(12) United States Patent
Staben et al.

(10) Patent No.: US 8,901,313 B2
(45) Date of Patent: Dec. 2, 2014

(54) 6,5-HETEROCYCLIC PROPARGYLIC ALCOHOL COMPOUNDS AND USES THEREFOR

(75) Inventors: Steven Staben, South San Francisco, CA (US); Jianwen Feng, South San Francisco, CA (US); Pui Leng Loke, Abingdon (GB); Christian A. G. N. Montalbetti, Abingdon (GB)

(73) Assignee: Genentech, Inc., South San Francisco, CA (US)

( * ) Notice: Subject to any disclaimer, the term of this patent is extended or adjusted under 35 U.S.C. 154(b) by 258 days.

(21) Appl. No.: 13/420,988

(22) Filed: Mar. 15, 2012

(65) Prior Publication Data

US 2012/0214762 A1 Aug. 23, 2012

Related U.S. Application Data

(60) Provisional application No. 61/453,494, filed on Mar. 16, 2011.

(51) Int. Cl.
| | |
|---|---|
| C07D 401/14 | (2006.01) |
| C07D 403/04 | (2006.01) |
| C07D 405/14 | (2006.01) |
| C07D 413/14 | (2006.01) |
| C07D 417/14 | (2006.01) |
| C07D 487/04 | (2006.01) |
| A61K 31/506 | (2006.01) |
| A61K 31/53 | (2006.01) |
| A61K 31/4184 | (2006.01) |
| A61P 19/02 | (2006.01) |
| C07D 403/14 | (2006.01) |
| C07D 491/10 | (2006.01) |

(52) U.S. Cl.
CPC ............ *C07D 417/14* (2013.01); *C07D 401/14* (2013.01); *C07D 403/04* (2013.01); *C07D 403/14* (2013.01); *C07D 405/14* (2013.01); *C07D 413/14* (2013.01); *C07D 487/04* (2013.01); *C07D 491/10* (2013.01)
USPC ...................... 548/304.7; 514/394; 514/231.5; 514/241; 514/256; 514/252.06; 514/252.12; 514/320; 514/365; 514/374; 514/381; 514/383; 514/406; 544/112; 544/114; 544/180; 544/296; 544/331; 544/238; 548/146; 548/240; 548/250; 548/255; 548/356.1; 546/192

(58) Field of Classification Search
USPC ................ 548/304.7; 514/394, 231.5, 24; 544/112, 114, 180, 296, 331
See application file for complete search history.

(56) References Cited

U.S. PATENT DOCUMENTS

| | | |
|---|---|---|
| 5,804,374 A | 9/1998 | Baltimore et al. |
| 6,841,549 B1 | 1/2005 | Asano et al. |
| 7,329,679 B2 | 2/2008 | Halfbrodt et al. |
| 7,485,456 B1 | 2/2009 | Wallach et al. |
| 7,521,447 B2 | 4/2009 | Munson et al. |
| 2011/0086384 A1 | 4/2011 | Eckstein et al. |
| 2011/0086834 A1 | 4/2011 | Chen et al. |

FOREIGN PATENT DOCUMENTS

| | | |
|---|---|---|
| WO | 2005/054230 A1 | 6/2005 |
| WO | 2007/058850 A2 | 5/2007 |
| WO | 2007/058850 A3 | 5/2007 |
| WO | 2008/043019 A1 | 4/2008 |
| WO | 2009/158011 A1 | 12/2009 |
| WO | 2010/071837 A1 | 6/2010 |
| WO | 2012/012478 A1 | 1/2012 |

OTHER PUBLICATIONS

Cecil Textbook of Medicine, edited by Bennet, J.C., and Plum F., 20th edition,vol. 1, 1004-101 O, 1996.*
Mass, R. D., Int. J. Radiation Oncology Bio. Phys.vol. 58(3): 932-940, 2004.*
Fabbro et al. Pharmacology & therapeutics 93, 79-98, 2002.*
Cohen et al., Current Opinion in Chemical Biology, 3,459-465, 1999.*
Freshney et al.,Culture of Animal Cells, A Manual of Basic Technique, Alan R. Liss, Inc., 1983, New York, p. 4.*
Dermer et al., Bio/Technology, 1994, 12:320.*
Chen et al., "Development of pyrimidine-based inhibitors of Janus tyrosine kinase 3" Bioorg Med Chem Lett. 16(21):5633-8 (Nov. 2006).
PCT ISA for PCT/EP2012/054518, Mar. 15, 2012.
Altmeyer et al., "Subtype-selectivity of metal-dependent methionine aminopeptidase inhibitors" Bioorg Med Chem Lett. 20(14):4038-44, 2010.
:International Search Report and Written Opinion for PCT/EP2012/054518, Jun. 12, 2012.

* cited by examiner

*Primary Examiner* — Venkataraman Balasubramanian
(74) *Attorney, Agent, or Firm* — Tamara Kale; Genentech, Inc.

(57) ABSTRACT

The invention relates to novel compounds of Formula I:

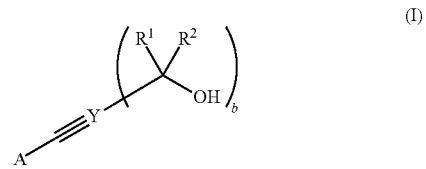

(I)

wherein A, Y, $R^1$, $R^2$ and the subscript b each has the meaning as described herein and compounds of Formula I, and stereoisomers, geometric isomers, tautomers, solvates, metabolites, isotopes, pharmaceutically acceptable salts, or prodrugs thereof. Compounds of Formula I and pharmaceutical compositions thereof are useful in the treatment of disease and disorders in which undesired or over-activation of NF-kB signaling is observed.

21 Claims, No Drawings

6,5-HETEROCYCLIC PROPARGYLIC ALCOHOL COMPOUNDS AND USES THEREFOR

CROSS-REFERENCE TO RELATED APPLICATION

This application claims the benefit of priority to U.S. Provisional Application No. 61/453,494 filed on Mar. 16, 2011 which is incorporated by reference in its entirety for all purposes.

FIELD OF THE INVENTION

The present invention relates to organic compounds useful for therapy and/or prophylaxis in a mammal, and in particular to inhibitors of NF-kB-inducing kinase (NIK) useful for treating cancer and inflammatory diseases and disorders, among others. NF-kB inducing kinase (NIK) is also known as MAPK kinase kinase 14 (MAP3K14) and is a serine/threonine kinase and a member of the MAPK family. It was originally identified in a two-hybrid screen as a binding partner of TNF receptor (TNFR) associated factor 2 (TRAF2) [See, Malinin, N L, et al, Nature, 1997, 385:540-4]. Overexpression of NIK leads to the activation of NF-kB and dominant negative forms of NIK lacking kinase activity were able to inhibit NF-kB activation in response to TNF and IL-1 treatment. Thus NIK has been identified as an important component of the NF-kB signaling pathway. Scientific research has shown that in blocking the NF-kB signaling pathway in cancer cells can cause such cells to stop proliferating, to die, and/or to become more sensitive to the action of other anticancer therapies. Additionally, research has shown that NF-κB controls the expression of many genes involved in inflammation and that NF-kB signalling is found to be chronically active in many inflammatory diseases, such as rheumatoid arthritis, inflammatory bowel disease, arthritis, sepsis, gastritis, asthma, among others. Accordingly, organic compounds capable of inhibiting NIK and thereby inhibiting, weakening and/or lessening the undesired or over-activation of the NF-kB signaling pathway can have a therapeutic benefit for the treatment diseases and disorders for which such undesired or over-activation of NF-kB signaling is observed.

SUMMARY OF THE INVENTION

In one aspect, the present invention provides for compounds of Formula I:

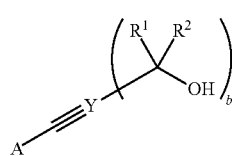

(I)

in which for compounds of Formula I, Y is nitrogen and the subscript b is the integer 0, or Y is carbon and the subscript b is the integer 1. $R^1$ is $C_{1-2}$ alkyl, $C_{1-2}$ haloalkyl or —$CH_2$—OH. $R^2$ is $C_{1-6}$ alkyl, $C_{1-6}$ haloalkyl, 3-7 membered cycloalkyl, $C_{1-6}$ alkylene-3-7 membered cycloalkyl, phenyl, 5-6 membered heteroaryl, —C(=O)$R^{x2a}$, —C(=O)O$R^{x2a}$ or —C(=O)N$R^{x2a}R^{x2b}$, in which $R^{x2a}$ is selected from the group consisting of hydrogen, $C_{1-6}$ alkyl, $C_{2-6}$ alkenyl, $C_{2-6}$ alkynyl, $C_{1-6}$ heteroalkyl, 3-8 membered cycloalkyl, 3-8 membered heteroalkyl, —($C_{1-6}$ alkylene)-(3-8 membered cycloalkyl), —($C_{1-6}$ alkylene)-(3-8 membered heterocycloalkyl), —($C_{1-6}$ alkylene)-(6-membered aryl) and —($C_{1-6}$ alkylene)-(5-6 membered heteroaryl), and $R^{x2b}$ is selected from the group consisting of hydrogen, $C_{1-6}$ alkyl, $C_{2-6}$ alkenyl, $C_{2-6}$ alkynyl and $C_{1-6}$ heteroalkyl. In Formula I, when $R^{x2a}$ and $R^{x2b}$ are attached to the same nitrogen atom, then they are optionally combined to form a 3-7 membered heterocycloalkyl further comprising 0-2 additional heteroatoms selected from N, O and S. Alternatively, in Formula I, $R^1$ and $R^2$ are combined to form a 3-8 membered cycloalkyl or 3-8 membered heterocycloalkyl and optionally fused thereto is a 5-6 membered heteroaryl ring comprising 1-3 heteroatoms selected from N, O and S. The aliphatic and/or aromatic portions of $R^1$ and $R^2$ either independently or when combined, are optionally substituted with 1 to 5 $R^{R1/2}$ substituents selected from the group consisting of F, Cl, Br, I, —OH, —$NH_2$, —SH, —$CF_3$, —$OCF_3$, —$SF_5$, —$OCH_3$, —$(X^a)_{0-1}$—CN, —$(X^a)_{0-1}$—$NO_2$, —$(X^a)_{0-1}$—$N_3$, —$(X^a)_{0-1}$—OH, —$(X^a)_{0-1}$—H, —$(X^a)_{0-1}$—$OR^a$, —$(X^a)_{0-1}$—N(H)$R^a$, —$(X^a)_{0-1}$—N(H)$_2$, —$(X^a)_{0-1}$—N($R^a$)$_2$, —$(X^a)_{0-1}$—$SR^a$, —$(X^a)_{0-1}$—SH, —$(X^a)_{0-1}$—C(O)$R^a$, —$(X^a)_{0-1}$—S(O)$_2R^a$, —$(X^a)_{0-1}$—S(O)$R^a$, —$(X^a)_{0-1}$—N(H)S(O)$_2R^a$, —$(X^a)_{0-1}$—N($R^a$)S(O)$_2R^a$, —$(X^a)_{0-1}$—OC(O)$R^a$, —$(X^a)_{0-1}$—N(H)C(O)$OR^a$, —$(X^a)_{0-1}$—N($R^a$)C(O)$OR^a$, —$(X^a)_{0-1}$—C(=O)$OR^a$, —$(X^a)_{0-1}$—C(=O)OH, —$(X^a)_{0-1}$—C(=O)N(H)$R^a$, —$(X^a)_{0-1}$—C(=O)N($R^a$)$R^a$, —$(X^a)_{0-1}$—N(H)C(=O)$R^a$, —$(X^a)_{0-1}$—N($R^a$)C(=O)$R^a$, —$(X^a)_{0-1}$—N(H)C(=O)$OR^a$ and —$(X^a)_{0-1}$—N($R^a$)C(=O)$OR^a$, in which $X^a$ is selected from the group consisting of $C_{1-6}$ alkylene, $C_{2-6}$ alkenylene, $C_{2-6}$ alkynylene, $C_{1-6}$ heteroalkylene, 3-6 membered cycloalkylene and 3-6 membered heterocycloalkylene, and $R^a$ at each occurrence is independently selected from the group consisting of $C_{1-6}$ alkyl, $C_{1-6}$ haloalkyl, $C_{1-6}$ heteroalkyl, $C_{2-6}$ alkenyl, $C_{2-6}$ alkynyl, 3-7 membered cycloalkyl and 3-7 membered heterocycloalkyl. In Formula I, A is selected from the group consisting of:

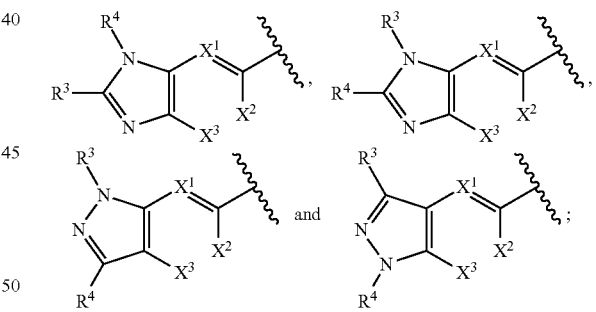

in which $X^1$, $X^2$ and $X^3$ are independently N or $CR^5$, wherein at least one of $X^1$, $X^2$ and $X^3$ is $CR^5$, where $R^5$ is selected from the group consisting of hydrogen, $C_{1-4}$ alkyl, $C_{1-4}$ haloalkyl, halogen, —$OC_{1-6}$ alkyl, 3-6 membered heterocycloalkyl-$C_{1-3}$alkyleneoxy-, —CN, —$NO_2$, —NH($C_{1-6}$ alkyl), —$NH_2$ and —N($C_{1-6}$ alkyl)$_2$. In Formula I, $R^3$ is 5-10 membered heteroaryl optionally substituted with —$NR^{x3a}R^{x3b}$, in which $R^{x3a}$ and $R^{x3b}$ are each independently selected from the group consisting of hydrogen, $C_{1-6}$ alkyl, $C_{1-6}$haloalkyl, $C_{2-6}$ alkenyl, $C_{2-6}$ alkynyl, $C_{1-6}$ alkoxy, $C_{1-6}$ heteroalkyl, 6-10 membered aryl and 5-10 membered heteroaryl. In Formula I, $R^3$ and the $R^{x3a}$ and $R^{x3b}$ groups of $R^3$, if present, are further each independently optionally substituted with 1 to 5 $R^{R3}$ substituents selected from the group consisting of F, Cl, Br, I, —OH, —$NH_2$, —SH, —$CF_3$, —$OCF_3$, —$SF_5$, —$OCH_3$, —(X$^b$)$_{0-1}$—CN, —(X$^b$)$_{0-1}$—NO$_2$, —(X$^b$)$_{0-1}$—N$_3$, —(X$^b$)—OH, —(X$^b$)—H, —(X$^b$)$_{0-1}$—OR$^b$, —(X$^b$)—N(H)$_2$, —(X$^b$)$_{0-1}$—N(R$^b$)$_2$, —(X$^b$)$_{0-1}$—SR$^b$, —(X$^b$)$_{0-1}$—SH, —(X$^b$)$_{0-1}$—C(O)R$^b$, —(X$^b$)$_{0-1}$—S(O)$_2$R$^b$, —(X$^b$)$_{0-1}$—S(O)R$^b$, —(X$^b$)$_{0-1}$—N(H)S(O)$_2$R$^b$, —(X$^b$)$_{0-1}$—N(R$^b$)S(O)$_2$R$^b$, —(X$^b$)$_{0-1}$—OC(O)R$^b$, —(X$^b$)$_{0-1}$—N(H)C(O)OR$^b$, —(X$^b$)$_{0-1}$—N(R$^b$)C(O)OR$^b$, —(X$^b$)$_{0-1}$—C(=O)OR$^b$, —(X$^b$)$_{0-1}$—C(=O)OH, —(X$^b$)$_{0-1}$—C(=O)N(H)R$^b$, —(X$^b$)$_{0-1}$—C(=O)N(R$^b$)R$^b$, —(X$^b$)$_{0-1}$—N(H)C(=O)R$^b$, —(X$^b$)$_{0-1}$—N(R$^b$)C(=O)R$^b$, —(X$^b$)$_{0-1}$—N(H)C(=O)OR$^b$ and —(X$^b$)$_{0-1}$—N(R$^b$)C(=O)OR$^b$, in which X$^b$ is selected from the group consisting of C$_{1-6}$ alkylene, C$_{2-6}$ alkenylene, C$_{2-6}$ alkynylene, C$_{1-6}$ heteroalkylene, C$_{3-6}$ cycloalkylene and C$_{3-6}$ heterocycloalkylene, and R$^b$ at each occurrence is independently selected from the group consisting of C$_{1-6}$ alkyl, C$_{1-6}$ haloalkyl, C$_{1-6}$ heteroalkyl, C$_{2-6}$ alkenyl, C$_{2-6}$ alkynyl, 3-7 membered cycloalkyl and 3-7 membered heterocycloalkyl. In Formula I, R$^4$ is -(L)$_{0-1}$-R$^{x4a}$, wherein L is selected from the group consisting of —O—, —N(H)—, —C(=O)—, C$_{1-4}$ alkylene, C$_{1-4}$ haloalkylene, C$_{2-4}$ alkenylene, C$_{2-4}$ alkynylene and C$_{1-4}$ heteroalkylene and R$^{x4a}$ is selected from the group consisting of hydrogen, C$_{1-6}$ alkyl, C$_{1-6}$ haloalkyl, C$_{2-6}$ alkenyl, C$_{2-6}$ alkynyl and C$_{1-6}$ heteroalkyl, 3-6 membered cycloalkyl, 3-9 membered heterocycloalkyl, 6-10 membered aryl and 5-10 membered heteroaryl. The aliphatic or aromatic portions of R$^4$ are independently substituted with 0 to 5 R$^{R4}$ substituents selected from the group consisting of C$_{1-6}$ alkyl, C$_{1-6}$ haloalkyl, C$_{1-6}$ heteroalkyl, C$_{1-6}$ alkoxy, C$_{1-6}$ alkylamino, C$_{1-6}$ dialkylamino, C$_{3-6}$ heterocycloalkyl, F, Cl, Br, I, —OH, —NH$_2$, —SH, —CF$_3$, —OCF$_3$, —SF$_5$, —(X$^c$)$_{0-1}$—CN, —(X$^c$)$_{0-1}$—NO$_2$, —(X$^c$)$_{0-1}$—N$_3$, —(X$^c$)—OH, —(X$^c$)$_{0-1}$—OR$^c$, —(X$^c$)—H, —(X$^c$)$_{0-1}$—R$^c$, —(X$^c$)$_{0-1}$-N(H)R$^c$, —(X$^c$)$_{0-1}$—N(R$^c$)$_2$, —(X$^c$)$_{0-1}$—SR$^c$, —(X$^c$)$_{0-1}$—C(O)R$^c$, —(X$^c$)$_{0-1}$—S(O)$_2$R$^c$, —(X$^c$)$_{0-1}$—S(O)R$^c$, —(X$^c$)$_{0-1}$—N(H)S(O)$_2$R$^c$, —(X$^c$)$_{0-1}$—N(R$^c$)S(O)$_2$R$^c$, —(X$^c$)$_{0-1}$—C(=O)OR$^c$, —(X$^c$)$_{0-1}$—C(=O)OH, —(X$^c$)$_{0-1}$—C(=O)N(H)R$^c$, —(X$^c$)$_{0-1}$—C(=O)N(R$^c$)R$^c$, —(X$^c$)$_{0-1}$—N(H)C(=O)R$^c$ and —(X$^c$)$_{0-1}$—N(R$^c$)C(=O)R$^c$, in which X$^c$ is selected from the group consisting of C$_{1-6}$ alkylene, C$_{2-6}$ alkenylene, C$_{2-6}$ alkynylene, C$_{1-6}$ heteroalkylene, C$_{3-6}$ cycloalkylene and C$_{3-6}$ heterocycloalkylene, and R$^c$ at each occurrence is independently selected from the group consisting of C$_{1-6}$ alkyl, C$_{1-6}$ haloalkyl, C$_{1-6}$ heteroalkyl, C$_{2-6}$ alkenyl, C$_{2-6}$ alkynyl, 3-7 membered cycloalkyl, 3-7 membered heterocycloalkyl, phenyl and 5-6 membered heteroaryl. In Formula I, any two R$^c$ groups attached to the same nitrogen atom are optionally combined to form a 3-7 membered heterocycloalkyl or 5-10 membered heteroaryl comprising 1-3 heteroatoms selected from N, O and S. In another aspect, the invention provides for stereoisomers, geometric isomers, tautomers, solvates, metabolites, isotopes, pharmaceutically acceptable salts, or prodrugs of compound of Formula I. In another aspect, the invention provides for pharmaceutical compositions comprising a compound of Formula I (or stereoisomers, geometric isomers, tautomers, solvates, metabolites, isotopes, pharmaceutically acceptable salts, or prodrugs thereof) and a therapeutically inert carrier. In another aspect, the invention provides for a method (and/or use) of compounds of Formula I in the treatment of diseases and disorders, such as, for example, cancer, inflammatory diseases, autoimmune diseases, among others. In another aspect, the invention provides for compounds of Formula I for the preparation of a medicament for the treatment of cancer, inflammatory diseases, autoimmune diseases, among others. In another aspect, the inventions provides for compounds of Formula I for the treatment of diseases and disorders, including, cancer, inflammatory disease, autoimmune disease, among others.

DETAILED DESCRIPTION OF THE INVENTION

The invention provides for compounds of Formula I, pharmaceutical compositions comprising compounds of Formula I and methods of using such compounds and compositions in treating diseases and disordered related to undesired or overactivation of NF-kB signaling pathway, such as, for example, certain cancers and inflammatory diseases and disorders.

DEFINITIONS

As used herein, the term "alkyl", by itself or as part of another substituent, means, unless otherwise stated, a straight or branched chain hydrocarbon radical, having the number of carbon atoms designated (i.e., C$_{1-8}$ means one to eight carbons). Examples of alkyl groups include methyl, ethyl, n-propyl, iso-propyl, n-butyl, t-butyl, iso-butyl, sec-butyl, n-pentyl, n-hexyl, n-heptyl, n-octyl, and the like. The term "alkenyl" refers to an unsaturated alkyl radical having one or more double bonds. Similarly, the term "alkynyl" refers to an unsaturated alkyl radical having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl," "carbocyclic," or "carbocycle" refers to hydrocarbon rings having the indicated number of ring atoms (e.g., 3-6 membered cycloalkyl) and being fully saturated or having no more than one double bond between ring vertices. As used herein, "cycloalkyl," "carbocyclic," or "carbocycle" is also meant to refer to bicyclic, polycyclic and spirocyclic hydrocarbon rings such as, for example, bicyclo[2.2.1]heptane, pinane, bicyclo[2.2.2]octane, adamantane, norborene, spirocyclic C$_{5-12}$ alkane, etc. As used herein, the terms, "alkenyl," "alkynyl," "cycloalkyl,", "carbocycle," and "carbocyclic," are meant to include mono and polyhalogenated variants thereof.

The term "heteroalkyl," by itself or in combination with another term, means, unless otherwise stated, a stable straight or branched chain hydrocarbon radical, consisting of the stated number of carbon atoms and from one to three heteroatoms selected from the group consisting of O, N, Si and S, and wherein the nitrogen and sulfur atoms can optionally be oxidized and the nitrogen heteroatom can optionally be quaternized. The heteroatom(s) O, N and S can be placed at any interior position of the heteroalkyl group. The heteroatom Si can be placed at any position of the heteroalkyl group, including the position at which the alkyl group is attached to the remainder of the molecule. A "heteroalkyl" can contain up to three units of unsaturation, and also include mono- and polyhalogenated variants, or combinations thereof. Examples include —CH$_2$—CH$_2$—O—CH$_3$, —CH$_2$—CH$_2$—O—CF$_3$, —CH$_2$—CH$_2$—NH—CH$_3$, —CH$_2$—CH$_2$—N(CH$_3$)—CH$_3$, —CH$_2$—S—CH$_2$—CH$_3$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH=N(CH$_3$)—CH$_3$. Up to two heteroatoms can be consecutive, such as, for example, —CH$_2$—NH—OCH$_3$ and —CH$_2$—O—Si(CH$_3$)$_3$.

The term "heterocycloalkyl," "heterocyclic," or "heterocycle" refers to a cycloalkane ring having the indicated number of ring atoms (e.g., 5-6 membered heterocycloalkyl) that contain from one to five heteroatoms selected from N, O, and S, wherein the nitrogen and sulfur atoms are optionally oxidized, nitrogen atom(s) are optionally quaternized, as ring atoms. Unless otherwise stated, a "heterocycloalkyl," "heterocyclic," or "heterocycle" ring can be a monocyclic, a bicyclic, spirocyclic or a polycyclic ring system. Non limiting examples of "heterocycloalkyl," "heterocyclic," or "heterocycle" rings include pyrrolidine, piperidine, N-methylpiperidine, imidazolidine, pyrazolidine, butyrolactam, valerolactam, imidazolidinone, hydantoin, dioxolane, phthalimide, piperidine, pyrimidine-2,4(1H,3H)-dione, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrahydrothiophene, quinuclidine, tropane and the like. A "heterocycloalkyl," "heterocyclic," or "heterocycle" group can be attached to the remainder of the molecule through one or more ring carbons or heteroatoms. A "heterocycloalkyl," "heterocyclic," or "heterocycle" can include mono- and poly-halogenated variants thereof.

The term "alkylene" by itself or as part of another substituent means a divalent radical derived from an alkane, as exemplified by —CH$_2$CH$_2$CH$_2$CH$_2$—. Typically, an alkyl (or alkylene) group will have from 1 to 24 carbon atoms, with those groups having 10 or fewer carbon atoms being preferred in the present invention. "Alkenylene" and "alkynylene" refer to the unsaturated forms of "alkylene" having double or triple bonds, respectively. "Alkylene", "alkenylene" and "alkynylene" are also meant to include mono and poly-halogenated variants.

The term "heteroalkylene" by itself or as part of another substituent means a divalent radical, saturated or unsaturated or polyunsaturated, derived from heteroalkyl, as exemplified by —CH$_2$—CH$_2$—S—CH$_2$CH$_2$— and —CH$_2$—S—CH$_2$—CH$_2$—NH—CH$_2$—, —O—CH$_2$—CH=CH—, —CH$_2$—CH=C(H)CH$_2$—O—CH$_2$— and —S—CH$_2$—C≡C—. For heteroalkylene groups, heteroatoms can also occupy either or both of the chain termini (e.g., alkyleneoxy, alkylenedioxy, alkyleneamino, alkylenediamino, and the like). The term "heteroalkylene" is also meant to include mono and poly-halogenated variants.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively, and further include mono- and poly-halogenated variants thereof. Additionally, for dialkylamino groups, the alkyl portions can be the same or different and can also be combined to form a 3-7 membered ring with the nitrogen atom to which each is attached. Accordingly, a group represented as —NR$^a$R$^b$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, difluoromethyl, and the like.

The term "aryl" means, unless otherwise stated, a polyunsaturated, typically aromatic, hydrocarbon ring, which can be a single ring or multiple rings (up to three rings) which are fused together. The term "heteroaryl" refers to aryl ring(s) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Optional substituents for each of the above noted aryl and heteroaryl ring systems can be selected from the group of acceptable substituents described further below.

The above terms (e.g., "alkyl," "aryl" and "heteroaryl"), in some embodiments, will include both substituted and unsubstituted forms of the indicated radical. Preferred substituents for each type of radical are provided below.

Substituents for the alkyl radicals (including those groups often referred to as alkylene, alkenyl, alkynyl, heteroalkyl and cycloalkyl) can be a variety of groups including, but not limited to, -halogen, —OR', —NR'R'', —SR', —SiR'R''R''', —OC(O)R', —C(O)R', —CO$_2$R', —CONR'R'', —OC(O)NR'R'', —N R''C(O)R', —NR'''C(O)NR'R'', —NR''C(O)$_2$R', —NHC(NH$_2$)=NH, —NR'C(NH$_2$)=NH, —NHC(NH$_2$)=NR', —NR'''C(NR'R'')=N—CN, —NR'''C(NR'R'')=NOR', —NHC(NH$_2$)=NR', —S(O)R', —S(O)$_2$R', —S(O)$_2$NR'R'', —NR'S(O)$_2$R'', —NR'''S(O)$_2$NR'R'', —CN, —NO$_2$, —(CH$_2$)$_{1-4}$—OR', —(CH$_2$)$_{1-4}$—NR'R'', —(CH$_2$)$_{1-4}$—SR', —(CH$_2$)$_{1-4}$—SiR'R''R''', —(CH$_2$)$_{1-4}$OC(O)R', —(CH$_2$)$_{1-4}$—C(O)R', —(CH$_2$)$_{1-4}$—CO$_2$R', —(CH$_2$)$_{1-4}$CONR'R'', in a number ranging from zero to (2m'+1), where m' is the total number of carbon atoms in such radical. R', R'' and R''' each independently refer groups including, for example, hydrogen, unsubstituted $C_{1-6}$ alkyl, unsubstituted heteroalkyl, unsubstituted aryl, aryl substituted with 1-3 halogens, unsubstituted $C_{1-6}$ alkyl, $C_{1-6}$ alkoxy or $C_{1-6}$ thioalkoxy groups, or unsubstituted aryl-$C_{1-4}$ alkyl groups, unsubstituted heteroaryl, substituted heteroaryl, among others. When R' and R'' are attached to the same nitrogen atom, they can be combined with the nitrogen atom to form a 3-, 4-, 5-, 6-, or 7-membered ring. For example, —NR'R'' is meant to include 1-pyrrolidinyl and 4-morpholinyl. Other substituents for alkyl radicals, including heteroalkyl, alkylene, include for example, =O, =NR', =N—OR', =N—CN, =NH, wherein R' include substituents as described above. When a substituent for the alkyl radicals (including those groups often referred to as alkylene, alkenyl, alkynyl, heteroalkyl and cycloalkyl) contains an alkylene linker (e.g., —(CH$_2$)$_{1-4}$—NR'R''), the alkylene linker includes halo variants as well. For example, the linker "—(CH$_2$)$_{1-4}$—" when used as part of a substituent is meant to include difluoromethylene, 1,2-difluoroethylene, etc.

Similarly, substituents for the aryl and heteroaryl groups are varied and are generally selected from the group including, but not limited to, -halogen, —OR', —OC(O)R', —NR'R'', —SW, —R', —CN, —NO$_2$, —CO$_2$R', —CONR'R'', —C(O)R', —OC(O)NR'R'', —NR''C(O)R', —NR''C(O)$_2$R', —NR'C(O)NR''R''', —NHC(NH$_2$)=NH, —NR'C(NH$_2$)=NH, —NHC(NH$_2$)=NR', —S(O)R', —S(O)$_2$R', —S(O)$_2$NR'R'', —NR'S(O)$_2$R'', —N$_3$, perfluoro-$C_{1-4}$ alkoxy, and perfluoro-$C_{1-4}$ alkyl, —(CH$_2$)$_{1-4}$—OR', —(CH$_2$)$_{1-4}$—NR'R'', —(CH$_2$)$_{1-4}$—SR', —(CH$_2$)$_{1-4}$—SiR'R''R''', —(CH$_2$)$_{1-4}$—OC(O)R', —(CH$_2$)$_{1-4}$—C(O)R', —(CH$_2$)$_{1-4}$—CO$_2$R', —(CH$_2$)$_{1-4}$CONR'R'', in a number ranging from zero to the total number of open valences on the aromatic ring system; and where R', R'' and R''' are independently selected from hydrogen, $C_{1-6}$ alkyl, $C_{3-6}$ cycloalkyl, $C_{2-6}$ alkenyl, $C_{2-6}$ alkynyl, unsubstituted aryl and heteroaryl, (unsubstituted aryl)-$C_{1-4}$ alkyl, and unsubstituted aryloxy-$C_{1-4}$ alkyl. Other suitable substituents include each of the above aryl substituents attached to a ring atom by an alkylene tether of from 1-4 carbon atoms. When a substituent for the aryl or heteroaryl group contains an alkylene linker (e.g., —(CH$_2$)$_{1-4}$—NR'R"), the alkylene linker includes halo variants as well. For example, the linker "—(CH$_2$)$_{1-4}$—" when used as part of a substituent is meant to include difluoromethylene, 1,2-difluoroethylene, etc.

As used herein, the term "heteroatom" is meant to include oxygen (O), nitrogen (N), sulfur (S) and silicon (Si).

As used herein, the term "chiral" refers to molecules which have the property of non-superimposability of the mirror image partner, while the term "achiral" refers to molecules which are superimposable on their mirror image partner.

As used herein, the term "stereoisomers" refers to compounds which have identical chemical constitution, but differ with regard to the arrangement of the atoms or groups in space.

As used herein a wavy line "〜〜〜" that intersects a bond in a chemical structure indicate the point of attachment of the atom to which the wavy bond is connected in the chemical structure to the remainder of a molecule, or to the remainder of a fragment of a molecule.

As used herein, the representation of a group (e.g., $X^d$) in parenthesis followed by a subscript integer range (e.g., $(X^d)_{0-2}$) means that the group can have the number of occurrences as designated by the integer range. For example, $(X^d)_{0-1}$ means the group $X^d$ can be absent or can occur one time.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers can separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

As used herein, the term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

As used herein, the term "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

As used herein, the term "protecting group" refers to a substituent that is commonly employed to block or protect a particular functional group on a compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl) ethyl, 2-(trimethylsilyl)ethoxymethyl, 2-(p-toluenesulfonyl) ethyl, 2-(p-nitrophenylsulfenyl)ethyl, 2-(diphenylphosphino)-ethyl, nitroethyl and the like. For a general description of protecting groups and their use, see P. G. M. Wuts and T. W. Greene, Greene's Protective Groups in Organic Synthesis 4$^{th}$ edition, Wiley-Interscience, New York, 2006.

As used herein, the term "mammal" includes, but is not limited to, humans, mice, rats, guinea pigs, monkeys, dogs, cats, horses, cows, pigs, and sheep As used herein, the term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. As used herein the term "prodrug" refers to those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Prodrugs of the invention include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methyl-alanine, para-benzoylphenylalanine, phenylglycine, propargylglycine, sarcosine, methionine sulfone and tert-butylglycine.

Additional types of prodrugs are also encompassed. For instance, a free carboxyl group of a compound of the invention can be derivatized as an amide or alkyl ester. As another example, compounds of this invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as $(C_{1-6})$alkanoyloxymethyl, 1-($(C_{1-6})$alkanoyloxy)ethyl, 1-methyl-1-($(C_{1-6})$alkanoyloxy)ethyl, $(C_{1-6})$alkoxycarbonyloxymethyl, N—$(C_{1-6})$alkoxycarbonylaminomethyl, succinoyl, $(C_{1-6})$alkanoyl, alpha-amino$(C_{1-4})$alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_{1-6})alkyl)_2$ or glycosyl (the radical resulting from the removal of a hydroxyl group of the hemiacetal form of a carbohydrate).

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Additionally, the present invention provides for metabolites of compounds of the invention. As used herein, a "metabolite" refers to a product produced through metabolism in the body of a specified compound or salt thereof. Such products can result for example from the oxidation, reduction, hydrolysis, amidation, deamidation, esterification, deesterification, enzymatic cleavage, and the like, of the administered compound.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention can exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention.

The compounds of the present invention can also contain unnatural proportions of atomic isotopes at one or more of the atoms that constitute such compounds. For example, the present invention also embraces isotopically-labeled variants of the present invention which are identical to those recited herein, bur the for the fact that one or more atoms are replace by an atom having the atomic mass or mass number different from the predominant atomic mass or mass number usually found in nature for the atom. All isotopes of any particular atom or element as specified are contemplated within the scope of the compounds of the invention, and their uses. Exemplary isotopes that can be incorporated in to compounds of the invention include isotopes of hydrogen, carbon, nitrogen, oxygen, phosphorous, sulfur, fluorine, chlorine and iodine, such as $^{2}H$ ("D"), $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Certain isotopically labeled compounds of the present invention (e.g., those labeled with $^{3}H$ or $^{14}C$) are useful in compound and/or substrate tissue distribution assays. Tritiated ($^{3}H$) and carbon-14 ($^{14}C$) isotopes are useful for their ease of preparation and detectability. Further substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$, and $^{18}F$ are useful for positron emission tomography (PET) studies to examine substrate receptor occupancy. Isotopically labeled compounds of the present inventions can generally be prepared by following procedures analogous to those disclosed in the Schemes and/or in the Examples herein below, by substituting an isotopically labeled reagent for a non-isotopically labeled reagent.

The terms "treat" and "treatment" refer to both therapeutic treatment and/or prophylactic treatment or preventative measures, wherein the object is to prevent or slow down (lessen) an undesired physiological change or disorder, such as, for example, the development or spread of cancer. For purposes of this invention, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treatment" can also mean prolonging survival as compared to expected survival if not receiving treatment. Those in need of treatment include those already with the disease or disorder as well as those prone to have the disease or disorder or those in which the disease or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. For cancer therapy, efficacy can, for example, be measured by assessing the time to disease progression (TTP) and/or determining the response rate (RR). In the case of immunological disease, the therapeutic effective amount is an amount sufficient to decrease or alleviate an allergic disorder, the symptoms of an autoimmune and/or inflammatory disease (e.g. psoriasis or inflammatory bowel disease), or the symptoms of an acute inflammatory reaction (e.g. asthma). In some embodiments, a therapeutically effective amount is an amount of a chemical entity described herein sufficient to significantly decrease the activity or number of B-cells.

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

"Inflammatory disease or disorder" as used herein can refer to any disease, disorder, or syndrome in which an excessive or unregulated inflammatory response leads to excessive inflammatory symptoms, host tissue damage, or loss of tissue function.

"Inflammation" as used herein refers to a localized, protective response elicited by injury or destruction of tissues, which serves to destroy, dilute, or wall off (sequester) both the injurious agent and the injured tissue. Inflammation is notably associated with influx of leukocytes and/or neutrophil chemotaxis. Inflammation can result from infection with pathogenic organisms and viruses and from noninfectious means such as trauma or reperfusion following myocardial infarction or stroke, immune response to foreign antigen, and autoimmune responses.

The terms "cancer" and "cancerous" refer to or describe the physiological condition in mammals that is typically characterized by unregulated cell growth and/or proliferation. A "tumor" comprises one or more cancerous cells. Examples of cancer include, but are not limited to, carcinoma, lymphoma, blastoma, sarcoma, and leukemia or lymphoid malignancies.

"Autoimmune disease" as used herein refers to any group of disorders in which tissue injury is associated with humoral or cell-mediated responses to the body's own constituents.

COMPOUNDS

The compounds of the invention have Formula I:

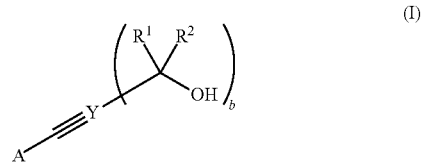

(I)

in which for compounds of Formula I, Y is nitrogen and the subscript b is the integer 0, or Y is carbon and the subscript b is the integer 1. $R^1$ is $C_{1-2}$ alkyl, $C_{1-2}$ haloalkyl or —$CH_2$—OH. $R^2$ is $C_{1-6}$ alkyl, $C_{1-6}$ haloalkyl, 3-7 membered cycloalkyl, $C_{1-6}$ alkylene-3-7 membered cycloalkyl, phenyl, 5-6 membered heteroaryl, —C(=O)$R^{x2a}$, —C(=O)O$R^{x2a}$ or —C(=O)N$R^{x2a}R^{x2b}$, in which $R^{x2a}$ is selected from the group consisting of hydrogen, $C_{1-6}$ alkyl, $C_{2-6}$ alkenyl, $C_{2-6}$ alkynyl, $C_{1-6}$ heteroalkyl, 3-8 membered cycloalkyl, 3-8 membered heteroalkyl, —($C_{1-6}$ alkylene)-(3-8 membered cycloalkyl), —($C_{1-6}$ alkylene)-(3-8 membered heterocycloalkyl), —($C_{1-6}$ alkylene)-(6-membered aryl) and —($C_{1-6}$ alkylene)-(5-6 membered heteroaryl), and $R^{x2b}$ is selected from the group consisting of hydrogen, $C_{1-6}$ alkyl, $C_{2-6}$ alkenyl, $C_{2-6}$ alkynyl and $C_{1-6}$ heteroalkyl. In Formula I, when $R^{x2a}$ and $R^{x2b}$ are attached to the same nitrogen atom, then they are optionally combined to form a 3-7 membered heterocycloalkyl further comprising 0-2 additional heteroatoms selected from N, O and S. Alternatively, in Formula I, $R^1$ and $R^2$ are combined to form a 3-8 membered cycloalkyl or 3-8 membered heterocycloalkyl and optionally fused thereto is a 5-6 membered heteroaryl ring comprising 1-3 heteroatoms selected from N, O and S. The aliphatic and/or aromatic portions of $R^1$ and $R^2$ either independently or when combined, are optionally substituted with 1 to 5 $R^{R1/2}$ substituents selected from the group consisting of F, Cl, Br, I, —OH, —$NH_2$, —SH, —$CF_3$, —$OCF_3$, —$SF_5$, —$OCH_3$, —$(X^a)_{0-1}$—CN, —$(X^a)_{0-1}$—$NO_2$, —$(X^a)_{0-1}$—$N_3$, —$(X^a)_{0-1}$—OH, —$(X^a)_{0-1}$—H, —$(X^a)_{0-1}$—$OR^a$, —$(X^a)_{0-1}$—$N(H)R^a$, —$(X^a)_{0-1}$—$N(H)_2$, —$(X^a)_{0-1}$—$N(R^a)_2$, —$(X^a)_{0-1}$—$SR^a$, —$(X^a)_{0-1}$—SH, —$(X^a)_{0-1}$—$C(O)R^a$, —$(X^a)_{0-1}$—$S(O)_2R^a$, —$(X^a)_{0-1}$—$S(O)R^a$, —$(X^a)_{0-1}$—$N(H)S(O)_2R^a$, —$(X^a)_{0-1}$—$N(R^a)S(O)_2R^a$, —$(X^a)_{0-1}$—$OC(O)R^a$, —$(X^a)_{0-1}$—$N(H)C(O)OR^a$, —$(X^a)_{0-1}$—$N(R^a)C(O)OR^a$, —$(X^a)_{0-1}$—$C(=O)OR^a$, —$(X^a)_{0-1}$—$C(=O)OH$, —$(X^a)_{0-1}$—$C(=O)N(H)R^a$, —$(X^a)_{0-1}$—$C(=O)N(R^a)R^a$, —$(X^a)_{0-1}$—$N(H)C(=O)R^a$, —$(X^a)_{0-1}$—$N(R^a)C(=O)R^a$, —$(X^a)_{0-1}$—$N(H)C(=O)OR^a$ and —$(X^a)_{0-1}$—$N(R^a)C(=O)OR^a$, in which $X^a$ is selected from the group consisting of $C_{1-6}$ alkylene, $C_{2-6}$ alkenylene, $C_{2-6}$ alkynylene, $C_{1-6}$ heteroalkylene, 3-6 membered cycloalkylene and 3-6 membered heterocycloalkylene, and $R^a$ at each occurrence is independently selected from the group consisting of $C_{1-6}$ alkyl, $C_{1-6}$ haloalkyl, $C_{1-6}$ heteroalkyl, $C_{2-6}$ alkenyl, $C_{2-6}$ alkynyl, 3-7 membered cycloalkyl and 3-7 membered heterocycloalkyl. In Formula I, A is selected from the group consisting of:

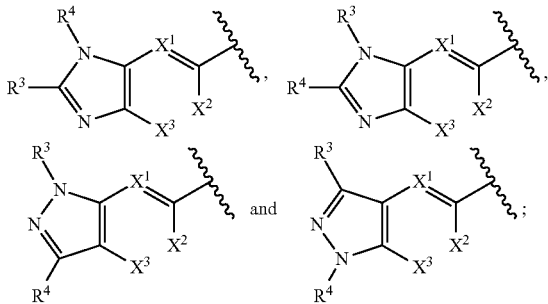

in which $X^1$, $X^2$ and $X^3$ are independently N or $CR^5$, wherein at least one of $X^1$, $X^2$ and $X^3$ is $CR^5$, where $R^5$ is selected from the group consisting of hydrogen, $C_{1-4}$ alkyl, $C_{1-4}$ haloalkyl, halogen, —$OC_{1-6}$ alkyl, 3-6 membered heterocycloalkyl-$C_{1-3}$alkyleneoxy-, —CN, —$NO_2$, —$NH(C_{1-6}$ alkyl), —$NH_2$ and —$N(C_{1-6}$ alkyl$)_2$. In Formula I, $R^3$ is 5-10 membered heteroaryl optionally substituted with —$NR^{x3a}R^{x3b}$, in which $R^{x3a}$ and $R^{x3b}$ are each independently selected from the group consisting of hydrogen, $C_{1-6}$ alkyl, $C_{1-6}$haloalkyl, $C_{2-6}$ alkenyl, $C_{2-6}$ alkynyl, $C_{1-6}$ alkoxy, $C_{1-6}$ heteroalkyl, 6-10 membered aryl and 5-10 membered heteroaryl. In Formula I, $R^3$ and the $R^{x3a}$ and $R^{x3b}$ groups of $R^3$, if present, are further each independently optionally substituted with 1 to 5 $R^{R3}$ substituents selected from the group consisting of F, Cl, Br, I, —OH, —$NH_2$, —SH, —$CF_3$, —$OCF_3$, —$SF_5$, —$OCH_3$, —$(X^b)_{0-1}$—CN, —$(X^b)_{0-1}$—$NO_2$, —$(X^b)_{0-1}$—$N_3$, —$(X^b)$—OH, —$(X^b)$—H, —$(X^b)_{0-1}$—$OR^b$, —$(X^b)_{0-1}$—$N(H)R^b$, —$(X^b)$—$N(H)_2$, —$(X^b)_{0-1}$—$N(R^b)_2$, —$(X^b)_{0-1}$—$SR^b$, —$(X^b)_{0-1}$—SH, —$(X^b)_{0-1}$—$C(O)R^b$, —$(X^b)_{0-1}$—$S(O)_2R^b$, —$(X^b)_{0-1}$—$S(O)R^b$, —$(X^b)_{0-1}$—$N(H)S(O)_2R^b$, —$(X^b)_{0-1}$—$N(R^b)S(O)_2R^b$, —$(X^b)_{0-1}$—$OC(O)R^b$, —$(X^b)_{0-1}$—$N(H)C(O)OR^b$, —$(X^b)_{0-1}$—$N(R^b)C(O)OR^b$, —$(X^b)_{0-1}$—$C(=O)OR^b$, —$(X^b)_{0-1}$—$C(=O)OH$, —$(X^b)_{0-1}$—$C(=O)N(H)R^b$, —$(X^b)_{0-1}$—$C(=O)N(R^b)R^b$, —$(X^b)_{0-1}$—$N(H)C(=O)R^b$, —$(X^b)_{0-1}$—$N(R^b)C(=O)R^b$, —$(X^b)_{0-1}$—$N(H)C(=O)OR^b$ and —$(X^b)_{0-1}$—$N(R^b)C(=O)OR^b$, in which $X^b$ is selected from the group consisting of $C_{1-6}$ alkylene, $C_{2-6}$ alkenylene, $C_{2-6}$ alkynylene, $C_{1-6}$ heteroalkylene, $C_{3-6}$ cycloalkylene and $C_{3-6}$ heterocycloalkylene, and $R^b$ at each occurrence is independently selected from the group consisting of $C_{1-6}$ alkyl, $C_{1-6}$ haloalkyl, $C_{1-6}$ heteroalkyl, $C_{2-6}$ alkenyl, $C_{2-6}$ alkynyl, 3-7 membered cycloalkyl and 3-7 membered heterocycloalkyl. In Formula I, $R^4$ is -$(L)_{0-1}$-$R^{x4a}$, wherein L is selected from the group consisting of —O—, —N(H)—, —C(=O)—, $C_{1-4}$ alkylene, $C_{1-4}$ haloalkylene, $C_{2-4}$ alkenylene, $C_{2-4}$ alkynylene and $C_{1-4}$ heteroalkylene and $R^{x4a}$ is selected from the group consisting of hydrogen, $C_{1-6}$ alkyl, $C_{1-6}$ haloalkyl, $C_{2-6}$ alkenyl, $C_{2-6}$ alkynyl and $C_{1-6}$ heteroalkyl, 3-6 membered cycloalkyl, 3-9 membered heterocycloalkyl, 6-10 membered aryl and 5-10 membered heteroaryl. The aliphatic or aromatic portions of $R^4$ are independently substituted with 0 to 5 $R^{R4}$ substituents selected from the group consisting of $C_{1-6}$ alkyl, $C_{1-6}$ haloalkyl, $C_{1-6}$ heteroalkyl, $C_{1-6}$ alkoxy, $C_{1-6}$ alkylamino, $C_{1-6}$ dialkylamino, $C_{3-6}$ heterocycloalkyl, F, Cl, Br, I, —OH, —$NH_2$, —SH, —$CF_3$, —$OCF_3$, —$SF_5$, —$(X^c)_{0-1}$—CN, —$(X^c)_{0-1}$—$NO_2$, —$(X^c)_{0-1}$—$N_3$, —$(X^c)$—OH, —$(X^c)_{0-1}$—$OR^c$, —$(X^c)$—H, —$(X^c)_{0-1}$—$N(H)R^c$, —$(X^c)_{0-1}$—$N(R^c)_2$, —$(X^c)_{0-1}$—$SR^c$, —$(X^c)_{0-1}$—$C(O)R^c$, —$(X^c)_{0-1}$—$S(O)_2R^c$, —$(X^c)_{0-1}$—$S(O)R^c$, —$(X^c)_{0-1}$—$N(H)S(O)_2R^c$, —$(X^c)_{0-1}$—$N(R^c)S(O)_2R^c$, —$(X^c)_{0-1}$—$C(=O)OR^c$, —$(X^c)_{0-1}$—$C(=O)OH$, —$(X^c)_{0-1}$—$C(=O)N(H)R^c$, —$(X^c)_{0-1}$—$C(=O)N(R^c)R^c$, —$(X^c)_{0-1}$—$N(H)C(=O)R^c$ and —$(X^c)_{0-1}$—$N(R^c)C(=O)R^c$, in which $X^c$ is selected from the group consisting of $C_{1-6}$ alkylene, $C_{2-6}$ alkenylene, $C_{2-6}$ alkynylene, $C_{1-6}$ heteroalkylene, $C_{3-6}$ cycloalkylene and $C_{3-6}$ heterocycloalkylene, and $R^c$ at each occurrence is independently selected from the group consisting of $C_{1-6}$ alkyl, $C_{1-6}$ haloalkyl, $C_{1-6}$ heteroalkyl, $C_{2-6}$ alkenyl, $C_{2-6}$ alkynyl, 3-7 membered cycloalkyl, 3-7 membered heterocycloalkyl, phenyl and 5-6 membered heteroaryl. In Formula I, any two $R^c$ groups attached to the same nitrogen atom are optionally combined to form a 3-7 membered heterocycloalkyl or 5-10 membered heteroaryl comprising 1-3 heteroatoms selected from N, O and S.

In another embodiment, in compounds of Formula I or in certain aspects of one or more embodiment(s) of compounds of Formula I, Y is nitrogen and the subscript b is the integer 0, or Y is carbon and the subscript b is the integer 1. $R^1$ is $C_{1-2}$ alkyl, $C_{1-2}$ haloalkyl or —$CH_2$—OH. $R^2$ is $C_{1-6}$ alkyl, $C_{1-6}$ haloalkyl, 3-7 membered cycloalkyl, phenyl, 5-6 membered heteroaryl, —$C(=O)R^{x2a}$, —$C(=O)OR^{x2a}$ or —$C(=O)NR^{x2a}R^{x2b}$, in which $R^{x2a}$ is selected from the group consisting of hydrogen, $C_{1-6}$ alkyl, $C_{2-6}$ alkenyl, $C_{2-6}$ alkynyl, $C_{1-6}$ heteroalkyl, 3-8 membered cycloalkyl, 3-8 membered heteroalkyl, —$(C_{1-6}$ alkylene)-(3-8 membered cycloalkyl), —$(C_{1-6}$ alkylene)-(3-8 membered heterocycloalkyl), —$(C_{1-6}$ alkylene)-(6-membered aryl) and —$(C_{1-6}$ alkylene)-(5-6 membered heteroaryl), and $R^{x2b}$ is selected from the group consisting of hydrogen, $C_{1-6}$ alkyl, $C_{2-6}$ alkenyl, $C_{2-6}$ alkynyl and $C_{1-6}$ heteroalkyl. In Formula I, when $R^{x2a}$ and $R^{x2b}$ are attached to the same nitrogen atom, then they are optionally combined to form a 3-7 membered heterocycloalkyl further comprising 0-2 additional heteroatoms selected from N, O and S. Alternatively, in Formula I, $R^1$ and $R^2$ are combined to form a 3-8 membered cycloalkyl or 3-8 membered heterocycloalkyl. The aliphatic and/or aromatic portions of $R^1$ and $R^2$ either independently or when combined, are optionally substituted with 1 to 5 $R^{R1/2}$ substituents selected from the group consisting of F, Cl, Br, I, —OH, —$NH_2$, —SH, —$CF_3$, —$OCF_3$, —$SF_5$, —$OCH_3$, —$(X^a)_{0-1}$—CN, —$(X^a)_{0-1}$—$NO_2$, —$(X^a)_{0-1}$—$N_3$, —$(X^a)_{0-1}$—OH, —$(X^a)_{0-1}$—H, —$(X^a)_{0-1}$—$OR^a$, —$(X^a)_{0-1}$—$N(H)R^a$, —$(X^a)_{0-1}$—$N(H)_2$, —$(X^a)_{0-1}$—$N(R^a)_2$, —$(X^a)_{0-1}$—$SR^a$, —$(X^a)_{0-1}$—SH, —$(X^a)_{0-1}$—$C(O)R^a$, —$(X^a)_{0-1}$—$S(O)_2R^a$, —$(X^a)_{0-1}$—$S(O)R^a$, —$(X^a)_{0-1}$—$N(H)S(O)_2R^a$, —$(X^a)_{0-1}$—$N(R^a)S(O)_2R^a$, —$(X^a)_{0-1}$—$OC(O)R^a$, —$(X^a)_{0-1}$—$N(H)C(O)OR^a$, —(X$^a$)$_{0-1}$—N(R$^a$)C(O)OR$^a$, —(X$^a$)$_{0-1}$—C(=O)OR$^a$, —(X$^a$)$_{0-1}$—C(=O)OH, —(X$^a$)$_{0-1}$—C(=O)N(H)R$^a$, —(X$^a$)$_{0-1}$—C(=O)N(R$^a$)R$^a$, —(X$^a$)$_{0-1}$—N(H)C(=O)R$^a$, —(X$^a$)$_{0-1}$—N(R$^a$)C(=O)R$^a$, —(X$^a$)$_{0-1}$—N(H)C(=O)OR$^a$ and —(X$^a$)$_{0-1}$—N(R$^a$)C(=O)OR$^a$, in which X$^a$ is selected from the group consisting of C$_{1-6}$ alkylene, C$_{2-6}$ alkenylene, C$_{2-6}$ alkynylene, C$_{1-6}$ heteroalkylene, 3-6 membered cycloalkylene and 3-6 membered heterocycloalkylene, and R$^a$ at each occurrence is independently selected from the group consisting of C$_{1-6}$ alkyl, C$_{1-6}$ haloalkyl, C$_{1-6}$ heteroalkyl, C$_{2-6}$ alkenyl, C$_{2-6}$ alkynyl, 3-7 membered cycloalkyl and 3-7 membered heterocycloalkyl. In Formula I, A is selected from the group consisting of:

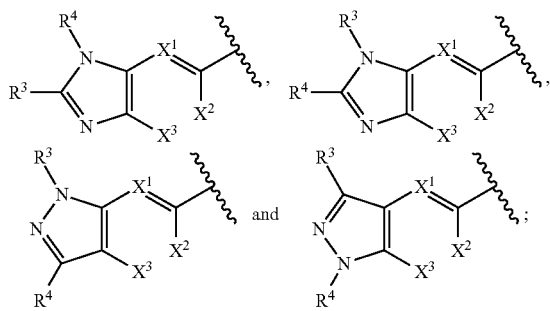

in which X$^1$, X$^2$ and X$^3$ are independently N or CR$^5$, wherein at least one of X$^1$, X$^2$ and X$^3$ is CR$^5$, where R$^5$ is selected from the group consisting of hydrogen, C$_{1-4}$ alkyl, C$_{1-4}$ haloalkyl, halogen, —OC$_{1-6}$ alkyl, 3-6 membered heterocycloalkyl-C$_{1-3}$alkyleneoxy-, —CN, —NO$_2$, —NH(C$_{1-6}$ alkyl), —NH$_2$ and —N(C$_{1-6}$ alkyl)$_2$. In Formula I, R$^3$ is 5-10 membered heteroaryl optionally substituted with —NR$^{x3a}$R$^{x3b}$, in which R$^{x3a}$ and R$^{x3b}$ are each independently selected from the group consisting of hydrogen, C$_{1-6}$ alkyl, C$_{1-6}$haloalkyl, C$_{2-6}$ alkenyl, C$_{2-6}$ alkynyl, C$_{1-6}$ alkoxy, C$_{1-6}$ heteroalkyl, 6-10 membered aryl and 5-10 membered heteroaryl. In Formula I, R$^3$ and the R$^{x3a}$ and R$^{x3b}$ groups of R$^3$, if present, are further each independently optionally substituted with 1 to 5 R$^{R3}$ substituents selected from the group consisting of F, Cl, Br, I, —OH, —NH$_2$, —SH, —CF$_3$, —OCF$_3$, —SF$_5$, —OCH$_3$, —(X$^b$)$_{0-1}$—CN, —(X$^b$)$_{0-1}$—NO$_2$, —(X$^b$)$_{0-1}$—N$_3$, —(X$^b$)—OH, —(X$^b$)—H, —(X$^b$)$_{0-1}$—OR$^b$, —(X$^b$)$_{0-1}$—N(H)R$^b$, —(X$^b$)—N(H)$_2$, —(X$^b$)$_{0-1}$—N(R$^b$)$_2$, —(X$^b$)$_{0-1}$—SR$^b$, —(X$^b$)$_{0-1}$—SH, —(X$^b$)$_{0-1}$—C(O)R$^b$, —(X$^b$)$_{0-1}$—S(O)$_2$R$^b$, —(X$^b$)$_{0-1}$—S(O)R$^b$, —(X$^b$)$_{0-1}$—N(H)S(O)$_2$R$^b$, —(X$^b$)$_{0-1}$—N(R$^b$)S(O)$_2$R$^b$, —(X$^b$)$_{0-1}$—OC(O)R$^b$, —(X$^b$)$_{0-1}$—N(H)C(O)OR$^b$, —(X$^b$)$_{0-1}$—N(R$^b$)C(O)OR$^b$, —(X$^b$)$_{0-1}$—C(=O)OR$^b$, —(X$^b$)$_{0-1}$—C(=O)OH, —(X$^b$)$_{0-1}$—C(=O)N(H)R$^b$, —(X$^b$)$_{0-1}$—C(=O)N(R$^b$)R$^b$, —(X$^b$)$_{0-1}$—N(H)C(=O)R$^b$, —(X$^b$)$_{0-1}$—N(R$^b$)C(=O)R$^b$, —(X$^b$)$_{0-1}$—N(H)C(=O)OR$^b$ and —(X$^b$)$_{0-1}$—N(R$^b$)C(=O)OR$^b$, in which X$^b$ is selected from the group consisting of C$_{1-6}$ alkylene, C$_{2-6}$ alkenylene, C$_{2-6}$ alkynylene, C$_{1-6}$ heteroalkylene, C$_{3-6}$ cycloalkylene and C$_{3-6}$ heterocycloalkylene, and R$^b$ at each occurrence is independently selected from the group consisting of C$_{1-6}$ alkyl, C$_{1-6}$ haloalkyl, C$_{1-6}$ heteroalkyl, C$_{2-6}$ alkenyl, C$_{2-6}$ alkynyl, 3-7 membered cycloalkyl and 3-7 membered heterocycloalkyl. In Formula I, R$^4$ is -(L)$_{0-1}$-R$^{x4a}$, wherein L is selected from the group consisting of —O—, —N(H)—, —C(=O)—, C$_{1-4}$ alkylene, C$_{1-4}$ haloalkylene, C$_{2-4}$ alkenylene, C$_{2-4}$ alkynylene and C$_{1-4}$ heteroalkylene and R$^{x4a}$ is selected from the group consisting of hydrogen, C$_{1-6}$ alkyl, C$_{1-6}$ haloalkyl, C$_{2-6}$ alkenyl, C$_{2-6}$ alkynyl and C$_{1-6}$ heteroalkyl, 3-6 membered cycloalkyl, 3-9 membered heterocycloalkyl, 6-10 membered aryl and 5-10 membered heteroaryl. The aliphatic or aromatic portions of R$^4$ are independently substituted with 0 to 5 R$^{R4}$ substituents selected from the group consisting of C$_{1-6}$ alkyl, C$_{1-6}$ haloalkyl, C$_{1-6}$ heteroalkyl, C$_{1-6}$ alkoxy, C$_{1-6}$ alkylamino, C$_{1-6}$ dialkylamino, C$_{3-6}$ heterocycloalkyl, F, Cl, Br, I, —OH, —NH$_2$, —SH, —CF$_3$, —OCF$_3$, —SF$_5$, —(X$^c$)$_{0-1}$—CN, —(X$^c$)$_{0-1}$—NO$_2$, —(X$^c$)$_{0-1}$—N$_3$, —(X$^c$)—OH, —(X$^c$)$_{0-1}$—OR$^c$, —(X$^c$)—H, —(X$^c$)$_{0-1}$—R$^c$, —(X$^c$)$_{0-1}$—N(H)R$^c$, —(X$^c$)$_{0-1}$—N(R$^c$)$_2$, —(X$^c$)$_{0-1}$—SR$^c$, —(X$^c$)$_{0-1}$—C(O)R$^c$, —(X$^c$)$_{0-1}$—S(O)$_2$R$^c$, —(X$^c$)$_{0-1}$—S(O)R$^c$, —(X$^c$)$_{0-1}$—N(H)S(O)$_2$R$^c$, —(X$^c$)$_{0-1}$—N(R$^c$)S(O)$_2$R$^c$, —(X$^c$)$_{0-1}$—C(=O)OR$^c$, —(X$^c$)$_{0-1}$—C(=O)OH, —(X$^c$)$_{0-1}$—C(=O)N(H)R$^c$, —(X$^c$)$_{0-1}$—C(=O)N(R$^c$)R$^c$, —(X$^c$)$_{0-1}$—N(H)C(=O)R$^c$ and —(X$^c$)$_{0-1}$—N(R$^c$)C(=O)R$^c$, in which X$^c$ is selected from the group consisting of C$_{1-6}$ alkylene, C$_{2-6}$ alkenylene, C$_{2-6}$ alkynylene, C$_{1-6}$ heteroalkylene, C$_{3-6}$ cycloalkylene and C$_{3-6}$ heterocycloalkylene, and R$^c$ at each occurrence is independently selected from the group consisting of C$_{1-6}$ alkyl, C$_{1-6}$ haloalkyl, C$_{1-6}$ heteroalkyl, C$_{2-6}$ alkenyl, C$_{2-6}$ alkynyl, 3-7 membered cycloalkyl, 3-7 membered heterocycloalkyl, phenyl and 5-6 membered heteroaryl. In Formula I, any two R$^c$ groups attached to the same nitrogen atom are optionally combined to form a 3-7 membered heterocycloalkyl or 5-10 membered heteroaryl comprising 1-3 heteroatoms selected from N, O and S.

In another embodiment, in compounds of Formula I or in certain aspects of one or more embodiment(s) of compounds of Formula I, R$^3$ is substituted with —NR$^{x3a}$R$^{x3b}$, in which R$^3$ and R$^{x3a}$ and R$^{x3b}$ are optionally substituted with 1 to 5 R$^{R3}$ substituents.

In another embodiment, in compounds of Formula I or in certain aspects of one or more embodiment(s) of compounds of Formula I, Y is nitrogen and the subscript b is the integer 0.

In another embodiment, in compounds of Formula I or in certain aspects of one or more embodiment(s) of compounds of Formula I, Y is carbon and the subscript b is the integer 1.

In another embodiment, in compounds of Formula I or in certain aspects of one or more embodiment(s) of compounds of Formula I, A is selected from the group consisting of

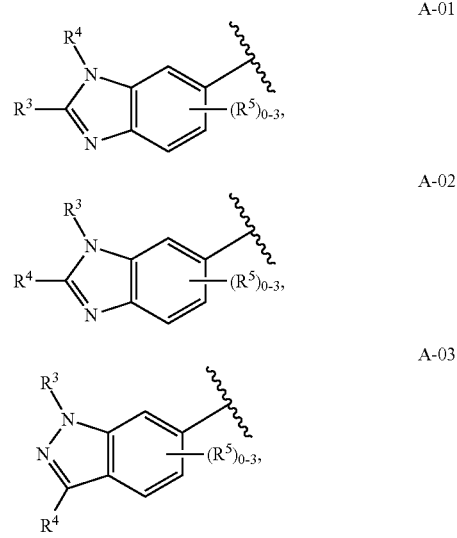

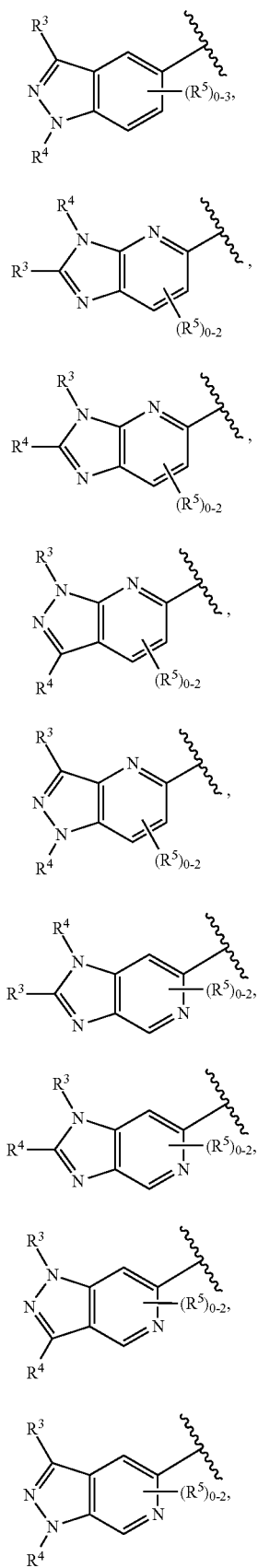
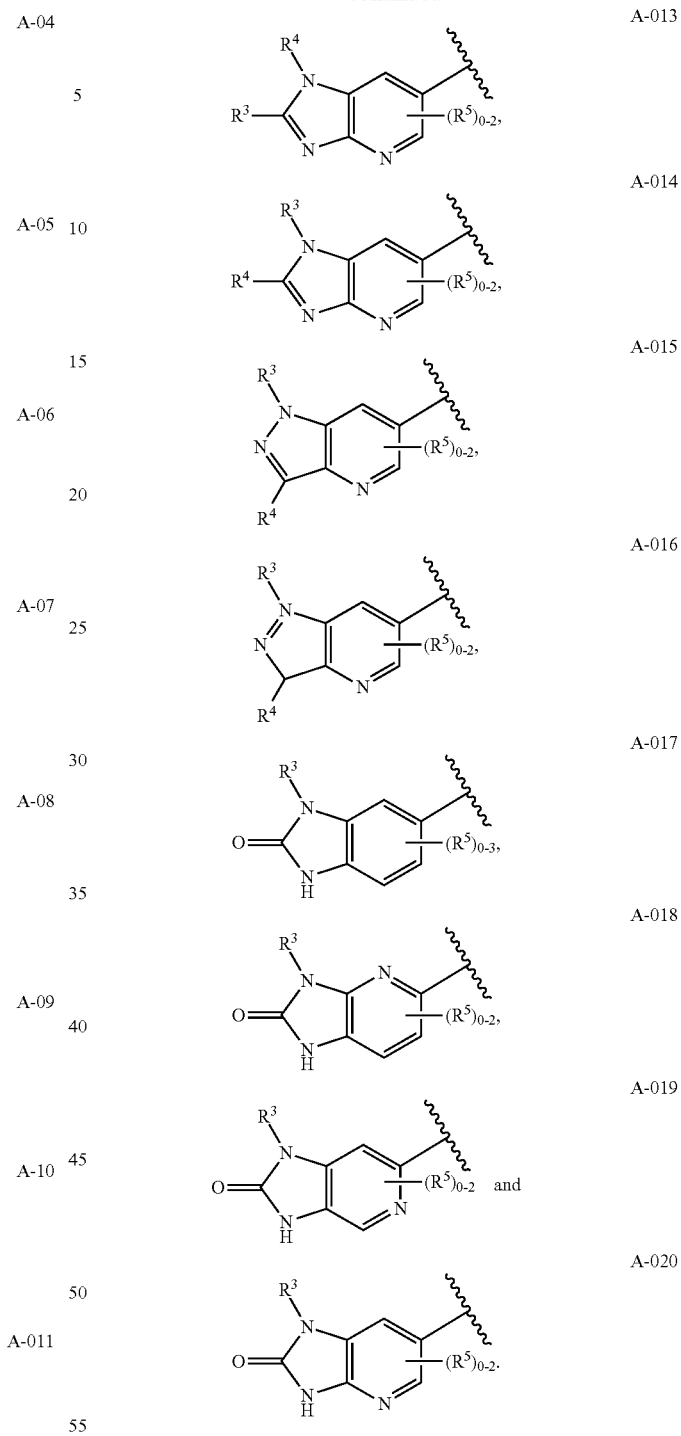

In another embodiment, in compounds of Formula I or in certain aspects of one or more embodiment(s) of compounds of Formula I, $R^3$ is selected from the group consisting of pyridyl, pyrimidinyl, pyrazinyl, pyridazinyl, triazinyl, purinyl, pyrrolopyrimidinyl, triazolopyrimidinyl, pyrazolopyrimidinyl, pyrrolopyrazinyl, pyrazolopyrazinyl, triazolopyrazinyl, imidazolopyrazinyl, pyrrolopyridazinyl, pyrazoloyridazinyl, triazoloyridazinyl, imidazoloyridazinyl, furopyrimidinyl, thienopyrimidinyl, oxazolopyrimidinyl, thiazolopyrimidinyl, pyrrolyl, imidazolyl, pyrazolyl, oxazolyl, isoxazolyl, oxadiazolyl, thiazolyl, isothiazolyl and thiadiazolyl, in which $R^3$ is substituted with —$NR^{x3a}R^{x3b}$, and in which $R^3$ and the $R^{x3a}$ and $R^{x3b}$ group are each independently further optionally substituted with 1 to 5 $R^{R3}$ substituents.

In another embodiment, in compounds of Formula I or in certain aspects of one or more embodiment(s) of compounds of Formula I, $R^3$ is selected from the group consisting of pyridyl, pyrimidinyl, pyrazinyl, pyridazinyl, triazinyl, pyrrolyl, imidazolyl, pyrazolyl, isoxazolyl, oxadiazolyl, thiazolyl, isothiazolyl and thiadiazolyl and wherein $R^3$ is substituted with —$NR^{x3a}R^{x3b}$, in which $R^3$ and the $R^{x3a}$ and $R^{x3b}$ group are further each independently optionally substituted with 1 to 3 $R^{R3}$ substituents.

In another embodiment, in compounds of Formula I or in certain aspects of one or more embodiment(s) of compounds of Formula I, $R^{x3a}$ and $R^{x3b}$ is each independently selected from the group consisting of hydrogen, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ heteroalkyl, 6-10 membered aryl and 5-10 membered heteroaryl, in which at least one of $R^{x3a}$ and $R^{x3b}$ is hydrogen.

In another embodiment, in compounds of Formula I or in certain aspects of one or more embodiment(s) of compounds of Formula I, $R^{x3a}$ and $R^{x3b}$ is each independently selected from the group consisting of hydrogen, methyl, ethyl, propyl, isopropyl, phenyl and pyridyl, and in which at least one of $R^{x3a}$ and $R^{x3b}$ is hydrogen.

In another embodiment, in compounds of Formula I or in certain aspects of one or more embodiment(s) of compounds of Formula I, $R^{x3a}$ and $R^{x3b}$ are each hydrogen.

In another embodiment, in compounds of Formula I or in certain aspects of one or more embodiment(s) of compounds of Formula I, $R^{R3}$ is selected from the group consisting F, Cl, Br, I, —OH, —$NH_2$, —$CF_3$, —$OCF_3$, —$OCH_3$, —$NO_2$, —$X^b$—$NO_2$, —$X^b$—OH, —$X^b$—H, —$X^b$—$OR^b$, —$OR^b$, —$X^b$—N(H)$R^b$, —N(H)$R^b$, —$X^b$—N(H)$_2$, —$X^b$—N($R^b$)$_2$, —N($R^b$)$_2$, —C(=O)N(H)$R^b$, —$X^b$—C(=O)N(H)$R^b$, —C(=O)N($R^b$)$R^b$, —$X^b$—C(=O)N($R^b$)$R^b$, —$X^b$—N(H)C(=O)$R^b$, —$X^b$—N(H)C(=O)$R^b$, —$X^b$—N($R^b$)C(=O)$R^b$ and —N($R^b$)C(=O)$R^b$, in which $X^b$ is selected from the group consisting of $C_{1-6}$ alkylene, $C_{2-6}$ alkenylene, $C_{2-6}$ alkynylene and $C_{1-6}$ heteroalkylene, and $R^b$ at each occurrence is independently selected from the group consisting of $C_{1-6}$ alkyl, $C_{1-6}$ haloalkyl, $C_{1-6}$ heteroalkyl, $C_{2-6}$ alkenyl, $C_{2-6}$ alkynyl, 3-7 membered cycloalkyl and 3-7 membered heterocycloalkyl.

In another embodiment, in compounds of Formula I or in certain aspects of one or more embodiment(s) of compounds of Formula I, $R^{R3}$ is selected from the group consisting of F, Cl, Br, I, —OH, —$NH_2$, —$CF_3$, —$OCF_3$, —$OCH_3$, —$NO_2$, —$X^b$—H, —$OR^b$, —N(H)$R^b$, —N($R^b$)$_2$, —C(=O)N(H)$R^b$ and —C(=O)N($R^b$)$R^b$.

In another embodiment, in compounds of Formula I or in certain aspects of one or more embodiment(s) of compounds of Formula I, $R^{R3}$ is selected from the group consisting of F, Cl, Br, I, —OH, —$NH_2$, —$CF_3$, —$OCF_3$, —$OCH_3$, —$NO_2$, —C(=O)N(CH$_3$)$_2$ and 3-methyloxetan-3yl-(C=O)N(H)—.

In another embodiment, in compounds of Formula I or in certain aspects of one or more embodiments of compounds of Formula I, $R^4$ is -(L)$_{0-1}$-$R^{x4a}$, in which L is selected from the group consisting of —O—, —N(H)—, —C(=O)—, $C_{1-6}$ alkylene, $C_{1-6}$ haloalkylene and $C_{1-6}$ heteroalkylene, in which $R^{x4a}$ is selected from the group consisting of hydrogen, 3-6 membered cycloalkyl, 3-9 membered heterocycloalkyl and 5-6 membered heteroaryl, and in which the aliphatic and/or aromatic portions of $R^4$ are independently optionally substituted with 1 to 5 $R^{R4}$ substituents.

In another embodiment, in compounds of Formula I or in certain aspects of one or more embodiment(s) of compounds of Formula I, $R^4$ is -(L)$_{0-1}$-$R^{x4a}$, in which L is selected from the group consisting of —O—, —N(H)—, —C(=O)—, $C_{1-6}$ alkylene, $C_{1-6}$ haloalkylene and $C_{1-6}$ heteroalkylene, in which $R^{x4a}$ is selected from the group consisting of hydrogen, cyclopropyl, cyclobutyl, cyclopentyl, cyclohexyl, aziridinyl, azetanyl, 2-oxa-6-azaspiro[3.3]heptanyl, 1,3-dioxolanyl, 2-oxa-5-azabicyclo[2.2.1]heptanyl, oxetanyl, tetrahydropyranyl, tetrahydrothiopyranyl, tetrahydrofuranyl, morpholinyl, piperidinyl, piperazinyl, thiomorpholinyl and pyrrolidinyl, in which the aliphatic and/or aromatic portions of $R^4$ are independently optionally substituted with 1 to 5 $R^{R4}$ substituents.

In another embodiment, in compounds of Formula I or in certain aspects of one or more embodiment(s) of compounds of Formula I, $R^4$ is -(L)$_{0-1}$-$R^{x4a}$, in which L is selected from the group consisting of —O—, —N(H)—, —C(=O)—, $C_{1-6}$ alkylene, $C_{1-6}$ haloalkylene and $C_{1-6}$ heteroalkylene, in which $R^{x4a}$ is selected from the group consisting of hydrogen, cyclopropyl, cyclobutyl, cyclopentyl, cyclohexyl, aziridinyl, oxetanyl, tetrahydropyranyl, tetrahydrothiopyranyl, tetrahydrofuranyl, morpholinyl, piperidinyl, piperazinyl, thiomorpholinyl and pyrrolidinyl, in which the aliphatic and/or aromatic portions of $R^4$ are independently optionally substituted with 1 to 5 $R^{R4}$ substituents.

In another embodiment, in compounds of Formula I or in certain aspects of one or more embodiment(s) of compounds of Formula I, $R^4$ is selected from the group consisting of hydrogen, —C(=O)N(CH$_3$)$_2$, —(CH$_2$)N(CH$_3$)$_2$, —(CH$_2$)NH(CH$_3$), morpholin-4-yl-(CH$_2$)—, cyclopropylmethyl, trifluoromethylethyl, —CH$_2$CH$_2$OCH$_3$, —OCH$_2$CH$_3$, methyl, ethyl, morpholin-4-yl-C(=O)—, pyrrolidin-1-yl-C(=O)—, CH$_3$OCH$_2$—, ethoxy and cyclopropyl.

In another embodiment, in compounds of Formula I or in certain aspects of one or more embodiment(s) of compounds of Formula I, $R^4$ is selected from the group consisting of

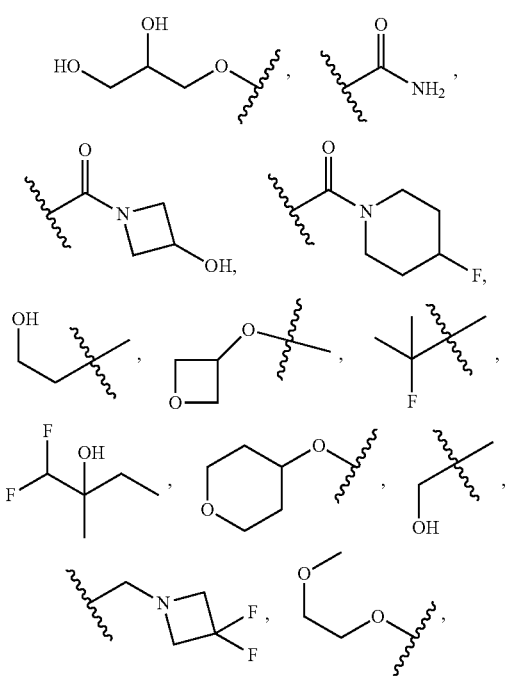

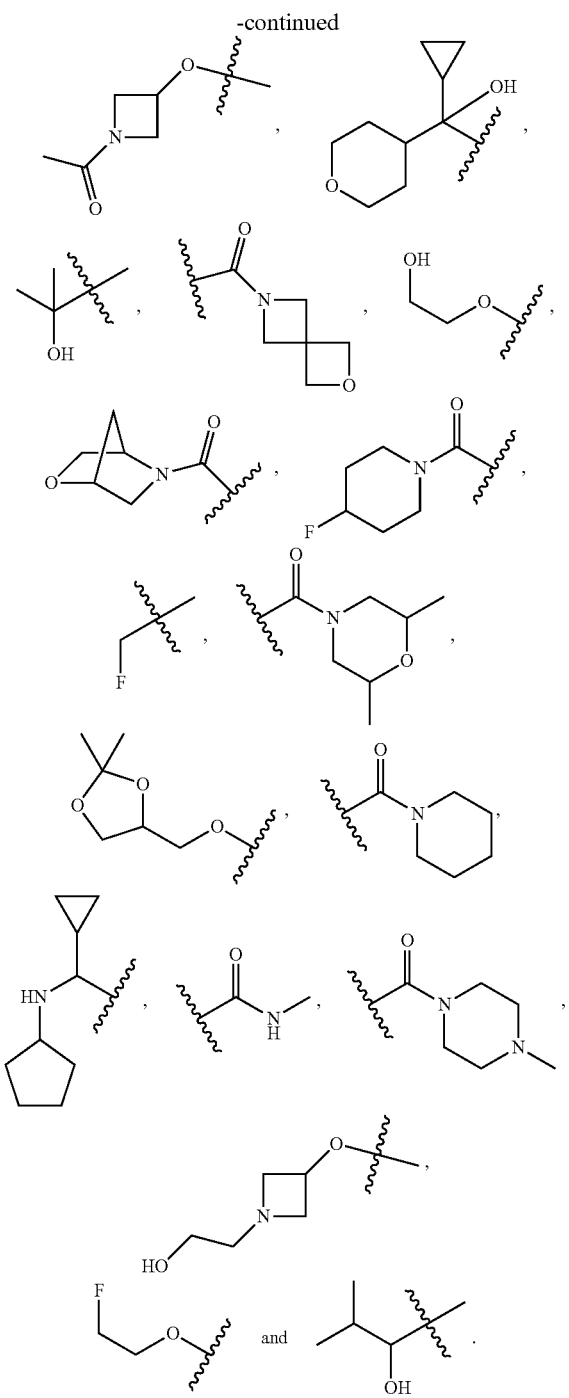

In another embodiment, in compounds of Formula I or in certain aspects of one or more embodiment(s) of compounds of Formula I, $R^2$ is selected from the group consisting of $C_{1-6}$ alkyl, $C_{1-6}$ haloalkyl, cyclopropyl, cyclopropylmethyl, cyclobutyl, cyclopentyl, cyclohexyl, oxetanyl, tetrahydrofuranyl, tetrahydropyranyl, thiazolyl, imidazolyl, oxadiazolyl, triazolyl, tetrazolyl, oxazolyl, pyrazolyl, pyridyl, pyrimidinyl, pyrazinyl, pyrrolyl; or alternatively $R^2$ and $R^1$ are combined to form 3-6 membered ring selected from the group consisting of cyclobutyl, cyclopentyl, cyclohexyl oxetanyl, tetrahydrofuranyl and tetrahydropyanyl, azetidinyl, pyrrolidinyl, piperidinyl, 6,7-dihydro-5H-pyrrolo[1,2-a]imidazole and 6,7-dihydro-5H-cyclopenta[b]pyridine, wherein the aliphatic and/or aromatic portions of $R^1$ and $R^2$ either independently or when combined, are optionally substituted with 1 to 5 $R^{R1/2}$ substituents.

In another embodiment, in compounds of Formula I or in certain aspects of one or more embodiment(s) of compounds of Formula I, $R^2$ is selected from the group consisting of $C_{1-6}$ alkyl, $C_{1-6}$ haloalkyl, cyclopropyl, cyclobutyl, cyclopentyl, cyclohexyl, oxetanyl, tetrahydrofuranyl, tetrahydropyranyl, thiazolyl, oxadiazolyl, triazolyl, tetrazolyl, oxazolyl, pyrazolyl, pyrimidinyl, pyrazinyl and pyrrolyl; or alternatively $R^2$ and $R^1$ are combined to form 3-6 membered ring selected from the group consisting of cyclobutyl, cyclopentyl, cyclohexyl oxetanyl, tetrahydrofuranyl and tetrahydropyanyl, azetidinyl, pyrrolidinyl and piperidinyl, wherein the aliphatic and/or aromatic portions of $R^1$ and $R^2$ either independently or when combined, are optionally substituted with 1 to 5 $R^{R1/2}$ substituents.

In another embodiment, in compounds of Formula I or in certain aspects of one or more embodiment(s) of compounds of Formula I, Formula I has a subformula selected from the group consisting of

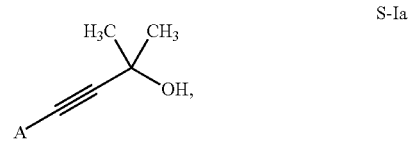

S-Ia

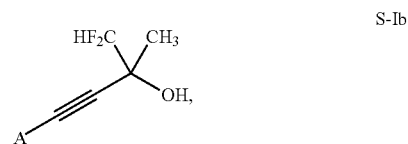

S-Ib

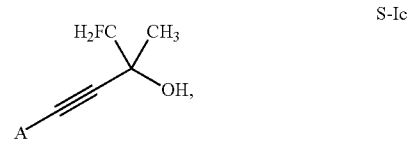

S-Ic

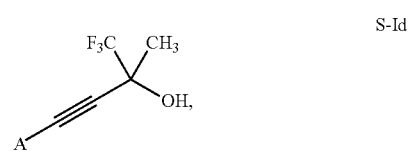

S-Id

In another embodiment, in compounds of Formula I or in certain aspects of one or more embodiment(s) of compounds of Formula I, $R^4$ is selected from the group consisting of In another embodiment, in compounds of Formula I or in certain aspects of one or more embodiment(s) of compounds of Formula I, $R^1$ is $C_{1-6}$ alkyl or $C_{1-6}$ haloalkyl; $R^2$ is $C_{1-6}$ alkyl, $C_{1-6}$ haloalkyl, 3-8 membered cycloalkyl, phenyl or 5-6 membered heteroaryl; or alternatively $R^1$ and $R^2$ are combined to form a 3-6 membered cycloalkyl or 3-6 membered heterocycloalkyl; and wherein the aliphatic and/or aromatic portions of $R^1$ and $R^2$ either independently or when combined, are optionally substituted with 1 to 5 $R^{R1/2}$ substituents.

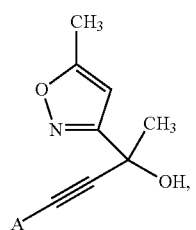 S-Ie
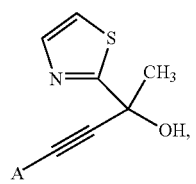 S-If
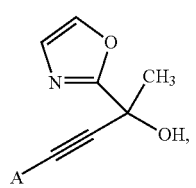 S-Ig
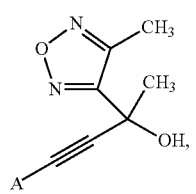 S-Ih
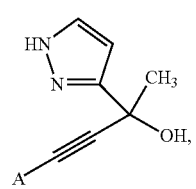 S-Ii
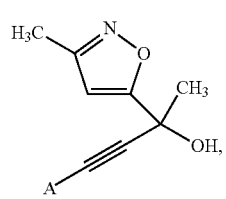 S-Ij
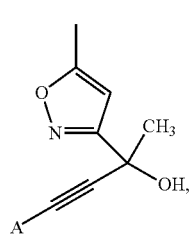 S-Ik
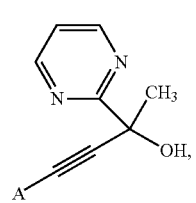 S-Il
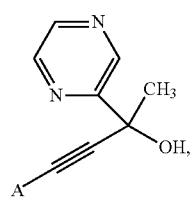 S-Im
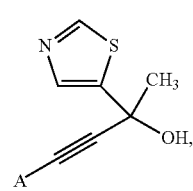 S-In
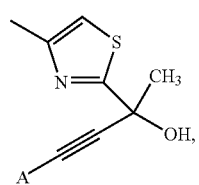 S-Io
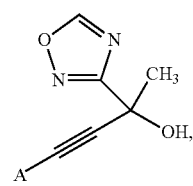 S-Ip
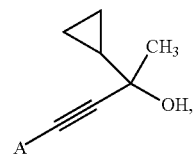 S-Iq
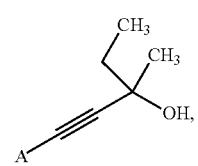 S-Ir
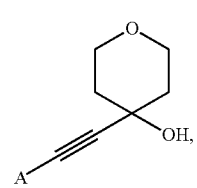 S-Is
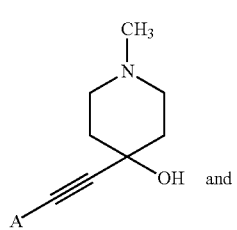 S-It
and -continued S-Iu
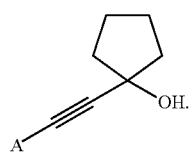

In another embodiment, in compounds of Formula I or in certain aspects of one or more embodiment(s) of compounds of Formula I, Formula I has a subformula selected from the group consisting of:

S-Iv
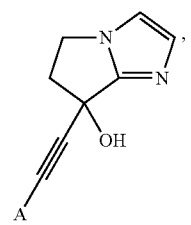

S-Iw
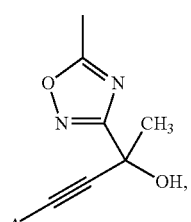

S-Ix
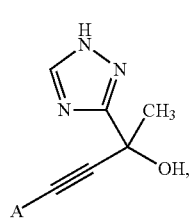

S-Iy
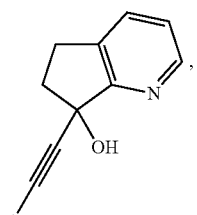

S-Iz
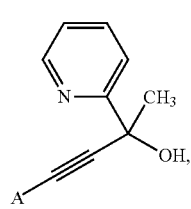

S-Iaa
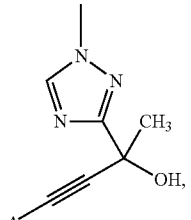

-continued

S-Iab
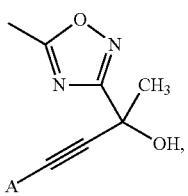

S-Iac
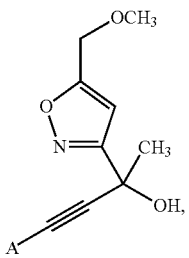

S-Iad
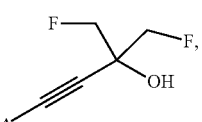

S-Iae
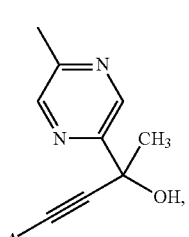

S-Iaf
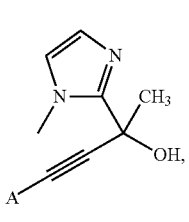

S-Iag
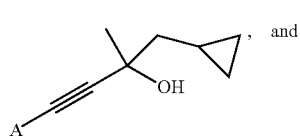

SI-ah
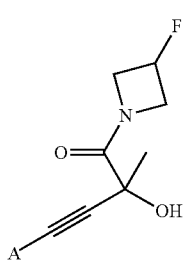

In another embodiment, in compounds of Formula I or in certain aspects of one or more embodiment(s) of compounds for Formula I having subformula S-Ib, S-Ic, S-Id, S-Ie, S-If, S-Ig, S-Ih, S-Ii, S-Ij, S-Ik, S-Il, S-Im, S-In, S-Io, S-Ip, S-Iq or S-Ir, the carbon to which $R^1$ and $R^2$ are attached has the (S)-stereochemical configuration.

In another embodiment, in compounds of Formula I or in certain aspects of one or more embodiment(s) of compounds for Formula I having subformula S-Iv, S-Iw, S-Ix, S-Iy S-Iz, S-Iaa, S-Iab, S-Iac, S-Iad, S-Iae, S-Iaf, S-Iag or SI-ah, the carbon to which $R^1$ and $R^2$ are attached has the (S)-stereochemical configuration.

In another embodiment, in compounds of Formula I or in certain aspects of one or more embodiment(s) of compounds for Formula I having subformula S-Ib, S-Ic, S-Id, S-Ie, S-If, S-Ig, S-Ih, S-Ii, S-Ij, S-Ik, S-Il, S-Im, S-In, S-Io, S-Ip, S-Iq or S-Ir, the carbon to which $R^1$ and $R^2$ are attached has the (R)-stereochemical configuration.

In another embodiment, in compounds of Formula I or in certain aspects of one or more embodiment(s) of compounds of Formula I, Y is carbon and the subscript b is the integer 1; $R^1$ is $C_{1-6}$ alkyl, $C_{1-6}$ haloalkyl or $CH_2$—OH; $R^2$ is $C_{1-6}$ alkyl, $C_{1-6}$ haloalkyl, 3-8 membered cycloalkyl, phenyl or 5-6 membered heteroaryl; or alternatively $R^1$ and $R^2$ are combined to form a 3-6 membered cycloalkyl or 3-6 membered heterocycloalkyl; and in which the aliphatic and/or aromatic portions of $R^1$ and $R^2$ either independently or when combined, are optionally substituted with 1 to 5 $R^{R1/2}$ substituents; A is selected from the group consisting of

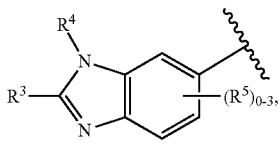
A-01

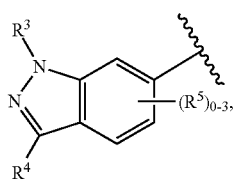
A-03

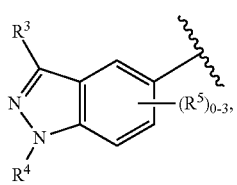
A-04

A-06

A-017 in which $R^3$ is selected from the group consisting of pyridyl, pyrimidinyl, pyrazinyl, pyridazinyl, triazinyl, purinyl, pyrrolopyrimidinyl, triazolopyrimidinyl, pyrazolopyrimidinyl, pyrrolopyrazinyl, pyrazolopyrazinyl, triazolopyrazinyl, imidazolopyrazinyl, pyrrolopyridazinyl, pyrazoloyridazinyl, triazoloyridazinyl, imidazoloyridazinyl, furopyrimidinyl, thienopyrimidinyl, oxazolopyrimidinyl, thiazolopyrimidinyl, pyrrolyl, imidazolyl, pyrazolyl, oxazolyl, isoxazolyl, oxadiazolyl, thiazolyl, isothiazolyl and thiadiazolyl, in which $R^3$ is substituted with —$NR^{x3a}R^{x3b}$, in which $R^3$ and the $R^{x3a}$ and $R^{x3b}$ group are each independently further optionally substituted with 1 to 5 $R^{R3}$ substituents; $R^4$ is -$(L)_{0-1}$-$R^{x4a}$, in which L is selected from the group consisting of —C(=O)—, $C_{1-6}$ alkylene, $C_{1-6}$ haloalkylene and $C_{1-6}$ heteroalkylene, $R^{x4a}$ is selected from the group consisting of hydrogen, cyclopropyl, cyclobutyl, cyclopentyl, cyclohexyl, aziridinyl, oxetanyl, tetrahydropyranyl, tetrahydrothiopyranyl, tetrahydrofuranyl, tetrahydromorpholinyl, piperidinyl, piperazinyl, thiomorpholinyl and pyrrolidinyl, wherein the aliphatic and/or aromatic portions of $R^4$ are independently optionally substituted with 1 to 5 $R^{R4}$ substituents; $R^5$ is selected from the group consisting of hydrogen, $C_{1-4}$ alkyl, $C_{1-4}$ haloalkyl, halogen, —$OC_{1-6}$ alkyl and 3-6 membered heterocycloalkyl-$C_{1-3}$ alkyleneoxy.

In one embodiment, compounds of Formula I have chemical structures as selected from those presented in Table 1 and Table 1.1 below.

TABLE 1

| No | Structure | Name |
|---|---|---|
| T1-1 | 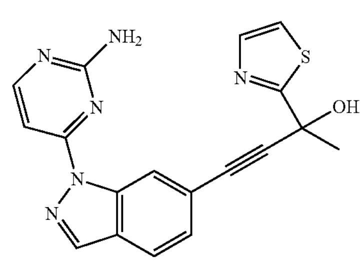 [SMILES: CC(O)(C#Cc1ccc2cnn(-c3ccnc(N)n3)c2c1)c1nccs1] | 4-(1-(2-aminopyrimidin-4-yl)-1H-indazol-6-yl)-2-(thiazol-2-yl)but-3-yn-2-ol |

TABLE 1-continued

| No | Structure | Name |
|---|---|---|
| T1-2 | 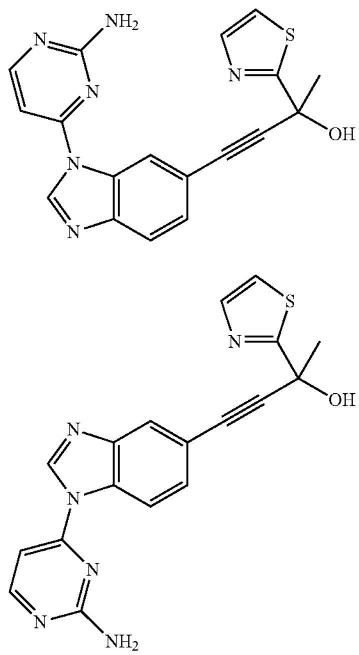 | 4-(1-(2-aminopyrimidin-4-yl)-1H-benzo[d]imidazol-5-yl)-2-(thiazol-2-yl)but-3-yn-2-ol compound with 4-(1-(2-aminopyrimidin-4-yl-1H-benzo[d]imidazol-6-yl)-2-(thiazol-2-yl)but-3-yn-2-ol (1:1) |
| T1-3 | 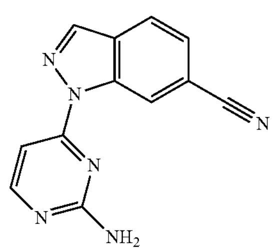 [SMILES: N#Cc1ccc2cnn(-c3ccnc(N)n3)c2c1] | 1-(2-aminopyrimidin-4-yl)-1H-indazole-6-carbonitrile |
| T1-4 | 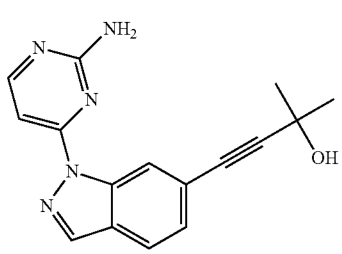 [SMILES: CC(C)(O)C#Cc1ccc2cnn(-c3ccnc(N)n3)c2c1] | 4-(1-(2-aminopyrimidin-4-yl)-1H-indazol-6-yl)-2-methyl but-3-yn-2-ol |
| T1-5 | 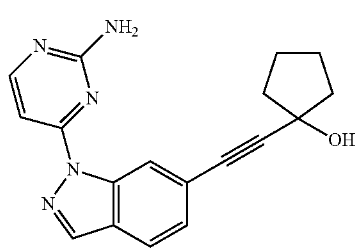 [SMILES: Nc1nccc(-n2ncc3ccc(C#CC4(O)CCCC4)cc32)n1] | 1-((1-(2-aminopyrimidin-4-yl)-1H-indazol-6-yl)ethynyl)cyclopentanol |

TABLE 1-continued

| No | Structure | Name |
| --- | --- | --- |
| T1-6 | 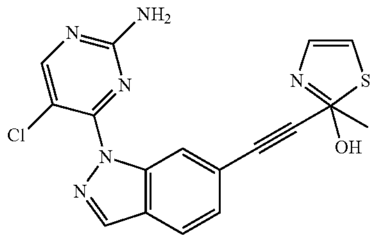 | 4-(1-(2-amino-5-chloro-pyrimidin-4-yl)-1H-indazol-6-yl)-2-(thiazol-2-yl)but-3-yn-2-ol |
| T1-7 | 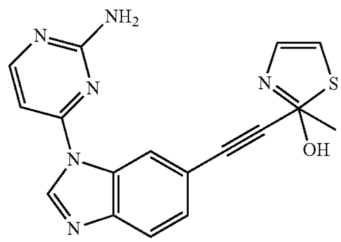 | 4-(1-(2-aminopyrimidin-4-yl)-1H-benzo[d]imidazol-6-yl)-2-(thiazol-2-yl)but-3-yn-2-ol |
| T1-8 | 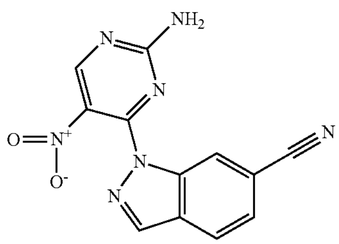 [SMILES: N#Cc1ccc2cnn(-c3nc(N)ncc3[N+](=O)[O-])c2c1] | 1-(2-amino-5-nitropyrimidin-4-yl)-1H-indazole-6-carbonitrile |
| T1-9 | 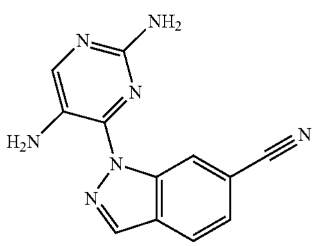 [SMILES: N#Cc1ccc2cnn(-c3nc(N)ncc3N)c2c1] | 1-(2,5-diaminopyrimidin-4-yl)-1H-indazole-6-carbonitrile |
| T1-10 | 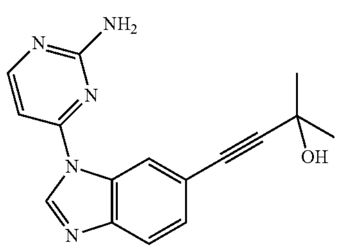 [SMILES: CC(C)(O)C#Cc1ccc2ncn(-c3ccnc(N)n3)c2c1] | 4-(1-(2-aminopyrimidin-4-yl)-1H-benzo[d]imidazol-6-yl)-2-methylbut-3-yn-2-ol |
| T1-11 | 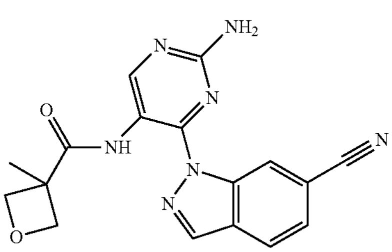 [SMILES: CC1(C(=O)Nc2cnc(N)nc2-n2ncc3ccc(C#N)cc32)COC1] | N-(2-amino-4-(6-cyano-1H-indazol-1-yl)pyrimidin-5-yl)-3-methyloxetane-3-carboxamide |

TABLE 1-continued

| No | Structure | Name |
|---|---|---|
| T1-12 | 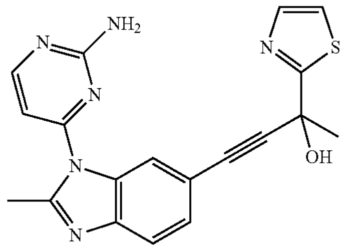 [SMILES: Cc1nc2ccc(C#CC(C)(O)c3nccs3)cc2n1-c1ccnc(N)n1] | 4-(1-(2-aminopyrimidin-4-yl)-2-methyl-1H-benzo[d]imidazol-6-yl)-2-(thiazol-2-yl)but-3-yn-2-ol |
| T1-13 | 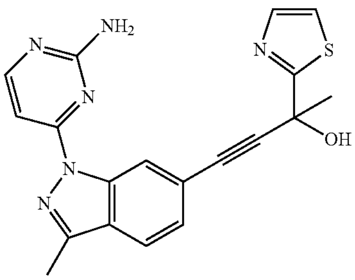 [SMILES: Cc1nn(-c2ccnc(N)n2)c2cc(C#CC(C)(O)c3nccs3)ccc12] | 4-(1-(2-aminopyrimidin-4-yl)-3-methyl-1H-indazol-6-yl)-2-(thiazol-2-yl)but-3-yn-2-ol |
| T1-14 | 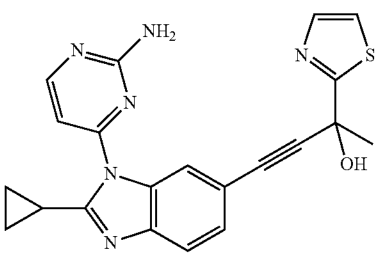 [SMILES: CC(O)(C#Cc1ccc2nc(C3CC3)n(-c3ccnc(N)n3)c2c1)c1nccs1] | 4-(1-(2-aminopyrimidin-4-yl)-2-cyclopropyl-1H-benzo[d]imidazol-6-yl)-2-(thiazol-2-yl)but-3-yn-2-ol |
| T1-15 | 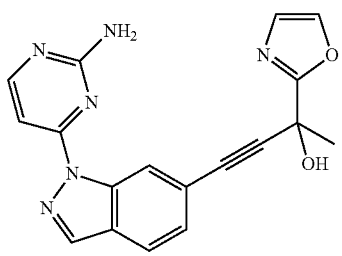 [SMILES: CC(O)(C#Cc1ccc2cnn(-c3ccnc(N)n3)c2c1)c1ncco1] | 4-(1-(2-aminopyrimidin-4-yl)-1H-indazol-6-yl)-2-(oxazol-2-yl)but-3-yn-2-ol |
| T1-16 | 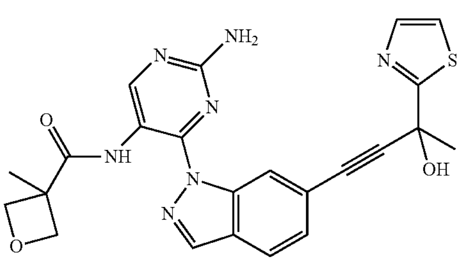 [SMILES: CC1(C(=O)Nc2cnc(N)nc2-n2ncc3ccc(C#CC(C)(O)c4nccs4)cc32)COC1] | N-(2-amino-4-(6-(3-hydroxy-3-(thiazol-2-yl)but-1-ynyl)-1H-indazol-1-yl)pyrimidin-5-yl)-3-methyloxetane-3-carboxamide |
| T1-17 | 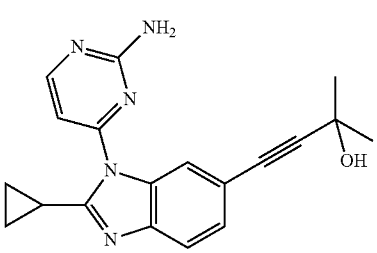 [SMILES: CC(C)(O)C#Cc1ccc2nc(C3CC3)n(-c3ccnc(N)n3)c2c1] | 4-(1-(2-aminopyrimidin-4-yl)-2-cyclopropyl-1H-benzo[d]imidazol-6-yl)-2-methylbut-3-yn-2-ol |

TABLE 1-continued

| No | Structure | Name |
|---|---|---|
| T1-18 | 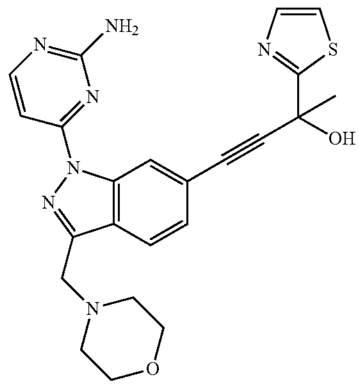 [SMILES: CC(O)(C#Cc1ccc2c(CN3CCOCC3)nn(-c3ccnc(N)n3)c2c1)c1nccs1] | 4-(1-(2-aminopyrimidin-4-yl)-3-(morpholinomethyl)-1H-indazol-6-yl)-2-(thiazol-2-yl)but-3-yn-2-ol |
| T1-19 | 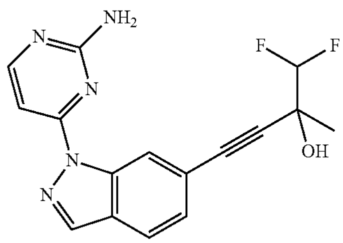 [SMILES: CC(O)(C#Cc1ccc2cnn(-c3ccnc(N)n3)c2c1)C(F)F] | 4-(1-(2-aminopyrimidin-4-yl)-1H-indazol-6-yl)-1,1-difluoro-2-methylbut-3-yn-2-ol |
| T1-20 | 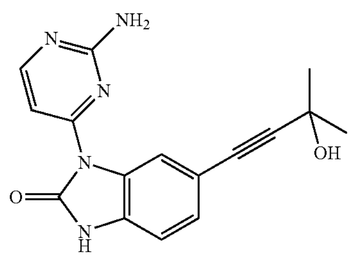 [SMILES: CC(C)(O)C#Cc1ccc2[nH]c(=O)n(-c3ccnc(N)n3)c2c1] | 1-(2-aminopyrimidin-4-yl)-6-(3-hydroxy-3-methylbut-1-ynyl)-1H-benzo[d]imidazol-2(3H)-one |
| T1-21 | 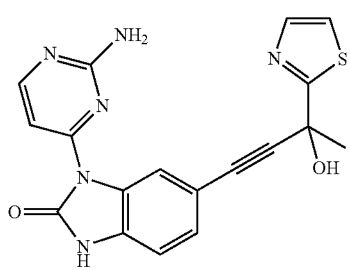 [SMILES: CC(O)(C#Cc1ccc2[nH]c(=O)n(-c3ccnc(N)n3)c2c1)c1nccs1] | 1-(2-aminopyrimidin-4-yl)-6-(3-hydroxy-3-(thiazol-2-yl)but-1-ynyl)-1H-benzo[d]imidazol-2(3H)-one |
| T1-22 | 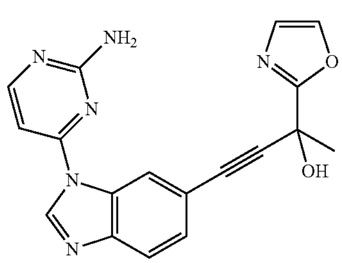 [SMILES: CC(O)(C#Cc1ccc2ncn(-c3ccnc(N)n3)c2c1)c1ncco1] | 4-(1-(2-aminopyrimidin-4-yl)-1H-benzo[d]imidazol-6-yl)-2-(oxazol-2-yl)but-3-yn-2-ol |

TABLE 1-continued

| No | Structure | Name |
|---|---|---|
| T1-23 | 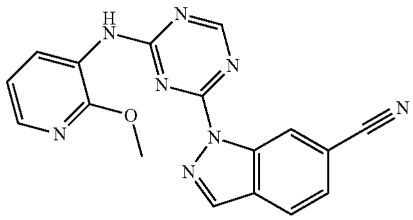 [SMILES: COc1ncccc1Nc1ncnc(-n2ncc3ccc(C#N)cc32)n1] | 1-(4-(2-methoxypyridin-3-yl amino)-1,3,5-triazin-2-yl)-1H-indazole-6-carbonitrile |
| T1-24 | 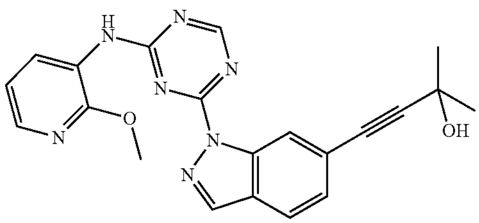 [SMILES: COc1ncccc1Nc1ncnc(-n2ncc3ccc(C#CC(C)(C)O)cc32)n1] | 4-(1-(4-(2-methoxypyridin-3-ylamino)-1,3,5-triazin-2-yl)-1H-indazol-6-yl)-2-methylbut-3-yn-2-ol |
| T1-25 | 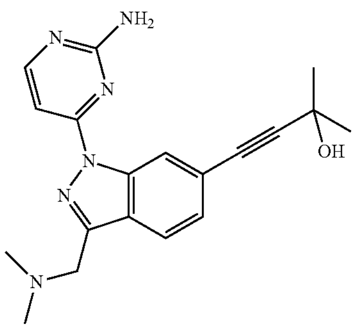 [SMILES: CN(C)Cc1nn(-c2ccnc(N)n2)c2cc(C#CC(C)(C)O)ccc12] | 4-(1-(2-aminopyrimidin-4-yl)-3-((dimethylamino)methyl)-1H-indazol-6-yl)-2-methylbut-3-yn-2-ol |
| T1-26 | 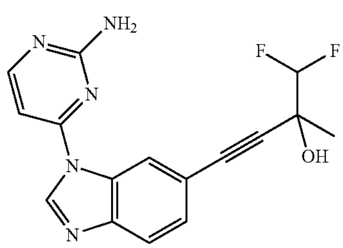 [SMILES: CC(O)(C#Cc1ccc2ncn(-c3ccnc(N)n3)c2c1)C(F)F] | 4-(1-(2-aminopyrimidin-4-yl)-1H-benzo[d]imidazol-6-yl)-1,1-difluoro-2-methylbut-3-yn-2-ol |
| T1-27 | 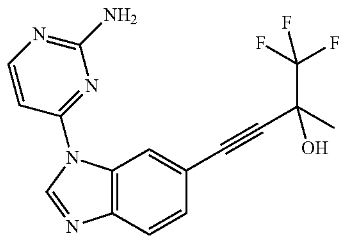 [SMILES: CC(O)(C#Cc1ccc2ncn(-c3ccnc(N)n3)c2c1)C(F)(F)F] | 4-(1-(2-aminopyrimidin-4-yl)-1H-benzo[d]imidazol-6-yl)-1,1,1-trifluoro-2-methylbut-3-yn-2-ol |
| T1-28 | 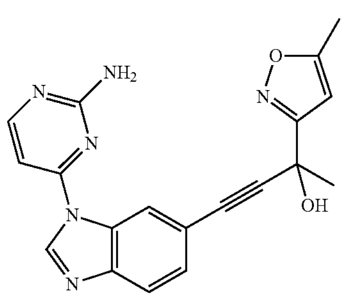 [SMILES: Cc1cc(C(C)(O)C#Cc2ccc3ncn(-c4ccnc(N)n4)c3c2)no1] | 4-(1-(2-aminopyrimidin-4-yl)-1H-benzo[d]imidazol-6-yl)-2-(5-methylisoxazol-3-yl)but-3-yn-2-ol |

TABLE 1-continued

| No | Structure | Name |
|---|---|---|
| T1-29 | 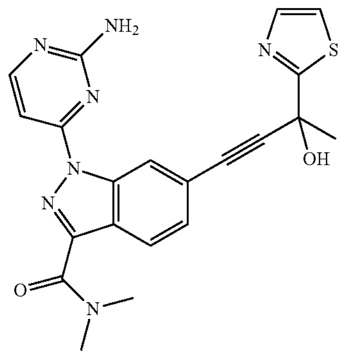 [SMILES: CN(C)C(=O)c1nn(-c2ccnc(N)n2)c2cc(C#CC(C)(O)c3nccs3)ccc12] | 1-(2-aminopyrimidin-4-yl)-6-(3-hydroxy-3-(thiazol-2-yl)but-1-ynyl)-N,N-dimethyl-1H-indazole-3-carboxamide |
| T1-30 | 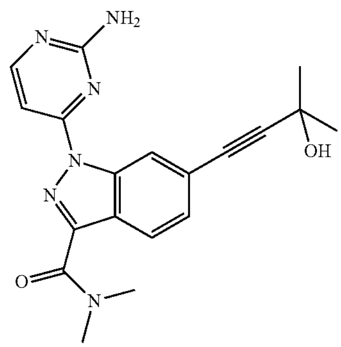 [SMILES: CN(C)C(=O)c1nn(-c2ccnc(N)n2)c2cc(C#CC(C)(C)O)ccc12] | 1-(2-aminopyrimidin-4-yl)-6-(3-hydroxy-3-methylbut-1-ynyl)-N,N-dimethyl-1H-indazole-3-carboxamide |
| T1-31 | 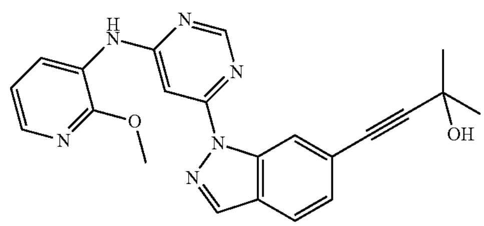 [SMILES: COc1ncccc1Nc1cc(-n2ncc3ccc(C#CC(C)(C)O)cc32)ncn1] | 4-(1-(6-(2-methoxypyridin-3-ylamino)pyrimidin-4-yl)-1H-indazol-6-yl)-2-methylbut-3-yn-2-ol |
| T1-32 | 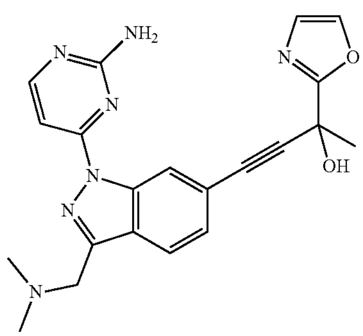 [SMILES: CN(C)Cc1nn(-c2ccnc(N)n2)c2cc(C#CC(C)(O)c3ncco3)ccc12] | 4-(1-(2-aminopyrimidin-4-yl)-3-((dimethylamino)methyl)-1H-indazol-6-yl)-2-(oxazol-2-yl)but-3-yn-2-ol |
| T1-33 | 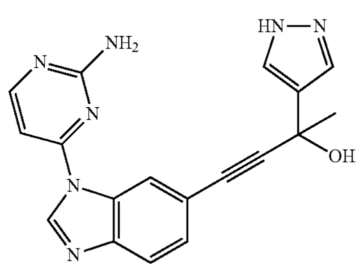 [SMILES: CC(O)(C#Cc1ccc2ncn(-c3ccnc(N)n3)c2c1)c1cn[nH]c1] | 4-(1-(2-aminopyrimidin-4-yl)-1H-benzo[d]imidazol-6-yl)-2-(1H-pyrazol-4-yl)but-3-yn-2-ol |

TABLE 1-continued

| No | Structure | Name |
|---|---|---|
| T1-34 | 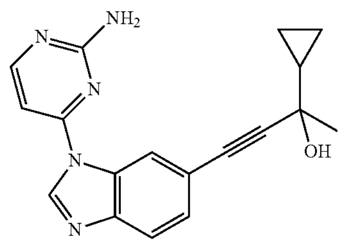 [SMILES: CC(O)(C#Cc1ccc2ncn(-c3ccnc(N)n3)c2c1)C1CC1] | 4-(1-(2-aminopyrimidin-4-yl)-1H-benzo[d]imidazol-6-yl)-2-cyclopropylbut-3-yn-2-ol |
| T1-35 | 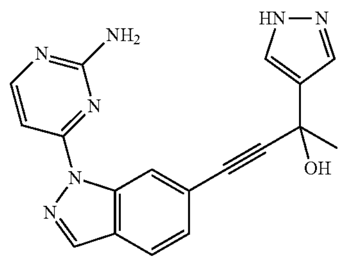 [SMILES: CC(O)(C#Cc1ccc2cnn(-c3ccnc(N)n3)c2c1)c1cn[nH]c1] | 4-(1-(2-aminopyrimidin-4-yl)-1H-indazol-6-yl)-2-(1H-pyrazol-4-yl)but-3-yn-2-ol |
| T1-36 | 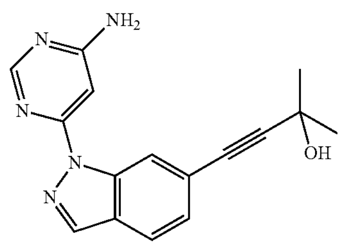 [SMILES: CC(C)(O)C#Cc1ccc2cnn(-c3cc(N)ncn3)c2c1] | 4-(1-(6-aminopyrimidin-4-yl)-1H-indazol-6-yl)-2-methylbut-3-yn-2-ol |
| T1-37 | 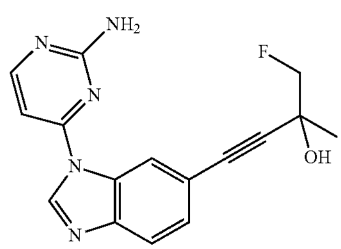 [SMILES: CC(O)(C#Cc1ccc2ncn(-c3ccnc(N)n3)c2c1)CF] | 4-(1-(2-aminopyrimidin-4-yl)-1H-benzo[d]imidazol-6-yl)-1-fluoro-2-methylbut-3-yn-2-ol |
| T1-38 | 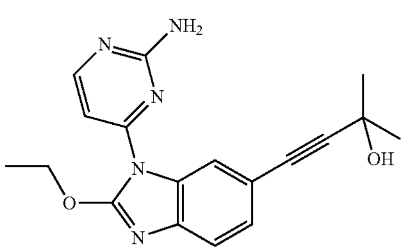 [SMILES: CCOc1nc2ccc(C#CC(C)(C)O)cc2n1-c1ccnc(N)n1] | 4-(1-(2-aminopyrimidin-4-yl)-2-ethoxy-1H-benzo[d]imidazol-6-yl)-2-methylbut-3-yn-2-ol |
| T1-39 | 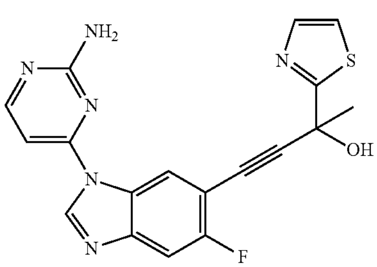 [SMILES: CC(O)(C#Cc1cc2c(cc1F)ncn2-c1ccnc(N)n1)c1nccs1] | 4-(1-(2-aminopyrimidin-4-yl)-5-fluoro-1H-benzo[d]imidazol-6-yl)-2-(thiazol-2-yl)but-3-yn-2-ol |

TABLE 1-continued

| No | Structure | Name |
|---|---|---|
| T1-40 | 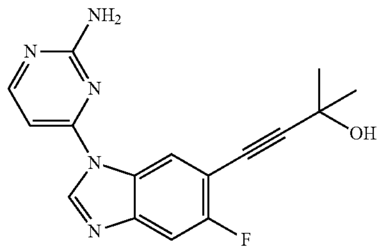 [SMILES: CC(C)(O)C#Cc1cc2c(cc1F)ncn2-c1ccnc(N)n1] | 4-(1-(2-aminopyrimidin-4-yl)-5-fluoro-1H-benzo[d]imidazol-6-yl)-2-methylbut-3-yn-2-ol |
| T1-41 | 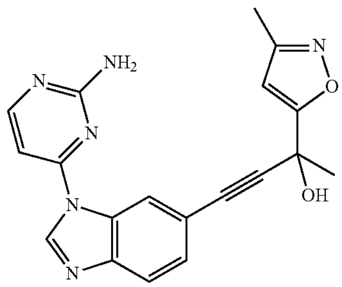 [SMILES: Cc1cc(C(C)(O)C#Cc2ccc3ncn(-c4ccnc(N)n4)c3c2)on1] | 4-(1-(2-aminopyrimidin-4-yl)-1H-benzo[d]imidazol-6-yl)-2-(3-methylisoxazol-5-yl)but-3-yn-2-ol |
| T1-42 | 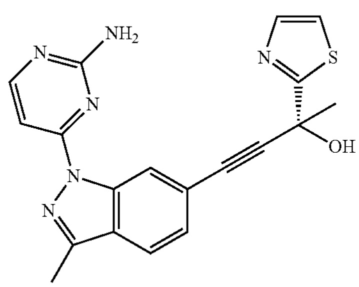 | 4-(1-(2-aminopyrimidin-4-yl)-3-methyl-1H-indazol-6-yl)-2-(thiazol-2-yl)but-3-yn-2-ol |
| T1-43 | 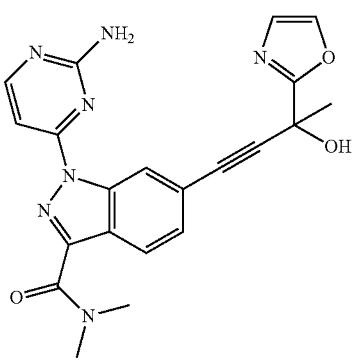 [SMILES: CN(C)C(=O)c1nn(-c2ccnc(N)n2)c2cc(C#CC(C)(O)c3ncco3)ccc12] | 1-(2-aminopyrimidin-4-yl)-6-(3-hydroxy-3-(oxazol-2-yl)but-1-ynyl)-N,N-dimethyl-1H-indazole-3-carboxamide |
| T1-44 | 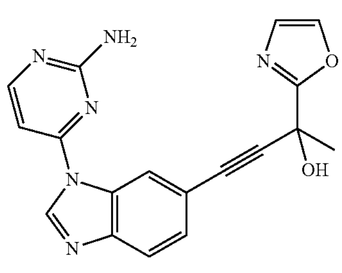 [SMILES: CC(O)(C#Cc1ccc2ncn(-c3ccnc(N)n3)c2c1)c1ncco1] | 4-(1-(2-aminopyrimidin-4-yl)-1H-benzo[d]imidazol-6-yl)-2-(oxazol-2-yl)but-3-yn-2-ol |

TABLE 1-continued

| No | Structure | Name |
|---|---|---|
| T1-45 | 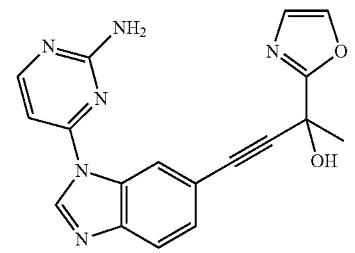 [SMILES: CC(O)(C#Cc1ccc2ncn(-c3ccnc(N)n3)c2c1)c1ncco1] | 4-(1-(2-aminopyrimidin-4-yl)-1H-benzo[d]imidazol-6-yl)-2-(oxazol-2-yl)but-3-yn-2-ol |
| T1-46 | 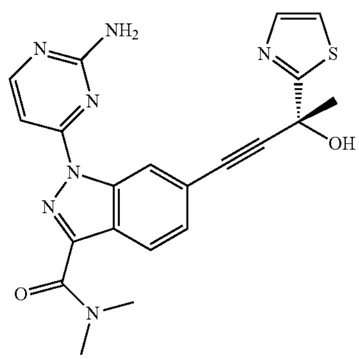 [SMILES: CN(C)C(=O)c1nn(-c2ccnc(N)n2)c2cc(C#C[C@@](C)(O)c3nccs3)ccc12] | (R)-1-(2-aminopyrimidin-4-yl)-6-(3-hydroxy-3-(thiazol-2-yl)but-1-ynyl)-N,N-dimethyl-1H-indazole-3-carboxamide |
| T1-47 | 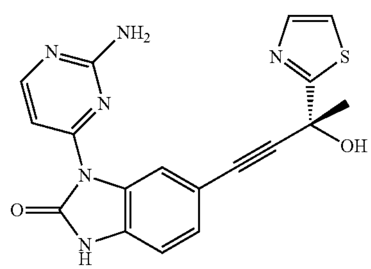 [SMILES: C[C@@](O)(C#Cc1ccc2[nH]c(=O)n(-c3ccnc(N)n3)c2c1)c1nccs1] | (R)-1-(2-aminopyrimidin-4-yl)-6-(3-hydroxy-3-(thiazol-2-yl)but-1-ynyl)-1H-benzo[d]imidazol-2(3H)-one |
| T1-48 | 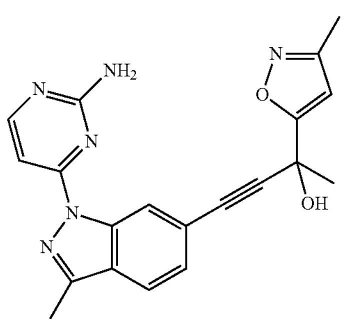 [SMILES: Cc1cc(C(C)(O)C#Cc2ccc3c(C)nn(-c4ccnc(N)n4)c3c2)on1] | 4-(1-(2-aminopyrimidin-4-yl)-3-methyl-1H-indazol-6-yl)-2-(3-methylisoxazol-5-yl)but-3-yn-2-ol |
| T1-49 | 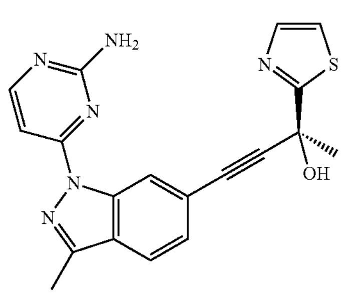 [SMILES: Cc1nn(-c2ccnc(N)n2)c2cc(C#C[C@](C)(O)c3nccs3)ccc12] | (S)-4-(1-(2-aminopyrimidin-4-yl)-3-methyl-1H-indazol-6-yl)-2-(thiazol-2-yl)but-3-yn-2-ol |

TABLE 1-continued

| No | Structure | Name |
|---|---|---|
| T1-50 | 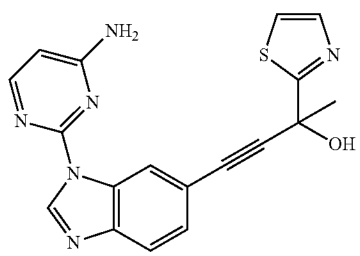 [SMILES: CC(O)(C#Cc1ccc2ncn(-c3nccc(N)n3)c2c1)c1nccs1] | 4-(1-(4-aminopyrimidin-2-yl)-1H-benzo[d]imidazol-6-yl)-2-(thiazol-2-yl)but-3-yn-2-ol |
| T1-51 | 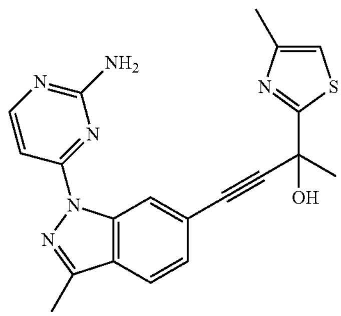 [SMILES: Cc1csc(C(C)(O)C#Cc2ccc3c(C)nn(-c4ccnc(N)n4)c3c2)n1] | 4-(1-(2-aminopyrimidin-4-yl)-3-methyl-1H-indazol-6-yl)-2-(4-methylthiazol-2-yl)but-3-yn-2-ol |
| T1-52 | 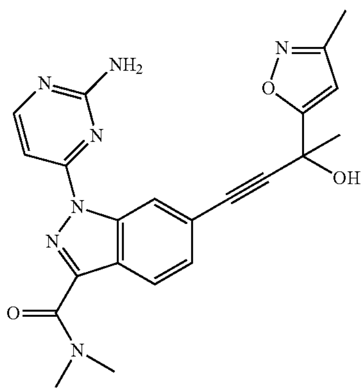 [SMILES: Cc1cc(C(C)(O)C#Cc2ccc3c(C(=O)N(C)C)nn(-c4ccnc(N)n4)c3c2)on1] | 1-(2-aminopyrimidin-4-yl)-6-(3-hydroxy-3-(3-methyl-isoxazol-5-yl)but-1-ynyl)-N,N-dimethyl-1H-indazole-3-carboxamide |
| T1-53 | 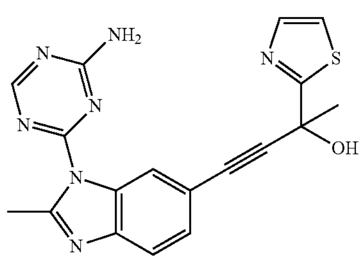 [SMILES: Cc1nc2ccc(C#CC(C)(O)c3nccs3)cc2n1-c1ncnc(N)n1] | 4-(1-(4-amino-1,3,5-triazin-2-yl)-2-methyl-1H-benzo[d]imidazol-6-yl)-2-(thiazol-2-yl)but-3-yn-2-ol |
| T1-54 | 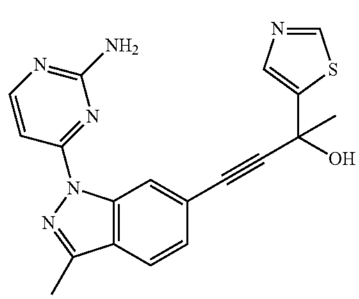 [SMILES: Cc1nn(-c2ccnc(N)n2)c2cc(C#CC(C)(O)c3cncs3)ccc12] | 4-(1-(2-aminopyrimidin-4-yl)-3-methyl-1H-indazol-6-yl)-2-(thiazol-5-yl)but-3-yn-2-ol |

TABLE 1-continued

| No | Structure | Name |
|---|---|---|
| T1-55 | 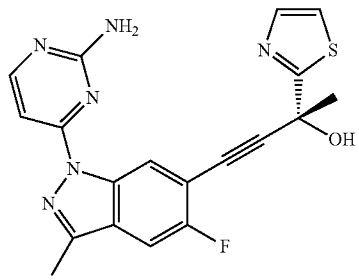 [SMILES: Cc1nn(-c2ccnc(N)n2)c2cc(C#C[C@@](C)(O)c3nccs3)c(F)cc12] | (R)-4-(1-(2-aminopyrimidin-4-yl)-5-fluoro-3-methyl-1H-indazol-6-yl)-2-(thiazol-2-yl)but-3-yn-2-ol |
| T1-56 | 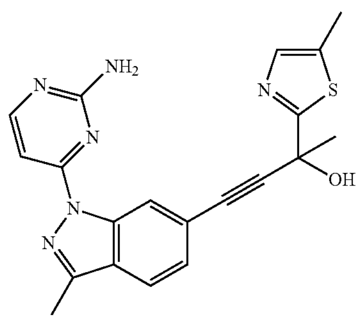 [SMILES: Cc1cnc(C(C)(O)C#Cc2ccc3c(C)nn(-c4ccnc(N)n4)c3c2)s1] | 4-(1-(2-aminopyrimidin-4-yl)-3-methyl-1H-indazol-6-yl)-2-(5-methylthiazol-2-yl)but-3-yn-2-ol |
| T1-57 | 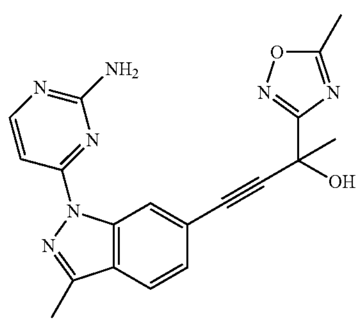 | 4-(1-(2-aminopyrimidin-4-yl)-3-methyl-1H-indazol-6-yl)-2-(5-methyl-1,2,4-oxadiazol-3-yl)but-3-yn-2-ol |
| T1-58 | 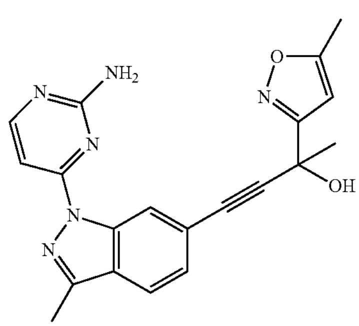 [SMILES: Cc1cc(C(C)(O)C#Cc2ccc3c(C)nn(-c4ccnc(N)n4)c3c2)no1] | 4-(1-(2-aminopyrimidin-4-yl)-3-methyl-1H-indazol-6-yl)-2-(5-methylisoxazol-3-yl)but-3-yn-2-ol |

TABLE 1-continued

| No | Structure | Name |
|---|---|---|
| T1-59 | 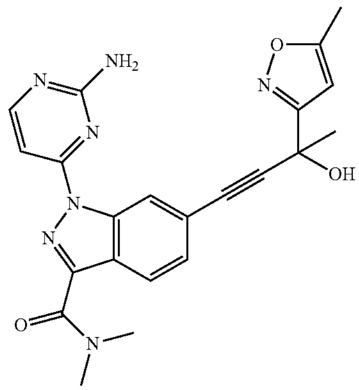 [SMILES: Cc1cc(C(C)(O)C#Cc2ccc3c(C(=O)N(C)C)nn(-c4ccnc(N)n4)c3c2)no1] | 1-(2-aminopyrimidin-4-yl)-6-(3-hydroxy-3-(5-methyl-isoxazol-3-yl)but-1-ynyl)-N,N-dimethyl-1H-indazole-3-carboxamide |
| T1-60 | 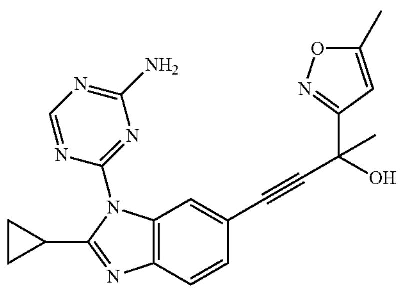 [SMILES: Cc1cc(C(C)(O)C#Cc2ccc3nc(C4CC4)n(-c4ncnc(N)n4)c3c2)no1] | 4-(1-(4-amino-1,3,5-triazin-2-yl)-2-cyclopropyl-1H-benzo[d]imidazol-6-yl)-2-(5-methyl-isoxazol-3-yl)but-3-yn-2-ol |
| T1-61 | 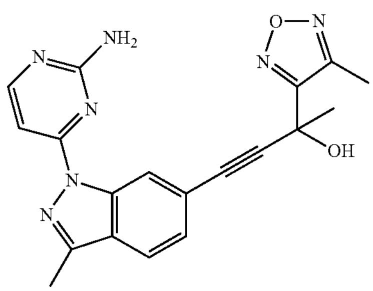 [SMILES: Cc1nonc1C(C)(O)C#Cc1ccc2c(C)nn(-c3ccnc(N)n3)c2c1] | 4-(1-(2-aminopyrimidin-4-yl)-3-methyl-1H-indazol-6-yl)-2-(4-methyl-1,2,5-oxadiazol-3-yl)but-3-yn-2-ol |
| T1-62 | 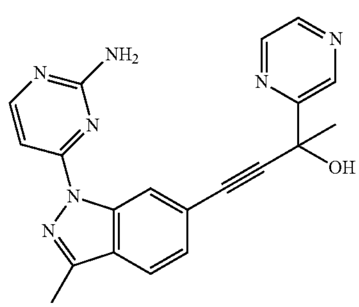 [SMILES: Cc1nn(-c2ccnc(N)n2)c2cc(C#CC(C)(O)c3cnccn3)ccc12] | 4-(1-(2-aminopyrimidin-4-yl)-3-methyl-1H-indazol-6-yl)-2-(pyrazin-2-yl)but-3-yn-2-ol |
| T1-63 | 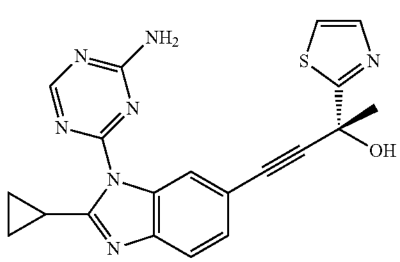 [SMILES: C[C@@](O)(C#Cc1ccc2nc(C3CC3)n(-c3ncnc(N)n3)c2c1)c1nccs1] | (R)-4-(1-(4-amino-1,3,5-triazin-2-yl)-2-cyclopropyl-1H-benzo[d]imidazol-6-yl)-2-(thiazol-2-yl)but-3-yn-2-ol |

TABLE 1-continued

| No | Structure | Name |
|---|---|---|
| T1-64 | 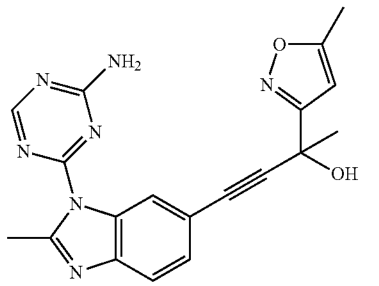 | 4-(1-(4-amino-1,3,5-triazin-2-yl)-2-methyl-1H-benzo[d]imidazol-6-yl)-2-(5-methyl-isoxazol-3-yl)but-3-yn-2-ol |
| T1-65 | 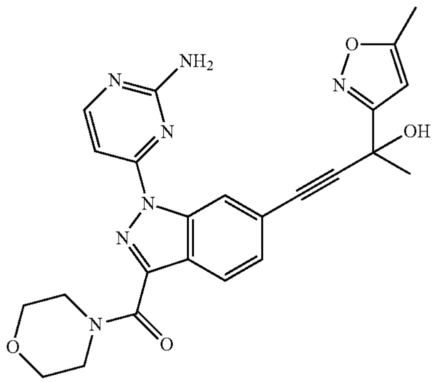 [SMILES: Cc1cc(C(C)(O)C#Cc2ccc3c(C(=O)N4CCOCC4)nn(-c4ccnc(N)n4)c3c2)no1] | (1-(2-aminopyrimidin-4-yl)-6-(3-hydroxy-3-(5-methyl-isoxazol-3-yl)but-1-ynyl)-1H-indazol-3-yl)(morpholino)methanone |
| T1-66 | 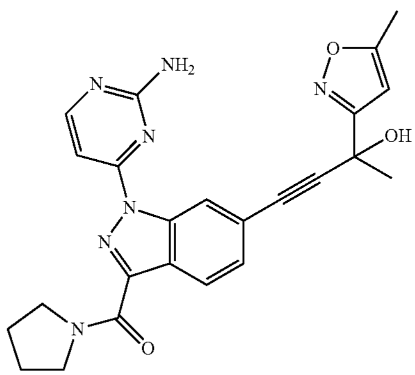 [SMILES: Cc1cc(C(C)(O)C#Cc2ccc3c(C(=O)N4CCCC4)nn(-c4ccnc(N)n4)c3c2)no1] | (1-(2-aminopyrimidin-4-yl)-6-(3-hydroxy-3-(5-methyl-isoxazol-3-yl)but-1-ynyl)-1H-indazol-3-yl)(pyrrolidin-1-yl)methanone |
| T1-67 | 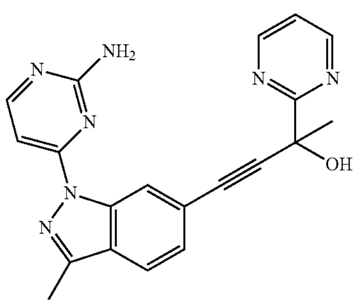 [SMILES: Cc1nn(-c2ccnc(N)n2)c2cc(C#CC(C)(O)c3ncccn3)ccc12] | 4-(1-(2-aminopyrimidin-4-yl)-3-methyl-1H-indazol-6-yl)-2-(pyrimidin-2-yl)but-3-yn-2-ol |
| T1-68 | 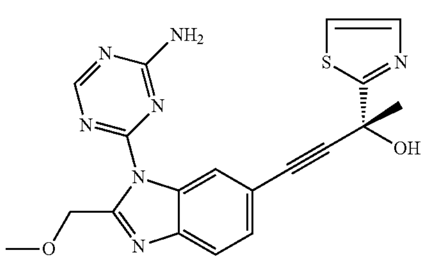 [SMILES: COCc1nc2ccc(C#C[C@@](C)(O)c3nccs3)cc2n1-c1ncnc(N)n1] | (R)-4-(1-(4-amino-1,3,5-triazin-2-yl)-2-(methoxymethyl)-1H-benzo[d]imidazol-6-yl)-2-(thiazol-2-yl)but-3-yn-2-ol |

TABLE 1-continued

| No | Structure | Name |
|---|---|---|
| T1-69 | 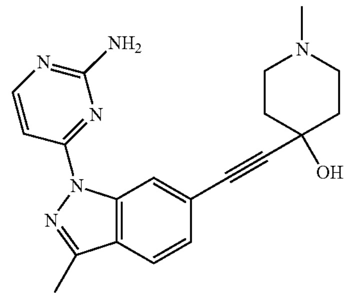 [SMILES: Cc1nn(-c2ccnc(N)n2)c2cc(C#CC3(O)CCN(C)CC3)ccc12] | 4-((1-(2-aminopyrimidin-4-yl)-3-methyl-1H-indazol-6-yl)ethynyl)-1-methylpiperidin-4-ol |
| T1-70 | 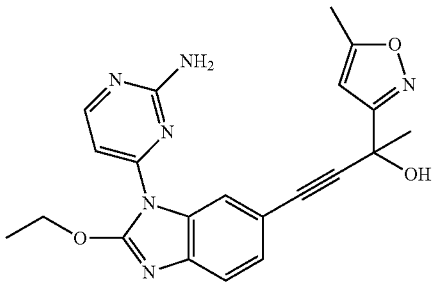 [SMILES: CCOc1nc2ccc(C#CC(C)(O)c3cc(C)on3)cc2n1-c1ccnc(N)n1] | 4-(1-(2-aminopyrimidin-4-yl)-2-ethoxy-1H-benzo[d]imidazol-6-yl)-2-(5-methyl-isoxazol-3-yl)but-3-yn-2-ol |

TABLE 1.1

| No. | Structure | Name |
|---|---|---|
| T1.1-1 | 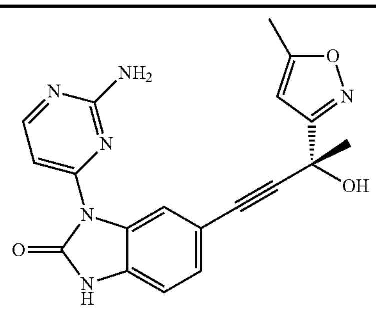 | 3-(2-aminopyrimidin-4-yl)-[(3R)-3-hydroxy-3-(5-methyl-isoxazol-3-yl)but-1-ynyl]-1H-benzimidazol-2-one |
| T1.1-2 | 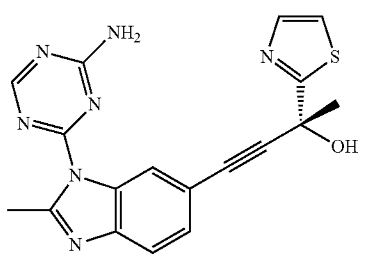 [SMILES: Cc1nc2ccc(C#C[C@@](C)(O)c3nccs3)cc2n1-c1ncnc(N)n1] | (2R)-4-[3-(4-amino-1,3,5-triazin-2-yl)-2-methyl-benzimidazol-5-yl]-2-thiazol-2-yl-but-3-yn-2-ol |
| T1.1-3 | 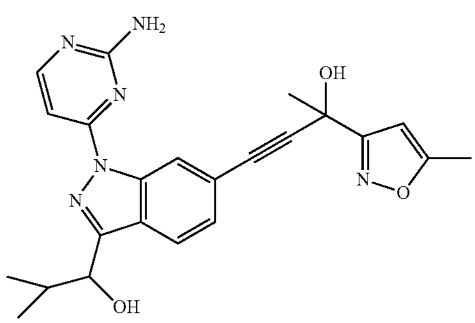 [SMILES: Cc1cc(C(C)(O)C#Cc2ccc3c(C(O)C(C)C)nn(-c4ccnc(N)n4)c3c2)no1] | 4-[1-(2-aminopyrimidin-4-yl)-3-(1-hydroxy-2-methyl-propyl)indazol-6-yl]-2-(5-methyl-isoxazol-3-yl)but-3-yn-2-ol |

TABLE 1.1-continued

| No. | Structure | Name |
|---|---|---|
| T1.1-4 | 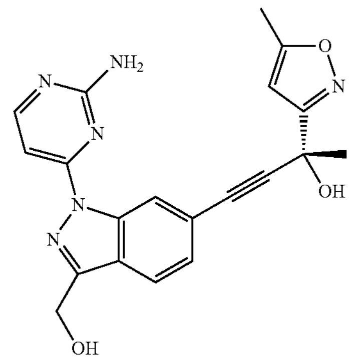 [SMILES: Cc1cc([C@](C)(O)C#Cc2ccc3c(CO)nn(-c4ccnc(N)n4)c3c2)no1] | (2R)-4-[1-(2-aminopyrimidin-4-yl)-3-(hydroxymethyl)indazol-6-yl]-2-(5-methyl-isoxazol-3-yl)but-3-yn-2-ol |
| T1.1-5 | 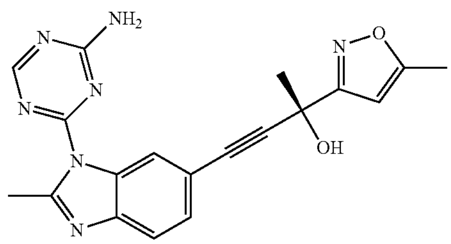 | (2R)-4-[3-(4-amino-1,3,5-triazin-2-yl)-2-methyl-benzimidazol-5-yl]-2-(5-methylisoxazol-3-yl)but-3-yn-2-ol |
| T1.1-6 | 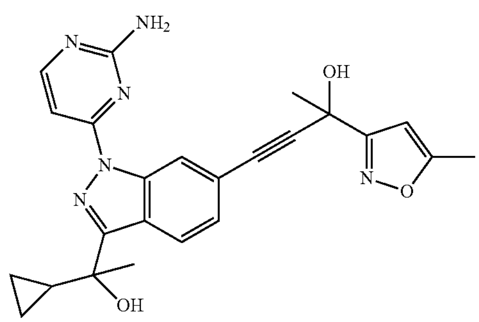 [SMILES: Cc1cc(C(C)(O)C#Cc2ccc3c(C(C)(O)C4CC4)nn(-c4ccnc(N)n4)c3c2)no1] | 4-[1-(2-aminopyrimidin-4-yl)-3-(1-cyclopropyl-1-hydroxy-ethyl)indazol-6-yl]-2-(5-methylisoxazol-3-yl)but-3-yn-2-ol |
| T1.1-7 | 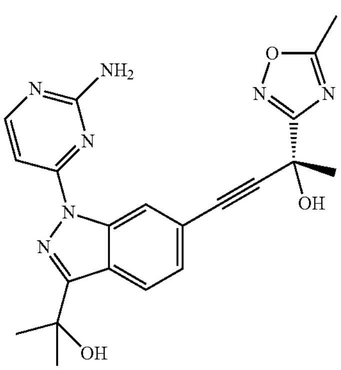 [SMILES: Cc1nc([C@](C)(O)C#Cc2ccc3c(C(C)(C)O)nn(-c4ccnc(N)n4)c3c2)no1] | (2R)-4-[1-(2-aminopyrimidin-4-yl)-3-(1-hydroxy-1-methyl-ethyl)indazol-6-yl]-2-(5-methyl-1,2,4-oxadiazol-3-yl)but-3-yn-2-ol |

TABLE 1.1-continued

| No. | Structure | Name |
|---|---|---|
| T1.1-8 | 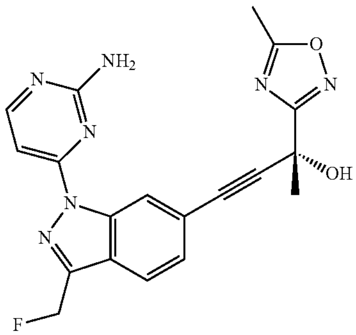 [SMILES: Cc1nc([C@](C)(O)C#Cc2ccc3c(CF)nn(-c4ccnc(N)n4)c3c2)no1] | (2R)-4-[1-(2-aminopyrimidin-4-yl)-3-(fluoromethyl)indazol-6-yl]-2-(5-methyl-1,2,4-oxadiazol-3-yl)but-3-yn-2-ol |
| T1.1-9 | 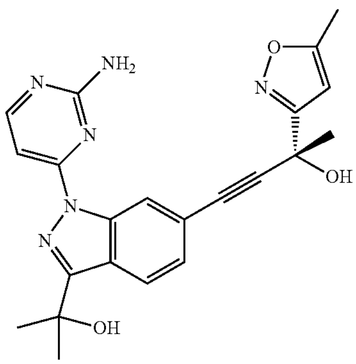 [SMILES: Cc1cc([C@](C)(O)C#Cc2ccc3c(C(C)(C)O)nn(-c4ccnc(N)n4)c3c2)no1] | (2R)-4-[1-(2-aminopyrimidin-4-yl)-3-(1-hydroxy-1-methyl-ethyl)indazol-6-yl]-2-(5-methyl-isoxazol-3-yl)but-3-yn-2-ol |
| T1.1-10 | 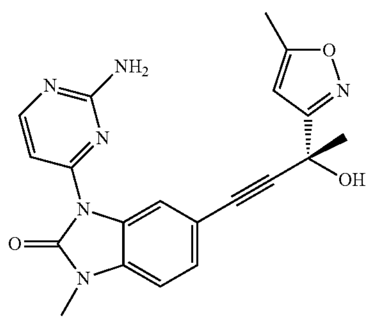 [SMILES: Cc1cc([C@](C)(O)C#Cc2ccc3c(c2)n(-c2ccnc(N)n2)c(=O)n3C)no1] | 3-(2-aminopyrimidin-4-yl)-5-[(3R)-3-hydroxy-3-(5-methylisoxazol-3-yl)but-1-ynyl]-1-methyl-benzimidazol-2-one |
| T1.1-11 | 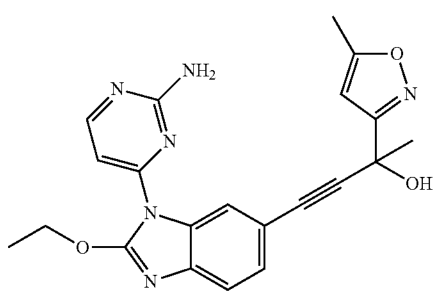 [SMILES: CCOc1nc2ccc(C#CC(C)(O)c3cc(C)on3)cc2n1-c1ccnc(N)n1] | 4-[3-(2-aminopyrimidin-4-yl)-2-ethoxy-benzimidazol-5-yl]-2-(5-methylisoxazol-3-yl) but-3-yn-2-ol |
| T1.1-12 | 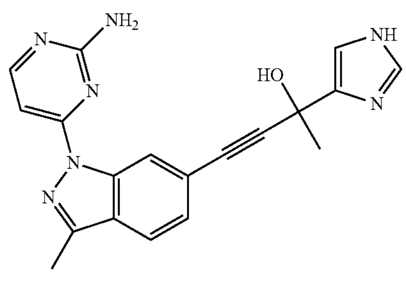 [SMILES: Cc1nn(-c2ccnc(N)n2)c2cc(C#CC(C)(O)c3c[nH]cn3)ccc12] | 4-[1-(2-aminopyrimidin-4-yl)-3-methyl-indazol-6-yl]-2-(1H-imidazol-4-yl)but-3-yn-2-ol |

TABLE 1.1-continued

| No. | Structure | Name |
|---|---|---|
| T1.1-13 | 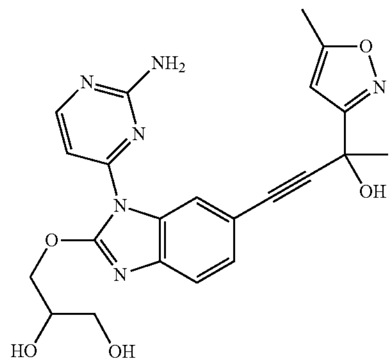 [SMILES: Cc1cc(C(C)(O)C#Cc2ccc3nc(OCC(O)CO)n(-c4ccnc(N)n4)c3c2)no1] | 3-[1-(2-aminopyrimidin-4-yl)-6-[3-hydroxy-3-(5-methylisoxazol-3-yl)but-1-ynyl]benzimidazol-2-yl]oxypropane-1,2-diol |
| T1.1-14 | 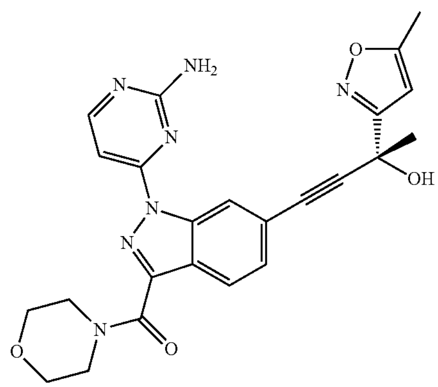 [SMILES: Cc1cc([C@](C)(O)C#Cc2ccc3c(C(=O)N4CCOCC4)nn(-c4ccnc(N)n4)c3c2)no1] | [1-(2-aminopyrimidin-4-yl)-6-[(3R)-3-hydroxy-3-(5-methylisoxazol-3-yl)but-1-ynyl]indazol-3-yl]-morpholino-methanone |
| T1.1-15 | 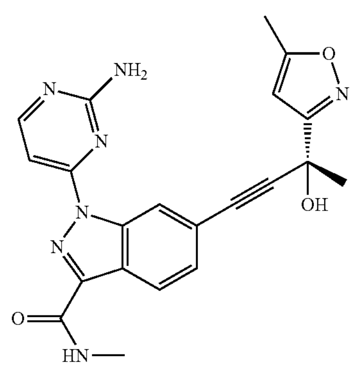 [SMILES: CNC(=O)c1nn(-c2ccnc(N)n2)c2cc(C#C[C@@](C)(O)c3cc(C)on3)ccc12] | 1-(2-aminopyrimidin-4-yl)-6-[(3R)-3-hydroxy-3-(5-methylisoxazol-3-yl)but-1-ynyl]-N-methyl-indazole-3-carboxamide |
| T1.1-16 | 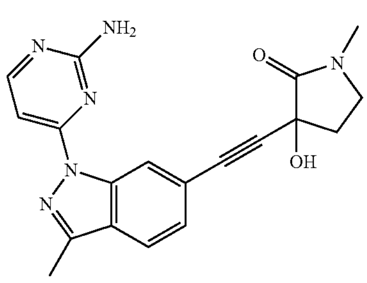 [SMILES: Cc1nn(-c2ccnc(N)n2)c2cc(C#CC3(O)CCN(C)C3=O)ccc12] | 3-[2-[1-(2-aminopyrimidin-4-yl)-3-methyl-indazol-6-yl]ethynyl]-3-hydroxy-1-methyl-pyrrolidin-2-one |

TABLE 1.1-continued

| No. | Structure | Name |
|---|---|---|
| T1.1-17 | 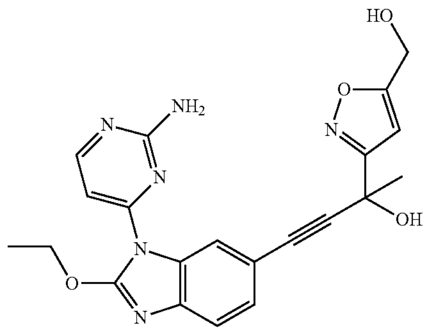 [SMILES: CCOc1nc2ccc(C#CC(C)(O)c3cc(CO)on3)cc2n1-c1ccnc(N)n1] | 4-[3-(2-aminopyrimidin-4-yl)-2-ethoxy-benzimidazol-5-yl]-2-[5-(hydroxymethyl)isoxdazol-3-yl]but-3-yn-2-ol |
| T1.1-18 | 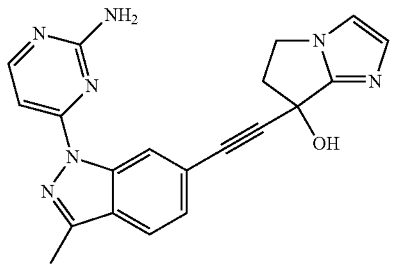 [SMILES: Cc1nn(-c2ccnc(N)n2)c2cc(C#CC3(O)CCn4ccnc43)ccc12] | 7-[2-[1-(2-aminopyrimidin-4-yl)-3-methyl-indazol-6-yl]ethynyl]-5,6-dihydropyrrolo[1,2-a]imidazol-7-ol |
| T1.1-19 | 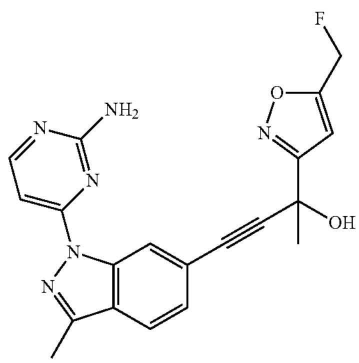 [SMILES: Cc1nn(-c2ccnc(N)n2)c2cc(C#CC(C)(O)c3cc(CF)on3)ccc12] | 4-[1-(2-aminopyrimidin-4-yl)-3-methyl-indazol-6-yl]-2-[5-(fluoromethyl)isoxazol-3-yl]but-3-yn-2-ol |
| T1.1-20 | 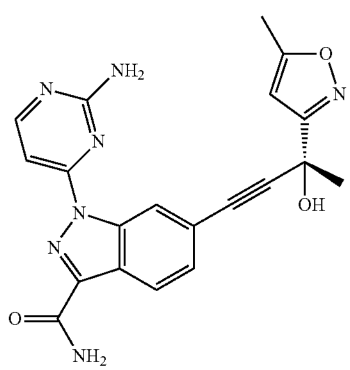 [SMILES: Cc1cc([C@](C)(O)C#Cc2ccc3c(C(N)=O)nn(-c4ccnc(N)n4)c3c2)no1] | 1-(2-aminopyrimidin-4-yl)-6-[(3R)-3-hydroxy-3-(5-methyl-isoxazol-3-yl)but-1-ynyl]indazole-3-carboxamide |
| T1.1-21 | 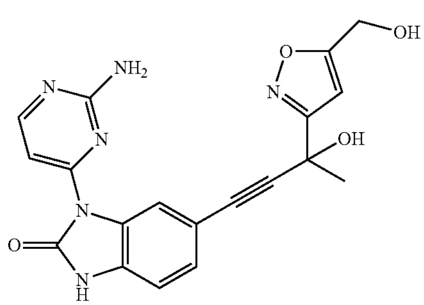 [SMILES: CC(O)(C#Cc1ccc2[nH]c(=O)n(-c3ccnc(N)n3)c2c1)c1cc(CO)on1] | 3-(2-aminopyrimidin-4-yl)-5-[3-hydroxy-3-[5-(hydroxymethyl)isoxazol-3-yl]but-1-ynyl]-1H-benzimidazol-2-one |

TABLE 1.1-continued

| No. | Structure | Name |
|---|---|---|
| T1.1-22 | 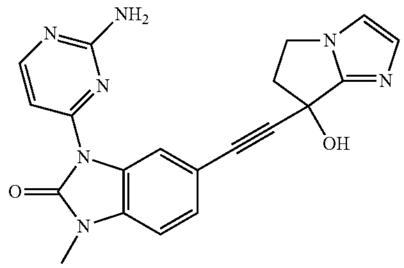 [SMILES: Cn1c(=O)n(-c2ccnc(N)n2)c2cc(C#CC3(O)CCn4ccnc43)ccc21] | 3-(2-aminopyrimidin-4-yl)-5-[2-(7-hydroxy-5,6-dihydropyrrolo[1,2-a]imidazol-7-yl)ethynyl]-1-methyl-benzimidazol-2-one |
| T1.1-23 | 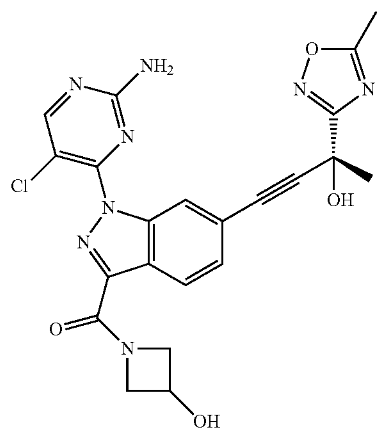 [SMILES: Cc1nc([C@](C)(O)C#Cc2ccc3c(C(=O)N4CC(O)C4)nn(-c4nc(N)ncc4Cl)c3c2)no1] | [1-(2-amino-5-chloro-pyrimidin-4-yl)-6-[(3R)-3-hydroxy-3-(5-methyl-1,2,4-oxadiazol-3-yl)but-1-ynyl]indazol-3-yl]-(3-hydroxy-azetidin-1-yl)methanone |
| T1.1-24 | 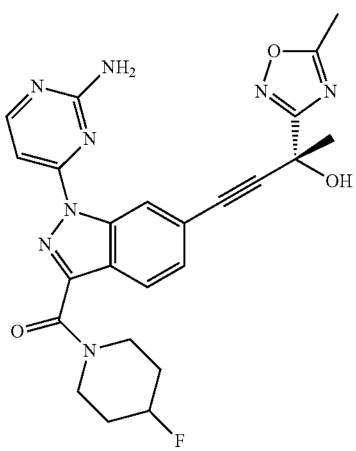 [SMILES: Cc1nc([C@](C)(O)C#Cc2ccc3c(C(=O)N4CCC(F)CC4)nn(-c4ccnc(N)n4)c3c2)no1] | [1-(2-aminopyrimidin-4-yl)-6-[(3R)-3-hydroxy-3-(5-methyl-1,2,4-oxadiazol-3-yl)but-1-ynyl]indazol-3-yl]-(4-fluoro-1-piperidyl)methanone |
| T1.1-25 | 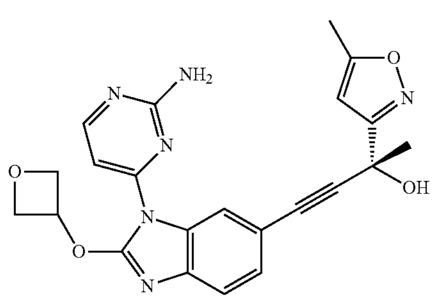 [SMILES: Cc1cc([C@](C)(O)C#Cc2ccc3nc(OC4COC4)n(-c4ccnc(N)n4)c3c2)no1] | (2R)-4-[3-(2-aminopyrimidin-4-yl)-2-(oxetan-3-yloxy)benzimidazol-5-yl]-2-(5-methylisoxazol-3-yl)but-3-yn-2-ol |

TABLE 1.1-continued

| No. | Structure | Name |
|---|---|---|
| T1.1-26 | 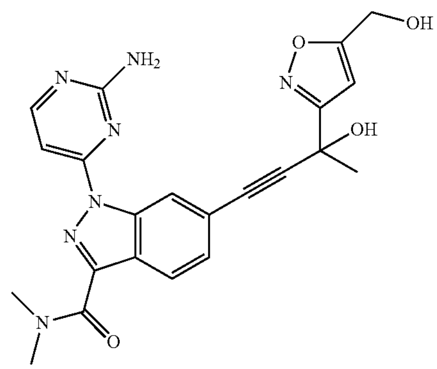 [SMILES: CN(C)C(=O)c1nn(-c2ccnc(N)n2)c2cc(C#CC(C)(O)c3cc(CO)on3)ccc12] | 1-(2-aminopyrimidin-4-yl)-6-[3-hydroxy-3-[5-(hydroxymethyl)isoxazol-3-yl]but-1-ynyl]-N,N-dimethyl-indazole-3-carboxamide |
| T1.1-27 | 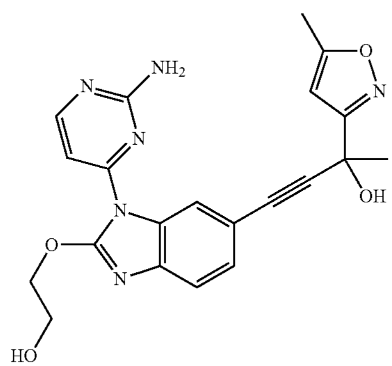 [SMILES: Cc1cc(C(C)(O)C#Cc2ccc3nc(OCCO)n(-c4ccnc(N)n4)c3c2)no1] | 4-[3-(2-aminopyrimidin-4-yl)-2-(2-hydroxyethoxy)benzimidazol-5-yl]-2-(5-methylisoxazol-3-yl)but-3-yn-2-ol |
| T1.1-28 | 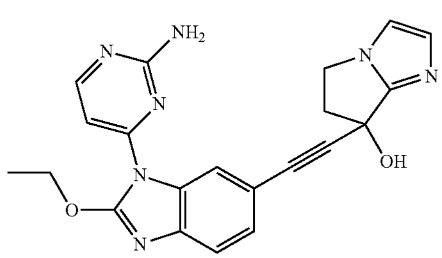 [SMILES: CCOc1nc2ccc(C#CC3(O)CCn4ccnc43)cc2n1-c1ccnc(N)n1] | 7-[2-[3-(2-aminopyrimidin-4-yl)-2-ethoxy-benzimidazol-5-yl]ethynyl]-5,6-dihydropyrrolo[1,2-a]imidazol-7-ol |
| T1.1-29 | 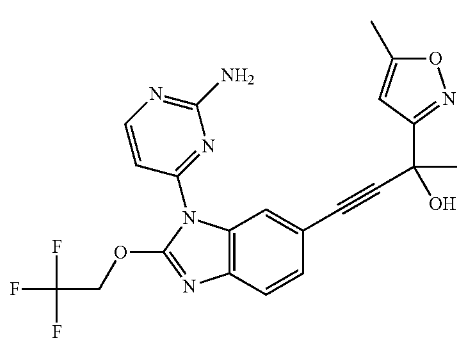 [SMILES: Cc1cc(C(C)(O)C#Cc2ccc3nc(OCC(F)(F)F)n(-c4ccnc(N)n4)c3c2)no1] | 4-[3-(2-aminopyrimidin-4-yl)-2-(2,2,2-trifluoroethoxy)benzimidazol-5-yl]-2-(5-methylisoxazol-3-yl)but-3-yn-2-ol |

TABLE 1.1-continued

| No. | Structure | Name |
|---|---|---|
| T1.1-30 | 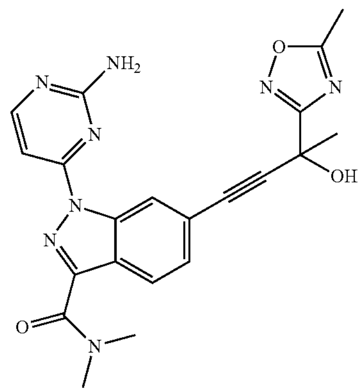 [SMILES: Cc1nc(C(C)(O)C#Cc2ccc3c(C(=O)N(C)C)nn(-c4ccnc(N)n4)c3c2)no1] | 1-(2-aminopyrimidin-4-yl)-6-[3-hydroxy-3-(5-methyl-1,2,4-oxadiazol-3-yl)but-1-ynyl]-N,N-dimethyl-indazole-3-carboxamide |
| T1.1-31 | 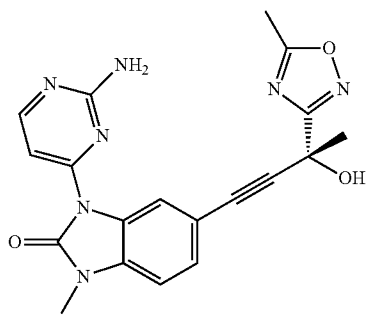 [SMILES: Cc1nc([C@](C)(O)C#Cc2ccc3c(c2)n(-c2ccnc(N)n2)c(=O)n3C)no1] | 3-(2-aminopyrimidin-4-yl)-5-[(3R)-3-hydroxy-3-(5-methyl-1,2,4-oxadiazol-3-yl)but-1-ynyl]-1-methyl-benzimidazol-2-one |
| T1.1-32 | 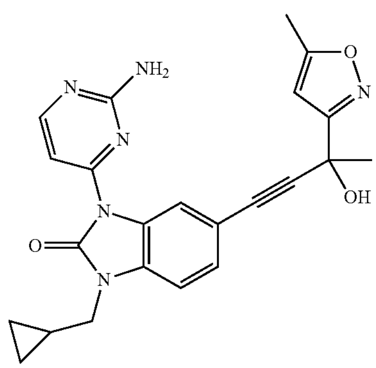 [SMILES: Cc1cc(C(C)(O)C#Cc2ccc3c(c2)n(-c2ccnc(N)n2)c(=O)n3CC2CC2)no1] | 3-(2-aminopyrimidin-4-yl)-1-(cyclopropylmethyl)-5-[3-hydroxy-3-(5-methylisoxazol-3-yl)but-1-ynyl]benzimidazol-2-one |
| T1.1-33 | 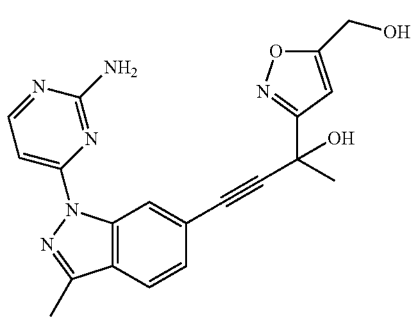 [SMILES: Cc1nn(-c2ccnc(N)n2)c2cc(C#CC(C)(O)c3cc(CO)on3)ccc12] | 4-[1-(2-aminopyrimidin-4-yl)-3-methyl-indazol-6-yl]-2-[5-(hydroxymethyl)isoxazol-3-yl]but-3-yn-2-ol |

TABLE 1.1-continued

| No. | Structure | Name |
|---|---|---|
| T1.1-34 | 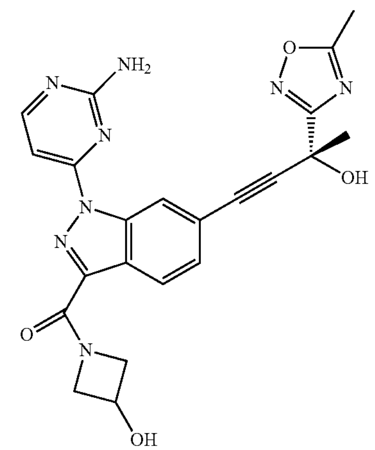 [SMILES: Cc1nc([C@](C)(O)C#Cc2ccc3c(C(=O)N4CC(O)C4)nn(-c4ccnc(N)n4)c3c2)no1] | [1-(2-aminopyrimidin-4-yl)-6-[(3R)-3-hydroxy-3-(5-methyl-1,2,4-oxadiazol-3-yl)but-1-ynyl]indazol-3-yl]-(3-hydroxyazetidin-1-yl)methanone |
| T1.1-35 | 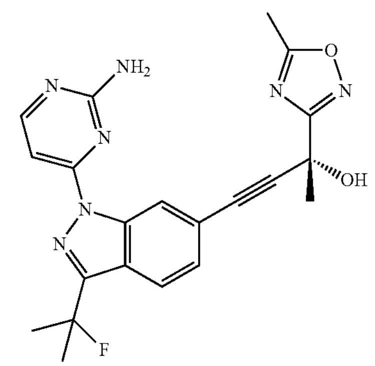 [SMILES: Cc1nc([C@](C)(O)C#Cc2ccc3c(C(C)(C)F)nn(-c4ccnc(N)n4)c3c2)no1] | (2R)-4-[1-(2-aminopyrimidin-4-yl)-3-(1-fluoro-1-methyl-ethyl)indazol-6-yl]-2-(5-methyl-1,2,4-oxadiazol-3-yl)but-3-yn-2-ol |
| T1.1-36 | 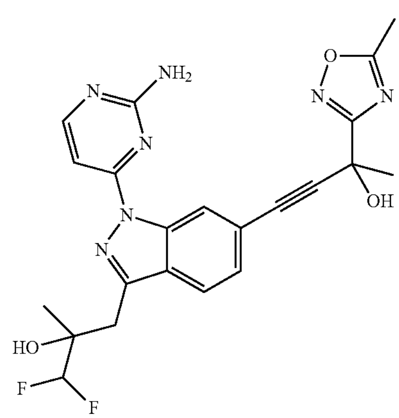 [SMILES: Cc1nc(C(C)(O)C#Cc2ccc3c(CC(C)(O)C(F)F)nn(-c4ccnc(N)n4)c3c2)no1] | 3-[1-(2-aminopyrimidin-4-yl)-6-[3-hydroxy-3-(5-methyl-1,2,4-oxadiazol-3-yl)but-1-ynyl]indazol-3-yl]-1,1-difluoro-2-methyl-propan-2-ol |

TABLE 1.1-continued

| No. | Structure | Name |
|---|---|---|
| T1.1-37 | 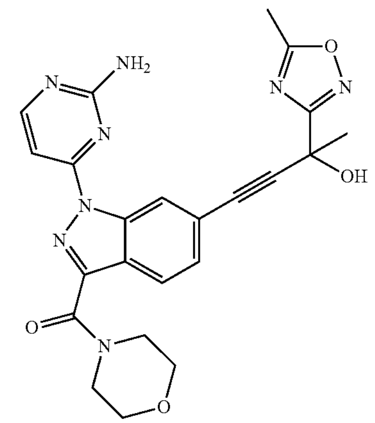 [SMILES: Cc1nc(C(C)(O)C#Cc2ccc3c(C(=O)N4CCOCC4)nn(-c4ccnc(N)n4)c3c2)no1] | [1-(2-aminopyrimidin-4-yl)-6-[3-hydroxy-3-(5-methyl-1,2,4-oxadiazol-3-yl)but-1-ynyl]indazol-3-yl]-morpholino-methanone |
| T1.1-38 | 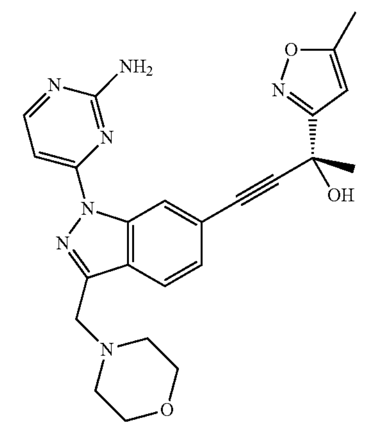 [SMILES: Cc1cc([C@](C)(O)C#Cc2ccc3c(CN4CCOCC4)nn(-c4ccnc(N)n4)c3c2)no1] | (2R)-4-[1-(2-aminopyrimidin-4-yl)-3-(morpholinomethyl)indazol-6-yl]-2-(5-methylisoxazol-3-yl)but-3-yn-2-ol |
| T1.1-39 | 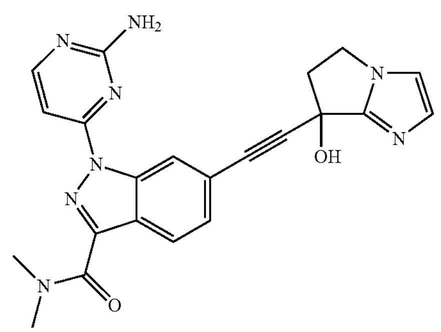 [SMILES: CN(C)C(=O)c1nn(-c2ccnc(N)n2)c2cc(C#CC3(O)CCn4ccnc43)ccc12] | 1-(2-aminopyrimidin-4-yl)-6-[2-(7-hydroxy-5,6-dihydropyrrolo[1,2-a]imidazol-7-yl)ethynyl]-N,N-dimethyl-indazole-3-carboxamide |
| T1.1-40 | 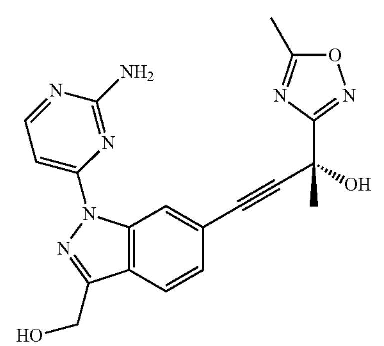 [SMILES: Cc1nc([C@](C)(O)C#Cc2ccc3c(CO)nn(-c4ccnc(N)n4)c3c2)no1] | (2R)-4-[1-(2-aminopyrimidin-4-yl)-3-(hydroxymethyl)indazol-6-yl]-2-(5-methyl-1,2,4-oxadiazol-3-yl)but-3-yn-2-ol |

TABLE 1.1-continued

| No. | Structure | Name |
|---|---|---|
| T1.1-41 | 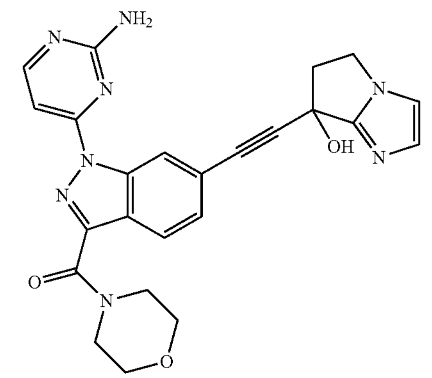 [SMILES: Nc1nccc(-n2nc(C(=O)N3CCOCC3)c3ccc(C#CC4(O)CCn5ccnc54)cc32)n1] | [1-(2-aminopyrimidin-4-yl)-6-[2-(7-hydroxy-5,6-dihydropyrrolo[1,2-a]imidazol-7-yl) ethynyl]indazol-3-yl]-morpholino-methanone |
| T1.1-42 | 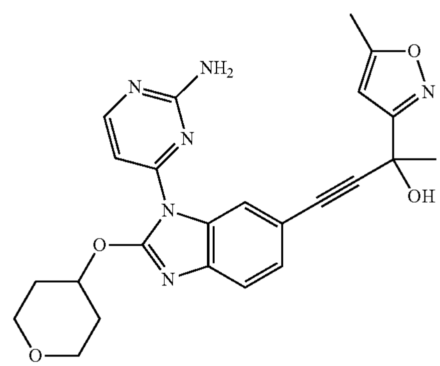 [SMILES: Cc1cc(C(C)(O)C#Cc2ccc3nc(OC4CCOCC4)n(-c4ccnc(N)n4)c3c2)no1] | 4-[3-(2-aminopyrimidin-4-yl)-2-tetrahydropyran-4-yloxy-benzimidazol-5-yl]-2-(5-methylisoxazol-3-yl)but-3-yn-2-ol |
| T1.1-43 | 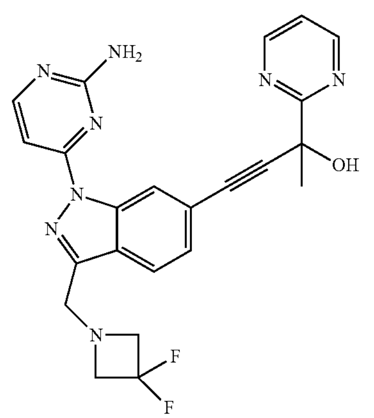 [SMILES: CC(O)(C#Cc1ccc2c(CN3CC(F)(F)C3)nn(-c3ccnc(N)n3)c2c1)c1ncccn1] | 4-[1-(2-aminopyrimidin-4-yl)-3-[(3,3-difluoroazetidin-1-yl)methyl]indazol-6-yl]-2-pyrimidin-2-yl-but-3-yn-2-ol |
| T1.1-44 | 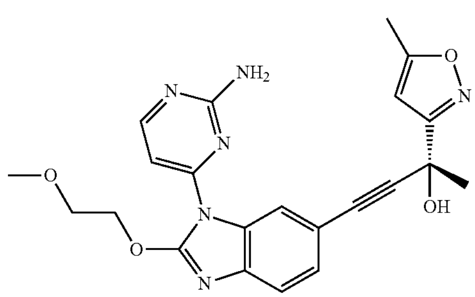 [SMILES: COCCOc1nc2ccc(C#C[C@@](C)(O)c3cc(C)on3)cc2n1-c1ccnc(N)n1] | (2R)-4-[3-(2-aminopyrimidin-4-yl)-2-(2-methoxyethoxy) benzimidazol-5-yl]-2-(5-methylisoxazol-3-yl)but-3-yn-2-ol |

TABLE 1.1-continued

| No. | Name |
|---|---|
| T1.1-45 | 4-[1-(2-aminopyrimidin-4-yl)-3-methyl-indazol-6-yl]-2-(1H-1,2,4-triazol-3-yl)but-3-yn-2-ol |
| T1.1-46 | 4-[3-(2-aminopyrimidin-4-yl)-2-(2,2,2-trifluoroethoxy)benzimidazol-5-yl]-2-pyrimidin-2-yl-but-3-yn-2-ol |
| T1.1-47 | (2R)-4-[3-(2-aminopyrimidin-4-yl)-2-(oxetan-3-yloxy)benzimidazol-5-yl]-2-(5-methyl-1,2,4-oxadiazol-3-yl)but-3-yn-2-ol |
| T1.1-48 | 4-[3-(2-aminopyrimidin-4-yl)-2-ethoxy-benzimidazol-5-yl]-2-pyrimidin-2-yl-but-3-yn-2-ol |
| T1.1-49 | 4-[1-(2-aminopyrimidin-4-yl)-3-(fluoromethyl)indazol-6-yl]-2-pyrimidin-2-yl-but-3-yn-2-ol |

TABLE 1.1-continued

| No. | Structure | Name |
|---|---|---|
| T1.1-50 | 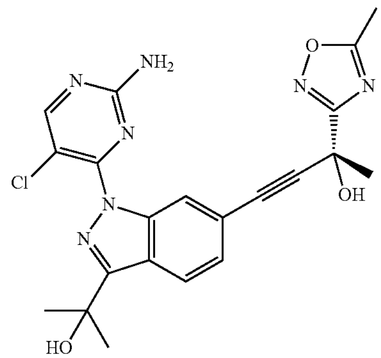 [SMILES: Cc1nc([C@](C)(O)C#Cc2ccc3c(C(C)(C)O)nn(-c4nc(N)ncc4Cl)c3c2)no1] | (2R)-4-[1-(2-amino-5-chloro-pyrimidin-4-yl)-3-(1-hydroxy-1-methyl-ethyl)indazol-6-yl]-2-(5-methyl-1,2,4-oxadiazol-3-yl)but-3-yn-2-ol |
| T1.1-51 | 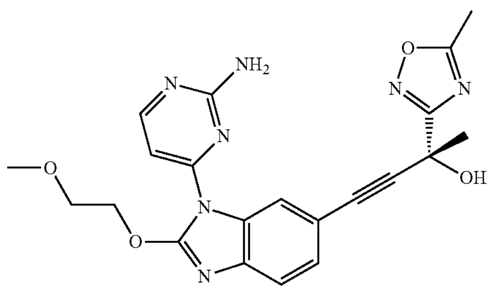 | (2R)-4-[3-(2-aminopyrimidin-4-yl)-2-(2-methoxyethoxy) benzimidazol-5-yl]-2-(5-methyl-1,2,4-oxadiazol-3-yl)but-3-yn-2-ol |
| T1.1-52 | 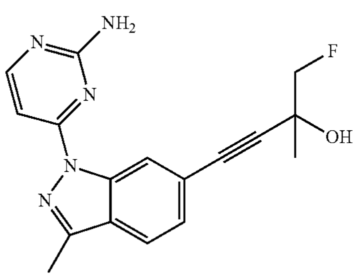 [SMILES: Cc1nn(-c2ccnc(N)n2)c2cc(C#CC(C)(O)CF)ccc12] | 4-[1-(2-aminopyrimidin-4-yl)-3-methyl-indazol-6-yl]-1-fluoro-2-methyl-but-3-yn-2-ol |
| T1.1-53 | 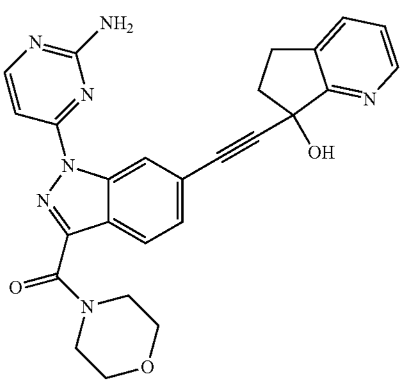 [SMILES: Nc1nccc(-n2nc(C(=O)N3CCOCC3)c3ccc(C#CC4(O)CCc5cccnc54)cc32)n1] | [1-(2-aminopyrimidin-4-yl)-6-[2-(7-hydroxy-5,6-dihydrocyclopenta[b]pyridin-7-yl)ethynyl]indazol-3-yl]-morpholino-methanone |

TABLE 1.1-continued

| No. | Structure | Name |
|---|---|---|
| T1.1-54 | 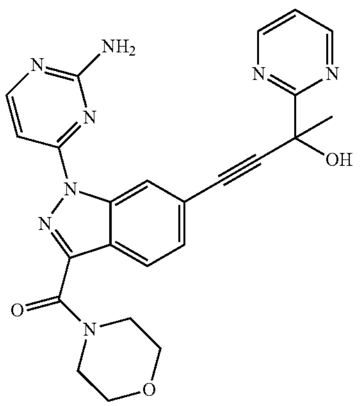 [SMILES: CC(O)(C#Cc1ccc2c(C(=O)N3CCOCC3)nn(-c3ccnc(N)n3)c2c1)c1ncccn1] | [1-(2-aminopyrimidin-4-yl)-6-(3-hydroxy-3-pyrimidin-2-yl-but-1-ynyl)indazol-3-yl]-morpholino-methanone |
| T1.1-55 | 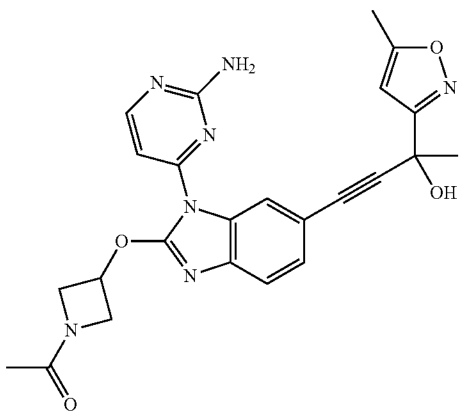 [SMILES: CC(=O)N1CC(Oc2nc3ccc(C#CC(C)(O)c4cc(C)on4)cc3n2-c2ccnc(N)n2)C1] | 1-[3-[1-(2-aminopyrimidin-4-yl)-6-[3-hydroxy-3-(5-methylisoxazol-3-yl)but-1-ynyl]benzimidazol-2-yl]oxyazetidin-1-yl]ethanone |
| T1.1-56 | 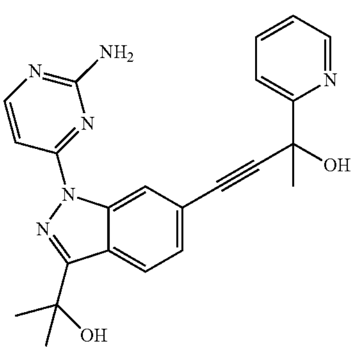 [SMILES: CC(C)(O)c1nn(-c2ccnc(N)n2)c2cc(C#CC(C)(O)c3ccccn3)ccc12] | 4-[1-(2-aminopyrimidin-4-yl)-3-(1-hydroxy-1-methyl-ethyl)indazol-6-yl]-2-(2-pyridyl)but-3-yn-2-ol |
| T1.1-57 | 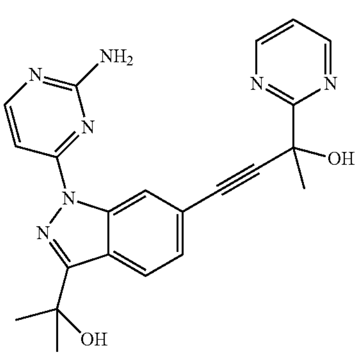 [SMILES: CC(C)(O)c1nn(-c2ccnc(N)n2)c2cc(C#CC(C)(O)c3ncccn3)ccc12] | 4-[1-(2-aminopyrimidin-4-yl)-3-(1-hydroxy-1-methyl-ethyl)indazol-6-yl]-2-pyrimidin-2-yl-but-3-yn-2-ol |

TABLE 1.1-continued

| No. | Structure | Name |
|---|---|---|
| T1.1-58 | 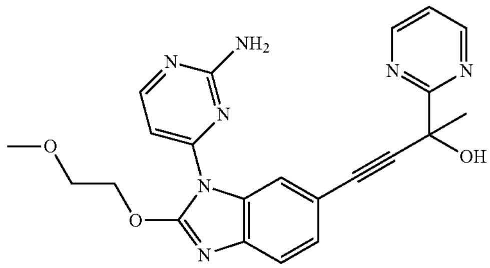 [SMILES: COCCOc1nc2ccc(C#CC(C)(O)c3ncccn3)cc2n1-c1ccnc(N)n1] | 4-[3-(2-aminopyrimidin-4-yl)-2-(2-methoxyethoxy)benzimidazol-5-yl]-2-pyrimidin-2-yl-but-3-yn-2-ol |
| T1.1-59 | 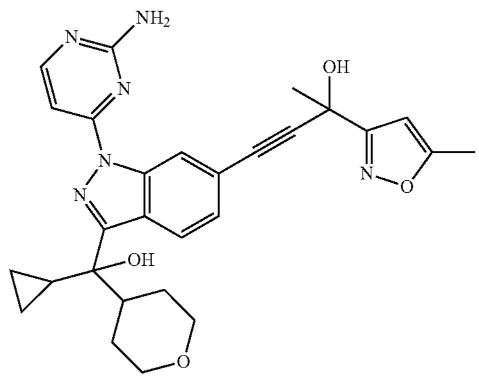 [SMILES: Cc1cc(C(C)(O)C#Cc2ccc3c(C(O)(C4CCOCC4)C4CC4)nn(-c4ccnc(N)n4)c3c2)no1] | 4-[1-(2-aminopyrimidin-4-yl)-3-(cyclopropyl-hydroxy-tetrahydropyran-4-yl-methyl)indazol-6-yl]-2-(5-methyl-isoxazol-3-yl)but-3-yn-2-ol |
| T1.1-60 | 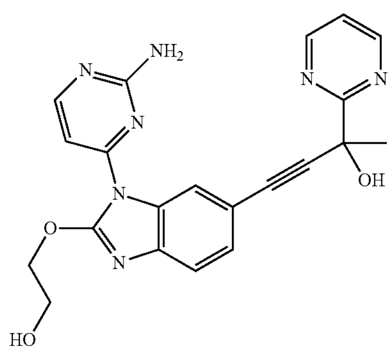 [SMILES: CC(O)(C#Cc1ccc2nc(OCCO)n(-c3ccnc(N)n3)c2c1)c1ncccn1] | 4-[3-(2-aminopyrimidin-4-yl)-2-(2-hydroxyethoxy)benzimidazol-5-yl]-2-pyrimidin-2-yl-but-3-yn-2-ol |
| T1.1-61 | 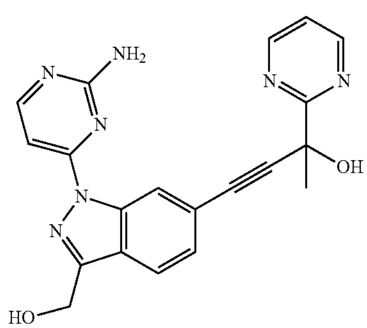 [SMILES: CC(O)(C#Cc1ccc2c(CO)nn(-c3ccnc(N)n3)c2c1)c1ncccn1] | 4-[1-(2-aminopyrimidin-4-yl)-3-(hydroxymethyl)indazol-6-yl]-2-pyrimidin-2-yl-but-3-yn-2-ol |
| T1.1-62 | 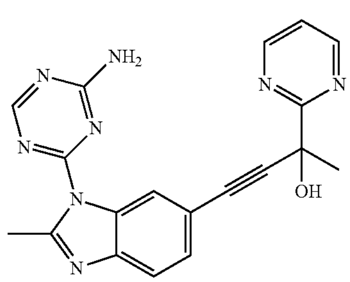 [SMILES: Cc1nc2ccc(C#CC(C)(O)c3ncccn3)cc2n1-c1ncnc(N)n1] | 4-[3-(4-amino-1,3,5-triazin-2-yl)-2-methyl-benzimidazol-5-yl]-2-pyrimidin-2-yl-but-3-yn-2-ol |

TABLE 1.1-continued

| No. | Structure | Name |
|---|---|---|
| T1.1-63 | 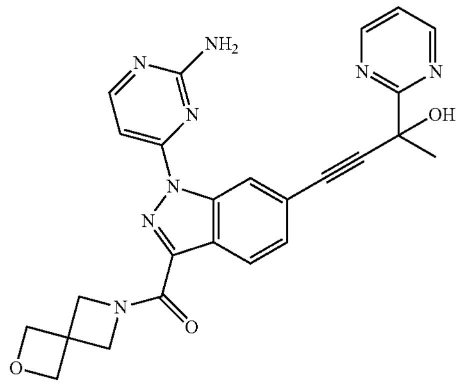 [SMILES: CC(O)(C#Cc1ccc2c(C(=O)N3CC4(COC4)C3)nn(-c3ccnc(N)n3)c2c1)c1ncccn1] | [1-(2-aminopyrimidin-4-yl)-6-(3-hydroxy-3-pyrimidin-2-yl-but-1-ynyl)indazol-3-yl]-(2-oxa-6-azaspiro[3.3]heptan-6-yl)methanone |
| T1.1-64 | 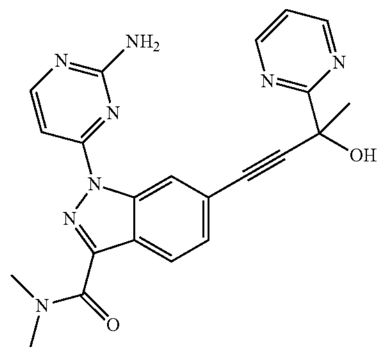 [SMILES: CN(C)C(=O)c1nn(-c2ccnc(N)n2)c2cc(C#CC(C)(O)c3ncccn3)ccc12] | 1-(2-aminopyrimidin-4-yl)-6-(3-hydroxy-3-pyrimidin-2-yl-but-1-ynyl)-N,N-dimethyl-indazole-3-carboxamide |
| T1.1-65 | 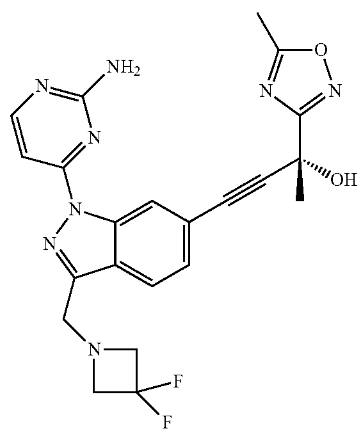 [SMILES: Cc1nc([C@](C)(O)C#Cc2ccc3c(CN4CC(F)(F)C4)nn(-c4ccnc(N)n4)c3c2)no1] | (2R)-4-[1-(2-aminopyrimidin-4-yl)-3-[(3,3-difluoroazetidin-1-yl)methyl]indazol-6-yl]-2-(5-methyl-1,2,4-oxadiazol-3-yl)but-3-yn-2-ol |
| T1.1-66 | 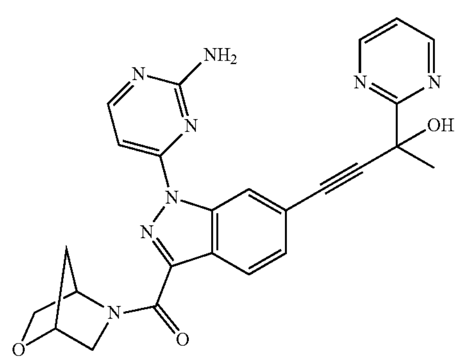 [SMILES: CC(O)(C#Cc1ccc2c(C(=O)N3CC4CC3CO4)nn(-c3ccnc(N)n3)c2c1)c1ncccn1] | [1-(2-aminopyrimidin-4-yl)-6-(3-hydroxy-3-pyrimidin-2-yl-but-1-ynyl)indazol-3-yl]-(2-oxa-5-azabicyclo[2.2.1]heptan-5-yl)methanone |

TABLE 1.1-continued

| No. | Structure | Name |
|---|---|---|
| T1.1-67 | 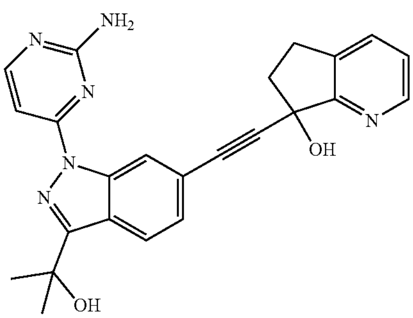 [SMILES: CC(C)(O)c1nn(-c2ccnc(N)n2)c2cc(C#CC3(O)CCc4cccnc43)ccc12] | 7-[2-[1-(2-aminopyrimidin-4-yl)-3-(1-hydroxy-1-methyl-ethyl)indazol-6-yl]ethynyl]-5,6-dihydrocyclopenta[b]pyridin-7-ol |
| T1.1-68 | 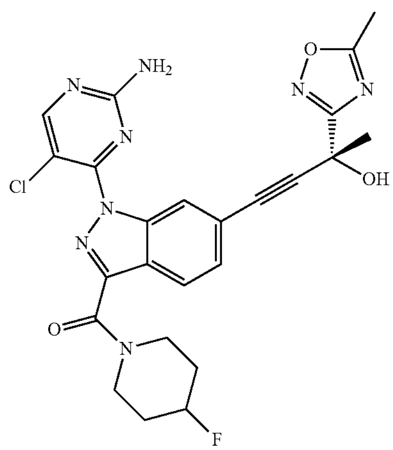 [SMILES: Cc1nc([C@](C)(O)C#Cc2ccc3c(C(=O)N4CCC(F)CC4)nn(-c4nc(N)ncc4Cl)c3c2)no1] | [1-(2-amino-5-chloro-pyrimidin-4-yl)-6-[(3R)-3-hydroxy-3-(5-methyl-1,2,4-oxadiazol-3-yl)but-1-ynyl]indazol-3-yl]-(4-fluoro-1-piperidyl)methanone |
| T1.1-69 | 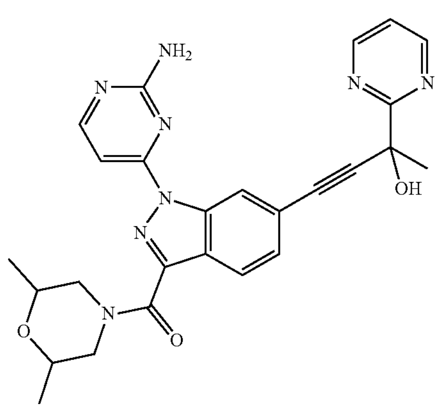 [SMILES: CC1CN(C(=O)c2nn(-c3ccnc(N)n3)c3cc(C#CC(C)(O)c4ncccn4)ccc23)CC(C)O1] | [1-(2-aminopyrimidin-4-yl)-6-(3-hydroxy-3-pyrimidin-2-yl-but-1-ynyl)indazol-3-yl]-(2,6-dimethylmorpholin-4-yl)methanone |

| No. | Structure | Name |
| --- | --- | --- |
| T1.1-70 | 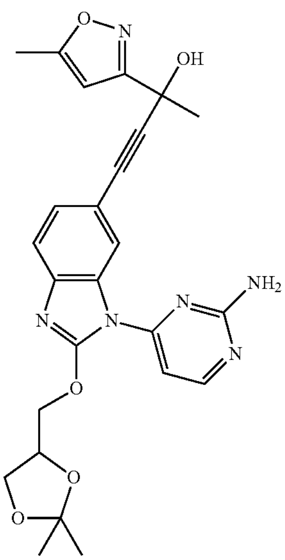 [SMILES: Cc1cc(C(C)(O)C#Cc2ccc3nc(OCC4COC(C)(C)O4)n(-c4ccnc(N)n4)c3c2)no1] | 4-[3-(2-aminopyrimidin-4-yl)-2-[(2,2-dimethyl-1,3-dioxolan-4-yl)methoxy]benzimidazol-5-yl]-2-(5-methylisoxazol-3-yl)but-3-yn-2-ol |
| T1.1-71 | 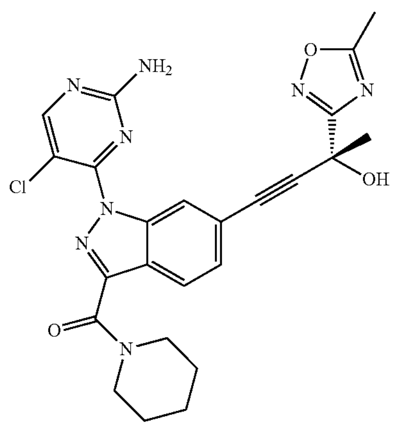 [SMILES: Cc1nc([C@](C)(O)C#Cc2ccc3c(C(=O)N4CCCCC4)nn(-c4nc(N)ncc4Cl)c3c2)no1] | [1-(2-amino-5-chloro-pyrimidin-4-yl)-6-[(3R)-3-hydroxy-3-(5-methyl-1,2,4-oxadiazol-3-yl)but-1-ynyl]indazol-3-yl]-(1-piperidyl)methanone |
| T1.1-72 | 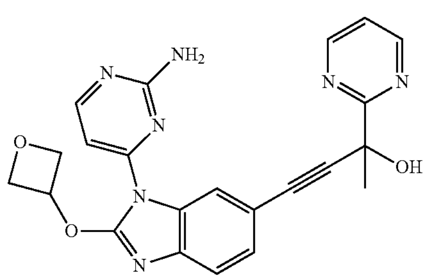 [SMILES: CC(O)(C#Cc1ccc2nc(OC3COC3)n(-c3ccnc(N)n3)c2c1)c1ncccn1] | 4-[3-(2-aminopyrimidin-4-yl)-2-(oxetan-3-yloxy)benzimidazol-5-yl]-2-pyrimidin-2-yl-but-3-yn-2-ol |
| T1.1-73 | 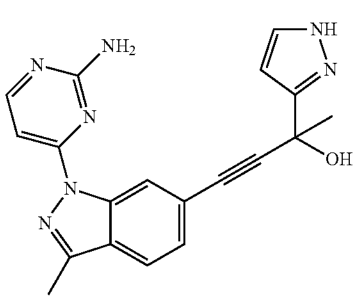 [SMILES: Cc1nn(-c2ccnc(N)n2)c2cc(C#CC(C)(O)c3cc[nH]n3)ccc12] | 4-[1-(2-aminopyrimidin-4-yl)-3-methyl-indazol-6-yl]-2-(1H-pyrazol-3-yl)but-3-yn-2-ol |

TABLE 1.1-continued

| No. | Structure | Name |
|---|---|---|
| T1.1-74 | 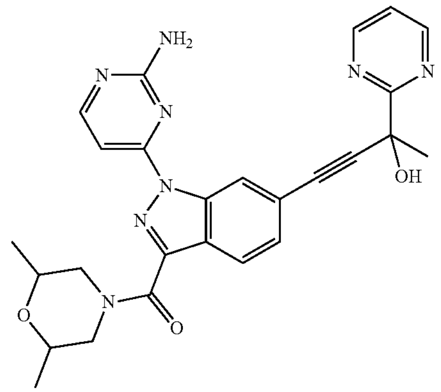 [SMILES: CC1CN(C(=O)c2nn(-c3ccnc(N)n3)c3cc(C#CC(C)(O)c4ncccn4)ccc23)CC(C)O1] | [1-(2-aminopyrimidin-4-yl)-6-(3-hydroxy-3-pyrimidin-2-yl-but-1-ynyl)indazol-3-yl]-(2,6-dimethylmorpholin-4-yl) methanone |
| T1.1-75 | 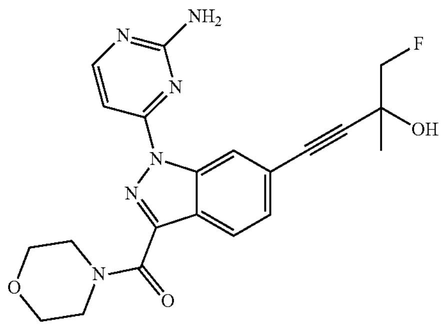 [SMILES: CC(O)(C#Cc1ccc2c(C(=O)N3CCOCC3)nn(-c3ccnc(N)n3)c2c1)CF] | [1-(2-aminopyrimidin-4-yl)-6-(4-fluoro-3-hydroxy-3-methyl-but-1-ynyl)indazol-3-yl]-morpholino-methanone |
| T1.1-76 | 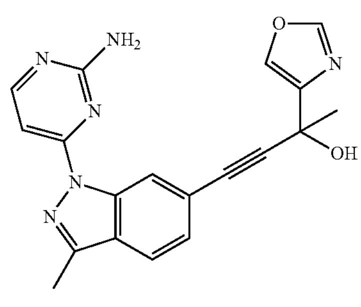 [SMILES: Cc1nn(-c2ccnc(N)n2)c2cc(C#CC(C)(O)c3cocn3)ccc12] | 4-[1-(2-aminopyrimidin-4-yl)-3-methyl-indazol-6-yl]-2-oxazol-4-yl-but-3-yn-2-ol |
| T1.1-78 | 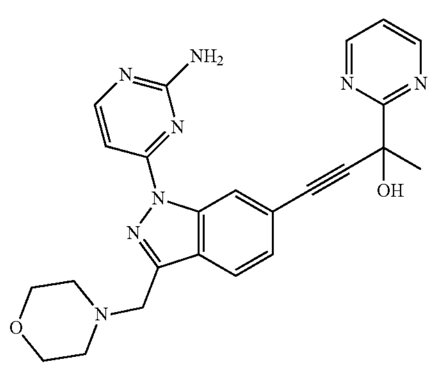 [SMILES: CC(O)(C#Cc1ccc2c(CN3CCOCC3)nn(-c3ccnc(N)n3)c2c1)c1ncccn1] | 4-[1-(2-aminopyrimidin-4-yl)-3-(morpholinomethyl)indazol-6-yl]-2-pyrimidin-2-yl-but-3-yn-2-ol |

TABLE 1.1-continued

| No. | Structure | Name |
|---|---|---|
| T1.1-79 | 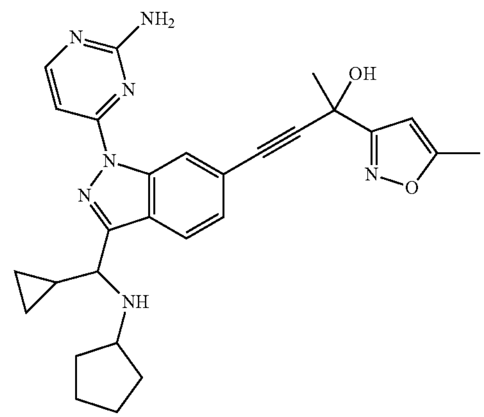 [SMILES: Cc1cc(C(C)(O)C#Cc2ccc3c(C(NC4CCCC4)C4CC4)nn(-c4ccnc(N)n4)c3c2)no1] | 4-[1-(2-aminopyrimidin-4-yl)-3-[(cyclopentylamino)-cyclopropyl-methyl]indazol-6-yl]-2-(5-methyl-isoxazol-3-yl)but-3-yn-2-ol |
| T1.1-80 | 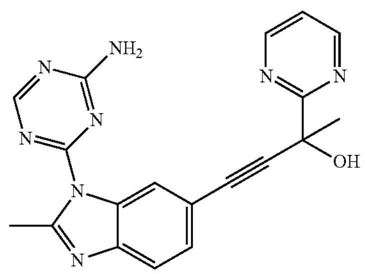 [SMILES: Cc1nc2ccc(C#CC(C)(O)c3ncccn3)cc2n1-c1ncnc(N)n1] | 4-[3-(4-amino-1,3,5-triazin-2-yl)-2-methyl-benzimidazol-5-yl]-2-pyrazin-2-yl-but-3-yn-2-ol |
| T1.1-81 | 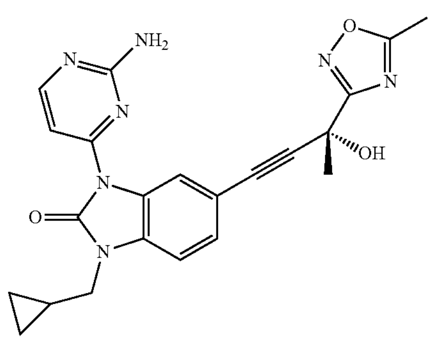 [SMILES: Cc1nc([C@](C)(O)C#Cc2ccc3c(c2)n(-c2ccnc(N)n2)c(=O)n3CC2CC2)no1] | 3-(2-aminopyrimidin-4-yl)-1-(cyclopropylmethyl)-5-[(3R)-3-hydroxy-3-(5-methyl-1,2,4-oxadiazol-3-yl)but-1-ynyl] benzimidazol-2-one |
| T1.1-82 | 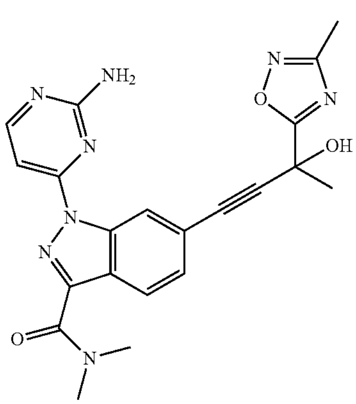 [SMILES: Cc1noc(C(C)(O)C#Cc2ccc3c(C(=O)N(C)C)nn(-c4ccnc(N)n4)c3c2)n1] | 1-(2-aminopyrimidin-4-yl)-6-[3-hydroxy-3-(3-methyl-1,2,4-oxadiazol-5-yl)but-1-ynyl]-N,N-dimethyl-indazole-3-carboxamide |

TABLE 1.1-continued

| No. | Structure | Name |
|---|---|---|
| T1.1-83 | 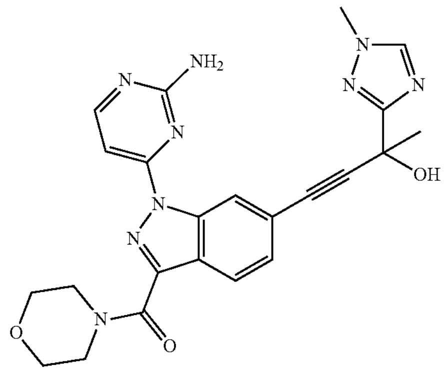 [SMILES: Cn1cnc(C(C)(O)C#Cc2ccc3c(C(=O)N4CCOCC4)nn(-c4ccnc(N)n4)c3c2)n1] | [1-(2-aminopyrimidin-4-yl)-6-[3-hydroxy-3-(1-methyl-1,2,4-triazol-3-yl)but-1-ynyl]indazol-3-yl]-morpholino-methanone |
| T1.1-84 | 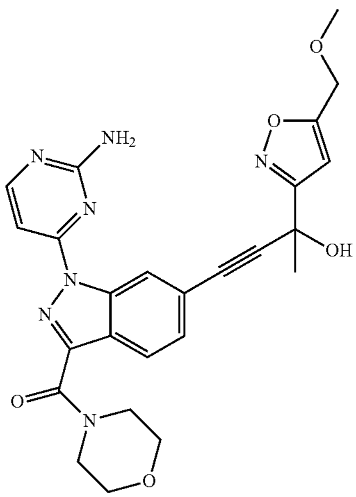 [SMILES: COCc1cc(C(C)(O)C#Cc2ccc3c(C(=O)N4CCOCC4)nn(-c4ccnc(N)n4)c3c2)no1] | [1-(2-aminopyrimidin-4-yl)-6-[3-hydroxy-3-[5-(methoxy methyl)isoxazol-3-yl]but-1-ynyl]indazol-3-yl]-morpholino-methanone |
| T1.1-85 | 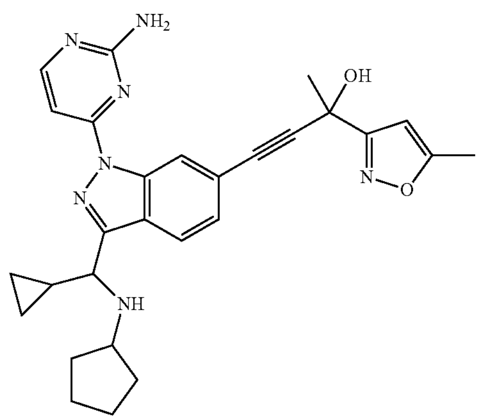 [SMILES: Cc1cc(C(C)(O)C#Cc2ccc3c(C(NC4CCCC4)C4CC4)nn(-c4ccnc(N)n4)c3c2)no1] | 4-[1-(2-aminopyrimidin-4-yl)-3-[(cyclopentylamino)-cyclopropyl-methyl]indazol-6-yl]-2-(5-methyl-isoxazol-3-yl)but-3-yn-2-ol |
| T1.1-86 | 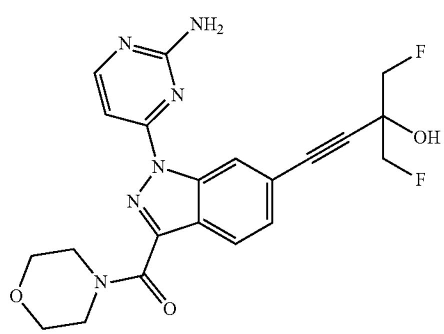 [SMILES: Nc1nccc(-n2nc(C(=O)N3CCOCC3)c3ccc(C#CC(O)(CF)CF)cc32)n1] | [1-(2-aminopyrimidin-4-yl)-6-[4-fluoro-3-(fluoromethyl)-3-hydroxy-but-1-ynyl]indazol-3-yl]-morpholino-methanone |

TABLE 1.1-continued

| No. | Structure | Name |
|---|---|---|
| T1.1-87 | 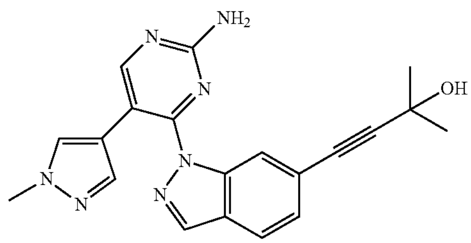 [SMILES: Cn1cc(-c2cnc(N)nc2-n2ncc3ccc(C#CC(C)(C)O)cc32)cn1] | 4-[1-[2-amino-5-(1-methyl-pyrazol-4-yl)pyrimidin-4-yl]indazol-6-yl]-2-methyl-but-3-yn-2-ol |
| T1.1-88 | 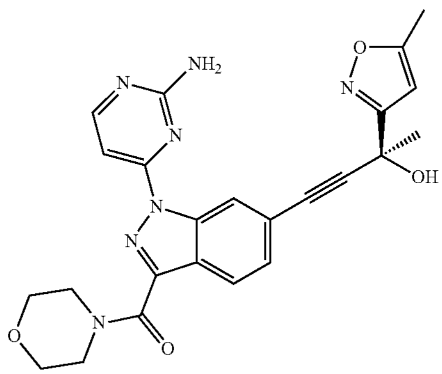 [SMILES: Cc1cc([C@@](C)(O)C#Cc2ccc3c(C(=O)N4CCOCC4)nn(-c4ccnc(N)n4)c3c2)no1] | [1-(2-aminopyrimidin-4-yl)-6-[(3S)-3-hydroxy-3-(5-methylisoxazol-3-yl)but-1-ynyl]indazol-3-yl]-morpholino-methanone |
| T1.1-89 | 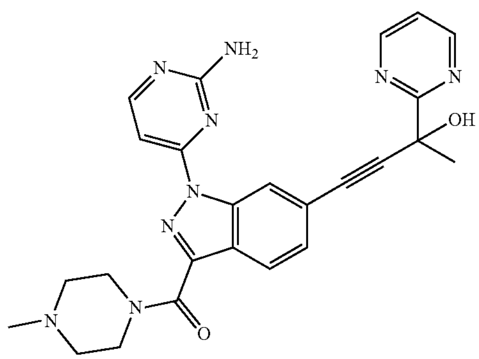 [SMILES: CN1CCN(C(=O)c2nn(-c3ccnc(N)n3)c3cc(C#CC(C)(O)c4ncccn4)ccc23)CC1] | [1-(2-aminopyrimidin-4-yl)-6-(3-hydroxy-3-pyrimidin-2-yl-but-1-ynyl)indazol-3-yl]-(4-methylpiperazin-1-yl)methanone |
| T1.1-90 | 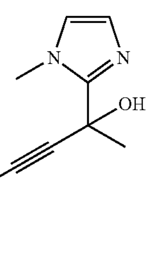 | 4-[1-(2-aminopyrimidin-4-yl)-3-methyl-indazol-6-yl]-2-(1-methyl-imidazol-2-yl)but-3-yn-2-ol |
| T1.1-91 | 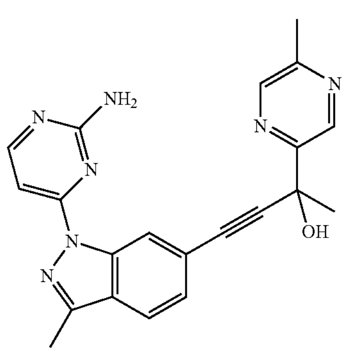 [SMILES: Cc1cnc(C(C)(O)C#Cc2ccc3c(C)nn(-c4ccnc(N)n4)c3c2)cn1] | 4-[1-(2-aminopyrimidin-4-yl)-3-methyl-indazol-6-yl]-2-(5-methyl-pyrazin-2-yl)but-3-yn-2-ol |

TABLE 1.1-continued

| No. | Structure | Name |
|---|---|---|
| T1.1-92 | 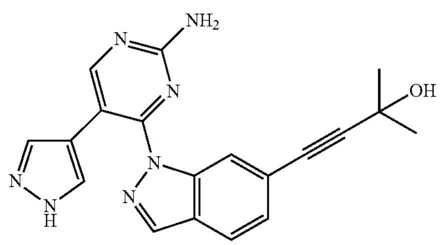 [SMILES: CC(C)(O)C#Cc1ccc2cnn(-c3nc(N)ncc3-c3cn[nH]c3)c2c1] | 4-[1-[2-amino-5-(1H-pyrazol-4-yl)pyrimidin-4-yl]indazol-6-yl]-2-methyl-but-3-yn-2-ol |
| T1.1-93 | 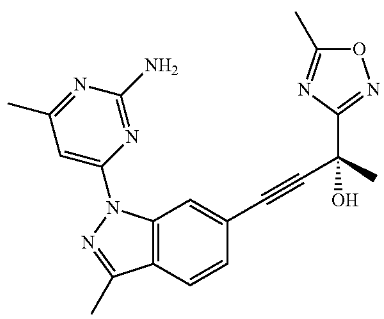 [SMILES: Cc1cc(-n2nc(C)c3ccc(C#C[C@@](C)(O)c4noc(C)n4)cc32)nc(N)n1] | (2R)-4-[1-(2-amino-6-methyl-pyrimidin-4-yl)-3-methyl-indazol-6-yl]-2-(5-methyl-1,2,4-oxadiazol-3-yl)but-3-yn-2-ol |
| T1.1-94 | 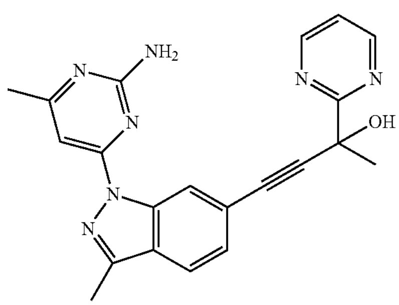 [SMILES: Cc1cc(-n2nc(C)c3ccc(C#CC(C)(O)c4ncccn4)cc32)nc(N)n1] | 4-[1-(2-amino-6-methyl-pyrimidin-4-yl)-3-methyl-indazol-6-yl]-2-pyrimidin-2-yl-but-3-yn-2-ol |
| T1.1-95 | 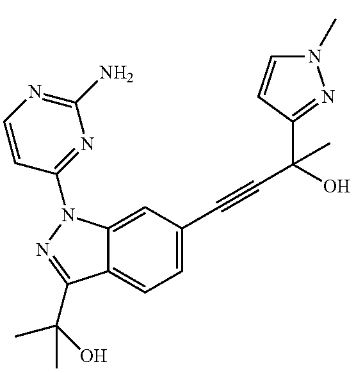 [SMILES: Cn1ccc(C(C)(O)C#Cc2ccc3c(C(C)(C)O)nn(-c4ccnc(N)n4)c3c2)n1] | 4-[1-(2-aminopyrimidin-4-yl)-3-(1-hydroxy-1-methyl-ethyl)indazol-6-yl]-2-(1-methyl pyrazol-3-yl)but-3-yn-2-ol |
| T1.1-96 | 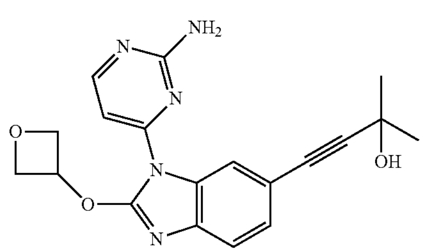 [SMILES: CC(C)(O)C#Cc1ccc2nc(OC3COC3)n(-c3ccnc(N)n3)c2c1] | 4-[3-(2-aminopyrimidin-4-yl)-2-(oxetan-3-yloxy)benzimidazol-5-yl]-2-methyl-but-3-yn-2-ol |

TABLE 1.1-continued

| No. | Structure | Name |
|---|---|---|
| T1.1-97 | 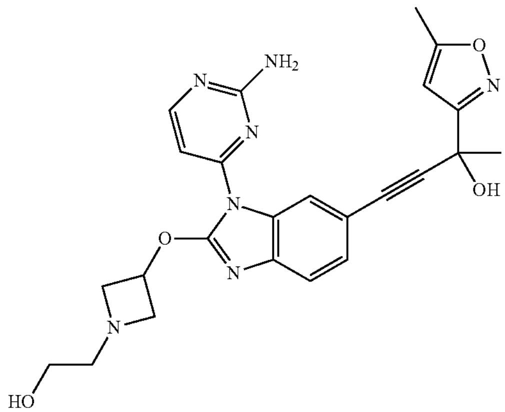 [SMILES: Cc1cc(C(C)(O)C#Cc2ccc3nc(OC4CN(CCO)C4)n(-c4ccnc(N)n4)c3c2)no1] | 4-[3-(2-aminopyrimidin-4-yl)-2-[1-(2-hydroxyethyl)azetidin-3-yl]oxy-benzimidazol-5-yl]-2-(5-methyl-isoxazol-3-yl)but-3-yn-2-ol |
| T1.1-98 | 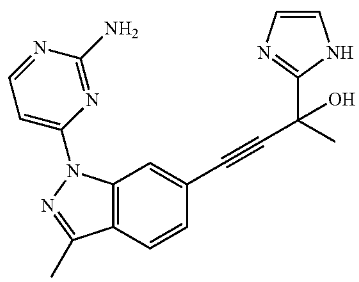 [SMILES: Cc1nn(-c2ccnc(N)n2)c2cc(C#CC(C)(O)c3ncc[nH]3)ccc12] | 4-[1-(2-aminopyrimidin-4-yl)-3-methyl-indazol-6-yl]-2-(1H-imidazol-2-yl)but-3-yn-2-ol |
| T1.1-99 | 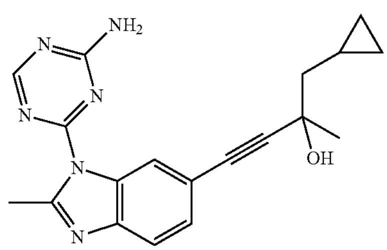 [SMILES: Cc1nc2ccc(C#CC(C)(O)CC3CC3)cc2n1-c1ncnc(N)n1] | 4-[3-(4-amino-1,3,5-triazin-2-yl)-2-methyl-benzimidazol-5-yl]-1-cyclopropyl-2-methyl-but-3-yn-2-ol |
| T1.1-100 | 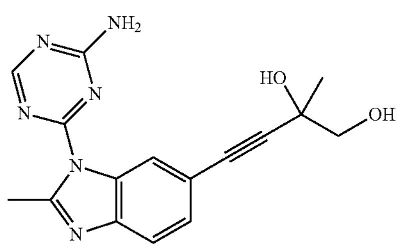 [SMILES: Cc1nc2ccc(C#CC(C)(O)CO)cc2n1-c1ncnc(N)n1] | 4-[3-(4-amino-1,3,5-triazin-2-yl)-2-methyl-benzimidazol-5-yl]-2-methyl-but-3-yne-1,2-diol |
| T1.1-101 | 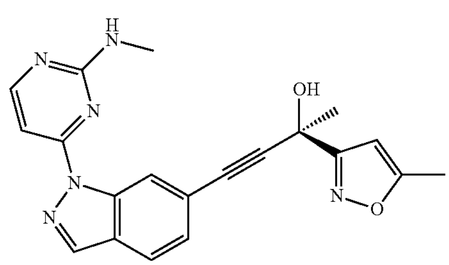 [SMILES: CNc1nccc(-n2ncc3ccc(C#C[C@@](C)(O)c4cc(C)on4)cc32)n1] | (2R)-4-[1-[2-(methylamino)pyrimidin-4-yl]indazol-6-yl]-2-(5-methylisoxazol-3-yl)but-3-yn-2-ol |

TABLE 1.1-continued

| No. | Name |
|---|---|
| T1.1-102 | 4-[1-(2-aminopyrimidin-4-yl)-3-methyl-indazol-6-yl]-2-hydroxy-1-(3-hydroxyazetidin-1-yl)-2-methyl-but-3-yn-1-one |
| T1.1-103 | 4-[1-(2-aminopyrimidin-4-yl)-3-methyl-indazol-6-yl]-2-hydroxy-N,N,2-trimethyl-but-3-ynamide |
| T1.1-104 | [1-(2-aminopyrimidin-4-yl)-6-[3-hydroxy-3-(5-methylisoxazol-3-yl)but-1-ynyl]benzimidazol-2-yl]-pyrrolidin-1-yl-methanone |
| T1.1-105 | [1-(2-aminopyrimidin-4-yl)-6-[3-hydroxy-3-(5-methyl-1,2,4-oxadiazol-3-yl)but-1-ynyl]indazol-3-yl]-morpholino-methanone |
| T1.1-106 | 1-[2-[3-(4-amino-1,3,5-triazin-2-yl)-2-methyl-benzimidazol-5-yl]ethynyl]cyclohexanol |

TABLE 1.1-continued

| No. | Structure | Name |
|---|---|---|
| T1.1-107 | 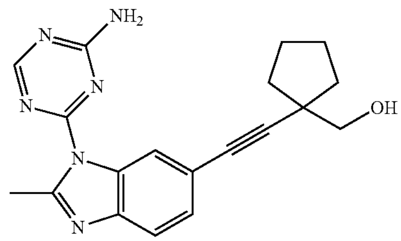 [SMILES: Cc1nc2ccc(C#CC3(CO)CCCC3)cc2n1-c1ncnc(N)n1] | [1-[2-[3-(4-amino-1,3,5-triazin-2-yl)-2-methyl-benzimidazol-5-yl]ethynyl]cyclopentyl]methanol |
| T1.1-108 | 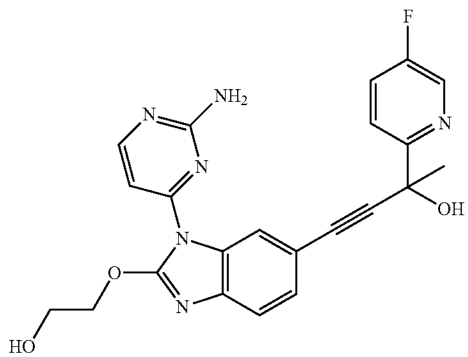 [SMILES: CC(O)(C#Cc1ccc2nc(OCCO)n(-c3ccnc(N)n3)c2c1)c1ccc(F)cn1] | 4-[3-(2-aminopyrimidin-4-yl)-2-(2-hydroxyethoxy)benzimidazol-5-yl]-2-(5-fluoro-2-pyridyl)but-3-yn-2-ol |
| T1.1-109 | 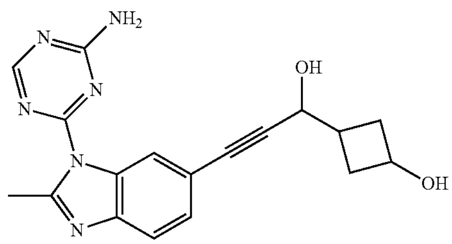 [SMILES: Cc1nc2ccc(C#CC(O)C3CC(O)C3)cc2n1-c1ncnc(N)n1] | 3-[3-[3-(4-amino-1,3,5-triazin-2-yl)-2-methyl-benzimidazol-5-yl]-1-hydroxy-prop-2-ynyl]cyclobutanol |
| T1.1-110 | 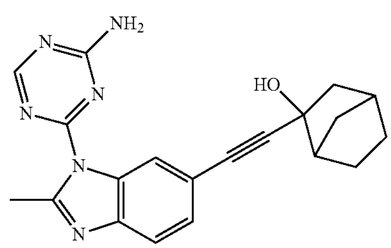 [SMILES: Cc1nc2ccc(C#CC3(O)CC4CCC3C4)cc2n1-c1ncnc(N)n1] | 2-[2-[3-(4-amino-1,3,5-triazin-2-yl)-2-methyl-benzimidazol-5-yl]ethynyl]norbornan-2-ol |
| T1.1-111 | 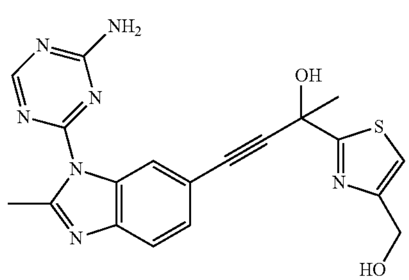 [SMILES: Cc1nc2ccc(C#CC(C)(O)c3nc(CO)cs3)cc2n1-c1ncnc(N)n1] | 4-[3-(4-amino-1,3,5-triazin-2-yl)-2-methyl-benzimidazol-5-yl]-2-[4-(hydroxymethyl)thiazol-2-yl]but-3-yn-2-ol |
| T1.1-112 | 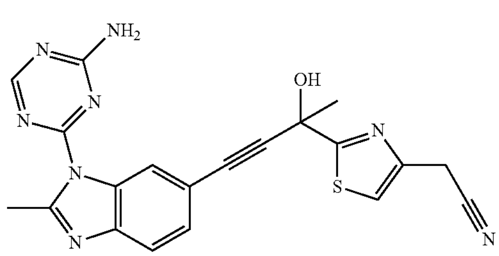 [SMILES: Cc1nc2ccc(C#CC(C)(O)c3nc(CC#N)cs3)cc2n1-c1ncnc(N)n1] | 2-[2-[3-[3-(4-amino-1,3,5-triazin-2-yl)-2-methyl-benzimidazol-5-yl]-1-hydroxy-1-methyl-prop-2-ynyl]thiazol-4-yl]acetonitrile |

TABLE 1.1-continued

| No. | Structure | Name |
|---|---|---|
| T1.1-113 | 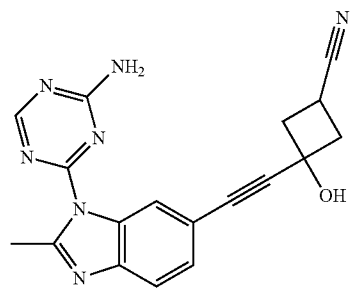 [SMILES: Cc1nc2ccc(C#CC3(O)CC(C#N)C3)cc2n1-c1ncnc(N)n1] | 3-[2-[3-(4-amino-1,3,5-triazin-2-yl)-2-methyl-benzimidazol-5-yl]ethynyl]-3-hydroxy-cyclobutanecarbonitrile |
| T1.1-114 | 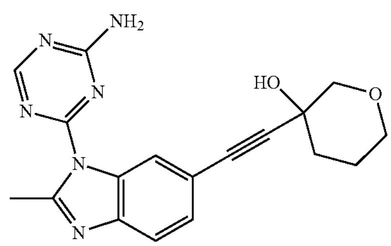 [SMILES: Cc1nc2ccc(C#CC3(O)CCCOC3)cc2n1-c1ncnc(N)n1] | 3-[2-[3-(4-amino-1,3,5-triazin-2-yl)-2-methyl-benzimidazol-5-yl]ethynyl] tetrahydropyran-3-ol |
| T1.1-115 | 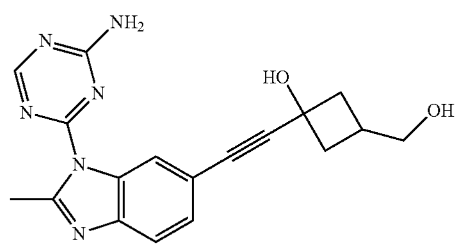 [SMILES: Cc1nc2ccc(C#CC3(O)CC(CO)C3)cc2n1-c1ncnc(N)n1] | 1-[2-[3-(4-amino-1,3,5-triazin-2-yl)-2-methyl-benzimidazol-5-yl]ethynyl]-3-(hydroxy methyl)cyclobutanol |
| T1.1-116 | 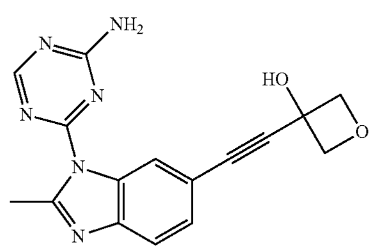 [SMILES: Cc1nc2ccc(C#CC3(O)COC3)cc2n1-c1ncnc(N)n1] | 3-[2-[3-(4-amino-1,3,5-triazin-2-yl)-2-methyl-benzimidazol-5-yl]ethynyl] oxetan-3-ol |
| T1.1-117 | 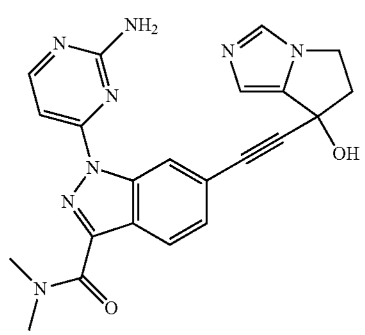 [SMILES: CN(C)C(=O)c1nn(-c2ccnc(N)n2)c2cc(C#CC3(O)CCn4cncc43)ccc12] | 1-(2-aminopyrimidin-4-yl)-6-[2-(7-hydroxy-5,6-dihydropyrrolo[1,2-c]imidazol-7-yl)ethynyl]-N,N-dimethyl-indazole-3-carboxamide |
| T1.1-118 | 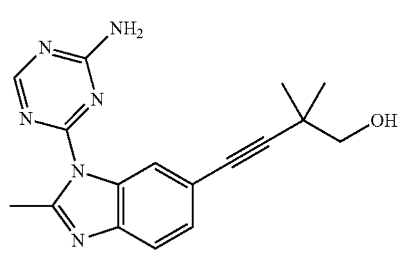 [SMILES: Cc1nc2ccc(C#CC(C)(C)CO)cc2n1-c1ncnc(N)n1] | 4-[3-(4-amino-1,3,5-triazin-2-yl)-2-methyl-benzimidazol-5-yl]-2,2-dimethyl-but-3-yn-1-ol |

| No. | Structure | Name |
|---|---|---|
| T1.1-119 | 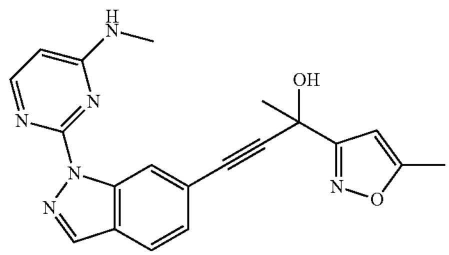 [SMILES: CNc1ccnc(-n2ncc3ccc(C#CC(C)(O)c4cc(C)on4)cc32)n1] | 4-[1-[4-(methylamino)pyrimidin-2-yl]indazol-6-yl]-2-(5-methyl-isoxazol-3-yl)but-3-yn-2-ol |
| T1.1-120 | 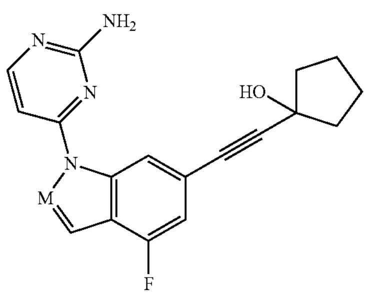 | 1-[2-[1-(2-aminopyrimidin-4-yl)-4-fluoro-indazol-6-yl]ethynyl]cyclopentanol |
| T1.1-121 | 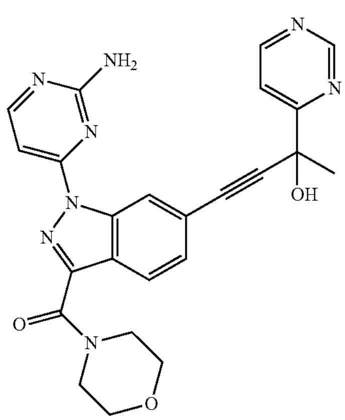 [SMILES: CC(O)(C#Cc1ccc2c(C(=O)N3CCOCC3)nn(-c3ccnc(N)n3)c2c1)c1ccncn1] | [1-(2-aminopyrimidin-4-yl)-6-(3-hydroxy-3-pyrimidin-4-yl-but-1-ynyl)indazol-3-yl]-morpholino-methanone |
| T1.1-122 | 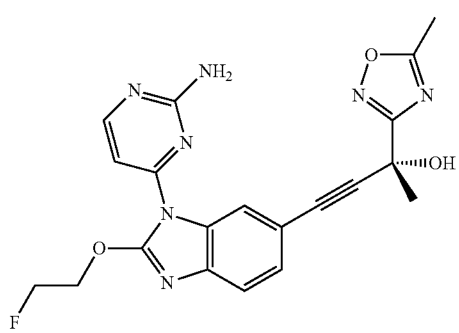 [SMILES: Cc1nc([C@](C)(O)C#Cc2ccc3nc(OCCF)n(-c4ccnc(N)n4)c3c2)no1] | (2R)-4-[3-(2-aminopyrimidin-4-yl)-2-(2-fluoroethoxy)benzimidazol-5-yl]-2-(5-methyl-1,2,4-oxadiazol-3-yl)but-3-yn-2-ol |

TABLE 1.1-continued

| No. | Structure | Name |
|---|---|---|
| T1.1-123 | 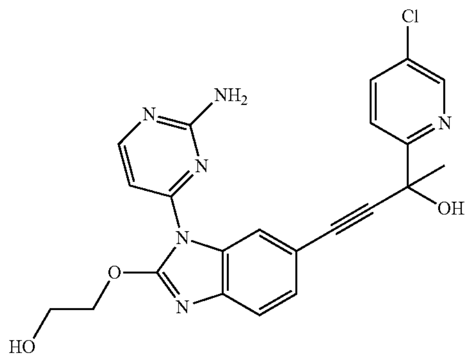 [SMILES: CC(O)(C#Cc1ccc2nc(OCCO)n(-c3ccnc(N)n3)c2c1)c1ccc(Cl)cn1] | 4-[3-(2-aminopyrimidin-4-yl)-2-(2-hydroxyethoxy)benzimidazol-5-yl]-2-(5-chloro-2-pyridyl)but-3-yn-2-ol |
| T1.1-124 | 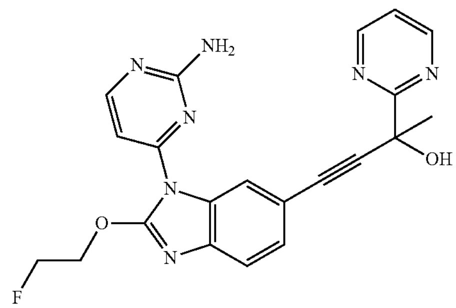 [SMILES: CC(O)(C#Cc1ccc2nc(OCCF)n(-c3ccnc(N)n3)c2c1)c1ncccn1] | 4-[3-(2-aminopyrimidin-4-yl)-2-(2-fluoroethoxy)benzimidazol-5-yl]-2-pyrimidin-2-yl-but-3-yn-2-ol |
| T1.1-125 | 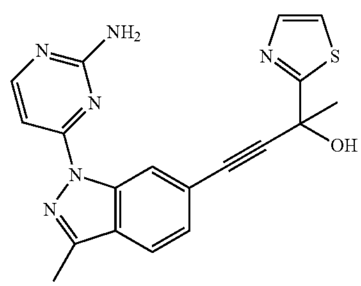 [SMILES: Cc1nn(-c2ccnc(N)n2)c2cc(C#CC(C)(O)c3nccs3)ccc12] | 4-[1-(2-aminopyrimidin-4-yl)-3-methyl-indazol-6-yl]-2-thiazol-2-yl-but-3-yn-2-ol |
| T1.1-126 | 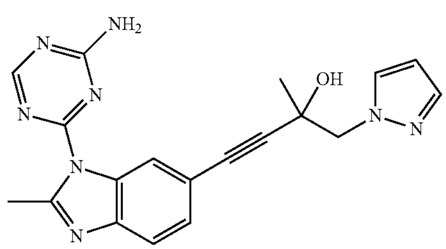 [SMILES: Cc1nc2ccc(C#CC(C)(O)Cn3cccn3)cc2n1-c1ncnc(N)n1] | 4-[3-(4-amino-1,3,5-triazin-2-yl)-2-methyl-benzimidazol-5-yl]-2-methyl-1-pyrazol-1-yl-but-3-yn-2-ol |
| T1.1-127 | 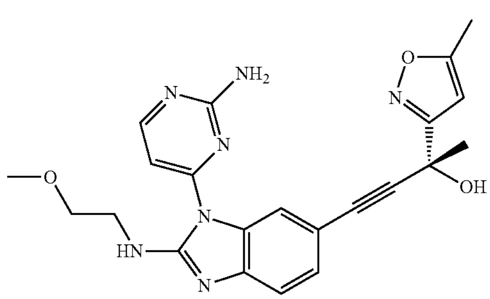 | (2R)-4-[3-(2-aminopyrimidin-4-yl)-2-(2-methoxyethylamino)benzimidazol-5-yl]-2-(5-methylisoxazol-3-yl)but-3-yn-2-ol |

| No. | Structure | Name |
| --- | --- | --- |
| T1.1-128 | 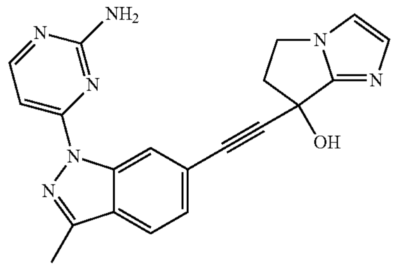 [SMILES: Cc1nn(-c2ccnc(N)n2)c2cc(C#CC3(O)CCn4ccnc43)ccc12] | 7-[2-[1-(2-aminopyrimidin-4-yl)-3-methyl-indazol-6-yl]ethynyl]-5,6-dihydropyrrolo[1,2-a]imidazol-7-ol |
| T1.1-129 | 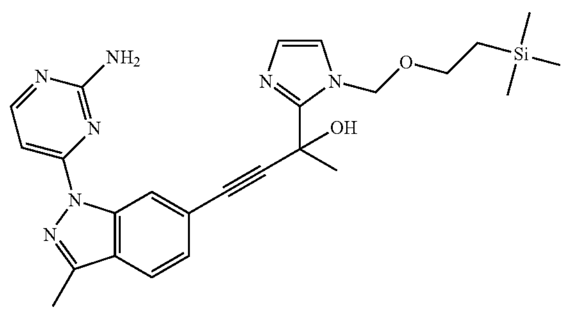 [SMILES: Cc1nn(-c2ccnc(N)n2)c2cc(C#CC(C)(O)c3nccn3COCC[Si](C)(C)C)ccc12] | 4-[1-(2-aminopyrimidin-4-yl)-3-methyl-indazol-6-yl]-2-[1-(2-trimethylsilyl-ethoxymethyl)imidazol-2-yl]but-3-yn-2-ol |
| T1.1-130 | 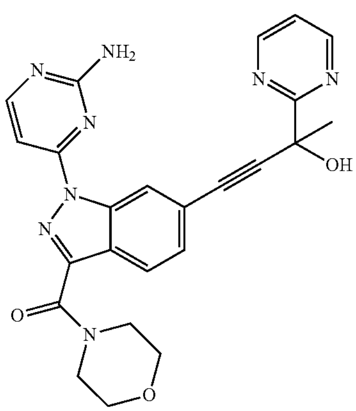 [SMILES: CC(O)(C#Cc1ccc2c(C(=O)N3CCOCC3)nn(-c3ccnc(N)n3)c2c1)c1ncccn1] | [1-(2-aminopyrimidin-4-yl)-6-(3-hydroxy-3-pyrimidin-2-yl-but-1-ynyl)indazol-3-yl]-morpholino-methanone |
| T1.1-131 | 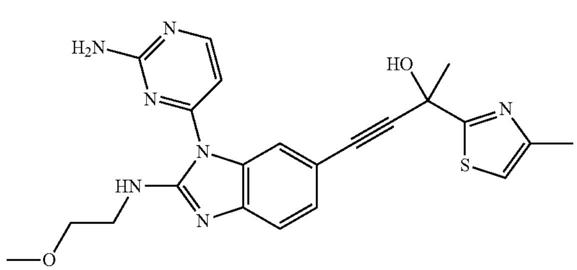 | 4-[3-(2-aminopyrimidin-4-yl)-2-(2-methoxyethylamino)benzimidazol-5-yl]-2-(4-methylthiazol-2-yl)but-3-yn-2-ol |

| No. | Structure | Name |
|---|---|---|
| T1.1-132 | 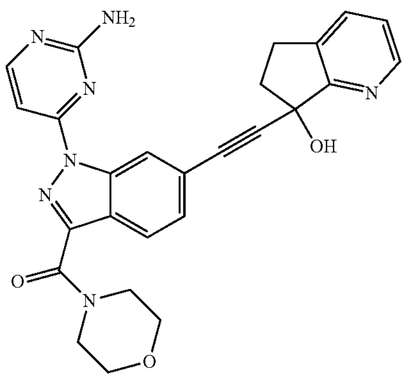 [SMILES: Nc1nccc(-n2nc(C(=O)N3CCOCC3)c3ccc(C#CC4(O)CCc5cccnc54)cc32)n1] | [1-(2-aminopyrimidin-4-yl)-6-[2-(7-hydroxy-5,6-dihydro cyclopenta[b]pyridin-7-yl)ethynyl]indazol-3-yl]-morpholino-methanone |
| T1.1-133 | 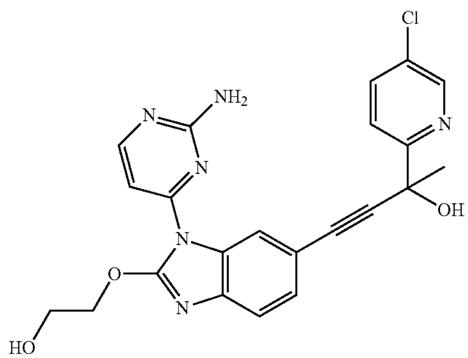 [SMILES: CC(O)(C#Cc1ccc2nc(OCCO)n(-c3ccnc(N)n3)c2c1)c1ccc(Cl)cn1] | 4-[3-(2-aminopyrimidin-4-yl)-2-(2-hydroxyethoxy)benzimidazol-5-yl]-2-(5-chloro-2-pyridyl)but-3-yn-2-ol |
| T1.134 | 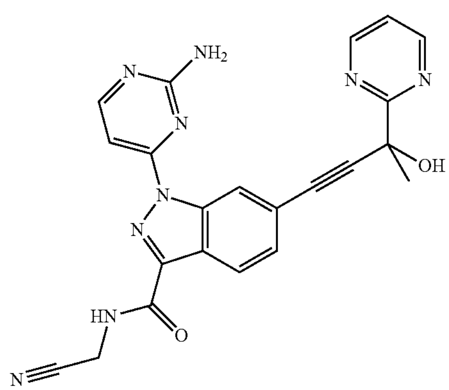 [SMILES: CC(O)(C#Cc1ccc2c(C(=O)NCC#N)nn(-c3ccnc(N)n3)c2c1)c1ncccn1] | 1-(2-aminopyrimidin-4-yl)-N-(cyanomethyl)-6-(3-hydroxy-3-pyrimidin-2-yl-but-1-ynyl)indazole-3-carboxamide |
| T1.1-135 | 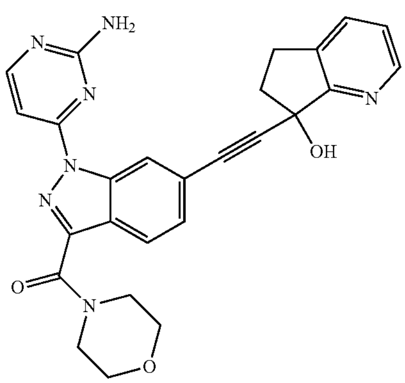 [SMILES: Nc1nccc(-n2nc(C(=O)N3CCOCC3)c3ccc(C#CC4(O)CCc5cccnc54)cc32)n1] | [1-(2-aminopyrimidin-4-yl)-6-[2-(7-hydroxy-5,6-dihydro cyclopenta[b]pyridin-7-yl)ethynyl]indazol-3-yl]-morpholino-methanone |

TABLE 1.1-continued

| No. | Structure | Name |
|---|---|---|
| T1.1-136 | 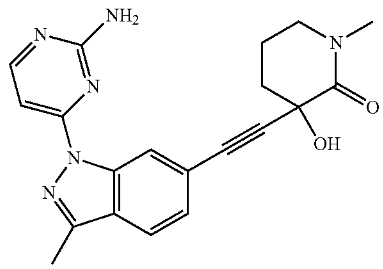 [SMILES: Cc1nn(-c2ccnc(N)n2)c2cc(C#CC3(O)CCCN(C)C3=O)ccc12] | 3-[2-[1-(2-aminopyrimidin-4-yl)-3-methyl-indazol-6-yl]ethynyl]-3-hydroxy-1-methyl-piperidin-2-one |
| T1.1-137 | 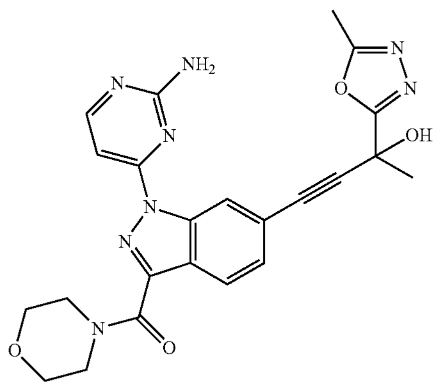 [SMILES: Cc1nnc(C(C)(O)C#Cc2ccc3c(C(=O)N4CCOCC4)nn(-c4ccnc(N)n4)c3c2)o1] | [1-(2-aminopyrimidin-4-yl)-6-[3-hydroxy-3-(5-methyl-1,3,4-oxadiazol-2-yl)but-1-ynyl]indazol-3-yl]-morpholino-methanone |
| T1.1-138 | 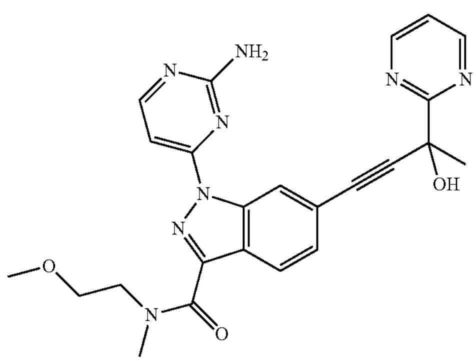 [SMILES: COCCN(C)C(=O)c1nn(-c2ccnc(N)n2)c2cc(C#CC(C)(O)c3ncccn3)ccc12] | 1-(2-aminopyrimidin-4-yl)-6-(3-hydroxy-3-pyrimidin-2-yl-but-1-ynyl)-N-(2-methoxyethyl)-N-methyl-indazole-3-carboxamide |
| T1.1-139 | 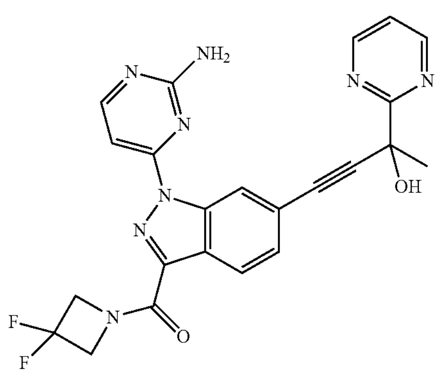 [SMILES: CC(O)(C#Cc1ccc2c(C(=O)N3CC(F)(F)C3)nn(-c3ccnc(N)n3)c2c1)c1ncccn1] | [1-(2-aminopyrimidin-4-yl)-6-(3-hydroxy-3-pyrimidin-2-yl-but-1-ynyl)indazol-3-yl]-(3,3-difluoroazetidin-1-yl)methanone |

TABLE 1.1-continued

| No. | Structure | Name |
|---|---|---|
| T1.1-140 | 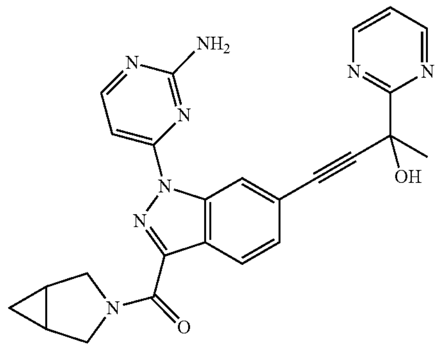 [SMILES: CC(O)(C#Cc1ccc2c(C(=O)N3CC4CC4C3)nn(-c3ccnc(N)n3)c2c1)c1ncccn1] | [1-(2-aminopyrimidin-4-yl)-6-(3-hydroxy-3-pyrimidin-2-yl-but-1-ynyl)indazol-3-yl]-(3-azabicyclo[3.1.0]hexan-3-yl)methanone |
| T1.1-141 | 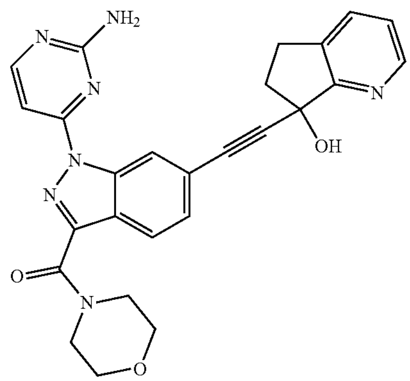 [SMILES: Nc1nccc(-n2nc(C(=O)N3CCOCC3)c3ccc(C#CC4(O)CCc5cccnc54)cc32)n1] | [1-(2-aminopyrimidin-4-yl)-6-[2-(7-hydroxy-5,6-dihydro cyclopenta[b]pyridin-7-yl)ethynyl]indazol-3-yl]-morpholino-methanone |
| T1.1-142 | 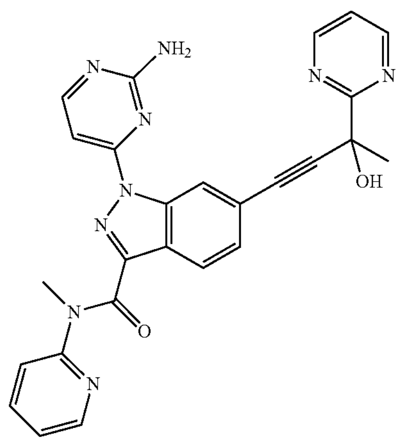 [SMILES: CN(C(=O)c1nn(-c2ccnc(N)n2)c2cc(C#CC(C)(O)c3ncccn3)ccc12)c1ccccn1] | 1-(2-aminopyrimidin-4-yl)-6-(3-hydroxy-3-pyrimidin-2-yl-but-1-ynyl)-N-methyl-N-(2-pyridyl)indazole-3-carboxamide |
| T1.1-143 | 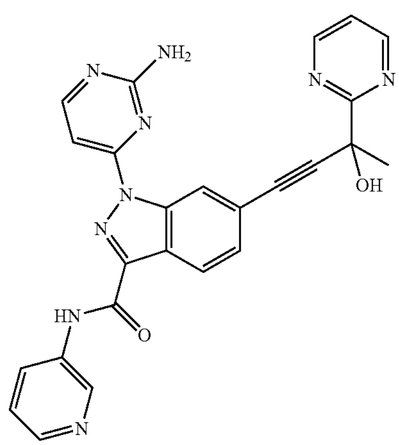 [SMILES: CC(O)(C#Cc1ccc2c(C(=O)Nc3cccnc3)nn(-c3ccnc(N)n3)c2c1)c1ncccn1] | 1-(2-aminopyrimidin-4-yl)-6-(3-hydroxy-3-pyrimidin-2-yl-but-1-ynyl)-N-(3-pyridyl)indazole-3-carboxamide |

| No. | Structure | Name |
|---|---|---|
| T1.1-144 | 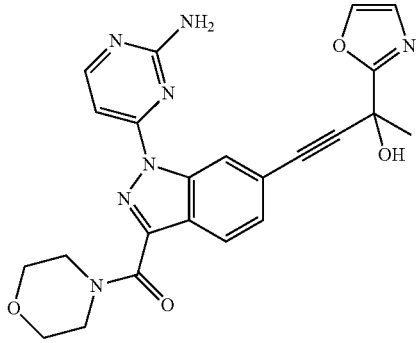 [SMILES: CC(O)(C#Cc1ccc2c(C(=O)N3CCOCC3)nn(-c3ccnc(N)n3)c2c1)c1ncco1] | [1-(2-aminopyrimidin-4-yl)-6-(3-hydroxy-3-oxazol-2-yl-but-1-ynyl)indazol-3-yl]-morpholino-methanone |
| T1.1-145 | 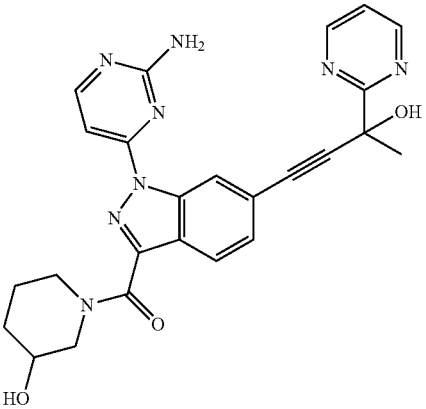 [SMILES: CC(O)(C#Cc1ccc2c(C(=O)N3CCCC(O)C3)nn(-c3ccnc(N)n3)c2c1)c1ncccn1] | [1-(2-aminopyrimidin-4-yl)-6-(3-hydroxy-3-pyrimidin-2-yl-but-1-ynyl)indazol-3-yl]-(3-hydroxy-1-piperidyl)methanone |
| T1.1-146 | 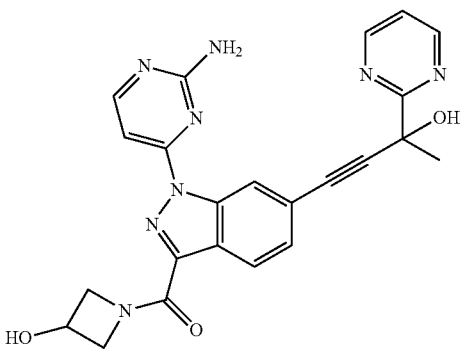 [SMILES: CC(O)(C#Cc1ccc2c(C(=O)N3CC(O)C3)nn(-c3ccnc(N)n3)c2c1)c1ncccn1] | [1-(2-aminopyrimidin-4-yl)-6-(3-hydroxy-3-pyrimidin-2-yl-but-1-ynyl)indazol-3-yl]-(3-hydroxyazetidin-1-yl)methanone |
| T1.1-147 | 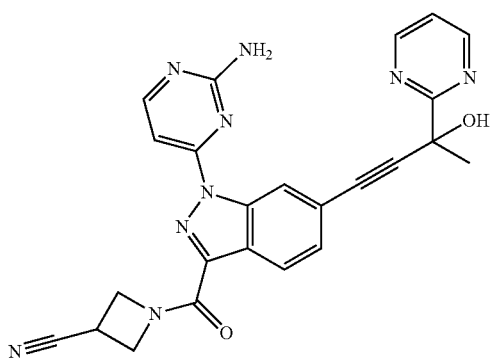 [SMILES: CC(O)(C#Cc1ccc2c(C(=O)N3CC(C#N)C3)nn(-c3ccnc(N)n3)c2c1)c1ncccn1] | 1-[1-(2-aminopyrimidin-4-yl)-6-(3-hydroxy-3-pyrimidin-2-yl-but-1-ynyl)indazole-3-carbonyl]azetidine-3-carbonitrile |

TABLE 1.1-continued

| No. | Structure | Name |
| --- | --- | --- |
| T1.1-148 | 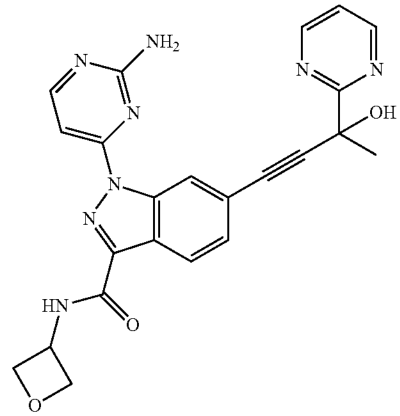 [SMILES: CC(O)(C#Cc1ccc2c(C(=O)NC3COC3)nn(-c3ccnc(N)n3)c2c1)c1ncccn1] | 1-(2-aminopyrimidin-4-yl)-6-(3-hydroxy-3-pyrimidin-2-yl-but-1-ynyl)-N-(oxetan-3-yl)indazole-3-carboxamide |
| T1.1-149 | 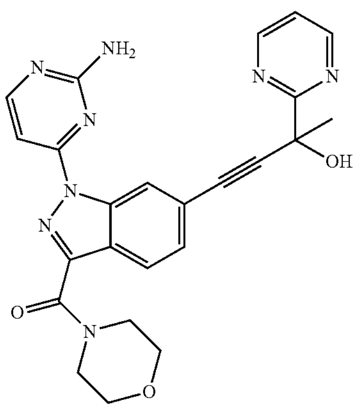 [SMILES: CC(O)(C#Cc1ccc2c(C(=O)N3CCOCC3)nn(-c3ccnc(N)n3)c2c1)c1ncccn1] | [1-(2-aminopyrimidin-4-yl)-6-(3-hydroxy-3-pyrimidin-2-yl-but-1-ynyl)indazol-3-yl]-morpholino-methanone |
| T1.1-150 | 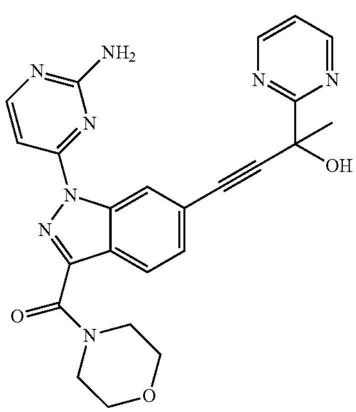 [SMILES: CC(O)(C#Cc1ccc2c(C(=O)N3CCOCC3)nn(-c3ccnc(N)n3)c2c1)c1ncccn1] | [1-(2-aminopyrimidin-4-yl)-6-(3-hydroxy-3-pyrimidin-2-yl-but-1-ynyl)indazol-3-yl]-morpholino-methanone |
| T1.1-151 | 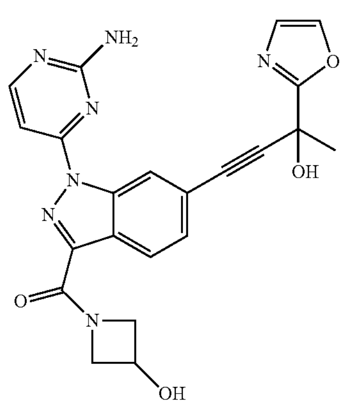 [SMILES: CC(O)(C#Cc1ccc2c(C(=O)N3CC(O)C3)nn(-c3ccnc(N)n3)c2c1)c1ncco1] | [1-(2-aminopyrimidin-4-yl)-6-(3-hydroxy-3-oxazol-2-yl-but-1-ynyl)indazol-3-yl]-(3-hydroxyazetidin-1-yl)methanone |

TABLE 1.1-continued

| No. | Structure | Name |
|---|---|---|
| T1.1-152 | 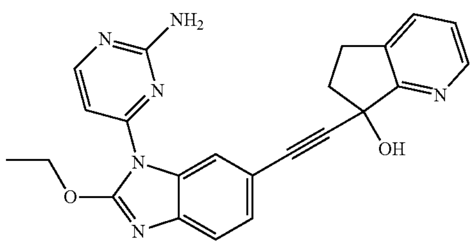 [SMILES: CCOc1nc2ccc(C#CC3(O)CCc4cccnc43)cc2n1-c1ccnc(N)n1] | 7-[2-[3-(2-aminopyrimidin-4-yl)-2-ethoxy-benzimidazol-5-yl]ethynyl]-5,6-dihydrocyclopenta[b]pyridin-7-ol |

In another embodiment, the invention provides for compound intermediates useful in the synthesis of compounds of Formula I.

Synthesis of Compounds

For illustrative purposes, Schemes 1-3 show general methods for preparing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In preparing compounds of Formulas I, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethylenoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Compounds of the invention of Formula I can be synthesized according to the Schemes presented below, in which, "R" at each occurrence independently represents a non-interfering substituent and LG represents a leaving group, (e.g., Cl, OTs, etc.)

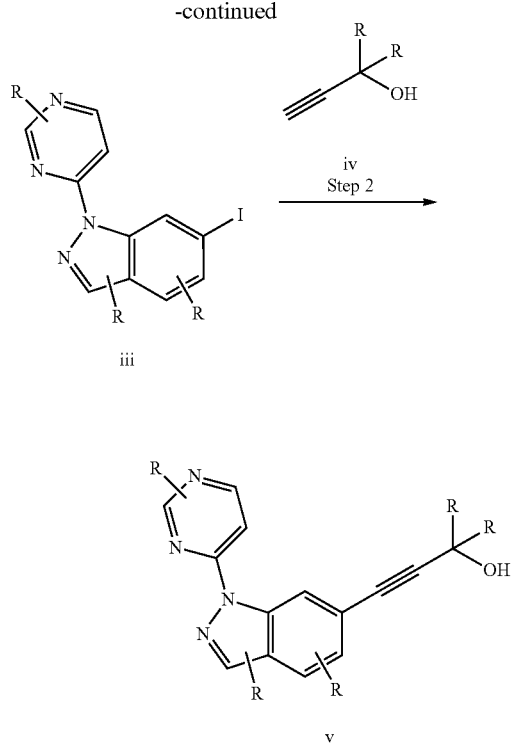

Step 1: Benzopyrazole (i) and heteroarene (ii) are combined under appropriate nucleophilic substitution conditions (e.g., with amine base, aprotic solvent), to form N-heteroarylated benzopyrazole (iii) (see, J. A. Zoltewicz Top. Curr. Chem. 59 (1975), p. 33). Step 2: Compound iii was combined with alkynyl alcohol (iv) under suitable Sonogashira type palladium mediated coupling conditions (see, Chincilla, C., Nájera, C. Chem. Rev. 2007, 107, 874-922) to form compounds of the invention, e.g., compound v.

Scheme 1

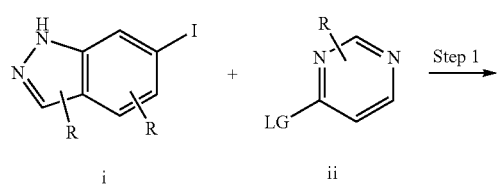

Scheme 2

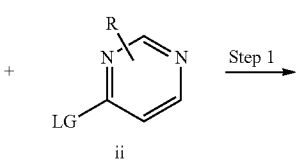

-continued

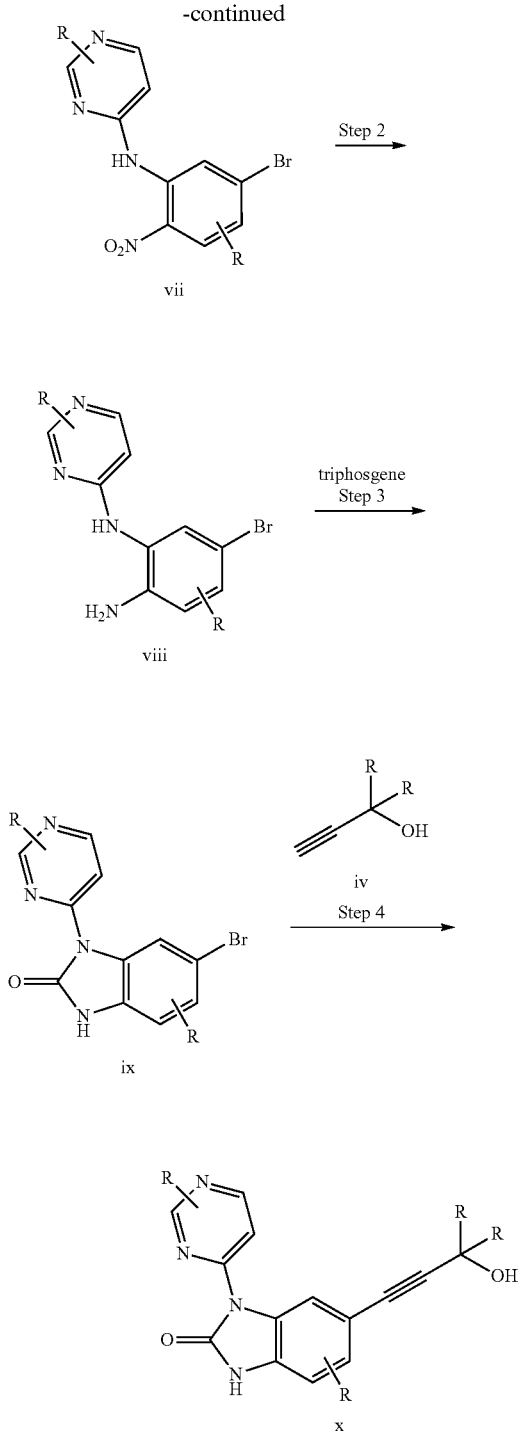

Step 1: Nitroaniline (vi) and heteroarene (ii) are combined under appropriate nucleophilic substitution conditions (e.g., with amine base, aprotic solvent), to form N-heteroarylated nitroaniline (vii). Step 2: Reduction of the nitro functional group of compound vii, preferably under conditions which avoids dehalogenation on aryl ring, produces aminoaniline (viii). Step 3: Treatment of amino-aniline (viii) with triphogene produces benzoimidazolone compound ix. Step 4: Sonogashira type coupling of compound ix with alkynyl alcohol iv produces benzimidazolone compounds of the invention, e.g., compound x.

Scheme 3

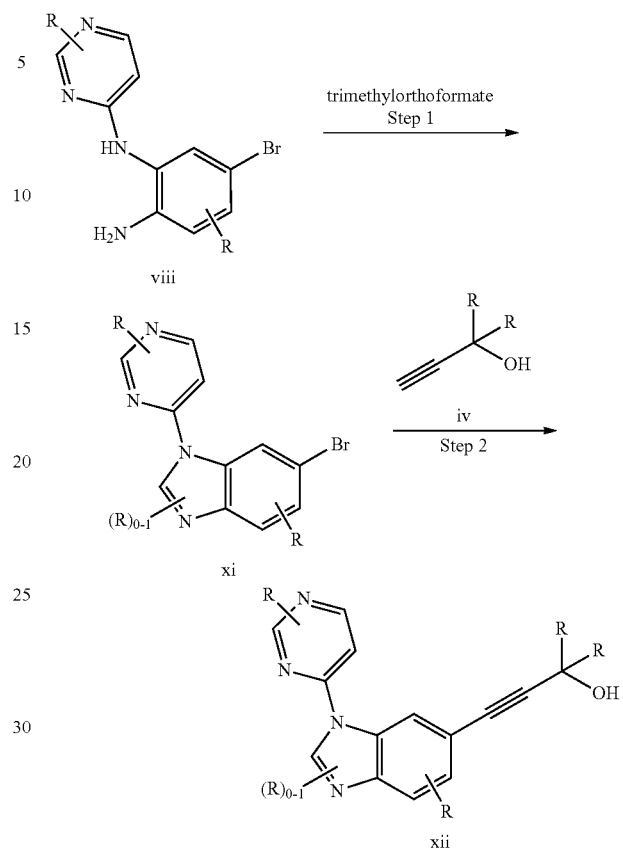

Step 1: Aminoanline (viii) can be treated with orthoformate to provide benzimidazole compound xi. Step 2: Sonogashira coupling of compound xi with alkynyl alcohol iv, will product benzimidazole compounds of the invention, e.g., compound xii.

Further synthetic detail and additional synthetic procedures are described in the Examples section below.

Pharmaceutical Compositions and Administration

In addition to one or more of the compounds provided above (or stereoisomers, geometric isomers, tautomers, solvates, metabolites, isotopes, pharmaceutically acceptable salts, or prodrugs thereof), the invention also provides for compositions and medicaments comprising a compound of Formula I and at least one pharmaceutically acceptable carrier, diluent or excipient. The compositions of the invention can be used inhibiting NF-kB signaling activity in mammals (e.g., human patients), by for example, inhibiting NIK activity The term "composition," as used herein, is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

In one embodiment, the invention provides for pharmaceutical compositions (or medicaments) comprising a compound of Formula I (or stereoisomers, geometric isomers, tautomers, solvates, metabolites, isotopes, pharmaceutically acceptable salts, or prodrugs thereof) and a pharmaceutically acceptable carrier, diluent or excipient. In another embodiment, the invention provides for preparing compositions (or medicaments) comprising compounds of the invention. In another embodiment, the invention provides for administering compounds of Formula I and compositions comprising compounds of Formula I to a mammal (e.g., a human patient) in need thereof.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The effective amount of the compound to be administered will be governed by such considerations, and is the minimum amount necessary to inhibit NIK activity as required to prevent or treat the undesired disease or disorder, such as for example, neurodegeneration, amyloidosis, formation of neurofibrillary tangles, or undesired cell growth (e.g., cancer cell growth). For example, such amount may be below the amount that is toxic to normal cells, or the mammal as a whole.

In one example, the therapeutically effective amount of the compound of the invention administered parenterally per dose will be in the range of about 0.01-100 mg/kg, alternatively about e.g., 0.1 to 20 mg/kg of patient body weight per day, with the typical initial range of compound used being 0.3 to 15 mg/kg/day. The daily does is, in certain embodiments, given as a single daily dose or in divided doses two to six times a day, or in sustained release form. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compositions comprising compounds of Formula I are normally formulated in accordance with standard pharmaceutical practice as a pharmaceutical composition. A typical formulation is prepared by mixing a compound of the present invention and a diluent, carrier or excipient. Suitable diluents, carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which a compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). A active pharmaceutical ingredient of the invention (e.g., compound of Formula I) can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy: Remington the Science and Practice of Pharmacy (2005) $21^{st}$ Edition, Lippincott Williams & Wilkins, Philadelphia, Pa.

Sustained-release preparations of a compound of the invention (e.g., compound of Formula I) can be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773, 919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations can conveniently be presented in unit dosage form and can be prepared by any of the methods well known in the art of pharmacy. Techniques and formulations generally are found in Remington: The Science and Practice of Pharmacy: Remington the Science and Practice of Pharmacy (2005) 21$^{st}$ Edition, Lippincott Williams & Wilkins, Philadelphia, Pa. Such methods include the step of bringing into association the active ingredient with the carrier which constitutes one or more accessory ingredients.

In general the formulations are prepared by uniformly and intimately bringing into association the active ingredient with liquid carriers, diluents or excipients or finely divided solid carriers, diluents or excipients, or both, and then, if necessary, shaping the product. A typical formulation is prepared by mixing a compound of the present invention and a carrier, diluent or excipient. The formulations can be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. A compound of the present invention is typically formulated into pharmaceutical dosage forms to provide an easily controllable dosage of the drug and to enable patient compliance with the prescribed regimen.

In one example, compounds of Formula I may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of Formula I is formulated in an acetate buffer, at pH 5. In another embodiment, the compounds of Formula I are sterile. The compound may be stored, for example, as a solid or amorphous composition, as a lyophilized formulation or as an aqueous solution.

Formulations of a compound of the invention (e.g., compound of Formula I) suitable for oral administration can be prepared as discrete units such as pills, capsules, cachets or tablets each containing a predetermined amount of a compound of the invention.

Compressed tablets can be prepared by compressing in a suitable machine the active ingredient in a free-flowing form such as a powder or granules, optionally mixed with a binder, lubricant, inert diluent, preservative, surface active or dispersing agent. Molded tablets can be made by molding in a suitable machine a mixture of the powdered active ingredient moistened with an inert liquid diluent. The tablets can optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs can be prepared for oral use. Formulations of a compound of the invention (e.g., compound of Formula I) intended for oral use can be prepared according to any method known to the art for the manufacture of pharmaceutical compositions and such compositions can contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients can be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets can be uncoated or can be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax can be employed.

An example of a suitable oral administration form is a tablet containing about 1 mg, 5 mg, 10 mg, 25 mg, 30 mg, 50 mg, 80 mg, 100 mg, 150 mg, 250 mg, 300 mg and 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredient can be employed with either a paraffinic or a water-miscible ointment base. Alternatively, the active ingredients can be formulated in a cream with an oil-in-water cream base.

If desired, the aqueous phase of the cream base can include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations can desirably include a compound which enhances absorption or penetration of the active ingredient through the skin or other affected areas. Examples of such dermal penetration enhancers include dimethyl sulfoxide and related analogs.

The oily phase of the emulsions of this invention can be constituted from known ingredients in a known manner. While the phase can comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of a compound of the invention (e.g., compound of Formula I) contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose or saccharin.

Formulations of a compound of the invention (e.g., compound of Formula I) can be in the form of a sterile injectable preparation, such as a sterile injectable aqueous or oleaginous suspension. This suspension can be formulated according to the known art using those suitable dispersing or wetting agents and suspending agents which have been mentioned above. The sterile injectable preparation can also be a sterile injectable solution or suspension in a non-toxic parenterally acceptable diluent or solvent, such as a solution in 1,3-butanediol or prepared as a lyophilized powder. Among the acceptable vehicles and solvents that can be employed are water, Ringer's solution and isotonic sodium chloride solution. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

The amount of active ingredient that can be combined with the carrier material to produce a single dosage form will vary depending upon the host treated and the particular mode of administration. For example, a time-release formulation intended for oral administration to humans can contain approximately 1 to 1000 mg of active material compounded with an appropriate and convenient amount of carrier material which can vary from about 5 to about 95% of the total compositions (weight:weight). The pharmaceutical composition can be prepared to provide easily measurable amounts for administration. For example, an aqueous solution intended for intravenous infusion can contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which can contain anti-oxidants, buffers, bacteriostats and solutes which render the formulation isotonic with the blood of the intended recipient; and aqueous and non-aqueous sterile suspensions which can include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration can be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration can be prepared according to conventional methods and can be delivered with other therapeutic agents such as compounds heretofore used in the treatment of disorders as described below.

Formulations suitable for vaginal administration can be presented as pessaries, tampons, creams, gels, pastes, foams or spray formulations containing in addition to the active ingredient such carriers as are known in the art to be appropriate.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

Indications and Methods of Treatment

The compounds of Formula I inhibit the activity of NIK. Accordingly, in another aspect of the invention the compounds of the invention (e.g., compounds of Formula I, or stereoisomers, geometric isomers, tautomers, solvates, metabolites, isotopes, pharmaceutically acceptable salts, or prodrugs thereof) can be used for the treatment of diseases and disorders in a mammal, for example a human patient, I which the inhibition of NIK in the patient would be therapeutically effective. For example, the compounds of the invention are useful for the treatment of diseases or disorders in a mammal (e.g., human patient) associated with overactive or undesired NF-kB signaling through, for example, the overactivation of NIK. In another embodiment, the compounds of the invention (e.g., compounds of Formula I, or stereoisomers, geometric isomers, tautomers, solvates, metabolites, isotopes, pharmaceutically acceptable salts, or prodrugs thereof) are used to inhibit the activity of NIK, for example in an in vitro assay setting, by contacting said compound of Formula I with NIK. For example, compounds of Formula I can be used as a control compound in an in vitro assay setting. In another embodiment, the compounds of the invention (e.g., compounds of Formula I, or stereoisomers, geometric isomers, tautomers, solvates, metabolites, isotopes, pharmaceutically acceptable salts, or prodrugs thereof) are used to inhibit the undesired signaling of NF-kB, e.g. in an cell proliferation assay, by introducing into a cell a compound of Formula I. In another embodiment, the present invention provides the treatment of diseases or disorders in a mammal (e.g., human patient) associated with overactive or undesired NF-kB signaling (e.g., cancer, inflammatory diseases, among others) said method comprising administering to a mammal (e.g., human patient) in need thereof a therapeutically effective amount of a compound of the invention (e.g., compounds of Formula I, or stereoisomers, geometric isomers, tautomers, solvates, metabolites, isotopes, pharmaceutically acceptable salts, or prodrugs thereof).

Diseases and disorders treatable according to the methods of this invention include, cancer, inflammatory diseases autoimmune disease and proliferation induced after medical procedures (e.g., arthritis, graft rejection, inflammatory bowel disease, cell proliferation induced after surgery angioplasty, among others). In one embodiment, a mammal (e.g., a human patient) is treated with a compound of the invention (e.g., compounds of Formula I, or stereoisomers, geometric isomers, tautomers, solvates, metabolites, isotopes, pharmaceutically acceptable salts, or prodrugs thereof) and a pharmaceutically acceptable carrier, adjuvant, or vehicle, wherein said compound of the invention (e.g., compounds of Formula I, or stereoisomers, geometric isomers, tautomers, solvates, metabolites, isotopes, pharmaceutically acceptable salts, or prodrugs thereof) is present in an amount to inhibit NF-kB signaling through, for example but not limited to, inhibition of NIK.

In one embodiment, a compound of the invention (e.g., compound of Formula I, or stereoisomers, geometric isomers, tautomers, solvates, metabolites, isotopes, pharmaceutically acceptable salts, or prodrugs thereof) can be used in the treatment of cell proliferative disorders, including cancers of the following categories: (1) Cardiac: sarcoma (angiosarcoma, fibrosarcoma, rhabdomyosarcoma, liposarcoma), myxoma, rhabdomyoma, fibroma, lipoma and teratoma; (2) Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma, non-small cell lung, small cell lung; (3) Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); (4) Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); (5) Liver: hepatoma (hepatocellular carcinoma), cholangiocarcinoma, hepatoblastoma, angiosarcoma, hepatocellular adenoma, hemangioma; (6) Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; (7) Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform. oligodendroglioma, schwannoma, retinoblastoma, congenital tumors), spinal cord neurofibroma, meningioma, glioma, sarcoma); (8) Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); (9) Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; (10) Skin: advanced melanoma, malignant melanoma, basal cell carcinoma, squamous cell carcinoma, Karposi's sarcoma, moles dysplastic nevi, lipoma, angioma, dermatofibroma, keloids, psoriasis; (11) Adrenal glands: neuroblastoma; (12) Breast: metastatic breast; breast adenocarcinoma; (13) Colon; (14) Oral cavity; (15) Hairy cell leukemia; (16) Head and neck; (17) and others including refractory metastatic disease; Kaposi's sarcoma; Bannayan-Zonana syndrome; and Cowden disease or Lhermitte-Duclos disease, among other kinds of cancers.

In one embodiment of the invention, cancers that may be treated by the compounds of Formula I (or stereoisomer, geometric isomer, tautomer, solvate, metabolite, pharmaceutically acceptable salt, or prodrug thereof), selected from the group consisting of Lung (brochogenic carcinoma (non-small cell lung); Gastrointestinal—rectal, colorectal and colon; Genitourinary tract—kidney (papillary renal cell carcinoma); and skin—head and neck squamous cell carcinoma.

In one embodiment, compound of Formula I (or stereoisomer, geometric isomer, tautomer, solvate, metabolite, pharmaceutically acceptable salt, or prodrug thereof), can be use for the treatment of a cancer selected from the group consisting of head and neck squamous cell carcinomas, histiocytic lymphoma, lung adenocarcinoma, small cell lung cancer, non-small cell lung cancer, pancreatic cancer, papillary renal cell carcinoma, liver cancer, gastric cancers, colon cancer, leukemias, lymphomas, multiple myeloma, glioblastomas and breast carcinoma.

In one embodiment, compound of Formula I (or stereoisomer, geometric isomer, tautomer, solvate, metabolite, pharmaceutically acceptable salt, or prodrug thereof), can be used for the treatment of a cancer selected from the group consisting of histiocytic lymphoma, lung adenocarcinoma, small cell lung cancer, pancreatic cancer, liver cancer, gastric cancer, colon cancer, leukemias, lymphomas, multiple myeloma, glioblastomas and breast carcinoma.

In one embodiment, compound of Formula I (or stereoisomer, geometric isomer, tautomer, solvate, metabolite, pharmaceutically acceptable salt, or prodrug thereof), can be used for the treatment of a cancer selected from the group consisting of histiocytic lymphoma, lung adenocarcinoma, small cell lung cancers, pancreatic cancer, liver cancer gastric cancer, colon cancer, leukemias, lymphomas, multiple myeloma, glioblastomas and breast carcinoma.

In one embodiment, compound of Formula I (or stereoisomer, geometric isomer, tautomer, solvate, metabolite, pharmaceutically acceptable salt, or prodrug thereof), can be used for the treatment of cancer selected from the group consisting of lymphomas, leukemias and multiple myeloma.

In one embodiment, the invention provide for the use of a compound of Formula I (or stereoisomers, geometric isomers, tautomers, solvates, metabolites, isotopes, pharmaceutically acceptable salts, or prodrugs thereof) for the treatment of lymphoma, leukemia or multiple myeloma.

In one embodiment, the invention provides for the preparation of a medicament comprising a compound of Formula I (or stereoisomers, geometric isomers, tautomers, solvates, metabolites, isotopes, pharmaceutically acceptable salts, or prodrugs thereof) for the treatment of lymphoma, leukemia or multiple myeloma.

In one embodiment, the invention provides for the treatment of lymphoma, leukemia or multiple myeloma, which method comprises administering an effective amount of a compound of Formula I (or stereoisomers, geometric isomers, tautomers, solvates, metabolites, isotopes, pharmaceutically acceptable salts, or prodrugs thereof).

In one embodiment, compound of the invention (e.g., compounds of Formula I, or stereoisomers, geometric isomers, tautomers, solvates, metabolites, isotopes, pharmaceutically acceptable salts, or prodrugs thereof) are useful for the treatment of inflammatory diseases and conditions including, but not limited to, asthma, lupus, COPD, rhinitis, multiple sclerosis, IBD, arthritis, gastritis, rheumatoid arthritis, dermatitis, endometriosis, transplant rejection, cardiac infarction, Alzheimer's diseases, diabetes Type II, inflammatory bowel disease, sepsis, and artherosclerosis.

In one embodiment, compound of the invention (e.g., compounds of Formula I, or stereoisomers, geometric isomers, tautomers, solvates, metabolites, isotopes, pharmaceutically acceptable salts, or prodrugs thereof) are useful for the treatment of inflammatory diseases and conditions including, but not limited to, lupus, COPD and rheumatoid arthritis.

In one embodiment, the invention provides for the use of a compound of Formula I (or stereoisomers, geometric isomers, tautomers, solvates, metabolites, isotopes, pharmaceutically acceptable salts, or prodrugs thereof) for the treatment of an inflammatory condition.

In one embodiment, the invention provides for the use of a compound of Formula I (or stereoisomers, geometric isomers, tautomers, solvates, metabolites, isotopes, pharmaceutically acceptable salts, or prodrugs thereof) for the preparation of a medicament for the treatment of an inflammatory condition.

In one embodiment, the invention provides for a compound of Formula I (or stereoisomers, geometric isomers, tautomers, solvates, metabolites, isotopes, pharmaceutically acceptable salts, or prodrugs thereof) for the treatment of an inflammatory condition.

In one embodiment, the invention provides for a method for the treatment of an inflammatory condition, which method comprises administering an effective amount of a compound of Formula I (or stereoisomers, geometric isomers, tautomers, solvates, metabolites, isotopes, pharmaceutically acceptable salts, or prodrugs thereof).

In one embodiment, the invention provides for the treatment of an inflammatory condition selected from the group consisting of asthma, lupus, COPD, rhinitis, multiple sclerosis, IBD, arthritis, rheumatoid arthritis, dermatisis, endometriosis and transplant rejection, which method comprises administering an effective amount of a compound of Formula I (or stereoisomers, geometric isomers, tautomers, solvates, metabolites, isotopes, pharmaceutically acceptable salts, or prodrugs thereof).

Combinations

The compounds of Formula I (or stereoisomer, geometric isomer, tautomer, solvate, metabolite, pharmaceutically acceptable salt, or prodrug thereof) may be employed alone or in combination with other therapeutic agents for treatment. In one embodiment, compounds of this invention may be employed alone or in combination with chemotherapeutic agents. In one embodiment, compounds of this invention may be employed alone or in combination with anti-inflammatory agents. The compounds of the present invention can be used in combination with one or more additional drugs, for example an anti-inflammatory compound or anti-cancer compound that works by a different mechanism of action. The second compound of the pharmaceutical combination formulation or dosing regimen preferably has complementary activities to the compound of this invention such that they do not adversely affect each other. Such molecules are suitably present in combination in amounts that are effective for the purpose intended. The compounds may be administered together in a unitary pharmaceutical composition or separately and, when administered separately this may occur simultaneously or sequentially in any order. Such sequential administration may be close in time or remote in time.

In certain embodiments, a compound of Formula I, or a subformula thereof is combined in a pharmaceutical combination formulation, or dosing regimen as combination therapy, with a second therapeutic compound that has anti-inflammatory or anti-cancer properties or that is useful for treating an inflammation, immune-response disorder, or hyperproliferative disorder (e.g., cancer). The second therapeutic agent may be a NSAID (Non-Steroidal Anti-Inflammatory Drug) or other anti-inflammatory agent. The second therapeutic agent may be a chemotherapeutic agent. In one embodiment, a pharmaceutical composition of this invention comprises a compound of Formula I, or a stereoisomer, geometric isomer, tautomer, solvate, metabolite, or pharmaceutically acceptable salt or prodrug thereof, in combination with a therapeutic agent such as an NSAID.

The combination therapy may provide "synergy" and prove "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g. by different injections in separate syringes. In general, during alternation therapy, an effective dosage of each active ingredient is administered sequentially, i.e. serially, whereas in combination therapy, effective dosages of two or more active ingredients are administered together.

Suitable dosages for any of the above coadministered agents are those presently used and may be lowered due to the combined action (synergy) of the newly identified agent and other chemotherapeutic agents or treatments.

EXAMPLES

The invention will be more fully understood by reference to the following examples. They should not, however, be construed as limiting the scope of the invention. These examples are not intended to limit the scope of the present invention, but rather to provide guidance to a skilled artisan to prepare and use the compounds, compositions, and methods of the present invention. While particular embodiments of the present invention are described, the skilled artisan will appreciate that various changes and modifications can be made without departing from the spirit and scope of the invention.

The chemical reactions in the Examples described can be readily adapted to prepare a number of other compounds of the invention, and alternative methods for preparing the compounds of this invention are deemed to be within the scope of this invention. For example, the synthesis of non-exemplified compounds according to the invention can be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

Description of General Reaction Conditions

Commercially available reagents were purchased from suppliers such as Aldrich Chemical Company, Lancaster, TCI or Maybridge, and were used without further purification unless otherwise indicated. 2-methylbut-3-yn-2-ol, 1-ethynylcyclopentan-1-ol and 3-methoxy-3-methylbut-1-yne were readily available and purchased from commercial sources. The reactions set forth below were done generally under a positive pressure of nitrogen or argon or with a drying tube (unless otherwise stated), in anhydrous solvents, and the reaction flasks were typically fitted with rubber septa for the introduction of substrates and reagents via syringe. Glassware was oven dried and/or heat dried. Column chromatography was conducted on a Biotage system (Isolera Four) having a silica gel column or, alternatively column chromatography was carried out using an Isolute® silica gel cartridge (Biotage). $^1$H NMR spectra were recorded on either on a Bruker DPX instrument operating at 250 MHz or a Bruker DRX instrument operating at 500 MHz. $^1$H NMR spectra were obtained in deuterated CDCl$_3$, d$_6$-DMSO or CH$_3$OD (reported in ppm), using chloroform as the reference standard (7.25 ppm). When peak multiplicities are reported, the following abbreviations are used: s (singlet), d (doublet), t (triplet), m (multiplet), br (broadened), dd (doublet of doublets), dt (doublet of triplets). Coupling constants, when given, were reported in Hertz (Hz). When possible, product formations in the reaction mixtures were monitored by LC-MS (Method B). LC-MS m/z data for the compounds described were obtained by LC-MS (Method A) unless otherwise stated.

| LC-MS (Method A) | | |
|---|---|---|
| Column | Waters Atlantis dC18 100 × 2.1 mm, 3 μm column 40° C. | |
| Mobile phase | A—0.1% Formic acid (water) B—0.1% Formic acid (acetonitrile) | |
| Flow rate | 0.6 ml/min | |
| Injection volume | 3 μL | |
| Detector | 215 nm and 254 nm | |
| Gradient | Time (mins) | % B |
| | 0 | 5 |
| | 5 | 100 |
| | 5.4 | 100 |
| | 5.42 | 5 |

| LC-MS (Method B) | | |
|---|---|---|
| Column | Waters Atlantis dC18 100 × 2.1 mm, 3 μm column | |
| Mobile phase | A—0.1% Formic acid (water) B—0.1% Formic acid (acetonitrile) | |
| Flow rate | 1.0 ml/min | |
| Injection volume | 3 μL | |
| Detector | 215 nm (nominal) | |
| Gradient | Time (mins) | % B |
| | 0 | 5 |
| | 2.5 | 100 |
| | 2.7 | 100 |
| | 2.71 | 5 |
| | 3.0 | 5 |

Reverse phase HPLC purification methods used anywhere from 0-100% acetonitrile in water and may contain 0.1% formic acid, 0.1% TFA or 0.2% ammonium hydroxide and used one of the following columns:

a) Waters Sunfire OBD C18 5 um, 30×150 mm column;

b) Phenomenex Gemini Axia C18 5 um, 30×100 mm column;

c) Waters XBridge Prep C18 5 um, 19×100 mm; or or using IntelFlash-1; Column, T3; mobile phase, acetonitrile/Water=10/90 increasing to acetonitrile/Water=95/5 within 16 min; Detector, UV 254 nm Alternatively, other reverse phase HPLC purification methods used anywhere from 0-100% acetonitrile in water and may contain 0.1% formic acid, 0.1% TFA or 0.2% ammonium hydroxide and used one of the following columns:

a) Waters Sunfire OBD C18 5 um, 30×150 mm column or 19×150 column;

b) Phenomenex Gemini Axia C18 5 μm, 30×100 mm column;

c) Waters XBridge Prep C18 5 μm, 19×100 mm; or d) Phenomenex Luna C18 10 μm 25-200 column.

Chemical structures were named according to: vendor designation; IUPAC convention; J Chem for Excel, Version 5.3.8.14, ChemAxon Ltd. or Autonom 2000 Name, MDL Inc. It is recognized by those skilled in the art that a compound may have more than one name, according to different conventions.

Example 1

Preparation of 4-[1-(2-aminopyrimidin-4-yl)-1H-indazol-6-yl]-2-(1,3-thiazol-2-yl)but-3-yn-2-ol

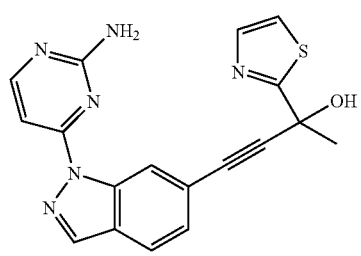

(1-b)

Step 1—Synthesis of 4-(6-iodo-1H-indazol-1-yl)pyrimidin-2-amine (1-a1) and 4-(6-iodo-2H-indazol-2-yl)pyrimidin-2-amine (1-a2)

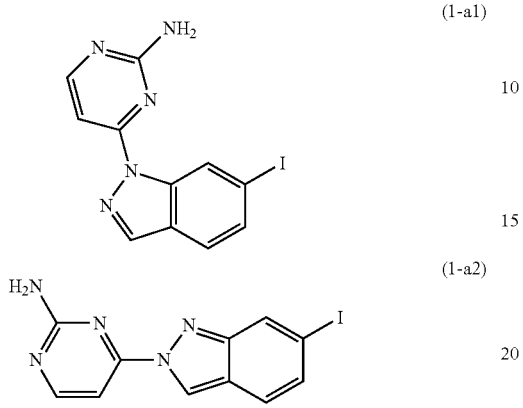

To a solution of 6-iodo-1H-indazole (500 mg, 1.95 mmol) in DMF (5 mL) was added NaH (60% oil dispersion) (125 mg, 3.11 mmol) at 0° C. The mixture was stirred at RT for 10 min before addition of 4-chloropyrimidin-2-amine (504 mg, 3.89 mmol). Stirring was continued at RT for 18 hr then the mixture was heated at 50° C. for 2 hr. LCMS showed formation of a (1:1) mixture of (1-a1) and (1-a2). These isomers were separated as follows:

The reaction mixture was quenched by addition of water (5 mL). Extraction with EtOAc (3×5 mL) resulted in precipitation. Suction filtration gave 4-(6-iodo-2H-indazol-2-yl)pyrimidin-2-amine (1-a2) as a pale brown solid: $^1$H NMR (250 MHz, DMSO)δ 7.13 (2H, s), 7.28 (1H, d, J=5.33 Hz), 7.39 (1H, d, J=1.37 Hz), 7.67 (1H, dd, J=8.91, 0.69 Hz), 8.21 (1H, d, J=0.91 Hz), 8.46 (1H, d, J=5.18 Hz), 9.12 (1H, d, J=1.07 Hz). LC-MS: m/z=+337.90 (M+H)+.

The filtrate was washed with water (5 mL), dried (Na$_2$SO$_4$), filtered and concentrated in vacuo. The residue was purified by flash chromatography (Isolute column, 50% EtOAc in heptanes) to give (6-iodo-1H-indazol-1-yl)pyrimidin-2-amine (1-a1) as a pale brown solid: $^1$H NMR (250 MHz, DMSO) δ 7.08 (1H, d, J=5.48 Hz), 7.11-7.16 (2H, m), 7.69 (2H, dd, J=1.75, 0.99 Hz), 8.30 (1H, d, J=5.63 Hz), 8.47 (1H, d, J=0.76 Hz), 9.31 (1H, d, J=0.91 Hz) LC-MS: m/z=+337.90 (M+H)+.

Step 2: Synthesis of 4-[1-(2-aminopyrimidin-4-yl)-1H-indazol-6-yl]-2-(1,3-thiazol-2-yl)but-3-yn-2-ol (1-b)

To a mixture of 4-(6-iodo-1H-indazol-1-yl)pyrimidin-2-amine (1-a1) (150 mg, 0.285 mmol) and piperidine (1 mL) was added tetrakis(triphenylphosphine)palladium (49.3 mg, 0.043 mmol), copper(I) iodide (8.1 mg, 0.043 mmol) and 2-(1,3-thiazol-2-yl)but-3-yn-2-ol (I-1) (131 mg, 0.854 mmol). The reaction was purged with N$_2$ and stirred at RT for 30 min. The reaction mixture was concentrated in vacuo and the residue purified by reverse phase preparative HPLC to afford the title compound: $^1$H NMR (500 MHz, DMSO) δ 1.95 (3H, s), 7.04 (2H, br. s.), 7.08-7.13 (2H, m), 7.35 (1H, dd, J=8.20, 1.26 Hz), 7.70 (1H, d, J=3.15 Hz), 7.79 (1H, d, J=3.15 Hz), 7.89 (1H, d, J=8.51 Hz), 8.30 (1H, d, J=5.67 Hz), 8.50 (1H, s), 8.91 (1H, s). LC-MS: m/z=+363.4 (M+H)+.

Example 2

Preparation of 4-[1-(2-aminopyrimidin-4-yl)-1H-indazol-6-yl]-2-(1,3-oxazol-2-yl)but-3-yn-2-ol

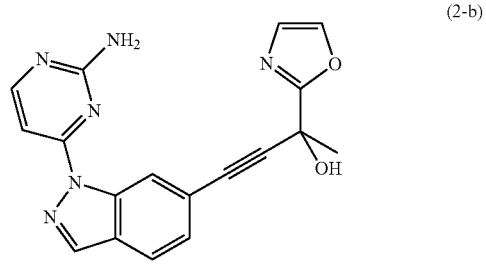 [SMILES: CC(O)(C#Cc1ccc2cnn(-c3ccnc(N)n3)c2c1)c1ncco1]

Step 1—Synthesis of 4-(6-bromo-1H-indazol-1-yl)pyrimidin-2-amine

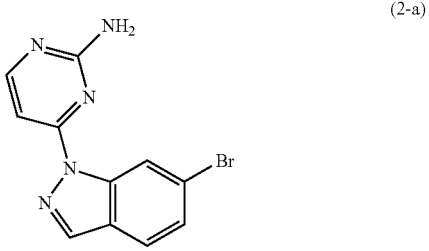 [SMILES: Nc1nccc(-n2ncc3ccc(Br)cc32)n1]

The title compound was prepared by procedure described in Example 1-a1, by substituting 6-iodo-1H-indazole with 6-bromo-1H-indazole in Step 1: $^1$H NMR (500 MHz, DMSO) δ 7.08 (3H, d, J=5.52 Hz), 7.52 (1H, d, J=1.58 Hz), 7.85 (1H, d, J=8.51 Hz), 8.30 (1H, d, J=5.36 Hz), 8.49 (1H, s), 9.14 (1H, s); LC-MS: m/z=+289.6/291.6 (M+H)+.

Step 2—Synthesis of 4-[1-(2-aminopyrimidin-4-yl)-1H-indazol-6-yl]-2-(1,3-oxazol-2-yl)but-3-yn-2-ol The title compound was prepared by adaption of procedure described in Example 1, by substituting 4-(6-iodo-1H-indazol-1-yl)pyrimidin-2-amine with 4-(6-bromo-1H-indazol-1-yl)pyrimidin-2-amine in Step 2. The reaction was carried out at 60° C. for 2 hr. The title compound, 4-[1-(2-aminopyrimidin-4-yl)-1H-indazol-6-yl]-2-(1,3-oxazol-2-yl)but-3-yn-2-ol, was obtained: $^1$H NMR (500 MHz, DMSO) δ 1.94 (3H, s), 6.79 (1H, s), 6.99-7.16 (3H, m), 7.24 (1H, s), 7.37 (1H, dd, J=8.28, 1.18 Hz), 7.90 (1H, d, J=8.20 Hz), 8.16 (1H, s), 8.31 (1H, d, J=5.52 Hz), 8.51 (1H, s), 8.93 (1H, s); LC-MS: m/z=+347.5 (M+H)+.

Example 3

Examples in Table 3 were prepared by procedures described in either Example 1 or Example 2 by reacting 4-(6-iodo-1H-indazol-1-yl)pyrimidin-2-amine (Example 1) or 4-(6-bromo-1H-indazol-1-yl)pyrimidin-2-amine (Example 2) with the appropriate but-3-yn-2-ol intermediates.

TABLE 2

| No. | Structure | Name | ¹H NMR | MS (M + H) |
|---|---|---|---|---|
| T2-3.1 | 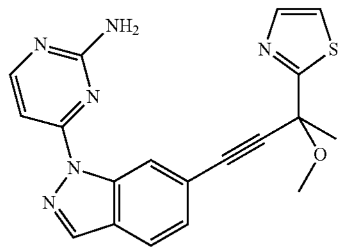 [SMILES: COC(C)(C#Cc1ccc2cnn(-c3ccnc(N)n3)c2c1)c1nccs1] | 4-{6-[3-methoxy-3-(1,3-thiazol-2-yl)but-1-yn-1-yl]-1H-indazol-1-yl}pyrimidin-2-amine | (500 MHz, DMSO) δ 1.96 (3 H, s), 3.42 (3 H, s), 7.13 (3 H, br. s.), 7.45 (1 H, dd, J = 8.35, 0.95 Hz), 7.81 (1 H, d, J = 3.15 Hz), 7.86 (1 H, d, J = 3.15 Hz), 7.93 (1 H, d, J = 8.35 Hz), 8.53 (1 H, s), 8.99 (1 H, s) | 377.5 |
| T2-3.2 | 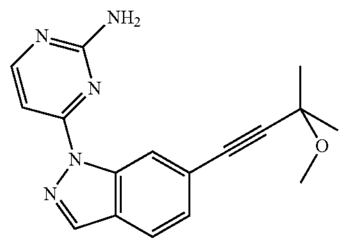 [SMILES: COC(C)(C)C#Cc1ccc2cnn(-c3ccnc(N)n3)c2c1] | 4-[6-(3-methoxy-3-methylbut-1-yn-1-yl)-1H-indazol-1-yl]pyrimidin-2-amine | (500 MHz, DMSO) δ 1.54 (6 H, s), 3.37 (3 H, s), 6.99-7.14 (3 H, m), 7.38 (1 H, dd, J = 8.20, 1.26 Hz), 7.88 (1 H, d, J = 8.20 Hz), 8.31 (1 H, br. s.), 8.50 (1 H, d, J = 0.63 Hz), 8.92 (1 H, s) | 308.2 |
| T2-3.3 | 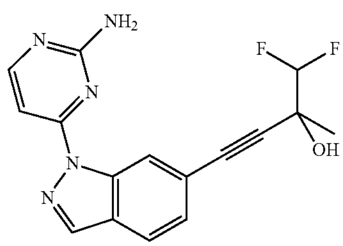 [SMILES: CC(O)(C#Cc1ccc2cnn(-c3ccnc(N)n3)c2c1)C(F)F] | 4-[1-(2-aminopyrimidin-4-yl)-1H-indazol-6-yl]-1,1-difluoro-2-methylbut-3-yn-2-ol | (500 MHz, DMSO) δ 1.54 (3 H, s), 5.81-6.18 (1 H, m), 6.47 (1 H, br. s.), 6.97-7.18 (3 H, m), 7.37 (1 H, dd, J = 8.20, 1.26 Hz), 7.91 (1 H, d, J = 8.35 Hz), 8.31 (1 H, d, J = 5.52 Hz), 8.51 (1 H, d, J = 0.79 Hz), 8.94 (1 H, s) | 330.4 |
| T2-3.4 | 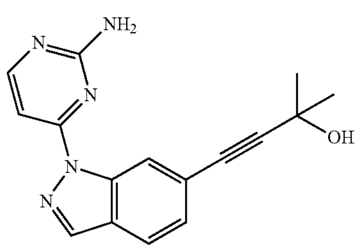 [SMILES: CC(C)(O)C#Cc1ccc2cnn(-c3ccnc(N)n3)c2c1] | 4-[1-(2-aminopyrimidin-4-yl)-1H-indazol-6-yl]-2-methylbut-3-yn-2-ol | (500 MHz, DMSO) δ 1.53 (6 H, s), 5.55 (1 H, br. s.), 6.96-7.18 (3 H, m), 7.33 (1H, dd, J = 8.24, 1.22 Hz), 7.87 (1 H, d, J = 8.24 Hz), 8.30 (1 H, d, J = 5.49 Hz), 8.49 (1 H, s), 8.88 (1 H, s) | 294.4 |
| T2-3.5 | 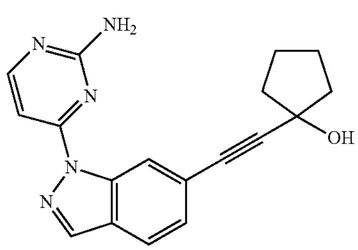 [SMILES: Nc1nccc(-n2ncc3ccc(C#CC4(O)CCCC4)cc32)n1] | 1-{2-[1-(2-aminopyrimidin-4-yl)-1H-indazol-6-yl]ethynyl}cyclopentan-1-ol | (500 MHz, DMSO) δ 1.68-1.80 (4H, m), 1.93-2.00 (4 H, m), 5.33-5.42 (1 H, m), 7.04 (2 H, br. s.), 7.10 (1 H, d, J = 5.49 Hz), 7.33 (1 H, dd, J = 8.24, 1.37 Hz), 7.87 (1 H, dd, J = 8.24, 0.61 Hz), 8.30 (1 H, d, J = 5.49 Hz), 8.48 (1 H, d, J = 0.76 Hz), 8.88 (1 H, s) | 320.1 |

Example 4

Preparation of 4-[1-(2-amino-5-chloropyrimidin-4-yl)-1H-indazol-6-yl]-2-(1,3-thiazol-2-yl)but-3-yn-2-ol

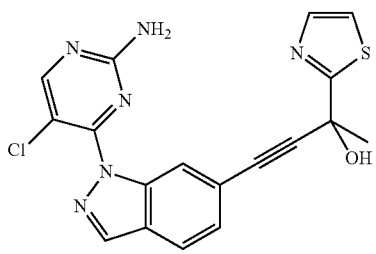
(4-b)

Step 1—Synthesis of 5-chloro-4-(6-iodo-1H-indazol-1-yl)pyrimidin-2-amine

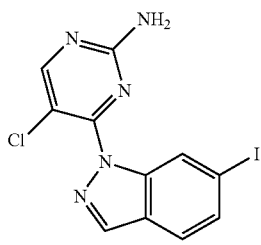
(4-a)

To a solution of 6-iodo-1H-indazole (100 mg, 0.41 mmol) in DMF (3 mL) was added NaH (60% oil dispersion, 32 mg, 0.82 mmol) at 0° C. The mixture was stirred at 0° C. to RT for 10 min before addition of 4,5-dichloropyrimidin-2-amine (134.4 mg, 0.82 mmol). The mixture was stirred at 50° C. for 2 hr, then quenched with water and extracted with DCM (2×). The combined organic layers were dried over $Na_2SO_4$, filtered and concentrated in vacuo. LC-MS (Method B) indicated a mixture of title compound [67%, Retention time=2.11 min, m/z=+371.9/373.9 (M+H)+] and an isomeric by-product [10%, Retention time=2.07 min, m/z=+371.9/373.9 (M+H)+]. Purification by flash chromatography (Isolute column, 50% EtOAc in heptane) afforded the title compound: $^1$H NMR (500 MHz, DMSO) δ 7.31 (2H, br. s.), 7.65 (1H, dd, J=8.51, 1.26 Hz), 7.71 (1H, d, J=8.20 Hz), 8.45-8.48 (1H, m), 8.56-8.71 (1H, m), 8.61 (1H, s); LC-MS: m/z=+371.9 (M+H)+.

Step 2—Synthesis of 4-[1-(2-amino-5-chloropyrimidin-4-yl)-1H-indazol-6-yl]-2-(1,3-thiazol-2-yl)but-3-yn-2-ol To a mixture of 5-chloro-4-(6-iodo-1H-indazol-1-yl)pyrimidin-2-amine (170 mg, 0.46 mmol) and piperidine (1.2 mL) was added tetrakis(triphenylphosphine)palladium (52.9 mg, 0.05 mmol), copper(I) iodide (8.7 mg, 0.05 mmol) and 2-(1,3-thiazol-2-yl)but-3-yn-2-ol (I-1) (140.2 mg, 0.92 mmol). The reaction was purged with $N_2$ and stirred at RT for 20 min. The reaction mixture was concentrated in vacuo and the resultant residue purified by flash chromatography (Isolute column, 1% MeOH in DCM), followed by reverse phase preparative HPLC to give the title compound as a solid: $^1$H NMR (500 MHz, DMSO) δ 1.91 (3H, s), 7.09 (1H, s), 7.23-7.39 (3H, m), 7.69 (1H, d, J=3.36 Hz), 7.78 (1H, d, J=3.20 Hz), 7.90 (1H, d, J=8.24 Hz), 8.17 (1H, d, J=0.76 Hz), 8.43-8.53 (2H, m); LC-MS: m/z=+397.40 (M+H)+.

Example 5

Preparation of 4-[1-(2-aminopyrimidin-4-yl)-3-methyl-1H-indazol-6-yl]-2-(1,3-thiazol-2-yl)but-3-yn-2-ol

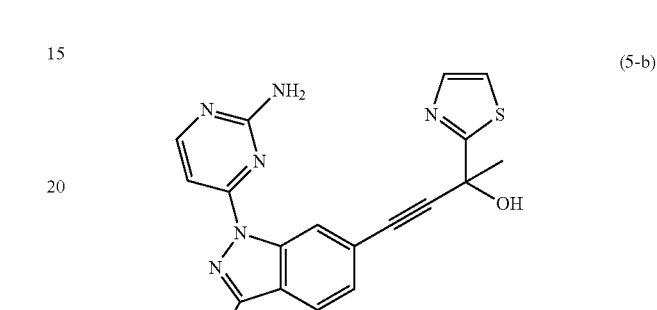
(5-b)

Step 1—Synthesis of 4-(6-bromo-3-methyl-1H-indazol-1-yl)pyrimidin-2-amine

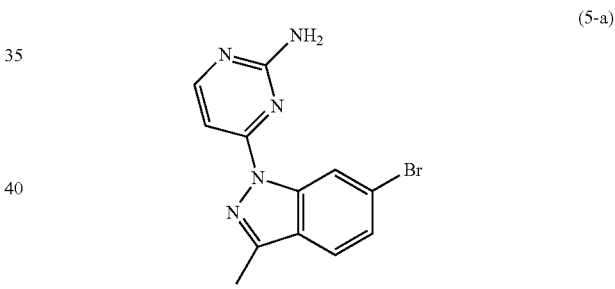
(5-a)

To a solution of 6-bromo-3-methylindazole (300 mg, 1.42 mmol) in DMF (6 mL) was added NaH (60% oil suspension) (91 mg, 2.27 mmol) at 0° C. The mixture was stirred at RT for 10 min before addition of 4-chloropyrimidin-2-amine (368 mg, 2.84 mmol). Stirring continued at 60° C. for 2 hr. After standing at RT overnight the reaction mixture was quenched by addition of water (10 mL). The mixture was extracted with EtOAc (2×15 mL). During the process of extraction solid formed was removed by suction filtration. The organic layer was washed with water (2×5 mL), dried over $Na_2SO_4$, filtered and concentrated in vacuo. The residue was triturated with EtOAc-heptane (1:1) to give the title intermediate as a white solid: $^1$H NMR (250 MHz, DMSO) δ 2.53-2.64 (3H, m), 6.69-7.21 (3H, m), 7.43-7.62 (1H, m), 7.76-7.89 (1H, m), 8.18-8.38 (1H, m), 8.92-9.15 (1H, m); LC-MS: m/z=+303.95/305.65 (M+H).

Step 2—Synthesis of 4-[1-(2-aminopyrimidin-4-yl)-3-methyl-1H-indazol-6-yl]-2-(1,3-thiazol-2-yl)but-3-yn-2-ol To a mixture of 4-(6-bromo-3-methyl-1H-indazol-1-yl)pyrimidin-2-amine (5-a) (240 mg, 0.489 mmol) and piperidine (1.2 mL) was added tetrakis(triphenylphosphine)palladium (53.5 mg, 0.049 mmol), copper(I) iodide (9.3 mg, 0.049 mmol) and 2-(1,3-thiazol-2-yl)but-3-yn-2-ol (I-1) (150 mg, 0.978 mmol). The reaction was purged with $N_2$ and stirred at 60° C. for 1.5 hr. The reaction mixture was concentrated in vacuo. EtOAc (2 mL) was added to the residue and concentration in vacuo was repeated. The resultant residue was purified by flash chromatography (Isolute column, 100% DCM to 3% MeOH in DCM) to afford the title compound as a white solid: $^1$H NMR (250 MHz, DMSO) δ 1.87-1.97 (3H, m), 2.56 (3H, s), 6.91-7.00 (1H, m), 7.01-7.07 (1H, m), 7.10-7.23 (1H, m), 7.29-7.40 (1H, m), 7.65-7.73 (1H, m), 7.74-7.80 (1H, m), 7.81-7.90 (1H, m), 8.19-8.32 (1H, m), 8.76-8.92 (1H, m); LC-MS: m/z=+377.5 (M+H)+.

Example 6

Preparation of 4-[1-(2-aminopyrimidin-4-yl)-3-[(dimethylamino)methyl]-1H-indazol-6-yl]-2-methylbut-3-yn-2-ol

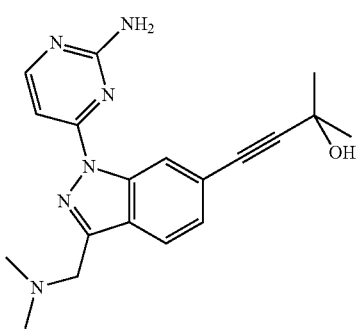

(6-c)

Step 1—Synthesis of 1-(6-bromo-1H-indazol-3-yl)-N,N-dimethylmethanamine

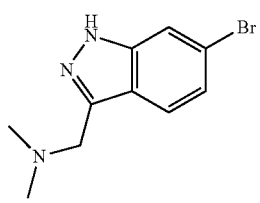

(10-a)

To a solution of 6-bromo-1H-indazole-3-carbaldehyde (300 mg, 1.33 mmol) in THF (1 mL) was added acetic acid (0.11 mL, 2 mmol), 2M dimethylamine in THF (1.33 mL, 2.66 mmol) and sodium triacetoxyborohydride (283 mg, 1.33 mmol). The reaction was stirred at RT for 2 hr then allowed to stand at RT for 18 hr. The mixture was concentrated in vacuo, then diluted with EtOAc (50 mL) and washed with 1M aqueous $NaHCO_3$ (10 mL). The organic layer was washed with brine (5 mL), followed by water (5 mL). The organic layer was then dried ($Na_2SO_4$), filtered and concentrated in vacuo to give the title compound as a beige solid: $^1$H NMR (500 MHz, MeOD) δ 2.31 (6H, s), 3.85 (2H, s), 7.27 (1H, dd, J=8.67, 1.58 Hz), 7.68-7.72 (1H, m), 7.77 (1H, d, J=8.67 Hz). LC-MS: m/z=+253.9/255.9 (M+H)+.

Step 2—Synthesis of 4-{6-bromo-3-[(dimethylamino)methyl]-1H-indazol-1-yl}pyrimidin-2-amine

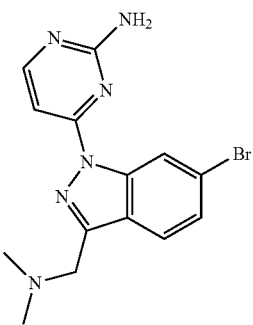

(6-b)

To a solution of (6-Bromo-1H-indazol-3-ylmethyl)-dimethyl-amine (523 mg, 2.05 mmol) in DMF (8 mL) was added NaH (60% oil dispersion) (132 mg, 3.29 mmol) at 0° C. The reaction mixture was allowed to warm up to RT and was stirred for 15 min. A solution of 4-chloropyrimidin-2-amine (533 mg, 4.11 mmol) in DMF (3 mL) was added slowly. The resulting mixture was stirred at 60° C. for 18 hr. When the reaction mixture was partitioned between EtOAc (25 mL) and water (10 mL), precipitation occurred. The solid was collected by suction filtration and was washed with EtOAc to give the title compound: $^1$H NMR (500 MHz, DMSO) δ 2.22 (6H, s), 3.81 (2H, s), 7.04 (1H, d, J=5.52 Hz), 7.06-7.19 (2H, m), 7.50 (1H, m, J=8.51 Hz), 7.92 (1H, d, J=8.51 Hz), 8.27 (1H, d, J=5.52 Hz), 9.11 (1H, d, J=1.26 Hz); LC-MS: m/z=+348.9 (M+H)+.

Step 3—Synthesis of -[1-(2-aminopyrimidin-4-yl)-3-[(dimethylamino)methyl]-1H-indazol-6-yl]-2-methylbut-3-yn-2-ol To a solution of 4-{6-bromo-3-[(dimethylamino)methyl]-1H-indazol-1-yl}pyrimidin-2-amine (80 mg, 0.23 mmol) in piperidine (2 mL) was added 2-methyl-but-3-yn-2-ol (38.8 mg, 0.461 mmol), CuI (4.4 mg, 0.023 mmol) and tetrakis(triphenylphosphine)palladium (13.3 mg, 0.012 mmol). The mixture was heated at 75° C. for 1 hr in a sealed tube. Volatiles were removed by concentration in vacuo. Purification by flash chromatography (Isolute column, 100% DCM to 5% MeOH in DCM) afforded the title compound as yellow solid: $^1$H NMR (500 MHz, DMSO) δ 1.53 (6H, s), 2.23 (6H, s), 3.80 (2H, s), 5.51 (1H, s), 6.93-7.09 (2H, m), 6.97-7.04 (1H, m), 7.32 (1H, d, J=8.20 Hz), 7.93 (1H, s), 8.19-8.35 (1H, m), 8.84 (1H, s); LC-MS: m/z=+351.10 (M+H)+.

Example 7

Preparation of 4-[1-(2-aminopyrimidin-4-yl)-3-(morpholin-4-ylmethyl)-1H-indazol-6-yl]-2-(1,3-thiazol-2-yl)but-3-yn-2-ol

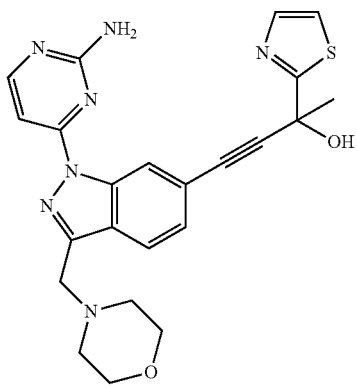

(7-c)

Step 1—Synthesis of 6-bromo-3-(morpholin-4-ylmethyl)-1H-indazole

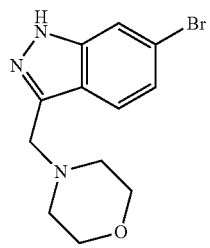

(7-a)

The title compound was prepared by the procedure described in Example 8-a by substituting 2M dimethylamine in THF with morpholine in Step 1: ¹H NMR (250 MHz, CDCl₃) δ 2.49-2.68 (4 H, m), 3.66-3.82 (4H, m), 3.93 (2H, s), 7.25-7.32 (1H, m), 7.65 (1H, d, J=0.91 Hz), 7.78 (1H, d, J=8.98 Hz), 8.17 (1H, br. s); LC-MS: m/z=+296.0/297.8 (M+H)+.

Step 2—Synthesis of 4-[6-bromo-3-(morpholin-4-ylmethyl)-1H-indazol-1-yl]pyrimidin-2-amine

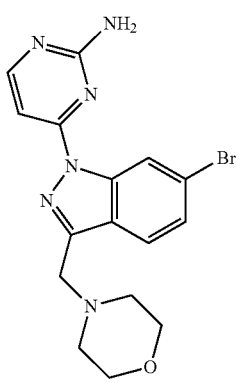

(7-b)

The title compound was prepared by the procedure described in Example 8-b by substituting 1-(6-bromo-1H-indazol-3-yl)-N,N-dimethylmethanamine with 6-bromo-3-(morpholin-4-ylmethyl)-1H-indazole in Step 2: ¹H NMR (250 MHz, DMSO) δ 2.44 (4H, d, J=3.81 Hz), 3.55 (4H, br. s.), 3.87 (2H, s), 7.02 (3H, d, J=5.63 Hz), 7.52 (1H, s), 7.95 (1H, s), 8.26 (1H, d, J=5.63 Hz), 9.09 (1H, d, J=1.37 Hz); LC-MS: m/z=+389.0/391.0 (M+H)+.

Step 3—Synthesis of 4-[1-(2-aminopyrimidin-4-yl)-3-(morpholin-4-ylmethyl)-1H-indazol-6-yl]-2-(1,3-thiazol-2-yl)but-3-yn-2-ol The title compound was prepared by the procedure described in Example 6-c by substituting 4-{6-bromo-3-[(dimethylamino)methyl]-1H-indazol-1-yl}pyrimidin-2-amine with 4-[6-bromo-3-(morpholin-4-ylmethyl)-1H-indazol-1-yl]pyrimidin-2-amine and 2-methyl-but-3-yn-2-ol with 2-(1,3-thiazol-2-yl)but-3-yn-2-ol. The reaction was carried out at 60° C. for 1.5 hr. Title compound was obtained: ¹H NMR (500 MHz, DMSO) δ 1.93 (3H, s), 2.45 (4H, br. s.), 3.55-3.57 (4H, m), 3.88 (2H, s), 6.98 (2H, br. s.), 7.05 (1H, d, J=5.52 Hz), 7.12 (1H, s), 7.35 (1H, dd, J=8.35, 1.26 Hz), 7.68 (1H, d, J=3.31 Hz), 7.78 (1H, d, J=3.31 Hz), 8.01 (1H, d, J=8.35 Hz), 8.27 (1H, d, J=5.52 Hz), 8.87 (1H, s); LC-MS: m/z=+462.1 (M+H)+.

Example 8

Preparation of 1-(2-aminopyrimidin-4-yl)-1H-indazole-6-carbonitrile

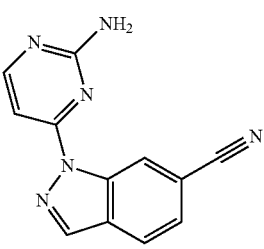

(8-a)

To a solution of 1H-indazole-6-carbonitrile (200 mg, 1.40 mmol) in DMF (2 mL), was added NaH (60% oil dispersion) (89.4 mg, 2.24 mmol). The reaction mixture was stirred for 10 min at RT before addition of 4-chloropyrimidin-2-amine (362 mg, 2.79 mmol). The reaction mixture was stirred at RT for 1 hr then heated at 50° C. in a sealed tube for 18 hr. LC-MS (Method B) indicated a mixture of desired product and a regiosiomer by-product [21%, Retention time=1.65 min, m/z=237.4 (M+H)+] and [29%, Retention time=1.43 min, m/z=237.4 (M+H)+]. The reaction was quenched by addition of water (1 mL) and EtOAc (3 mL). The precipitated solid was collected by suction filtration: LC-MS (Method B): Retention time=1.65 min.

LC-MS (Method B) of the filtrate showed Retention time=1.43 min as the major peak. Further trituration with EtOAc gave a second crop of solid, which was the title compound: ¹H NMR (500 MHz, MeOD) δ 7.29 (1H, d, J=5.65 Hz), 7.63 (1H, dd, J=8.24, 1.22 Hz), 8.03 (1H, dd, J=8.24, 0.46 Hz), 8.29 (1H, d, J=5.80 Hz), 8.45 (1H, s), 9.45 (1H, s); LC-MS: m/z=+236.90 (M+H)+.

Example 9

Preparation of N-[2-amino-4-(6-cyano-1H-indazol-1-yl)pyrimidin-5-yl]-3-methyloxetane-3-carboxamide

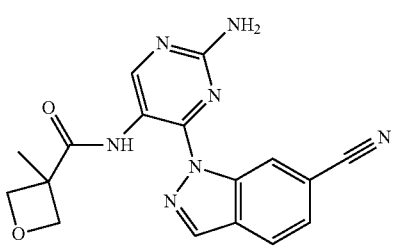

(9-e)

Step 1—Synthesis of 2-amino-5-nitro-3,4-dihydropyrimidin-4-one

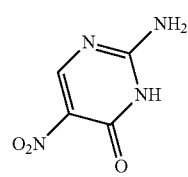

(9-a)

Concentrated sulfuric acid (2.4 mL) was added to 2-amino-3,4-dihydropyrimidin-4-one (1 g, 9.0 mmol). The mixture was stirred and cooled in ice bath before dropwise addition of concentrated nitric acid (0.56 mL). The mixture was stirred at RT for 30 min before being heated at 70° C. for 2 hr. The mixture was allowed to cool to RT and was slowly added to water (10 mL), cooled in an ice bath. The resultant precipitate was collected by suction filtration, washed with diethyl ether (5 mL) and then thoroughly dried under high vacuum to give the title compound: $^1$H NMR (250 MHz, DMSO) δ 7.18 (1H, br. s.), 8.61 (1H, br. s.), 8.81 (1H, s); LC-MS: m/z=+156.9 (M+H)+.

Step 2—Synthesis of 6-chloro-5-nitro-1,6-dihydropyrimidin-2-amine

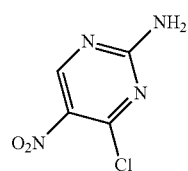

(9-b)

A suspension mixture of 2-amino-5-nitro-3,4-dihydropyrimidin-4-one (1.5 g, 9.61 mmol) and phosphorus oxychloride (27 mL, 0.29 mol) was heated under reflux (100° C.) for 18 hr. The reaction mixture turned into a yellow solution. The mixture was cooled to RT before being concentrated in vacuo. DCM (10 mL) was added and concentrated in vacuo was repeated. Ice (ca 5 g) was added, resulted in a sticky solid. DCM (20 mL) was added and the mixture was quenched by addition to an ice-cold saturated aqueous NaHCO$_3$ solution (150 mL). The pH of mixture was adjusted to basic by final addition of 2M aq K$_2$CO$_3$. Attempt to extract product with DCM resulted in emulsion formation. Emulsion was removed by suction filtration. The aqueous layer was extracted with EtOAc (3×50 mL). The EtOAc extracts were combined with the DCM extract, dried over Na$_2$SO$_4$, filtered and concentrated in vacuo to afford the title compound as a yellow powder: $^1$H NMR (500 MHz, DMSO) δ 8.40-8.48 (2H, m), 9.02 (1H, s). LC-MS: m/z=+174.9 (M+H)+.

Step 3—Synthesis of 1-(2-amino-5-nitro-3,4-dihydropyrimidin-4-yl)-1H-indazole-6-carbonitrile

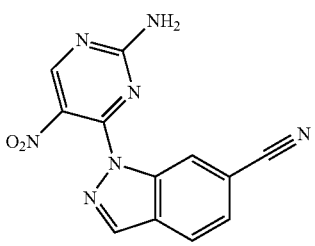

(9-c)

To a solution of 6-chloro-5-nitro-1,6-dihydropyrimidin-2-amine (538.5 mg, 60% purity, 2.00 mmol) in DMF (10 mL) was added NaH (60% oil suspension, 172 mg, 4.30 mmol) at 0° C. Mixture was stirred at RT for 10 min before addition of 1H-indazole-6-carbonitrile (410 mg, 2.87 mmol). Stirring was continued at RT for 18 hr. The reaction mixture was quenched with water (25 mL) cooled in an ice bath and extracted with EtOAc (3×20 mL). Insoluble solid formed during extraction was separated out. Combined EtOAc extract was washed with water (20 mL), dried over Na$_2$SO$_4$, filtered and concentrated in vacuo. A portion (70 mg) of the crude product was purified by reverse phase preparative HPLC to give the title compound: $^1$H NMR (250 MHz, DMSO) δ 7.79 (1 H, dd, J=8.22, 1.07 Hz), 8.14 (1H, d, J=8.22 Hz), 8.20 (1H, br. s.), 8.33 (1H, br. s.), 8.65 (1H, s), 8.91 (1H, s), 9.03 (1H, s); LC-MS: m/z=+281.95 (M+H)+.

Step 4—Synthesis of 1-(2,5-diaminopyrimidin-4-yl)-1H-indazole-6-carbonitrile

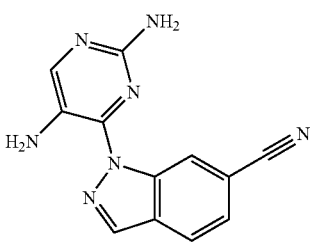

(9-d)

A mixture of 1-(2-amino-5-nitro-3,4-dihydropyrimidin-4-yl)-1H-indazole-6-carbonitrile (40% purity, 400 mg, 0.64 mmol) and tin (II) chloride (577 mg, 2.56 mmol) in ethanol (15 mL) was heated at 60° C. for 2 hr then at 70° C. for 3 hr. LC-MS (Method B) showed 11% desired product and 74% degradation. The reaction mixture was concentrated in vacuo. The residue was vigorously stirred with a mixture of saturated aqueous Rochelle salt (potassium sodium tartrate (20 mL), saturated aqueous NaHCO$_3$ (20 mL) and EtOAc (30 mL) for 30 min. The EtOAc layer was washed with brine (10 mL), dried over Na$_2$SO$_4$, filtered and concentrated in vacuo. The crude was purified by column chromatography (Biotage) (100% EtOAc) to give the title compound as a pale yellow solid: $^1$H NMR (250 MHz, DMSO) δ 5.40 (2H, br. s.), 6.30 (2H, s), 7.69 (1H, dd, J=8.38, 1.22 Hz), 8.01-8.25 (2H, m), 8.62 (1H, d, J=0.76 Hz), 9.31 (1H, s); LC-MS: m/z=+252.0 (M+H)+.

Step 5—Synthesis of N-[2-amino-4-(6-cyano-1H-indazol-1-yl)pyrimidin-5-yl]-3-methyloxetane-3-carboxamide To a mixture of 3-methyloxetane-3-carboxylic acid (17 mg, 0.143 mmol) and HATU (54.5 mg, 0.143 mmol) was added a solution of 1-(2,5-diaminopyrimidin-4-yl)-1H-indazole-6-carbonitrile (30 mg, 0.072 mmol) in DMF (0.5 mL) followed by triethylamine (0.030 mL, 0.215 mmol). The mixture was stirred at RT for 10 min, then diluted with EtOAc (10 mL) and washed with water (2×3 mL). The combined organic layer was dried over Na$_2$SO$_4$, filtered and concentrated in vacuo to give the crude compound. The crude product was purified by flash chromatography (Isolute column, 90% EtOAc in heptane to 100% EtOAc and then 0.5% MeOH/EtOAc) to afford the title compound as a pale yellow solid: $^1$H NMR (250 MHz, DMSO) δ 1.61 (3H, s), 4.31 (2H, d, J=5.94 Hz), 4.83 (2H, d, J=5.94 Hz), 7.20 (2H, br. s.), 7.65-7.92 (1H, m), 8.12 (1H, dd, J=8.22, 0.76 Hz), 8.49 (1H, s), 8.64 (1H, d, J=0.91 Hz), 9.14 (1H, s), 9.70 (1H, s); LC-MS: m/z=+350.1 (M+H)+.

Example 10

Preparation of N-(2-amino-4-{6-[3-hydroxy-3-(1,3-thiazol-2-yl)but-1-yn-1-yl]-1H-indazol-1-yl}pyrimidin-5-yl)-3-methyloxetane-3-carboxamide

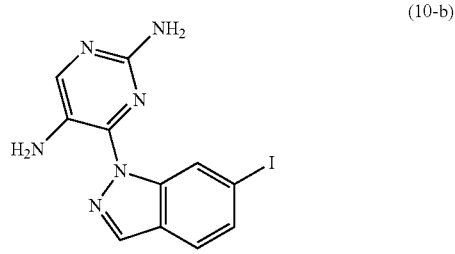
(10-d)

Step 1—Synthesis of 4-(6-iodo-1H-indazol-1-yl)-5-nitropyrimidin-2-amine

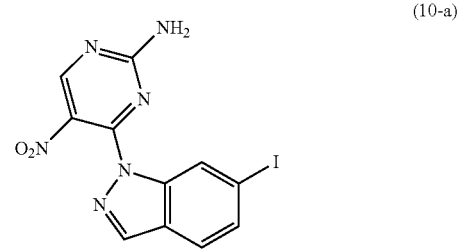 [SMILES: Nc1ncc([N+](=O)[O-])c(-n2ncc3ccc(I)cc32)n1]
(10-a)

To a solution of 6-iodo-1H-indazole (537 mg, 2.20 mmol) in DMF (16 mL) was added NaH (60% oil dispersion) (132 mg, 3.30 mmol) at 0° C. Mixture was stirred at RT for 10 min before addition of a portion of 6-chloro-5-nitro-1,6-dihydropyrimidin-2-amine (60% pure, 500 mg, 1.71 mmol). The mixture was stirred at RT for 20 min. Another portion of NaH (60% oil dispersion) (132 mg, 3.30 mmol) was added at RT. After 10 min, another portion of 6-chloro-5-nitro-1,6-dihydropyrimidin-2-amine (60% pure, 300 mg, 1.03 mmol) was added. Stirring continued for 30 min. The reaction mixture was cooled in an ice bath before quenching with water. The mixture was acidified by addition of 1 M aq HCl then the pH was adjusted to 8-9 by dropwise addition of saturated aq NaHCO$_3$.

The mixture was further diluted with water (20 mL) and extracted with EtOAc (20 mL×3). During the first extraction with EtOAc the insoluble solid was removed by suction filtration. The combined EtOAc layer was washed with water (20 mL), dried over Na$_2$SO$_4$ filtered and concentrated in vacuo to give the crude title compound: LC-MS (Method B): m/z=+382.9 (M+H)+, (purity=45%) This intermediate was used in the next step without further purification.

Step 2—Synthesis of 4-(6-iodo-1H-indazol-1-yl)pyrimidine-2,5-diamine

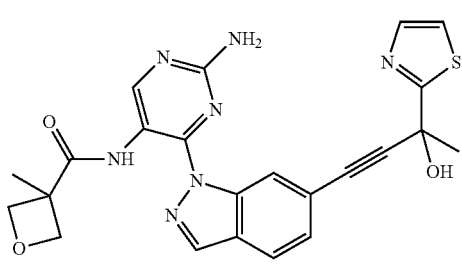
(10-b)

To a suspension of 4-(6-iodo-1H-indazol-1-yl)-5-nitropyrimidin-2-amine (200 mg, 45% purity, 0.236 mmol) in a mixture of methanol (4 mL), DMF (3 mL) and water (3 mL) was added sodium dithionite (205 mg, 1.178 mmol) and sodium bicarbonate (99 mg, 1.178 mmol). The suspension was stirred at RT for 2 hr. After 2 hr LC-MS (Method B) showed 11% of desired product, 15% of starting 4-(6-iodo-1H-indazol-1-yl)-5-nitropyrimidin-2-amine (16-a) and 67% of degraded by-product. The reaction mixture was diluted with EtOAc (30 mL) and washed with water (2×10 mL), then dried over Na$_2$SO$_4$, filtered and concentrated in vacuo to give the crude title compound; m/z=+352.9 (M+H)+, (purity=11%). This intermediate was used in the next step without further purification.

Step 3—Synthesis of N-[2-amino-4-(6-iodo-1H-indazol-1-yl)pyrimidin-5-yl]-3-methyloxetane-3-carboxamide

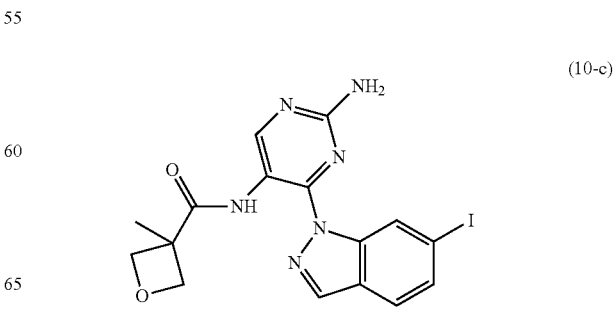
(10-c)

To a mixture of 3-methyloxetane-3-carboxylic acid (8.7 mg, 0.075 mmol) and HATU (28.5 mg, 0.075 mmol) was added a solution of crude 4-(6-iodo-1H-indazol-1-yl)pyrimidine-2,5-diamine (11% purity, 120 mg, 0.037 mmol) in DMF (0.5 mL) followed by triethylamine (0.016 mL, 0.112 mmol). The mixture was stirred at RT for 10 min, then diluted with EtOAc (10 mL) and washed with water (2×3 mL). The combined organic layer was dried over $Na_2SO_4$, filtered and concentrated in vacuo to give the crude compound. Purification by flash chromatography (Isolute column, 100% DCM to 3% MeOH in DCM) gave the title compound; m/z=+451.30 (M+H)+, (purity=76%). This intermediate was used in the next step without further purification.

Step 4—Synthesis of N-(2-amino-4-{6-[3-hydroxy-3-(1,3-thiazol-2-yl)but-1-yn-1-yl]-1H-indazol-1-yl}pyrimidin-5-yl)-3-methyloxetane-3-carboxamide To a mixture of N-[2-amino-4-(6-iodo-1H-indazol-1-yl)pyrimidin-5-yl]-3-methyloxetane-3-carboxamide (76% purity, 20 mg, 0.034 mmol) and piperidine (0.1 mL) was added tetrakis(triphenylphosphine)palladium (7.8 mg, 0.007 mmol), copper(I) iodide (1.2 mg, 0.007 mmol) and 2-(1,3-thiazol-2-yl)but-3-yn-2-ol (I-1) (10.3 mg, 0.068 mmol). The reaction was purged with $N_2$ and stirred at RT for 2 hr. Reaction mixture was concentrated in vacuo. Purification by flash chromatography (Isolute column, 100% DCM to 2% MeOH-DCM) followed by recrystallization (1:1 MeOH-EtOAc mixture) gave the title compound: $^1$H NMR (500 MHz, MeOD) δ 1.73 (3H, s), 1.98 (3H, s), 4.47 (2H, d, J=5.99 Hz), 5.01 (2H, d, J=6.15 Hz), 7.43 (1H, dd, J=8.28, 1.18 Hz), 7.57 (1H, d, J=3.31 Hz), 7.79 (1H, d, J=3.31 Hz), 7.83 (1H, d, J=8.35 Hz), 8.39 (1H, s), 8.82 (1H, s), 8.92 (1H, s); m/z=+476.1 (M+H)+.

Example 11

Preparation of 1-{4-[(2-methoxypyridin-3-yl)amino]-1,3,5-triazin-2-yl}-1H-indazole-6-carbonitrile

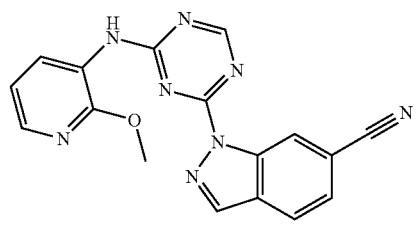

(11-b)

Step 1—Synthesis of 4-chloro-N-(2-methoxypyridin-3-yl)-1,3,5-triazin-2-amine

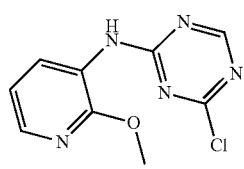

(11-a)

To a solution of 2,4-dichloro-1,3,5-triazine (265.77 mg, 1.77 mmol) in THF (5 mL) was added DIPEA (0.266 mL, 1.61 mmol) followed by 2-methoxypyridin-3-amine (200 mg, 1.61 mmol). The resultant mixture was stirred at RT for 2 hr, then DCM was added and the organics washed with water (×2) and 0.5M aqueous HCl solution. Combined organics were dried over $Na_2SO_4$, filtered and concentrated in vacuo to give a beige solid: $^1$H NMR (250 MHz, DMSO) δ 3.88 (3H, s), 7.05 (1H, dd, J=7.54, 4.95 Hz), 7.86 (1H, dd, J=7.61, 1.68 Hz), 8.07 (1H, dd, J=4.95, 1.75 Hz), 8.56 (1H, s), 10.14 (1H, s); =+238.0/239.9 (M+H)+.

Step 2—Synthesis of 1-{4-[(2-methoxypyridin-3-yl)amino]-1,3,5-triazin-2-yl}-1H-indazole-6-carbonitrile To a solution of 1H-indazole-6-carbonitrile (70 mg, 0.49 mmol) in DMF (5 mL) was added NaH (60% oil dispersion, 39.12 mg, 0.98 mmol) at 0° C. The reaction mixture was stirred at 0° C. for 10 minutes before the addition of 4-chloro-N-(2-methoxypyridin-3-yl)-1,3,5-triazin-2-amine (139.45 mg, 0.59 mmol). Stirring at RT was continued for 2 hr. The reaction mixture was then quenched with water and EtOAc was added. Precipitate formed was collected by suction filtration, then redissolved in DCM and washed with water. Further trituration (9:1 mixture of heptane/$Et_2O$) gave the title compound: $^1$H (250 MHz, $CDCl_3$, VT @ 323K) δ 4.10 (3H, s), 7.06 (1H, br. s.), 7.60 (1H, dd, J=8.22, 1.37 Hz), 7.91 (1H, dd, J=8.22, 0.76 Hz), 7.97 (2H, d), 8.42 (1H, d, J=0.76 Hz), 8.74 (1H, dd, J=7.84, 1.60 Hz), 8.86 (1H, s), 9.20 (1H, s); m/z=+345.0 (M+H)+.

Example 12

Preparation of 4-(6-bromo-1H-indazol-1-yl)-N-(2-methoxypyridin-3-yl)-1,3,5-triazin-2-amine

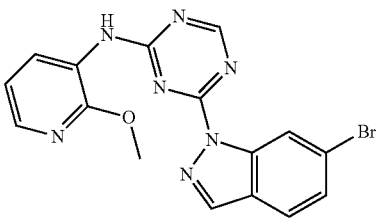

(12-a)

To a solution of 6-bromo-1H-indazole (172 mg, 0.87 mmol) in DMF (8 mL) was added NaH (60% in oil, 69.8 mg, 1.75 mmol) at 0° C. The reaction mixture was stirred at 0° C. for 10 minutes before the addition of 4-chloro-N-(2-methoxypyridin-3-yl)-1,3,5-triazin-2-amine (311.18 mg, 1.31 mmol). Stirring was continued at RT for 2 hr. The reaction mixture was quenched with water and EtOAc added. The resultant precipitate was collected and further drying under vacuum gave the title compound as a beige solid; $^1$H NMR (250 MHz, $CDCl_3$) δ 4.09 (3H, s), 7.05 (1H, d, J=2.28 Hz), 7.50 (1H, dd, J=8.53, 1.68 Hz), 7.62-7.70 (1H, m), 7.88-8.09

(2H, m), 8.30 (1H, d, J=0.76 Hz), 8.74 (1H, dd, J=7.77, 1.68 Hz), 8.83 (1H, s), 9.01 (1H, s); LC-MS: m/z=+397.9/399.8 (M+H)+.

Example 13

Preparation of 4-(1-{4-[(2-methoxypyridin-3-yl)amino]-1,3,5-triazin-2-yl}-1H-indazol-6-yl)-2-methylbut-3-yn-2-ol

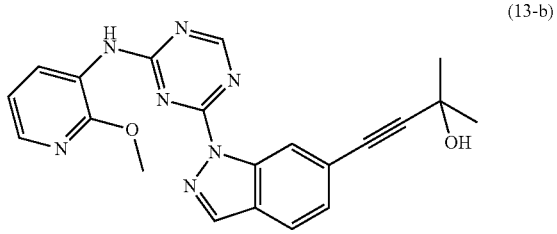 [SMILES: COc1ncccc1Nc1ncnc(-n2ncc3ccc(C#CC(C)(C)O)cc32)n1]

(13-b)

Step 1—Synthesis of 4-(6-iodo-1H-indazol-1-yl)-N-(2-methoxypyridin-3-yl)-1,3,5-triazin-2-amine

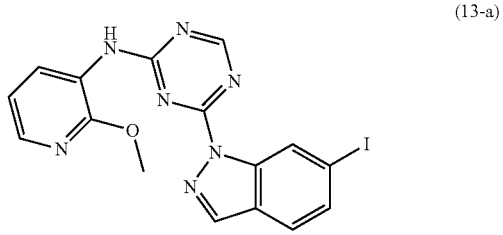 [SMILES: COc1ncccc1Nc1ncnc(-n2ncc3ccc(I)cc32)n1]

(13-a)

The title compound was prepared by the procedure described in Example 12 by substituting 6-bromo-1H-indazole with 6-iodo-1H-indazole; ¹H NMR (500 MHz, CDCl₃) δ 4.06 (3H, s), 6.88-7.24 (1H, m), 7.52 (1H, d, J=8.35 Hz), 7.67 (1H, dd, J=8.35, 0.79 Hz), 7.80-8.16 (2H, m), 8.29 (1 H, d, J=0.63 Hz), 8.64-8.91 (2H, m), 9.03-9.34 (1H, m); LC-MS (Method B): m/z=+446.0 (M+H)+.

Step 2—Synthesis of 4-(1-{4-[(2-methoxypyridin-3-yl)amino]-1,3,5-triazin-2-yl}-1H-indazol-6-yl)-2-methylbut-3-yn-2-ol To a pressure tube was added 4-(6-iodo-1H-indazol-1-yl)-N-(2-methoxypyridin-3-yl)-1,3,5-triazin-2-amine (100 mg, 0.22 mmol), followed by triethylamine (0.7 mL) and THF (0.7 mL). Copper(I) iodide (4.28 mg, 0.022 mmol), PdCl₂(PPh₃)₂ (15.76 mg, 0.022 mmol) and 2-methylbut-3-yn-2-ol (0.04 ml, 0.45 mmol) were then added and the reaction vessel was sealed and stirred at RT for 1 hr.

The reaction was concentrated in vacuo and DCM was added. The organics were washed with 0.1M aq HCl, water and brine. Combined organics were dried over Na₂SO₄, filtered and concentrated in vacuo to give a red solid which was purified by flash chromatography (Isolute column, 1% MeOH in DCM to 2.5% MeOH in DCM). Further trituration (10% diethyl ether in heptane) afforded the title compound as a red solid; ¹H NMR (250 MHz, CDCl₃, VT @ 323K) δ 1.70 (6H, s), 2.15 (1H, br. s.), 4.09 (3H, s), 7.04 (1H, br. s.), 7.33-8.92 (7H, m); LC-MS: m/z=+401.4 (M+H)+.

Example 14

Preparation of 4-[1-(2-aminopyrimidin-4-yl)-1H-1,3-benzodiazol-6-yl]-2-(1,3-thiazol-2-yl)but-3-yn-2-ol

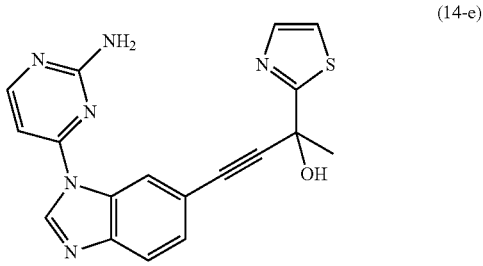 [SMILES: CC(O)(C#Cc1ccc2ncn(-c3ccnc(N)n3)c2c1)c1nccs1]

(14-e)

Step 1—Synthesis of N-(5-bromo-2-nitrophenyl)-2-chloropyrimidin-4-amine

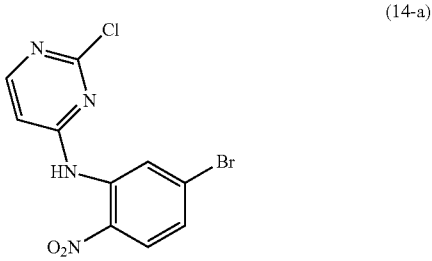 [SMILES: O=[N+]([O-])c1ccc(Br)cc1Nc1ccnc(Cl)n1]

(14-a)

To a solution of 2-chloropyrimidin-4-amine (8.83 g, 68.18 mmol) in THF (250 mL) at 0° C. was added sodium hydride (60% dispersion in oil, 4.36 g, 181.82 mmol) portionwise. The reaction mixture was stirred at 0° C. to RT for 10 minutes before addition of 4-bromo-2-fluoro-1-nitrobenzene (10 g, 45.45 mmol). The reaction mixture was stirred at 65° C. for 1 hr, then after cooling to RT, water was added resulting in formation of a yellow precipitate. The solid was collected by suction filtration and was washed with water. The filtrate was extracted with DCM. The organics were washed with water, dried over Na₂SO₄, filtered and concentrated in vacuo. The residue was purified by flash chromatography (Isolute column, 1% MeOH in DCM) then combined with the solid collected by suction filtration to give the title compound: ¹HNMR (250 MHz, DMSO) δ 6.91 (1H, d, J=5.79 Hz), 7.61 (1H, dd, J=8.76, 2.21 Hz), 7.91-8.05 (2H, m), 8.29 (1H, d, J=5.79 Hz), 10.40 (1H, s); LC-MS: m/z=+328.9, 330.8 (M+H)+.

Step 2—Synthesis of 4-N-(5-bromo-2-nitrophenyl)pyrimidine-2,4-diamine

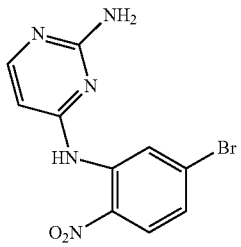

(14-b)

To a solution of N-(5-bromo-2-nitrophenyl)-2-chloropyrimidin-4-amine (6 g, 18.21 mmol) in 2-propanol (70 mL), in a pressure vessel, was carefully added ammonium hydroxide solution (150 mL) at RT. The reaction vessel was sealed and stirred at 90° C. (at 4.5 bar pressure) for 20 hr. The reaction mixture was cooled to 0° C. The resulting precipitate was collected by vacuum filtration, washed with water and dried in the vacuum oven to afford the title compound as an orange solid: $^1$H NMR (250 MHz, DMSO) δ 6.17 (1H, d, J=5.63 Hz), 6.34 (2H, br. s.), 7.39 (1H, dd, J=8.83, 1.98 Hz), 7.89-7.99 (2H, m), 8.34 (1H, d, J=2.13 Hz), 9.62 (1H, s); LC-MS: m/z+309.9, 311.7 (M+H)+.

Step 3—Synthesis of 4-N-(2-amino-5-bromophenyl)pyrimidine-2,4-diamine

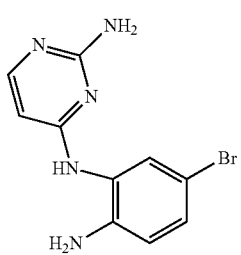

(14-c)

To a solution of 4-N-(5-bromo-2-nitrophenyl)pyrimidine-2,4-diamine (5.06 g, 16.32 mmol) in ethanol (110 mL) was added tin(II) chloride dihydrate (12.89 g, 57.11 mmol). The reaction mixture was stirred at 65° C. for 2 hr. The reaction mixture was evaporated to dryness and ice-water added. The pH of the mixture was adjusted to 10 using saturated aqueous $Na_2CO_3$ solution. EtOAc was added followed by saturated aqueous Rochelles salt (potassium sodium tartrate). The resulting mixture was stirred until separate layers were observed. The organic layer was extracted and the extraction repeated (2×) with EtOAc and DCM. Combined organic layer were washed with brine, dried over $Na_2SO_4$, filtered and concentrated in vacuo to give the title compound as a pale yellow solid: $^1$H NMR (250 MHz, DMSO) δ 5.05 (2H, br. s), 5.79 (1H, d, J=5.79 Hz), 6.08 (2H, br. s), 6.68 (1H, d, J=8.53 Hz), 7.02 (1H, dd, J=8.60, 2.36 Hz), 7.36 (1H, d, J=2.28 Hz), 7.75 (1H, d, J=5.63 Hz), 8.15 (1H, s); LC-MS: m/z=+279.9, 281.9 (M+H)+.

Step 4—Synthesis of 4-(6-bromo-1H-1,3-benzodiazol-1-yl)pyrimidin-2-amine

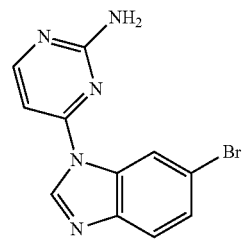

(14-d)

To a solution of 4-N-(2-amino-5-bromophenyl)pyrimidine-2,4-diamine (750 mg, 2.68 mmol) in mixture of methanol (7 mL) and THF (30 mL) was added trimethyl orthoformate (8.81 ml, 80.32 mmol) and TsOH (0.04 ml, 0.27 mmol). The reaction mixture was stirred at 70° C. for 1 h. Then another portion of trimethyl orthoformate (4.4 ml, 40.16 mmol) was added. Stirring at 70° C. was continued for another 6 hr. The reaction mixture was allowed to cool down to RT then a saturated aqueous solution of $NaHCO_3$ was added. The product was extracted into DCM (×3) and the combined organic layers were washed with brine and dried over $Na_2SO_4$, filtered and concentrated in vacuo to give the title compound; $^1$H NMR (500 MHz, DMSO) δ 7.08-7.24 (3H, m), 7.50 (1H, dd, J=8.51, 1.89 Hz), 7.71 (1H, d, J=8.51 Hz), 8.37 (1H, d, J=5.52 Hz), 8.83 (1H, d, J=1.73 Hz), 9.08 (1H, s); LC-MS (Method B): m/z=+289.9, 291.8 (M+H)+. This compound, with LC-MS purity=70%, was used in the next step without further purification.

Step 5—Synthesis of 4-[1-(2-aminopyrimidin-4-yl)-1H-1,3-benzodiazol-6-yl]-2-(1,3-thiazol-2-yl)but-3-yn-2-ol To a pressure tube was added 4-(6-bromo-1H-1,3-benzodiazol-1-yl)pyrimidin-2-amine (70% purity, 790 mg, 1.91 mmol), followed by piperidine (4 mL), tetrakis(triphenylphosphine)palladium (220 mg, 0.19 mmol), copper(I) iodide (36.3 mg, 0.19 mmol)) and 2-(1,3-thiazol-2-yl)but-3-yn-2-ol (584.04 mg, 3.81 mmol). The reaction was capped and stirred at 75° C. for 3.5 hr. The reaction mixture was concentrated in vacuo and purified by flash chromatography (Isolute column, 2% MeOH in DCM to 3% MeOH in DCM) followed by reverse phase preparative HPLC to give the title compound as a pale yellow solid: $^1$H NMR (500 MHz, DMSO) δ 1.92 (3H, s), 7.03 (1H, br. s.), 7.08-7.20 (3H, m), 7.38 (1H, dd, J=8.35, 1.58 Hz), 7.69 (1H, d, J=3.15 Hz), 7.74 (1H, d, J=8.35 Hz), 7.78 (1H, d, J=3.31 Hz), 8.38 (1H, d, J=5.52 Hz), 8.56 (1H, d, J=0.95 Hz), 9.08 (1H, s); LC-MS: m/z=+363.4 (M+H)+.

Example 15

Examples in Table 3 were prepared by procedure described in Example 14 by reacting 4-(6-bromo-1H-1,3-benzodiazol-1-yl)pyrimidin-2-amine (14-d) with the appropriate but-3-yn-2-ol intermediates.

TABLE 3

| No. | Structure | Name | ¹H NMR | MS (M + H) |
|---|---|---|---|---|
| T3-15.1 | 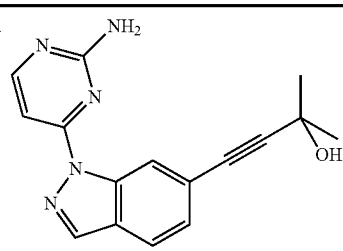 | 4-[1-(2-aminopyrimidin-4-yl)-1H-1,3-benzodiazol-6-yl]-2-methylbut-3-yn-2-ol | (500 MHz, DMSO) δ 1.51 (6 H, s), 5.46 (1H, br. s.), 7.07-7.25 (3 H, m), 7.35 (1 H, dd, J = 8.35, 1.58 Hz), 7.72 (1 H, d, J = 8.35 Hz), 8.38 (1 H, d, J = 5.52 Hz), 8.55 (1 H, d, J = 0.95 Hz), 9.07 (1 H, s) | 294.4 |
| T3-15.2 | 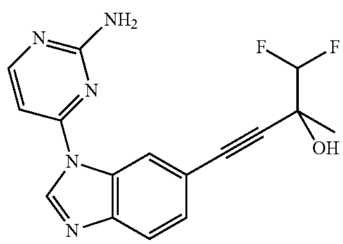 [SMILES: CC(O)(C#Cc1ccc2ncn(-c3ccnc(N)n3)c2c1)C(F)F] | 4-[1-(2-aminopyrimidin-4-yl)-1H-1,3-benzodiazol-6-yl]-1,1-difluoro-2-methylbut-3-yn-2-ol | (500 MHz, DMSO) δ 1.52 (3 H, s), 5.83-6.09 (1 H, m), 6.43 (1 H, s), 7.14 (1 H, d, J = 5.67 Hz), 7.17 (2 H, br. s.), 7.40 (1 H, dd, J = 8.20, 1.58 Hz), 7.76 (1 H, d, J = 8.20 Hz), 8.39 (1 H, d, J = 5.52 Hz), 8.61 (1H, d, J = 0.95 Hz), 9.11 (1 H, s) | 330.4 |
| T3-15.3 | 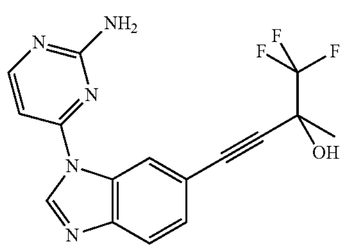 [SMILES: CC(O)(C#Cc1ccc2ncn(-c3ccnc(N)n3)c2c1)C(F)(F)F] | 4-[1-(2-aminopyrimidin-4-yl)-1H-1,3-benzodiazol-6-yl]-1,1,1-trifluoro-2-methylbut-3-yn-2-ol | (500 MHz, DMSO) δ 1.67 (3 H, s), 7.13-7.16 (2 H, m), 7.19 (2 H, br. s.), 7.43 (1 H, dd, J = 8.35, 1.58 Hz), 7.78 (1H, d, J = 8.35 Hz), 8.39 (1 H, d, J = 5.36 Hz), 8.65 (1H, d, J = 0.95 Hz), 9.13 (1 H, s) | 348.4 |
| T3-15.4 | 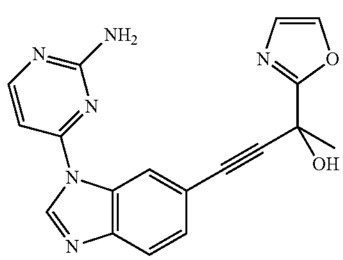 [SMILES: CC(O)(C#Cc1ccc2ncn(-c3ccnc(N)n3)c2c1)c1ncco1] | 4-[1-(2-aminopyrimidin-4-yl)-1H-1,3-benzodiazol-6-yl]-2-(1,3-oxazol-2-yl)but-3-yn-2-ol | (500 MHz, DMSO) δ 1.92 (3 H, s), 6.73 (1 H, s), 7.13 (1H, d, J = 5.67 Hz), 7.18 (2 H, br. s), 7.23 (1H, s), 7.39 (1 H, dd, J = 8.35, 1.58 Hz), 7.75 (1 H, d, J = 8.35 Hz), 8.15 (1 H, d, J = 0.79 Hz), 8.38 (1 H, d, J = 5.52 Hz), 8.60 (1H, d, J = 0.95 Hz), 9.11 (1 H, s) | 347.4 |

Example 16

Preparation of 1-(2-aminopyrimidin-4-yl)-1H-1,3-benzodiazole-6-carbonitrile

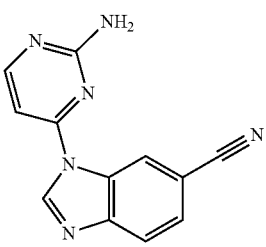

(16-a)

To a round bottom flask equipped with a condenser and nitrogen bubbler attached to a bleach scrubber bath was added 4-(6-bromo-1H-1,3-benzodiazol-1-yl)pyrimidin-2-amine (90% purity, 83 mg, 0.26 mmol) and zinc cyanide (30.23 mg, 0.26 mmol) in de-gassed DMF (2 mL). Tetrakis(triphenylphosphine)palladium (29.75 mg, 0.03 mmol) was then added and the reaction heated stirred at 100° C. under nitrogen for 30 min. The reaction mixture was allowed to cool to RT and poured into saturated aqueous ammonium chloride (6 mL) and extracted into DCM (×2). The combined organics were dried over Na₂SO₄, filtered and concentrated in vacuo. The residue was combined with the precipitate formed during the aqueous work up process and was purified by flash chromatography (Isolute column, 10% MeOH in DCM) to afford the title compound as a pale beige solid; ¹H NMR (500 MHz, DMSO) δ 6.90-7.42 (3H, m), 7.76 (1H, dd, J=8.35, 1.58 Hz), 7.94 (1H, d, J=8.04 Hz), 8.40 (1H, d, J=5.52 Hz), 9.20 (1H, d, J=0.95 Hz), 9.33 (1H, s); LC-MS: m/z=+236.95 (M+H)+.

Example 17

Preparation of 4-[1-(2-aminopyrimidin-4-yl)-2-methyl-1H-1,3-benzodiazol-6-yl]-2-(1,3-thiazol-2-yl)but-3-yn-2-ol

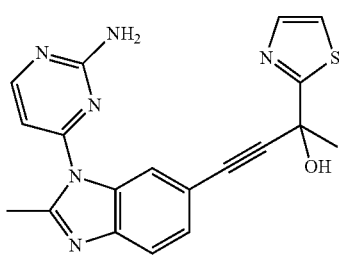
(17-b)

Step 1—Synthesis of 4-(6-bromo-2-methyl-1H-1,3-benzodiazol-1-yl)pyrimidin-2-amine

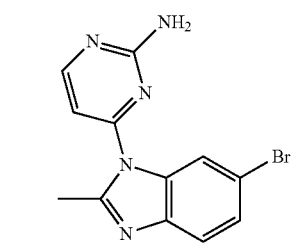
(17-a)

To a solution of 4-N-(2-amino-5-bromophenyl)pyrimidine-2,4-diamine (300 mg, 1.07 mmol) in a mixture of methanol (5 mL) and THF (20 mL) was added trimethyl orthoacetate (2.02 ml, 0.02 mol) and TsOH (0.02 ml, 0.11 mmol). The reaction mixture was stirred at 70° C. for 40 min then allowed to stand at RT for 3 days. A saturated aqueous solution of NaHCO$_3$ was added. The product was extracted into DCM (×3) and the organic layers were washed with brine and then dried with Na$_2$SO$_4$, filtered and concentrated in vacuo. The residue was purified by flash chromatography (Isolute column, 1-2% MeOH in DCM) to give the title compound as a yellow solid; $^1$H NMR (500 MHz, DMSO) δ 2.67 (3H, s), 6.88 (1H, d, J=5.20 Hz), 7.13 (2H, br. s.), 7.41 (1H, dd, J=8.51, 1.89 Hz), 7.58 (1H, d, J=8.51 Hz), 7.86 (1H, d, J=1.89 Hz), 8.48 (1H, d, J=5.20 Hz); LC-MS: m/z=+303.9, 305.7 (M+H)+.

Step 2—Synthesis of 4-[1-(2-aminopyrimidin-4-yl)-2-methyl-1H-1,3-benzodiazol-6-yl]-2-(1,3-thiazol-2-yl)but-3-yn-2-ol The title compound was prepared by procedure described in Example 20 by substituting 4-(6-bromo-1H-1,3-benzodiazol-1-yl)pyrimidin-2-amine with 4-(6-bromo-2-methyl-1H-1,3-benzodiazol-1-yl)pyrimidin-2-amine in Step 5: $^1$H NMR (500 MHz, DMSO) δ 1.87 (3H, s), 2.67 (3H, s), 6.88 (1H, d, J=5.20 Hz), 7.00 (1H, s), 7.12 (1H, br. s.), 7.29 (1H, dd, J=8.28, 1.50 Hz), 7.61 (1H, d, J=8.35 Hz), 7.64 (1H, d, J=0.79 Hz), 7.67 (1H, d, J=3.31 Hz), 7.76 (1H, d, J=3.31 Hz), 8.48 (1H, d, J=5.20 Hz); LC-MS: m/z=+377.45 (M+H)+.

Example 18

Preparation of 4-[1-(2-aminopyrimidin-4-yl)-2-cyclopropyl-1H-1,3-benzodiazol-6-yl]-2-(1,3-thiazol-2-yl)but-3-yn-2-ol

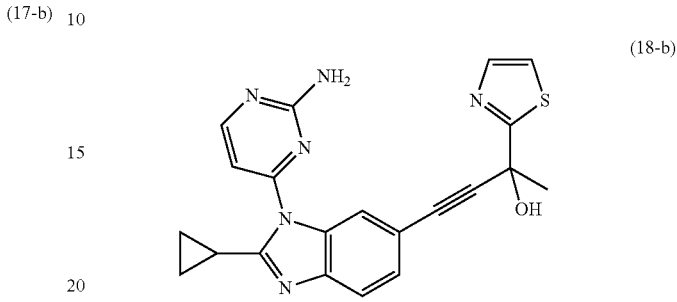
(18-b)

Step 1—Synthesis of 4-(6-bromo-2-cyclopropyl-1H-1,3-benzodiazol-1-yl)pyrimidin-2-amine

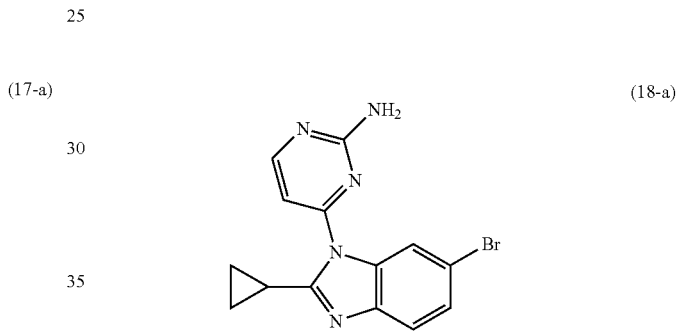
(18-a)

To a solution of 4-N-(2-amino-5-bromophenyl)pyrimidine-2,4-diamine (400 mg, 1.43 mmol) in DMF (4 mL) were added cyclopropanecarbaldehyde (130 mg, 1.86 mmol) and oxone (527 mg, 0.86 mmol). The reaction was stirred at RT for 3 days. The mixture was diluted with EtOAc (20 mL) and washed with water. The aqueous layer was extracted with more EtOAc. The combined organics were dried over Na$_2$SO$_4$, filtered and concentrated in vacuo. Purification by flash chromatography (Isolute column, 100% DCM to 2% MeOH/DCM) afforded the title compound as an orange solid: $^1$H NMR (500 MHz, MeOD) δ 1.16-1.24 (2H, m), 1.24-1.29 (2H, m), 2.32-2.48 (1H, m), 6.98 (1H, d, J=5.36 Hz), 7.41-7.45 (1H, m), 7.47-7.52 (1H, m), 7.90 (1H, d, J=1.89 Hz), 8.51 (1H, d, J=5.20 Hz); LC-MS (Method B): m/z=+330.0, 331.8 (M+H)+.

Step 2—Synthesis of 4-[1-(2-aminopyrimidin-4-yl)-2-cyclopropyl-1H-1,3-benzodiazol-6-yl]-2-(1,3-thiazol-2-yl)but-3-yn-2-ol The title compound was prepared by adaptation of procedure described in Example 14 by substituting 4-(6-bromo-1H-1,3-benzodiazol-1-yl)pyrimidin-2-amine with 4-(6-bromo-2-cyclopropyl-1H-1,3-benzodiazol-1-yl)pyrimidin-2-amine in Step 5: $^1$H NMR (500 MHz, DMSO) δ 1.07-1.14 (2H, m), 1.14-1.21 (2H, m), 1.86 (3H, s), 2.30-2.40 (1H, m), 6.91 (1H, d, J=5.04 Hz), 7.02 (1H, br.s.), 7.19 (2H, br. s.), 7.23-7.30 (1H, m), 7.55 (1H, d, J=8.20 Hz), 7.61-7.65 (1H, m), 7.68 (1H, d, J=3.31 Hz), 7.76 (1H, d, J=3.15 Hz), 8.37-8.61 (1H, m); LC-MS: m/z=+403.5 (M+H)+.

Example 19

Preparation of 4-[1-(2-aminopyrimidin-4-yl)-2-cyclopropyl-1H-1,3-benzodiazol-6-yl]-2-methylbut-3-yn-2-ol

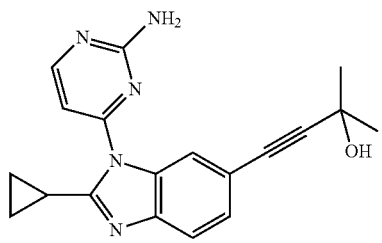
(19-a)

The title compound was prepared by procedure described in Example 25 by substituting 2-(1,3-thiazol-2-yl)but-3-yn-2-ol (I-1) with 2-methylbut-3-yn-2-ol (I-6) in Step 2: $^1$H NMR (500 MHz, DMSO) δ 1.08-1.15 (2H, m), 1.14-1.21 (2H, m), 1.47 (6H, s), 2.30-2.40 (1H, m), 5.42 (1 H, s), 6.91 (1H, d, J=5.20 Hz), 7.17 (2H, s), 7.21-7.28 (1H, m), 7.54 (1H, d, J=8.35 Hz), 7.60-7.64 (1H, m), 8.51 (1H, d, J=5.20 Hz); LC-MS: m/z=+334.5 (M+H)+.

Example 20

Preparation of 1-(2-aminopyrimidin-4-yl)-6-[3-hydroxy-3-(1,3-thiazol-2-yl)but-1-yn-1-yl]-2,3-dihydro-1H-1,3-benzodiazol-2-one

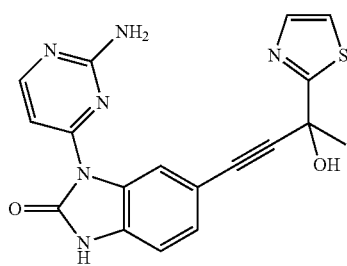
(20-b)

Step 1—Synthesis of 1-(2-aminopyrimidin-4-yl)-6-bromo-2,3-dihydro-1H-1,3-benzodiazol-2-one

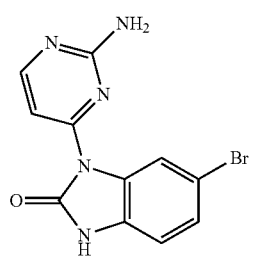
(20-a)

To a solution of 4-N-(2-amino-5-bromophenyl)pyrimidine-2,4-diamine (400 mg, 1.43 mmol) in DMF (4 mL) was added N,N'-carbonyldiimidazole (255 mg, 1.57 mmol). The reaction was stirred at 80° C. overnight. Another portion of N,N'-carbonyldiimidazole (69 mg, 0.43 mmol) was added and heating was continued for another 2 hr at 80° C. The reaction mixture was concentrated in vacuo, diluted with water (10 mL) and extracted with ethyl acetate (2×20 mL). The organics were dried over $Na_2SO_4$, filtered and concentrated in vacuo. The resulting yellow solid was slurried in ethyl acetate and filtered off to give the title compound as a yellow solid: $^1$H (500 MHz, DMSO) δ 6.93 (2H, br. s.), 7.00 (1H, d, J=8.35 Hz), 7.31 (1H, d, J=10.25 Hz), 7.45 (1H, d, J=5.67 Hz), 8.25 (1H, d, J=5.52 Hz), 8.58 (1H, s); LC-MS: m/z=+306.0, 307.9 (M+H)+.

Step 2—Synthesis of 1-(2-aminopyrimidin-4-yl)-6-[3-hydroxy-3-(1,3-thiazol-2-yl)but-1-yn-1-yl]-2,3-dihydro-1H-1,3-benzodiazol-2-one To a solution of 1-(2-aminopyrimidin-4-yl)-6-bromo-2,3-dihydro-1H-1,3-benzodiazol-2-one (230 mg, 0.751 mmol) in EtOAc was added charcoal (5 mol %). The mixture was stirred at RT for 20 min then filtered and concentrated in vacuo. To the residue in a sealed tube was added 2-(1,3-thiazol-2-yl)but-3-yn-2-ol (230 mg, 1.50 mmol), piperidine (2 mL), tetrakis(triphenylphosphine)palladium (43.4 mg, 0.038 mmol) and copper(I) iodide (14.3 mg, 0.075 mmol). The reaction mixture was then heated at 75° C. for 18 hr then partitioned between EtOAc (15 mL) and water (2 mL). The organic layer was concentrated in vacuo and the residue purified by reverse phase preparative HPLC to afford the title compound: $^1$H NMR (500 MHz, DMSO) δ 1.90 (3 H, s), 6.92 (2H, s), 6.95 (1H, s), 7.04 (1H, d, J=8.04 Hz), 7.21 (1H, dd, J=8.04, 1.42 Hz), 7.40 (1H, d, J=5.52 Hz), 7.68 (1H, d, J=3.31 Hz), 7.77 (1H, d, J=3.15 Hz), 8.26-8.36 (2H, m), 11.57 (1H, br. s.); LC-MS: m/z=+379.0 (M+H)+.

Example 21

Preparation of 1-(2-aminopyrimidin-4-yl)-6-(3-hydroxy-3-methylbut-1-yn-1-yl)-2,3-dihydro-1H-1,3-benzo diazol-2-one

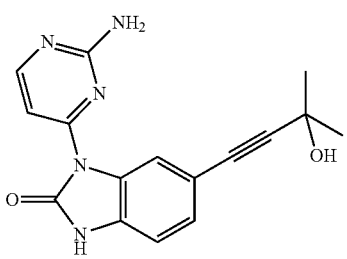
(21-a)

The title compound was prepared by adaptation of procedure described in Example 20 by substituting 2-(1,3-thiazol-2-yl)but-3-yn-2-ol with 2-methylbut-3-yn-2-ol in Step 2; $^1$H NMR (500 MHz, DMSO) δ1.49 (6H, s), 5.39 (1H, s), 6.92 (2H, br. s.), 7.03 (1H, d, J=8.04 Hz), 7.18 (1H, dd, J=8.04, 1.58 Hz), 7.42 (1H, d, J=5.67 Hz), 8.25-8.35 (2H, m), 11.54 (1H, br. s.); LC-MS: m/z=+310.4 (M+H)+.

Example 22

The following intermediates (I-1 to I-4) in Table 4 were prepared by modifying procedures described in WO 2009/158011.

TABLE 4

| No | Structure | Name | 1H NMR | MS (M + H) |
|---|---|---|---|---|
| T4-I.1 | 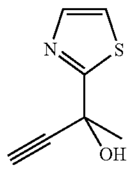 | 2-(1,3-thiazol-2-yl)but-3-yn-2-ol | (250 MHz, CDCl₃) δ 1.97 (3 H, s), 2.70 (1 H, s), 3.92 (1 H, br. s.), 7.34 (1 H, d, J = 3.20 Hz), 7.76 (1 H, d, J = 3.20 Hz) | 153.9 |
| T4-I.2 | 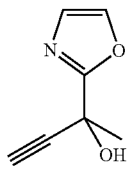 | 2-(1,3-oxazol-2-yl)but-3-yn-2-ol | (250 MHz, CDCl₃) δ 1.94 (3 H, s), 2.66 (1 H, s), 3.90 (1 H, br. s.), 7.13 (1 H, d, J = 0.76 Hz), 7.67 (1 H, d, J = 0.76 Hz) | 137.9 |
| T4-I.3 | 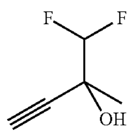 | 1,1-difluoro-2-methylbut-3-yn-2-ol | (250 MHz, CDCl₃) δ 1.53-1.58 (3 H, m), 2.50 (1 H, br. s.), 2.58 (1 H, s), 5.26-5.91 (1 H, m) | n/a |
| T4-I.4 | 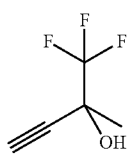 | 1,1,1-trifluoro-2-methylbut-3-yn-2-ol | (250 MHz, CDCl₃) δ 1.66 (3 H, s), 2.62 (1 H, s), 2.77 (1 H, br. s.) | n/a |
| T4-I.5 | 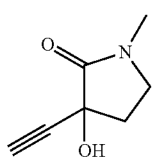 | 3-ethynyl-3-hydroxy-1-methylpyrrolidin-2-one | (500 MHz, CDCl3) delta ppm 2.29 (dt, J = 12.85, 8.24 Hz, 1 H) 2.54 (td, J = 6.46, 2.84 Hz, 1 H) 2.57 (s, 1 H) 2.93 (s, 3 H) 3.32-3.38 (m, 1 H) 3.39-3.47 (m, 1 H) 3.72 (br. s., 1 H) | 140 |
| T4-I.6 | 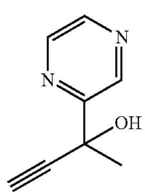 | 2-(pyrazin-2-yl)but-3-yn-2-ol | (500 MHz, CDCl₃) delta 1.87 (3 H, s), 2.65 (1 H, s), 4.45 (1 H, s), 8.51-8.56 (1 H, m), 8.59 (1 H, d, J = 2.52 Hz), 8.99 (1 H, d, J = 1.42 Hz) | 148.9 |
| T4-I.7 | 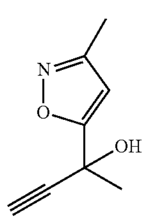 | 2-(3-methyl-1,2-oxazol-5-yl)but-3-yn-2-ol | n/a | |
| T4-I.8 | 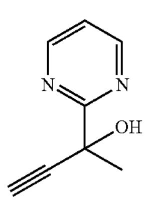 | 2-(pyrimidin-2-yl)but-3-yn-2-ol | (250 MHz, CDCl₃) delta 1.92 (3 H, s), 2.56 (1 H, s), 5.15 (1 H, s), 7.32 (1 H, t, J = 4.95 Hz), 8.82 (2 H, d, J = 4.87 Hz) | 148.9 |

TABLE 4-continued

| No | Name | 1H NMR | MS (M + H) |
|---|---|---|---|
| T4-I.9 | 4-ethynyl-1-methylpiperidin-4-ol | (250 MHz, CDCl$_3$) delta 2.08-1.74 (4 H, m), 2.27 (3 H, s), 2.43-2.30 (2 H, m), 2.48 (1 H, s), 2.75-2.56 (2 H, m), 3.49 (1 H, s). | 139.9 |
| T4-I.10 | 2-(1H-pyrazol-3-yl)but-3-yn-2-ol | n/a | 136.9 |
| T4-I.11 | 2-(5-methyl-1,2,4-oxadiazol-3-yl)but-3-yn-2-ol | (500 MHz, CDCl$_3$) delta 1.94 (3 H, s), 2.64 (3 H, s), 2.67 (1 H, s), 3.29 (1 H, br. s.) | 152.9 |
| T4-I.12 | 2-(1H-imidazol-4-yl)but-3-yn-2-ol | n/a | 136.9 |
| T4-I.13 | 7-ethynyl-5H,6H-pyrrolo[1,2-c]imidazol-7-ol | (250 MHz, DMSO) delta 3.07-2.59 (2 H, m), 3.57 (1 H, s), 4.31-3.92 (2 H, m), 6.26 (1 H, s), 6.77 (1 H, s), 7.52 (1 H, s). | 148.9 |
| T4-I.14 | 2-(3-methyl-1,2,4-oxadiazol-5-yl)but-3-yn-2-ol | (250 MHz, CDCl$_3$) delta 1.96 (3 H, s), 2.44 (3 H, s), 2.72 (1 H, s), 3.39 (1 H, s). | 152.9 |
| T4-I.15 | 1-fluoro-2-methylbut-3-yn-2-ol | (500 MHz, CDCl$_3$) delta 1.62-1.66 (3 H, m), 2.53 (1 H, s), 3.49-3.56 (1 H, m), 3.60-3.65 (1 H,m) | — |
| T4-I.16 | 1-fluoro-2-(fluoromethyl)but-3-yn-2-ol | (500 MHz, CDCl$_3$) delta ppm 3.64 (1 H, s), 4.41-4.64 (4 H, m) | — |
| T4-I.17 | 2-cyclopropylbut-3-yn-2-ol | (500 MHz, MeOD) delta 0.33-0.52 (3 H, m), 0.54-0.69 (1 H, m), 0.96-1.12 (1 H, m), 1.50 (3 H, s), 2.71 (1 H, s) | — |

TABLE 4-continued

| No | Structure | Name | 1H NMR | MS (M + H) |
|---|---|---|---|---|
| T4-I.18 | 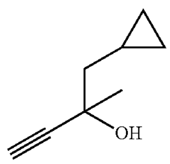 | 1-cyclopropyl-2-but-3-yn-2-ol | (250 MHz, CDCl₃) delta 2.36-2.51 (2 H,m), 1.74 (1 H, dd, J = 13.9, 6.1 Hz), 1.44-1.58 (4 H, m), 0.79-1.06 (1 H,m), 0.40-0.66 (2 H, m), 0.03-0.29 (2 H, m) | |
| T4-I.19 | 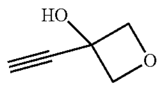 | 3-ethynyloxetan-3-ol | (400 MHz, CDCl₃): delta 2.73 (s, 1 H), 3.41 (s, 1H), 4.70 (d, J = 7.2 Hz, 2H), 4.85 (d, J = 7.2 Hz, 2H). | |
| T4-I.20 | 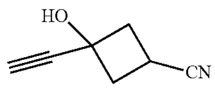 | 3-ethynyl-3-hydroxycyclobutanecarbonitrile | | |
| T4-I.21 | 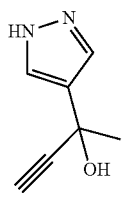 | 2-(1H-pyrazol-4-yl)but-3-yn-2-ol | (500 MHz, DMSO) delta 1.63 (3 H, s), 3.35 (1 H, s), 5.74 (1 H, s), 7.46 (1 H, s), 7.62 (1 H, s), 12.64 (1 H, br. s.) | 136.9 |
| T4-I.22 | 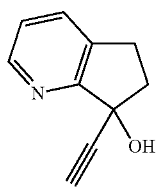 | 7-ethynyl-5H,6H-cyclopenta[b]pyridin-7-ol | | |

Example 23

Preparation of intermediate compound 2-(2-methoxybut-3-yn-2-yl)-1,3-thiazole (I.5)

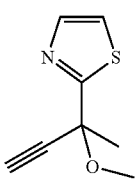
(I.5)

To a solution of 2-(1,3-thiazol-2-yl)but-3-yn-2-ol (I-1) (1.0 g, 6.33 mmol) in DMF (15 mL) cooled to 0° C., was slowly added sodium hydride (60% oil dispersion) (0.30 g, 7.6 mmol). After stirring at 0° C. for 20 min, methyl iodide (0.47 mL, 7.6 mmol) was added. The solution was warmed to RT. The mixture was partition between EtOAc (50 mL) and water (20 mL). The organic layer was washed with water, dried (Na₂SO₄), filtered and concentrated in vacuo. Purification by flash chromatography (Isolute column, 20% EtOAc in heptane) gave the title compound as a pale yellow oil: ¹H NMR (250 MHz, CDCl₃) δ 1.91 (3H, s), 2.78 (1H, s), 3.41 (3H, s), 7.35 (1H, d, J=3.20 Hz), 7.80 (1H, d, J=3.20 Hz); LC-MS: m/z=+167.9 (M+H)+.

Example 24

Preparation of 2-(4-methyl-1,3-thiazol-2-yl)but-3-yn-2-ol

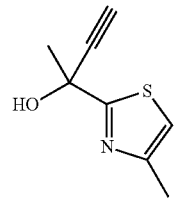

Step 1—Synthesis of 1-(4-methyl-1,3-thiazol-2-yl)ethan-1-one

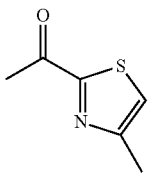
(24-a)

To a solution of n-butyllithium (2.5M in hexane, 14.4 mL) maintained under nitrogen at −78° C. was added a solution of 4-methyl-1,3-thiazole (3 g, 30.26 mmol) in ether (20 mL). The reaction mixture was stirred at −78° C. for 20 min. N-Methoxy-N-methylacetamide (3.4 g, 32.97 mmol) was then added dropwise to the reaction mixture over 10 min. The resulting solution was stirred at −78° C. for 2 hr and then quenched by the addition of aqueous sodium bicarbonate (20 mL). The resulting solution was extracted with ether (3×50 mL). The combined organic layers were dried over Na$_2$SO$_4$, filtered and concentrated in vacuo. The residue was purified on a silica gel column with ethyl acetate/petroleum ether (1/5) to give 2.1 g (39%) of 1-(4-methyl-1,3-thiazol-2-yl)ethan-1-one as a yellow oil: $^1$H NMR (300 MHz, CDCl$_3$) delta 7.25 (s, 1H), 2.71 (s, 3H), 2.51 (s, 3H).

Step 2: Synthesis of 2-(4-methyl-1,3-thiazol-2-yl)but-3-yn-2-ol

To a stirred solution of ethynylmagnesium bromide (0.5 M in THF, 30.6 mL, 15.30 mmol) maintained under nitrogen at −20° C. was added slowly a solution of 1-(4-methyl-1,3-thiazol-2-yl)ethan-1-one (1.8 g, 10.20 mmol, 80%) in tetrahydrofuran (10 mL) over a period of 20 min. The resulting solution was stirred for 3 hr at 20-30° C. and then quenched by the addition of water (20 mL). The resulting mixture was extracted with ethyl acetate (3×30 mL). The combined organic layers were dried over Na$_2$SO$_4$, filtered and concentrated in vacuo. The crude residue was purified on a silica gel column eluted with ethyl acetate/petroleum ether (1/6) to yield 0.5 g (26%) of the title compound as a yellow solid: LC-MS: m/z=+168 (M+H)+.

Example 25

Preparation of 2-(5-fluoropyridin-2-yl)but-3-yn-2-ol

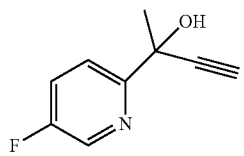

Step 1: Synthesis of 2-(5-fluoropyridin-2-yl)-4-(trimethylsilyl)but-3-yn-2-ol

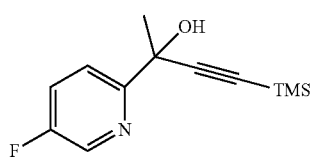
(25-a)

To a stirred solution of 2-bromo-5-fluoropyridine (1.76 g, 10.00 mmol) in ether (20 mL) maintained under nitrogen at −78° C. was added a solution of s-butyllithium (1.3M in hexane, 10 mL, 13.00 mmol) dropwise. The reaction mixture was then stirred at −78° C. for 1 hr and 4-(trimethylsilyl)but-3-yn-2-one (1.54 g, 10.98 mmol) was added to the reaction mixture dropwise with stirring at −78° C. The resulting solution was stirred at −78° C. for 2 hr and then quenched by the addition of saturated ammonium chloride solution (5 mL) and water (10 mL). The resulting solution was extracted with ethyl acetate (3×20 mL). The combined organic layers were dried over Na$_2$SO$_4$, filtered and concentrated in vacuo. The crude residue was purified on a silica gel column with ethyl acetate/petroleum ether (1:3) to give 1 g (42%) of the title compound as a yellow oil: LC-MS: m/z=+238 (M+H)+.

Step 2: Synthesis of 2-(5-fluoropyridin-2-yl)but-3-yn-2-ol

A solution of 2-(5-fluoropyridin-2-yl)-4-(trimethylsilyl)but-3-yn-2-ol (1 g, 4.21 mmol) and potassium fluoride (987 mg, 16.99 mmol) in methanol (10 mL) was stirred for 2 hr at 50° C. The resulting solution was diluted with ethyl acetate (20 mL) and the solid material was removed by filtration. The filtrate was concentrated in vacuo to give 600 mg (86%) of the title compound as yellow oil: LC-MS: m/z=+166 (M+H)+.

Example 26

Preparation of 2-(1-methyl-1,2,4-triazol-3-yl)but-3-yn-2-ol

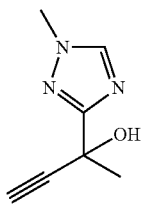

Step 1—Synthesis of 1-(1-methyl-1,2,4-triazol-3-yl)ethanone

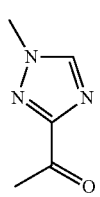
(26-a)

The title compound was prepared according to methods described in Chem. Pharm. Bull. 41(7) 1226-1231 (1993) and Organic Syntheses, Coll. Vol. 6, p. 601 (1988); Vol. 56, p. 72 (1977); $^1$H NMR (500 MHz, CDCl$_3$) delta 2.66 (3H, s), 4.01 (3H, s), 8.11 (1H, s); LC-MS: m/z=+125.90 (M+H)+.

Step 2: Synthesis of 2-(1-methyl-1,2,4-triazol-3-yl)but-3-yn-2-ol

To a solution of ethynylmagnesium bromide (0.5M in THF, 4.32 mL, 2.16 mmol) at 0° C. was added 1-(1-methyl-1,2,4-triazol-3-yl)ethanone (180 mg, 1.44 mmol) in THF (5 mL) slowly. The reaction mixture was allowed to warm to RT and stirred for a further 1.5 hr. The reaction mixture was quenched with saturated aqueous NH$_4$Cl solution (10 mL) and the organics were removed in vacuo. The product was extracted into EtOAc (×2) and the combined organics were dried (Na₂SO₄), filtered and concentrated in vacuo. Purification by column chromatography eluting with 2-10% methanol in DCM afforded the title compound: ¹H NMR (500 MHz, CDCl₃) delta 1.93 (3H, s), 2.62 (1H, s), 3.53 (1H, s), 3.93 (3H, s), 8.01 (1H, s); LC-MS: m/z=+152.0 (M+H)+.

Example 27

Preparation of 7-ethynyl-5H,6H-pyrrolo[1,2-a]imidazol-7-ol

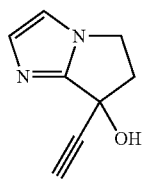

(27-c)

Step 1—Synthesis of 5H,6H,7H-pyrrolo[1,2-a]imidazol-7-ol

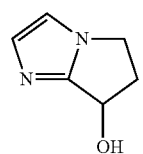

(27-a)

To a solution of imidazole (2 mL, 30.26 mmol) and acetic acid (0.12 mL, 2.12 mmol) in dry dioxane (20 mL) under N₂ was added acrolein (3.03 mL, 45.39 mmol) in 1 portion and the resultant solution heated to reflux for 4 hr. The reaction mixture was concentrated in vacuo and the yellow-brown residue was purified by column chromatography, (elution with 25% methanol in DCM) to give the title product; ¹H NMR (500 MHz, DMSO) delta 2.25 (1H, ddt, J=13.06, 7.90, 3.94, 3.94 Hz), 2.70-2.87 (1H, m), 3.85 (1H, ddd, J=10.72, 8.51, 4.26 Hz), 4.03 (1H, ddd, J=10.72, 7.80, 6.23 Hz), 4.86 (1H, dd, J=7.09, 3.00 Hz), 5.58 (1H, br. s.), 6.94 (1H, s), 7.06 (1H, d, J=0.95 Hz); LC-MS: m/z=+124.9 (M+H)+.

Step 2—Synthesis of 5H,6H-pyrrolo[1,2-a]imidazol-7-one

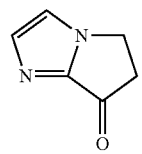

(27-b)

To a solution of 5H,6H,7H-pyrrolo[1,2-a]imidazol-7-ol (7.1 g, 57.2 mmol) in DCM (70 mL) was added MnO₂ (34.8 g, 400.3 mmol) portionwise. The reaction mixture was stirred vigorously at RT for 3 days under N₂. The reaction mixture was filtered through Celite and washed with DCM (200 mL) and EtOAc (200 mL). The filtrate was concentrated in vacuo to give the title compound as a yellow solid (4.04 g, 58% yield); ¹H NMR (500 MHz, CDCl₃) delta 3.08-3.23 (2H, m), 4.39 (2H, t, J=5.83 Hz), 7.26 (1H, s), 7.56 (1H, s); LC-MS: m/z=+122.9 (M+H)+.

Step 3—Synthesis of 7-ethynyl-5H,6H-pyrrolo[1,2-a]imidazol-7-ol

To a solution of ethynylmagnesium bromide (0.5M in THF, 14.6 mL, 7.3 mmol) at 0° C. was added 5H,6H-pyrrolo[1,2-a]imidazol-7-one (900 mg, 4.86 mmol) in THF (10 mL) slowly. The reaction mixture was allowed to warm to RT and stirred for 1 hr. The reaction mixture was quenched with saturated aqueous NH₄Cl solution (10 mL) and the organics were removed in vacuo. The product was extracted into EtOAc (10 mL×2) and the combined organics were dried (Na₂SO₄), filtered and concentrated in vacuo. Purification by column chromatography (Biotage), eluting with 3-10% methanol in DCM afforded the title product; ¹H NMR (500 MHz, CDCl₃) delta 2.55 (1H, s), 2.96 (1H, ddd, J=13.24, 7.57, 4.26 Hz), 3.03-3.12 (1H, m), 3.16-3.22 (1H, m), 4.01 (1H, ddd, J=10.56, 8.12, 4.33 Hz), 4.15 (1H, ddd, J=10.52, 7.29, 6.62 Hz), 6.84 (1H, d, J=1.10 Hz), 7.11 (1H, d, J=0.79 Hz); LC-MS: m/z=+136.9 (M+H)+.

Example 28

Preparation of 3-ethynyl-3-hydroxy-1-methylpiperidin-2-one

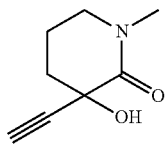

(28-f)

Step 1—Synthesis of 3-(benzyloxy)pyridin-2-ol

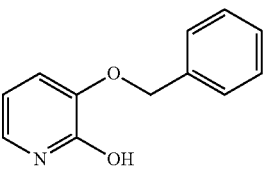

(28-a)

Pyridine-2,3-diol (38 g, 342.04 mmol) was added to a solution of potassium hydroxide (21 g, 374.26 mmol) in methanol (400 mL) in portions while maintaining the reaction temperature below 30° C. Benzyl bromide (64.4 g, 376.53 mmol) was then added dropwise with stirring to the reaction mixture at room temperature. The resulting solution was stirred at 40° C. for 5 hr then concentrated in vacuo. The residue was diluted with water (500 mL) and the mixture was extracted with of dichloromethane (2×500 mL). The combined organic layer was dried over anhydrous sodium sulfate and concentrated in vacuo. Recrystallization from ethanol afforded the title compound (30 g, 43%) as a white solid: ¹H NMR (400 MHz, DMSO) delta 11.60 (s, 1H), 7.45-7.28 (m, 5H), 6.96-6.89 (m, 2H), 6.10-6.06 (m, 1H), 5.01 (s, 2H).

Step 2—Synthesis of 3-(benzyloxy)-1-methyl-1H-pyridin-2-one

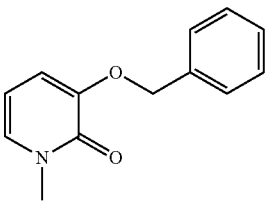
(28-b)

To a solution of 3-(benzyloxy)pyridin-2-ol (25 g, 123.00 mmol) and potassium hydroxide (10 g, 178.22 mmol, 1.45 equiv) in dimethylsulfoxide (250 mL) maintained under nitrogen atmosphere was added methyl iodide (27 g, 190.14 mmol) dropwise with stirring. The resulting solution was stirred overnight at room temperature then concentrated under vacuum. The residue was diluted with water (500 mL) then extracted with dichloromethane (2×400 mL). The combined organic layer was washed with water (3×500 mL), dried over anhydrous sodium sulfate and concentrated under vacuum to give the title compound (25 g, 93%) as a light brown oil: $^1$H NMR (400 MHz, DMSO) delta 7.44-7.32 (m, 5H), 7.29-7.27 (m, 1H), 6.91-6.88 (m, 1H), 6.12-6.09 (m, 1H), 5.02 (s, 2H), 3.44 (s, 3H).

Step 3—Synthesis of 3-hydroxy-1-methyl-1H-pyridin-2-one

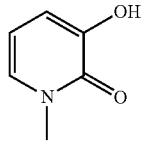
(28-c)

A mixture of 3-(benzyloxy)-1-methyl-1H-pyridin-2-one (23 g, 106.85 mmol) and 10% palladium on carbon (2.3 g) in methanol (250 mL) was stirred under 1 atmosphere of hydrogen for 5 hr at room temperature. The catalyst was removed by filtration. The filtrate was concentrated in vacuo to give the title compound (12 g, 90%) as a purple solid: $^1$H NMR (400 MHz, DMSO) delta 8.96 (s, 1H), 7.15-7.13 (m, 1H), 6.70-6.68 (m, 1H), 6.07 (t, J=7.0 Hz, 1H), 3.47 (s, 3H).

Step 4—Synthesis of 3-hydroxy-1-methylpiperidin-2-one

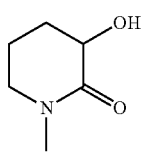
(28-d)

A mixture of 3-hydroxy-1-methyl-1H-pyridin-2-one (11.5 g, 91.91 mmol) and Ru/Al2O3 (2.5 g) in methanol (120 mL) was stirred under hydrogen (10 bar) in a 250-mL pressure reactor for 48 hr at 50° C. The catalyst was removed by filtration and the filtrate was concentrated in vacuo to give the title compound (11.3 g, 90%) as a brown oil: $^1$H NMR (400 MHz, DMSO delta 3.85-3.82 (m, 1H), 3.28-3.18 (m, 2H), 2.79 (s, 3H), 1.98-1.92 (m, 1H), 1.87-1.81 (m, 1H), 1.75-1.69 (m, 1H), 1.64-1.55 (m, 1H).

Step 5—Synthesis of 1-methylpiperidine-2,3-dione

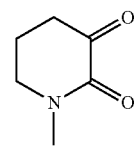
(28-e)

To a solution of 3-hydroxy-1-methylpiperidin-2-one (1 g, 7.59 mmol) in acetone (50 mL) was added Jones-reagent (2 mL) dropwise at room temperature. The resulting solution was stirred for 10 min at room temperature. The solid material was removed by filtration. The filtrate was concentrated in vacuo at 30-40° C. The residue was dissolved in DCM (50 mL), dried over anhydrous sodium sulfate and concentrated in vacuo to afford the title compound (220 mg, 11%) which was used in next step immediately without further purification.

Step 6—Synthesis of 3-ethynyl-3-hydroxy-1-methylpiperidin-2-one

To a solution of ethynylmagnesium bromide (0.5M in tetrahydrofuran, 4 mL, 2 mmol) maintained under nitrogen at −20° C. was added a solution of 1-methylpiperidine-2,3-dione (220 mg, 0.87 mmol) in tetrahydrofuran (3 mL) dropwise with stirring within 1 min. The reaction mixture was stirred for 2 hr at room temperature and then quenched by the addition of saturated ammonium chloride solution (1 mL). The mixture was diluted with DCM (50 mL), dried over anhydrous sodium sulfate and concentrated under vacuum. The crude residue was purified on a silica gel column, elution with ethyl acetate/petroleum ether (0:1-1:0) afforded the title compound (40 mg, 30%) as a brown oil: $^1$H NMR (400 MHz, CDCl$_3$) delta 4.23 (s, 1H), 3.35-3.30 (m, 2H), 2.95 (s, 3H), 2.47 (s, 1H), 2.35-2.16 (m, 2H), 1.97-1.90 (m, 2H). LC-MS m/z=+154 [M+H]+.

Example 29

Preparation of 2-(1,3-oxazol-4-yl)but-3-yn-2-ol

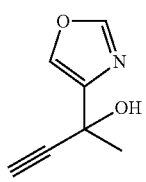
(29-b)

Step 1—Synthesis of 1-(1,3-oxazol-4-yl)ethanone

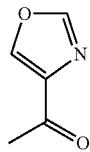

(29-a)

To a solution of methylmagnesium bromide (3M solution in Et2O, 8.86 mL, 26.58 mmol) was added slowly a solution of 1,3-oxazole-4-carbonitrile (500 mg, 5.32 mmol) in anhydrous Et$_2$O (10 mL). After addition the reaction mixture was stirred at 40° C. for 3 hr. The reaction mixture was cooled to ambient temperature, and of methanol (5 mL) was added dropwise. The reaction mixture was stirred for 3 hr and then filtered. The filtrate was collected and silica (5 g) was added and the mixture stirred at room temperature for 3 hr. The silica was filtered off and the volume reduced (removed methanol). EtOAc and water were added and the organics were extracted (repeated with CHCl$_3$:isopropanol 3:1), washed with water and dried (Na$_2$SO$_4$), filtered and concentrated in vacuo. The crude material was purified by column chromatography (Biotage) (Eluted with 2-8% methanol in DCM) to give the title compound; $^1$H NMR (250 MHz, CDCl$_3$) delta 2.56 (3H, s), 7.91 (1H, d, J=0.7 Hz), 8.25 (1H, d, J=0.9 Hz); LC-MS: m/z=+112 (M+H)+.

Step 2—Synthesis of 2-(1,3-oxazol-4-yl)but-3-yn-2-ol

To a solution of n-butyllithium (2.5M in hexane, 1.03 mL, 2.57 mmol) in THF (3 mL) at −78° C. was added dropwise ethynyl(trimethyl)silane (0.34 mL, 2.38 mmol). The reaction was stirred at −78° C. for 10 minutes and then 1-(1,3-oxazol-4-yl)ethanone (220 mg, 1.98 mmol) was added in more THF (2 mL). The reaction was stirred at −78° C. to RT for 1 hr. The mixture was then diluted with water and the volatiles removed. The product was then extracted with EtOAc (2×15 mL) and the combined organics washed with water (2×5 mL) and dried (Na$_2$SO$_4$), filtered and concentrated in vacuo. The crude material was purified by column chromatography (eluted with 2-13% methanol) to give the title compound; $^1$H NMR (500 MHz, CDCl$_3$) delta 1.85 (3H, s), 2.61 (1H, s), 2.92 (1H, s), 7.71 (1H, s), 7.87 (1H, s).

Example 30

Preparation and separation of 2-(pyrimidin-4-yl)but-3-yn-2-ol (30-1) and 2-(pyrimidin-4-yl)-4-(trimethylsilyl)but-3-yn-2-ol (30-2)

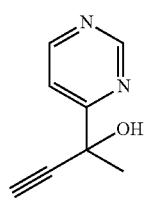

(30-1)

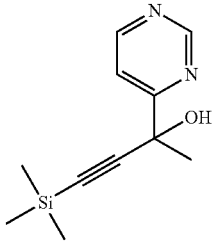

(30-2)

To a solution of n-butyllithium (2.5M in hexane, 2.1 ml, 5.32 mmol) in THF (3 mL) at −78° C. was added dropwise ethynyl(trimethyl)silane (0.7 mL, 4.91 mmol). The reaction was stirred at −78° C. for 10 minutes and then 1-(pyrimidin-4-yl)ethanone (0.5 g, 4.09 mmol) was added in more THF (2 mL). The reaction was stirred at −78° C. to RT overnight. The mixture was diluted with water and the volatiles removed in vacuo. The product was then extracted with CHCl$_3$:IPA (2:1 ratio, 2×25 mL). The organic phase was washed with water (20 mL), brine (20 mL); dried over Na$_2$SO$_4$ and the solvent removed in vacuo. Purification by column chromatography (Biotage), eluting with 0-100% EtOAc-heptane afforded 2-(pyrimidin-4-yl)-4-(trimethylsilyl)but-3-yn-2-ol; $^1$H NMR (500 MHz, CDCl$_3$) delta 0.19 (9H, s), 1.78 (3H, s), 4.65 (1H, s), 7.65 (1H, dd, J=5.20, 1.10 Hz), 8.79 (1H, d, J=5.36 Hz), 9.20 (1H, s); LC-MS: m/z=+221 (M+H)+; and 2-(pyrimidin-4-yl)but-3-yn-2-ol; $^1$H NMR (500 MHz, CDCl$_3$) delta 1.79 (3H, s), 2.62 (1H, s), 4.99 (1H, s), 7.67 (1H, dd, J=5.28, 0.87 Hz), 8.77 (1H, d, J=5.36 Hz), 9.19 (1H, s); LC-MS: m/z=+148.95 (M+H)+.

Example 31

Preparation of 7-ethynyl-5H,6H-cyclopenta[b]pyridin-7-ol

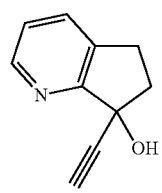

To a solution of n-butyllithium (2.5M in hexane, 19.5 ml, 48.75 mmol) in THF (15 ml) at −78° C. was added dropwise ethynyl(trimethyl)silane (6.41 ml, 45.06 mmol). The reaction was stirred at −78° C. for 20 minutes and then a solution of 5,6-dihydro-7H-cyclopenta[b]pyridin-7-one (5 g, 7.51 mmol) in THF (25 mL) was added. The reaction mixture was stirred at −78° C. to RT for 4 hr. The mixture was then diluted with water and the volatiles removed in vacuo. The product was extracted with CHCl$_3$:IPA (2:1 ratio, 3×30 ml) and the organic phase was washed with water (30 mL), brine (30 mL); dried over Na$_2$SO$_4$, filtered and concentrated in vacuo. Purification by column chromatography (Biotage), eluting with 0-5% MeOH-DCM followed by another column chromatography purification with 30% EtOAc/heptanes gave the title compound; $^1$H NMR (500 MHz, CDCl$_3$) 2.49 (1H, ddd, J=13.44, 8.24, 6.07 Hz), 2.63-2.76 (2H, m), 2.90-3.02 (1H, m), 3.03-3.13 (1H, m), 3.42 (1H, s), 7.22 (1H, dd, J=7.57,

Example 32

Preparation of 2-(pyridin-2-yl)but-3-yn-2-ol

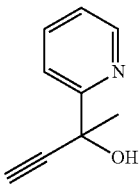

The title compound was prepared using the method described for the preparation of 7-ethynyl-5H,6H-cyclopenta[b]pyridin-7-ol, by replacing 5,6-dihydro-7H-cyclopenta[b]pyridin-7-one with 2-acetylpyridine; $^1$H NMR (500 MHz, CDCl$_3$) delta 1.80 (3H, s), 2.55 (1H, s), 5.50 (1H, s), 7.20-7.32 (1H, m), 7.62 (1H, d, J=7.88 Hz), 7.78 (1 H, td, J=7.72, 1.58 Hz), 8.54 (1H, d, J=4.73 Hz); LC-MS: m/z=+147.9 (M+H)+.

Example 33

Preparation of 2-(5-methylpyrazin-2-yl)but-3-yn-2-ol

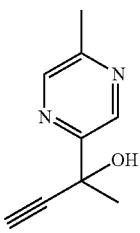

The title compound was prepared using the method described for the preparation of 7-ethynyl-5H,6H-cyclopenta[b]pyridin-7-ol, by replacing 5,6-dihydro-7H-cyclopenta[b]pyridin-7-one with 1-(5-methylpyrazin-2-yl)ethanone; $^1$H NMR (500 MHz, CDCl$_3$) delta 1.65 (3H, s), 2.45 (3H, s), 4.32 (1H, s), 8.22 (1H, s), 8.77 (1H, s); LC-MS: m/z=+162.9 (M+H)+.

Example 34

Preparation of 2-ethynylbicyclo[2.2.1]heptan-2-ol

(34-b)

Step 1—Synthesis of 2-((trimethylsilyl)ethynyl)bicyclo[2.2.1]heptan-2-ol

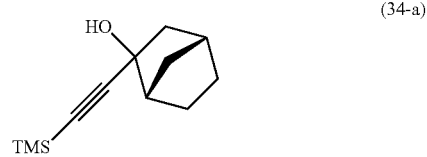 [SMILES: C[Si](C)(C)C#CC1(O)C[C@@H]2CC[C@H]1C2]
(34-a)

Bicyclo[2.2.1]heptan-2-one (1.1 g, 10 mmol) in THF was treated with n-BuLi (6 mL, 2.5 M in n-hexane) at −78° C. for about 30 min. Ethynyltrimethylsilane (1.1 g, 11 mmol) was then added and the reaction mixture was stirred for 3 hr. Purification by gel chromatography afforded the title compound (1.6 g); $^1$H NMR (400 MHz, DMSO) delta 0.16 (s, 9H), 1.15-1.44 (m, 4H), 1.64-1.67 (m, 1H), 1.88-1.93 (m, 2H), 2.07-2.22 (m, 3H), 3.94 (s, 1H).

Step 2: Synthesis of 2-ethynylbicyclo[2.2.1]heptan-2-ol 2-((trimethylsilyl)ethynyl)bicyclo[2.2.1]heptan-2-ol (700 mg, 5.1 mmol) was dissolved in THF (25 mL) and treated with TBAF (2.7 g, 10.2 mmol) at 0° C. for 30 min. Purification by gel chromatography afforded the title compound; $^1$H NMR (400 MHz, DMSO) delta 1.15-1.44 (m, 4H), 1.64-1.67 (m, 1H), 1.88-1.93 (m, 2H), 2.07-2.22 (m, 3H), 3.25 (s, 1H)

Example 35

Preparation of 3-ethynyltetrahydro-2H-pyran-3-ol

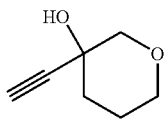
(35-b)

Step 1—Synthesis of 3-((trimethylsilyl)ethynyl)tetrahydro-2H-pyran-3-ol

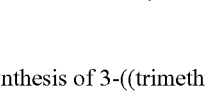
(35-a)

A solution of dihydro-2H-pyran-3(4H)-one (200 mg, 2 mmol) in THF was treated with n-BuLi (2 mL) at −78° C. for about 30 min. Ethynyltrimethylsilane (300 mg, 3 mmol) was then added and the reaction mixture was stirred for 3 hr. Purification by gel chromatography afforded the title compound (200 mg, 50%); $^1$H NMR (400 MHz, DMSO) delta 0.15 (s, 9H), 1.52-1.55 (m, 1H), 1.62-1.67 (m, 1H), 1.80-1.88 (m, 1H), 3.23-3.26 (m, 1H), 3.37-3.44 (m, 1H), 3.49-3.56 (m, 2H), 5.52 (s, 1H).

Step 2—Synthesis of 3-ethynyltetrahydro-2H-pyran-3-ol

The title compound was prepared by the procedure described in Example 34, by substituting 2-((trimethyl-silyl)ethynyl)bicyclo[2.2.1]heptan-2-ol with 3-((trimethylsilyl)ethynyl)tetrahydro-2H-pyran-3-ol in Step 2.

Example 36

Preparation of 3-(tert-butyl-dimethyl-silanyloxymethyl)-1-ethynyl-cyclobutanol (36-d1) and 1-[3-(tert-butyl-dimethyl-silanyloxy)-cyclobutyl]-prop-2-yn-1-ol (36-d2)

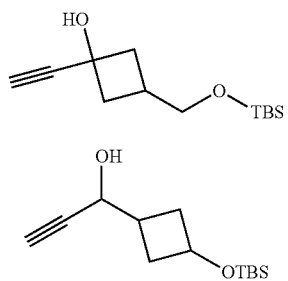

(36-d1)

(36-d2)

Step 1—Synthesis of 3-hydroxymethyl-cyclobutanol (36-a)

(36-a)

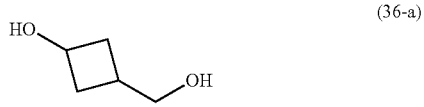

To a solution of 3-oxo-cyclobutanecarboxylic acid (5.0 g, 44 mmol) in tetrahydrofuran (50 mL) was added slowly BH3S(CH3)2 (5.9 mL, 14.7 mmol) at −78° C. The solution was stirred overnight at room temperature. The reaction mixture was then quenched with methanol and purified by flash chromatography (Isolute column). Elution with 5% methanol in DCM afforded the title compound; (3.4 g, 76%).

Step 2—Synthesis of 3-(tert-butyl-dimethyl-silanyloxymethyl)-cyclobutanol (36-b1) and [3-(tert-butyl-dimethyl-silanyloxy)-cyclobutyl]-methanol (36-b2)

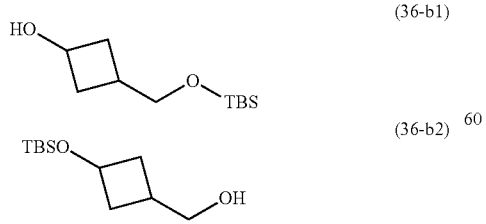

(36-b1)

(36-b2)

To a solution of 3-hydroxymethyl-cyclobutanol (0.4 g, 4 mmol) in DCM (20 mL) was added triethylamine (1.2 g, 12 mmol) and tert-butyl-chloro-dimethyl-silane (1.2 g, 8 mmol). The solution was stirred overnight at room temperature. The reaction mixture was then washed with water (×3) and the organic layers concentrated in vacuo. The crude residue was purified by flash chromatography to afford a mixture of 3-(tert-butyl-dimethyl-silanyloxymethyl)cyclobutanol and [3-(tert-butyl-dimethyl-silanyloxy)-cyclobutyl]-methanol (0.6 g, 69%).

Step 3—Synthesis of 3-(tert-butyl-dimethyl-silanyloxymethyl)-cyclobutanone (36-c1) and 3-(tert-butyl-dimethyl-silanyloxy)-cyclobutanecarbaldehyde (36-c2)

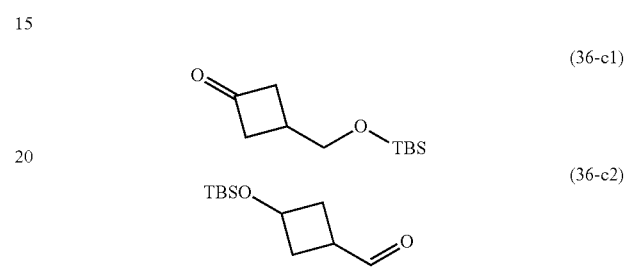

(36-c1)

(36-c2)

To a mixture of 3-(tert-butyl-dimethyl-silanyloxymethyl)-cyclobutanol (36-b1) and [3-(tert-butyl-dimethyl-silanyloxy)-cyclobutyl]-methanol (36-b2) (0.5 g, 2.31 mmol) in DCM (10 mL) was added Dess-Martin reagent (1.47 g, 3.5 mmol). The reaction mixture was stirred for 3 hr at room temperature and then washed with water. The crude residue was purified by flash chromatography (Isolute column), elution with 5% petroleum ether in EtOAc afforded a mixture of 3-(tert-butyl-dimethyl-silanyloxymethyl)-cyclobutanone (36-c1) and 3-(tert-butyl-dimethyl-silanyloxy)-cyclobutanecarbaldehyde (36-c2), (0.44 g, 89%).

Step 4—Synthesis of 3-(tert-butyl-dimethyl-silanyloxymethyl)-1-ethynyl-cyclobutanol (36-d1) and 1-[3-(tert-butyl-dimethyl-silanyloxy)-cyclobutyl]-prop-2-yn-1-ol (36-d2)

To a mixture of 3-(tert-butyl-dimethyl-silanyloxymethyl)-cyclobutanone (36-c1) and 3-(tert-butyl-dimethyl-silanyloxy)-cyclobutanecarbaldehyde (36-c2) (0.44 g, 2.2 mmol) in tetrahydrofuran (20 mL) was added ethynyl magnesium bromide (6.7 mL, 3.3 mmol) at −78° C. The solution was stirred for 5 hr at room temperature and then quenched with saturated aqueous NH$_4$Cl solution. The product was extracted with DCM and the organics dried (Na$_2$SO$_4$), filtered and concentrated in vacuo to afford a mixture of 3-(tert-butyl-dimethyl-silanyloxymethyl)-1-ethynyl-cyclobutanol and 1-[3-(tert-butyl-dimethyl-silanyloxy)-cyclobutyl]-prop-2-yn-1-ol (0.41 g, 78%).

Example 37

Preparation of tert-butyl-(2,2-dimethyl-but-3-ynyloxy)-dimethyl-silane

(37-c)

Step 1—Synthesis of 3-(tert-butyl-dimethyl-silanyloxy)-2,2-dimethyl-propan-1-ol

(37-a)

To a solution of 2,2-dimethyl-propane-1,3-diol (5.0 g, 48 mmol) in DCM (20 mL) was added triethylamine (14.6 g, 144.3 mmol) and tert-butyl-chloro-dimethyl-silane (7.2 g, 48.1 mmol). The solution was stirred overnight at room temperature. The reaction mixture was then washed with water (×3) and concentrated in vacuo. The residue was purified by flash chromatography to afford the title compound (6.1 g, 58%): $^1$H NMR (CDCl$_3$, 400 MHz) delta 0.04 (s, 6H), 0.86 (s, 6H), 0.87 (s, 9H), 2.94 (s, 1H), 3.43 (s, 4H).

Step 2—Synthesis of 3-(tert-butyl-dimethyl-silanyloxy)-2,2-dimethyl-propionaldehyde

(37-b)

To a solution of 3-(tert-butyl-dimethyl-silanyloxy)-2,2-dimethyl-propan-1-ol (3.0 g, 13.8 mmol) in DCM (30 ml) was added Dess-Martin reagent (8.6 g, 20.6 mmol) and the reaction mixture was stirred overnight at room temperature. The reaction mixture was then washed with water and concentrated in vacuo. The crude residue was purified by flash chromatography (eluted with petroleum ether:EtOAc=100:1) to afford the title compound (1.6 g, 54%): $^1$H NMR (CDCl$_3$, 400 MHz) delta 0.05 (s, 6H), 0.88 (s, 9H), 1.17 (s, 6H), 3.59 (s, 2H).

Step 3—Synthesis of tert-butyl-(2,2-dimethyl-but-3-ynyloxy)-dimethyl-silane

To a solution of 3-(tert-butyl-dimethyl-silanyloxy)-2,2-dimethyl-propionaldehyde (0.84 g, 3.9 mmol) in methanol (20 mL) was added (1-diazo-2-oxo-propyl)-phosphonic acid dimethyl ester (0.9 g, 4.7 mmol) and K$_2$CO$_3$ (1.1 g, 7.8 mmol). The solution was stirred overnight at room temperature and then the reaction mixture was washed with water. The crude residue was purified by flash chromatography (eluted with: petroleum ether:EtOAc=100:2) to afford the title compound (0.17 g, 21%): $^1$H NMR (CDCl$_3$, 400 MHz) delta 0.05 (s, 6H), 0.90 (s, 9H), 1.19 (s, 6H), 2.06 (s, 1H), 3.45 (s, 2H).

Example 38

Preparation of tert-butyl-(1-ethynyl-cyclopentyl-methoxy)-dimethylsilane

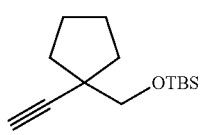

(38-d)

Step 1—Synthesis of [1-(tert-butyl-dimethyl-silanyloxymethyl)-cyclopentyl]-methanol

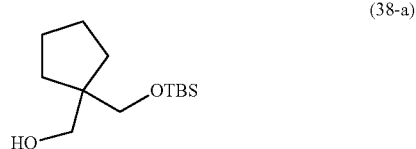 [SMILES: CC(C)(C)[Si](C)(C)OCC1(CO)CCCC1]

(38-a)

(1-hydroxymethyl-cyclopentyl)-methanol (1.0 g, 7.7 mmol) was dissolved in DCM (30 ml) and TEA (1.15 g, 7.7 mmol) and DMAP (0.14 g, 1.15 mmol) were added. TBSCl (1.17 g, 11.5 mmol) was then added in portions and the mixture was stirred at room temperature for 16 hr. The reaction mixture was washed with saturated aqueous NaHCO$_3$ solution and extracted with EtOAc. The organic phase was concentrated and the crude residue was purified by chromatography on silica gel (eluted with hexanes:EtOAc, 10:1) to afford the title compound (1.1 g, yield 59%): $^1$H NMR (400 MHz, DMSO) delta 0.00 (s, 6H), 0.84 (s, 9H), 1.28-1.31 (m, 4H), 1.46-1.50 (m, 4H), 3.20 (d, J=5.2 Hz, 2H), 3.36 (s, 2H), 4.38 (t, J=5.2 Hz, 1H).

Step 2—Synthesis of 1-(tert-butyl-dimethyl-silanyloxymethyl)-cyclopentanecarbaldehyde

(38-b)

[1-(tert-butyl-dimethyl-silanyloxymethyl)-cyclopentyl]-methanol (1.1 g, 4.51 mmol) was dissolved in DCM (30 ml) and Dess-Martin reagent (3.82 g, 9.0 mmol) was added in portions. The reaction mixture was stirred at room temperature for 4 hr and filtered. The filtrate was concentrated in vacuo and purified by silica gel chromatography (eluted with hexanes:EtOAc, 10:1) to afford the title compound (0.75 g, 64%): $^1$H NMR (400 MHz, DMSO) delta 0.00 (s, 6H), 0.84 (s, 9H), 1.28-1.31 (m, 4H), 1.46-1.50 (m, 4H), 3.76 (s, 2H), 9.54 (s, 1H).

Step 3—Synthesis of (1-diazo-2-oxo-propyl)-phosphonic acid dimethyl ester

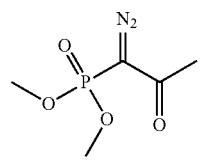

(38-c)

(2-oxo-propyl)-phosphonic acid dimethyl ester (20 g, 0.12 mol) was dissolved in toluene (500 mL) at 0° C. and NaH (4.8 g, 0.12 mol) was added in portions. After the gas evolution had ceased, a solution of 4-methyl-benzenesulfonyl azide (21.4 g, 1.1 mol) was added drop-wise and the mixture was stirred at room temperature for 16 hr. The mixture was diluted with hexanes, filtered through a pad of celite and rinsed with TMBE. The filtrate was concentrated to afford the title compound (16 g, 70%): $^1$H NMR (400 MHz, DMSO) delta 2.22 (s, 3H), 3.74 (s, 3H), 3.79 (s, 3H).

Step 4—Synthesis of tert-butyl-(1-ethynyl-cyclopentylmethoxy)-dimethylsilane

To a mixture of 1-(tert-butyl-dimethyl-silanyloxymethyl)-cyclopentanecarbaldehyde (750 mg, 3.1 mmol) in methanol (20 mL) was added $K_2CO_3$ (855 mg, 6.2 mmol) followed by dropwise addition of (1-diazo-2-oxo-propyl)-phosphonic acid dimethyl ester (714 mg, 3.6 mmol). The mixture was stirred at room temperature for 4 hr and then diluted with TMBE and washed with $NaHCO_3$. The product was extracted with EtOAc and the organic phase was concentrated and purified by flash chromatography to afford the title compound (400 mg, 54.2%): $^1$H NMR (400 MHz, DMSO) delta 0.00 (s, 6H), 0.83 (s, 9H), 1.53-1.64 (m, 8H), 2.82 (s, 1H), 3.44 (s, 2H).

Example 39

Preparation of 2-methyl-1-(1H-pyrazol-1-yl)but-3-yn-2-ol

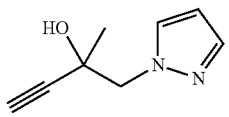
(39-b)

Step 1—Synthesis of 1-(1H-pyrazol-1-yl)propan-2-one

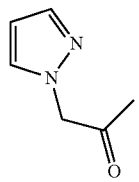
(39-a)

1H-pyrazole (1.0 g, 15 mmol) was dissolved in chloroacetone (3.0 g, 32 mmol) and heated at 90° C. for 10 hr. Purification by silica gel column, elution with 1:1 hexanes:DCM afforded the title compound (700 mg): $^1$H NMR (400 MHz DMSO) delta 2.05 (s, 3H), 5.09 (s, 2H), 6.29 (t, J=2.0 Hz, 1H), 7.47 (dd, J=0.4, 1.6 Hz, 1H), 7.67 (dd, J=0.4, 2.0 Hz, 1H).

Step 2—Synthesis of 2-methyl-1-(1H-pyrazol-1-yl)but-3-yn-2-ol

The title compound was prepared by procedure described in Example 22 (T4-119), by substituting oxetan-3-one with 1-(1H-pyrazol-1-yl)propan-2-one (39-a). Purification by gel chromatography afforded 2-methyl-1-(1H-pyrazol-1-yl)but-3-yn-2-ol (yield 28%).

Example 40

Preparation of 1-(tert-butyl-dimethyl-silanyloxy)-2-methyl-but-3-yn-2-ol

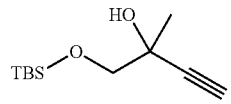

1-(tert-butyl-dimethyl-silanyloxy)-propan-2-one (500 mg, 2.6 mmol) was dissolved in THF (20 mL) and treated with ethynylmagnesium bromide (0.5 M, 8 mL) for 10 hr. The solution was extracted with EtOAc, and the organic layer was dried over $Na_2SO_4$ and concentrated in vacuo to afford the title compound (380 mg, 68.3%): $^1$H NMR (400 MHz DMSO) delta 0.10 (s, 6H), 0.92 (s, 9H), 1.40 (s, 3H), 2.74 (s, 1H), 3.58 (d, J=9.6 Hz, 1H), 3.61 (d, J=9.6 Hz, 1H).

Example 41

Preparation of 2-[5-(hydroxymethyl)isoxazol-3-yl]but-3-yn-2-ol

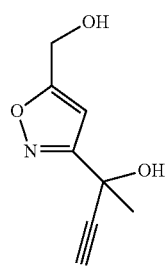

To a solution of ethynylmagnesium bromide (0.5M in THF, 99 mL, 49.0 mmol) at 0° C. under N2 was added a solution of 1-[5-(hydroxymethyl)isoxazol-3-yl]ethanone (prepared according to Synthesis 2005, 20, 3541) (4.10 g, 29.0 mmol) in dry THF (25 mL) over 20 minutes. The reaction mixture was warmed to RT for 1.5 hr, quenched by dropwise addition of saturated aqueous ammonium chloride (20 mL) and concentrated in vacuo. After re-dissolving the residue in EtOAc (100 mL), the aqueous phase was removed, diluted with water to dissolve all suspended solids and washed with EtOAc (100 mL). The combined organic extracts were dried ($Na_2SO_4$), filtered and concentrated in vacuo to furnish the crude title compound as a red-brown syrup: $^1$H NMR (500 MHz, $CDCl_3$) delta 1.88 (3H, s), 2.67 (1H, s), 4.77 (2H, s), 6.39 (1H, s); LC-MS: m/z=+167.9 (M+H)+. This compound, with LC-MS purity=88% UV, was used in the next step without further purification.

Example 42

Preparation of 2-[5-(fluoromethyl)isoxazol-3-yl]but-3-yn-2-ol

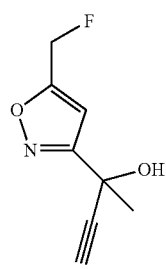

(42-b)

Step 1—Synthesis of [3-(2-hydroxybut-3-yn-2-yl)isoxazol-5-yl]methyl 4-methylbenzenesulfonate

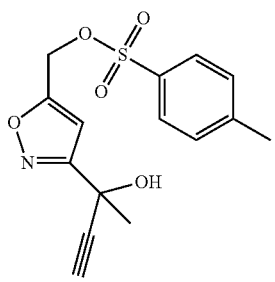

(42-a)

To a solution of 2-[5-(hydroxymethyl)isoxazol-3-yl]but-3-yn-2-ol (500 mg, 2.99 mmol) in DCM (5 mL) at 0° C. under an atmosphere of nitrogen was introduced triethylamine (333 mg, 3.29 mmol) and p-toluenesulfonyl chloride (627 mg, 3.29 mmol) in one portion. After warming to RT for 3 hr, the reaction mixture was diluted with DCM (10 mL) and washed with brine (5 mL). The organic extract was dried (Na$_2$SO$_4$), filtered and the filtrate adsorbed onto silica gel in vacuo. Purification by silica gel flash column chromatography (heptane/EtOAc gradient of increasing polarity) furnished the title compound as a colorless oil: $^1$H NMR (500 MHz, CDCl$_3$) delta 1.84 (3H, s), 2.26 (3H, s), 2.66 (1H, s), 2.86 (1H, br. s), 5.14 (2H, s), 6.41 (1H, s), 7.36 (2H, d, J=8.1 Hz), 7.80 (2H, d, J=8.1 Hz); LC-MS: m/z=+321.9 (M+H)+.

Step 2—Synthesis of 2-[5-(fluoromethyl)isoxazol-3-yl]but-3-yn-2-ol

To a solution of [3-(2-hydroxybut-3-yn-2-yl)isoxazol-5-yl]methyl 4-methylbenzenesulfonate (259 mg, 0.81 mmol) in dry acetonitrile (10 mL) was introduced potassium fluoride (94 mg, 1.61 mmol) and Kryptopfix® 222 (606 mg, 1.61 mmol). After 5 hr rapid stirring at RT, the reaction mixture was concentrated in vacuo and the residue partitioned between EtOAc (40 mL) and water (2×40 mL). The organic extract was washed with brine (30 mL), dried (Na$_2$SO$_4$), filtered and the filtrate adsorbed onto silica gel in vacuo. Purification by silica gel flash column chromatography (heptane/EtOAc gradient of increasing polarity) furnished the title compound as a colorless oil: $^1$H NMR (500 MHz, CDCl$_3$) delta 1.91 (3H, s), 2.69 (1H, s), 2.86 (1H, s), 5.42 (1H, d, J=47.3 Hz), 6.55 (1H, d, J=2.8 Hz); $^{19}$F NMR-decoupled (235 MHz, CDCl$_3$) delta −218.8 (s); LC-MS: m/z=+169.9 (M+H)+.

Example 43

Preparation of 2-hydroxy-N,N,2-trimethylbut-3-ynamide

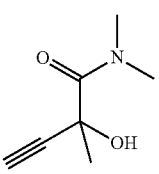

(43-b)

Step 1—Synthesis of N,N-dimethyl-2-oxopropanamide

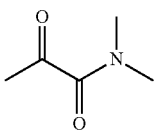

(43-a)

To a solution of pyruvoyl chloride (3.28 g, 30.80 mmol) in dry DCM (25 mL) at 0° C. under an atmosphere of nitrogen was introduced a pre-mixed solution of dimethylamine (18 mL of a 2M solution in THF, 36.00 mmol) and triethylamine (5.0 mL, 35.94 mmol) dropwise over 10 min. After 1 hr at this temperature, the reaction mixture was diluted with DCM (50 mL), washed with hydrochloric acid (3×20 ml 1.0M HCl aq.), brine (20 ml) and dried (Na$_2$SO$_4$). Following filtration, the filtrate was concentrated in vacuo to furnish the crude title compound as an orange-brown oil: $^1$H NMR (500 MHz, CDCl$_3$) delta 2.44 (3H, s), 3.00 (3H, s), 3.03 (3H, s). This compound, estimated as 90%+ purity by $^1$H NMR, was used in the next step without further purification.

Step 2—Synthesis of 2-hydroxy-N,N,2-trimethylbut-3-ynamide

To a solution of N,N-dimethyl-2-oxopropanamide (413 mg, 3.59 mmol) in dry THF (10 mL) at 0° C. under an atmosphere of nitrogen was introduced ethynylmagnesium bromide (10 mL of a 0.5M solution in THF, 5.00 mmol) dropwise over 10 minutes. After warming to RT for 1 hr, water was introduced dropwise until gas evolution ceased and the resulting slurry concentrated in vacuo. The residue was slurried in DCM (50 mL) with sonication for 5 min. and the mixture filtered. Following re-suspension of the filter cake in water (10 mL), the pH was adjusted to 2 with 1M aqueous hydrochloric acid and the resulting hazy solution re-extracted with DCM (30 mL). The DCM extract was combined with the DCM filtrate, dried (Na$_2$SO$_4$), filtered and the filtrate concentrated in vacuo to furnish the crude title compound as a brown oil: ¹H NMR (500 MHz, CDCl₃) delta 1.68 (3H, s), 2.64 (1H, s), 3.08 (3H, s), 3.31 (3H, s), 5.25 (1H, br. s); LC-MS: m/z=+ 141.95 (M+H)+.

Example 44

Preparation of 2-[5-(methoxymethyl)isoxazol-3-yl]but-3-yn-2-ol

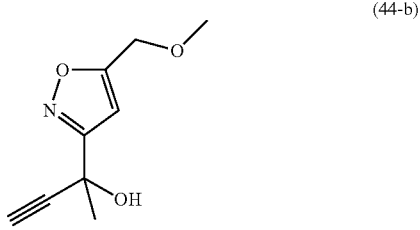
(44-b)

Step 1—Synthesis of 1-[5-(methoxymethyl)isoxazol-3-yl]ethanone

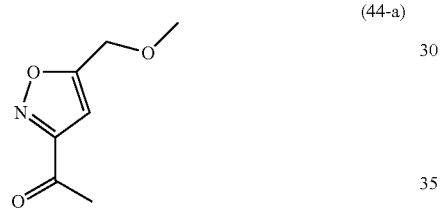
(44-a)

To a solution of 1-[5-(hydroxymethyl)-1,2-oxazol-3-yl]ethanone (1.00 g, 7.09 mmol) in dry THF (20 mL) under an atmosphere of nitrogen was introduced cesium carbonate (2.31 g, 7.09 mmol) and methyl iodide (5.03 g, 35.43 mmol). The reaction mixture was warmed to 60° C. for 16 hr, cooled to RT and the solids removed by filtration. The filtrate was re-treated with additional cesium carbonate (4.31 g, 13.23 mmol) and methyl iodide (9.59 g, 67.58 mmol) and warmed to 60° C. for 34 hr. After cooling to RT, the reaction mixture was filtered, concentrated in vacuo and the residue re-dissolved in EtOAc (50 mL). The EtOAc solution was washed with water (25 mL), brine (25 mL), dried (Na₂SO₄) and filtered. After concentrating the filtrate in vacuo, the residual oil was purified by silica gel flash column chromatography (95:5-50:50 gradient of heptane/EtOAc) to furnish the title compound as a colorless oil: ¹H NMR (500 MHz, CDCl₃) delta 2.66 (3H, s), 3.44 (3H, s), 4.59 (2H, s), 6.64 (1H, s).

Step 2—Synthesis of 2-[5-(methoxymethyl)isoxazol-3-yl]but-3-yn-2-ol

To a solution of 1-[5-(methoxymethyl)isoxazol-3-yl]ethanone (220 mg, 1.42 mmol) in dry THF (4 mL) at 0° C. under an atmosphere of nitrogen, was introduced ethynylmagnesium bromide (4.4 mL of a 0.5M solution in THF, 2.20 mmol) dropwise over 5 min. After 1.5 hr at this temperature, the reaction was carefully quenched with water (0.2 mL) and the resulting suspension concentrated in vacuo. The residual syrup was slurried in water (5 mL) and the pH adjusted to 2 with 5M aqueous hydrochloric acid for 5 min., then saturated sodium bicarbonate solution introduced until the pH was ~7.5. Following extraction of the basic aqueous solution with EtOAc (2×100 ml), the combined EtOAc extracts were dried (Na₂SO₄), filtered and the filtrate concentrated in vacuo to furnish the crude title compound as a pale brown oil: ¹H NMR (500 MHz, CDCl₃) delta 1.89 (3H, s), 2.66 (1H, s), 3.02 (1H, br. s), 3.45 (3H, s), 4.55 (2H, s), 6.39 (1H, s); LC-MS: m/z=+ 181.95 (M+H)+.

Examples 45 (i) and 45 (ii)

Preparation of (2R)-2-(5-methyl-1,2-oxazol-3-yl)but-3-yn-2-ol [Example 45 (i)] and (2S)-2-(5-methyl-1,2-oxazol-3-yl)but-3-yn-2-ol [Example 45 (ii)]

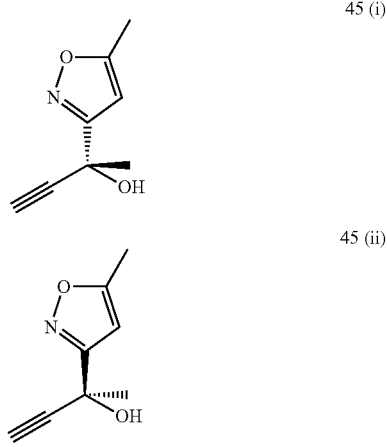

45 (i)

45 (ii)

Step 1—Synthesis of 1-(5-methylisoxazol-3-yl)ethanone (1-a)

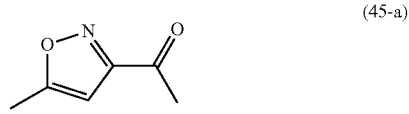
(45-a)

Ethyl nitrite gas was generated in situ by addition of a solution of sodium nitrite (100 g, 1.44 mol) in 50 mL of ethanol and 400 mL of water dropwise into a solution of 50 mL of concentrated sulfuric acid in 50 mL of ethanol and 400 mL of water in a stand-alone reaction vessel. The ethyl nitrite gas generated was bubbled into another reaction flask containing a mixture of hexane-2,5-dione (80 g, 700.88 mmol) in concentrated hydrochloric acid (10 mL). The resulting solution was stirred for 6 hr at 50° C. After cooling to room temperature, the reaction mixture was diluted with ether (600 mL) then washed with of saturated sodium carbonate solution (2×500 mL) and brine (500 mL). The organic layer was dried with anhydrous sodium sulphate then concentrated in vacuo. The crude product was purified by distillation under reduced pressure (12 mm Hg) and the fraction with the boiling point of 70° C. was collected to give 61 g (69%) of the title compound as a colorless liquid: 1H NMR (300 MHz, CDCl₃) delta 6.36 (s, 1H), 2.63 (s, 3H), 2.49 (s, 3H).

Step 2—Synthesis of 2-(5-methylisoxazol-3-yl)but-3-yn-2-ol

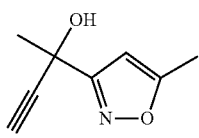
(45-b)

To a stirred solution of ethynylmagnesium bromide (0.5 M in THF, 50 mL, 25 mmol) maintained under nitrogen below 0° C. was added a solution of 1-(5-methyl-1,2-oxazol-3-yl)ethan-1-one (2.5 g, 19.98 mmol) in tetrahydrofuran (20 mL) dropwise over 5 min. The resulting solution was warmed to room temperature and then stirred for a further 3 hr. The reaction was quenched by the addition of saturated ammonium chloride solution (100 mL) then extracted with ethyl acetate (2×100 mL). The combined organic layers was washed with brine (200 mL), dried with anhydrous sodium sulphate and concentrated in vacuo. The residue was purified on a silica gel column, elution with ethyl acetate/petroleum ether (0:1-1:4) afforded the title compound (2.3 g, 75%) as a colorless oil: ¹H NMR (300 MHz, CDCl₃) delta 6.12 (s, 1H), 3.47 (s, 1H), 2.63 (s, 1H), 2.42 (s, 3H), 1.86 (s, 3H).

Step 3—Chiral separation of (2R)-2-(5-methyl-1,2-oxazol-3-yl)but-3-yn-2-ol and (2S)-2-(5-methyl-1,2-oxazol-3-yl)but-3-yn-2-ol

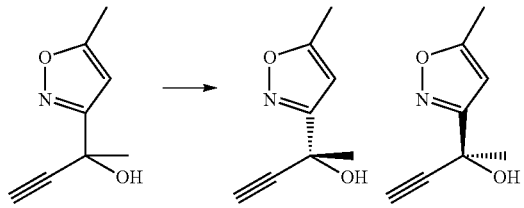

The racemic mixture of (45-b) was separated on preparative chiral column by the method described in WO 2009/158011 to give (2R)-2-(5-methyl-1,2-oxazol-3-yl)but-3-yn-2-ol and (2S)-2-(5-methyl-1,2-oxazol-3-yl)but-3-yn-2-ol.

Examples 46 (i) and 46 (ii)

Preparation of (2R)-2-(1,3-thiazol-2-yl)but-3-yn-2-ol [Examples 46 (i)] and (2S)-2-(1,3-thiazol-2-yl)but-3-yn-2-ol [Examples 46 (ii)]

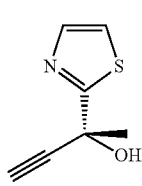
46(i)

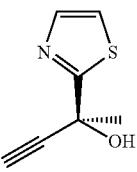
46(ii)

Step 1—Chiral separation of (2R)-2-(1,3-thiazol-2-yl)but-3-yn-2-ol and (2S)-2-(1,3-thiazol-2-yl)but-3-yn-2-ol

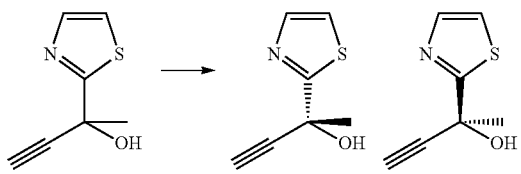

The racemic mixture was separated on preparative chiral column by the method described in WO 2009/158011 to give (2R)-2-(1,3-thiazol-2-yl)but-3-yn-2-ol and (2S)-2-(1,3-thiazol-2-yl)but-3-yn-2-ol.

Example 47

Preparation of (2R)-2-(5-methyl-1,2,4-oxadiazol-3-yl)but-3-yn-2-ol [Example 47 (i)] and (2S)-2-(5-methyl-1,2,4-oxadiazol-3-yl)but-3-yn-2-ol [Example 47 (ii)]

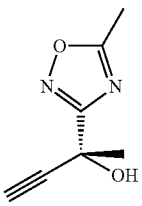
[Example 47 (i)]

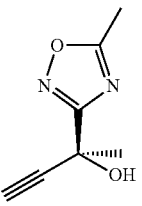
[Example 47 (ii)]

Step 1—Synthesis of 1-(5-methyl-1,2,4-oxadiazol-3-yl)ethanone (47-a)

A mixture of acetonitrile (8.1 L), acetone (522.0 g, 9.0 mol) and iron (III) nitrate (727.2 g, 1.8 mol) was stirred under reflux for 16 h. The suspension was filtered through a pad of celite and the pad was washed with DCM. The combined filtrates were concentrated to dryness. The residue was distilled at 80-110° C. at 13 mm to afford 80 g of crude product. Flash column with DCM, followed by re-distillation at 100-109° C. at 13 mm afforded the title compound (54 g, 8%); $^1$H NMR (CDCl$_3$, 400 MHz): delta 2.63 (s, 6H); LC-MS: m/z=+126 (M+H)+.

Step 2—Synthesis of 2-(5-methyl-1,2,4-oxadiazol-3-yl)but-3-yn-2-ol

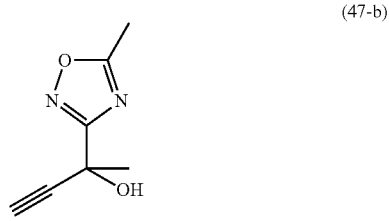

(47-b)

To a solution of ethynylmagnesium bromide (0.5 M in THF, 800 mL, 400 mmol) at 0° C. was added 1-(5-methyl-1,2,4-oxadiazol-3-yl)ethanone (33.5 g, 266 mmol) in THF (533 mL) slowly. The reaction was allowed to warm to room temperature and stirred for 5 hours. After being quenched with saturated NH$_4$Cl (750 mL) at 0° C., the THF was removed in vacuo and the aqueous residue was extracted with ethyl acetate (600 mL×2). The combined organic extracts were dried over Na$_2$SO$_4$, filtered, and concentrated under reduced pressure to give dark brown oil. The dark brown oil was purified by silica gel column chromatography use 10% of ethyl acetate in hexanes as eluent to give the title compound (36 g, 89%), $^1$H NMR (CDCl$_3$, 400 MHz): delta 3.93 (s, 1H), 2.63 (s, 1H), 2.61 (s, 3H), 1.91 (s, 3H).

Step 3—Chiral separation of (2R)-2-(5-methyl-1,2,4-oxadiazol-3-yl)but-3-yn-2-ol [Example 47 (i)] and (2S)-2-(5-methyl-1,2,4-oxadiazol-3-yl)but-3-yn-2-ol [Example 47 (ii)]

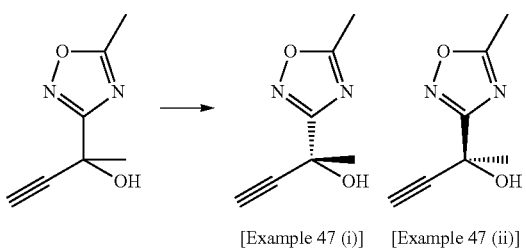

[Example 47 (i)]    [Example 47 (ii)]

The racemic mixture of 2-(5-methyl-1,2,4-oxadiazol-3-yl)but-3-yn-2-ol (161 g) was separated by preparative SFC using the following conditions to give the first eluting compound, [Example 47 (i)] (51.3 g, >95% chiral purity) and second eluting compound [Example 47 (ii)] (54.1 g, >95% chiral purity). Separation conditions: Instrument: Thar 200 preparative SFC; Column: ChiralCel OZ-H, 250×30 mmI.D, Mobile phase: A for CO2 and B for IPA; Gradient: B 10%; Flow rate: 100 mL/min; Back pressure: 100 bar; Column temperature: 38° C.; Wavelength: 210 nm; Cycletime: 2 min; Sample preparation: Compound was dissolved in Methanol to ~50 mg/ml; Injection: 1 ml per injection.

Example 48

Preparation of (2R)-2-(pyrimidin-2-yl)but-3-yn-2-ol [Example 48 (ii)] and (2S)-2-(pyrimidin-2-yl)but-3-yn-2-ol [Example 48 (i)]

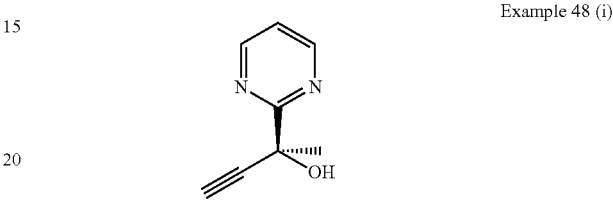

Example 48 (i)

Example 48 (ii)

Step 1—Synthesis of 2-(pyrimidin-2-yl)but-3-yn-2-ol

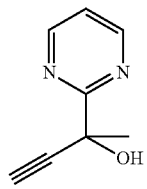

(48-a)

A solution of 1-(pyrimidin-2-yl)ethan-1-one (2.5 g, 20.47 mmol) in tetrahydrofuran (60 mL) was added dropwise into a ethynylmagnesium bromide (0.5 M in tetrahydrofuran, 60 mL, 30 mmol) solution with stirring at room temperature under nitrogen atmosphere. The reaction mixture was stirred at room temperature for 1 hr and then quenched by the addition of saturated aqueous ammonium chloride (200 mL). The resulting solution was extracted with ethyl acetate (2×300 mL) and the combined organic layers were washed with brine (300 mL), dried over anhydrous sodium sulphate and concentrated in vacuo. The residue was purified on a silica gel column, elution with ethyl acetate/petroleum ether (0:1-1:1) afforded 2-(pyrimidin-2-yl)but-3-yn-2-ol (1.5 g, 50%) as yellow oil. $^1$H NMR (400 MHz, CDCl$_3$) delta 8.82 (d, J=4.4 Hz, 2H), 7.33-7.29 (m, 1H), 5.1 (s, 1H), 2.56 (s, 1H), 1.93 (s, 3H); LC-MS: m/z=149 (M+H)$^+$.

Chiral separation of (2R)-2-(pyrimidin-2-yl)but-3-yn-2-ol [Example 48 (ii)] and (2S)-2-(pyrimidin-2-yl)but-3-yn-2-ol [Example 48 (i)]

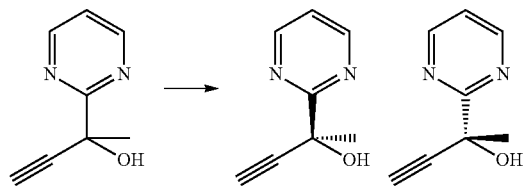

The racemic mixture of 2-(pyrimidin-2-yl)but-3-yn-2-ol was separated by preparative SFC using the following conditions to give the first eluting compound (2S)-2-(pyrimidin-2-yl)but-3-yn-2-ol Example 48 (i) and second eluting compound (2R)-2-(pyrimidin-2-yl)but-3-yn-2-ol [Example 48 (ii)]. Separation conditions: Column: Chiralpak IC, 3×25 cm, 5 um column; Mobile phase A: CO2; Mobile phase B: Isopropanol (0.1% NH4OH); Isocratic condition: 90% A/10% B; Flow rate: 200 mL/min; UV: 254 nm; Backpressure: 120 Bar; Temp: 40 degrees C.

Example 49

Examples in Table 5 were prepared by procedure described in Example 5 by reacting 4-(6-bromo-3-methyl-1H-indazol-1-yl)pyrimidin-2-amine with the appropriate but-3-yn-2-ol intermediates.

TABLE 5

| No. | Structure | Name | 1H NMR | MS (M + H) |
|---|---|---|---|---|
| T5-49.1 | 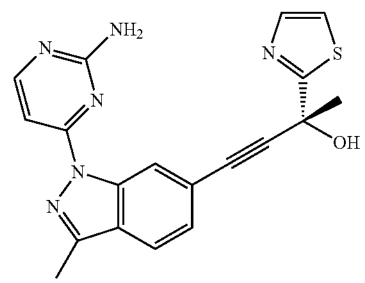 | (2R)-4-[1-(2-aminopyrimidin-4-yl)-3-methyl-1H-indazol-6-yl]-2-(1,3-thiazol-2-yl)but-3-yn-2-ol | (500 MHz, DMSO) delta 1.94 (3 H, s), 2.57 (3 H, s), 6.97 (2 H, br. s.), 7.04 (1 H, d, J = 5.36 Hz), 7.08 (1 H, s), 7.34 (1 H, d, J = 8.20 Hz), 7.70 (1 H, d, J = 3.15 Hz), 7.78 (1 H, d, J = 3.15 Hz), 7.84 (1 H, d, J = 8.20 Hz), 8.27 (1 H, br. s.), 8.85 (1 H, s) | 377.35 |
| T5-49-2 | 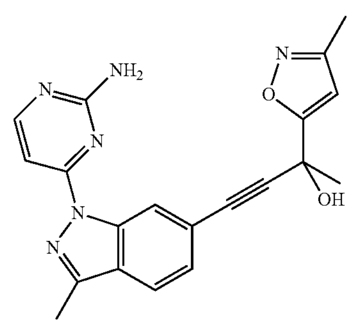 [SMILES: Cc1cc(C(C)(O)C#Cc2ccc3c(C)nn(-c4ccnc(N)n4)c3c2)on1] | 4-[1-(2-aminopyrimidin-4-yl)-3-methyl-1H-indazol-6-yl]-2-(3-methyl-1,2-oxazol-5-yl)but-3-yn-2-ol | (500 MHz, DMSO) delta 1.86 (3 H, s), 2.25 (3 H, s), 2.58 (3 H, s), 6.45 (1 H, s), 6.76 (1 H, s), 6.99 (2 H, br. s.), 7.05 (1 H, s), 7.39 (1 H, d, J = 8.35 Hz), 7.87 (1 H, d, J = 8.20 Hz), 8.27 (1 H, d, J = 5.36 Hz), 8.90 (1 H, s) | 375.45 |
| T5-49.3 | 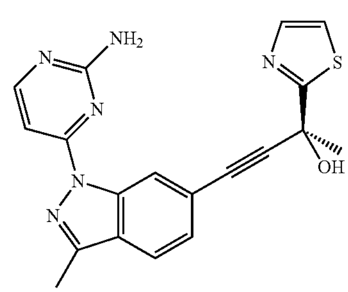 [SMILES: Cc1nn(-c2ccnc(N)n2)c2cc(C#C[C@](C)(O)c3nccs3)ccc12] | (2S)-4-[1-(2-aminopyrimidin-4-yl)-3-methyl-1H-indazol-6-yl]-2-(1,3-thiazol-2-yl)but-3-yn-2-ol | (500 MHz, DMSO) delta 1.94 (3 H, s), 2.57 (3 H, s), 6.98 (2 H, br. s.), 7.06 (1H, br. s.), 7.08 (1H, s), 7.34 (1 H, d, J = 7.88 Hz), 7.70 (1 H, d, J = 2.36 Hz), 7.76-7.82 (1 H, m), 7.84 (1H, d, J = 8.20 Hz), 8.31 (1 H, br. s.), 8.85 (1 H, s) | 377.1 |

TABLE 5-continued

| No. | Structure | Name | 1H NMR | MS (M + H) |
|---|---|---|---|---|
| T5-49.4 | 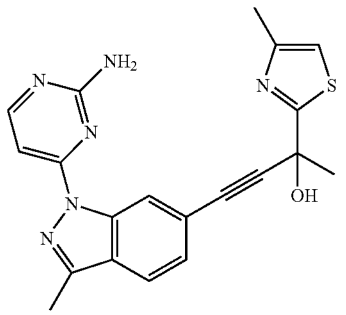 [SMILES: Cc1csc(C(C)(O)C#Cc2ccc3c(C)nn(-c4ccnc(N)n4)c3c2)n1] | 4-[1-(2-aminopyrimidin-4-yl)-3-methyl-1H-indazol-6-yl]-2-(4-methyl-1,3-thiazol-2-yl)but-3-yn-2-ol | (500 MHz, DMSO) delta 1.92 (3 H, s), 2.37 (3 H, s), 2.58 (3 H, s), 6.97 (2 H, br. s.), 7.01 (1 H, s), 7.04 (1 H, d, J = 5.36 Hz), 7.20-7.24 (1 H, m), 7.35 (1 H, d, J = 8.67 Hz), 7.85 (1 H, d, J = 8.20 Hz), 8.26 (1H, br. s.), 8.85 (1 H, s) | 391.05 |
| T5-49.5 | 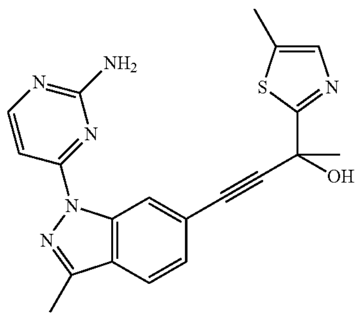 [SMILES: Cc1cnc(C(C)(O)C#Cc2ccc3c(C)nn(-c4ccnc(N)n4)c3c2)s1] | 4-[1-(2-aminopyrimidin-4-yl)-3-methylindazol-6-yl]-2-(5-methyl-1,3-thiazol-2-yl)but-3-yn-2-ol | (500 MHz, DMSO) delta 1.91(3 H, s), 2.44 (3 H, d, J = 1.10 Hz), 2.57 (3 H, s), 6.91-7.00 (3 H, m), 7.04 (1 H, d, J = 5.52 Hz), 7.34 (1 H, dd, J = 8.28, 1.18 Hz), 7.44 (1 H, d, J = 1.26 Hz), 7.84 (1 H, d, J = 8.20 Hz), 8.26 (1 H, d, J = 5.52 Hz), 8.85 (1 H, s) | 391.4 |
| T5-49.6 | 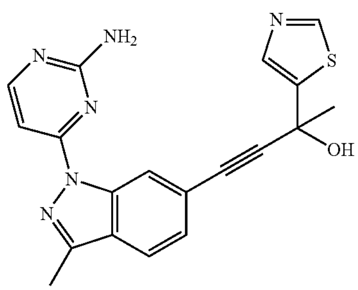 [SMILES: Cc1nn(-c2ccnc(N)n2)c2cc(C#CC(C)(O)c3cncs3)ccc12] | 4-[1-(2-aminopyrimidin-4-yl)-3-methyl-1H-indazol-6-yl]-2-(1,3-thiazol-5-yl)but-3-yn-2-ol | (500 MHz, DMSO) delta 1.93 (3 H, s), 2.58 (3 H, s), 6.79 (1H, s), 6.98 (2 H, br. s.), 7.04 (1 H, d, J = 5.52 Hz), 7.40 (1 H, dd, J = 8.20, 1.10 Hz), 7.86 (1 H, d, J = 8.20 Hz), 8.00 (1 H, s), 8.26 (1 H, d, J = 5.52 Hz), 8.90 (1 H, s), 9.03 (1 H, s) | 377.35 |
| T5-49.7 | 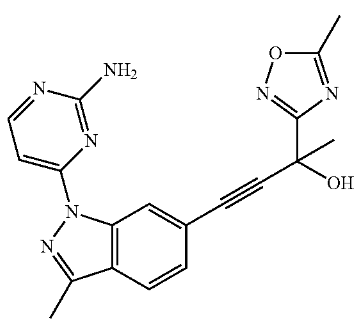 [SMILES: Cc1nc(C(C)(O)C#Cc2ccc3c(C)nn(-c4ccnc(N)n4)c3c2)no1] | 4-[1-(2-aminopyrimidin-4-yl)-3-methyl-1H-indazol-6-yl]-2-(5-methyl-1,2,4-oxadiazol-3-yl)but-3-yn-2-ol | (500 MHz, DMSO) delta 1.90 (3 H, s), 2.58 (3 H, s), 2.63 (3 H, s), 6.76 (1 H, s), 6.97 (2 H, br. s.), 7.04 (1 H, d, J = 5.52 Hz), 7.36 (1 H, dd, J = 8.20, 1.26 Hz), 7.86 (1 H, d, J = 8.20 Hz), 8.26 (1 H, d, J = 5.52 Hz), 8.87 (1 H, s) | 376.4 |
| T5-49.8 | 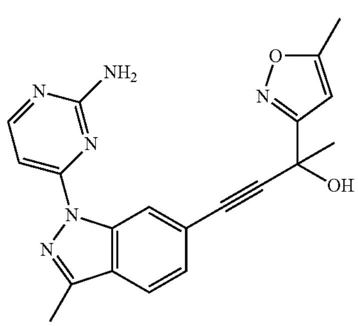 [SMILES: Cc1cc(C(C)(O)C#Cc2ccc3c(C)nn(-c4ccnc(N)n4)c3c2)no1] | 4-[1-(2-aminopyrimidin-4-yl)-3-methyl-1H-indazol-6-yl]-2-(5-methyl-1,2-oxazol-3-yl)but-3-yn-2-ol | (500 MHz, DMSO) delta 1.86 (3 H, s), 2.42 (3 H, s), 2.57 (3 H, s), 6.41 (1 H, s), 6.55 (1 H, s), 6.97 (2 H, br. s.), 7.04 (1 H, d, J = 5.52 Hz), 7.35 (1 H, dd, J = 8.20, 1.26 Hz), 7.85 (1 H, d, J = 8.20 Hz), 8.26 (1 H, d, J = 5.52 Hz), 8.86 (1 H, s) | 375.45 |

TABLE 5-continued

| No. | Structure | Name | 1H NMR | MS (M + H) |
|---|---|---|---|---|
| T5-49.9 | 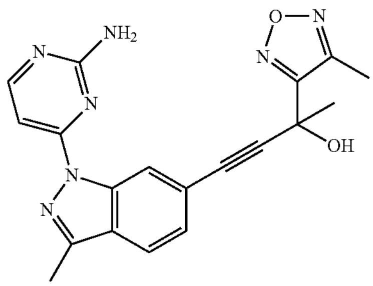 [SMILES: Cc1nonc1C(C)(O)C#Cc1ccc2c(C)nn(-c3ccnc(N)n3)c2c1] | 4-[1-(2-aminopyrimidin-4-yl)-3-methyl-1H-indazol-6-yl]-2-(4-methyl-1,2,5-oxadiazol-3-yl)but-3-yn-2-ol | (500 MHz, DMSO) delta 2.01 (3 H, s), 2.58 (3 H, s), 2.59 (3 H, s), 6.91(1 H, s), 6.97 (2 H, br. s.), 7.04 (1 H, d, J = 5.36 Hz), 7.39 (1 H, dd, J = 8.20, 1.10 Hz), 7.87 (1 H, d, J = 8.20 Hz), 8.28 (1 H, s), 8.91 (1 H, s) | 376.4 |
| T5-49.10 | 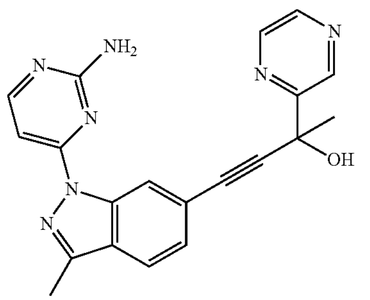 [SMILES: Cc1nn(-c2ccnc(N)n2)c2cc(C#CC(C)(O)c3cnccn3)ccc12] | 4-[1-(2-aminopyrimidin-4-yl)-3-methyl-1H-indazol-6-yl]-2-(pyrazin-2-yl)but-3-yn-2-ol | (500 MHz, DMSO) delta 1.91 (3 H, s), 2.57 (3 H, s), 6.69 (1 H, s), 6.97 (2 H, br. s.), 7.04 (1 H, d, J = 5.36 Hz), 7.35 (1H, dd, J = 8.20, 1.26 Hz), 7.83 (1 H, d, J = 8.20 Hz), 8.26 (1 H, s), 8.60-8.71 (2 H,m), 8.86 (1H, s), 9.06 (1H, s) | 372.4 |
| T5-49.11 | 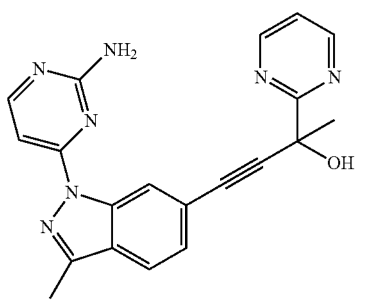 [SMILES: Cc1nn(-c2ccnc(N)n2)c2cc(C#CC(C)(O)c3ncccn3)ccc12] | 4-[1-(2-aminopyrimidin-4-yl)-3-methyl-1H-indazol-6-yl]-2-(pyrimidin-2-yl)but-3-yn-2-ol | (500 MHz, DMSO) delta 1.92 (3 H, s), 2.56 (3 H, s), 6.23 (1 H, s), 6.97 (2 H, br. s.), 7.03 (1 H, d, J = 5.52 Hz), 7.30 (1 H, dd, J = 8.28, 1.18 Hz), 7.51 (1 H, t, J = 4.81 Hz), 7.82 (1 H, d, J = 8.20 Hz), 8.25 (1 H, d, J = 5.52 Hz), 8.82 (1 H, s), 8.90 (2 H, d, J = 4.89 Hz) | 372.4 |
| T5-49.12 | 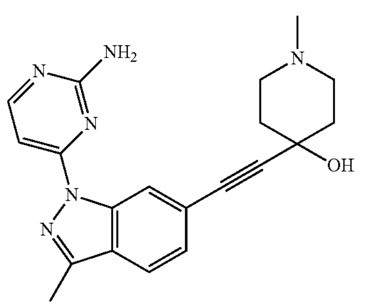 [SMILES: Cc1nn(-c2ccnc(N)n2)c2cc(C#CC3(O)CCN(C)CC3)ccc12] | 4-{2-[1-(2-aminopyrimidin-4-yl)-3-methyl-1H-indazol-6-yl]ethynyl}-1-methylpiperidin-4-ol | (500 MHz, DMSO) delta 1.82 (2 H, br. s.), 1.97 (2 H, d, J = 12.61 Hz), 2.26 (3 H, br. s.), 2.32-2.69 (4 H, m), 2.57 (3 H, s), 5.64 (1 H, br. s.), 6.96 (2 H, br. s.), 7.04 (1 H, d, J = 5.52 Hz), 7.34 (1 H, dd, J = 8.20, 1.10 Hz), 7.83 (1 H, d, J = 8.20 Hz), 8.26 (1 H, d, J = 5.52 Hz), 8.84 (1 H, s) | 363.05 |
| T5-49.13 | 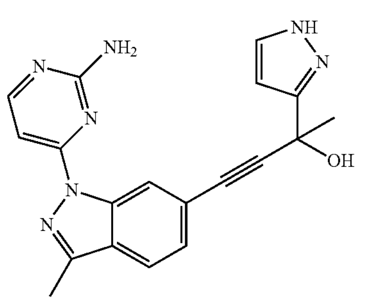 [SMILES: Cc1nn(-c2ccnc(N)n2)c2cc(C#CC(C)(O)c3cc[nH]n3)ccc12] | 4-[1-(2-aminopyrimidin-4-yl)-3-methyl-1H-indazol-6-yl]-2-(1H-pyrazol-3-yl)but-3-yn-2-ol | (250 MHz, DMSO) delta 1.88 (3 H, s), 2.57 (3 H, s), 5.63 (1 H, s), 6.37 (1 H, d, J = 1.83 Hz), 6.51 (2 H, br. s.), 7.07 (1H, d, J = 5.48 Hz), 7.32-7.40 (1 H, m), 7.51 (1 H, s), 7.78 (1H, d, J = 8.22 Hz), 8.25 (1 H, d, J = 5.63 Hz), 8.81 (1 H, s) | 360.05 |

TABLE 5-continued

| No. | Name | 1H NMR | MS (M + H) |
|---|---|---|---|
| T5-49.14 | 4-[1-(2-aminopyrimidin-4-yl)-3-methyl-1H-indazol-6-yl]-2-(1H-imidazol-4-yl)but-3-yn-2-ol | (250 MHz, MeOD) delta 1.92 (3 H, s), 2.60 (3 H, s), 7.20 (2 H, d, J = 5.63 Hz), 7.40 (1 H, d, J = 8.53 Hz), 7.64-7.81 (2 H, m), 8.20 (1 H, d, J = 5.63 Hz), 9.00 (1H, s) | 360.05 |
| T5-49.15 | 4-[1-(2-aminopyrimidin-4-yl)-3-methyl-1H-indazol-6-yl]-2-[5-(hydroxymethyl)-1,2-oxazol-3-yl]but-3-yn-2-ol | (500 MHz, DMSO) delta 1.88 (3 H, s), 2.58 (3 H, s), 4.57 (2 H, d, J = 6.15 Hz), 5.68 (1 H, t, J = 6.07 Hz), 6.55 (1 H, s), 6.64 (1 H, s), 6.99 (2 H, br. s.), 7.04 (1 H, d, J = 5.52 Hz), 7.36 (1 H, dd, J = 8.20, 1.26 Hz), 7.86 (1 H, d, J = 8.20 Hz), 8.26 (1 H, d, J = 4.89 Hz), 8.87 (1 H, s) | 391.4 |
| T5-49.16 | 7-{2-[1-(2-aminopyrimidin-4-yl)-3-methyl-1H-indazol-6-yl]ethynyl}-5H,6H,7H-pyrrolo[1,2-a]imidazol-7-ol | (500 MHz, DMSO) delta 2.58 (3 H, s), 2.83 (1 H, d, J = 13.40 Hz), 3.12 (1 H, d, J = 13.24 Hz), 4.02-4.14 (2 H, m), 6.57 (1 H, s), 7.00 (1 H, s), 6.98 (1H, s), 7.04 (1 H, d, J = 5.52 Hz), 7.15 (1 H, s), 7.37 (1 H, d, J = 8.20 Hz), 7.86 (1 H, d, J = 8.35 Hz), 8.26 (1 H, d, J = 5.52 Hz), 8.89 (1 H, s) | 372.05 |
| T5-49.17 | 4-[1-(2-aminopyrimidin-4-yl)-3-methyl-1H-indazol-6-yl]-2-hydroxy-N,N,2-trimethylbut-3-ynamide | (500 MHz, DMSO) delta 1.66 (3 H, s), 2.53 (3 H, s), 2.87 (3 H, s), 3.33 (3 H, s), 7.04 (1H, d, J = 5.67 Hz), 7.34 (1 H, dd, J = 8.20, 0.95 Hz), 7.81 (1 H, d, J = 8.20 Hz), 8.22 (1 H, d, J = 5.36 Hz), 8.82 (1 H, s) | 365.1 |
| T5-49.18 | 4-[1-(2-aminopyrimidin-4-yl)-3-methyl-1H-indazol-6-yl]-1-fluoro-2-methylbut-3-yn-2-ol | (500 MHz, MeOD) delta 1.61 (3 H, d, J = 1.89 Hz), 2.58 (3 H, s), 4.43 (2 H, dd, J = 47.29, 1.26 Hz), 5.49 (1H, s), 7.20 (1H, d, J = 5.83 Hz), 7.36 (1 H, dd, J = 8.35, 1.26 Hz), 7.71 (1 H, dd, J = 8.20, 0.63 Hz), 8.19 (1H, d, J = 5.83 Hz), 8.91 (1 H, s) | 326 |

TABLE 5-continued

| No. | Structure | Name | 1H NMR | MS (M + H) |
|---|---|---|---|---|
| T5-49.19 | 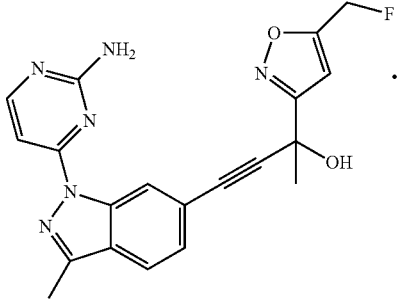 | 4-[1-(2-aminopyrimidin-4-yl)-3-methyl-1H-indazol-6-yl]-2-[5-(fluoromethyl)isoxazol-3-yl]but-3-yn-2-ol mono-formate salt | (500 MHz, MeOD) delta 1.96 (3 H, s), 2.59 (3 H, s), 5.49 (1 H, d, J = 47.3 Hz), 6.79 (1 H, d, J = 3.5 Hz), 7.21 (1 H, d, J = 5.8 Hz), 7.40 (1 H, dd, J = 8.20, 1.1 Hz), 7.74 (1 H, d, J = 8.2 Hz), 8.13 (1H, s), 8.19 (1H, d, J = 5.8 Hz), 8.98 (1 H, s); | 393.0 |
| T5-49.20 | 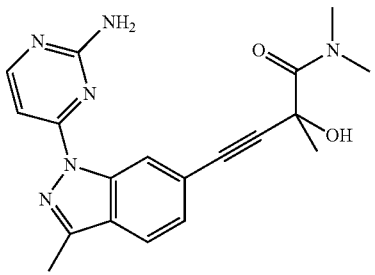 [SMILES: Cc1nn(-c2ccnc(N)n2)c2cc(C#CC(C)(O)C(=O)N(C)C)ccc12] | 4-[1-(2-aminopyrimidin-4-yl)-3-methyl-1H-indazol-6-yl]-2-hydroxy-N,N,2-trimethylbut-3-ynamide: | (500 MHz, DMSO) delta 1.66 (3 H, s), 2.53 (3 H, s), 2.87 (3 H, s), 3.33 (3 H, s), 7.04 (1 H, d, J = 5.67 Hz), 7.34 (1 H, dd, J = 8.20, 0.95 Hz), 7.81 (1 H, d, J = 8.20 Hz), 8.22 (1 H, d, J = 5.36 Hz), 8.82 (1 H, s); | 365.10 |
| T5-49.21 | 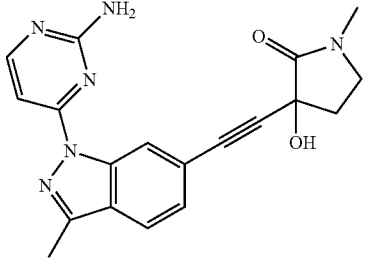 [SMILES: Cc1nn(-c2ccnc(N)n2)c2cc(C#CC3(O)CCN(C)C3=O)ccc12] | 3-{[1-(2-aminopyrimidin-4-yl)-3-methyl-1H-indazol-6-yl]ethynyl}-3-hydroxy-1-methylpyrrolidin-2-one | (500 MHz, 9:1 Methanol-d4:CDCl3) delta 2.32-2.38 (1 H, m), 2.59 (3 H, s), 2.64 (1 H, ddd, J = 12.93, 6.78, 4.57 Hz), 2.95 (3 H, s), 3.47-3.53 (2 H, m), 4.53 (1 H, s), 7.19 (1 H, d, J = 5.67 Hz), 7.37 (1 H, dd, J = 8.51, 1.26 Hz), 7.70 (1 H, dd, J = 8.20, 0.95 Hz), 8.18 (1H, d, J = 5.36 Hz), 9.01 (1 H, s); | 363.1 |

Example 50

Preparation of 4-[1-(2-aminopyrimidin-4-yl)-1H-indazol-6-yl]-2-(1H-pyrazol-4-yl)but-3-yn-2-ol

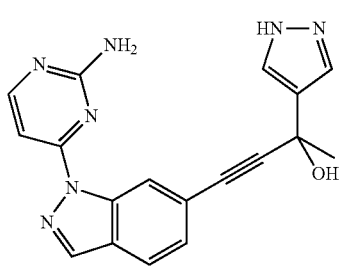 [SMILES: CC(O)(C#Cc1ccc2cnn(-c3ccnc(N)n3)c2c1)c1cn[nH]c1]

The title compound was prepared by the procedure described in Example 2 (Step 2-b) by reacting 4-(6-bromo-1H-indazol-1-yl)pyrimidin-2-amine with 2-(1H-pyrazol-4-yl)but-3-yn-2-ol. The reaction was carried out at 75° C. for 1 hr: $^1$H NMR (500 MHz, DMSO) delta 1.81 (3H, s), 5.95 (1 H, br. s.), 6.93-7.17 (3H, m), 7.38 (1H, d, J=9.30 Hz), 7.70 (2H, br. s.), 7.88 (1H, d, J=8.35 Hz), 8.31 (1H, d, J=5.52 Hz), 8.49 (1H, s), 8.91 (1H, s), 12.71 (1H, br. s.); LC-MS: m/z=+346.50 (M+H)+.

Example 51

Preparation of 4-[1-(2-aminopyrimidin-4-yl)-3-methyl-1H-indazol-6-yl]-2-(1,3-oxazol-4-yl)but-3-yn-2-ol

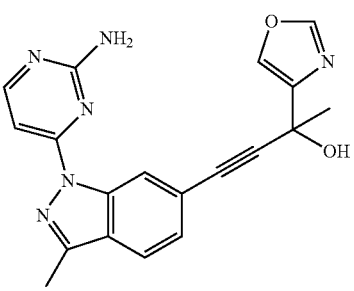

(51-b)

Step 1—Synthesis of
4-(6-iodo-3-methylindazol-1-yl)pyrimidin-2-amine

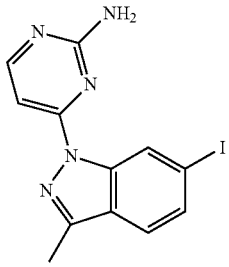

(51-a)

A pressure tube containing copper (1) iodide (37.57 mg, 0.20 mmol), sodium iodide (591.42 mg, 3.95 mmol) and 4-(6-bromo-3-methyl-1H-indazol-1-yl)pyrimidin-2-amine (600 mg, 1.97 mmol) was flushed with nitrogen before the addition of 1,4-dioxane, DMF (3 ml each) and N,N'-dimethylethane-1,2-diamine (0.021 ml, 0.20 mmol). The vessel was sealed and stirred at 115° C. overnight. Reaction was cooled and added to ice water (15 ml) before extracting into DCM (2×20 mL). Combined organics were dried (Na$_2$SO$_4$), filtered and concentrated in vacuo. Crude material purified by column chromatography (Elution with 2% MeOH-DCM to 12% MeOH-DCM) to give the title compound: $^1$H NMR (500 MHz, DMSO) delta 7.02 (3H, dd, J=5.5, 3.1 Hz), 7.73-7.53 (2H, m), 8.25 (1H, d, J=5.5 Hz), 9.25 (1H, s); LC-MS: m/z=+ 351.90 (M+H)+. This compound of 79% purity LC-MS was used for the next step without further purification Step 2—Synthesis of 4-[1-(2-aminopyrimidin-4-yl)-3-methyl-1H-indazol-6-yl]-2-(1,3-oxazol-4-yl)but-3-yn-2-ol To a vial was added 4-(6-iodo-3-methylindazol-1-yl)pyrimidin-2-amine (150 mg, 0.43 mmol), piperidine (1.5 mL), tetrakis(triphenylphosphine)palladium (49.36 mg, 0.04 mmol), copper(I) iodide (8.14 mg, 0.04 mmol) and 2-(1,3-oxazol-4-yl)but-3-yn-2-ol (87.87 mg, 0.64 mmol). The mixture was stirred at RT for 20 mins. Reaction mixture was concentrated in vacuo. DCM (5 mL) added and mixture was concentrated in vacuo. This was repeated twice. The crude material was purified by column chromatography (Biotage, 98:2 to 88:12 DCM: methanol gradient). Further purification by flash column chromatography gave the title compound: $^1$H (500 MHz, DMSO) delta 1.81 (3H, s), 2.58 (3H, s), 6.26 (1H, s), 6.99 (2H, s), 7.04 (1H, d, J=5.5 Hz), 7.39 (1H, dd, J=8.2, 1.1 Hz), 7.85 (1H, d, J=8.1 Hz), 8.13 (1H, s), 8.26 (1H, d, J=5.5 Hz), 8.36 (1H, s), 8.87 (1H, s); LC-MS: m/z=+361.05 (M+H)+.

Example 52

Examples in Table 6 were prepared by procedure as described in Example 51 (Step 2) by reacting 4-(6-iodo-3-methylindazol-1-yl)pyrimidin-2-amine with the appropriate but-3-yn-2-ol.

TABLE 6

| No. | Structure | Name | 1H NMR | MS (M + H) |
|---|---|---|---|---|
| T6-52.1 | 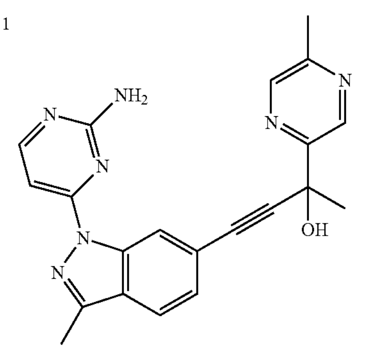 | 4-[1-(2-aminopyrimidin-4-yl)-3-methyl-1H-indazol-6-yl]-2-(5-methylpyrazin-2-yl)but-3-yn-2-ol; formic acid | (500 MHz, DMSO) delta 1.88 (3 H, s), 2.52 (3 H, s), 2.57 (2 H, s), 6.62 (1H, br. s.), 6.99 (2 H, br. s.), 7.03 (1 H, d, J = 5.67 Hz), 7.34 (1 H, dd, J = 8.28, 1.18 Hz), 7.83 (1 H, d, J = 8.20 Hz), 8.14 (1H, s), 8.25 (1 H, d, J = 5.52 Hz), 8.53 (1 H, s), 8.85 (1H, s), 8.90 (1 H, d, J = 1.26 Hz) | 385.95 |
| T6-52.2 | 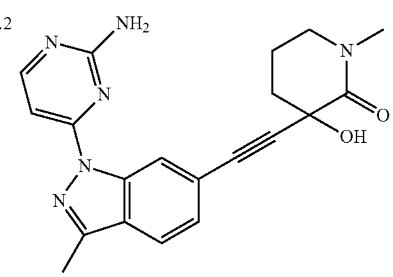 | 3-{2-[1-(2-aminopyrimidin-4-yl)-3-methyl-1H-indazol-6-yl]ethynyl}-3-hydroxy-1-methylpiperidin-2-one; formic acid | (500 MHz, DMSO) delta 1.89-2.13 (3 H, m), 2.26 (1 H, td, J = 5.99, 3.78 Hz), 2.33-2.39 (1 H, m), 2.58 (3 H, s), 2.64 (1 H, d, J = 1.73 Hz), 2.88 (3 H, s), 6.16 (1 H, br.s.), 6.99 (2 H, br. s.), 7.04 (1 H, d, J = 5.52 Hz), 7.34 (1 H, dd, J = 8.20, 1.10 Hz), 7.85 (1H, d, J = 8.20 Hz), 8.27 (1 H, d, J = 5.52 Hz), 8.35 (1 H, br. s.), 8.85 (1 H, s) | 377.15 |

Example 53

Preparation of 4-[1-(2-aminopyrimidin-4-yl)-3-methyl-1H-indazol-6-yl]-2-(1-methyl-1H-imidazol-2-yl)but-3-yn-2-ol

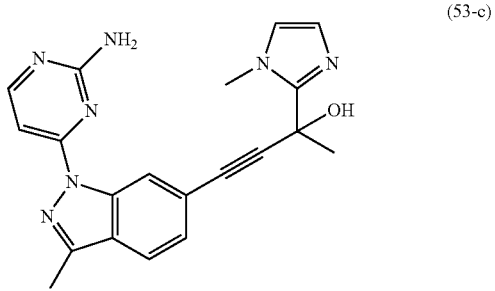 [SMILES: Cc1nn(-c2ccnc(N)n2)c2cc(C#CC(C)(O)c3nccn3C)ccc12]
(53-c)

Step 1—Synthesis of 4-{3-methyl-6-[2-(trimethylsilyl)ethynyl]indazol-1-yl}pyrimidin-2-amine

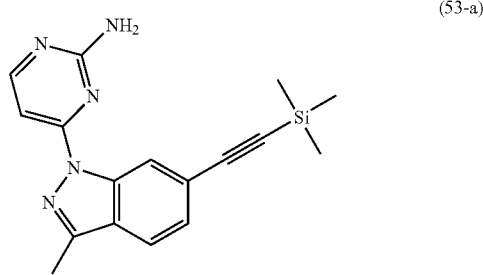 [SMILES: Cc1nn(-c2ccnc(N)n2)c2cc(C#C[Si](C)(C)C)ccc12]
(53-a)

To a pressure tube was added 4-(6-bromo-3-methylindazol-1-yl)pyrimidin-2-amine (0.5 g, 1.64 mmol), piperidine (3.5 mL) tetrakis(triphenylphosphine)palladium (113.98 mg, 0.1 mmol), copper(I) iodide (18.79 mg, 0.1 mmol) and ethynyl(trimethyl)silane (0.47 ml, 3.29 mmol). The mixture was purged with nitrogen for 2 minutes and then stirred at 65° C. for 1.5 hr. The reaction mixture was concentrated in vacuo, DCM (5 mL) was added and the concentration repeated (×2). The mixture was purified by column chromatography (Biotage, 3-8% MeOH gradient in DCM) to give the title intermediate as a white solid (116 mg): $^1$H NMR (250 MHz, DMSO) delta 0.28 (9H, s), 2.57 (3H, s), 7.03 (3H, d, J=5.5), 7.38 (1H, d, J=8.2), 7.84 (1H, d, J=8.2), 8.26 (1H, d, J=5.5), 8.90 (1H, s); LC-MS: m/z=+322.50 (M+H)+.

Step 2—Synthesis of 4-(6-ethynyl-3-methylindazol-1-yl)pyrimidin-2-amine

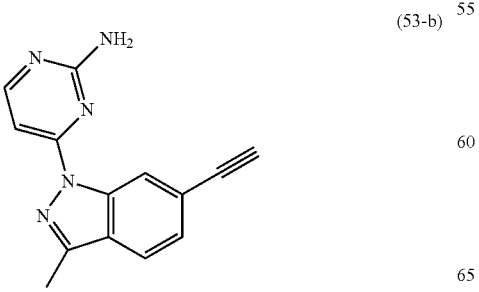
(53-b)

To a solution of 4-{3-methyl-6-[2-(trimethylsilyl)ethynyl]indazol-1-yl}pyrimidin-2-amine (600 mg, 1.87 mmol) in THF (15 ml) was added TBAF (2.24 mL of a 1M solution in THF, 2.24 mmol) and the reaction mixture was allowed to stand for 0.5 hr. The reaction mixture was concentrated in vacuo, DCM (5 ml) was added and the concentration repeated (×2). The crude product was purified by flash chromatography (Biotage, 3-10% methanol in DCM) to give the title intermediate as a yellow solid (300 mg): $^1$H NMR (500 MHz, DMSO) delta 2.58 (3H, s), 4.37 (1H, s), 7.14-6.86 (3H, m), 7.40 (1H, dd, J=8.2, 1.1 Hz), 7.85 (1H, d, J=8.2 Hz), 8.26 (1H, d, J=5.5 Hz), 8.98 (1H, s); LC-MS: m/z=+250.35 (M+H)+.

Step 3—Synthesis of 4-[1-(2-aminopyrimidin-4-yl)-3-methyl-1H-indazol-6-yl]-2-(1-methyl-1H-imidazol-2-yl)but-3-yn-2-ol To a solution of 4-(6-ethynyl-3-methylindazol-1-yl)pyrimidin-2-amine (150 mg, 0.6 mmol) in THF (2 mL) at −78° C. under nitrogen was added 2M LDA in THF (0.75 mL, 1.50 mmol). After 5 minutes, 1-(1-methyl-1H-imidazol-2-yl)ethanone (225 mg, 1.81 mmol) in THF (1.0 mL) was added, and after a further 20 minutes the mixture was allowed to warm to RT and stirred for 1.5 hours. The reaction mixture was then cooled to −78° C. and treated with additional 2M LDA in THF (0.3 mL, 0.6 mmol) and 1-(1-methyl-1H-imidazol-2-yl)ethanone (90 mg, 0.6 mmol). After stirring at RT for 4 hr, the reaction mixture was quenched by addition of saturated aqueous NH$_4$Cl (2 mL). The volatiles were removed in vacuo and the mixture was diluted with DCM (10 ml) and washed with water (2 mL), dried (Na$_2$SO$_4$), filtered and concentrated in vacuo. The crude product was purified by flash chromatography (Biotage, 3-12% methanol gradient in DCM) to give the title compound: $^1$H NMR (500 MHz, DMSO) delta 2.00 (3H, s), 2.57 (3H, s), 3.92 (3H, s), 6.32 (1H, s), 6.77 (1H, s), 6.98 (2 H, s), 7.03 (1H, d, J=5.5 Hz), 7.15 (1H, s), 7.36 (1H, d, J=8.2), 7.84 (1H, d, J=8.2 Hz), 8.25 (1H, d, J=5.5 Hz), 8.84 (1H, s); LC-MS: m/z=+374.05 (M+H)+.

Example 54

Preparation of 4-[1-(2-aminopyrimidin-4-yl)-3-methyl-1H-indazol-6-yl]-2-(1H-1,2,4-triazol-3-yl)but-3-yn-2-ol

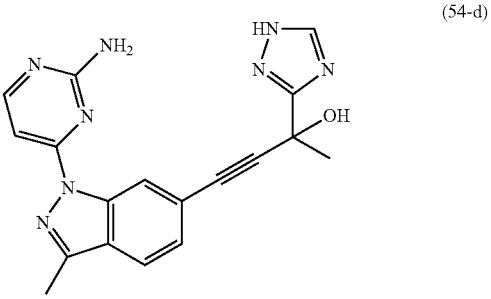 [SMILES: Cc1nn(-c2ccnc(N)n2)c2cc(C#CC(C)(O)c3nc[nH]n3)ccc12]
(54-d)

Step 1—Synthesis of 1-(oxan-2-yl)-1,2,4-triazole-3-carbonitrile

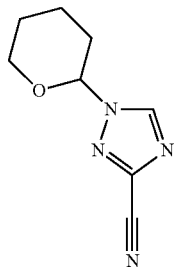

(54-a)

To a solution of 1H-1,2,4-triazole-3-carbonitrile (1.00 g, 10.63 mmol) in DCE (10 mL) was added 3,4-dihydro-2H-pyran (1.94 ml, 21.26 mmol) and p-toluenesulfonic acid (183 mg, 1.06 mmol). The resulting mixture was stirred at room temperature under nitrogen for 15 minutes. Saturated aqueous sodium bicarbonate solution (25 mL) was added and the product extracted into DCM (25 mL×3). The combined organics were washed with brine (10 mL), dried ($Na_2SO_4$) and concentrated in vacuo. The crude product was purified by flash chromatography (Biotage, 0-10% methanol gradient in DCM) to give the title intermediate as a yellow oil: $^1$H NMR (500 MHz, $CDCl_3$) delta 1.81-1.63 (3H, m), 2.11-1.95 (2H, m), 2.19 (1H, dd, J=8.1, 5.6 Hz), 3.87-3.65 (1H, m), 4.18-3.97 (1H, m), 5.53 (1H, dd, J=8.5, 2.9 Hz), 8.37 (1H, s).

Step 2—Synthesis of 1-[1-(oxan-2-yl)-1,2,4-triazol-3-yl]ethanone

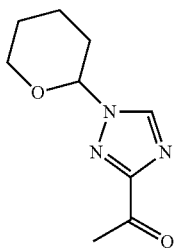

(54-b)

To a solution of methylmagnesium bromide (13.75 mL of a 3.2M solution in 2-methyltetrahydrofuran, 6.29 mmol) was added slowly 1-(oxan-2-yl)-1,2,4-triazole-3-carbonitrile (1.12 g, 6.29 mmol) in anhydrous THF (20 mL). The reaction mixture was stirred at 40° C. for 3 h, cooled to ambient temperature and methanol (10 mL) added dropwise. The reaction mixture was stirred for 3 h and the precipitate removed by vacuum filtration. The filtrate was collected, silica gel (10 g) was added and the mixture stirred at RT for 15 hr. Water (10 ml) was introduced and the volatiles were removed in vacuo. The product was extracted into EtOAc (25 mL×2) and the combined organics were washed with water (10 mL) and dried ($Na_2SO_4$), filtered and concentrated in vacuo. The aqueous phase was re-extracted with chloroform:isopropanol (3:1, 2×25 mL extractions) and the washes repeated before combining with the EtOAc extracts and concentrating in vacuo. The crude product was purified by flash chromatography (Biotage, 0-8% methanol gradient in DCM) to give of the title intermediate as a yellow oil: $^1$H NMR (250 MHz, $CDCl_3$) delta 1.70 (3H, dd, J=4.7, 2.9 Hz), 2.39-1.94 (3H, m), 2.67 (3H, s), 3.91-3.63 (1H, m), 4.27-4.01 (1H, m), 5.71-5.42 (1H, m), 8.35 (1H, s); LC-MS: m/z=+391.10 (2M+1)+. This compound of 78% purity LC-MS (UV) was used without further purification.

Step 3—Synthesis of 4-[1-(2-aminopyrimidin-4-yl)-3-methylindazol-6-yl]-2-[1-(oxan-2-yl)-1,2,4-triazol-3-yl]but-3-yn-2-ol

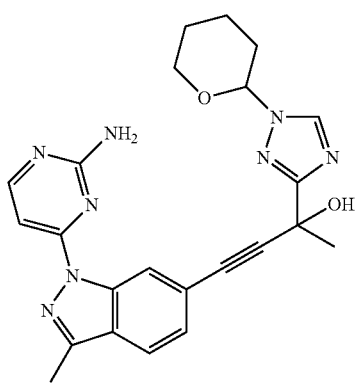

(54-c)

To a solution of 4-(6-ethynyl-3-methylindazol-1-yl)pyrimidin-2-amine (90 mg, 0.36 mmol) in dry THF (1.5 mL) at −78° C. under an atmosphere of nitrogen was added 2M LDA in THF (0.45 mL, 0.903 mmol). After 5 minutes, 1-[1-(oxan-2-yl)-1,2,4-triazol-3-yl]ethanone (211.45 mg in 1.5 mL dry THF, 1.08 mmol) was added. After 20 minutes the mixture was allowed to warm up to RT, then stirred for a further 30 minutes. The reaction mixture was quenched by addition of saturated aqueous $NH_4Cl$ (0.5 mL). The volatiles were removed in vacuo and the mixture was diluted with DCM (10 ml) and washed with water (2 mL), dried ($Na_2SO_4$), filtered and concentrated in vacuo. The crude product was purified by flash chromatography (Biotage, 2-11% methanol gradient in DCM) to give the title intermediate as a pale yellow oil: $^1$H NMR (500 MHz, DMSO) delta 1.76-1.56 (3H, m), 1.90 (3H, s), 2.18-1.94 (3H, m), 2.58 (3H, s), 3.74-3.60 (1H, m), 4.03-3.87 (1H, m), 5.60-5.43 (1H, m), 6.27 (1H, s), 6.96 (2H, s), 7.04 (1H, d, J=5.5 Hz), 7.34 (1H, d, J=8.1 Hz), 7.84 (1H, d, J=8.4 Hz), 8.26 (1H, d, J=5.5 Hz), 8.68 (1H, s), 8.84 (1H, s); LC-MS: m/z=+445.05 (M+H)+.

Step 4—Synthesis of 4-[1-(2-aminopyrimidin-4-yl)-3-methyl-1H-indazol-6-yl]-2-(1H-1,2,4-triazol-3-yl)but-3-yn-2-ol To a solution of 4-[1-(2-aminopyrimidin-4-yl)-3-methylindazol-6-yl]-2-[1-(oxan-2-yl)-1,2,4-triazol-3-yl]but-3-yn-2-ol (60 mg, 0.13 mmol) in methanol (3 mL) was added p-toluenesulfonic acid (25.38 mg, 0.15 mmol). The reaction mixture was stirred at 55° C. for 1 hr, and then concentrated in vacuo. The crude residue was partitioned between saturated $NaHCO_3$ solution (2 ml) and DCM (2×5 ml). The combined organic extracts were washed with brine (2 mL), dried ($Na_2SO_4$), filtered and concentrated in vacuo. The crude product was purified by flash chromatography (Isolute column, 2-10% methanol gradient in DCM) to give the title compound: $^1$H NMR (500 MHz, DMSO) delta 1.92 (3H, s), 2.58 (3H, s), 6.96 (2H, s), 7.05 (1H, d, J=5.5 Hz), 7.46-7.28 (1H, m), 7.85 (1H, d, J=8.2 Hz), 8.26 (1H, d, J=5.5 Hz), 8.86 (1H, s), 14.01 (1H, s); LC-MS: m/z=+361.05 (M+H)+.

Example 55

Preparation of 4-[1-(2-aminopyrimidin-4-yl)-3-methyl-1H-indazol-6-yl]-2-(1H-imidazol-4-yl)but-3-yn-2-ol

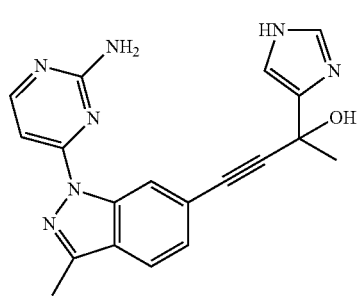

(55-c)

Step 1—Synthesis of 1-[1-(triphenylmethyl)imidazol-4-yl]ethanone

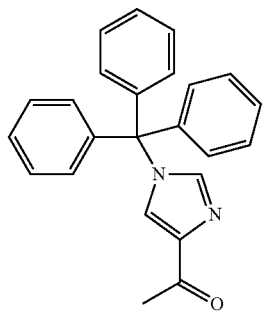

(55-a)

To a solution of 1-(1H-imidazol-4-yl)ethanone (200 mg, 1.82 mmol) in DMF (4 mL) was introduced triethylamine (0.38 mL, 2.72 mmol) and trityl chloride (506.34 mg, 1.82 mmol). The reaction mixture was stirred at room temperature for 2 h. Aqueous brine solution (5 mL) was added to the reaction mixture and the product extracted with EtOAc (2×10 mL). The combined organics were dried (Na₂SO₄), filtered and concentrated in vacuo. The crude product was purified by flash chromatography (Isolute, 1-10% methanol gradient in DCM) to give the title intermediate as a clear oil: $^1$H NMR (500 MHz, CDCl₃) delta 2.55 (3H, s), 7.18-7.06 (6H, m), 7.40-7.29 (9H, m), 7.44 (1 H, d, J=1.3 Hz), 7.58 (1H, d, J=1.4 Hz); LC-MS: m/z=+375.10 (M+Na)+.

Step 2—Synthesis of 4-[1-(2-aminopyrimidin-4-yl)-3-methylindazol-6-yl]-2-[1-(triphenylmethyl)imidazol-4-yl]but-3-yn-2-ol

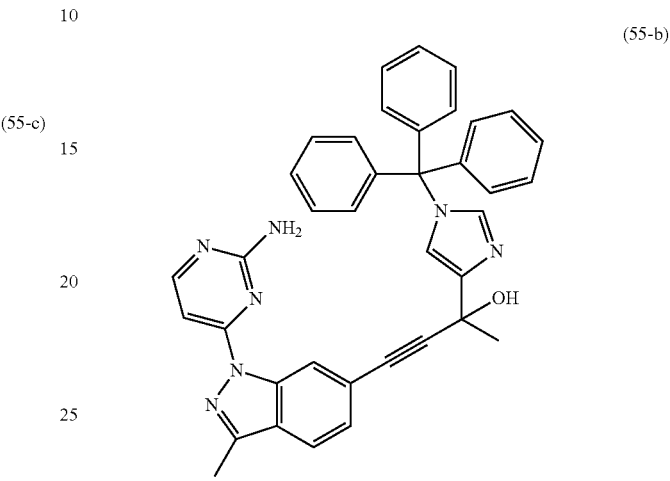

(55-b)

To a solution of 4-(6-ethynyl-3-methylindazol-1-yl)pyrimidin-2-amine (180 mg at 90% purity, 0.65 mmol) in THF (2.5 mL) at −78° C. under nitrogen was added 2M LDA in THF (0.81 mL, 1.63 mmol). After 5 minutes 1-[1-(triphenylmethyl)imidazol-4-yl]ethanone (458.08 mg, 1.3 mmol) in THF (1.5 mL) was added. After 20 minutes, the mixture was allowed to warm up to RT and stirred for a further 1 hr. The reaction mixture was quenched by addition of saturated aqueous NH₄Cl (1 mL). The volatiles were removed in vacuo and the mixture was diluted with DCM (10 ml) and washed with water (2 mL), dried (Na₂SO₄), filtered and concentrated in vacuo. The crude product was purified by flash chromatography (Biotage, 2-12% methanol gradient in DCM) to give the title intermediate as a yellow oil: $^1$H NMR (500 MHz, CDCl₃) delta 1.96 (3H, s), 2.58 (3H, s), 4.41 (1H, s), 5.36 (2H, s), 6.96 (1H, d, J=1.0), 7.19-7.09 (6H, m), 7.24 (1H, d, J=5.7 Hz), 7.35-7.30 (10H, m), 7.44 (1H, d, J=1.0 Hz), 7.53 (1H, d, J=8.2), 8.24 (1H, d, J=5.7), 8.83 (1H, s); LC-MS: m/z=+360.35 (M-C(C₆H₅)₃)+.

Step 3—Synthesis of 4-[1-(2-aminopyrimidin-4-yl)-3-methyl-1H-indazol-6-yl]-2-(1H-imidazol-4-yl)but-3-yn-2-ol To a solution of 4-[1-(2-aminopyrimidin-4-yl)-3-methylindazol-6-yl]-2-[1-(triphenylmethyl)imidazol-4-yl]but-3-yn-2-ol (45 mg, 0.07 mmol) in DCM (2 ml) was added trifluoroacetic acid (0.4 ml). The reaction was allowed to stand at RT for 0.5 hr and then concentrated in vacuo. DCM (5 mL) and saturated aqueous sodium bicarbonate (2 mL) were added and the organics extracted (4×5 mL DCM extractions). The combined extracts were dried (Na₂SO₄), filtered and concentrated in vacuo. The crude product was purified by flash chromatography (Isolute, 0-10% methanol gradient in DCM) to surrender the title compound as a pale brown solid: $^1$H NMR (250 MHz, MeOD) delta 1.92 (3H, s), 2.58 (3H, s), 7.28-7.14 (2H, m), 7.39 (1H, dd, J=8.2, 1.2 Hz), 7.82-7.64 (2H, m), 8.19 (1H, d, J=5.8 Hz), 8.98 (1H, s); LC-MS: m/z=+ 360.05 (M+H)+.

Example 56

Preparation of 4-[1-(2-aminopyrimidin-4-yl)-3-methyl-1H-indazol-6-yl]-2-(1-{[2-(trimethylsilyl) ethoxy]methyl}-1H-imidazol-2-yl)but-3-yn-2-ol

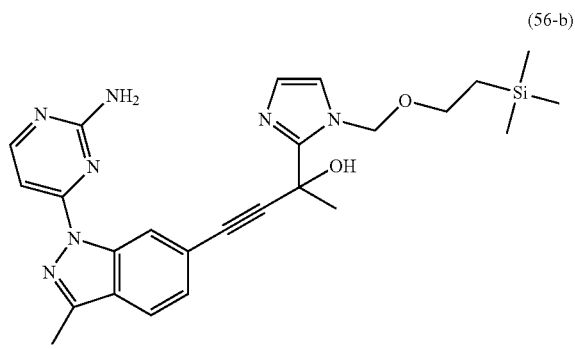 [SMILES: Cc1nn(-c2ccnc(N)n2)c2cc(C#CC(C)(O)c3nccn3COCC[Si](C)(C)C)ccc12]

(56-b)

Step 1—Synthesis of 1-(1-{[2-(trimethylsilyl) ethoxy]methyl}imidazol-2-yl)ethanone

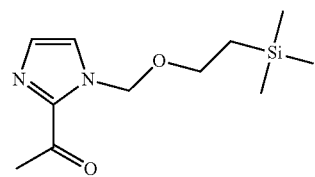

(56-a)

To a solution of 1-(1H-imidazol-2-yl)ethanone (550 mg, 4.99 mmol), 3.18 mmol) in DCM (20 mL) was added DIPEA (1.74 ml, 9.99 mmol) and SEM chloride (0.87 ml dissolved in 5 mL DCM, 4.99 mmol). The resulting mixture was stirred at RT for 1 hr. Saturated aqueous sodium bicarbonate (10 mL) was then added and the aqueous phase was extracted with DCM (3×10 mL extractions). The combined organic extracts were dried (Na$_2$SO$_4$), filtered and concentrated in vacuo to give the title intermediate as a yellow oil: $^1$H NMR (500 MHz, CDCl$_3$) delta 0.00 (9H, s), 1.03-0.82 (2H, m), 2.66 (3H, s), 3.66-3.38 (2H, m), 5.76 (2H, s), 7.18 (1H, s), 7.28 (1H, s); LC-MS: m/z=+241.00 (M+H)+.

Step 2—Synthesis of 4-[1-(2-aminopyrimidin-4-yl)-3-methyl-1H-indazol-6-yl]-2-(1-{[2-(trimethylsilyl) ethoxy]methyl}-1H-imidazol-2-yl)but-3-yn-2-ol To a solution of 1-(2-aminopyrimidin-4-yl)-6-ethynyl-N,N-dimethylindazole-3-carboxamide (200 mg, 0.8 mmol) in THF (2 mL) at −78° C. under nitrogen was added 2M LDA in THF (1.40 mL, 2.81 mmol). After 1 hour, 1-(1-{[2-(trimethylsilyl)ethoxy]methyl}imidazol-2-yl)ethanone (771.45 mg, 3.21 mmol) in THF (1.0 mL) was added. After stirring for 15 minutes, the reaction mixture was allowed to warm to RT and stirred for 2 hr. The reaction mixture was quenched by addition of saturated aqueous ammonium chloride (3 mL) and the volatiles were removed in vacuo. The reaction mixture was diluted with DCM (10 ml) and washed with water (2 mL), dried (Na$_2$SO$_4$), filtered and concentrated in vacuo. The crude product was purified by flash chromatography (Biotage, 1-12% methanol gradient in DCM) to surrender the title compound as a yellow solid: $^1$H NMR (500 MHz, DMSO) delta −0.19 (9H, s), 0.83-0.77 (2H, m), 2.01 (3H, s), 2.57 (3H, s), 3.59-3.49 (2H, m), 5.62 (1H, d, J=10.3 Hz), 5.78 (1H, d, J=10.2 Hz), 6.42 (1H, s), 6.86 (1H, d, J=1.1 Hz), 6.96 (2H, s), 7.03 (1 H, d, J=5.5 Hz), 7.27 (1H, d, J=1.0 Hz), 7.36 (1H, dd, J=8.1, 1.1 Hz), 7.84 (1H, d, J=8.2 Hz), 8.25 (1H, d, J=5.5 Hz), 8.85 (1H, s); LC-MS: m/z=+490.10 (M+H)+

Example 57

Preparation of 4-[1-(2-aminopyrimidin-4-yl)-3-methyl-1H-indazol-6-yl]-2-(1H-imidazol-2-yl)but-3-yn-2-ol

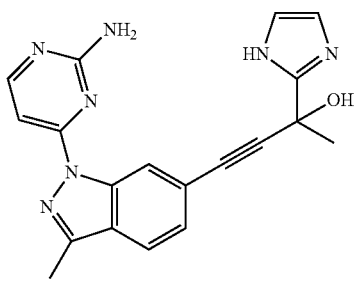

A solution of 4-[1-(2-aminopyrimidin-4-yl)-3-methyl-1H-indazol-6-yl]-2-(1-{[2-(trimethylsilyl)ethoxy]methyl}-1H-imidazol-2-yl)but-3-yn-2-ol in 4M HCl in dioxane (2.5 ml) was stirred at 40° C. for 2 h and then at 50° C. for a further 1 hr. The reaction mixture was then concentrated in vacuo and basified using saturated aqueous sodium bicarbonate solution. The product was extracted into DCM (2×3 mL) and the combined organics were washed with brine solution (2 ml), dried (Na$_2$SO$_4$), filtered and concentrated in vacuo. The crude product was purified by flash chromatography (Biotage, 5-12% methanol gradient in DCM) to give the title compound as an off-white solid: $^1$H NMR (500 MHz, DMSO) delta 1.90 (3H, s), 2.57 (3H, s), 6.42 (1H, s), 6.83 (1H, s), 6.96 (2H, s), 7.10-6.99 (2H, m), 7.35 (1H, d, J=8.2 Hz), 7.84 (1H, d, J=8.2 Hz), 8.25 (1H, d, J=5.5 Hz), 8.86 (1H, s), 12.01 (1H, s); LC-MS: m/z=+360.05 (M+H)+.

Example 58

Preparation of 4-[1-(2-aminopyrimidin-4-yl)-3-methyl-1H-indazol-6-yl]-2-hydroxy-1-(3-hydroxyazetidin-1-yl)-2-methylbut-3-yn-1-one

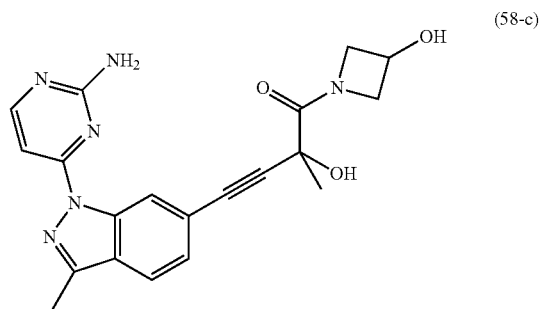 [SMILES: Cc1nn(-c2ccnc(N)n2)c2cc(C#CC(C)(O)C(=O)N3CC(O)C3)ccc12]

(58-c)

Step 1—Synthesis of ethyl 4-[1-(2-aminopyrimidin-4-yl)-3-methyl-1H-indazol-6-yl]-2-hydroxy-2-methylbut-3-ynoate

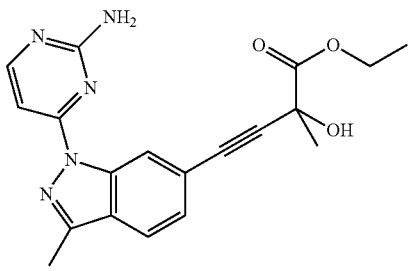

(58-a)

To a solution of 4-(6-iodo-3-methyl-1H-indazol-1-yl)pyrimidin-2-amine (170 mg, 0.38 mmol) in dry THF (3 mL) was introduced bis(triphenylphosphine)palladium(II) chloride (27 mg, 0.04 mmol), ethyl 2-hydroxy-2-methyl-4-(trimethylsilyl)but-3-ynoate (164 mg, 0.76 mmol) and TBAF (0.46 mL of a 1M solution in THF, 0.46 mmol). The solution was warmed to 50° C. for 1.5 hr. After cooling, sodium bicarbonate (4 mL of saturated aqueous NaHCO₃) was introduced and the solution extracted with EtOAc (3×10 mL extractions). The combined organic extracts were washed with brine (10 mL), dried (Na₂SO₄), filtered and concentrated in vacuo. Purification by silica gel flash column chromatography (DCM containing a 1-10% gradient of methanol) furnished the title compound as an orange oil: ¹H NMR (250 MHz, Chloroform-d) delta 1.39 (3H, t, J=7.1 Hz), 1.83 (3 H, s), 2.60 (3H, s), 4.38 (2H, q, J=7.1 Hz), 5.20 (2H, s), 7.29 (1H, s), 7.34 (1H, dd, J=8.2, 1.3 Hz), 7.60 (1H, dd, J=8.2, 0.7 Hz), 8.29 (1H, d, J=5.7 Hz), 8.83 (1H, s); LC-MS: m/z=+366.05 (M+H)+.

Step 2—Synthesis of 4-[1-(2-aminopyrimidin-4-yl)-3-methyl-1H-indazol-6-yl]-2-hydroxy-2-methylbut-3-ynoic acid

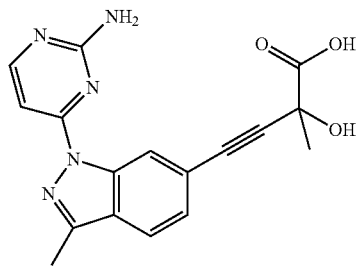

(58-b)

To a solution of ethyl 4-[1-(2-aminopyrimidin-4-yl)-3-methyl-1H-indazol-6-yl]-2-hydroxy-2-methylbut-3-ynoate (120 mg, 0.33 mmol) in methanol (0.5 mL) was introduced sodium hydroxide (0.16 mL of a 2M aqueous solution, 0.33 mmol). After 15 hr at RT, the reaction mixture was concentrated in vacuo and the pH of the aqueous residue adjusted to 7 with 0.5M aqueous hydrochloric acid. The solution was extracted with 3:1 chloroform/isopropanol (5×5 mL extractions) and the combined organic extracts dried (Na₂SO₄), filtered and concentrated in vacuo to furnish the crude title compound as a yellow solid: ¹H NMR (250 MHz, DMSO) delta 1.68 (3H, s), 2.59 (3H, s), 7.07-7.29 (3H, m), 7.37 (2H, dd, J=8.4, 1.2 Hz), 7.87 (1H, d, J=7.7 Hz), 8.28 (1H, d, J=5.9 Hz), 8.85 (1H, s); LC-MS: m/z=+338.00 (M+H)+. This compound, with LC-MS purity=100% UV, was used in the next step without further purification.

Step 3—Synthesis of 4-[1-(2-aminopyrimidin-4-yl)-3-methyl-1H-indazol-6-yl]-2-hydroxy-1-(3-hydroxyazetidin-1-yl)-2-methylbut-3-yn-1-one To a solution of 4-[1-(2-aminopyrimidin-4-yl)-3-methyl-1H-indazol-6-yl]-2-hydroxy-2-methylbut-3-ynoic acid (100 mg, 0.30 mmol) in DMF (3 mL) was introduced O-(7-azabenzotriazol-1-yl)-N,N,N',N'-tetramethyluronium hexafluorophosphate (225 mg, 0.59 mmol), azetidin-3-ol hydrochloride (65 mg, 0.59 mmol) and triethylamine (0.12 mL, 0.89 mmol). After 18 hr at RT, the solution was re-treated with O-(7-azabenzotriazol-1-yl)-N,N,N',N'-tetramethyluronium hexafluorophosphate (225 mg, 0.59 mmol), azetidin-3-ol hydrochloride (65 mg, 0.59 mmol) and triethylamine (0.12 mL, 0.89 mmol). After 3 hr at RT, the reaction mixture was diluted with water (2 mL) and extracted with EtOAc (2×5 mL extractions). The combined organic extracts were washed with water (5 mL) and brine (5 ml), dried (Na₂SO₄), filtered and concentrated in vacuo. Purification of the residue by silica gel flash column chromatography (DCM containing a 2-10% gradient of methanol) furnished the title compound as a colorless solid: ¹H NMR (500 MHz, DMSO) delta 1.64 (3H, s), 2.58 (3H, s), 3.58-3.75 (1H, m), 4.09-4.19 (1H, m), 4.19-4.28 (1H, m), 4.49 (1H, s), 4.63-4.76 (1H, m), 5.67-5.81 (1H, m), 6.14 (1H, d, J=17.5 Hz), 6.98 (2H, s), 7.05 (1H, d, J=5.5 Hz), 7.38 (1H, d, J=8.7 Hz), 7.87 (1H, dd, J=8.2, 1.8 Hz), 8.27 (1H, d, J=5.5 Hz), 8.87 (1H, s); LC-MS: m/z=+393.05 (M+H)+.

Example 59

Preparation of (2R)-4-[1-(2-aminopyrimidin-4-yl)-3-[(3,3-difluoroazetidin-1-yl)methyl]-1H-indazol-6-yl]-2-(5-methyl-1,2,4-oxadiazol-3-yl)but-3-yn-2-ol

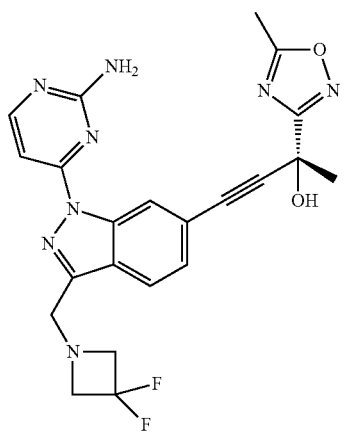

(59-c)

Step 1—Synthesis of 6-bromo-3-[(3,3-difluoroazetidin-1-yl)methyl]-1H-indazole

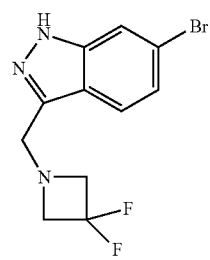

(59-a)

The title compound was prepared by the procedure described in Example 12-a by substituting 2M dimethylamine in THF with 3,3-difluoroazetidine in Step 1: ¹H NMR (500 MHz, CDCl₃) delta 2.55 (4H, br. s.), 3.73 (4H, t, J=4.57 Hz), 3.91 (2H, s), 7.22-7.30 (1H, m), 7.63 (1H, s), 7.72 (1H, s), 7.78 (1H, d, J=8.67 Hz); LC-MS: m/z=+295.90/297.85 (M+H)+.

Step 2—Synthesis of 4-{6-bromo-3-[(3,3-difluoroazetidin-1-yl)methyl]indazol-1-yl}pyrimidin-2-amine

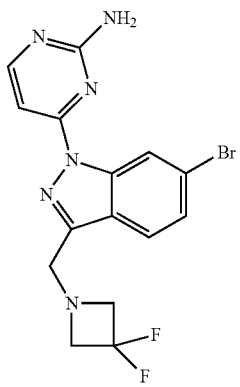

(59-b)

The title compound was prepared by the procedure described in Example 12-b by substituting 1-(6-bromo-1H-indazol-3-yl)-N,N-dimethylmethanamine with 6-bromo-3-[(3,3-difluoroazetidin-1-yl)methyl]-1H-indazole in Step 2: ¹H NMR (250 MHz, CDCl₃) delta 2.89 (1H, s), 2.96 (1H, s), 3.73 (4H, t, J=12.03 Hz), 4.13 (2H, s), 7.15-7.33 (1H, m), 7.43 (1 H, dd, J=8.45, 1.60 Hz), 7.76 (1H, d, J=8.53 Hz), 8.32 (1H, d, J=5.63 Hz), 8.98 (1H, d, J=1.22 Hz); LC-MS: m/z=+395.00/396.80 (M+H)+.

Step 3—Synthesis of (2R)-4-[1-(2-aminopyrimidin-4-yl)-3-[(3,3-difluoroazetidin-1-yl)methyl]-1H-indazol-6-yl]-2-(5-methyl-1,2,4-oxadiazol-3-yl)but-3-yn-2-ol The title compound was prepared by the procedure described in Example 10-c by substituting 4-{6-bromo-3-[(dimethylamino)methyl]-1H-indazol-1-yl}pyrimidin-2-amine with of 4-{6-bromo-3-[(3,3-difluoroazetidin-1-yl)methyl]indazol-1-yl}pyrimidin-2-amine and 2-methyl-but-3-yn-2-ol with (2R)-2-(5-methyl-1,2,4-oxadiazol-3-yl)but-3-yn-2-ol: ¹H NMR (500 MHz, CDCl₃) delta 2.09 (3H, s), 2.67 (3H, s), 3.73 (4H, t, J=12.06 Hz), 4.12 (2H, s), 4.80-5.13 (1 H, m), 5.51 (2H, s), 7.28 (1H, d, J=5.67 Hz), 7.37 (1H, dd, J=8.28, 1.02 Hz), 7.79 (1H, d, J=8.20 Hz), 8.30 (1H, d, J=5.67 Hz), 8.86 (1H, s); LC-MS: m/z=+467.1 (M+H)+.

Example 60

Examples in Table 7 were prepared by procedure described in Example 6 by reacting the 4-[6-bromo-1H-indazol-1-yl]pyrimidin-2-amine derivatives with the appropriate but-3-yn-2-ol.

TABLE 7

| No. | Structure | Name | 1H NMR | MS (M + H) |
|---|---|---|---|---|
| T7-60.1 | 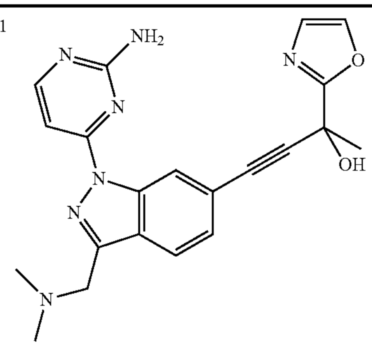 | 4-[1-(2-aminopyrimidin-4-yl)-3-[(dimethylamino)methyl]-1H-indazol-6-yl]-2-(1,3-oxazol-2-yl)but-3-yn-2-ol | (500 MHz, DMSO) delta 1.95 (3 H, s), 2.24 (6 H, s), 3.82 (2 H, s), 6.96-7.09 (3 H, m), 7.24 (1 H, s), 7.37 (1 H, d, J = 8.20 Hz), 7.98 (1 H, d, J = 8.35 Hz), 8.15 (1 H, s), 8.28 (1 H, d, J = 5.52 Hz), 8.90 (1 H, s) | 404.1 |
| T7-60.2 | 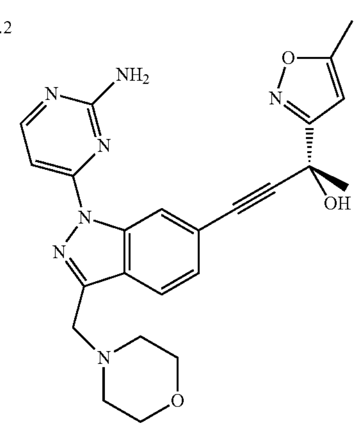 | (2R)-4-[1-(2-aminopyrimidin-4-yl)-3-(morpholin-4-ylmethyl)-1H-indazol-6-yl]-2-(5-methyl-1,2-oxazol-3-yl)but-3-yn-2-ol | (500 MHz, DMSO) delta 1.86 (3 H, s), 2.42 (3 H, s), 2.47 (4 H, br. s.), 3.57 (4 H, t, J = 4.18 Hz), 3.90 (2 H, s), 6.41 (1 H, s), 6.57 (1 H, s), 7.03 (2 H, br. s.), 7.06 (1 H, d, J = 5.52 Hz), 7.37 (1 H, dd, J = 8.35, 1.10 Hz), 8.03 (1H, d, J = 8.20 Hz), 8.28 (1 H, d, J = 5.52 Hz), 8.88 (1 H, s) | 460.1 |

TABLE 7-continued

| No. | Structure | Name | 1H NMR | MS (M + H) |
|---|---|---|---|---|
| T7-60.3 | 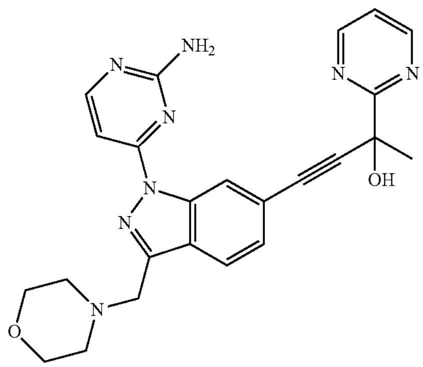 [SMILES: CC(O)(C#Cc1ccc2c(CN3CCOCC3)nn(-c3ccnc(N)n3)c2c1)c1ncccn1] | 4-[1-(2-aminopyrimidin-4-yl)-3-(morpholin-4-ylmethyl)-1H-indazol-6-yl]-2-(pyrimidin-2-yl)but-3-yn-2-ol | (500 MHz, CDCl$_3$) delta 2.17 (3 H, s), 2.45-2.63 (4 H,m), 3.71 (4 H, t, J = 4.49 Hz), 3.88 (2 H, s), 5.35 (2 H, br. s.), 5.52 (1 H, br. s.), 7.26 (1 H, br. s.), 7.30-7.39 (2 H, m), 7.85 (1 H, d, J = 8.20 Hz), 8.28 (1 H, br. s.), 8.84 (3 H, br. s.) | 457.1 |
| T7-60.4 | 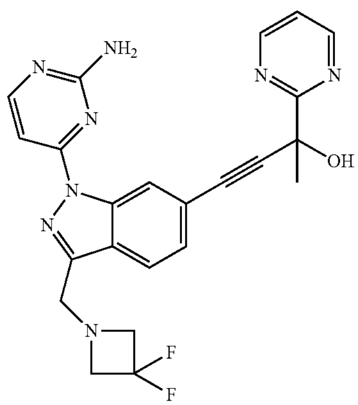 [SMILES: CC(O)(C#Cc1ccc2c(CN3CC(F)(F)C3)nn(-c3ccnc(N)n3)c2c1)c1ncccn1] | 4-[1-(2-aminopyrimidin-4-yl)-3-[(3,3-difluoroazetidin-1-yl)methyl]-1H-indazol-6-yl]-2-(pyrimidin-2-yl)but-3-yn-2-ol | (500 MHz, CDC13) delta 2.06 (3 H, s), 3.73 (4 H, t, J = 12.14 Hz), 4.12 (2 H, s), 5.21 (2 H, s), 5.38 (1 H, s), 7.29 (1 H, d, J = 5.52 Hz), 7.32-7.40 (2 H, m), 7.76 (1 H, d, J = 8.35 Hz), 8.31 (1 H, br. s.), 8.86 (3 H, d, J = 2.84 Hz) | 463.05 |

Example 61

Preparation of 1-(2-aminopyrimidin-4-yl)-6-[3-hydroxy-3-(1,3-thiazol-2-yl)but-1-yn-1-yl]-N,N-dimethyl-1H-indazole-3-carboxamide

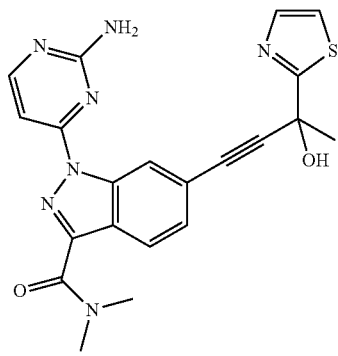

(61-c)

Step 1—Synthesis of 6-bromo-N,N-dimethyl-1H-indazole-3-carboxamide

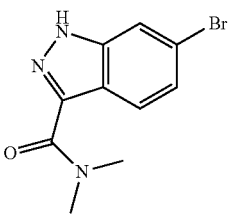

(61-a)

To a mixture of 6-bromo-1H-indazole-3-carboxylic acid (1 g, 4.15 mmol) and EDC.HCl (1.2 g, 6.2 mmol) in DMF (5 mL) was added 2 M dimethylamine in THF (3.45 mL, 10.3 mmol). Mixture was stirred at RT overnight. The reaction mixture was concentrated in vacuo to remove the volatiles, then diluted with EtOAc (30 mL) and washed with water. The aqueous layer was extracted with more EtOAc (20 mL). The combined organics were washed with water (30 mL), dried (Na$_2$SO$_4$), filtered and concentrated in vacuo to give the title compound as a white solid: $^1$H NMR (250 MHz, DMSO) delta 3.06 (3H, s), 7.34 (1H, dd, J=8.68, 1.52 Hz), 7.84 (1H, d, J=1.07 Hz), 7.92 (1H, d, J=8.68 Hz), 13.62 (1H, br. s.); LC-MS: m/z=+269.75 (M+H)+.

Step 2: Synthesis of 1-(2-aminopyrimidin-4-yl)-6-bromo-N,N-dimethylindazole-3-carboxamide

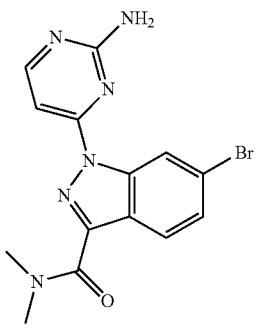

(61-b)

To a solution of 6-bromo-N,N-dimethyl-1H-indazole-3-carboxamide (95%, 450 mg, 1.59 mmol) in DMF (10 mL) was added NaH (60% dispension in mineral oil) (60 mg, 1.02 mmol) at 0° C. Mixture was stirred at rt for 10 mins before addition of 4-chloropyrimidin-2-amine (413 mg, 3.19 mmol). The mixture was stirred at 65° C. overnight. The mixture was quenched by addition of water (10 mL). The mixture was extracted with EtOAc (2×15 mL). The combined organics washed with water (10 mL), dried ($Na_2SO_4$), filtered and concentrated in vacuo. Trituration with DCM:heptane (4:1) gave the desired product. The filtrate was re-filtered. The solids were combined to give the title compound; $^1$H NMR (250 MHz, DMSO) delta 3.11 (3H, s), 3.32 (3H, s), 7.08 (1H, d, J=5.48 Hz), 7.19 (1H, d, J=3.35 Hz), 7.58 (1H, dd, J=8.68, 1.68 Hz), 7.95 (1H, d, J=8.53 Hz), 8.34 (1H, d, J=5.63 Hz), 9.18 (1H, d, J=1.22 Hz); LC-MS: m/z=+362.8 (M+H)+.

Step 3: Synthesis of 1-(2-aminopyrimidin-4-yl)-6-[3-hydroxy-3-(1,3-thiazol-2-yl)but-1-yn-1-yl]-N,N-dimethyl-1H-indazole-3-carboxamide To a sealed tube was added 1-(2-aminopyrimidin-4-yl)-6-bromo-N,N-dimethylindazole-3-carboxamide (55%, 113 mg, 0.172 mmol), followed by piperidine (2 mL), tetrakis(triphenylphosphine)palladium (40 mg, 0.034 mmol), copper (I) iodide (7 mg, 0.034 mmol) and 2-(1,3-thiazol-2-yl)but-3-yn-2-ol (105 mg, 0.688 mmol). The reaction mixture was purged with nitrogen gas, capped and stirred at 60° C. for 1.5 hr. Reaction mixture was concentrated in vacuo. EtOAc (5 mL) added. Concentration in vacuo was repeated. The residue was purified using column chromatography (Biotage, 100% DCM to 10% MeOH/DCM) to give a brown solid. Trituration of the solid with DCM gave the title compound; $^1$H NMR (500 MHz, DMSO) delta 1.95 (3H, s), 3.12 (3H, s), 3.33 (3H, s), 7.12 (2H, s), 7.13-7.19 (2H, m), 7.42 (1H, dd, J=8.35, 1.42 Hz), 7.71 (1H, d, J=3.31 Hz), 7.80 (1H, d, J=3.15 Hz), 7.97-8.07 (1H, m), 8.35 (1 H, d, J=5.52 Hz), 8.94 (1H, s); LC-MS: m/z=+434.45 (M+H)+.

Example 62

Preparation of 4-[1-(2-aminopyrimidin-4-yl)-3-[(morpholin-4-yl)carbonyl]-1H-indazol-6-yl]-2-(5-methyl-1,2-oxazol-3-yl)but-3-yn-2-ol

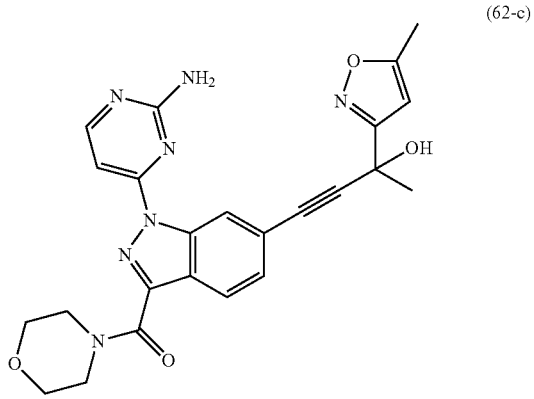 [SMILES: Cc1cc(C(C)(O)C#Cc2ccc3c(C(=O)N4CCOCC4)nn(-c4ccnc(N)n4)c3c2)no1]

(62-c)

Step 1: Synthesis of 6-bromo-3-[(morpholin-4-yl)carbonyl]-1H-indazole

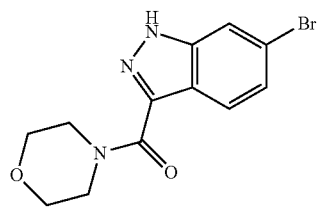

(62-a)

To a solution of 6-bromo-1H-indazole-3-carboxylic acid (500 mg, 2.07 mmol) in DMF (10 mL) was added CDI (403.62 mg, 2.49 mmol) and the reaction mixture stirred at 45° C. for 40 minutes. Morpholine (0.36 ml, 4.16 mmol) was then added and the reaction mixture stirred at RT. The reaction mixture was quenched by diluting with water. The product was extracted into EtOAc (×2) and the combined organic extracts were then washed with water and brine and dried ($Na_2SO_4$), filtered and concentrated in vacuo to give the crude (78% pure) title compound: $^1$H NMR (500 MHz, DMSO) delta 3.58-3.79 (6H, m), 3.96-4.13 (2H, m), 7.36 (1H, dd, J=8.59, 1.66 Hz), 7.86 (1H, d, J=1.10 Hz), 7.93 (1H, s), 13.66 (1H, br. s.); LC-MS: m/z=+311.70 (M+H)+.

Step 2: Synthesis of 4-{6-bromo-3-[(morpholin-4-yl)carbonyl]indazol-1-yl}pyrimidin-2-amine

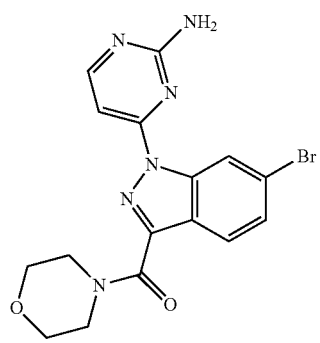

(62-b)

To a solution of 6-bromo-3-[(morpholin-4-yl)carbonyl]-1H-indazole (78%, 458 mg, 1.15 mmol) in DMF (8 mL) was added NaH (60% oil suspension, 73.71 mg, 1.84 mmol) at 0° C. Mixture was stirred at RT for 10 minutes before addition of 4-chloropyrimidin-2-amine (298.44 mg, 2.3 mmol). The mixture was stirred at RT for 10 minutes and then at 65° C. for 5 hr. Reaction mixture was quenched by addition of water (5 mL) and a little EtOAc (2 mL) was added. Precipitate formed was collected and dried under vacuum to give the title compound: $^1$H NMR (500 MHz, DMSO) delta 3.58-3.80 (6H, m), 3.87-4.13 (2H, m), 7.07 (1H, d, J=5.52 Hz), 7.59 (1H, dd, J=8.51, 1.42 Hz), 7.94 (1H, d, J=8.83 Hz), 8.35 (1H, d, J=5.52 Hz), 9.19 (1H, d, J=1.26 Hz); LC-MS: m/z=+404.8 (M+H)+.

Step 3: Synthesis of 4-[1-(2-aminopyrimidin-4-yl)-3-[(morpholin-4-yl)carbonyl]-1H-indazol-6-yl]-2-(5-methyl-1,2-oxazol-3-yl)but-3-yn-2-ol The title compound was prepared by procedure described in Example 61-c, by substituting 1-(2-aminopyrimidin-4-yl)-6-bromo-N,N-dimethylindazole-3-carboxamide with 4-{6-bromo-3-[(morpholin-4-yl)carbonyl]indazol-1-yl}pyrimidin-2-amine and 2-(1,3-thiazol-2-yl)but-3-yn-2-ol with 2-(5-methyl-1,2-oxazol-3-yl)but-3-yn-2-ol in Step 3: $^1$H NMR (500 MHz, DMSO) delta 1.86 (3H, s), 2.42 (3H, s), 3.63-3.70 (2H, m), 3.70-3.80 (4H, m), 3.89-3.97 (2H, m), 6.41 (1H, s), 6.58 (1H, s), 7.08 (1H, d, J=5.36 Hz), 7.16 (2H, br. s.), 7.44 (1H, dd, J=8.35, 1.26 Hz), 8.02 (1H, d, J=8.35 Hz), 8.35 (1H, d, J=5.36 Hz), 8.94 (1H, s); LC-MS: m/z=+474.4 (M+H)+.

Example 63

Examples in Table 8 were prepared by procedure described in Example 61-c by reacting either 1-(2-aminopyrimidin-4-yl)-6-bromo-N,N-dimethylindazole-3-carboxamide or 4-{6-bromo-3-[(morpholin-4-yl)carbonyl]indazol-1-yl}pyrimidin-2-amine with the appropriate but-3-yn-2-ol

TABLE 8

| No. | Structure | Name | 1H NMR | MS (M + H) |
|---|---|---|---|---|
| T8-63.1 | 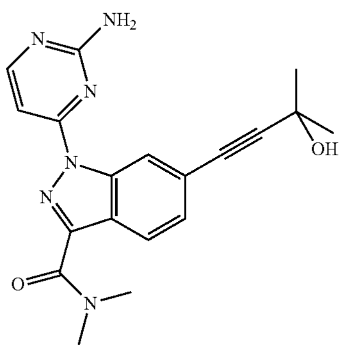 [SMILES: CN(C)C(=O)c1nn(-c2ccnc(N)n2)c2cc(C#CC(C)(C)O)ccc12] | 1-(2-aminopyrimidin-4-yl)-6-(3-hydroxy-3-methylbut-1-yn-1-yl)-N,N-dimethyl-1H-indazole-3-carboxamide | (500 MHz, DMSO) delta 1.53 (6 H, s), 3.11 (3 H, s), 3.32 (3 H, s), 5.54 (1 H, s), 7.11 (1 H, d, J = 4.26 Hz), 7.16 (2 H, br. s.), 7.39 (1 H, dd, J = 8.35, 1.26 Hz), 7.98 (1 H, d, J = 8.35 Hz), 8.40 (1 H, br. s.), 8.90 (1 H, s) | 365.45 |
| T8-63.2 | 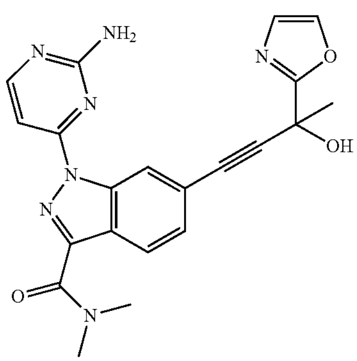 [SMILES: CN(C)C(=O)c1nn(-c2ccnc(N)n2)c2cc(C#CC(C)(O)c3ncco3)ccc12] | 1-(2-aminopyrimidin-4-yl)-6-[3-hydroxy-3-(1,3-oxazol-2-yl)but-1-yn-1-yl]-N,N-dimethyl-1H-indazole-3-carboxamide | (250 MHz, DMSO) delta 1.95 (3 H, s), 3.12 (3 H, s), 3.31-3.33 (3 H, m), 6.82 (1 H, s), 7.10 (1 H, d, J = 5.48 Hz), 7.17 (1H, br. s.), 7.25 (1 H, d, J = 0.61 Hz), 7.44 (1 H, dd, J = 8.38, 1.37 Hz), 7.96-8.07 (1H,m), 8.17 (1 H, d, J = 0.76 Hz), 8.35 (1 H, d, J = 5.33 Hz), 8.96 (1H, s) | 418.45 |
| T8-63.3 | 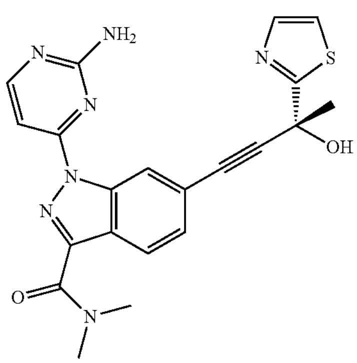 [SMILES: CN(C)C(=O)c1nn(-c2ccnc(N)n2)c2cc(C#C[C@@](C)(O)c3nccs3)ccc12] | 1-(2-aminopyrimidin-4-yl)-6-[(3R)-3-hydroxy-3-(1,3-thiazol-2-yl)but-1-yn-1-yl]-N,N-dimethyl-1H-indazole-3-carboxamide | (500 MHz, DMSO) delta 1.94 (3 H,s), 3.11 (3 H, s), 7.06-7.12 (2 H, m), 7.14 (2 H, br. s.), 7.41 (1 H, dd, J = 8.43, 1.18 Hz), 7.70 (1 H, d, J = 3.31 Hz), 7.79 (1 H, d, J = 3.15 Hz), 8.00 (1 H, d, J = 8.35 Hz), 8.34 (1 H, d, J = 5.52 Hz), 8.93 (1 H, s) | 434.4 |

TABLE 8-continued

| No. | Structure | Name | 1H NMR | MS (M + H) |
|---|---|---|---|---|
| T8-63.4 | 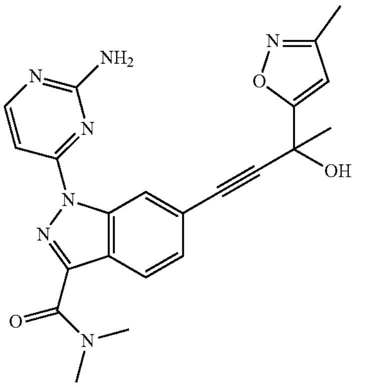 [SMILES: Cc1cc(C(C)(O)C#Cc2ccc3c(C(=O)N(C)C)nn(-c4ccnc(N)n4)c3c2)on1] | 1-(2-aminopyrimidin-4-yl)-6-[3-hydroxy-3-(3-methyl-1,2-oxazol-5-yl)but-1-yn-1-yl]-N,N-dimethyl-1H-indazole-3-carboxamide | (500 MHz, DMSO) delta 1.86 (3 H, s), 2.25 (3 H, s), 3.11 (3 H, s), 6.45 (1H, s), 6.79 (1 H, s), 7.10 (2 H, d, J = 5.52 Hz), 7.15 (2 H, br. s.), 7.46 (1 H, d, J = 8.35 Hz), 8.02 (1 H, d, J = 8.20 Hz), 8.35 (1 H, d, J = 5.36 Hz), 8.97 (1 H, s) | 432.45 |
| T8-63.5 | 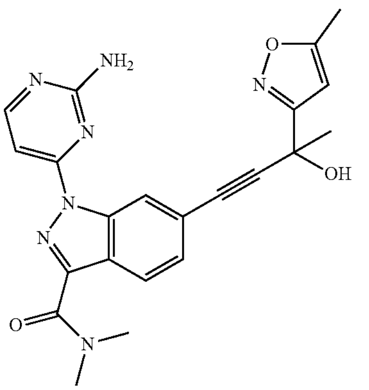 [SMILES: Cc1cc(C(C)(O)C#Cc2ccc3c(C(=O)N(C)C)nn(-c4ccnc(N)n4)c3c2)no1] | 1-(2-aminopyrimidin-4-yl)-6-[3-hydroxy-3-(5-methyl-1,2-oxazol-3-yl)but-1-yn-1-yl]-N,N-dimethyl-1H-indazole-3-carboxamide | (500 MHz, DMSO) delta 1.86 (3 H, s), 2.42 (3 H, s), 3.11 (3 H, s), 6.41 (1 H, s), 6.58 (1H, s), 7.10 (1 H, d, J = 5.52 Hz), 7.14 (2 H, br. s.), 7.43 (1 H, dd, J = 8.35, 1.26 Hz), 8.01 (1 H, d, J = 8.35 Hz), 8.35 (1 H, d, J = 5.52 Hz), 8.94 (1 H, s) | 432.45 |
| T8-63.6 | 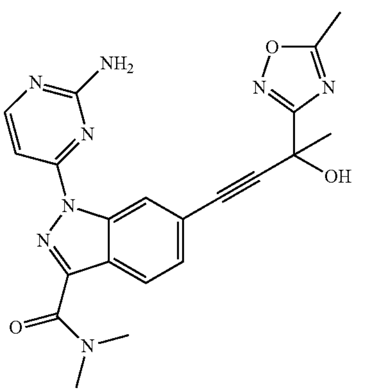 [SMILES: Cc1nc(C(C)(O)C#Cc2ccc3c(C(=O)N(C)C)nn(-c4ccnc(N)n4)c3c2)no1] | 1-(2-aminopyrimidin-4-yl)-6-[3-hydroxy-3-(5-methyl-1,2,4-oxadiazol-3-yl)but-1-yn-1-yl]-N,N-dimethyl-1H-indazole-3-carboxamide | (250 MHz, DMSO) delta 1.88 (3 H, s), 2.61 (3 H, s), 3.10 (3 H, s), 6.80 (1H, s), 7.08 (1H, d, J = 5.79 Hz), 7.14 (2 H, br. s.), 7.42 (1 H, d, J = 8.53 Hz), 8.00 (1 H, d, J = 8.38 Hz), 8.33 (1 H, d, J = 5.63 Hz), 8.94 (1 H, s) | 433.1 |
| T8-63.7 | 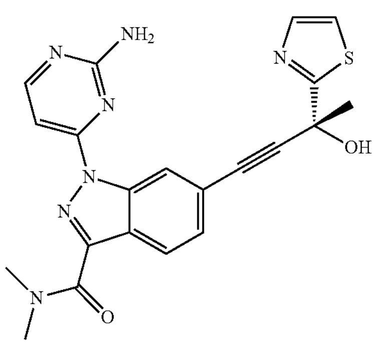 [SMILES: CN(C)C(=O)c1nn(-c2ccnc(N)n2)c2cc(C#C[C@@](C)(O)c3nccs3)ccc12] | 1-(2-aminopyrimidin-4-yl)-6-[(3R)-3-hydroxy-3-(1,3-thiazol-2-yl)but-1-yn-1-yl]-N,N-dimethyl-1H-indazole-3-carboxamide | (250 MHz, DMSO) delta 1.95 (3 H, s), 3.11 (3 H, s), 3.32 (3 H, s), 7.09 (1H, d, J 5.5), 7.24-7.12 (3 H, m), 7.42 (1 H, dd, J = 8.4, 1.3 Hz), 7.71 (1 H, d, J = 3.2 Hz), 7.79 (1 H, d, J = 3.2 Hz), 8.00 (1H, dd, J = 8.4, 0.6 Hz), 8.34 (1 H, d, J = 5.5 Hz), 8.93 (1 H, s). | 434.05 |

TABLE 8-continued

| No. | Structure | Name | 1H NMR | MS (M + H) |
|---|---|---|---|---|
| T8-63.8 | 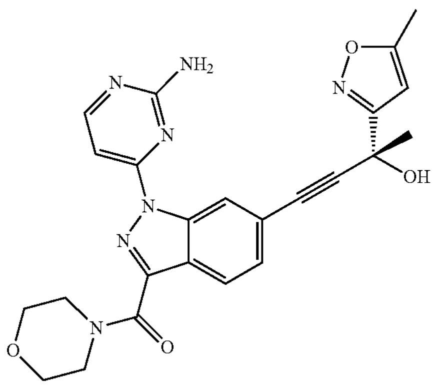 [SMILES: Cc1cc([C@](C)(O)C#Cc2ccc3c(C(=O)N4CCOCC4)nn(-c4ccnc(N)n4)c3c2)no1] | (2R)-4-[1-(2-amino pyrimidin-4-yl)-3-[(morpholin-4-yl) carbonyl]-1H-indazol-6-yl]-2-(5-methyl-1,2-oxazol-3-yl)but-3-yn-2-ol | (500 MHz, DMSO) delta 1.86 (3 H, s), 2.42 (3 H, s), 3.79-3.62 (6 H, m), 3.99-3.91 (2 H, m), 6.42 (1 H, s), 6.60 (1 H, s), 7.08 (1 H, d, J = 5.5 Hz), 7.17 (2 H, s), 7.44 (1H, dd, J = 8.4, 1.2 Hz), 8.02 (1 H, d, J = 8.4 Hz), 8.36 (1 H, d, J = 5.5 Hz), 8.95 (1H, s). | 474.5 |
| T8-63.9 | 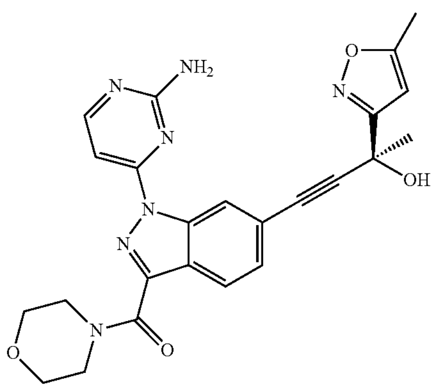 [SMILES: Cc1cc([C@@](C)(O)C#Cc2ccc3c(C(=O)N4CCOCC4)nn(-c4ccnc(N)n4)c3c2)no1] | (2S)-4-[1-(2-amino pyrimidin-4-yl)-3-[(morpholin-4-yl) carbonyl]-1H-indazol-6-yl]-2-(5-methyl-1,2-oxazol-3-yl)but-3-yn-2-ol | (500 MHz, DMSO) delta 1.86 (3 H, s), 2.42 (3 H, s), 3.81-3.60 (6 H, m), 4.01-3.87 (2 H, m), 6.42 (1 H, s), 6.60 (1 H, s), 7.08 (1 H, d, J = 5.5 Hz), 7.17 (2 H, s), 7.44 (1H, dd, J = 8.4, 1.1 Hz), 8.03 (1 H, d, J = 8.3 Hz), 8.36 (1 H, d, J = 5.5 Hz), 8.95 (1 H, s). | 474.45 |
| T8-63.10 | 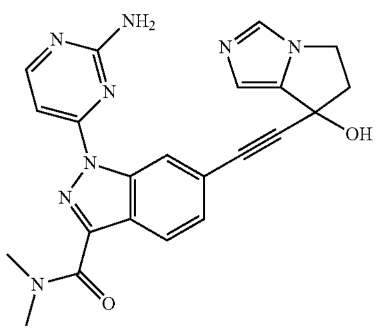 [SMILES: CN(C)C(=O)c1nn(-c2ccnc(N)n2)c2cc(C#CC3(O)CCn4cncc43)ccc12] | 1-(2-aminopyrimidin-4-yl)-6-(2-{7-hydroxy-5H,6H,7H-pyrrolo[1,2-c]imidazol-7-yl}ethynyl)-N,N-dimethyl-1H-indazole-3-carboxamide | (500 MHz, DMSO) delta 2.93-2.77 (1 H, m), 3.18-3.02 (4 H, m), 3.32 (3 H, s), 4.26-4.05 (2 H, m), 6.47 (1 H, s), 6.93 (1H, s), 7.09(1 H, d, J = 5.5 Hz), 7.17 (2 H, s), 7.45 (1 H, dd, J = 8.4, 1.2 Hz), 7.58 (1 H, s), 8.00 (1 H, d, J = 8.4 Hz), 8.34 (1 H, d, J = 5.5 Hz), 8.97 (1 H, s) | 429.05 |
| T8-63.11 | 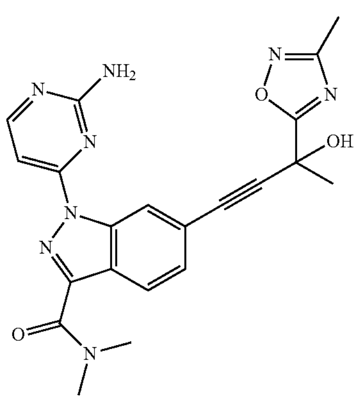 [SMILES: Cc1noc(C(C)(O)C#Cc2ccc3c(C(=O)N(C)C)nn(-c4ccnc(N)n4)c3c2)n1] | 1-(2-aminopyrimidin-4-yl)-6-[3-hydroxy-3-(3-methyl-1,2,4-oxadiazol-5-yl)but-1-yn-1-yl]-N,N-dimethyl-1H-indazole-3-carboxamide | (500 MHz, DMSO) delta 1.95 (3 H, s), 2.37 (3 H, s), 3.09 (3 H, s), 7.16-7.01 (3 H, m), 7.22 (1 H, s), 7.43 (1 H, dd, J = 8.4, 1.3 Hz), 8.01 (1 H, d, J = 7.7 Hz), 8.33 (1 H, d, J = 5.6 Hz), 8.97 (1 H, s). | 433.1 |

TABLE 8-continued

| No. | Structure | Name | 1H NMR | MS (M + H) |
|---|---|---|---|---|
| T8-63.12 | 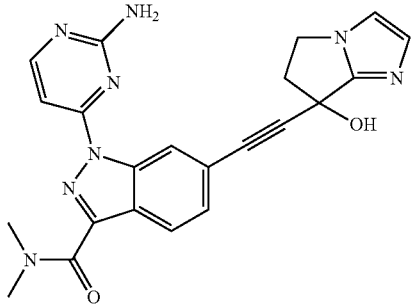 [SMILES: CN(C)C(=O)c1nn(-c2ccnc(N)n2)c2cc(C#CC3(O)CCn4ccnc43)ccc12] | 1-(2-aminopyrimidin-4-yl)-6-(2-{7-hydroxy-5H,6H,7H-pyrrolo[1,2-a]imidazol-7-yl}ethynyl)-N,N-dimethyl-1 H-indazole-3-carboxamide | (500 MHz, DMSO) delta 2.79-2.88 (1 H, m), 3.07-3.19 (4 H, m), 3.32 (3 H, s), 3.99-4.15 (2 H, m), 6.60 (1 H, s), 7.01 (1H, s), 7.05-7.22 (4 H, m), 7.43 (1 H, dd, J = 8.20, 1.42 Hz), 8.01 (1 H, d, J = 8.20 Hz), 8.34 (1 H, d, J = 5.83 Hz), 8.96 (1 H, s) | 429.15 |
| T8-63.13 | 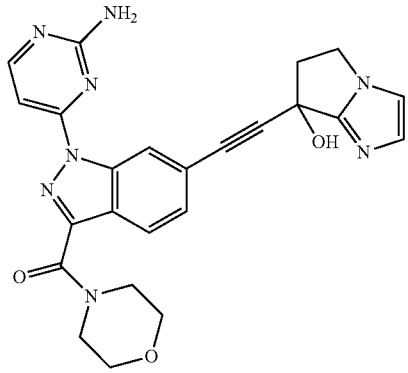 [SMILES: Nc1nccc(-n2nc(C(=O)N3CCOCC3)c3ccc(C#CC4(O)CCn5ccnc54)cc32)n1] | 7-{2-[1-(2-aminopyrimidin-4-yl)-3-[(morpholin-4-yl)carbonyl]-1H-indazol-6-yl]ethynyl}-5H,6H,7H-pyrrolo[1,2-a]imidazol-7-ol | (500 MHz, DMSO) delta 2.78-2.91 (1 H, m), 3.06- 3.19 (1H,m), 3.66 (2 H, br. s.), 3.74 (4 H, d, J = 5.99 Hz), 3.94 (2 H, br. s.), 4.07-4.15 (2 H, m), 6.60 (1 H, s), 7.00 (1 H, s), 7.07 (1 H, d, J = 5.52 Hz), 7.15 (2 H, s), 7.45 (1 H, d, J = 8.35 Hz), 8.03 (1 H, d, J = 8.35 Hz), 8.35 (1 H, d, J = 5.36 Hz), 8.97 (1 H, s) | 471.1 |
| T8-63.14 | 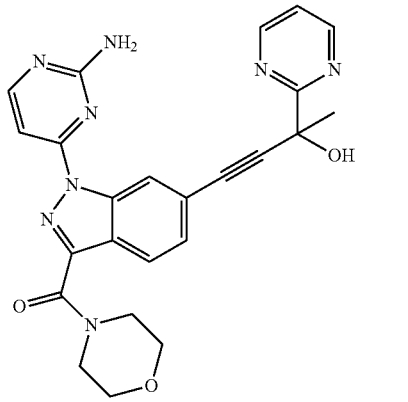 [SMILES: CC(O)(C#Cc1ccc2c(C(=O)N3CCOCC3)nn(-c3ccnc(N)n3)c2c1)c1ncccn1] | 4-[1-(2-aminopyrimidin-4-yl)-3-[(morpholin-4-yl)carbonyl]-1H-indazol-6-yl]-2-(pyrimidin-2-yl)but-3-yn-2-ol | (250 MHz, DMSO) delta 1.94 (3 H, s), 3.78-3.59 (6 H, m), 4.00-3.89 (2 H, m), 6.28 (1 H, s), 7.09 (1 H, d, J = 5.5 Hz), 7.17 (2 H, s), 7.40 (1H, dd, J = 8.4, 1.4 Hz), 7.52 (1 H, t, J = 4.9 Hz), 8.01 (1 H, d, J = 8.4 Hz), 8.36 (1 H, d, J = 5.4 Hz), 9.15-8.68 (3 H, m). | 471.05 |
| T8-63.15 | 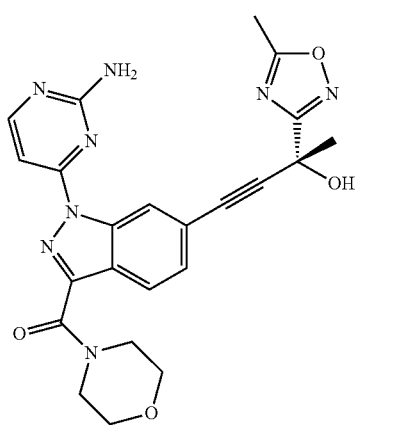 [SMILES: Cc1nc([C@](C)(O)C#Cc2ccc3c(C(=O)N4CCOCC4)nn(-c4ccnc(N)n4)c3c2)no1] | (2R)-4-[1-(2-amino pyrimidin-4-yl)-3-[(morpholin-4-yl)carbonyl]indazol-6-yl]-2-(5-methyl-1,2,4-oxadiazol-3-yl)but-3-yn-2-ol | (250 MHz, DMSO) delta 1.90 (3 H, s), 2.63 (3 H, s), 3.66 (2 H, br. s.), 3.74 (4 H, s), 3.94 (2 H, br. s.), 6.81 (1 H, s), 7.07 (1H, s), 7.16 (2 H, br. s.), 7.44 (1 H, dd, J = 8.38, 1.22 Hz), 8.03 (1 H, d, J = 8.22 Hz), 8.35(1 H, d, J = 5.48 Hz), 8.95 (1 H, s) | 475.05 |

TABLE 8-continued

| No. | Structure | Name | 1H NMR | MS (M + H) |
|---|---|---|---|---|
| T8-63.16 | 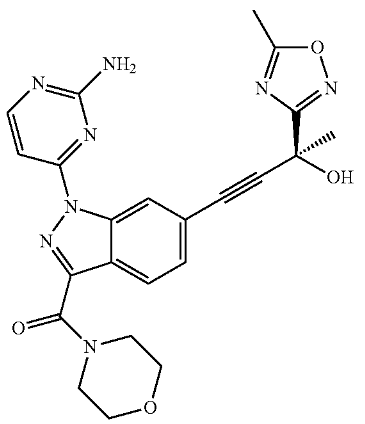 [SMILES: Cc1nc([C@@](C)(O)C#Cc2ccc3c(C(=O)N4CCOCC4)nn(-c4ccnc(N)n4)c3c2)no1] | (2S)-4-[1-(2-amino pyrimidin-4-yl)-3-[(morpholin-4-yl)carbonyl]indazol-6-yl]-2-(5-methyl-1,2,4-oxadiazol-3-yl)but-3-yn-2-ol | (250 MHz, DMSO) delta 1.89 (3 H, s), 2.62 (3 H, s), 3.61-3.80 (6 H, m), 3.92 (2 H, d, J = 3.65 Hz), 6.80 (1 H, s), 7.04-7.10 (1 H, m), 7.10-7.23 (2 H, m), 7.43 (1 H, dd, J = 8.38, 1.22 Hz), 8.02 (1 H, d, J = 8.53 Hz), 8.35 (1 H, d, J = 5.48 Hz), 8.95 (1 H, s) | 475.1 |
| T8-63.17 | 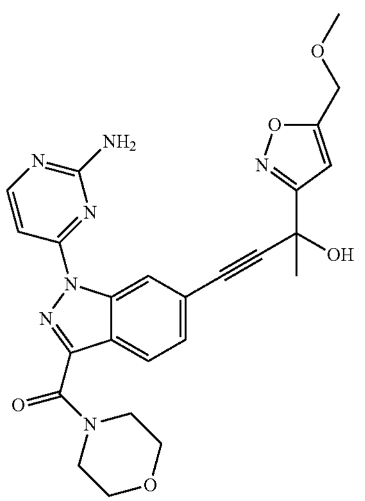 [SMILES: COCc1cc(C(C)(O)C#Cc2ccc3c(C(=O)N4CCOCC4)nn(-c4ccnc(N)n4)c3c2)no1] | 4-[1-(2-aminopyrimidin-4-yl)-3-[(morpholin-4-yl)carbonyl]-1H-indazol-6-yl]-2-[5-(methoxymethyl)-1,2-oxazol-3-yl]but-3-yn-2-ol | (500 MHz, CDCl3) delta 2.03 (3 H, s), 3.47 (3 H, s), 3.80 (2 H, d, J = 4.10 Hz), 3.87 (2 H, d, J = 4.73 Hz), 3.91 (2 H, d, J = 4.10 Hz), 3.94-4.05 (1 H, m), 4.11 (2 H, br. s.), 4.57 (2 H, s), 5.39 (2 H, br. s.), 6.49 (1 H, s), 7.21 (1 H, d, J = 5.36 Hz), 7.44 (1 H, d, J = 8.20 Hz), 8.08 (1 H, d, J = 8.20 Hz), 8.34 (1H, br. s.), 8.86 (1 H, s) | 504.05 |
| T8-63.18 | 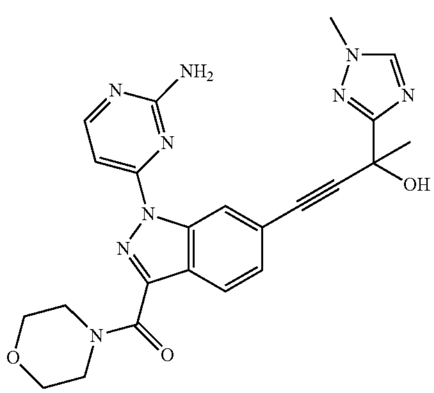 [SMILES: Cn1cnc(C(C)(O)C#Cc2ccc3c(C(=O)N4CCOCC4)nn(-c4ccnc(N)n4)c3c2)n1] | 4-[1-(2-aminopyrimidin-4-yl)-3-[(morpholin-4-yl)carbonyl-1H-indazol-6-yl]-2-(1-methyl-1H-1,2,4-triazol-3-yl)but-3-yn-2-ol | (500 MHz, DMSO) delta 1.89 (3 H, s), 3.68-3.64 (2 H, m), 3.77-3.71 (4 H, m), 3.87 (3 H, s), 3.97-3.91 (2 H, m), 6.24 (1 H, s), 7.08 (1 H, d, J = 5.5 Hz), 7.15 (2H, s), 7.41 (1 H, dd, J = 8.4, 1.1 Hz), 8.01 (1 H, d, J = 8.4 Hz), 8.35 (1 H, d, J = 5.5 Hz), 8.42 (1H, s), 8.91 (1H, s). | 474.1 |

TABLE 8-continued

| No. | Name | 1H NMR | MS (M + H) |
|---|---|---|---|
| T8-63.19 | 4-[1-(2-aminopyrimidin-4-yl)-3-[(morpholin-4-yl)carbonyl]-1H-indazol-6-yl]-2-(pyrimidin-4-yl)but-3-yn-2-ol | (500 MHz, DMSO) delta 1.86 (3 H, s), 3.61-3.81 (6H, m), 3.92 (2 H, s), 6.79 (1 H, s), 7.08 (1 H, d, J = 5.36 Hz), 7.15 (2 H, br. s.), 7.42 (1 H, d, J = 8.51 Hz), 7.86 (1 H, d, J = 5.20 Hz), 8.00 (1 H, d, J = 8.51 Hz), 8.34 (1 H, d, J = 4.89 Hz), 8.89 (1 H, d, J = 4.89 Hz), 8.93 (1 H, s), 9.21 (1 H, s) | 471.1 |
| T8-63.20 | 4-[1-(2-aminopyrimidin-4-yl)-3-[(morpholin-4-yl)carbonyl]-1H-indazol-6-yl]-1-fluoro-2-methyl]-but-3-yn-2-ol | (500 MHz, MeOD) delta 1.61 (3 H, d, J = 1.89 Hz), 3.71-3.80 (2 H, m), 3.81-3.92 (4 H, m), 3.98-4.10 (2 H, m), 4.42 (2 H, d, J = 51.07 Hz), 7.21 (1 H, d, J = 5.67 Hz), 7.45 (1 H, d, J = 7.09 Hz), 7.99 (1 H, d, J = 8.35 Hz), 8.29 (1 H, d, J = 5.67 Hz), 9.03 (1H, s) | 425.05 |
| T8-63.21 | 4-[1-(2-aminopyrimidin-4-yl)-3-[(morpholin-4-yl)carbonyl]-1H-indazol-6-yl]-1-fluoro-2-(fluoromethyl)but-3-yn-2-ol | (500 MHz, DMSO) delta 3.57-3.83 (6 H, m), 3.93 (2 H, d, J = 4.10 Hz), 4.41-4.72 (4 H, m), 6.70 (1 H, br. s.), 7.08 (1 H, d, J = 5.36 Hz), 7.19 (2 H, br. s.), 7.46 (1 H, d, J = 8.35 Hz), 8.04 (1 H, d, J = 8.35 Hz), 8.36 (1 H, d, J = 5.52 Hz), 9.00 (1 H, s) | 443.05 |
| T8-63.22 | 7-{2-[1-(2-aminopyrimidin-4-yl)-3-[(morpholin-4-yl)carbonyl]-1H-indazol-6-yl]ethynyl}-5H,6H,7H-cyclopenta[b]pyridin-7-ol | (500 MHz, CDCl₃) delta 2.38-2.46(1 H, m), 2.59-2.71 (1H, m), 2.89-2.99 (1 H, m), 3.00-3.09 (1 H, m), 3.66 (2 H, d, J = 4.26 Hz), 3.74 (4 H, d, J = 5.52 Hz), 3.93 (2 H, br. s.), 6.28(1 H, s), 7.07 (1H, d, J = 5.36 Hz), 7.15 (2 H, br. s.), 7.30 (1 H, dd, J = 7.49, 4.81 Hz), 7.41 (1 H, dd, J = 8.43, 1.02 Hz), 7.75 (1 H, d, J = 7.57 Hz), 8.01 (1 H, d, J = 8.35 Hz), 8.35 (1H, d, J = 4.57 Hz), 8.47 (1 H, d, J = 3.78 Hz), 8.92(1 H, s) | 482.15 |

TABLE 8-continued

| No. | Structure | Name | 1H NMR | MS (M + H) |
|---|---|---|---|---|
| T8-63.23 | 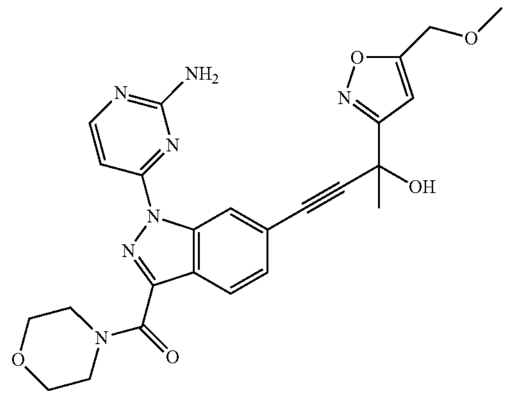 [SMILES: COCc1cc(C(C)(O)C#Cc2ccc3c(C(=O)N4CCOCC4)nn(-c4ccnc(N)n4)c3c2)no1] | 4-[1-(2-aminopyrimidin-4-yl)-3-[(morpholin-4-yl)carbonyl]-1H-indazol-6-yl]-2-[5-(methoxymethyl)-1,2-oxazol-3-yl]but-3-yn-2-ol | (500 MHz. CDCl₃) delta 2.03 (3 H, s), 3.47 (3 H, s), 3.80 (2 H, d, J = 4.10 Hz), 3.87 (2 H, d, J = 4.73 Hz), 3.91 (2 H, d, J = 4.10 Hz), 3.94-4.05 (1 H, m), 4.11 (2 H, br. s.), 4.57 (2 H, s), 5.39 (2 H, br. s.), 6.49 (1 H, s), 7.21 (1 H, d, J = 5.36 Hz), 7.44 (1 H, d, J = 8.20 Hz), 8.08 (1 H, d, J = 8.20 Hz), 8.34 (1 H, br. s.), 8.86 (1 H, s) | 504.05 |

Example 64

Preparation of 4-[1-(2-aminopyrimidin-4-yl)-3-[(pyrrolidin-1-yl)carbonyl]-1H-indazol-6-yl]-2-(5-methyl-1,2-oxazol-3-yl)but-3-yn-2-ol

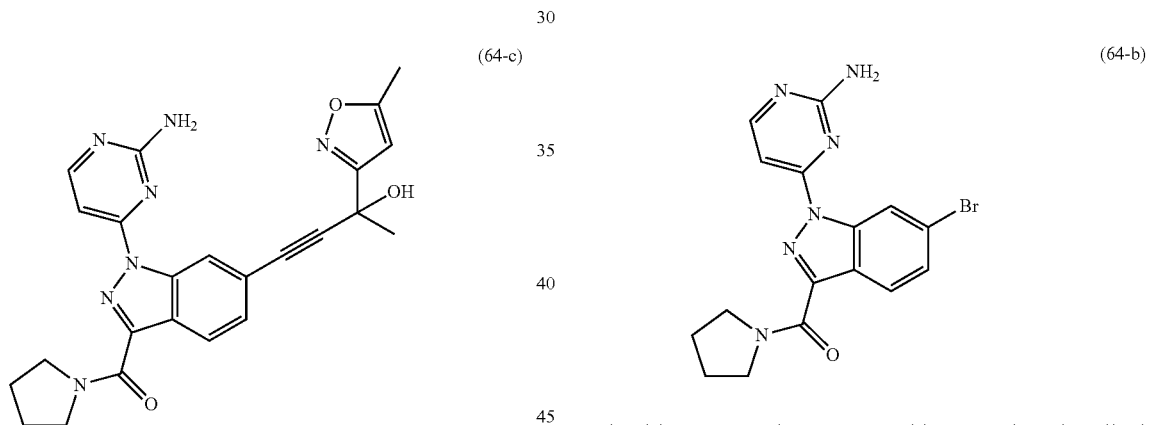

Step 1: Synthesis of 6-bromo-3-[(pyrrolidin-1-yl)carbonyl]-1H-indazole

The title compound was prepared by procedure described in Example 62-a, by substituting morpholine with pyrrolidine in Step 1: ¹H NMR (250 MHz, DMSO) delta 1.89 (4H, dt, J=18.24, 6.64 Hz), 3.56 (2H, t, J=6.62 Hz), 3.93 (2H, t, J=6.47 Hz), 7.36 (1H, dd, J=8.60, 1.60 Hz), 7.84 (1H, d, J=1.37 Hz), 8.09 (1H, d, J=8.68 Hz); LC-MS: m/z=+293.85/295.75 (M+H)+.

Step 2—Synthesis of 4-[6-bromo-3-[(pyrrolidin-1-yl)carbonyl]indazol-1-yl]pyrimidin-2-amine The title compound was prepared by procedure described in Example 62-b, by substituting 6-bromo-3-[(morpholin-4-yl)carbonyl]-1H-indazole with 6-bromo-3-[(pyrrolidin-1-yl)carbonyl]-1H-indazole in Step 2: ¹H NMR (250 MHz, DMSO) delta 1.79-2.09 (4 μl, m), 3.60 (2H, t, J=6.47 Hz), 3.87-4.08 (2H, m), 7.10 (1H, d, J=5.48 Hz), 7.20 (2 H, br. s.), 7.59 (1H, dd, J=8.60, 1.29 Hz), 8.16 (1H, d, J=8.53 Hz), 8.35 (1H, d, J=5.48 Hz), 9.18 (1 H, s); LC-MS: m/z=+387.00/388.80 (M+H)+.

Step 3—Synthesis of 4-[1-(2-aminopyrimidin-4-yl)-3-[(pyrrolidin-1-yl)carbonyl]-1H-indazol-6-yl]-2-(5-methyl-1,2-oxazol-3-yl)but-3-yn-2-ol The title compound was prepared by procedure described in Example 62-c, by substituting 1-(2-aminopyrimidin-4-yl)-6-bromo-N,N-dimethylindazole-3-carboxamide with 4-{6-bromo-3-[(pyrrolidin-1-yl)carbonyl]indazol-1-yl}pyrimidin-2-amine and 2-(1,3-thiazol-2-yl)but-3-yn-2-ol with 2-(5-methyl-1,2-oxazol-3-yl)but-3-yn-2-ol in Step 3: ¹H NMR (500 MHz, DMSO) delta 1.84-1.93 (5H, m), 1.93-1.98 (2H, m), 2.42 (3H, s), 3.60 (2H, t, J=6.86 Hz), 3.99 (2H, t, J=6.78 Hz), 6.41 (1H, s), 6.57 (1H, s), 7.13 (1H, d, J=5.36 Hz), 7.15 (2H, br. s.), 7.44 (1H, dd, J=8.43, 1.18 Hz), 8.22 (1H, d, J=8.35 Hz), 8.36 (1H, d, J=5.52 Hz), 8.94 (1H, s); LC-MS: m/z=+458.45 (M+H)+.

Example 65

Preparation of 1-(2-aminopyrimidin-4-yl)-6-[(3R)-3-hydroxy-3-(5-methyl-1,2-oxazol-3-yl)but-1-yn-1-yl]-N-methy 1-1H-indazole-3-carboxamide

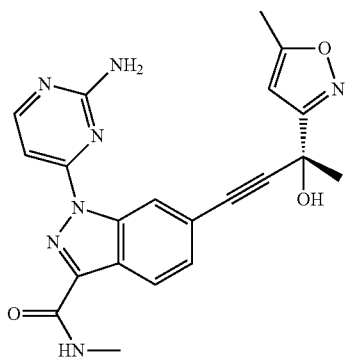
(65-c)

Step 1—Synthesis of 1-(2-aminopyrimidin-4-yl)-6-bromoindazole-3-carboxylic acid

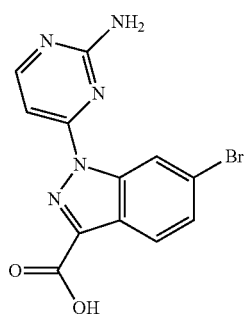
(65-a)

To suspension of 6-bromo-1H-indazole-3-carboxylic acid (5 g, 20.77 mmol) in DMF (40 mL) was added NaH (60%, 1.7 g, 41.5 mmol). The mixture was stirred at RT for 10 min, followed by addition of 4-chloro-pyrimidin-2-ylamine (4.0 g, 31 mmol). The mixture was heated at 65° C. for 2 hr. The reaction cooled to RT, then another 1 eq NaH added (ca 0.78 g). Heating continued at 65° C. overnight. Reaction mixture was allowed to cool to RT. The mixture was quenched by portionwise addition to water (10 mL) resulting in formation of a precipitate. The mixture was acidified with 0.5M aq citric acid. The precipitate was collected by suction filtration through a fritted sinter funnel and washed with MeOH/EtOAc (1/1) and was thoroughly dried under high vacuum to give the title compound as a beige solid (5.8 g, LC-MS purity=88%); LC-MS: m/z=+333.85/335.80 (M+H)+.

Step 2—Synthesis of 1-(2-aminopyrimidin-4-yl)-6-bromo-N-methylindazole-3-carboxamide
(65-b)

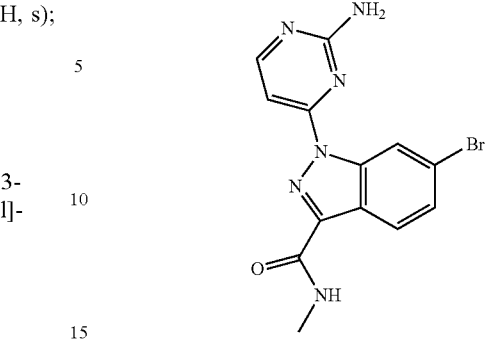

To a solution of 1-(2-aminopyrimidin-4-yl)-6-bromoindazole-3-carboxylic acid (300 mg, 0.79 mmol) in DCM (2 mL), was added thionyl chloride (0.28 mL, 3.9 mmol). DMF (0.01 mL) added The mixture was stirred at RT for 1 hr. The mixture was cooled to RT, concentrated in vacuo, DCM (2 mL) added and concentration in vacuo was repeated. To this residue was added 2M methylamine in MeOH (2.0 mL, 3.95 mmol). The resultant mixture stirred for 30 min, then concentrated in vacuo and partitioned between EtOAc and water. The precipitate formed was collected by suction filtration. The aqueous layer of the filtrate was extracted with more EtOAc. Combined organics dried (Na₂SO₄); filtered and concentrated in vacuo. This product was combined with the precipitate collected to give the title compound (290 mg, LC-MS purity=77%). LC-MS: m/z=+346.90/348.75 (M+H)+.

Step 3—Synthesis of 1-(2-aminopyrimidin-4-yl)-6-[(3R)-3-hydroxy-3-(5-methyl-1,2-oxazol-3-yl)but-1-yn-1-yl]-N-methyl-1H-indazole-3-carboxamide The title compound was prepared by procedure described in Example 62-c, by substituting 1-(2-aminopyrimidin-4-yl)-6-bromo-N,N-dimethylindazole-3-carboxamide with 1-(2-aminopyrimidin-4-yl)-6-bromo-N-methylindazole-3-carboxamide and 2-(1,3-thiazol-2-yl)but-3-yn-2-ol with (2R)-2-(5-methyl-1,2-oxazol-3-yl)but-3-yn-2-ol in Step 3: ¹H NMR (500 MHz, DMSO) delta 1.87 (3H, s), 2.42 (3H, s), 2.87 (3H, d, J=4.73 Hz), 6.42 (1H, s), 6.60 (1H, s), 7.17 (2H, br. s.), 7.32 (1H, d, J=5.36 Hz), 7.46 (1H, dd, J=8.35, 1.10 Hz), 8.27 (1H, d, J=8.20 Hz), 8.40 (1H, d, J=5.36 Hz), 8.78 (1H, d, J=4.73 Hz), 8.94 (1H, s); LC-MS: m/z=+418.05 (M+H)+.

Example 66

Preparation of 1-(2-aminopyrimidin-4-yl)-6-[(3R)-3-hydroxy-3-(5-methyl-1,2-oxazol-3-yl)but-1-yn-1-yl]-1H-indazole-3-carboxamide

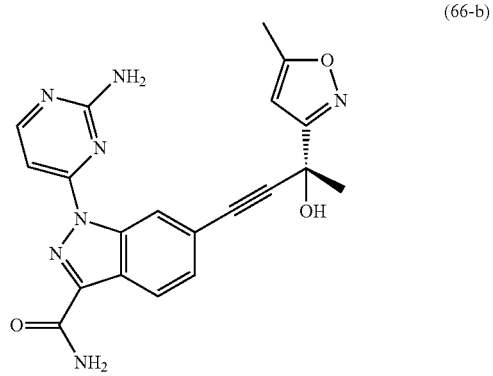 [SMILES: Cc1cc([C@](C)(O)C#Cc2ccc3c(C(N)=O)nn(-c4ccnc(N)n4)c3c2)no1]
(66-b)

Step 1—Synthesis of 1-(2-aminopyrimidin-4-yl)-6-bromoindazole-3-carboxamide

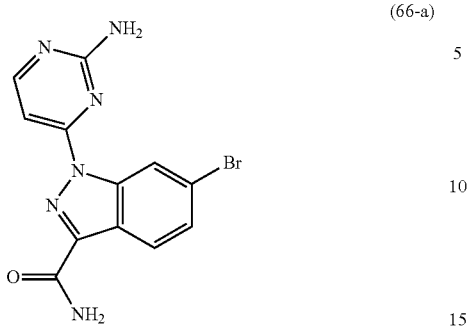

(66-a)

To a solution of 1-(2-aminopyrimidin-4-yl)-6-bromoindazole-3-carboxylic acid (500 mg, 1.32 mmol) in DCM (5 mL), was added thionyl chloride (0.6 mL, 7.9 mmol) followed by DMF (0.02 mL). The mixture was stirred at RT for 1 hr. The mixture was concentrated in vacuo, DCM (2 mL) added and concentration in vacuo was repeated. To this residue was added THF (5 mL) and conc. aq $NH_3$ (0.5 mL). The mixture stirred for 30 min, then diluted with water and the resultant solid was collected by suction filtration. The solid was thoroughly dried under high vacuum, to give the title compound (360 mg): $^1$H NMR (250 MHz, DMSO) delta 7.15 (1H, br. s.), 7.32 (1H, d, J=5.48 Hz), 7.60 (1H, dd, J=8.60, 1.60 Hz), 7.74 (1H, br. s.), 8.20 (1H, d, J=8.38 Hz), 8.38 (1H, d, J=5.48 Hz), 9.18 (1H, d, J=1.22 Hz); LC-MS: m/z=+332.90/334.70 (M+H)+.

Step 2—Synthesis of 1-(2-aminopyrimidin-4-yl)-6-[(3R)-3-hydroxy-3-(5-methyl-1,2-oxazol-3-yl)but-1-yn-1-yl]-1H-indazole-3-carboxamide The title compound was prepared by procedure as described in Example 62-c by reacting 1-(2-aminopyrimidin-4-yl)-6-bromoindazole-3-carboxamide and (2R)-2-(5-methyl-1,2-oxazol-3-yl)but-3-yn-2-ol: $^1$H NMR (500 MHz, DMSO) delta 1.86 (3H, s), 2.42 (3H, s), 6.41 (1H, s), 6.59 (1H, s), 7.16 (2H, br. s.), 7.34 (1H, d, J=5.52 Hz), 7.44 (1H, dd, J=8.43, 1.18 Hz), 7.75 (1H, s), 8.21 (1H, s), 8.26 (1H, d, J=8.35 Hz), 8.38 (1H, d, J=5.52 Hz), 8.93 (1H, s); LC-MS: m/z=+404 (M+H)+.

Example 67

Preparation of 1-{[1-(2-aminopyrimidin-4-yl)-6-[(3R)-3-hydroxy-3-(5-methyl-1,2,4-oxadiazol-3-yl)but-1-yn-1-yl]-1H-indazol-3-yl]carbonyl}azetidin-3-ol (67-b)

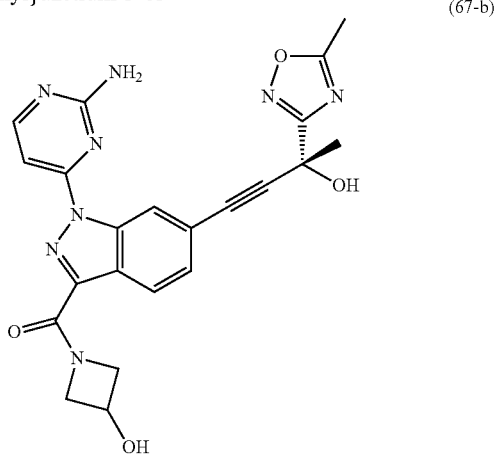 [SMILES: Cc1nc([C@](C)(O)C#Cc2ccc3c(C(=O)N4CC(O)C4)nn(-c4ccnc(N)n4)c3c2)no1]

Step 1—Synthesis of 1-{[1-(2-aminopyrimidin-4-yl)-6-bromoindazol-3-yl]carbonyl}azetidin-3-ol

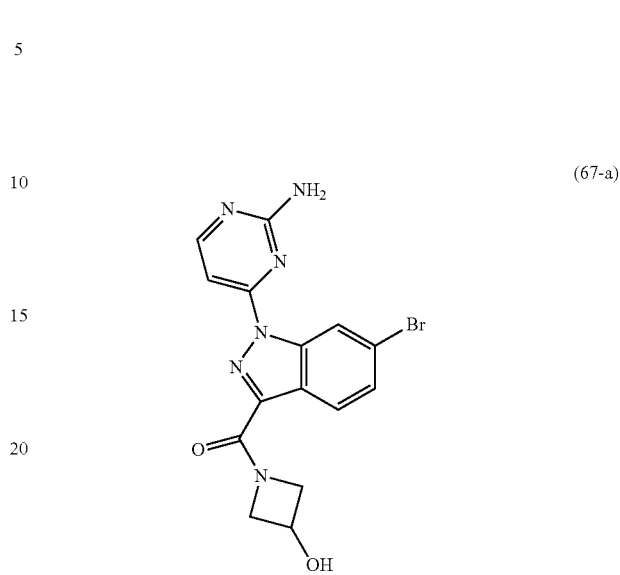

(67-a)

To a solution of 1-(2-aminopyrimidin-4-yl)-6-bromoindazole-3-carboxylic acid (0.38 g, 1.12 mmol)) in DCM (5 mL), was added thionyl chloride (0.49 ml, 6.74 mmol) followed by a drop of DMF. The mixture was stirred at 40° C. overnight. The reaction mixture was concentrated in vacuo and DCM added and the concentration repeated (×2). The acid chloride intermediate was suspended in DCM (10 ml), azetidin-3-ol hydrochloride (491.82 mg, 4.49 mmol) followed by DIPEA (0.86 ml, 4.94 mmol). The reaction was stirred at RT for 0.5 hr and then concentrated in vacuo. The residue was diluted with more DCM and water and the organics extracted (2×20 ml DCM). The combined organic layers were dried ($Na_2SO_4$), filtered and concentrated in vacuo to give the title intermediate (214 mg, LC-MS purity=63%); LC-MS: m/z=+388.95/390.80 (M+H)+.

Step 2—Synthesis of 1-{[1-(2-aminopyrimidin-4-yl)-6-[(3R)-3-hydroxy-3-(5-methyl-1,2,4-oxadiazol-3-yl)but-1-yn-1-yl]-1H-indazol-3-yl]carbonyl}azetidin-3-ol The title compound was prepared according to the procedure described in Example 62-c by reacting 1-{[1-(2-aminopyrimidin-4-yl)-6-bromoindazol-3-yl]carbonyl}azetidin-3-ol and (2R)-2-(5-methyl-1,2-oxazol-3-yl)but-3-yn-2-ol; 1H NMR (500 MHz, CDCl$_3$) delta 1.93 (3H, s), 2.54 (3H, s), 4.01 (1H, dd, J=10.8, 3.8 Hz), 4.42-4.35 (1H, m), 4.50-4.44 (1H, m), 4.63 (1H, dd, J=6.0, 4.5 Hz), 4.83 (1H, dd, J=10.6, 6.7 Hz), 5.12 (1H, d, J=6.0 Hz), 5.65-5.54 (2H, m), 5.76 (1H, s), 7.05 (1H, d, J=5.5 Hz), 7.33 (1H, dd, J=8.4, 1.2 Hz), 8.33-8.10 (2H, m), 8.80 (1H, d, J=6.5 Hz); LC-MS: m/z=+461.1 (M+H)+.

Example 68 (i) and Example 68 (ii)

Preparation of 4-[1-(2-aminopyrimidin-4-yl)-3-{[cis-2,6-dimethylmorpholin-4-yl]carbonyl}-1H-indazol-6-yl]-2-(pyrimidin-2-yl)but-3-yn-2-ol [Example 68 (i)] and 4-[1-(2-aminopyrimidin-4-yl)-3-{[(trans)-2,6-dimethylmorpholin-4-yl]carbonyl}-1H-indazol-6-yl]-2-(pyrimidin-2-yl)but-3-yn-2-ol [Example 68 (ii)]

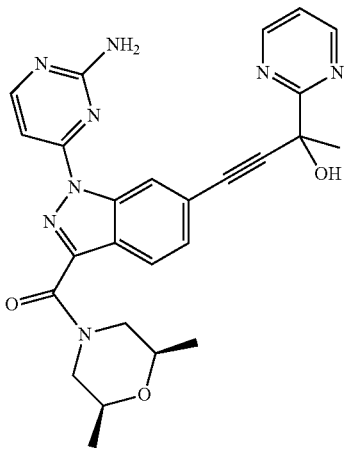
(68 (i)-b)

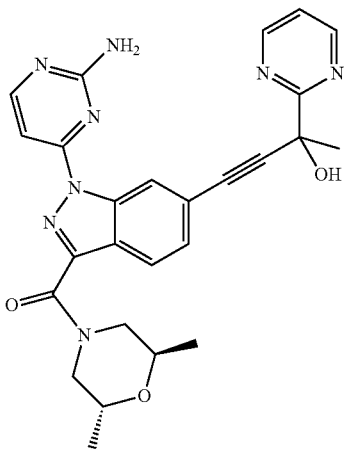
(68(ii)-b)

Absolute stereochemistry to be assigned.

Step 1—Synthesis of 4-{6-bromo-3-[(2,6-dimethylmorpholin-4-yl)carbonyl]indazol-1-yl}pyrimidin-2-amine

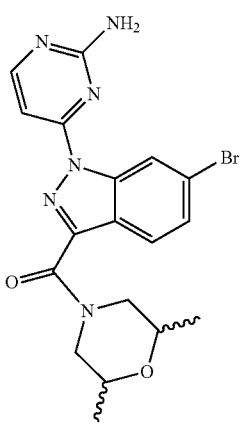
(68-a)

To a solution of 1-(2-aminopyrimidin-4-yl)-6-bromoindazole-3-carboxylic acid (0.38 g, 1.12 mmol)) in DCM (5 mL), was added thionyl chloride (0.49 ml, 6.74 mmol) followed by a drop of DMF. The mixture was stirred at 40° C. overnight. The reaction mixture was concentrated in vacuo and DCM added and the concentration repeated (×2). The acid chloride intermediate was suspended in DCM (10 ml), 2,6-dimethylmorpholine (0.55 ml, 4.49 mmol) added. The reaction was stirred at RT for 0.5 hr and then concentrated in vacuo. The residue was diluted with more DCM and water and the organics extracted (2×20 ml). The combined organic layers were dried (Na$_2$SO$_4$), filtered and concentrated in vacuo. Crude material purified by column chromatography, (9:1 DCM:methanol, Rf=0.6). Elution with DCM:methanol 98:2 to 90:10 gave the mixture of cis and trans 2,6-dimethylmorpholin-4-yl compound (200 mg): $^1$H NMR (500 MHz, CDCl$_3$) delta 1.21 (3H, d, J=6.2 Hz), 1.30 (3H, d, J=6.1 Hz), 2.64 (1H, dd, J=13.1, 10.8 Hz), 2.99 (1H, dd, J=13.2, 10.6 Hz), 4.84-3.26 (6H, m), 5.23 (2H, s), 7.23-7.19 (1H, m), 7.50 (1H, dd, J=8.6, 1.6 Hz), 7.98 (1H, d, J=8.6 Hz), 8.37 (1H, dd, J=5.6, 2.2 Hz), 9.01 (1H, d, J=1.2 Hz); LC-MS: m/z=+430.95/432.85 (M+H)+.

Step 2—Synthesis and separation of 4-[1-(2-aminopyrimidin-4-yl)-3-{[cis-2,6-dimethylmorpholin-4-yl]carbonyl}-1H-indazol-6-yl]-2-(pyrimidin-2-yl)but-3-yn-2-ol [Example 68 (i)] and 4-[1-(2-aminopyrimidin-4-yl)-3-[(trans)-2,6-dimethylmorpholin-4-yl]carbonyl}-1H-indazol-6-yl]-2-(pyrimidin-2-yl)but-3-yn-2-ol [Example 68 (ii)]

To a pressure tube was added 4-{6-bromo-3-[(2,6-dimethylmorpholin-4-yl)carbonyl]indazol-1-yl}pyrimidin-2-amine (170 mg, 0.39 mmol) followed by piperidine (1.0 mL), tetrakis(triphenylphosphine)palladium (45.55 mg, 0.04 mmol), copper(I) iodide (7.51 mg, 0.04 mmol) and 2-(pyrimidin-2-yl)but-3-yn-2-ol (116.8 mg, 0.79 mmol) in more piperidine (1.0 mL). The reaction was capped and stirred at 65° C. for 1.5 h. The reaction mixture was concentrated in vacuo after 1 hr 20 mm. DCM (5 mL×2) was added and the mixture was concentrated in vacuo. Crude material was purified by column chromatography (Biotage, DCM:methanol 98:2 to 90:10) to give the product as a mixture of cis and trans isomers. The isomeric mixture was then separated by reverse phase preparative HPLC (MeCN/Water+0.2% ammonium hydroxide) to give Example 68 (i) and Example 68 (ii).

Example 68(i)

$^1$H NMR (500 MHz, CDCl$_3$) delta 1.19 (3H, d, J=6.2 Hz), 1.29 (3H, d, J=6.2 Hz), 2.06 (3H, s), 2.68-2.57 (1H, m), 2.97 (1H, dd, J=13.3, 10.8 Hz), 3.72 (2H, d, J=6.5, 4.0 Hz), 4.58 (1H, d, J=13.3 Hz), 4.68 (1H, d, J=13.2 Hz), 5.25 (2H, s), 5.36 (1H, s), 7.21 (1H, d, J=5.5 Hz), 7.35 (1H, t, J=4.9 Hz), 7.42 (1H, dd, J=8.4, 1.2 Hz), 7.99 (1H, d, J=8.4 Hz), 8.35 (1H, d, J=4.7 Hz), 8.85 (2H, d, J=4.9 Hz), 8.89 (1H, s); LC-MS: m/z=+499.1 (M+H)+.

Example 68 (ii)

$^1$H NMR (500 MHz, CDCl$_3$) 1.38-1.20 (6H, m), 2.05 (3H, s), 3.45 (1H, dd, J=13.1, 6.8 Hz), 3.87 (1H, dd, J=13.3, 5.5 Hz), 4.08-3.96 (2H, m), 4.13 (2H, ddd, J=13.7, 8.1, 4.8 Hz), 5.80-4.93 (3H, m), 7.18 (1H, d, J=5.6 Hz), 7.34 (1H, t, J=4.9 Hz), 7.42 (1H, dd, J=8.4, 1.1 Hz), 8.02 (1H, d, J=8.4 Hz), 8.34 (1H, d, J=5.3 Hz), 8.85 (2H, d, J=4.9 Hz), 8.88 (1H, s); LC-MS: m/z=+499.1 (M+H)+.

Example 69

Preparation and chiral separation of (7R)-7-{2-[1-(2-aminopyrimidin-4-yl)-3-[(morpholin-4-yl)carbonyl]indazol-6-yl]ethynyl}-5H,6H-cyclopenta[b]pyridin-7-ol [Example 69(i)] and (7S)-7-{2-[1-(2-aminopyrimidin-4-yl)-3-[(morpholin-4-yl)carbonyl]indazol-6-yl]ethynyl}-5H,6H-cyclopenta[b]pyridin-7-ol [Example 69(ii)]

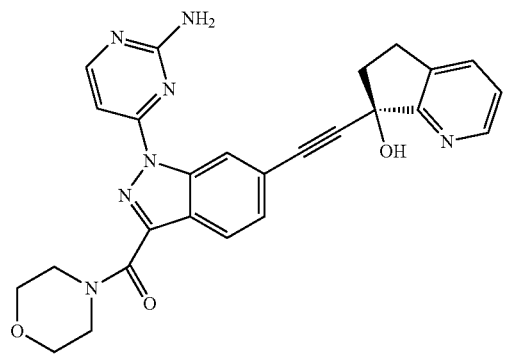

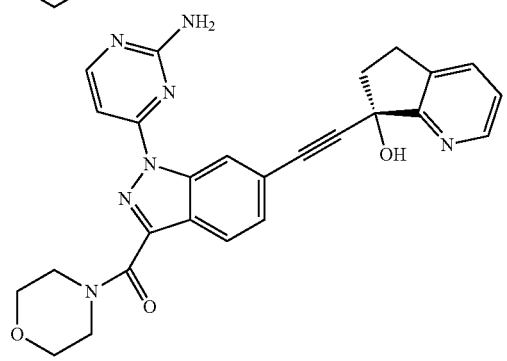

Example 69(i) Example 69(ii)

To a pressure tube was added 4-[6-bromo-3-[(morpholin-4-yl)carbonyl]indazol-1-yl]pyrimidin-2-amine (150 mg, 0.37 mmol) followed by piperidine (2.0 mL), tetrakis(triphenylphosphine)palladium (42.99 mg, 0.037 mmol), copper(I) iodide (7.1 mg, 0.037 mmol) and 7-ethynyl-5H,6H-cyclopenta[b]pyridin-7-ol (118.43 mg, 0.74 mmol). The reaction was capped and stirred at 65° C. for 2.5 hr. The reaction mixture was concentrated in vacuo. DCM (5 mL×2) added and the mixture was concentrated in vacuo. The crude material was purified by column chromatography (elution with 99:1 to 90:10 DCM: methanol) to give a residue which was triturated with MeCN/diethyl ether (3:1), giving the racemic product.

The enantiomers were separated using the following method. Instrument: Gilson 215 Liquid Handler, 2× Gilson 306 Pumps, Gilson 805 Manometric Module, Gilson 119 UV/Vis Dual Detector. Flow rate: 18 ml/min. Mobile Phase: Methanol+0.1% DEA. Column: Chiralcel OJ, 25 cm. Particle Size: 10 µm. Loading: 1.5 ml (<2 mg).

The first peak eluted gave (7R)-7-{2-[1-(2-aminopyrimidin-4-yl)-3-[(morpholin-4-yl)carbonyl]indazol-6-yl]ethynyl}-5H,6H-cyclopenta[b]pyridin-7-ol (Example 69(i)): $^1$H NMR (500 MHz, DMSO) delta 2.43 (1H, ddd, J=13.04, 8.00, 4.81 Hz), 2.60-2.70 (1H, m), 2.89-3.00 (1H, m), 3.00-3.10 (1H, m), 3.61-3.69 (2 H, m), 3.74 (4H, d, J=5.52 Hz), 3.93 (2H, d, J=4.41 Hz), 6.30 (1H, br. s.), 7.08 (1H, d, J=5.52 Hz), 7.15 (2H, br. s.), 7.31 (1H, dd, J=7.65, 4.81 Hz), 7.38-7.48 (1H, m), 7.76 (1H, d, J=7.41 Hz), 8.01 (1H, d, J=8.35 Hz), 8.35 (1H, d, J=5.52 Hz), 8.47 (1H, d, J=4.57 Hz), 8.92 (1H, s); LC-MS: m/z=+482.15 (M+H)+.

The second peak eluted gave (7S)-7-{2-[1-(2-aminopyrimidin-4-yl)-3-[(morpholin-4-yl)carbonyl]indazol-6-yl]ethynyl}-5H,6H-cyclopenta[b]pyridin-7-ol (Example 69(ii)): $^1$H NMR (500 MHz, DMSO) delta 2.19-2.27 (1H, m), 2.43-2.52 (1H, m), 2.71-2.81 (1H, m), 2.81-2.90 (1H, m), 3.48 (2H, d, J=4.57 Hz), 3.55 (4H, d, J=5.52 Hz), 3.74 (2H, d, J=4.41 Hz), 6.89 (1H, d, J=5.52 Hz), 7.12 (1H, dd, J=7.57, 4.89 Hz), 7.23 (1H, d, J=8.35 Hz), 7.57 (1H, d, J=7.41 Hz), 7.82 (1H, d, J=8.20 Hz), 8.16 (1H, d, J=5.52 Hz), 8.28 (1H, d, J=4.57 Hz), 8.74 (1H, s); LC-MS: m/z=+482.15 (M+H)+.

Absolute stereochemistry to be assigned.

Example 70

Preparation of 4-[1-(2-aminopyrimidin-4-yl)-3-[(morpholin-4-yl)carbonyl]-1H-indazol-6-yl]-2-(1,3-oxazol-2-yl)but-3-yn-2-ol

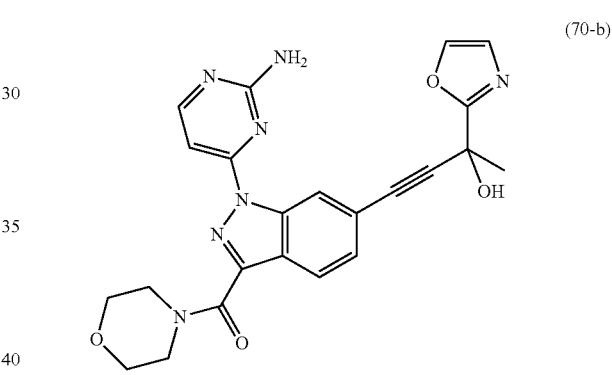

(70-b)

Step 1: Synthesis of 4-{6-iodo-3-[(morpholin-4-yl)carbonyl]indazol-1-yl}pyrimidin-2-amine

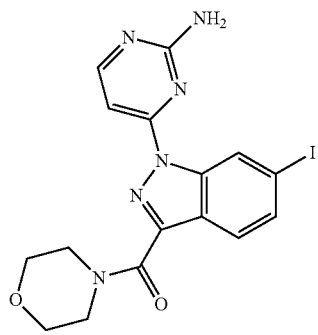 [SMILES: Nc1nccc(-n2nc(C(=O)N3CCOCC3)c3ccc(I)cc32)n1]

To a solution of 1-(2-aminopyrimidin-4-yl)-6-iodoindazole-3-carboxylic acid (3 g, 7.87 mmol)) in DCM (40 mL), was added thionyl chloride (6.85 ml, 94.46 mmol) followed by DMF (catalytic, 3 drops). The mixture was stirred at 50° C. for 1 hour. The reaction mixture was concentrated in vacuo and DCM added and the concentration repeated (×2). The crude acid chloride (assumed 7.87 mmol) was suspended in more DCM (30 mL) and morpholine (1.37 ml, 15.74 mmol) was added at 0 dropwise. The reaction was stirred at RT overnight. The reaction mixture was diluted with more DCM (25 ml) and 2M $Na_2CO_3$ added (35 ml). A pale brown precipitate was collected by filtration and washed with more DCM. The precipitate was slurried in water:acetonitrile (3:1, 10 ml) and the off-white solid collected by filtration and washed with more water:acetonitrile (3:1, 2×1 ml). The solid was then dried under vacuum to give the title compound (2.72 g, LC-MS purity=86%): $^1$H NMR (500 MHz, DMSO) delta 3.41-3.76 (6H, m), 3.85-3.97 (2H, m), 7.05 (1H, d, J=5.5 Hz), 7.18 (2H, s), 7.74 (1H, dd, J=8.4, 1.1 Hz), 7.80 (1H, d, J=8.4 Hz), 8.34 (1H, d, J=5.5 Hz), 9.33 (1H, s); LC-MS: m/z=+450.90 (M+H)+.

Step 2—Synthesis of 4-[1-(2-aminopyrimidin-4-yl)-3-[(morpholin-4-yl)carbonyl]-1H-indazol-6-yl]-2-(1,3-oxazol-2-yl)but-3-yn-2-ol To a pressure tube was added 4-{6-iodo-3-[(morpholin-4-yl)carbonyl]-1H-indazol-1-yl}pyrimidin-2-amine (150 mg, 0.33 mmol) followed by piperidine (2.0 mL), tetrakis(triphenylphosphine)palladium(0) (38.5 mg, 0.03 mmol), copper (I) iodide (6.35 mg, 0.03 mmol) and 2-(1,3-oxazol-2-yl)but-3-yn-2-ol (68.53 mg, 0.5 mmol). The reaction was capped and stirred at 35° C. for 2.5 hr. The reaction mixture was concentrated in vacuo. DCM (5 mL×2) added and the mixture was concentrated in vacuo. Purification by column chromatography (1% to 10% MeOH in DCM), followed by trituration with a mixture of MeCN/diethyl ether mixture (3/1) gave the title compound as an off-white solid (62 mg): $^1$H NMR (500 MHz, DMSO) delta 3.67 (2H, d, J=4.26 Hz), 3.75 (4H, d, J=5.67 Hz), 3.94 (2H, d, J=3.94 Hz), 4.06 (3H, s), 6.72-6.89 (1H, m), 6.93-7.33 (4H, m), 7.45 (1H, d, J=7.57 Hz), 8.04 (1H, d, J=7.88 Hz), 8.11-8.23 (1H, m), 8.97 (1H, s); LC-MS: m/z=+460.15 (M+H)+.

Example 71

Preparation of 1-(2-aminopyrimidin-4-yl)-6-[3-hydroxy-3-(pyrimidin-2-yl)but-1-yn-1-yl]-N-methyl-N-(pyridin-2-yl)-1H-indazole-3-carboxamide

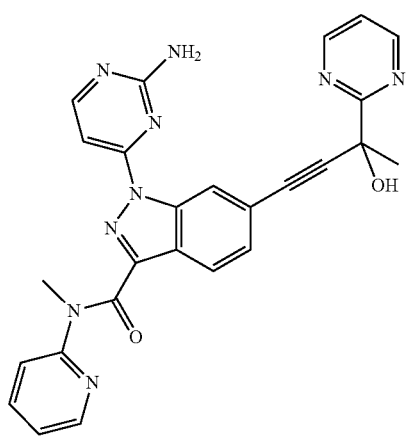

(71-c)

Step 1—Synthesis of 1-(2-aminopyrimidin-4-yl)-6-iodoindazole-3-carbonyl chloride

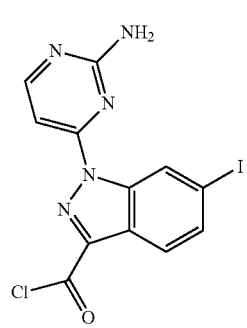

(71-a)

To a solution of 1-(2-aminopyrimidin-4-yl)-6-iodoindazole-3-carboxylic acid (1.00 g, 2.62 mmol) in DCM (10 mL), was added thionyl chloride (1.9 ml, 26.24 mmol)) followed by a drop of DMF. The mixture was stirred at 50° C. for 45 minutes. The reaction mixture was concentrated in vacuo and DCM (5 mL) was added and the concentration repeated (×2). The crude acid chloride was used directly in the next step: LC-MS m/z=+395.95 (M+H)+(after conversion to methyl ester derivative)

Step 2—Synthesis of 1-(2-aminopyrimidin-4-yl)-6-iodo-N-methyl-N-(pyridin-2-yl)indazole-3-carboxamide

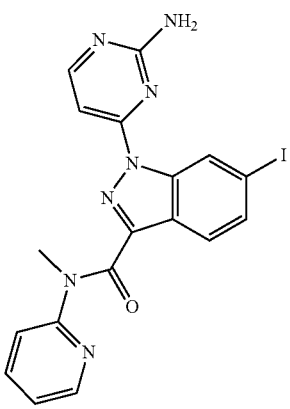

(71-b)

To a solution of 1-(2-aminopyrimidin-4-yl)-6-iodoindazole-3-carbonyl chloride (330 mg, 0.83 mmol) in DCM (5 mL) was added N-methylpyridin-2-amine (0.1 ml, 0.99 mmol) followed by triethylamine (0.29 ml, 2.06 mmol). The reaction was stirred at RT overnight and then concentrated in vacuo. The residue was diluted with water (10 ml) and extracted with DCM (2×20 ml). The title intermediate was obtained as a precipitate which was collected by suction filtration. The combined organic layers were dried ($Na_2SO_4$), filtered and concentrated in vacuo. The precipitate and organic extracts were combined to give the crude title intermediate; LC-MS purity=79%: $^1$H NMR (500 MHz, DMSO) delta 3.54 (3H, s), 6.28 (1H, d, J=5.5 Hz), 7.15 (2H, s), 7.25 (1H, dd, J=6.7, 5.0 Hz), 7.40 (1H, d, J=8.1 Hz), 7.74 (1H, dd, J=8.5, 1.3 Hz), 7.79-7.84 (2H, m), 8.19 (1H, d, J=5.5 Hz), 8.32 (1H, dd, J=4.6, 1.5 Hz), 9.24 (1H, s); LC-MS: m/z=+ 472.00 (M+H)+.

Step 3—Synthesis of 1-(2-aminopyrimidin-4-yl)-6-[3-hydroxy-3-(pyrimidin-2-yl)but-1-yn-1-yl]-N-methyl-N-(pyridin-2-yl)-1H-indazole-3-carboxamide The title compound was prepared according to the procedure described in Example 70-b, by substituting 4-{6-iodo-3-[(morpholin-4-yl)carbonyl]-1H-indazol-1-yl}pyrimidin-2-amine with 1-(2-aminopyrimidin-4-yl)-6-iodo-N-methyl-N-(pyridin-2-yl)indazole-3-carboxamide and 2-(1,3-oxazol-2-yl)but-3-yn-2-ol with 2-(pyrimidin-2-yl)but-3-yn-2-ol in Step 2: ¹H NMR (500 MHz, DMSO) delta 1.91 (3H, s), 3.54 (3H, s), 6.25 (1H, s), 6.28 (1H, d, J=5.5 Hz), 7.10 (2H, s), 7.25 (1H, dd, J=6.9, 5.1 Hz), 7.37 (1H, dd, J=8.4, 1.0 Hz), 7.41 (1H, d, J=8.1 Hz), 7.50 (1H, t, J=4.9 Hz), 7.80 (1H, td, J=7.8, 1.8 Hz), 8.00 (1H, d, J=8.4 Hz), 8.19 (1H, d, J=5.4 Hz), 8.32 (1H, d, J=3.4 Hz), 8.80 (1H, s), 8.86-8.96 (2H, m); LC-MS: m/z=+492.15 (M+H)+.

Example 72

Preparation of 1-(2-aminopyrimidin-4-yl)-6-[3-hydroxy-3-(pyrimidin-2-yl)but-1-yn-1-yl]-N-(pyridin-3-yl)-1H-indazole-3-carboxamide

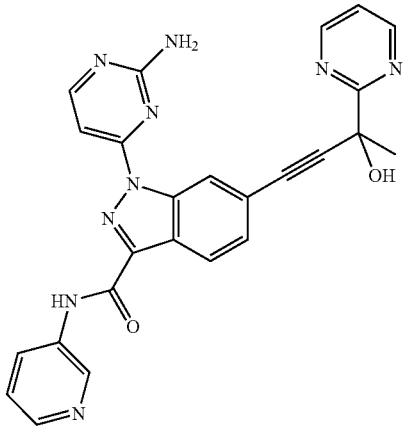 [SMILES: CC(O)(C#Cc1ccc2c(C(=O)Nc3cccnc3)nn(-c3ccnc(N)n3)c2c1)c1ncccn1]

The title compound was prepared according to the procedure described for the preparation of 1-(2-aminopyrimidin-4-yl)-6-[3-hydroxy-3-(pyrimidin-2-yl)but-1-yn-1-yl]-N-methyl-N-(pyridin-2-yl)-1H-indazole-3-carboxamide (Example 71-c); 1H NMR (500 MHz, DMSO) delta 1.94 (3H, s), 6.29 (1H, s), 7.21 (2H, s), 7.42-7.57 (4H, m), 8.24-8.33 (2H, m), 8.38 (1H, d, J=3.9 Hz), 8.45 (1H, d, J=5.3 Hz), 8.91 (2H, d, J=4.9 Hz), 8.96 (1H, s), 9.04 (1H, s), 10.78 (1H, s); LC-MS: m/z=+478.1 (M+H)+.

Example 73

Preparation of 1-{[1-(2-aminopyrimidin-4-yl)-6-[3-hydroxy-3-(1,3-oxazol-2-yl)but-1-yn-1-yl]indazol-3-yl]carbonyl}azetidin-3-ol

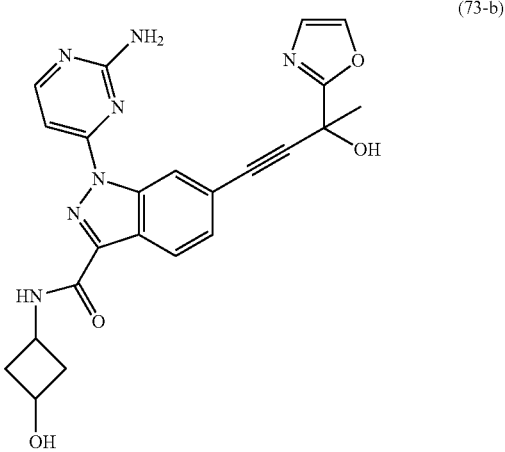 [SMILES: CC(O)(C#Cc1ccc2c(C(=O)NC3CC(O)C3)nn(-c3ccnc(N)n3)c2c1)c1ncco1]

Step 1 Synthesis of 1-{[1-(2-aminopyrimidin-4-yl)-6-iodo-1H-indazol-3-yl]carbonyl}azetidin-3-ol

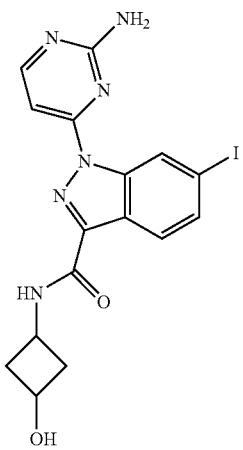

To a solution of 1-(2-amino-pyrimidin-4-yl)-6-iodo-1H-indazole-3-carboxylic acid (500 mg, 1.08 mmol) in DMF (5 ml) was added HATU (823.46 mg, 2.17 mmol) followed by azetidin-3-ol HCl (237.26 mg, 2.17 mmol) and triethylamine (0.45 ml, 3.25 mmol). The reaction mixture was stirred at RT for 3 hr. A white precipitate was also observed which was not soluble in EtOAc and water. The solid was filtered and washed with EtOAc and the filtrate worked up. The solid was dried and analysed by LCMS found to be clean title compound. To the filtrate water (6 ml) was added and the product extracted into EtOAc (2×10 ml). The combined organics were washed with water and brine and concentrated in vacuo. The material was then purified by column chromatography, (9:1 DCM: methanol). The combined column fractions were then triturated from acetonitrile to give the title compound; $^1$H NMR (500 MHz, DMSO) 3.86 (1H, dd, J=10.56, 3.94 Hz), 4.26-4.46 (2H, m), 4.52-4.64 (1H, m), 4.88 (1H, dd, J=9.77, 7.25 Hz), 5.83 (1H, d, J=6.62 Hz), 7.10 (1H, d, J=5.36 Hz), 7.17 (2H, br. s), 7.77 (1H, d, J=8.51 Hz), 8.04 (1H, d, J=8.51 Hz), 8.36 (1H, d, J=5.67 Hz), 9.34 (1 H, s). LC-MS: m/z=+436.95 (M+H)+.

Step 2 Synthesis of 1-{[1-(2-aminopyrimidin-4-yl)-6-[(3R)-3-hydroxy-3-(pyrimidin-2-yl)but-1-yn-1-yl]-1H-indazol-3-yl]carbonyl}azetidin-3-ol To a pressure tube was added 1-{[1-(2-aminopyrimidin-4-yl)-6-iodo-1H-indazol-3-yl]carbonyl}azetidin-3-ol (150 mg, 0.34 mmol) followed by piperidine (2.0 mL), Pd(PPh$_3$)$_4$ (39.74 mg, 0.03 mmol), copper(I) iodide (6.5 mg, 0.03 mmol) and 2-(1,3-oxazol-2-yl)but-3-yn-2-ol (70.74 mg, 0.5 mmol). The reaction vessel was capped and stirred at 35° C. for 2.5 hr. The reaction mixture was concentrated in vacuo. DCM (5 mL×2) added and the mixture was concentration in vacuo. The crude material purified by column chromatography (elution with 1-10% MeOH in DCM) and was then triturated from a MeCN/Ether mixture (3:1) to give the title compound; $^1$H NMR (DMSO-d6, 500 MHz) delta 1.94 (3H, s), 3.87 (1H, dd, J=10.4, 3.9 Hz), 4.31-4.44 (2H, m), 4.51-4.64 (1H, m), 4.88 (1H, dd, J=9.9, 6.9 Hz), 5.83 (1H, d, J=6.5 Hz), 6.81 (1H, s), 7.12 (1H, d, J=5.5 Hz), 7.18 (2H, s), 7.24 (1H, s), 7.46 (1H, d, J=8.4 Hz), 8.16 (1H, s), 8.27 (1H, d, J=8.4 Hz), 8.37 (1H, d, J=5.5 Hz), 8.96 (1H, s). LC-MS: m/z+388.05 (M+H)+.

Example 74

Preparation of (2S)-4-[1-(2-aminopyrimidin-4-yl)-3-[(morpholin-4-yl)carbonyl]-1H-indazol-6-yl]-2-(pyrimidin-2-yl)but-3-yn-2-ol

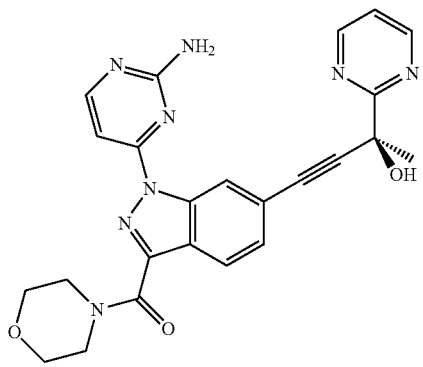 [SMILES: C[C@](O)(C#Cc1ccc2c(C(=O)N3CCOCC3)nn(-c3ccnc(N)n3)c2c1)c1ncccn1]

To solution of 4-{6-iodo-3-[(morpholin-4-yl)carbonyl]-1H-indazol-1-yl}pyrimidin-2-amine (60 mg, 0.13 mmol) in triethylamine (2 mL) was introduced tetrakis(triphenylphosphine)palladium (0) (15.4 mg, 0.01 mmol), copper(I) iodide (2.5 mg, 0.01 mmol) and (2S)-2-(pyrimidin-2-yl)but-3-yn-2-ol (30 mg, 0.20 mmol). After 18 hr at RT, the reaction mixture was concentrated in vacuo, DCM (10 mL) was added and the solution re-evaporated to dryness in vacuo (re-evaporation process repeated twice). Purification of the residue by column chromatography (Biotage, DCM containing a 0-10% gradient of methanol) furnished the title compound as an off-white solid: $^1$H NMR (500 MHz, DMSO-d6) delta 1.79-2.05 (3H, m), 3.59-3.68 (2H, m), 3.71-3.79 (4H, m), 3.89-4.01 (2H, m), 6.17-6.37 (1H, m), 6.98-7.10 (1H, m), 7.12-7.27 (2H, m), 7.32-7.42 (1H, m), 7.47-7.58 (1H, m), 7.92-8.05 (1H, m), 8.26-8.39 (1H, m), 8.80-9.04 (3H, m); LC-MS: m/z=+471.05 (M+H)+.

Example 75

Preparation of (2R)-4-[1-(2-aminopyrimidin-4-yl)-3-[(morpholin-4-yl)carbonyl]-1H-indazol-6-yl]-2-(pyrimidin-2-yl)but-3-yn-2-ol

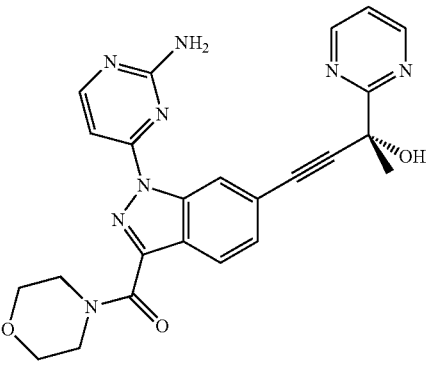 [SMILES: C[C@@](O)(C#Cc1ccc2c(C(=O)N3CCOCC3)nn(-c3ccnc(N)n3)c2c1)c1ncccn1]

Title compound prepared and purified according to procedure described for (2S)-4-[1-(2-aminoprimidin-4-yl)-3-[(morpholin-4-yl)carbonyl]-1H-indazol-6-yl]-2-(pyrimidin-2-yl)but-3-yn-2-ol (Example 74) to furnish the title compound as an off-white solid: $^1$H NMR (500 MHz, DMSO-d6) delta 1.86-2.00 (3H, m), 3.58-3.69 (2H, m), 3.69-3.82 (4H, m), 3.87-4.02 (2H, m), 6.17-6.31 (1H, m), 7.03-7.09 (1H, m), 7.10-7.27 (2H, m), 7.34-7.45 (1H, m), 7.47-7.58 (1H, m), 7.90-8.04 (1H, m), 8.27-8.41 (1H, m), 8.82-8.97 (3H, m); LC-MS: m/z=+471.05 (M+H)+.

Example 76

Preparation of (2R)-4-[1-(2-aminopyrimidin-4-yl)-3-[(4-fluoropiperidin-1-yl)carbonyl]-1H-indazol-6-yl]-2-(5-methyl-1,2,4-oxadiazol-3-yl)but-3-yn-2-ol mono-formate salt (76-b)

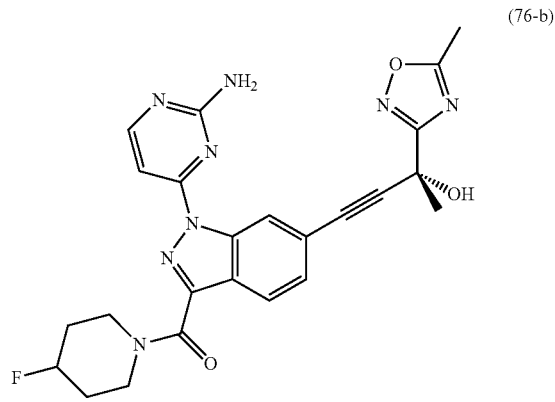 [SMILES: Cc1nc([C@](C)(O)C#Cc2ccc3c(C(=O)N4CCC(F)CC4)nn(-c4ccnc(N)n4)c3c2)no1]

Step 1—Synthesis of 1-(2-aminopyrimidin-4-yl)-6-[(3R)-3-hydroxy-3-(5-methyl-1,2,4-oxadiazol-3-yl)but-1-yn-1-yl]-1H-indazole-3-carboxylic acid

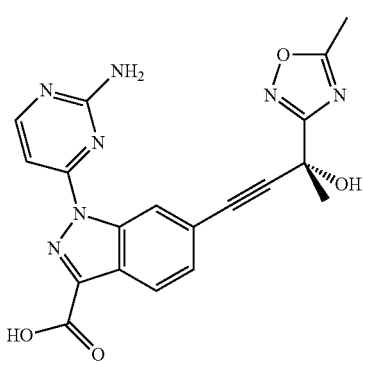

(76-a)

To a solution of 1-(2-aminopyrimidin-4-yl)-6-iodo-1H-indazole-3-carboxylic acid (150 mg, 0.39 mmol) in piperidine (1.5 mL) was introduced tetrakis(triphenylphosphine)palladium (0) (45.5 mg, 0.04 mmol), copper(I) iodide (7.4 mg, 0.04 mmol) and (2R)-2-(5-methyl-1,2,4-oxadiazol-3-yl)but-3-yn-2-ol (120 mg, 0.79 mmol). The reaction was warmed to 35° C. for 1 hr. After cooling to RT, the reaction mixture was concentrated in vacuo and the residue purified by silica gel flash column chromatography (eluent: DCM containing a 1-15% MeOH gradient followed by 85:15 DCM:7M ammonia in methanol). The partially purified product was suspended in 2M aqueous citric acid (3 mL) and extracted with 3:1 chloroform/isopropanol (5×5 mL). The combined extracts were dried (Na$_2$SO$_4$), filtered and concentrated in vacuo to furnish the title compound as a yellow-brown solid: $^1$H NMR (500 MHz, DMSO) delta 1.91 (3H, s), 2.64 (3H, s), 6.81 (1H, s), 7.27 (1H, d, J=5.9 Hz), 7.54 (1H, dd, J=8.4, 1.2 Hz), 7.80 (2H, s), 8.22 (1H, d, J=8.3 Hz), 8.42 (1H, d, J=6.0 Hz), 8.97 (1H, s), 13.92 (1H, s); LC-MS: m/z=+406.00 (M+H)+.

Step 2—Synthesis of (2R)-4-[1-(2-aminopyrimidin-4-yl)-3-[(4-fluoropiperidin-1-yl)carbonyl]-1H-indazol-6-yl]-2-(5-methyl-1,2,4-oxadiazol-3-yl)but-3-yn-2-ol mono-formate salt To a solution of 1-(2-aminopyrimidin-4-yl)-6-[(3R)-3-hydroxy-3-(5-methyl-1,2,4-oxadiazol-3-yl)but-1-yn-1-yl]-1H-indazole-3-carboxylic acid (50 mg, 0.12 mmol) in DMF (3 mL) was introduced O-(7-azabenzotriazol-1-yl)-N,N,N',N'-tetramethyluronium hexafluorophosphate (94 mg, 0.25 mmol), 4-fluoropiperidine hydrochloride (22 mg, 0.16 mmol) and triethylamine (0.05 mL, 0.37 mmol). After 30 minutes at RT, the reaction mixture was diluted with water (2 ml) and extracted with EtOAc (2×5 mL extractions). The combined organic extracts were washed with water (5 mL) and brine (5 ml), dried (Na$_2$SO$_4$), filtered and concentrated in vacuo. The residue was purified by silica gel flash column chromatography (DCM containing a 2-10% gradient of methanol). Further purification by reverse phase preparative HPLC furnished the title compound as a mono-formate salt: $^1$H NMR (500 MHz, CDCl$_3$) delta 2.20-1.67 (7H, m), 2.65 (3H, s), 3.78-3.64 (1H, m), 3.96-3.80 (1H, m), 4.25-4.06 (2H, m), 5.09-4.90 (1H, m), 6.42 (2H, s), 7.15 (1H, d, J=5.8 Hz), 7.37 (1H, d, J=8.4 Hz), 7.97 (1H, d, J=8.3 Hz), 8.30-8.12 (2H, m), 8.74 (1H, d, J=4.4 Hz); LC-MS: m/z=+491.10 (M+H)+.

Example 77

Preparation of 4-[1-(2-aminopyrimidin-4-yl)-3-({2-oxa-6-azaspiro[3.3]heptan-6-yl}carbonyl)-1H-indazol-6-yl]-2-(pyrimidin-2-yl)but-3-yn-2-ol

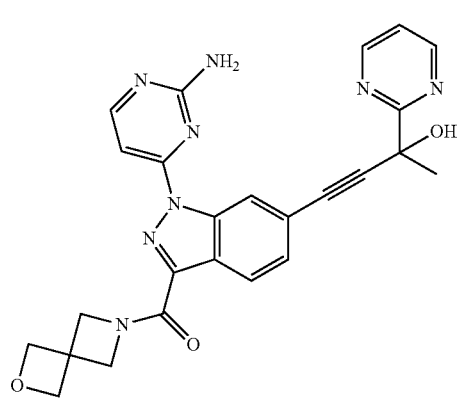

(77-b)

Step 1—Synthesis of 1-(2-aminopyrimidin-4-yl)-6-[3-hydroxy-3-(pyrimidin-2-yl)but-1-yn-1-yl]indazole-3-carboxylic acid

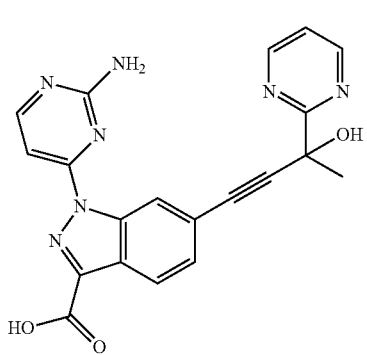

(77-a)

To a pressure tube containing 1-(2-aminopyrimidin-4-yl)-6-iodoindazole-3-carboxylic acid (550 mg, 1.44 mmol), copper(I) iodide (27.48 mg, 0.14 mmol), bis(triphenylphosphine)palladium(II) chloride (101.29 mg, 0.14 mmol) in triethylamine (4 mL) and THF (4 mL), was added 2-(pyrimidin-2-yl)but-3-yn-2-ol (427.62 mg, 2.89 mmol). The reaction was sealed and stirred at 55° C. for 1 hr. The reaction mixture was concentrated in vacuo and the crude product was purified by column chromatography (Biotage, 5-10% methanol in DCM followed by 10-20% [7M NH$_3$ in methanol] in DCM) to give the title intermediate as an orange/brown oil: $^1$H NMR (250 MHz, DMSO) delta 1.92 (3H, s), 6.27 (1H, s), 6.98 (3H, s), 7.09 (1H, d, J=5.5 Hz), 7.26 (1H, d, J=9.5 Hz), 7.50 (1H, t, J=4.9 Hz), 8.20-8.41 (3H, m), 8.73-9.02 (2H, m); LC-MS: m/z=+402.00 (M+H)+.

Step 2—Synthesis of 4-[1-(2-aminopyrimidin-4-yl)-3-({2-oxa-6-azaspiro[3.3]heptan-6-yl}carbonyl)-1H-indazol-6-yl]-2-(pyrimidin-2-yl)but-3-yn-2-ol To a solution of 1-(2-aminopyrimidin-4-yl)-6-[3-hydroxy-3-(pyrimidin-2-yl)but-1-yn-1-yl]indazole-3-carboxylic acid (100 mg, 0.25 mmol) in DMF (2 ml) was added HATU (189.46 mg, 0.5 mmol) followed by 2-oxa-6-azaspiro[3.3]heptane oxalate (94.26 mg, 0.5 mmol) and triethylamine (0.1 ml, 0.75 mmol). The reaction mixture was stirred at RT for 16 hr. Water (2 ml) was added to the reaction mixture and the product extracted into EtOAc (2×5 ml). The combined organics were washed with water (3 mL) and brine (3 mL) and concentrated in vacuo. The crude product was purified twice by flash chromatography (Biotage, 2-12% methanol in DCM) to give the title compound: $^1$H NMR (500 MHz, DMSO) delta 1.93 (3H, s), 4.31 (2H, s), 4.74 (4H, q, J=6.9 Hz), 4.87 (2H, s), 6.26 (1H, s), 7.02-7.32 (3H, m), 7.41 (1H, dd, J=8.4, 1.2 Hz), 7.51 (1H, t, J=4.9 Hz), 8.23 (1H, d, J=8.0 Hz), 8.39 (1H, d, J=5.5 Hz), 8.75-9.10 (3H, m); LC-MS: m/z=+483.10 (M+H)+.

Example 78

Examples in Table 9 were prepared by procedure described in Example 77-b by reacting 1-(2-aminopyrimidin-4-yl)-6-[3-hydroxy-3-(pyrimidin-2-yl)but-1-yn-1-yl]indazole-3-carboxylic acid with the appropriate amine

TABLE 9

| No. | Structure | Name | 1H NMR | MS (M + H) |
|---|---|---|---|---|
| T9-78.1 | 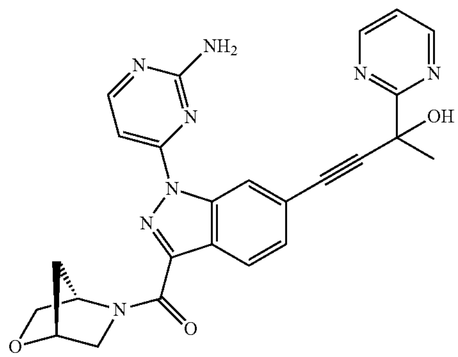 [SMILES: CC(O)(C#Cc1ccc2c(C(=O)N3C[C@@H]4C[C@H]3CO4)nn(-c3ccnc(N)n3)c2c1)c1ncccn1] | 4-[1-(2-aminopyrimidin-4-yl)-3-{[(1S,4S)-2-oxa-5-aza bicyclo[2.2.1]heptan-5-yl]carbonyl}-1H-indazol-6-yl]-2-(pyrimidin-2-yl)but-3-yn-2-ol | (500 MHz, DMSO) delta 1.81-2.02 (5H, m), 3.59 (1H, d, J = 10.7 Hz), 3.82 (1H, s), 3.90-3.95 (1H, m), 3.99 (1H, q, J = 11.2 Hz), 4.71 (1H, d, J = 6.8 Hz), 5.02- 5.59 (1H, m), 6.26 (1H, s), 7.10 (1H, dd, J = 20.8, 5.5 Hz), 7.16 (2H, s), 7.40(1H, ddd, J = 8.4, 2.8, 1.3 Hz), 7.51 (1H, t, J = 4.9 Hz), 8.10-8.30 (1H, m), 8.35 (1H, dd, J = 5.4, 3.7 Hz), 8.77-8.99 (3H, m) | 483.1 |
| T9-78.2 | 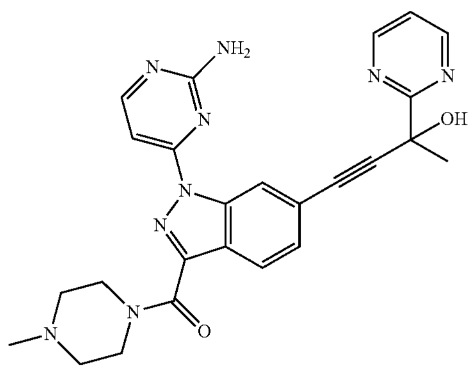 [SMILES: CN1CCN(C(=O)c2nn(-c3ccnc(N)n3)c3cc(C#CC(C)(O)c4ncccn4)ccc23)CC1] | 4-[1-(2-aminopyrimidin-4-yl)-3-[(4-methylpiperazin-1-yl)carbonyl]-1H-indazol-6-yl]-2-(pyrimidin-2-yl)but-3-yn-2-ol | (DMSO, 500 MHz) delta 1.93 (3H, s), 2.22 (3H, s), 2.37-2.44 (4H, m), 3.71-3.78 (2H, m), 3.80-3.88 (2H, m), 6.28 (1H, s), 7.06 (1H, d, J = 5.5 Hz), 7.15 (2H, s), 7.38 (1H, d, J = 9.6 Hz), 7.51 (1H, t, J = 4.9 Hz), 7.95 (1H, d, J = 8.4 Hz), 8.35 (1H, d, J = 5.5 Hz), 8.82-9.01 (3H, m) | 484.15 |
| T9-78.3 | 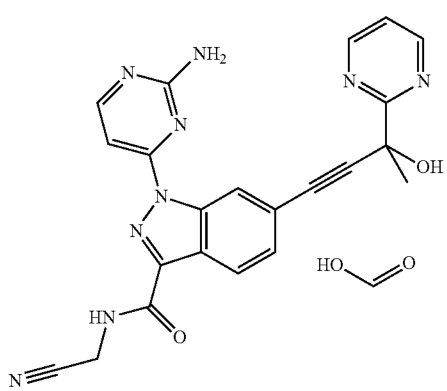 [SMILES: CC(O)(C#Cc1ccc2c(C(=O)NCC#N)nn(-c3ccnc(N)n3)c2c1)c1ncccn1 ; O=CO] | 1-(2-aminopyrimidin-4-yl)-N-(cyanomethyl)-6-[3-hydroxy-3-(pyrimidin-2-yl)but-1-yn-1-yl]-1H-indazole-3-carboxamide; formic acid | (DMSO, 500 MHz) delta 1.93 (3H, s), 4.41 (2H, d, J = 5.7 Hz), 6.28 (1H, s), 7.19 (2H, s), 7.31 (1H, d, J = 5.5 Hz), 7.44 (1H, dd, J = 8.4, 1.2 Hz), 7.51 (1H, t, J = 4.9 Hz), 8.24 (1H, d, J = 8.5 Hz), 8.42 (1H, d, J = 5.5 Hz), 8.71-9.06 (3H, m), 9.52 (1H, t, J = 5.7 Hz) | 440.05 |

TABLE 9-continued

| No. | Structure | Name | 1H NMR | MS (M + H) |
|---|---|---|---|---|
| T9-78.4 | 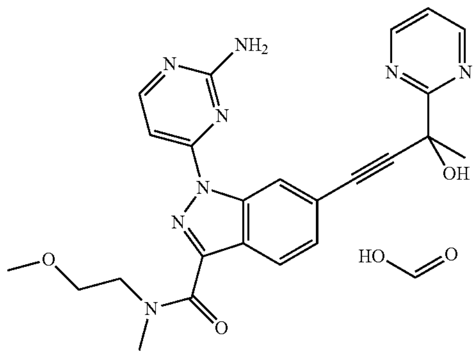 [SMILES: COCCN(C)C(=O)c1nn(-c2ccnc(N)n2)c2cc(C#CC(C)(O)c3ncccn3)ccc12 ; O=CO] | 1-(2-aminopyrimidin-4-yl)-6-[3-hydroxy-3-(pyrimidin-2-yl)but-1-yn-1-yl]-N-(2-methoxyethyl)-N-methyl-1H-indazole-3-carboxamide; formic acid | (DMSO, 250 MHz) delta 1.98 (3H, s), 3.23-3.33 (6H, m), 3.65 (2H, t, J = 5.7 Hz), 3.85 (2H, t, J = 5.6 Hz), 5.76 (1H, s), 6.73 (2H, s), 7.11 (1H, d, J = 5.5 Hz), 7.39 (1H, dd, J = 8.4, 1.3 Hz), 7.49 (1H, t, J = 4.9 Hz), 7.99 (1H, dd, J = 8.3, 0.7 Hz), 8.36 (1H, d, J = 5.5 Hz), 8.78-8.96 (3H, m) | 473.15 |
| T9-78.5 | 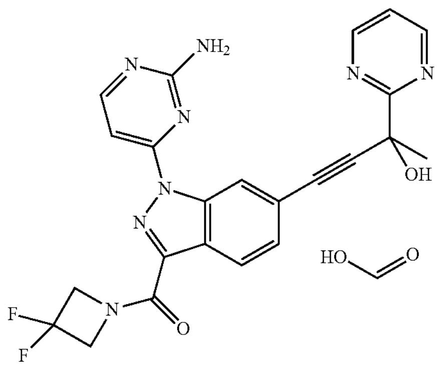 [SMILES: CC(O)(C#Cc1ccc2c(C(=O)N3CC(F)(F)C3)nn(-c3ccnc(N)n3)c2c1)c1ncccn1 ; O=CO] | 4-[1-(2-aminopyrimidin-4-yl)-3-[(3,3-difluoroazetidin-1-yl)carbonyl]-1H-indazol-6-yl]-2-(pyrimidin-2-yl)but-3-yn-2-ol; formic acid | (DMSO, 500 MHz) delta 1.92 (3H, s), 4.59 (2H, t, J = 12.2 Hz), 5.14 (2H, t, J = 12.3 Hz), 6.27 (1H, s), 7.10-7.29 (3H, m), 7.43 (1H, dd, J = 8.4, 1.2 Hz), 7.51 (1H, t, J = 4.9 Hz), 8.24 (1H, d, J = 8.6 Hz), 8.36 (1H, d, J = 5.5 Hz), 8.85-9.03 (3H, m) | 477.1 |
| T9-78.6 | 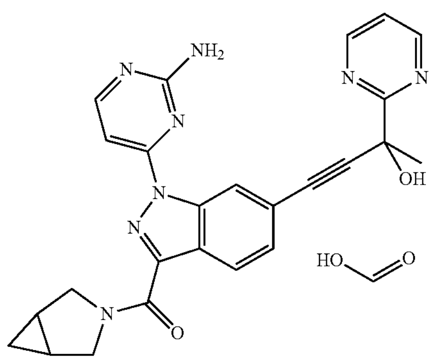 [SMILES: CC(O)(C#Cc1ccc2c(C(=O)N3CC4CC4C3)nn(-c3ccnc(N)n3)c2c1)c1ncccn1 ; O=CO] | 4-[1-(2-aminopyrimidin-4-yl)-3-({3-azabicyclo[3.1.0]hexan-3-yl}carbonyl)-1H-indazol-6-yl]-2-(pyrimidin-2-yl)but-3-yn-2-ol; formic acid | (DMSO, 500 MHz) delta 0.16 (1H, q, J = 4.2 Hz), 0.69-0.80 (1H, m), 1.58-1.67 (1H, m), 1.68-1.77 (1H, m), 1.92 (3H, s), 3.57 (1H, dd, J = 12.1, 4.4 Hz), 3.95 (1H, d, J = 12.2 Hz), 4.01 (1H, dd, J = 11.6, 4.3 Hz), 4.25 (1H, d, J = 11.5 Hz), 6.26 (1H, s), 7.04-7.23 (3H, m), 7.38 (1H, dd, J = 8.4, 1.3 Hz), 7.50 (1H, t, J = 4.9 Hz), 8.03-8.19 (1H, m), 8.36 (1H, d, J = 5.5 Hz), 8.90 (3H, d, J = 4.8 Hz) | 467.1 |
| T9-78.7 | 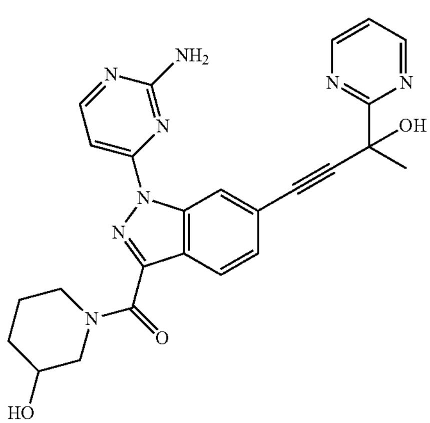 [SMILES: CC(O)(C#Cc1ccc2c(C(=O)N3CCCC(O)C3)nn(-c3ccnc(N)n3)c2c1)c1ncccn1] | 1-{[1-(2-aminopyrimidin-4-yl)-6-[3-hydroxy-3-(pyrimidin-2-yl)but-1-yn-1-yl]-1H-indazol-3-yl]carbonyl}piperidin-3-ol | (500 MHz, DMSO) delta 1.42-1.55 (2H, m), 1.73-1.89 (2H, m), 1.93 (3H, s), 2.96-3.06 (1H, m), 3.54-3.65 (1H, m), 3.86-4.31 (2H, m), 4.74-5.13 (1H, m), 6.28 (1H, s), 7.07 (1H, dd, J = 16.7, 5.5 Hz), 7.15 (2H, s), 7.38 (1H, dd, J = 8.4, 1.2 Hz), 7.52 (1H, t, J = 4.9 Hz), 7.93 (1H, d, J = 8.1 Hz), 8.35 (1H, d, J = 5.5 Hz), 8.74-9.20 (3H, m) | 485.1 |

TABLE 9-continued

| No. | Structure | Name | 1H NMR | MS (M + H) |
|---|---|---|---|---|
| T9-78.8 | 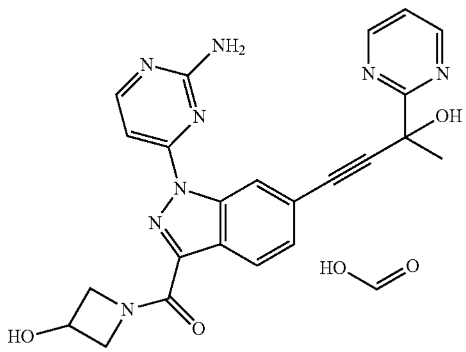 | 1-{[1-(2-aminopyrimidin-4-yl)-6-[3-hydroxy-3-(pyrimidin-2-yl)but-1-yn-1-yl]-1H-indazol-3-yl]carbonyl}azetidin-3-ol; formic acid | (500 MHz, DMSO) delta 1.93 (3H, s), 3.87 (1H, dd, J = 11.1, 3.4 Hz), 4.23-4.47 (2H, m), 4.53-4.66 (1H, m), 4.88 (1H, dd, J = 9.3, 6.9 Hz), 5.83 (1H, d, J = 6.4 Hz), 6.27 (1H, s), 7.04-7.22 (3H, m), 7.41 (1H, dd, J = 8.4, 1.2 Hz), 7.51 (1H, t, J = 4.9 Hz), 8.24 (1H, d, J = 8.3 Hz), 8.37 (1H, d, J = 5.5 Hz), 8.84-8.93 (3H, m) | 466.05 |
| T9-78.9 | 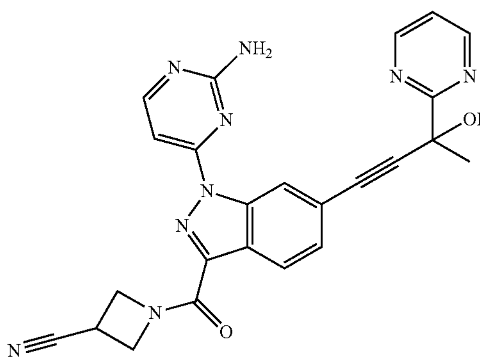 | 1-{[1-(2-aminopyrimidin-4-yl)-6-[3-hydroxy-3-(pyrimidin-2-yl)but-1-yn-1-yl]-1H-indazol-3-yl]carbonyl}azetidine-3-carbonitrile | (500 MHz, DMSO) delta 1.93 (3H, s), 3.88-4.01 (1H, m), 4.28-4.36 (1H, m), 4.44 (1H, t, J = 9.6 Hz), 4.86-4.94 (1H, m), 4.97 (1H, t, J = 9.4 Hz), 7.27 (1H, d, J = 5.7 Hz), 7.45 (1H, d, J = 8.4 Hz), 7.51 (1H, t, J = 4.9 Hz), 7.67 (2H, s), 8.24 (1H, d, J = 8.3 Hz), 8.38 (1H, d, J = 5.9 Hz), 8.75-9.00 (3H, m) | 457.1 |
| T9-78.10 | 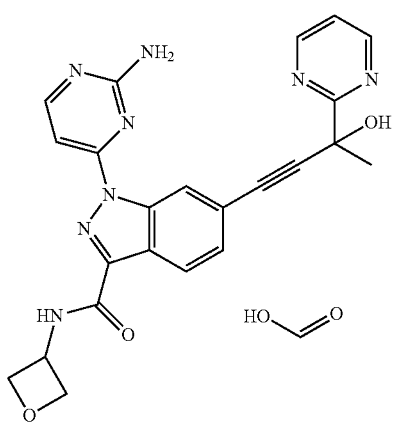 [SMILES: CC(O)(C#Cc1ccc2c(C(=O)NC3COC3)nn(-c3ccnc(N)n3)c2c1)c1ncccn1 ; O=CO] | 1-(2-aminopyrimidin-4-yl)-6-[3-hydroxy-3-(pyrimidin-2-yl)but-1-yn-1-yl]-N-(oxetan-3-yl)-1H-indazole-3-carboxamide; formic acid | (500 MHz, DMSO) delta 1.99 (3H, s), 4.77 (2H, t, J = 6.5 Hz), 4.87 (2H, t, J = 7.0 Hz), 5.19 (1H, q, J = 7.0 Hz), 7.42 (2H, s), 7.48 (1H, dd, J = 8.3, 1.2 Hz), 7.53 (1H, d, J = 5.6 Hz), 7.57 (1H, t, J = 4.8 Hz), 8.27 (1H, d, J = 8.3 Hz), 8.49 (1H, d, J = 5.7 Hz), 8.89-9.01 (3H, m), 9.57 (1H, d, J = 7.1 Hz) | 457.1 |

Example 79

Preparation of 1-(2-aminopyrimidin-4-yl)-6-{3-hydroxy-3-[5-(hydroxymethyl)-1,2-oxazol-3-yl]but-1-yn-1-yl}-N,N-dimethyl-1H-indazole-3-carboxamide (79-e)

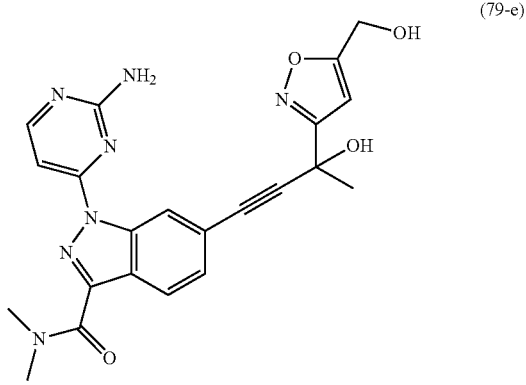 [SMILES: CN(C)C(=O)c1nn(-c2ccnc(N)n2)c2cc(C#CC(C)(O)c3cc(CO)on3)ccc12]

Step 1—Synthesis of 1-[5-(hydroxymethyl)-1,2-oxazol-3-yl]ethanone (79-a)

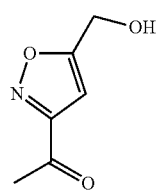

A mixture of 2-(prop-2-yn-1-yloxy)tetrahydro-2H-pyran (0.5 ml, 3.57 mmol) and iron(III) nitrate hydrate (0.86 ml, 3.57 mmol) in acetone (12 mL) was stirred at 55° C. for 15 hr. The reaction mixture was cooled, filtered through a pad of Celite® and EtOAc (50 mL) was added. The organics were then washed with saturated NaHCO$_3$ solution (2×5 mL), saturated brine solution (5 mL) and water (5 mL) and then dried (Na$_2$SO$_4$) and concentrated in vacuo. The crude product was purified by flash chromatography (Isolute, 0-60% EtOAc in heptane) to give the title intermediate: $^1$H NMR (250 MHz, CDCl$_3$) delta 2.63 (3H, s), 4.80 (2H, s), 6.60 (1H, s); LC-MS: m/z=+141.90 (M+H)+.

Step 2—Synthesis of 1-{5-[(oxan-2-yloxy)methyl]-1,2-oxazol-3-yl}ethanone (79-b)

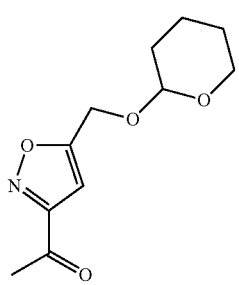

A solution of 1-[5-(hydroxymethyl)-1,2-oxazol-3-yl]ethanone (252 mg, 1.79 mmol), 3,4-dihydro-2H-pyran (0.24 ml, 2.68 mmol) and pyridinium 4-methylbenzenesulfonate (44.69 mg, 0.18 mmol) in DCM (10 mL) was stirred at RT for 16 hr and then for a further 0.5 hr at 40° C. after the addition of more 3,4-dihydro-2H-pyran (0.24 ml, 2.68 mmol) and pyridinium 4-methylbenzenesulfonate (44.69 mg, 0.18 mmol). The reaction mixture was diluted with water (5 ml) and the solution extracted with DCM (2×20 ml). The combined organic layers were washed with brine (5 ml), dried (Na$_2$SO$_4$), filtered and evaporated in vacuo. The crude product was purified by flash chromatography (Isolute, 9:1 heptane:EtOAc) to give the title intermediate: $^1$H NMR (500 MHz, CDCl$_3$) delta 1.56-1.53 (2H, m), 1.68-1.60 (2H, m), 1.89-1.69 (2H, m), 2.65 (3H, s), 3.62-3.51 (1H, m), 3.93-3.78 (1H, m), 4.68 (1H, d, J=13.9 Hz), 4.75 (1H, t, J=3.3 Hz), 4.86-4.80 (1 H, m), 6.63 (1H, s).

Step 3—Synthesis of 2-{5-[(oxan-2-yloxy)methyl]-1,2-oxazol-3-yl}but-3-yn-2-ol (79-c)

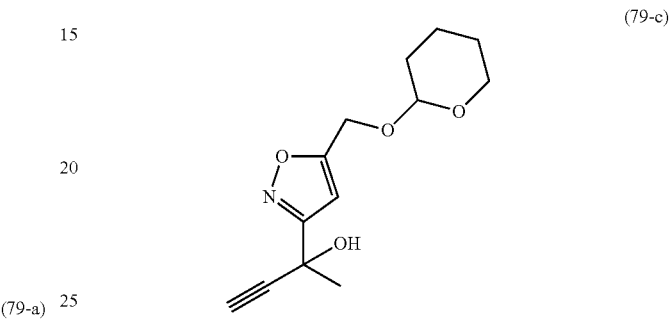

To a solution of ethynylmagnesium bromide (2.93 mL of a0.5M solution in THF, 1.47 mmol) at 0° C. was slowly added 1-{5-[(oxan-2-yloxy)methyl]-1,2-oxazol-3-yl}ethanone (220 mg, 0.98 mmol) in THF (5 mL). The reaction mixture was allowed to warm to RT and stirred for 45 minutes. The reaction mixture was quenched with aqueous saturated NH$_4$Cl solution (10 mL) and the organics were removed in vacuo. The product was extracted into EtOAc (20 ml×2) and the combined organics were dried (Na$_2$SO$_4$), filtered and concentrated in vacuo. The crude product was purified by flash chromatography (Isolute column, 10-30% EtOAc in heptanes) to give the title product as a pale yellow oil: $^1$H NMR (250 MHz, CDCl$_3$) delta 1.93-1.40 (9H, m), 2.66 (1H, s), 2.85 (1H, s), 3.69-3.46 (1H, m), 3.93-3.79 (1H, m), 4.94-4.54 (3H, m), 6.38 (1H, s); LC-MS: m/z=+251.95 (M+H)+.

Step 4—Synthesis of 1-(2-aminopyrimidin-4-yl)-6-(3-hydroxy-3-{5-[(oxan-2-yloxy)methyl]-1,2-oxazol-3-yl}but-1-yn-1-yl)-N,N-dimethylindazole-3-carboxamide (79-d)

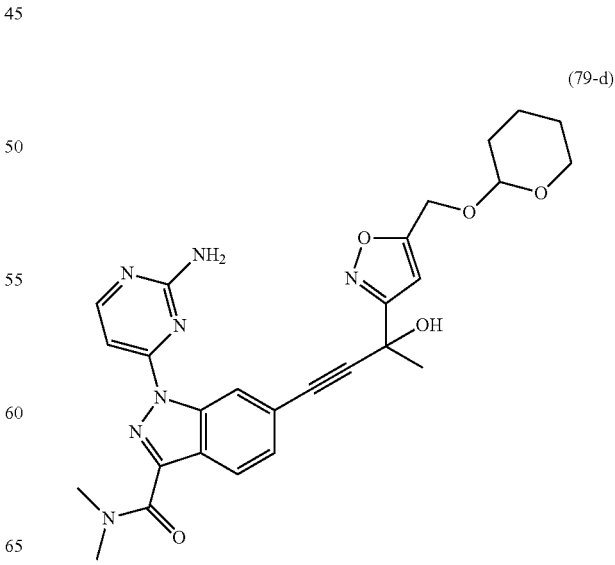

The title compound was prepared by procedure described in Example 61 step 3, by substituting 2-(1,3-thiazol-2-yl)but-3-yn-2-ol with 2-{5-[(oxan-2-yloxy)methyl]-1,2-oxazol-3-yl}but-3-yn-2-ol in Step 3. The title compound was isolated as brown solid: LC-MS: m/z=+532.10 (M+H)+. This compound of 79% purity LC-MS (UV) was used without further purification.

Step 5—Synthesis of 1-(2-aminopyrimidin-4-yl)-6-{3-hydroxy-3-[5-(hydroxymethyl)-1,2-oxazol-3-yl]but-1-yn-1-yl}-N,N-dimethyl-1H-indazole-3-carboxamide A solution of 1-(2-aminopyrimidin-4-yl)-6-(3-hydroxy-3-{5-[(oxan-2-yloxy)methyl]-1,2-oxazol-3-yl}but-1-yn-1-yl)-N,N-dimethylindazole-3-carboxamide (110 mg, 0.21 mmol) and pyridinium 4-methylbenzenesulfonate (5.18 mg, 0.2 mmol) in methanol (3 mL) was stirred at 60° C. for 1 hr, and then at RT for 3 days. Additional pyridinium 4-methylbenzenesulfonate was then added (20 mg, 0.8 mmol) and the reaction stirred at 55° C. for 1 hr. The reaction mixture was concentrated in vacuo and then saturated aqueous NaHCO$_3$ (3 ml) solution was added. The product was extracted into DCM (5 ml×2). The combined organics were washed with brine and dried (Na$_2$SO$_4$), filtered and concentrated in vacuo. The crude product was purified by flash chromatography (Isolute column). Elution with 3% methanol in DCM gave the title compound: $^1$H NMR (500 MHz, DMSO) delta 1.88 (3H, s), 3.12 (3H, s), 4.57 (2H, d, J 6.0), 5.67 (1H, t, J 6.1), 6.55 (1H, s), 6.66 (1H, s), 7.10 (1 H, d, J 5.5), 7.16 (2H, s), 7.43 (1H, d, J 8.4), 8.01 (1H, d, J 8.5), 8.35 (1H, d, J 5.5), 8.95 (1H, s); LC-MS m/z=+448.05 (M+H)+.

Example 80

Preparation of 1-(2-aminopyrimidin-4-yl)-6-[3-hydroxy-3-(pyrimidin-2-yl)but-1-yn-1-yl]-N,N-dimethyl-1H-indazole-3-carboxamide

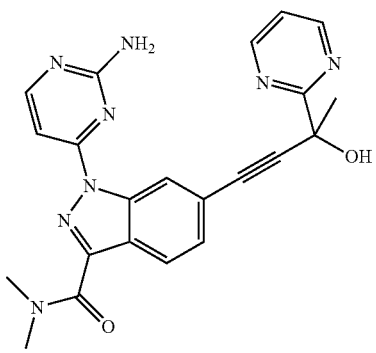
(80-c)

Step 1—Synthesis of 1-(2-aminopyrimidin-4-yl)-N,N-dimethyl-6-[2(trimethylsilyl)ethynyl]indazole-3-carboxamide

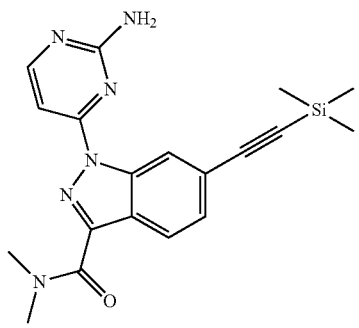
(80-a)

To a mixture of 1-(2-aminopyrimidin-4-yl)-6-bromo-N,N-dimethylindazole-3-carboxamide (61-b) (500 mg, 1.27 mmol), tetrakis(triphenylphosphine)palladium (118 mg, 0.102 mmol), copper(I) iodide (19.4 mg, 0.102 mmol) and ethynyl(trimethyl)silane 0.39 ml, 2.54 mmol) was added piperidine (3.1 mL). The mixture was purged with nitrogen for 2 minutes and then stirred at 65° C. for 4 hr. The reaction mixture was concentrated in vacuo, DCM (5 mL) was added and the concentration repeated (×2). The crude product was purified by flash chromatography (Biotage, 2-8% methanol in DCM) to give the title intermediate (250 mg): LC-MS: m/z=+379.45 (M+H)+.

Step 2—Synthesis of 1-(2-aminopyrimidin-4-yl)-6-ethynyl-N,N-dimethylindazole-3-carboxamide

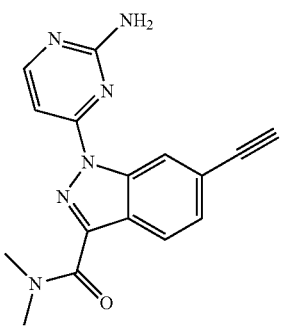
(80-b)

To a solution of 1-(2-aminopyrimidin-4-yl)-N,N-dimethyl-6-[2-(trimethylsilyl)ethynyl]indazole-3-carboxamide (250 mg, 0.66 mmol) in methanol (5 mL) and DCM (10 mL) was added K$_2$CO$_3$(182.57 mg, 1.32 mmol). The reaction mixture was stirred for 1 hr and then filtered by suction filtration. The precipitate was washed with DCM and methanol and the filtrate was concentrated in vacuo to give the title intermediate: $^1$H NMR (250 MHz, DMSO) delta 3.08 (3H, s), 3.29 (3H, br. s.), 4.42 (1H, s), 7.06 (1H, d, J=5.63 Hz), 7.14 (2H, br. s.), 7.41-7.48 (1H, m), 7.97 (1H, d, J=8.22 Hz), 8.31 (1H, d, J=5.48 Hz), 9.04 (1H, s); LC-MS: m/z=+307.00 (M+H)+.

Step 3—Synthesis of 1-(2-aminopyrimidin-4-yl)-6-[3-hydroxy-3-(pyrimidin-2-yl)but-1-yn-1-yl]-N,N-dimethyl-1H-indazole-3-carboxamide To a solution of 1-(2-aminopyrimidin-4-yl)-6-ethynyl-N,N-dimethylindazole-3-carboxamide (80 mg, 0.217 mmol) in THF (1.0 mL) at −78° C. under nitrogen was added 2M LDA in THF (0.27 mL, 0.54 mmol). After 5 minutes 1-pyrimidin-2-yl-ethanone (79 mg, 0.65 mmol) in THF (0.5 mL) was added and the reaction was allowed to warm to RT after 20 minutes. After a further 30 minutes the reaction mixture was quenched by addition of saturated aqueous NH$_4$Cl (0.5 mL). The volatiles were removed in vacuo and the mixture was diluted with DCM (10 ml) and washed with water (2 mL), dried (Na$_2$SO$_4$), filtered and concentrated in vacuo. The crude product was purified by flash chromatography (Biotage, 0-2% methanol in DCM). Trituration of the partially purified product from EtOAc-heptane gave the title compound: $^1$H NMR (250 MHz, MeOD) delta 1.93-2.02 (3H, m), 3.22 (3H, s), 3.41 (3H, s), 7.24 (1H, d, J=5.79 Hz), 7.40-7.55 (2H, m), 7.97 (1H, d, J=8.38 Hz), 8.29 (1H, d, J=5.79 Hz), 8.88 (2H, d, J=5.03 Hz), 9.12 (1H, s); LC-MS: m/z=+429.45 (M+H)+.

Example 81

Preparation of 1-(2-aminopyrimidin-4-yl)-6-[3-hydroxy-3-(1H-pyrazol-1-ylmethyl)but-1-yn-1-yl]-N,N-dimethyl-1H-indazole-3-carboxamide

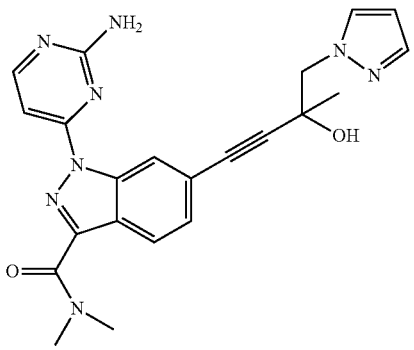 [SMILES: CN(C)C(=O)c1nn(-c2ccnc(N)n2)c2cc(C#CC(C)(O)Cn3cccn3)ccc12]

The title compound was prepared by procedure described for Example 80-c by substituting 1-pyrimidin-2-yl-ethanone with 1-pyrazol-1-yl-propan-2-one in Step 3: $^1$H NMR (500 MHz, MeOD) delta 1.54 (3H, s), 3.22 (3H, s), 3.40 (3H, s), 4.45 (2H, s), 6.35 (1H, t, J=2.13 Hz), 7.30 (1H, d, J=5.99 Hz), 7.41 (1H, dd, J=8.43, 1.18 Hz), 7.53 (1H, d, J=1.58 Hz), 7.80 (1H, d, J=2.05 Hz), 7.97 (1H, d, J=8.35 Hz), 8.29 (1H, d, J=5.99 Hz), 9.01 (1H, s); LC-MS: m/z=+431.05 (M+H)+.

Example 82

Preparation of 4-[1-(2-aminopyrimidin-4-yl)-3-[(morpholin-4-yl)carbonyl]-1H-indazol-6-yl]-2-(5-methyl-1,3,4-oxadiazol-2-yl)but-3-yn-2-ol (82-c)

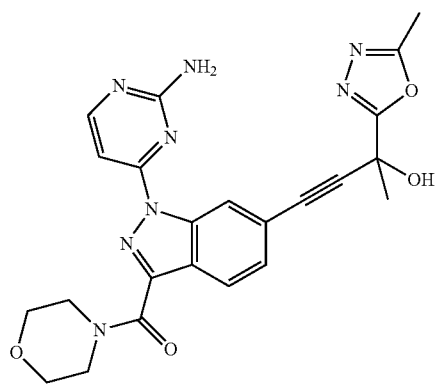

Step 1—Synthesis of 2-(5-methyl-1,3,4-oxadiazol-2-yl)-4-(trimethylsilyl)but-3-yn-2-ol (82-a)

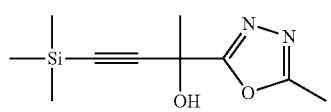

To a solution of isopropylmagnesium chloride lithium chloride complex (1.56 mL of a 1.3M solution in THF, 2.02 mmol) in dry THF (5 mL) at −15° C. under an atmosphere of nitrogen was introduced 2-bromo-5-methyl-1,3,4-oxadiazole (300 mg, 1.84 mmol). The reaction mixture was warmed to −10° C. for 30 minutes. A solution of 4-(trimethylsilyl)but-3-yn-2-one (0.37 ml, 2.21 mmol) in dry THF (5 mL) was added and the reaction mixture warmed to 0° C. for 1 hr. After further warming to RT for 30 minutes, the solution was cooled to 0° C. and saturated aqueous ammonium chloride (5 mL) introduced. The reaction mixture was extracted with DCM (3×10 mL extractions) and the combined organic extracts were dried (Na$_2$SO$_4$), filtered and concentrated in vacuo. Purification of the residue by flash chromatography (Biotage, heptane/EtOAc followed by an EtOAc/MeOH gradient) furnished the title compound as an orange oil: $^1$H NMR (500 MHz, CDCl$_3$) delta 0.18 (9H, s), 1.95 (3H, s), 2.57 (3H, s), 3.13 (1H, s); LC-MS: m/z=+224.95 (M+H)+.

Step 2—Synthesis of 4-[6-iodo-3-[(morpholin-4-yl)carbonyl]-1H-indazol-1-yl]pyrimidin-2-amine (82-b)

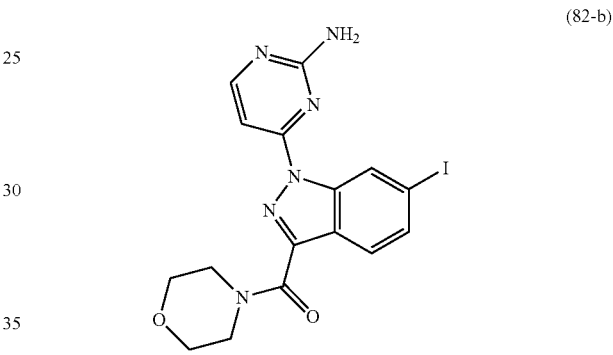

To a solution of 1-(2-aminopyrimidin-4-yl)-6-iodo-1H-indazole-3-carboxylic acid (3.00 g, 7.87 mmol) in dry DCM (40 mL) was introduced thionyl chloride (6.85 mL, 94.46 mmol) and DMF (3 drops, cat.). The reaction mixture was warmed to 50° C. for 1 hr. After cooling to RT, the reaction mixture was concentrated in vacuo. The residue was re-dissolved in dry DCM (20 mL) and concentrated in vacuo (twice). After suspending the residue in dry DCM (30 mL), the solution was cooled to 0° C. under an atmosphere of nitrogen, and morpholine (1.37 mL, 15.74 mmol) added dropwise. The reaction mixture was warmed to RT for 16 hr. Following dilution with DCM (25 mL), 2M aqueous sodium carbonate (35 mL) was introduced. The resulting precipitate was collected by filtration and washed on the filter with DCM (5 mL) and dried. After suspension of the precipitate in 3:1 water/acetonitrile (10 mL), the slurry was collected by filtration and washed on the filter with further 3:1 water/acetonitrile (2×1 mL washes). The filter cake was dried under vacuum to furnish the title compound as an off-white solid: $^1$H NMR (500 MHz, DMSO) delta 3.41-3.76 (6H, m), 3.85-3.97 (2H, m), 7.05 (1H, d, J=5.5 Hz), 7.18 (2H, s), 7.74 (1H, dd, J=8.4, 1.1 Hz), 7.80 (1H, d, J=8.4 Hz), 8.34 (1H, d, J=5.5 Hz), 9.33 (1H, s); LC-MS: m/z=+450.90 (M+H)+.

Step 3—Synthesis of 4-[1-(2-aminopyrimidin-4-yl)-3-[(morpholin-4-yl)carbonyl]-1H-indazol-6-yl]-2-(5-methyl-1,3,4-oxadiazol-2-yl)but-3-yn-2-ol To a solution of 4-6-iodo-3-[(morpholin-4-yl)carbonyl]-1H-indazol-1-yl)pyrimidin-2-amine (95 mg, 0.19 mmol) in dry THF (3 mL) under an atmosphere of nitrogen was introduced bis(triphenylphosphine)palladium(II) chloride (13.3 mg, 0.02 mmol), TBAF (0.23 mL of a 1M solution in THF, 0.23 mmol) and 2-(5-methyl-1,3,4-oxadiazol-2-yl)-4-(trimethylsilyl)but-3-yn-2-ol. The reaction mixture was warmed to 50° C. for 1.5 hr. After cooling to RT, the reaction mixture was diluted with saturated aqueous sodium bicarbonate solution (4 ml) and extracted with EtOAc (2×10 mL extractions). The combined extracts were washed with water (5×5 mL), brine (5 mL), dried (Na$_2$SO$_4$) and filtered. After concentration of the filtrate in vacuo, the residue was purified by flash chromatography (Biotage, DCM containing a 2-12% methanol gradient) to furnish the title compound as a pale brown solid: $^1$H NMR (500 MHz, DMSO) delta 1.98 (3H, s), 2.56 (3H, s), 3.61-3.78 (6H, m), 3.90-3.97 (2H, m), 7.08 (1H, d, J=5.5 Hz), 7.10 (1H, s), 7.17 (2H, s), 7.48 (1H, dd, J=8.4, 1.1 Hz), 8.05 (1H, d, J=8.4 Hz), 8.36 (1H, d, J=5.5 Hz), 9.00 (1H, s); LC-MS: m/z=+475.10 (M+H)+.

Example 83

Preparation of (2R)-4-[1-(2-aminopyrimidin-4-yl)-3-(2-hydroxypropan-2-yl)-1H-indazol-6-yl]-2-(5-methyl-1,2-oxazol-3-yl)but-3-yn-2-ol

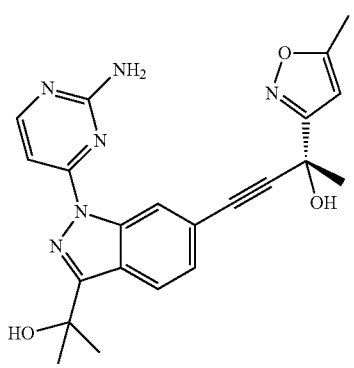

(83-d)

Step 1—Synthesis of methyl 6-bromo-1H-indazole-3-carboxylate

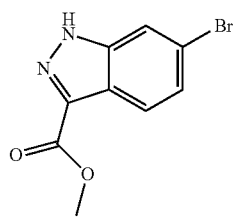

(83-a)

To a solution of 6-bromo-1H-indazole-3-carboxylic acid (1.5 g, 6.22 mmol) in methanol (25 mL) was added thionyl chloride (2.26 ml, 31.12 mmol). The mixture was heated at 60° C. for 1 hr. The reaction mixture was cooled and concentrated in vacuo. The crude residue was dissolved in EtOAc (30 mL) and washed with saturated aqueous NaHCO$_3$ (10 mL), water (10 mL) and dried (Na$_2$SO$_4$), filtered and concentrated in vacuo to give the title intermediate: $^1$H NMR (500 MHz, CDCl$_3$) delta 4.08 (3H, s), 7.44 (1H, d, J=8.6 Hz), 7.89 (1H, s), 8.09 (1H, d, J=8.7 Hz), 11.70 (1H, s); LC-MS: m/z=+254.85/256.75 (M+H)+.

Step 2—Synthesis of 2-(6-bromo-1H-indazol-3-yl)propan-2-ol

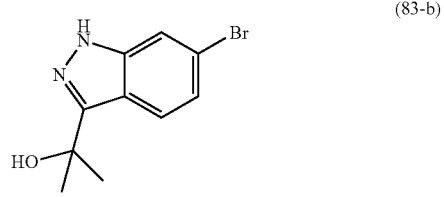

(83-b)

To a suspension of methyl 6-bromo-1H-indazole-3-carboxylate (500 mg, 1.96 mmol) at 0° C. in THF (15 mL) was added methylmagnesium bromide (1M in THF, 15.29 ml, 15.29 mmol) dropwise. The reaction mixture was stirred at RT for 15 hr. Saturated aqueous NH$_4$Cl solution (75 mL) was added and the product extracted into EtOAc (2×50 ml). The combined organics were washed with water (20 mL) and dried (Na$_2$SO$_4$), filtered and concentrated in vacuo. The crude product was purified by flash chromatography (Biotage, 20-100% EtOAc in heptanes) gave the title intermediate as a yellow solid: $^1$H NMR (500 MHz, CDCl$_3$) delta 1.75 (6H, s), 2.70 (1H, s), 7.28 (1 H, d, J=1.5 Hz), 7.63 (1H, d, J=1.0 Hz), 7.83 (1H, d, J=8.6 Hz), 9.82 (1H, s); LC-MS: m/z=+254.85/256.90 (M+H)+.

Step 3—Synthesis of 2-[1-(2-aminopyrimidin-4-yl)-6-bromoindazol-3-yl]propan-2-ol (83-c)

To a solution of 2-(6-bromo-1H-indazol-3-yl)propan-2-ol (317 mg, 1.24 mmol) in DMF (10 mL) was added NaH (60% oil dispersion, 79.5 mg, 1.99 mmol) at 0° C. The reaction mixture was stirred at RT for 20 minutes before addition of 4-chloropyrimidin-2-amine (321.95 mg, 2.49 mmol). The mixture was stirred at RT for 10 minutes and then at 65° C. for 23 hr. The reaction mixture was quenched by addition of water (10 mL) and EtOAc (2 mL) was added. The resultant precipitate was collected by suction filtration and then thoroughly dried under high vacuum and triturated from diethyl ether. The crude product was purified by flash chromatography (Biotage, 1-5% methanol in DCM) to give the title intermediate as a pale yellow solid: $^1$H NMR (500 MHz, DMSO) delta 1.63 (6 H, s), 5.59 (1H, s), 7.23-6.93 (3H, m), 7.49 (1H, dd, J=8.6, 1.5 Hz), 8.07 (1H, d, J=8.6 Hz), 8.27 (1H, d, J=5.5 Hz), 9.11 (1H, d, J=1.4 Hz); LC-MS m/z=+347.95/349.80 (M+H)+.

Step 4—Synthesis of (2R)-4-[1-(2-aminopyrimidin-4-yl)-3-(2-hydroxypropan-2-yl)-1H-indazol-6-yl]-2-(5-methyl-1,2-oxazol-3-yl)but-3-yn-2-ol To a pressure tube was added 2-[1-(2-aminopyrimidin-4-yl)-6-bromoindazol-3-yl]propan-2-ol followed by piperidine (2.5 mL), tetrakis(triphenylphosphine)palladium (102.88 mg, 0.09 mmol), copper(I) iodide (16.96 mg, 0.09 mmol) and (2R)-2-(5-methyl-1,2-oxazol-3-yl)but-3-yn-2-ol (269.16 mg, 1.78 mmol). The reaction was capped and stirred at 65° C. for 1.5 hr and then concentrated in vacuo. DCM (5 mL) was added to the reaction mixture and the concentration was repeated (×2). The crude product was purified by flash chromatography (Biotage, 1-10% methanol in DCM) gave the title compound: $^1$H NMR (500 MHz, DMSO) delta 1.63 (6H, s), 1.85 (3H, s), 2.41 (3H, s), 5.57 (1H, s), 6.41 (1H, s), 6.56 (1H, s), 7.00 (2H, s), 7.05 (1H, d, J=5.5 Hz), 7.33 (1H, dd, J=8.3, 1.2 Hz), 8.13 (1H, d, J=8.3 Hz), 8.27 (1H, d, J=5.2 Hz), 8.88 (1H, s); LC-MS: m/z=+419.10 (M+H)+.

Example 84

Preparation of (2R)-4-[1-(2-aminopyrimidin-4-yl)-3-(2-hydroxypropan-2-yl)-1H-indazol-6-yl]-2-(5-methyl-1,2,4-oxadiazol-3-yl)but-3-yn-2-ol

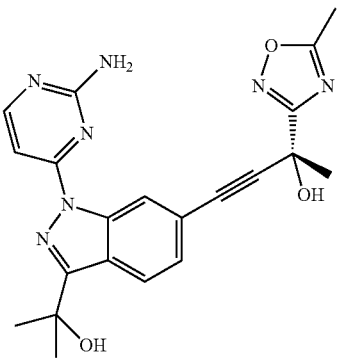 [SMILES: Cc1nc([C@](C)(O)C#Cc2ccc3c(C(C)(C)O)nn(-c4ccnc(N)n4)c3c2)no1]

The title compound was prepared by the procedure described in Example 83-d; $^1$H NMR (500 MHz, DMSO) delta 1.64 (6H, s), 1.90 (3H, s), 2.63 (3H, s), 5.58 (1H, s), 6.78 (1H, s), 7.01 (2 H, s), 7.05 (1H, d, J=5.5 Hz), 7.34 (1H, d, J=8.3 Hz), 8.27 (1H, d, J=5.5 Hz), 8.90 (1H, s); LC-MS: m/z=+420.

Example 85

The examples in Table 10 were prepared by procedure described in Example 83-d by reacting 2-(6-bromo-1H-indazol-3-yl)propan-2-ol with the appropriate but-3-yn-2-ol intermediates.

TABLE 10

| No. | Structure | Name | 1H NMR | MS (M + H) |
|---|---|---|---|---|
| T10-85.1 | 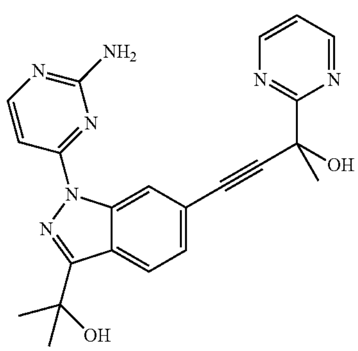 [SMILES: CC(C)(O)c1nn(-c2ccnc(N)n2)c2cc(C#CC(C)(O)c3ncccn3)ccc12] | 4-[1-(2-aminopyrimidin-4-yl)-3-(2-hydroxy propan-2-yl)-1H-indazol-6-yl]-2-(pyrimidin-2-yl)but-3-yn-2-ol | (500 MHz, DMSO) delta 8.91 (d, J = 4.89 Hz, 2 H) 8.85 (s, 1 H) 8.27 (d, J = 5.52 Hz, 1 H) 8.11 (d, J = 8.35 Hz, 1 H) 7.52 (t, J = 4.81 Hz, 1 H) 7.29 (d, J = 8.35 Hz, 1 H) 7.06 (d, J = 5.52 Hz, 1 H) 7.00 (br. s., 2 H) 6.24 (s, 1 H) 5.57 (s, 1H) 1.93 (s, 3 H) 1.64 (s, 6 H) | 416.05 |
| T10-85.2 | 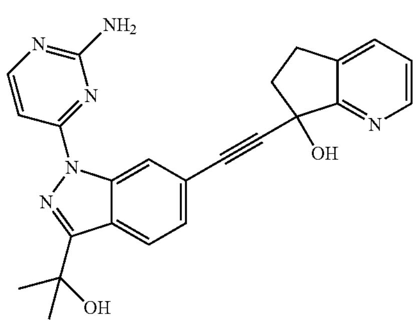 [SMILES: CC(C)(O)c1nn(-c2ccnc(N)n2)c2cc(C#CC3(O)CCc4cccnc43)ccc12] | 7-{2-[1-(2-aminopyrimidin-4-yl)-3-(2-hydroxypropan-2-yl)-1H-indazol-6-yl]ethynyl}-5H,6H,7H-cyclopenta[b]pyridin-7-ol | (500 MHz, DMSO) delta 1.63 (6 H, s), 2.36-2.46 (1 H, m), 2.60-2.70 (1 H, m), 2.96 (1 H, dd, J = 8.12, 4.81 Hz), 3.02 (1 H, t, J = 7.41 Hz), 5.56 (1H, s), 6.25 (1H, s), 6.98 (2 H, br. s.), 7.05 (1 H, d, J = 5.52 Hz), 7.26-7.37 (2 H, m), 7.75 (1H, d, J = 7.57 Hz), 8.12 (1 H, d, J = 8.35 Hz), 8.27 (1 H, d, J = 5.52 Hz), 8.46 (1 H, d, J = 4.26 Hz), 8.86 (1 H, s) | 427.15 |

Example 86

Preparation of 4-[1-(2-aminopyrimidin-4-yl)-3-(2-hydroxypropan-2-yl)-1H-indazol-6-yl]-2-(pyridin-2-yl)but-3-yn-2-ol

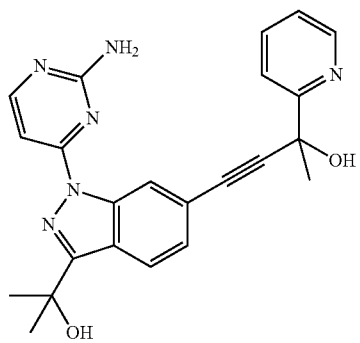
(86-d)

Step 1—Synthesis of methyl 6-iodo-1H-indazole-3-carboxylate

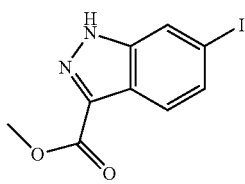
(86-a)

Preparation as described for methyl 6-bromo-1H-indazole-3-carboxylate: $^1$H NMR (500 MHz, MeOD) delta 4.03 (3H, s), 7.56 (1H, d, J=8.51 Hz), 7.91 (1H, d, J=8.51 Hz), 8.06 (1H, s); LC-MS: m/z=+302.85 (M+H)+.

Step 2—Synthesis of 2-(6-iodo-1H-indazol-3-yl)propan-2-ol

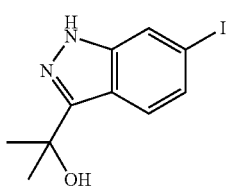
(86-b)

Preparation as described for 2-(6-bromo-1H-indazol-3-yl)propan-2-ol: $^1$H NMR (500 MHz, CDCl$_3$) delta 1.75 (6H, s), 2.69 (1H, s), 7.45 (1H, dd, J=8.51, 1.42 Hz), 7.72 (1H, d, J=8.51 Hz), 7.87 (1H, s), 9.74 (1H, br. s.); LC-MS: m/z=+ 302.85 (M+H)+.

Step 3—Synthesis of 2-[1-(2-aminopyrimidin-4-yl)-6-iodo-1H-indazol-3-yl]propan-2-ol

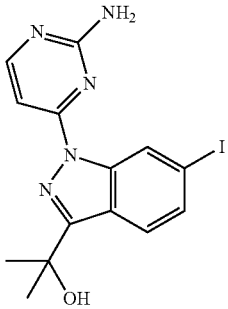
(86-c)

To a solution of 2-(6-iodo-1H-indazol-3-yl)propan-2-ol (1.00 g, 3.31 mmol) in dry DMF (30 mL) at 0° C. under an atmosphere of nitrogen was introduced sodium hydride (212 mg of a 60% dispersion in mineral oil, 5.3 mmol). After 20 minutes at this temperature, 4-chloropyrimidin-2-amine (858 mg, 6.62 mmol) was added and the solution warmed to RT for 10 minutes, then to 65° C. for 23 hr. The reaction mixture was cooled to RT, quenched carefully with water (20 mL) and extracted with EtOAc (2×20 mL extractions). The organic extracts were combined, dried (MgSO$_4$), filtered and concentrated in vacuo. Purification of the residue by silica gel flash column chromatography (4:1 to 1:1 heptane/EtOAc gradient) furnished the title compound as an off-white solid: $^1$H NMR (250 MHz, CDCl$_3$) delta 1.73-1.83 (6H, m), 2.77 (1H, s), 5.16 (2H, s), 7.23-7.33 (1H, m), 7.55-7.64 (1H, m), 7.68-7.78 (1H, m), 8.30 (1H, d, J=5.79 Hz), 9.15-9.28 (1 H, m); LC-MS: m/z=+395.90 (M+H)+.

Step 4—Synthesis of 4-[1-(2-aminopyrimidin-4-yl)-3-(2-hydroxypropan-2-yl)-1H-indazol-6-yl]-2-(pyridin-2-yl)but-3-yn-2-ol To a solution of 2-[1-(2-aminopyrimidin-4-yl)-6-iodo-1H-indazol-3-yl]propan-2-ol (150 mg, 0.36 mmol) in piperidine (2 mL) was introduced tetrakis(triphenylphosphine)palladium (0) (16.8 mg, 0.02 mmol), copper(I) iodide (2.8 mg, 0.02 mmol) and 2-(pyridin-2-yl)but-3-yn-2-ol (112 mg, 0.73 mmol). The reaction was warmed to 35° C. for 1 hr. After cooling to RT, the reaction mixture was concentrated in vacuo and the residue purified by flash chromatography (Biotage, DCM containing a 1-10% MeOH gradient) to furnish the title compound as a brown oil: $^1$H NMR (500 MHz, CDCl$_3$) delta 1.78 (6H, s), 1.94 (3H, s), 2.84 (1H, br. s.), 5.18 (2H, br. s.), 5.80 (1H, br. s.), 7.19-7.39 (1H, m), 7.74 (1H, d, J=7.88 Hz), 7.82 (1H, td, J=7.72, 1.58 Hz), 7.90 (1H, d, J=8.35 Hz), 8.29 (1H, d, J=5.36 Hz), 8.58 (1H, d, J=4.73 Hz), 8.89 (1 H, s); LCMS: m/z=+415.05 (M+H)+.

Example 87

Preparation of 4-[1-(2-aminopyrimidin-4-yl)-3-(2-hydroxypropan-2-yl)-1H-indazol-6-yl]-2-(1-methyl-1H-pyrazol-3-yl)but-3-yn-2-ol

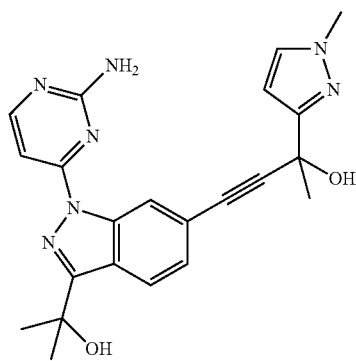

(87-b)

Step 1—Synthesis of 2-(1-methyl-1H-pyrazol-3-yl)-4-(trimethylsilyl)but-3-yn-2-ol

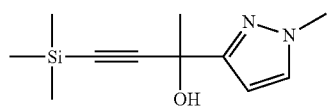

(87-a)

To a solution of 3-iodo-1-methyl-1H-pyrazole (378 mg, 1.82 mmol) in dry DCM (15 mL) at 0° C. under an atmosphere of nitrogen, was introduced ethylmagnesium bromide (2.0 mL of a 1.0M solution in THF, 2.0 mmol). After 30 minutes at 0° C., the reaction mixture was warmed to RT for 15 minutes, then introduced to a solution of 4-(trimethylsilyl)but-3-yn-2-one (0.37 ml, 2.18 mmol) in dry DCM (5 ml) at 0° C. under an atmosphere of nitrogen. The reaction mixture was warmed to RT for 16 hr. Following addition of saturated aqueous ammonium chloride (5 ml), the reaction mixture was extracted with DCM (3×5 mL extractions). The combined organic extracts were dried (Na$_2$SO$_4$), filtered and concentrated in vacuo. Purification of the residue by silica gel flash column chromatography (heptane/EtOAc gradient) furnished the title compound as an orange-brown oil: $^1$H NMR (500 MHz, CDCl$_3$) delta 0.15 (9H, d, J=3.5 Hz), 1.82 (3H, s), 3.18 (1H, s), 3.86 (3H, s), 6.28 (1H, d, J=2.2 Hz), 7.26 (1H, d, J=2.2 Hz); LC-MS: m/z=+222.95 (M+H)+.

Step 2—Synthesis of 4-[1-(2-aminopyrimidin-4-yl)-3-(2-hydroxypropan-2-yl)-1H-indazol-6-yl]-2-(1-methyl-1H-pyrazol-3-yl)but-3-yn-2-ol To a solution of 2-[1-(2-aminopyrimidin-4-yl)-6-iodo-1H-indazol-3-yl]propan-2-ol (135 mg, 0.31 mmol) in dry THF (4 mL) under an atmosphere of nitrogen was introduced bis(triphenylphosphine)palladium(II) chloride (21.6 mg, 0.03 mmol), TBAF (0.37 mL of a 1M solution in THF, 0.37 mmol) and 2-(1-methyl-1H-pyrazol-3-yl)-4-(trimethylsilyl)but-3-yn-2-ol (137 mg, 0.62 mmol). The reaction mixture was warmed to 50° C. for 1.5 hr. After cooling to RT, the reaction mixture was diluted with saturated aqueous sodium bicarbonate solution (4 ml) and extracted with EtOAc (2×10 mL extractions). The combined extracts were washed with water (5×5 mL), brine (5 mL), dried (Na$_2$SO$_4$) and filtered. After concentration of the filtrate in vacuo, the residue was purified by silica gel flash column chromatography (DCM containing a 1-10% methanol gradient) to furnish the title compound as an off-white solid: $^1$H NMR (DMSO, 500 MHz) delta 1.63 (6H, s), 1.83 (3H, s), 3.82 (3H, s), 5.57 (1H, s), 6.02 (1H, s), 6.36 (1H, d, J=2.1 Hz), 6.99 (2H, s), 7.05 (1H, d, J=5.5 Hz), 7.31 (1H, d, J=8.4 Hz), 7.61 (1H, d, J=2.0 Hz), 8.11 (1H, d, J=8.3 Hz), 8.27 (1H, d, J=5.5 Hz), 8.84 (1H, s); LC-MS: m/z=+418.10 (M+H)+.

Example 88

Preparation of (R)-4-[1-(2-Amino-pyrimidin-4-yl)-3-hydroxymethyl-1H-indazol-6-yl]-2-(5-methyl-isoxazol-3-yl)-but-3-yn-2-ol

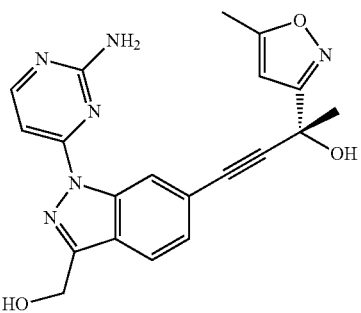 [SMILES: Cc1cc([C@](C)(O)C#Cc2ccc3c(CO)nn(-c4ccnc(N)n4)c3c2)no1]

The title compound was prepared under the same conditions as described for Example 83-d using (2R)-2-(5-methyl-1,2,4-oxadiazol-3-yl)but-3-yn-2-ol; $^1$H NMR (250 MHz, DMSO) delta 1.85 (3H, s), 2.41 (3H, s), 4.84 (2H, d, J=5.94 Hz), 5.47-5.66 (1H, m), 6.41 (1H, d, J=0.76 Hz), 6.57 (1 H, s), 7.04 (3H, d, J=5.63 Hz), 7.36 (1H, dd, J=8.22, 1.22 Hz), 7.96 (1H, d, J=8.22 Hz), 8.27 (1H, d, J=5.48 Hz), 8.88 (1H, s); LC-MS: m/z=+391.0 (M+H)+

Example 89

Preparation of (2R)-4-[1-(2-aminopyrimidin-4-yl)-3-(hydroxymethyl)-1H-indazol-6-yl]-2-(5-methyl-1,2,4-oxadiazol-3-yl)but-3-yn-2-ol

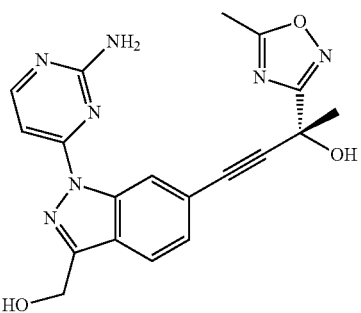 [SMILES: Cc1nc([C@](C)(O)C#Cc2ccc3c(CO)nn(-c4ccnc(N)n4)c3c2)no1]

The title compound was prepared under the same conditions as described for Example 83-d using (2R)-2-(5-methyl- 1,2,4-oxadiazol-3-yl)but-3-yn-2-ol; $^1$H NMR (500 MHz, MeOD) delta 1.98 (3H, s), 2.65 (3H, s), 4.97 (2H, s), 7.23 (1H, d, J=5.67 Hz), 7.40 (1H, dd, J=8.28, 1.18 Hz), 7.90 (1 H, d, J=8.20 Hz), 8.22 (1H, d, J=5.52 Hz), 9.03 (1H, s); LC-MS: m/z=+392.00 (M+H)+.

Example 90

Preparation of 4-[1-(2-aminopyrimidin-4-yl)-3-(hydroxymethyl)-1H-indazol-6-yl]-2-(pyrimidin-2-yl)but-3-yn-2-ol

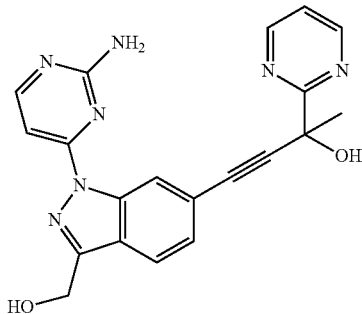 [SMILES: CC(O)(C#Cc1ccc2c(CO)nn(-c3ccnc(N)n3)c2c1)c1ncccn1]

The title compound was prepared under the same conditions as described for Example 83-d using 2-(pyrimidin-2-yl)but-3-yn-2-ol; $^1$H NMR (500 MHz, DMSO) delta 1.92 (3H, s), 4.79-4.88 (2H, m), 5.59 (1H, t, J=5.83 Hz), 6.26 (1H, s), 7.00 (2H, br. s.), 7.05 (1H, d, J=5.52 Hz), 7.32 (1H, dd, J=8.28, 1.18 Hz), 7.50 (1H, t, J=4.89 Hz), 7.94 (1H, d, J=11.98 Hz), 8.27 (1H, d, J=6.62 Hz), 8.82-8.86 (1H, m), 8.90 (2H, d, J=6.46 Hz); LC-MS: m/z=+388.05 (M+H)+.

Example 91

Preparation of (2R)-4-[1-(2-aminopyrimidin-4-yl)-3-(fluoromethyl)-1H-indazol-6-yl]-2-(5-methyl-1,2,4-oxadiazol-3-yl)but-3-yn-2-ol

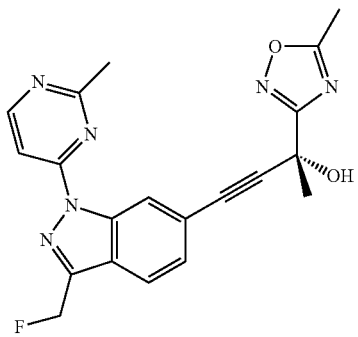

Step 1—Synthesis of ethyl 1-(2-aminopyrimidin-4-yl)-6-bromo-1H-indazole-3-carboxylate

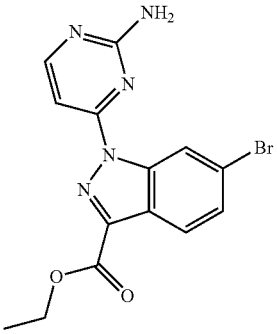

To a solution of 1-(2-aminopyrimidin-4-yl)-6-bromo-1H-indazole-3-carboxylic acid (2.00 g, 5.62 mmol) in dry DCM (10 mL) was introduced thionyl chloride (8.2 mL, 112.6 mmol) and DMF (0.1 mL, cat.). The solution was warmed to reflux for 18 hr under an atmosphere of nitrogen. After cooling to room temperature, the precipitous solution was filtered and the filter cake washed with DCM (5 mL). The washed precipitate was quickly introduced to ethanol (25 mL) at RT with rapid stirring for 3 hr. Following concentration of the reaction mixture in vacuo, the residue was suspended in sodium bicarbonate (20 mL of 1M aq NaHCO$_3$) and extracted with EtOAc (3×50 mL extractions). The combined organic extracts were washed with brine (20 mL), dried (Na$_2$SO$_4$), filtered and evaporated to furnish the crude title compound as a pale brown solid: $^1$H NMR (500 MHz, DMSO) delta 1.40 (3H, t, J=7.09 Hz), 4.46 (2H, q, J=7.09 Hz), 7.12 (1H, d, J=5.52 Hz), 7.24 (2H, br. s.), 7.66 (1H, dd, J=8.67, 1.58 Hz), 8.10 (1H, d, J=8.67 Hz), 8.38 (1H, d, J=5.52 Hz), 9.21 (1H, d, J=1.26 Hz); LC-MS: m/z=+361.95/363.80 (M+H)+. This compound, with LC-MS purity=64% UV, was used in the next step without further purification.

Step 2—Synthesis of [1-(2-aminopyrimidin-4-yl)-6-bromo-1H-indazol-3-yl]methanol

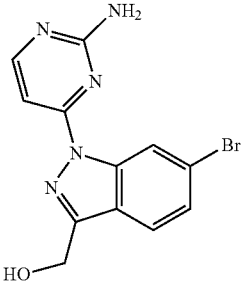

To a solution ethyl 1-(2-aminopyrimidin-4-yl)-6-bromo-1H-indazole-3-carboxylate (500 mg, 0.88 mmol) in dry THF (4 mL) at 0° C. under an atmosphere of nitrogen was introduced lithium aluminium hydride (3.5 mL of a 1M solution in THF, 3.50 mmol). After 10 minutes at this temperature, the reaction mixture was quenched by carefully transferring into a rapidly stirred saturated aqueous solution of Rochelle's salt (5 mL). The suspension was extracted with DCM (10 mL) and the organic extract filtered through a pad of Celite®. The filtrate was washed with water (5 mL) and brine (5 mL), dried (Na$_2$SO$_4$), filtered and the filtrate concentrated in vacuo to furnish the crude title compound as a colorless solid: $^1$H NMR (250 MHz, DMSO) delta 4.84 (2H, d, J=5.48 Hz), 5.61 (1H, t, J=5.71 Hz), 7.04 (3H, s), 7.51 (1H, dd, J=8.45, 1.75 Hz), 7.92 (1H, d, J=8.53 Hz), 8.28 (1H, d, J=5.48 Hz), 9.11 (1H, d, J=1.22 Hz); LC-MS: m/z=+319.90/321.80 (M+H)+. This compound, with LC-MS purity=76% UV, was used in the next step without further purification.

Step 3—Synthesis of 4-[6-bromo-3-(fluoromethyl)-1H-indazol-1-yl]pyrimidin-2-amine

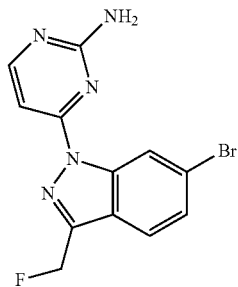 [SMILES: Nc1nccc(-n2nc(CF)c3ccc(Br)cc32)n1]

To a solution of [1-(2-aminopyrimidin-4-yl)-6-bromo-1H-indazol-3-yl]methanol (200 mg, 0.47 mmol) in dry DCM (10 mL) at RT under an atmosphere of nitrogen was introduced (diethylamino)sulphur trifluoride (0.08 mL, 0.63 mmol). After 16 hr at this temperature, the reaction mixture was treated with sodium bicarbonate (25 mL of saturated aq NaHCO$_3$) and extracted with DCM (2×20 mL extractions). The combined organic extracts were dried (Na$_2$SO$_4$), filtered and concentrated in vacuo. The residue was purified by column chromatography (Biotage, heptane/EtOAc gradient) to furnish the title compound as a colorless solid: $^1$H NMR (500 MHz, DMSO) delta 5.86 (2H, d, J=48.24 Hz), 7.06 (1H, d, J=5.04 Hz), 7.14 (2H, br. s.), 7.58 (1H, dd, J=8.04, 2.05 Hz), 7.92 (1H, d, J=8.98 Hz), 8.31 (1H, d, J=6.31 Hz), 9.17 (1H, d, J=1.42 Hz); LC-MS: m/z=+321.90/323.90 (M+H)+.

Step 4—Synthesis of (2R)-4-[1-(2-aminopyrimidin-4-yl)-3-(fluoromethyl)-1H-indazol-6-yl]-2-(5-methyl-1,2,4-oxadiazol-3-yl)but-3-yn-2-ol To a solution of 4-[6-bromo-3-(fluoromethyl)-1H-indazol-1-yl]pyrimidin-2-amine (70 mg, 0.21 mmol) in piperidine (2 mL) was introduced tetrakis(triphenylphosphine)palladium (0) (19 mg, 0.02 mmol), copper(I) iodide (3 mg, 0.02 mmol) and (2R)-2-(5-methyl-1,2,4-oxadiazol-3-yl)but-3-yn-2-ol (90 mg, 0.41 mmol). The reaction mixture was warmed to 66° C. for 2 hr, re-treated with (2R)-2-(5-methyl-1,2,4-oxadiazol-3-yl)but-3-yn-2-ol (45 mg, 0.20 mmol) and warming continued at 66° C. for a further 1 hr. Following cooling to RT, the reaction mixture was concentrated in vacuo, DCM (10 mL) was added and the solution re-evaporated to dryness in vacuo (re-evaporation process repeated twice). Purification of the residue by column chromatography (Biotage, DCM containing a 0-10% gradient of methanol) furnished a brown oil which was suspended in acetonitrile and concentrated in vacuo. The residue was slurried in diethyl ether (0.5 mL) to which was introduced acetonitrile until a fine cream precipitate resulted. Filtration furnished the title compound as a cream solid: $^1$H NMR (500 MHz, DMSO) delta 1.90 (3H, s), 2.62 (3H, s), 5.85 (2H, d, J=47.45 Hz), 6.82 (1H, s), 6.95-7.23 (3H, m), 7.43 (1H, dd, J=8.28, 1.18 Hz), 7.98 (1H, d, J=8.20 Hz), 8.33 (1H, d, J=5.36 Hz), 8.94 (1H, s); LC-MS: m/z=+394.00 (M+H)+.

Example 92

Preparation of 4-[1-(2-aminopyrimidin-4-yl)-3-(fluoromethyl)-1H-indazol-6-yl]-2-(pyrimidin-2-yl)but-3-yn-2-ol

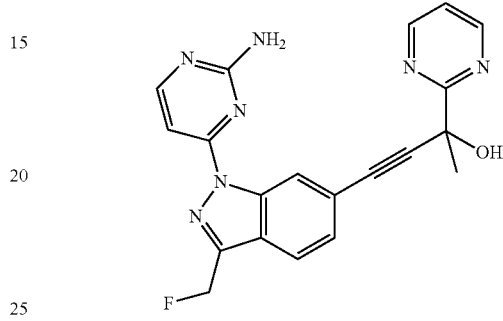

To a solution of 4-[6-bromo-3-(fluoromethyl)-1H-indazol-1-yl]pyrimidin-2-amine (49 mg, 0.12 mmol) in piperidine (2 mL) was introduced tetrakis(triphenylphosphine)palladium (0) (11.5 mg, 0.01 mmol), copper(I) iodide (1.9 mg, 0.01 mmol) and 2-(pyrimidin-2-yl)but-3-yn-2-ol (39 mg, 0.25 mmol). The reaction mixture was warmed to 66° C. for 2 hr. After cooling to RT, the reaction mixture was concentrated in vacuo, DCM (10 mL) was added and the solution re-evaporated to dryness in vacuo (re-evaporation process repeated twice). Purification of the residue by column chromatography (Biotage, DCM containing a 0-10% gradient of methanol) furnished a brown oil which was suspended in acetonitrile and concentrated in vacuo. The residue was re-suspended in acetonitrile (1 mL), whereupon a brown solid precipitated and was collected by filtration to furnish the title compound as a brown solid: $^1$H NMR (500 MHz, METHANOL-d4) delta 1.99 (3H, s), 5.75 (2H, d, J=47.92 Hz), 7.23 (1H, d, J=5.36 Hz), 7.42 (1H, dd, J=8.28, 1.02 Hz), 7.48 (1H, t, J=4.89 Hz), 7.85 (1H, d, J=8.20 Hz), 8.25 (1H, d, J=4.73 Hz), 8.88 (2H, d, J=4.89 Hz), 9.06 (1H, s); LC-MS: m/z=+390.05 (M+H)+.

Example 93

Preparation of (2R)-4-[1-(2-aminopyrimidin-4-yl)-3-(2-fluoropropan-2-yl)-1H-indazol-6-yl]-2-(5-methyl-1,2,4-oxa diazol-3-yl)but-3-yn-2-ol

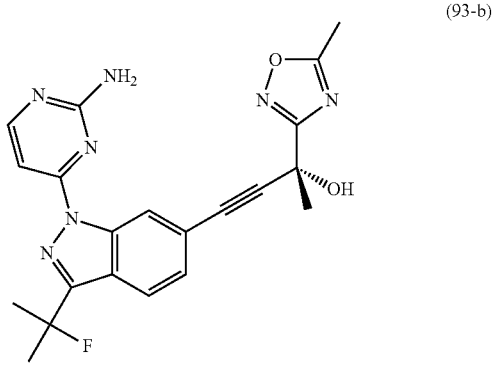 [SMILES: Cc1nc([C@](C)(O)C#Cc2ccc3c(C(C)(C)F)nn(-c4ccnc(N)n4)c3c2)no1]

(93-b)

Step 1—Synthesis of 4-[6-bromo-3-(2-fluoropropan-2-yl)-1H-indazol-1-yl]pyrimidin-2-amine (93-a)

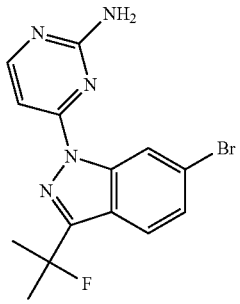

To a solution of 2-[1-(2-aminopyrimidin-4-yl)-6-bromo-1H-indazol-3-yl]propan-2-ol (200 mg, 0.57 mmol) in dry DCM (2 mL) at 0° C. under an atmosphere of nitrogen was introduced (diethylamino)sulphur trifluoride (0.14 mL, 1.15 mmol). The reaction was left to warm to RT for 1 hr. Following addition of sodium bicarbonate (5 mL of a saturated aqueous solution), the reaction mixture was washed with DCM (2×5 mL), and the combined organic extracts dried ($Na_2SO_4$), filtered and concentrated in vacuo. The residue was purified by flash chromatography (Biotage, eluent heptane:EtOAc [0-100%] gradient) to furnish the title compound as a yellow solid: $^1$H NMR (500 MHz, $CDCl_3$) delta 1.81-1.97 (6H, m), 5.18 (2H, br. s.), 7.28 (1H, s), 7.40-7.50 (1H, m), 7.78-7.92 (1H, m), 8.32 (1H, d, J=5.67 Hz), 9.01 (1H, d, J=1.10 Hz); LC-MS: m/z=+349.95/351.80 (M+H)+.

Step 2—Synthesis of (2R)-4-[1-(2-aminopyrimidin-4-yl)-3-(2-fluoropropan-2-yl)-1H-indazol-6-yl]-2-(5-methyl-1,2,4-oxa diazol-3-yl)but-3-yn-2-ol To a solution of 4-[6-bromo-3-(2-fluoropropan-2-yl)-1H-indazol-1-yl]pyrimidin-2-amine (95 mg, 0.26 mmol) in piperidine (1 mL) was introduced tetrakis(triphenylphosphine)palladium (0) (24 mg, 0.02 mmol), copper(I) iodide (4 mg, 0.02 mmol) and (2R)-2-(5-methyl-1,2,4-oxadiazol-3-yl)but-3-yn-2-ol (79 mg, 0.52 mmol). The reaction mixture was warmed to 66° C. for 2 hr. After cooling to RT, the reaction mixture was concentrated in vacuo and the residue purified by flash chromatography (Biotage, eluent:DCM containing a 1-10% MeOH gradient). Further purification by reverse phase preparative HPLC furnished the title compound as an orange solid: $^1$H NMR (500 MHz, DMSO) delta 1.76-2.00 (9H, m), 2.62 (3H, s), 6.82 (1H, s), 6.95-7.15 (3H, m), 7.39 (1H, d, J=9.93 Hz), 7.95 (1H, d, J=9.93 Hz), 8.33 (1H, br. s.), 8.94 (1H, s); LC-MS: m/z=+422.05 (M+H)+.

Example 94

Preparation of (2R)-4-[1-(2-aminopyrimidin-4-yl)-3-(3,3-difluoro-2-hydroxy-2-methylpropyl)-1H-indazol-6-yl]-2-(5-methyl-1,2,4-oxadiazol-3-yl)but-3-yn-2-ol (94-b)

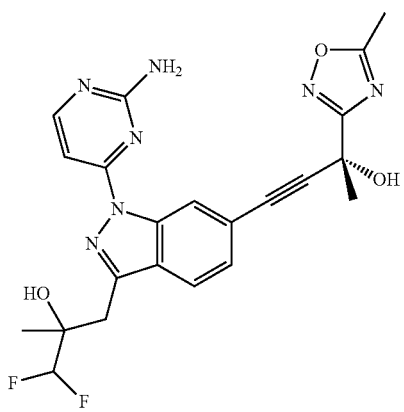

Step 1—Synthesis of 3-[1-(2-aminopyrimidin-4-yl)-6-bromo-1H-indazol-3-yl]-1,1-difluoro-2-methylpropan-2-ol (94-a)

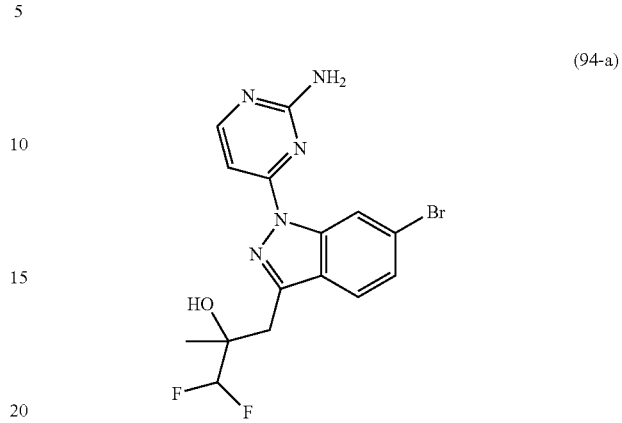

To a solution of 4-(6-bromo-3-methyl-1H-indazol-1-yl)pyrimidin-2-amine (500 mg, 1.64 mmol) in dry THF (5 mL) at −78° C. under an atmosphere of nitrogen, was introduced lithium diisopropylamide (2.1 mL of a 2M solution in THF, 4.11 mmol). After 5 minutes, a solution of 1,1-difluoropropan-2-one (0.4 mL, 4.93 mmol) in dry THF (2 mL) was added. The reaction mixture was warmed to RT after 20 minutes at −78° C. After 30 minutes at RT, the reaction mixture was quenched (5 mL of sat. aq. ammonium chloride) and concentrated in vacuo. The residue was diluted with DCM (10 mL), washed with water (2 mL) and the organic extract dried ($Na_2SO_4$), filtered and concentrated in vacuo. Purification of the residue by flash chromatography (Biotage, elution with DCM containing a 1-12% gradient of MeOH) furnished the title compound as a yellow solid: $^1$H NMR (500 MHz, $CDCl_3$) delta 1.36 (3H, s), 3.19 (1H, d, J=15.1 Hz), 3.34 (1H, d, J=14.9 Hz), 3.40 (1H, s), 5.17 (2H, s), 5.67 (1H, t, J=56.3 Hz), 7.24 (1H, d, J=8.5, 1.5 Hz), 7.45 (1H, dd, J=8.5, 1.5 Hz), 7.61 (1H, d, J=8.5 Hz), 8.32 (1H, d, J=5.6 Hz), 9.00 (1H, d, J=1.4 Hz); LC-MS: m/z=+397.90/399.90 (M+H)+.

Step 2—Synthesis of (2R)-4-[1-(2-aminopyrimidin-4-yl)-3-(3,3-difluoro-2-hydroxy-2-methylpropyl)-1H-indazol-6-yl]-2-(5-methyl-1,2,4-oxadiazol-3-yl)but-3-yn-2-ol To a solution of 3-[1-(2-aminopyrimidin-4-yl)-6-bromo-1H-indazol-3-yl]-1,1-difluoro-2-methylpropan-2-ol (75 mg, 0.19 mmol) in piperidine (1 mL) was introduced tetrakis(triphenylphosphine)palladium (0) (21.7 mg, 0.02 mmol), copper(I) iodide (3.6 mg, 0.02 mmol) and (2R)-2-(5-methyl-1,2,4-oxadiazol-3-yl)but-3-yn-2-ol (57 mg, 0.38 mmol). The reaction mixture was warmed to 65° C. for 1.5 hr under an atmosphere of nitrogen. After cooling to RT, the reaction mixture was re-treated with additional tetrakis(triphenylphosphine)palladium (0) (21.7 mg, 0.02 mmol), copper (I) iodide (3.6 mg, 0.02 mmol) and (2R)-2-(5-methyl-1,2,4-oxadiazol-3-yl)but-3-yn-2-ol (57 mg, 0.38 mmol). The reaction mixture was warmed to 65° C. for a further 3 hr. After cooling to RT, the reaction mixture was concentrated in vacuo. Purification of the residue by flash chromatography (Biotage, eluent 9:1 DCM/MeOH) furnished a partially purified product. Further purification by reverse phase preparative HPLC gave the title compound as a brown solid: $^1$H NMR (500 MHz, DMSO) delta 1.17 (3H, s), 1.90 (3H, s), 2.63 (3H, s), 3.09 (1H, d, J 14.2), 3.21 (1H, d, J 14.2), 5.50 (1H, s), 5.92 (1H, t, J 56.1), 6.78 (1H, s), 7.01 (2H, s), 7.08 (1H, d, J 5.5), 7.36 (1H, dd, J 8.3, 1.2), 7.94 (1H, d, J 8.3), 8.29 (1H, d, J 5.5), 8.89 (1H, s); LC-MS: m/z=+470.05 (M+H)+.

Example 95

Preparation of (2R)-4-[1-(2-aminopyrimidin-4-yl)-5-fluoro-3-methyl-1H-indazol-6-yl]-2-(1,3-thiazol-2-yl)but-3-yn-2-ol

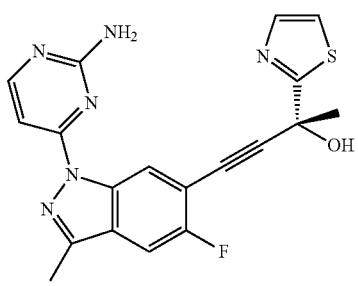

(95-e)

Step 1—Synthesis of 1-(4-bromo-2,5-difluorophenyl)ethanone

(95-a)

To a stirred mixture of 2-bromo-1,4-difluorobenzene (3.24 g, 16.81 mmol) and aluminium chloride (5.82 g, 43.7 mmol) at 60° C. under nitrogen was added dropwise acetyl chloride (1.98 g, 25.28 mmol 1). The mixture was stirred at 95° C. for 1.5 hr and then poured into ice (50 mL). To the mixture was added HCl (3 mL) followed by extraction into ether (20 mL×2). The ether extracts were washed with brine (20 mL) and then concentrated under reduced pressure to obtain the desired crude product (brown oil) as mixture with starting material (55:45) (2.67 g, 33%); 1H NMR (250 MHz, CHLOROFORM-d) delta 2.64 (3H, d, J=5.18 Hz), 7.42 (1H, dd, J=9.44, 5.18 Hz), 7.65 (1H, dd, J=8.45, 6.17 Hz).

Step 2—Synthesis of (E)-[1-(4-bromo-2,5-difluorophenyl)ethylidene]hydrazine

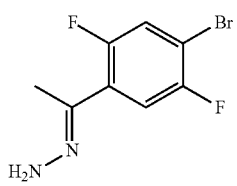

(95-b)

1-(4-bromo-2,5-difluorophenyl)ethanone (500 mg, 1.042 mmol) was dissolved in ethanol (10 mL), then hydrazine hydrate (57.4 mg, 1.147 mmol) added and stirred at RT for 16 hr. A pale yellow solid was filtered off and the filtrate was concentrated under reduced pressure to obtain the crude title compound as a brown-yellow solid (249 mg, 54% yield); 1H NMR (500 MHz, CHLOROFORM-d)delta 2.13 (3H, d, J=2.99 Hz), 7.28 (1H, dd, J=9.85, 5.60 Hz), 7.34 (1H, dd, J=9.14, 6.62 Hz).

Step 3—Synthesis of 6-bromo-5-fluoro-3-methyl-1H-indazole

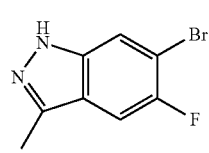

(95-c)

A solution of (E)-[1-(4-bromo-2,5-difluorophenyl)ethylidene]hydrazine in ethylene glycol (3 mL) was heated at 165° C. for 3 hours in a sealed tube. The mixture was cooled to RT and saturated NaHCO₃ was added (3 mL) and stirred for 10 minutes. The mixture was filtered and solid was washed with water (5 mL×2) to obtain the desired product brown solid (163 mg, 62%).
¹H NMR (500 MHz, METHANOL-d4) delta 2.51-2.55 (3H, m), 7.52 (1H, d, J=9.30 Hz), 7.75 (1H, d, J=5.52 Hz), 7.72-7.78 (1H, m). LC-MS: m/z: +229, 231 (M+H)+.

Step 4—Synthesis of 4-(6-bromo-5-fluoro-3-methylindazol-1-yl)pyrimidin-2-amine

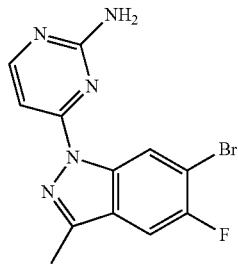

(95-d)

To a solution of 6-bromo-5-fluoro-3-methyl-1H-indazole (130 mg, 0.284 mmol, 50% purity) in DMF (2 ml) was added NaH (60% oil dispersion, 18.16 mg, 0.454 mmol) at 0° C. The reaction mixture stirred for 15 minutes before the slow addition of a solution of 4-chloropyrimidin-2-amine (73.53 mg, 0.568 mmol) in DMF (2 mL). The resulting mixture was stirred at 60° C. for 16 hr. The reaction mixture was cooled and partitioned between water (15 ml) and EtOAc (15 ml). A precipitate formed and was collected by suction filtration. The filtrate was concentrated in vacuo and purified by flash chromatography (Isolute column, 1-2% methanol in DCM) to give the title intermediate as a yellow oil: ¹H NMR (500 MHz, DMSO) delta 2.56 (3H, s), 7.00 (1H, s), 7.04-7.14 (2H, m), 7.92 (1H, d, J=8.35 Hz), 8.26 (1H, d, J=5.52 Hz), 9.22 (1H, d, J=5.99 Hz); LC-MS: m/z=+321.90, 323.80 (M+H)+.

Step 5—Synthesis of (2R)-4-[1-(2-aminopyrimidin-4-yl)-5-fluoro-3-methyl-1H-indazol-6-yl]-2-(1,3-thiazol-2-yl)but-3-yn-2-ol The title compound was prepared by the procedure described in Example 2-b by reacting 4-(6-bromo-5-fluoro-3-methylindazol-1-yl)pyrimidin-2-amine with (2R)-2-(1,3- thiazol-2-yl)but-3-yn-2-ol: $^1$H NMR (500 MHz, DMSO) delta 1.96 (3H, s), 2.55 (3H, s), 7.02 (3H, s), 7.15 (1H, br. s), 7.71 (1H, d, J=3.15 Hz), 7.79 (1H, s), 7.82 (1H, d, J=8.83 Hz), 8.26 (1H, d, J=5.52 Hz), 8.92 (1H, d, J=6.46 Hz); LC-MS m/z=+395.35 (M+H)+.

Example 96

Preparation of 4-[1-(2-amino-6-chloropyrimidin-4-yl)-3-[(morpholin-4-yl)carbonyl]-1H-indazol-6-yl]-2-(pyrimidin-2-yl)but-3-yn-2-ol mono formate salt

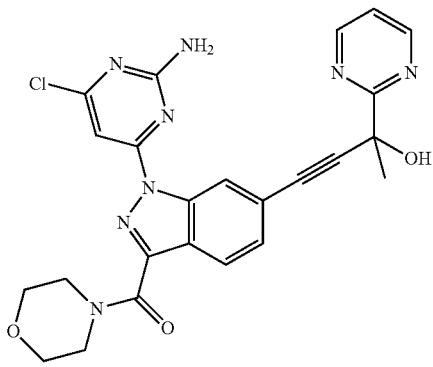

(96-c)

Step 1—Synthesis of 1-(2-amino-6-chloropyrimidin-4-yl)-6-iodo-1H-indazole-3-carboxylic acid (96-a)

To a solution of 6-iodo-1H-indazole-3-carboxylic acid (3.00 g, 10.42 mmol) in dry DMF (50 mL) at 0° C. under an atmosphere of nitrogen was introduced sodium hydride (1.25 g of a 60% dispersion in mineral oil, 31.25 mmol). The reaction mixture was warmed to RT for 15 mins. 4,6-Dichloropyrimidin-2-amine (2.56 g, 15.62 mmol) was then added, and the solution warmed to 60° C. for 18 hr. After cooling to 0° C., the reaction was carefully quenched with water (50 mL) and acidified by addition of 0.5M aqueous citric acid. The resulting precipitate was collected by filtration, washed on the filter with 1:1 methanol/EtOAc and dried under vacuum to furnish the title compound as a beige solid: LC-MS: m/z=+ 415.85/417.90 (M+H)+. This compound, with LC-MS purity=70% UV, was used in the next step without further purification.

Step 2—Synthesis of 1-(2-amino-6-chloropyrimidin-4-yl)-6-[3-hydroxy-3-(pyrimidin-2-yl)but-1-yn-1-yl]-1H-indazole-3-carboxylic acid

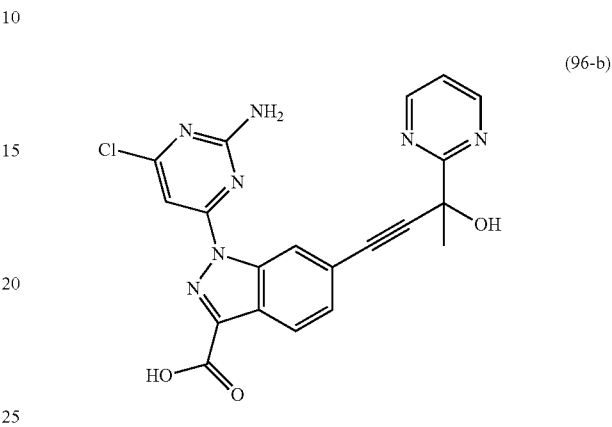

(96-b)

To a solution of 1-(2-amino-6-chloropyrimidin-4-yl)-6-iodo-1H-indazole-3-carboxylic acid (750 mg, 1.81 mmol) in 1:1 triethylamine/dry THF (12 mL) was introduced bis(triphenylphosphine)palladium(II) chloride (127 mg, 0.18 mmol), copper(I) iodide (34 mg, 0.18 mmol) and 2-(pyrimidin-2-yl)but-3-yn-2-ol (535 mg, 3.61 mmol). The reaction mixture was warmed to 55° C. for 1 hr. After cooling to RT, the reaction mixture was concentrated in vacuo to furnish the crude title compound: $^1$H NMR (500 MHz, DMSO) delta 1.92 (3H, s), 6.26 (1H, s), 7.09 (1H, s), 7.39 (1H, d, J=8.2 Hz), 7.51 (1H, t, J=4.9 Hz), 8.23 (1H, d, J=8.6 Hz), 8.82 (1H, s), 8.90 (2H, d, J=4.9 Hz); LC-MS: m/z=+436.05/437.70 (M+H)+. This compound, with LC-MS purity=91% UV, was used in the next step without further purification.

Step 3—Synthesis of 4-[1-(2-amino-6-chloropyrimidin-4-yl)-3-[(morpholin-4-yl)carbonyl]-1H-indazol-6-yl]-2-(pyrimidin-2-yl)but-3-yn-2-ol mono formate salt To a solution of 1-(2-amino-6-chloropyrimidin-4-yl)-6-[3-hydroxy-3-(pyrimidin-2-yl)but-1-yn-1-yl]-1H-indazole-3-carboxylic acid (250 mg, 0.51 mmol) in DMF (5 mL) was introduced O-(7-azabenzotriazol-1-yl)-N,N,N',N'-tetramethyluronium hexafluorophosphate (262 mg, 0.69 mmol), morpholine (60 mg, 0.69 mmol) and triethylamine (0.1 mL, 0.69 mmol). After 3 hr at RT, the reaction mixture was diluted with water (2 ml) and extracted with EtOAc (2×5 mL extractions). The combined organic extracts were washed with water (5 mL) and brine (5 ml), dried (Na$_2$SO$_4$), filtered and concentrated in vacuo. Purification of the residue by reverse phase preparative HPLC furnished the title compound as a beige solid: $^1$H NMR (500 MHz, DMSO) delta 1.92 (3H, s), 3.59-3.77 (6H, m), 3.86-3.92 (2H, m), 6.27 (1H, s), 7.06 (1H, s), 7.40 (1H, dd, J=8.4, 1.1 Hz), 7.51 (1H, t, J=4.9 Hz), 7.67

(2H, s), 7.98 (1H, d, J=8.3 Hz), 8.85 (1H, s), 8.90 (2H, d, J=4.9 Hz); LC-MS: m/z=+505.15/507.20 (M+H)+.

Example 97

Preparation of 1-[2-amino-6-(methylamino)pyrimidin-4-yl]-6-[3-hydroxy-3-(pyrimidin-2-yl)but-1-yn-1-yl]-N,N-dimethyl-1H-indazole-3-carboxamide

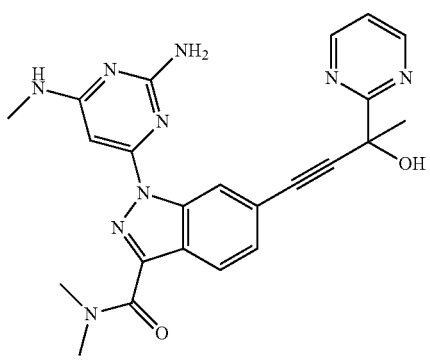

(97-b)

Step 1—Synthesis of 1-[2-amino-6-(methylamino)pyrimidin-4-yl]-6-iodo-N,N-dimethyl-1H-indazole-3-carboxamide

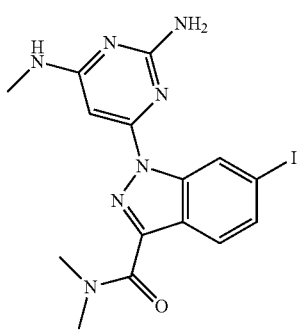

(97-a)

To a suspension of 6-iodo-N,N-dimethyl-1H-indazole-3-carboxamide (100 mg, 0.32 mmol) at 0° C. in DMF (3 mL) was added sodium hydride (19 mg of a 60% dispersion in mineral oil, 0.47 mmol). The reaction mixture was allowed to warm to RT over 15 minutes before the addition of 6-chloro-4-N-methylpyrimidine-2,4-diamine (75 mg, 0.47 mmol). The reaction mixture was then heated at 180° C. for 2 hr. The reaction mixture was allowed to cool to RT. The mixture was cooled to 0° C. and quenched by addition of water (1 mL) and the volatiles evaporated in vacuo. The mixture was diluted with sat ammonium chloride (20 mL) and extracted with ethyl acetate (3×50 mL). The combined organic extracts were dried (Na$_2$SO$_4$), filtered and evaporated in vacuo. Purification of the residue by column chromatography (Biotage, 55-100% ethyl acetate: heptanes) gave the title compound: $^1$H NMR (500 MHz, DMSO) delta 2.78 (3H, s), 3.08 (3H, s), 3.42 (3H, s), 6.24 (1H, s), 6.48 (2H, s), 7.08 (1H, s), 7.64 (1H, m), 7.79 (1H, m), 9.40 (1H, s); LC-MS: m/z=+438.0 (M+H)+.

Step 2—Synthesis of 1-[2-amino-6-(methylamino) pyrimidin-4-yl]-6-[3-hydroxy-3-(pyrimidin-2-yl)but-1-yn-1-yl]-N,N-dimethyl-1H-indazole-3-carboxamide To a sealed tube was added 1-[2-amino-6-(methylamino) pyrimidin-4-yl]-6-iodo-N,N-dimethyl-1H-indazole-3-carboxamide (86 mg, 0.20 mmol), followed by piperidine (2 mL), tetrakis(triphenylphosphine)palladium (23 mg, 0.02 mmol), copper(I) iodide (4 mg, 0.02 mmol) and 2-(pyrimidin-2-yl)but-3-yn-2-ol (58 mg, 0.39 mmol). The reaction mixture was purged with nitrogen gas, capped and stirred at room temperature for 1.5 hr. After cooling to RT, the reaction mixture was concentrated in vacuo. EtOAc (5 mL) was added and concentration in vacuo repeated. The residue was purified using column chromatography (Biotage, 0-10% gradient of methanol in DCM) to give a brown solid. Trituration of the solid with ethyl acetate/heptane gave the title compound. $^1$H NMR (DMSO, 500 MHz) delta 1.92 (3H, s), 2.80 (3H, d, J=4.1 Hz), 3.10 (3H, s), 3.31 (3H, s), 6.26 (2H, s), 6.49 (2H, s), 7.11 (1H, s), 7.30 (1H, d, J=8.4 Hz), 7.51 (1H, t, J=4.9 Hz), 7.94 (1H, d, J=8.4 Hz), 8.78-9.04 (3H, m); LC-MS: m/z=+458.10 (M+H)+.

Example 98

Preparation of (2R)-4-[1-(2-amino-6-methylpyrimidin-4-yl)-3-methyl-1H-indazol-6-yl]-2-(5-methyl-1,2,4-oxadiazol-3-yl)but-3-yn-2-ol mono formate salt

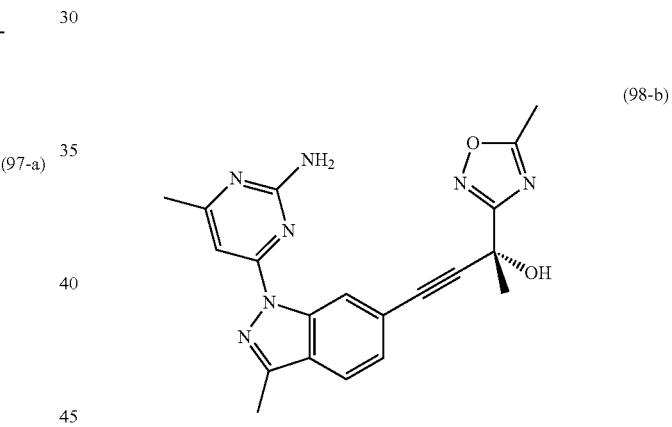

(98-b)

Step 1—Synthesis of 4-(6-bromo-3-methyl-1H-indazol-1-yl)-6-methylpyrimidin-2-amine

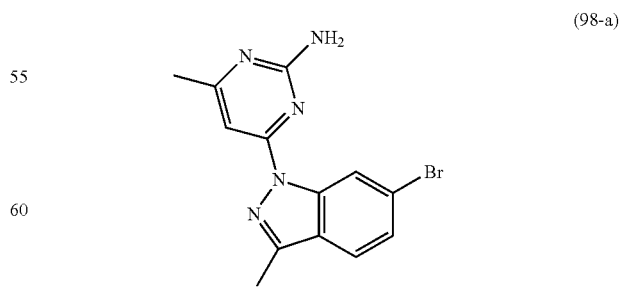

(98-a)

To a solution of 6-bromo-3-methyl-1H-indazole (500 mg, 2.37 mmol) in dry DMF (5 mL) at 0° C. under an atmosphere of nitrogen was introduced sodium hydride (684 mg of a 60% dispersion in mineral oil, 7.11 mmol). After warming to RT for 30 minutes, 4-chloro-6-methylpyrimidin-2-amine (510 mg, 3.55 mmol) was added and the solution warmed to 65° C. for 18 hr. The reaction mixture was cooled to RT, quenched by dropwise addition of water (5 mL) and extracted with 2:1 chloroform/isopropanol (3×10 mL extractions). The combined organic extracts were washed with water (5 mL) and brine (5 mL), dried (Na$_2$SO$_4$), filtered and concentrated in vacuo. Purification of the residue by column chromatography (Biotage, DCM containing a 0-10% gradient of methanol) furnished a yellow semi-solid which was slurried in acetonitrile (3 mL). The precipitate was collected by filtration to furnish the title compound as a yellow solid: $^1$H NMR (500 MHz, DMSO) delta 2.29 (3H, s), 2.56 (3H, s), 6.79-6.93 (2H, m), 6.93-6.95 (1H, m), 7.48 (1H, dd, J=8.43, 1.66 Hz), 7.78 (1H, d, J=8.35 Hz), 9.07 (1H, d, J=1.42 Hz); LC-MS: m/z=+ 317.95/319.95.

Step 2—Synthesis of (2R)-4-[1-(2-amino-6-methylpyrimidin-4-yl)-3-methyl-1H-indazol-6-yl]-2-(5-methyl-1,2,4-oxadiazol-3-yl)but-3-yn-2-ol mono formate salt To a solution of 4-(6-bromo-3-methyl-1H-indazol-1-yl)-6-methylpyrimidin-2-amine (100 mg, 0.29 mmol) in piperidine (1 mL) was introduced tetrakis(triphenylphosphine)palladium (0) (27 mg, 0.02 mmol), copper(I) iodide (5 mg, 0.02 mmol) and (2R)-2-(5-methyl-1,2,4-oxadiazol-3-yl)but-3-yn-2-ol (89 mg, 0.58 mmol). The reaction mixture was warmed to 66° C. for 2 hr. After cooling to RT, the reaction mixture was concentrated in vacuo, DCM (10 mL) was added and the solution re-evaporated to dryness in vacuo (re-evaporation process repeated twice). Purification of the residue by column chromatography (Biotage, DCM containing a 0-10% gradient of methanol) furnished a brown oil which was suspended in acetonitrile and concentrated in vacuo. The residue was re-suspended in acetonitrile (1 mL), whereupon a brown solid precipitated and was collected by filtration. Further purification by reverse phase preparative HPLC furnished the title compound as a pink solid: $^1$H NMR (500 MHz, DMSO) delta 1.89 (3H, s), 2.29 (3H, s), 2.57 (3H, s), 2.62 (3H, s), 6.66-6.92 (3H, m), 6.96 (1H, s), 7.34 (1H, dd, J=8.20, 1.10 Hz), 7.84 (1H, d, J=8.20 Hz), 8.18 (1H, br. s.), 8.86 (1H, s); LC-MS: m/z=+390.05 (M+H)+.

Example 99

Preparation of 4-[1-(2-amino-6-methylpyrimidin-4-yl)-3-methyl-1H-indazol-6-yl]-2-(pyrimidin-2-yl) but-3-yn-2-ol mono formate salt

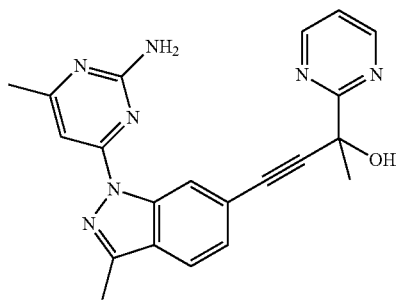 [SMILES: Cc1cc(-n2nc(C)c3ccc(C#CC(C)(O)c4ncccn4)cc32)nc(N)n1]

To a solution of 4-(6-bromo-3-methyl-1H-indazol-1-yl)-6-methylpyrimidin-2-amine (191 mg, 0.56 mmol) in piperidine (2 mL) was introduced tetrakis(triphenylphosphine)palladium (0) (52 mg, 0.05 mmol), copper(I) iodide (58.5 mg, 0.05 mmol) and 2-(pyrimidin-2-yl)but-3-yn-2-ol (171 mg, 1.12 mmol). The reaction mixture was warmed to 66° C. for 2 hr. After cooling to RT, the reaction mixture was concentrated in vacuo, DCM (10 mL) was added and the solution re-evaporated to dryness in vacuo (re-evaporation process repeated twice). Purification of the residue by column chromatography (Biotage, DCM containing a 0-10% gradient of methanol) furnished a brown oil which was suspended in acetonitrile and concentrated in vacuo. The residue was re-suspended in acetonitrile (1 mL), whereupon a brown solid precipitated and was collected by filtration. Further purification by reverse phase preparative HPLC furnished the title compound as a colorless solid: $^1$H NMR (500 MHz, CHLOROFORM-d) delta 2.06 (3H, s), 2.41 (3H, s), 2.59 (3H, s), 5.41 (2H, br. s.), 7.16 (1H, s), 7.31-7.38 (2H, m), 7.55 (1H, d, J=8.20 Hz), 8.83 (1H, s), 8.85 (2H, d, J=4.89 Hz); LC-MS: m/z=+386.05 (M+H)+.

Example 100

Preparation of (2R)-4-[1-(2-amino-5-chloropyrimidin-4-yl)-3-[(4-fluoropiperidin-1-yl)carbonyl]-1H-indazol-6-yl]-2-(5-methyl-1,2,4-oxadiazol-3-yl)but-3-yn-2-ol mono formate salt

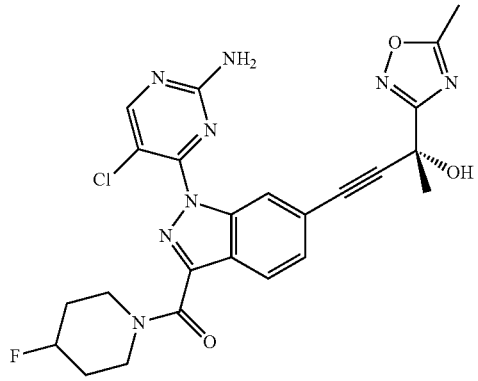

(100-c)

Step 1—Synthesis of 1-(2-amino-5-chloropyrimidin-4-yl)-6-iodo-1H-indazole-3-carboxylic acid

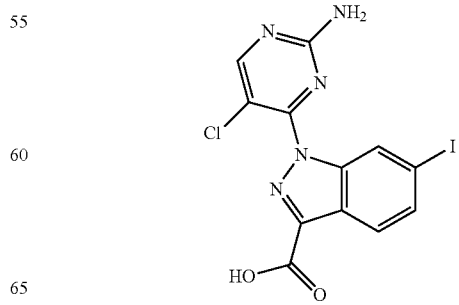

(100-a)

To a solution of 6-iodo-1H-indazole-3-carboxylic acid (300 mg, 1.04 mmol) in dry DMF (68 mL) at 0° C. under an atmosphere of nitrogen was introduced sodium hydride (100 mg of a 60% dispersion in mineral oil, 2.5 mmol). After 10 minutes at this temperature, 4,5-chloropyrimidin-2-amine (342 mg, 2.08 mmol) was added and the solution warmed to RT for 30 minutes, then to 65° C. for 18 hr. The reaction mixture was cooled to RT, quenched carefully by pouring into ice-water (50 mL) and the resulting precipitate collected by filtration. Following adjustment of the pH to 7 by addition of 2M aqueous hydrochloric acid, the filtrate was extracted with DCM (3×10 mL extraction) and 3:1 chloroform/isopropanol (3×10 mL extractions), and the combined extracts dried ($Na_2SO_4$) and concentrated in vacuo. The filtrate residue was combined with the precipitate to furnish the crude title compound as a tan solid: $^1$H NMR (500 MHz, DMSO) delta 7.34 (2H, s), 7.68 (1H, d, J=8.3 Hz), 8.04 (1H, d, J=8.4 Hz), 8.63-8.42 (2H, m); LC-MS: m/z=+415.85/417.55 (M+H)+. This compound, with LC-MS purity=58% UV, was used in the next step without further purification.

Step 2—Synthesis of 1-(2-amino-5-chloropyrimidin-4-yl)-6-[(3R)-3-hydroxy-3-(5-methyl-1,2,4-oxadiazol-3-yl)but-1-yn-1-yl]-1H-indazole-3-carboxylic acid (100-b)

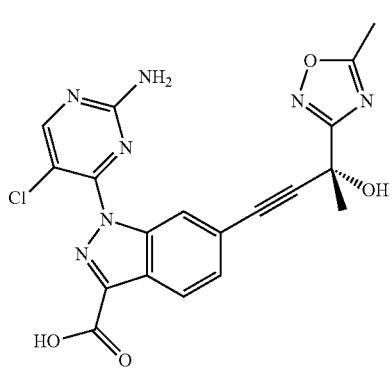

To a solution of 1-(2-amino-5-chloropyrimidin-4-yl)-6-iodo-1H-indazole-3-carboxylic acid (400 mg at 58% purity, 0.56 mmol) in piperidine (3 mL) was introduced tetrakis(triphenylphosphine)palladium (0) (111 mg, 0.10 mmol), copper(I) iodide (18.3 mg, 0.10 mmol) and (2R)-2-(5-methyl-1,2,4-oxadiazol-3-yl)but-3-yn-2-ol (293 mg, 1.93 mmol). The reaction was warmed to 35° C. under an atmosphere of nitrogen for 1 hr. After cooling to RT, the reaction mixture was concentrated in vacuo and the residue purified by silica gel flash column chromatography (eluent: DCM containing a 1-15% MeOH gradient followed by 85:15 DCM:7M ammonia in methanol). The partially purified compound was dissolved in DCM (20 mL) and washed with 2M aqueous citric acid (10 mL). The organic phase was dried ($Na_2SO_4$), filtered and concentrated in vacuo to furnish the title compound as a dark oil: $^1$H NMR (500 MHz, DMSO) delta 1.86 (3H, s), 2.62 (3H, s), 6.80 (1H, s), 7.53-7.35 (3H, m), 8.09 (1H, s), 8.23 (1H, d, J=8.4 Hz), 8.56 (1H, s); LC-MS: m/z=+ 439.90/441.90 (M+H)+. This compound, with LC-MS purity=61% UV, was used in the next step without further purification.

Step 3—Synthesis of (2R)-4-[1-(2-amino-5-chloropyrimidin-4-yl)-3-[(4-fluoropiperidin-1-yl)carbonyl]-1H-indazol-6-yl]-2-(5-methyl-1,2,4-oxadiazol-3-yl)but-3-yn-2-ol mono formate salt To a solution of 1-(2-amino-5-chloropyrimidin-4-yl)-6-[(3R)-3-hydroxy-3-(5-methyl-1,2,4-oxadiazol-3-yl)but-1-yn-1-yl]-1H-indazole-3-carboxylic acid (120 mg at 61% purity, 0.17 mmol) in DMF (3 mL) was introduced O-(7-azabenzotriazol-1-yl)-N,N,N',N'-tetramethyluronium hexafluorophosphate (127 mg, 0.33 mmol), 4-fluoropiperidine hydrochloride (47 mg, 0.33 mmol) and triethylamine (0.07 mL, 0.5 mmol). After 2 hr at RT, the reaction mixture was diluted with water (2 ml) and extracted with EtOAc (2×5 mL extractions). The combined organic extracts were washed with water (5 mL) and brine (5 ml), dried ($Na_2SO_4$), filtered and concentrated in vacuo. Purification of the residue by reverse phase preparative HPLC furnished the title compound as an off-white solid: $^1$H NMR (DMSO, 500 MHz) delta 1.76-1.91 (5H, m), 1.95-2.06 (2H, m), 2.62 (3H, s), 3.73-3.85 (2H, m), 4.01 (2H, t, J=5.4 Hz), 4.89-5.06 (1H, m), 6.82 (1H, s), 7.33-7.52 (3H, m), 8.05 (1H, d, J=8.3 Hz), 8.27 (1H, s), 8.54 (1H, s); LC-MS: m/z=+525.10/526.75.

Example 101

Preparation of (2R)-4-[1-(2-amino-5-chloropyrimidin-4-yl)-3-[(piperidin-1-yl)carbonyl]-1H-indazol-6-yl]-2-(5-methyl-1,2,4-oxadiazol-3-yl)but-3-yn-2-ol mono formate salt

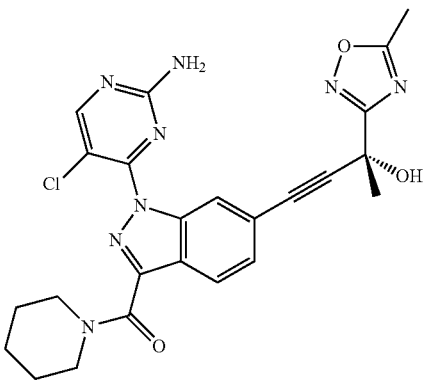 [SMILES: Cc1nc([C@](C)(O)C#Cc2ccc3c(C(=O)N4CCCCC4)nn(-c4nc(N)ncc4Cl)c3c2)no1]

The title compound was isolated by reverse phase preparative HPLC from the synthesis described for (2R)-4-[1-(2-amino-5-chloropyrimidin-4-yl)-3-[(4-fluoropiperidin-1-yl)carbonyl]-1H-indazol-6-yl]-2-(5-methyl-1,2,4-oxadiazol-3-yl)but-3-yn-2-ol mono formate salt, as a side product due the presence of piperidine impurity in the starting material. The title compound was furnished as a pale yellow solid: $^1$H NMR (DMSO, 500 MHz) delta 1.51-1.73 (6H, m), 1.87 (3H, s), 2.62 (3H, s), 3.66-3.79 (2H, m), 3.83-3.90 (2H, m), 6.82 (1H, s), 7.23-7.62 (3H, m), 8.01 (1H, d, J=8.5 Hz), 8.26 (1H, s), 8.53 (1H, s); LC-MS: m/z=+507.10/508.80 (M+H)+.

Example 102

Preparation of 1-{[1-(2-amino-5-chloropyrimidin-4-yl)-6-[(3R)-3-hydroxy-3-(5-methyl-1,2,4-oxadiazol-3-yl)but-1-yn-1-yl]-1H-indazol-3-yl]carbonyl}azetidin-3-ol

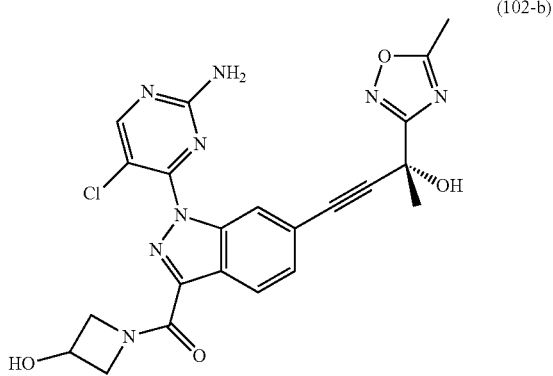 [SMILES: Cc1nc([C@](C)(O)C#Cc2ccc3c(C(=O)N4CC(O)C4)nn(-c4nc(N)ncc4Cl)c3c2)no1]

(102-b)

Step 1—Synthesis of 1-(2-amino-5-chloropyrimidin-4-yl)-6-[(3R)-3-hydroxy-3-(5-methyl-1,2,4-oxadiazol-3-yl)but-1-yn-1-yl]-1H-indazole-3-carboxylic acid

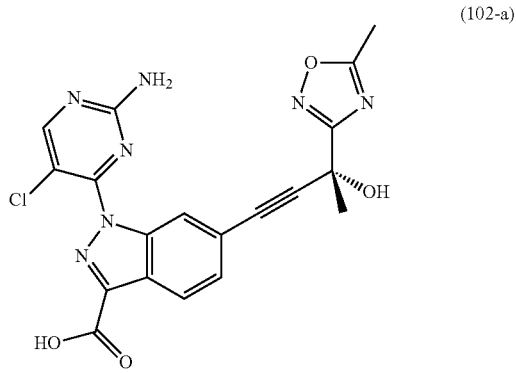 [SMILES: Cc1nc([C@](C)(O)C#Cc2ccc3c(C(=O)O)nn(-c4nc(N)ncc4Cl)c3c2)no1]

(102-a)

To a solution of 1-(2-amino-5-chloropyrimidin-4-yl)-6-iodo-1H-indazole-3-carboxylic acid (400 mg, 0.96 mmol) in piperidine (4 mL) was introduced tetrakis(triphenylphosphine)palladium (0) (111 mg, 0.10 mmol), copper(I) iodide (18.3 mg, 0.10 mmol) and (2R)-2-(5-methyl-1,2,4-oxadiazol-3-yl)but-3-yn-2-ol (292 mg, 1.92 mmol). The reaction was warmed to 35° C. for 1 hr. After cooling to RT, the reaction mixture was concentrated in vacuo and the residue purified by silica gel flash column chromatography (eluent: DCM containing a 1-15% MeOH gradient followed by 85:15 DCM:7M ammonia in methanol). The partially purified compound was dissolved in DCM (20 mL) and washed with 2M aqueous citric acid (10 mL). The organic phase was dried (Na$_2$SO$_4$), filtered and concentrated in vacuo to furnish the title compound as a dark oil: $^1$H NMR (500 MHz, DMSO) delta 1.86 (3H, s), 2.62 (3H, s), 6.80 (1H, s), 7.53-7.35 (3H, m), 8.09 (1H, s), 8.23 (1H, d, J=8.4 Hz), 8.56 (1H, s); LC-MS: m/z=+439.90 (M+H)+. This compound, with LC-MS purity=65% UV, was used in the next step without further purification.

Step 2—Synthesis of 1-{[1-(2-amino-5-chloropyrimidin-4-yl)-6-[(3R)-3-hydroxy-3-(5-methyl-1,2,4-oxadiazol-3-yl)but-1-yn-1-yl]-1H-indazol-3-yl]carbonyl}azetidin-3-ol To a solution of 1-(2-amino-5-chloropyrimidin-4-yl)-6-[(3R)-3-hydroxy-3-(5-methyl-1,2,4-oxadiazol-3-yl)but-1-yn-1-yl]-1H-indazole-3-carboxylic acid (100 mg at 65% purity, 0.14 mmol) in DMF (3 mL) was introduced O-(7-azabenzotriazol-1-yl)-N,N,N',N'-tetramethyluronium hexafluorophosphate (105 mg, 0.28 mmol), azetidin-3-ol hydrochloride (30 mg, 0.28 mmol) and triethylamine (0.06 mL, 0.42 mmol). After 5 hr at RT, the reaction mixture was retreated with O-(7-azabenzotriazol-1-yl)-N,N,N',N'-tetramethyluronium hexafluorophosphate (105 mg, 0.28 mmol), azetidin-3-ol hydrochloride (30 mg, 0.28 mmol) and triethylamine (0.06 mL, 0.42 mmol). The reaction was given a further 1 hr at RT, then diluted with water (2 ml) and extracted with EtOAc (2×5 mL extractions). The combined organic extracts were washed with water (5 mL) and brine (5 ml), dried (Na$_2$SO$_4$), filtered and concentrated in vacuo. Purification of the residue by silica gel flash column chromatography (DCM containing a 2-12% gradient of methanol) furnished a solid which was suspended in acetonitrile (2 mL). Filtration furnished the title compound as a colorless solid: $^1$H NMR (500 MHz, DMSO-d6) delta 1.86 (3H, s), 2.62 (3H, s), 3.85 (1H, dd, J=10.9, 4.1 Hz), 4.19-4.45 (2H, m), 4.45-4.67 (1H, m), 4.71-4.97 (1H, m), 5.80 (1H, s), 6.76 (1H, s), 7.26-7.58 (3H, m), 8.02-8.35 (2H, m), 8.54 (1H, s); LC-MS: m/z=+495.05/497.10 (M+H)+.

Example 103

Preparation of (2R)-4-[1-(2-amino-5-chloropyrimidin-4-yl)-3-(2-hydroxypropan-2-yl)-1H-indazol-6-yl]-2-(5-methyl-1,2,4-oxadiazol-3-yl)but-3-yn-2-ol

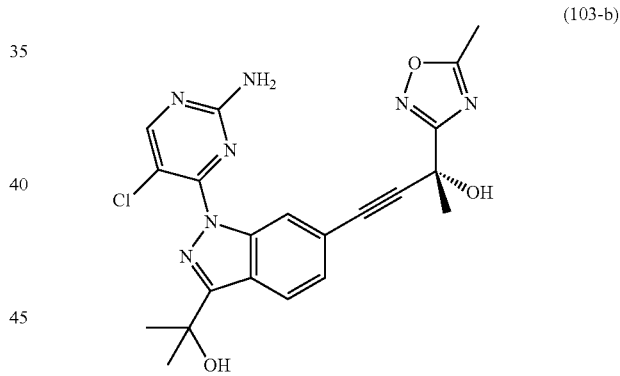

(103-b)

Step 1—Synthesis of 2-[1-(2-amino-5-chloropyrimidin-4-yl)-6-iodo-1H-indazol-3-yl]propan-2-ol

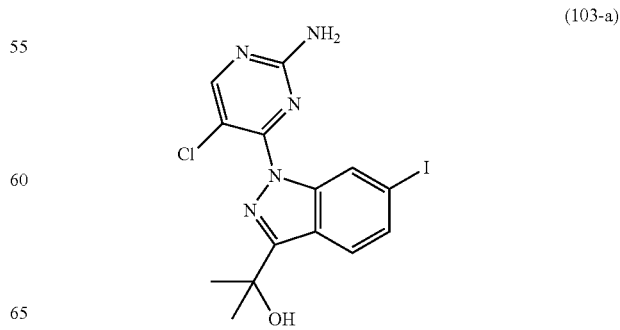

(103-a)

To a solution of 2-(6-iodo-1H-indazol-3-yl)propan-2-ol (300 mg, 0.99 mmol) in dry DMF (10 mL) at 0° C. under an atmosphere of nitrogen was introduced sodium hydride (63 mg of a 60% dispersion in mineral oil, 1.59 mmol). After 20 minutes at this temperature, 4,5-dichloropyrimidin-2-amine (326 mg, 1.99 mmol) was added and the solution warmed to RT for 10 minutes, then to 65° C. for 18 hr. Following cooling to RT, the reaction mixture was re-treated with additional sodium hydride (24 mg of a 60% dispersion in mineral oil) then warmed to 75° C. under nitrogen for 6 hr. The reaction mixture was cooled to RT, quenched carefully with water (20 mL) and extracted with EtOAc (2×20 mL extractions). The organic extracts were combined, dried (MgSO$_4$), filtered and concentrated in vacuo. Purification of the residue by silica gel flash column chromatography (4:1 to 1:1 heptane/EtOAc gradient) furnished the title compound as an off-white solid: $^1$H NMR (500 MHz, CDCl$_3$) delta 1.79 (6H, s), 5.19 (2H, br. s.), 7.61 (1H, dd, J=8.35, 1.42 Hz), 7.76 (1H, d, J=8.51 Hz), 8.42 (1H, s), 8.64 (1H, d, J=0.95 Hz); LC-MS: m/z=+429.90/431.65 (M+H)+.

Step 2—Synthesis of (2R)-4-[1-(2-amino-5-chloropyrimidin-4-yl)-3-(2-hydroxypropan-2-yl)-1H-indazol-6-yl]-2-(5-methyl-1,2,4-oxadiazol-3-yl)but-3-yn-2-ol To a solution of 2-[1-(2-amino-5-chloropyrimidin-4-yl)-6-iodo-1H-indazol-3-yl]propan-2-ol (150 mg, 0.35 mmol) in piperidine (2 mL) was introduced tetrakis(triphenylphosphine)palladium (0) (40.3 mg, 0.02 mmol), copper(I) iodide (6.6 mg, 0.02 mmol) and (2R)-2-(5-methyl-1,2,4-oxadiazol-3-yl)but-3-yn-2-ol (106 mg, 0.70 mmol). The reaction was warmed to 35° C. for 1.5 hr. After cooling to RT, the reaction mixture was concentrated in vacuo and the residue purified by silica gel flash column chromatography (heptane/EtOAc gradient) to furnish the title compound as a dark red solid: $^1$H NMR (500 MHz, DMSO-d6) delta 1.69 (6H, s), 1.93 (3H, s), 2.69 (3H, s), 5.65 (1H, s), 6.85 (1H, s), 7.34 (2H, br. s.), 7.39 (1H, dd, J=8.35, 1.10 Hz), 8.21 (1H, d, J=8.35 Hz), 8.26 (1H, s), 8.51 (1H, s); LC-MS: m/z=+454.05/456.05 (M+H)+.

Example 104

Preparation of 4-{1-[2-amino-5-(1-methylpyrazol-4-yl)pyrimidin-4-yl]indazol-6-yl}-2-methylbut-3-yn-2-ol

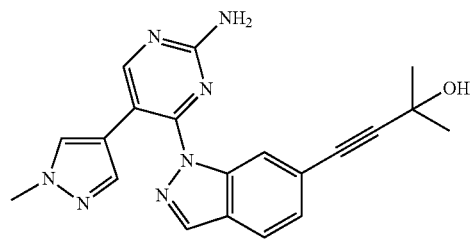 [SMILES: Cn1cc(-c2cnc(N)nc2-n2ncc3ccc(C#CC(C)(C)O)cc32)cn1]

5-bromo-4-(6-bromoindazol-1-yl)pyrimidin-2-amine (3 g) was reacted with 2-methyl-3-butyn-2-ol (1 eq) via Sonagashira Coupling to afford 0.7 g of 4-[1-(2-amino-5-bromo-pyrimidin-4-yl)indazol-6-yl]-2-methyl-but-3-yn-2-ol following flash column chromatography. 4-[1-(2-amino-5-bromo-pyrimidin-4-yl)indazol-6-yl]-2-methyl-but-3-yn-2-ol (0.1 g) was reacted with 1-methyl-4-pyrazoleboronic acid pinacol ester via Suzuki Coupling to afford 12.2 mg of 4-[1-[2-amino-5-(1-methylpyrazol-4-yl)pyrimidin-4-yl]indazol-6-yl]-2-methyl-but-3-yn-2-ol following reverse phase hplc purification. MS (Q1) 374. $^1$H NMR (400 MHz, DMSO) delta 8.57 (s, 1H), 8.30 (s, 1H), 7.88-7.81 (m, 2H), 7.48 (s, 1H), 7.24 (dd, J=8.3, 1.1 Hz, 1H), 7.05 (s, 2H), 6.98 (s, 1H), 5.47 (s, 1H), 3.73 (s, 3H), 1.48 (s, 6H).

Example 105

Preparation of 4-{1-[2-amino-5-(1H-pyrazol-4-yl)pyrimidin-4-yl]indazol-6-yl}-2-methylbut-3-yn-2-ol

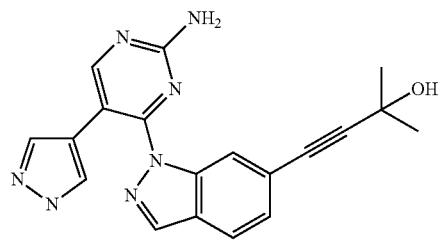 [SMILES: CC(C)(O)C#Cc1ccc2cnn(-c3nc(N)ncc3-c3cn[nH]c3)c2c1]

4-[1-(2-amino-5-bromo-pyrimidin-4-yl)indazol-6-yl]-2-methyl-but-3-yn-2-ol (0.075 g) was reacted 1-Boc-4-pyrazoleboronic acid pinacol ester via Suzuki Coupling to afford 9.5 mg of 4-[1-[2-amino-5-(1-methylpyrazol-4-yl)pyrimidin-4-yl]indazol-6-yl]-2-methyl-but-3-yn-2-ol following reverse phase hplc purification. MS (Q1) 360. $^1$H NMR (400 MHz, DMSO) delta 12.71 (s, 1H), 8.62 (s, 1H), 8.30 (s, 1H), 7.84 (d, J=8.3 Hz, 1H), 7.76 (s, 1H), 7.46 (s, 1H), 7.23 (d, J=8.2 Hz, 1H), 7.02 (s, 2H), 5.45 (s, 1H), 1.47 (s, 6H).

Example 106

Preparation of 4-(1-{6-[(2-methoxypyridin-3-yl)amino]pyrimidin-4-yl}-1H-indazol-6-yl)-2-methylbut-3-yn-2-ol (106-c)

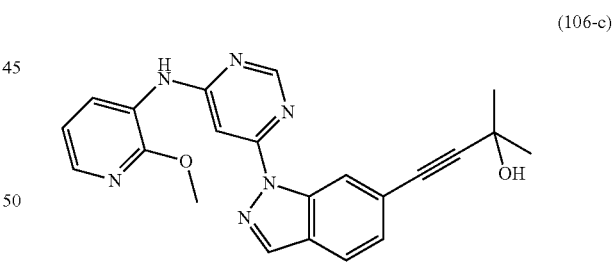

Step 1—Synthesis of 6-chloro-N-(2-methoxypyridin-3-yl)pyrimidin-4-amine

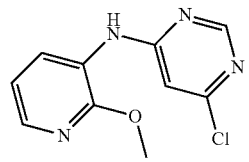 [SMILES: COc1ncccc1Nc1cc(Cl)ncn1]

To a solution of 4,6-dichloropyrimidine (660.04 mg, 4.43 mmol) in 1-butanol (10 mL) was added DIPEA (0.67 ml, 4.03 mmol) followed by 2-methoxypyridin-3-amine (500 mg, 4.03 mmol). The reaction mixture was then heated to 90° C. for 2 hr. The reaction mixture was then concentrated in vacuo and partitioned between DCM and water. A precipitate was removed by filtration and the organics extracted (2×20 ml DCM). The combined organic extracts were then washed with 0.5M HCl (5 ml) and then dried (Na₂SO₄), filtered and concentrated in vacuo to give the title intermediate (300 mg, LC-MS purity=83%); LC-MS: m/z=+236.95/238.90 (M+H)+.

Step 2—Synthesis of 6-(6-iodoindazol-1-yl)-N-(2-methoxypyridin-3-yl)pyrimidin-4-amine

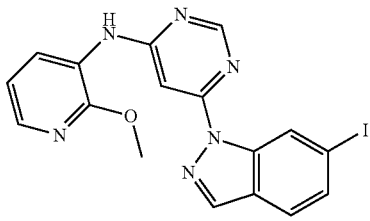 [SMILES: COc1ncccc1Nc1cc(-n2ncc3ccc(I)cc32)ncn1]

To a solution of 6-iodo-1H-indazole (100 mg, 0.41 mmol) in DMF (5 mL) was added NaH (60% oil dispersion, 32.78 mg, 0.82 mmol)) at 0° C. The reaction mixture was stirred at 0° C. for 10 minutes before the addition of 6-chloro-N-(2-methoxypyridin-3-yl)pyrimidin-4-amine (126.7 mg, 0.55 mmol). The reaction mixture was then stirred at 110° C. for 18 hr. The reaction mixture was then cooled to RT, quenched by the addition of water (2 ml), EtOAc (a few drops) was added and the resultant precipitate was collected by suction filtration and thoroughly dried under high vacuum to give the title compound (120 mg, LC-MS: m/z=+444.90). This compound of 62% purity LC-MS (UV) was used without further purification.

Step 3—Synthesis of 4-(1-{6-[(2-methoxypyridin-3-yl)amino]pyrimidin-4-yl}-1H-indazol-6-yl)-2-methylbut-3-yn-2-ol To a pressure tube was added 6-(6-iodoindazol-1-yl)-N-(2-methoxypyridin-3-yl)pyrimidin-4-amine (120 mg, 0.27 mmol) followed by triethylamine (2 mL) and THF (2 mL). Next, copper(I) iodide (5.15 mg, 0.027 mmol), bis(triphenylphosphine)palladium(II) chloride (18.96 mg, 0.027 mmol) and 2-methylbut-3-yn-2-ol (0.05 ml, 0.54 mmol) were added and the reaction vessel was sealed and stirred at RT for 1 h. The reaction mixture was concentrated in vacuo and DCM (5 ml) was added. The organics were washed with 0.5M HCl (2×3 ml), water (3 ml) and brine (3 ml), and dried (Na₂SO₄), filtered and concentrated in vacuo. The crude product was purified by flash chromatography (Isolute column, 4:6 to 1:1 EtOAc:heptanes) to surrender the title compound as a white solid: ¹H NMR (500 MHz, CDCl₃) delta 1.69 (6H, s), 2.08 (1H, br. s.), 4.07 (3H, s), 6.99 (1H, dd, J=7.80, 4.97 Hz), 7.32-7.41 (2H, m), 7.69 (1H, d, J=8.20 Hz), 7.88 (1H, dd, J=4.97, 1.66 Hz), 8.19 (1H, s), 8.54-8.61 (1H, m), 8.77 (1H, s), 8.99 (1H, s); LC-MS: m/z=+401.10 (M+H)+.

Example 107

Preparation of 4-[1-(6-aminopyrimidin-4-yl)-1H-indazol-6-yl]-2-methylbut-3-yn-2-ol

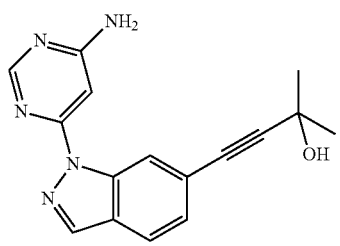

(107-b)

Step 1—Synthesis of 6-(6-iodoindazol-1-yl)pyrimidin-4-amine

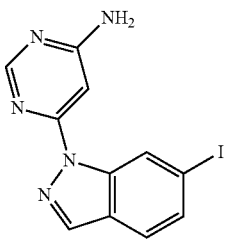

(107-a)

To a solution of 6-iodoindazole (500 mg, 2.05 mmol) in DMF (8 mL) was added NaH (60% oil dispersion, 131.12 mg, 3.28 mmol) at 0° C. The mixture was stirred at 0° C. to RT for 10 minutes before addition of 6-chloropyrimidin-4-amine (477.78 mg, 3.69 mmol) and stirring at 60° C. for 17 hr and then transferred to a pressure tube and heated at 70° C. for a further 6 hr. The reaction mixture was cooled and quenched by the addition of water (10 ml) and EtOAc (a few drops) was added. The resultant precipitate was collected by suction filtration and then thoroughly dried under high vacuum to give the title intermediate (248 mg): LC-MS: m/z=+338.20 (M+H)+.

Step 2—Synthesis of 4-[1-(6-aminopyrimidin-4-yl)-1H-indazol-6-yl]-2-methylbut-3-yn-2-ol The title compound was prepared by the procedure described in Example 1-b by reacting 6-(6-iodomoindazol-1-yl)pyrimidin-4-amine with 2-methylbut-3-yn-2-ol: ¹H NMR (500 MHz, DMSO) delta 1.50 (6H, s), 5.56 (1H, s), 6.95 (1H, s), 7.10 (2H, br. s.), 7.29 (1H, dd, J=8.20, 1.26 Hz), 7.86 (1H, d, J=8.20 Hz), 8.46 (2H, d, J=9.30 Hz), 8.81 (1H, s); LC-MS: m/z=+294.50.

Example 108

Examples in Table 11 were prepared by procedure described in Example 14-e by reacting 4-(6-bromo-1H-1,3-benzodiazol-1-yl)pyrimidin-2-amine with the appropriate but-3-yn-2-ol

TABLE 11

| No | Structure | Name | 1H NMR | LCMS (M + H) |
|---|---|---|---|---|
| T11-108.1 | 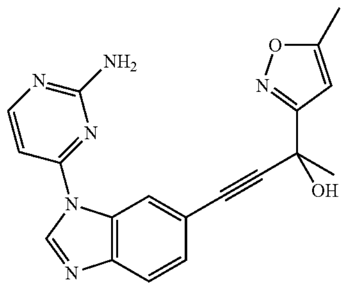 [SMILES: Cc1cc(C(C)(O)C#Cc2ccc3ncn(-c4ccnc(N)n4)c3c2)no1] | 4-[1-(2-aminopyrimidin-4-yl)-1H-1,3-benzodiazol-6-yl]-2-(5-methyl-1,2-oxazol-3-yl)but-3-yn-2-ol | (500 MHz, DMSO) delta 1.84 (3 H, s), 2.41 (3 H, s), 6.39 (1 H, d, J = 0.79 Hz), 6.49 (1 H, s), 7.07-7.25 (3 H, m), 7.39 (1 H, dd, J = 8.35, 1.58 Hz), 7.75 (1H, d, J = 8.20 Hz), 8.39 (1 H, br. s.), 8.58 (1 H, d, J = 0.95 Hz), 9.09 (1 H, s) | 361.05 |
| T11-108.2 | | 4-[1-(2-aminopyrimidin-4-yl)-1H-1,3-benzodiazol-6-yl]-2-(3-methyl-1,2-oxazol-5-yl)but-3-yn-2-ol | (500 MHz, DMSO) delta 1.84 (3 H, s), 2.25 (3 H, s), 6.42 (1 H, s), 6.71 (1 H, s), 7.22-7.11 (3 H, m), 7.43 (1 H, d, J = 8.2 Hz), 7.76 (1 H, d, J = 8.1 Hz), 8.41 (1 H, s), 8.62 (1 H, s), 9.12 (1 H, s). | 361.5 |
| T11-108.2 | | 4-[1-(2-aminopyrimidin-4-yl)-1H-1,3-benzodiazol-6-yl]-2-(1H-pyrazol-4-yl)but-3-yn-2-ol | (500 MHz, DMSO) delta 1.86 (3 H, s), 5.95 (1 H, s), 7.16-7.28 (3 H, m), 7.47 (1 H, dd, J = 8.35, 1.58 Hz), 7.75 (2 H, br. s.), 7.80 (1 H, d, J = 8.20 Hz), 8.45 (1H, d, J = 5.52 Hz), 8.64 (1 H, d, J = 0.79 Hz), 9.14 (1 H, s), 12.76 (1 H, br. s.) | 346.0 |
| T11-108.3 | 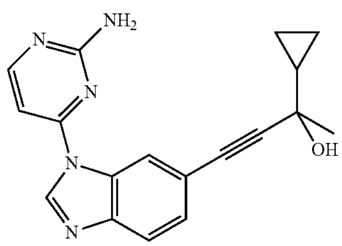 [SMILES: CC(O)(C#Cc1ccc2ncn(-c3ccnc(N)n3)c2c1)C1CC1] | 4-[1-(2-aminopyrimidin-4-yl)-1H-1,3-benzodiazol-6-yl]-2-cyclopropylbut-3-yn-2-ol | (500 MHz, DMSO) delta 0.42 (2 H, tdd, J = 8.63, 8.63, 5.12, 3.47 Hz), 0.47-0.53 (1 H, m), 0.53-0.61 (1 H, m), 1.11-1.21 (1 H, m), 1.54 (3 H, s), 5.33 (1H, s), 7.07-7.17 (3 H, m), 7.33 (1 H, dd, J = 8.20, 1.58 Hz), 7.69-7.74 (1 H, m), 8.38 (1 H, d, J = 5.67 Hz), 8.52 (1 H, d, J = 0.95 Hz), 9.06 (1 H, s) | 320.05 |
| T11-108.4 | 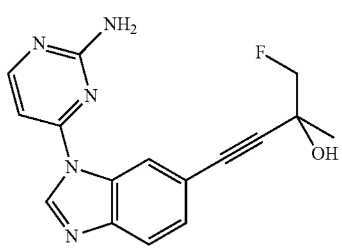 [SMILES: CC(O)(C#Cc1ccc2ncn(-c3ccnc(N)n3)c2c1)CF] | 4-[1-(2-aminopyrimidin-4-yl)-1H-1,3-benzodiazol-6-yl]-1-fluoro-2-methylbut-3-yn-2-ol | (500 MHz, MeOD) delta 1.59 (3 H, d, J = 1.89 Hz), 4.31-4.49 (2 H, m), 7.06 (1 H, d, J = 5.52 Hz), 7.45 (1 H, d, J = 8.35 Hz), 7.69 (1 H, d, J = 8.35 Hz), 8.36 (1 H, d, J = 5.52 Hz), 8.58 (1 H, s), 8.95 (1 H, s) | 312.05 |

Examples 109

Examples in Table 12 were prepared by adaptation of procedure described in Example 21 by substituting 2-(1,3-thiazol-2-yl)but-3-yn-2-ol with the appropriate but-3-yn-2-ol.

TABLE 12

| No | Structure | Name | $^1$H NMR | LC-MS (M + H) |
|---|---|---|---|---|
| T12-109.1 | 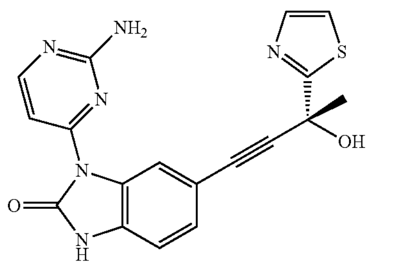 [SMILES: C[C@@](O)(C#Cc1ccc2[nH]c(=O)n(-c3ccnc(N)n3)c2c1)c1nccs1] | 1-(2-aminopyrimidin-4-yl)-6-[(3R)-3-hydroxy-3-(1,3-thiazol-2-yl)but-1-yn-1-yl]-2,3-dihydro-1H-1,3-benzodiazol-2-one | (500 MHz, DMSO) delta 1.89 (3 H, s), 6.91 (2 H, s), 6.94 (1 H, s), 7.04 (1 H, d, J = 8.1), 7.20 (1 H, dd, J = 8.1, 1.5 Hz), 7.38 (1 H, d, J = 5.6 Hz), 7.67 (1 H, d, J = 3.2 Hz), 7.76 (1 H, d, J = 3.2 Hz), 8.34-8.27 (2 H, m), 11.57 (1 H, s | 378.95 |
| T12-109.2 | 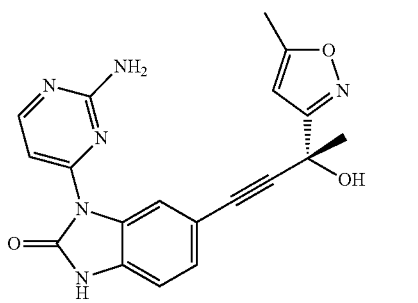 [SMILES: Cc1cc([C@](C)(O)C#Cc2ccc3[nH]c(=O)n(-c4ccnc(N)n4)c3c2)no1] | 1-(2-aminopyrimidin-4-yl)-6-[(3R)-3-hydroxy-3-(5-methyl-1,2-oxazol-3-yl)but-1-yn-1-yl]-2,3-dihydro-1H-1,3-benzodiazol-2-one | (250 MHz, DMSO) delta 1.81 (3 H, s), 2.40 (3 H, s), 6.38 (1 H, s), 6.44 (1 H, s), 6.95 (2 H, s), 7.04 (1 H, d, J = 8.07 Hz), 7.21 (1 H, dd, J = 8.07, 1.52 Hz), 7.40 (1 H, d, J = 5.63 Hz), 8.24-8.39 (2 H, m), 11.59 (1 H, s) | 377.4 |
| T12-109.3 | 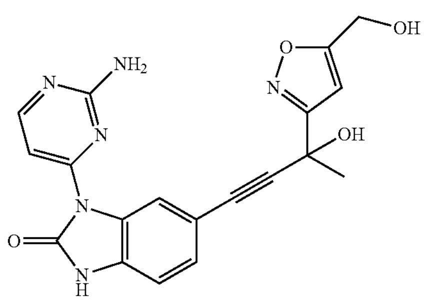 [SMILES: CC(O)(C#Cc1ccc2[nH]c(=O)n(-c3ccnc(N)n3)c2c1)c1cc(CO)on1] | 1-(2-aminopyrimidin-4-yl)-6-{3-hydroxy-3-[5-(hydroxymethyl)-1,2-oxazol-3-yl]but-1-yn-1-yl}-2,3-dihydro-1H-1,3-benzodiazol-2-one | (500 MHz, DMSO) delta 1.83 (3 H, s), 4.56 (2 H, d, J = 5.7 Hz), 5.65 (1 H, t, J = 6.0 Hz), 6.56-6.43 (2 H, m), 6.94 (2 H, s), 7.05 (1 H, d, J = 8.0 Hz), 7.22 (1 H, dd, J = 8.1, 1.5 Hz), 7.40 (1 H, d, J = 5.6 Hz), 8.30 (1 H, d, J = 5.6 Hz), 8.33 (1 H, d, J = 1.1 Hz), 11.08 (1H, s). | 393.0 |

Example 110

Preparation of 3-(2-aminopyrimidin-4-yl)-5-[(3R)-3-hydroxy-3-(5-methyl-1,2-oxazol-3-yl)but-1-yn-1-yl]-1-methyl-2,3-dihydro-1H-1,3-benzodiazol-2-one Step 1—Synthesis of 3-(2-aminopyrimidin-4-yl)-5-bromo-1-methyl-2,3-dihydro-1H-1,3-benzodiazol-2-one

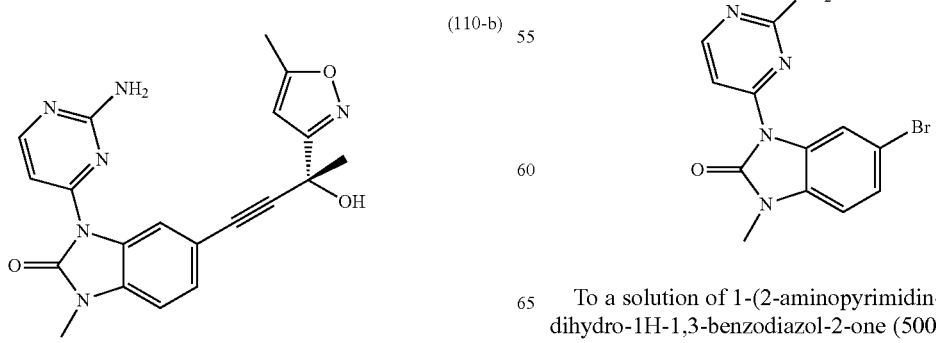

To a solution of 1-(2-aminopyrimidin-4-yl)-6-bromo-2,3-dihydro-1H-1,3-benzodiazol-2-one (500 mg, 1.63 mmol) in DMF (10 ml) at 0° C. was added sodium hydride (60% oil suspension, 65.33 g, 1.63 mmol). The reaction mixture was allowed to warm to RT over 5 minutes before addition of iodomethane (0.1 ml, 1.63 mmol) and stirring for 30 minutes. The mixture was quenched by addition of water (5 mL), EtOAc was then added resulting in formation of a precipitate. The precipitate was collected by suction filtration. The filtrate was extracted with EtOAc (×2). The combined organic fractions were washed with water and dried (Na$_2$SO$_4$), filtered and concentrated in vacuo. Combining the extract residue and the precipitate gave the crude title compound (600 mg); $^1$H NMR (500 MHz, CDCl$_3$) delta 3.23 (3H, s), 5.55 (2H, s), 6.72 (1H, d, J=8.3 Hz), 7.20-7.04 (1H, m), 7.42 (1H, d, J=5.7 Hz), 8.12 (1H, d, J=5.7 Hz), 8.39 (1H, d, J=1.8 Hz); LC-MS: m/z=+321.8 (M+H)+.

Step 2—Synthesis of 3-(2-aminopyrimidin-4-yl)-5-[(3R)-3-hydroxy-3-(5-methyl-1,2-oxazol-3-yl)but-1-yn-1-yl]-1-methyl-2,3-dihydro-1H-1,3-benzodiazol-2-one The title compound was prepared by the method described in Step 2 of Example 142-b by reacting 3-(2-aminopyrimidin-4-yl)-5-bromo-1-methyl-2,3-dihydro-1H-1,3-benzodiazol-2-one with (2R)-2-(5-methyl-1,2-oxazol-3-yl)but-3-yn-2-ol: $^1$H NMR (500 MHz, DMSO) delta 1.82 (3H, s), 2.40 (3H, s), 3.38 (3H, s), 6.38 (1H, s), 6.44 (1H, s), 6.97 (2H, s), 7.33-7.22 (2H, m), 7.42 (1H, d, J=5.6 Hz), 8.32 (1H, d, J=5.6 Hz), 8.38 (1H, s); LC-MS: m/z=+391 (M+H)+.

Example 111

Examples in Table 13 were prepared by the procedure described in Example 142-b by reacting 3-(2-aminopyrimidin-4-yl)-5-bromo-1-methyl-2,3-dihydro-1H-1,3-benzodiazol-2-one with the appropriate but-3-yn-2-ol intermediates.

Example 112

Preparation of 4-[1-(2-aminopyrimidin-4-yl)-2-ethoxy-1H-1,3-benzodiazol-6-yl]-2-methylbut-3-yn-2-ol

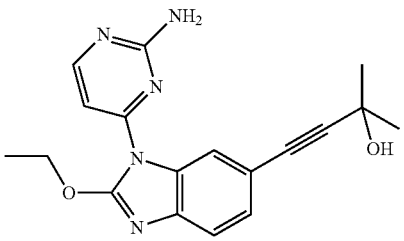

(112-b)

Step 1—Synthesis of 4-(6-bromo-2-ethoxy-1,3-benzodiazol-1-yl)pyrimidin-2-amine

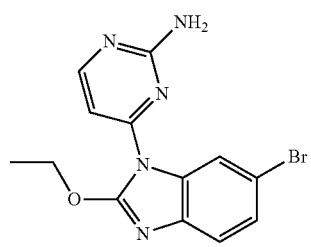

(112-a)

A mixture of 4-N-(2-amino-5-bromophenyl)pyrimidine-2,4-diamine (652 mg, 1.98 mmol), (triethoxymethoxy)ethane

TABLE 13

| No | Structure | Name | $^1$H NMR | LC-MS (M + H) |
|---|---|---|---|---|
| T13-111.1 | 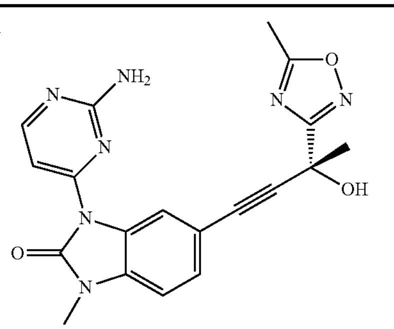 | 3-(2-aminopyrimidin-4-yl)-5-[(3R)-3-hydroxy-3-(5-methyl-1,2,4-oxadiazol-3-yl)but-1-yn-1-yl]-1-methyl-2,3-dihydro-1H-1,3-benzodiazol-2-one | (500 MHz, CDCl$_3$) delta 2.06 (3 H, s), 2.65 (3 H, s), 3.44 (3 H, s), 4.54 (1 H, br. s.), 5.42 (2 H, s), 6.93 (1 H, d, J = 8.20 Hz), 7.34 (1 H, dd, J = 8.04, 1.42 Hz), 7.70 (1 H, d, J = 5.83 Hz), 8.35 (1 H, d, J = 5.83 Hz), 8.44 (1 H, d, J = 1.10 Hz) | 392 |
| T13-111.2 | 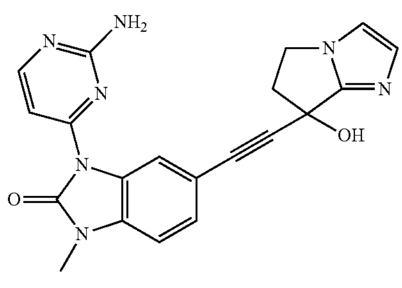 [SMILES: Cn1c(=O)n(-c2ccnc(N)n2)c2cc(C#CC3(O)CCn4ccnc43)ccc21] | 3-(2-aminopyrimidin-4-yl)-5-(2-{7-hydroxy-5H,6H,7H-pyrrolo[1,2-a]imidazol-7-yl}ethynyl)-1-methyl-2,3-dihydro-1H-1,3-benzodiazol-2-one | (500 MHz, DMSO) delta 2.72-2.84 (1 H, m), 3.01-3.12 (1 H, m), 3.30-3.36 (3 H, m), 3.99-4.09 (2 H, m), 6.47 (1 H, s), 6.87-7.04 (3 H, m), 7.09-7.15 (1 H, m), 7.26 (1 H, d, J = 8.04 Hz), 7.32 (1 H, dd, J = 8.04, 1.26 Hz), 7.42 (1 H, d, J = 5.52 Hz), 8.32 (1 H, d, J = 5.67 Hz), 8.42 (1 H, s) | 388.05 |

(2.0 mL, 9.89 mmol) and acetic acid (0.09 mL) was heated at 80° C. for 40 minutes. After cooling to room temperature, the mixture was concentrated in vacuo. The residue was dissolved in ethyl acetate (5 mL) and washed with saturated aqueous sodium hydrogencarbonate (2×10 mL) and then brine. The organic layer was dried over sodium sulfate, filtered and concentrated in vacuo to give the crude product as an orange solid $^1$H NMR (500 MHz, CDCl$_3$) delta 1.55 (3H, t, J=7.09 Hz), 4.71 (2H, q, J=7.25 Hz), 5.21 (2H, br. s.), 7.13 (1H, d, J=5.67 Hz), 7.35-7.42 (2H, m), 8.36-8.40 (2H, m); LC-MS: m/z=+334.00/335.75 (M+H)+.

Step 2—Synthesis of 4-[1-(2-aminopyrimidin-4-yl)-2-ethoxy-1H-1,3-benzodiazol-6-yl]-2-methylbut-3-yn-2-ol The title compound was prepared by the procedure described in Step 2 of Example 142-b by reacting 4-(6-bromo-2-ethoxy-1,3-benzodiazol-1-yl)pyrimidin-2-amine with 2-methyl-3-butyn-2-ol; $^1$H NMR (500 MHz, MeOD) delta 1.54 (3H, t, J=7.09 Hz), 1.58 (6H, s), 4.68 (2H, q, J=7.09 Hz), 7.11 (1H, d, J=5.67 Hz), 7.25-7.32 (1H, m), 7.39 (1H, d, J=8.20 Hz), 8.29 (1H, s), 8.31-8.43 (1H, m); LC-MS: m/z=+338.5 (M+H)+.

Example 113

Examples in Table 14 are prepared by the procedures described in Example 112-b, by reacting 4-(6-bromo-2-ethoxy-1H-1,3-benzodiazol-1-yl)pyrimidin-2-amine with the appropriate but-3-yn-2-ol intermediates.

TABLE 14

| No | Structure | Name | $^1$H NMR | LC-MS (M + H) |
|---|---|---|---|---|
| T14-113.1 | 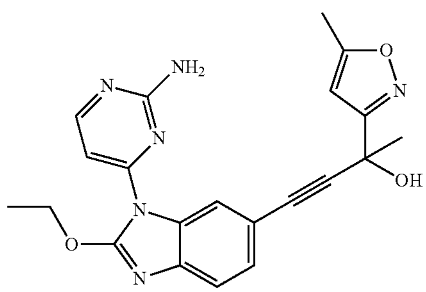 [SMILES: CCOc1nc2ccc(C#CC(C)(O)c3cc(C)on3)cc2n1-c1ccnc(N)n1] | 4-[1-(2-aminopyrimidin-4-yl)-2-ethoxy-1H-1,3-benzodiazol-6-yl]-2-(5-methyl-1,2-oxazol-3-yl)but-3-yn-2-ol | (250 MHz, DMSO) delta 1.44 (3 H, t, J = 7.01 Hz), 1.80 (3 H, s), 2.39 (3 H, s), 4.63 (2 H, q, J = 7.11 Hz), 6.36 (1 H, d, J = 0.91 Hz), 6.44 (1 H, s), 6.97 (1 H, d, J = 5.48 Hz), 7.08 (2 H, s), 7.26 (1 H, dd, J = 8.15, 1.60 Hz), 7.44 (1 H, d, J = 8.22 Hz), 8.14 (1 H, d, J = 1.22 Hz), 8.38 (1 H, d, J = 5.33 Hz) | 405.45 |
| T14-113.2 | 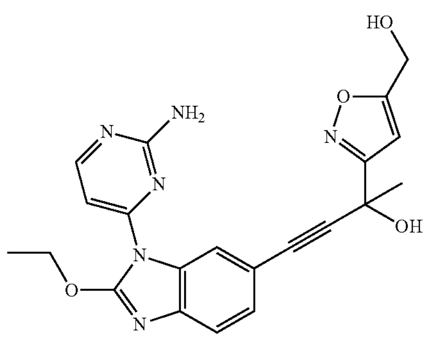 [SMILES: CCOc1nc2ccc(C#CC(C)(O)c3cc(CO)on3)cc2n1-c1ccnc(N)n1] | 4-[1-(2-aminopyrimidin-4-yl)-2-ethoxy-1H-1,3-benzodiazol-6-yl]-2-[5-(hydroxymethyl)-1,2-oxazol-3-yl]but-3-yn-2-ol | (500 MHz, DMSO) delta 1.44 (3 H, t, J = 7.1 Hz), 1.82 (3 H, s), 4.55 (2 H, d, J = 6.1 Hz), 4.63 (2 H, q, J = 7.1 Hz), 5.64 (1 H, t, J = 6.0 Hz), 6.50 (2 H, s), 6.97 (1 H, d, J = 5.5 Hz), 7.08 (2 H, s), 7.27 (1 H, dd, J = 8.2, 1.4 Hz), 7.45 (1 H, d, J = 8.2 Hz), 8.15 (1 H, s), 8.38 (1 H, d, J = 5.5 Hz). | 421.05 |
| T14-113.3 | 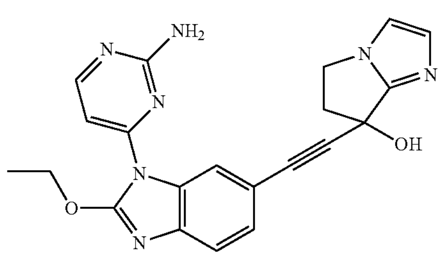 [SMILES: CCOc1nc2ccc(C#CC3(O)CCn4ccnc43)cc2n1-c1ccnc(N)n1] | 7-{2-[1-(2-aminopyrimidin-4-yl)-2-ethoxy-1H-1,3-benzodiazol-6-yl]ethynyl}-5H,6H,7H-pyrrolo[1,2-a]imidazol-7-ol | (250 MHz, DMSO) delta 1.45 (3 H, t, J = 7.08 Hz), 2.77 (1 H, br. s.), 2.92-3.11 (1 H, m), 4.01-4.12 (2 H, m), 4.64 (2 H, q, J = 6.85 Hz), 6.92-7.02 (2 H, m), 7.09 (2 H, s), 7.12 (1 H, d, J = 1.07 Hz), 7.28 (1 H, dd, J = 8.15, 1.60 Hz), 7.46 (1 H, d, J = 8.22 Hz), 8.18 (1 H, d, J = 1.37 Hz), 8.38 (1 H, d, J = 5.48 Hz) | 402.1 |

Example 114

Preparation of 7-{(2-[1-(2-aminopyrimidin-4-yl)-2-ethoxy-1H-1,3-benzodiazol-6-yl]ethynyl}-5H,6H,7H-cyclopenta[b]pyridin-7-ol

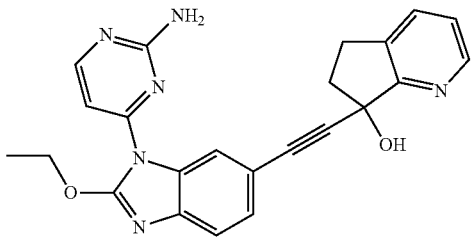

(114-c)

Step 1—Synthesis of 4-N-(2-amino-5-iodophenyl)pyrimidine-2,4-diamine

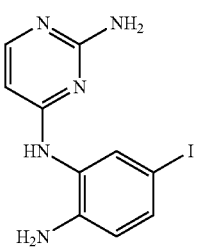

(114-a)

A pressure tube containing copper(I) iodide (61.2 mg, 0.32 mmol), sodium iodide (963.18 mg, 6.43 mmol) and 4-N-(2-amino-5-bromophenyl)pyrimidine-2,4-diamine (900 mg, 3.21 mmol) was flushed with nitrogen before the addition of 1,4-dioxane (4.0 mL), DMF (4.0 ml) and N,N'-dimethylethane-1,2-diamine (0.035 ml, 0.32 mmol). The vessel was sealed and stirred at 115° C. overnight. After cooling to RT, the reaction mixture was poured into ice water (7 ml) and the resulting solution extracted with DCM (2×100 mL). The combined organics were dried (Na₂SO₄), filtered and concentrated in vacuo. Purification by column chromatography (Biotage, 3-14% methanol gradient in DCM) furnished the title compound (600 mg, 57% yield); ¹H NMR (500 MHz, DMSO) delta 5.04 (2H, d, J=11.6 Hz), 5.78-5.73 (1H, m), 6.11-6.02 (2H, m), 6.57 (1H, d, J=8.4 Hz), 7.18 (1H, dd, J=8.4, 2.0 Hz), 7.47-7.38 (1H, m), 7.75 (1H, d, J=5.3 Hz), 8.20-8.12 (1H, m); LC-MS: m/z=+327.8 (M+H)+.

Step 2—Synthesis of 4-(2-ethoxy-6-iodo-1H-1,3-benzodiazol-1-yl)pyrimidin-2-amine

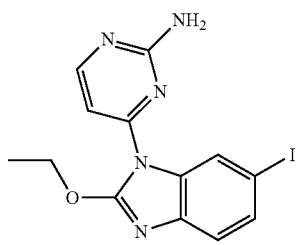

(114-b)

The title compound was prepared by replacing 4-N-(2-amino-5-bromophenyl)pyrimidine-2,4-diamine with 4-N-(2-amino-5-iodophenyl)pyrimidine-2,4-diamine in the procedure described in Example 112-a Step 1: ¹H NMR (500 MHz, DMSO) delta 1.46-1.59 (3H, m), 4.63-4.77 (2H, m), 7.01-7.10 (1H, m), 7.17 (2H, br. s.), 7.36 (1H, d, J=8.35 Hz), 7.54-7.68 (1H, m), 8.43 (1H, d, J=5.52 Hz), 8.58 (1 H, d, J=1.58 Hz), 12.04 (1H, br. s.); LC-MS: m/z=+381.9 (M+H)+.

Step 3—Synthesis of 7-{2-[1-(2-aminopyrimidin-4-yl)-2-ethoxy-1H-1,3-benzodiazol-6-yl]ethynyl}-5H,6H,7H-cyclopenta[b]pyridin-7-ol A mixture of 4-(2-ethoxy-6-iodo-1H-1,3-benzodiazol-1-yl)pyrimidin-2-amine (150 mg, 0.394 mmol) and 7-ethynyl-5H,6H-cyclopenta[b]pyridin-7-ol (118 mg, 0.59 mmol) was dissolved in piperidine (1 mL). The solution was de-gassed with nitrogen for 2 mins. Tetrakis(triphenylphosphine)palladium(0) (36 mg, 0.031 mmol) and copper(I) iodide (6 mg, 0.031 mmol) were added and the resultant solution heated to 30° C. for 2 hr. The mixture was concentrated in vacuo, DCM (10 mL) added and re-concentrated in vacuo (twice). The residue was purified by column chromatography (Biotage, 0-10% MeOH gradient in DCM), followed by reverse phase preparative HPLC purification to give the title compound; ¹H NMR (500 MHz, DMSO) delta 1.44 (3H, t, J=7.1 Hz), 2.36-2.42 (1H, m), 2.52-2.62 (1H, m), 2.83-2.95 (1H, m), 2.94-3.08 (1H, m), 4.63 (2H, q, J=7.0 Hz), 6.96 (1H, d, J=5.5 Hz), 7.08 (2H, s), 7.19-7.32 (2H, m), 7.44 (1H, d, J=8.2 Hz), 7.72 (1H, d, J=7.6 Hz), 8.13 (1H, s), 8.38 (1H, d, J=5.5 Hz), 8.44 (1H, d, J=4.8 Hz), 8.51 (1H, s); LC-MS: m/z=+413.05 (M+H)+.

Example 115

Preparation of 4-[1-(2-aminopyrimidin-4-yl)-2-ethoxy-1H-1,3-benzodiazol-6-yl]-2-(pyrimidin-2-yl)but-3-yn-2-ol

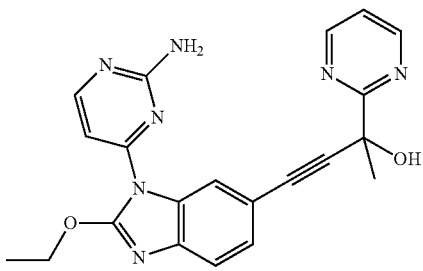

(115-c)

Step 1—Synthesis of 4-{2-ethoxy-6-[2-(trimethylsilyl)ethynyl]-1H-1,3-benzodiazol-1-yl}pyrimidin-2-amine

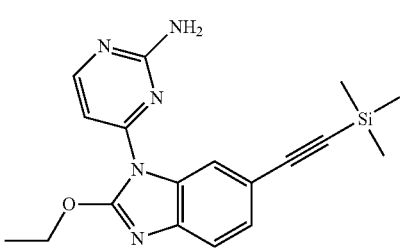

(115-a)

To a solution of 4-(6-bromo-2-ethoxy-1H-1,3-benzodiazol-1-yl)pyrimidin-2-amine (270 mg, 0.74 mmol) in piperidine (1.8 mL) was introduced tetrakis(triphenylphosphine)palladium(0) (69 mg, 0.06 mmol), copper(I) iodide (11 mg, 0.06 mmol) and ethynyltrimethylsilane (0.53 mL, 3.71 mmol). The reaction mixture was warmed to 65° C. for 3 hr. After cooling to RT, the reaction mixture was re-treated with further tetrakis(triphenylphosphine)palladium(0) (10 mg, 0.01 mmol), copper(I) iodide (5 mg, 0.03 mmol), ethynyltrimethylsilane (0.20 mL, 1.4 mmol) and warmed to 65° C. for an additional 2 hr. The reaction mixture was concentrated in vacuo and the residue re-dissolved in DCM (10 mL) and re-evaporated to dryness in vacuo (this procedure was repeated twice). Purification of the residue by column chromatography (Biotage, DCM containing a 2-8% gradient of methanol) furnished the title compound as an off-white solid: $^1$H NMR (250 MHz, DMSO) delta −0.07-0.07 (9 H, m), 1.21 (3H, t, J=7.01 Hz), 4.40 (2H, q, J=7.06 Hz), 6.65-6.81 (1H, m), 6.88 (2H, br. s.), 7.06 (1H, dd, J=8.15, 1.60 Hz), 7.20 (1H, d, J=8.22 Hz), 7.98 (1H, d, J=1.22 Hz), 8.12-8.25 (1H, m); LCMS: m/z=+352.45 (M+H)+.

Step 2—Synthesis of 4-(2-ethoxy-6-ethynyl-1H-1,3-benzodiazol-1-yl)pyrimidin-2-amine

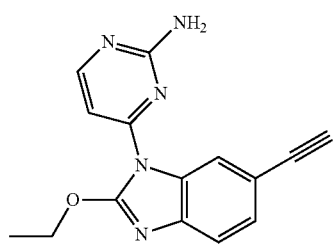

(115-b)

To a solution of 4-{2-ethoxy-6-[2-(trimethylsilyl)ethynyl]-1H-1,3-benzodiazol-1-yl}pyrimidin-2-amine (170 mg, 0.48 mmol) in dry THF (5 mL) at RT was introduced TBAF (0.58 mL of a 1M solution in THF, 0.58 mmol). After 20 minutes, the reaction mixture was concentrated in vacuo, DCM (5 mL) added, and the solution re-evaporated to dryness in vacuo (re-evaporation process repeated twice). Purification of the residue by column chromatography (Biotage, DCM containing a 1-7% gradient of methanol) furnished the title compound as a beige solid: $^1$H NMR (500 MHz, DMSO) delta 1.46 (3H, t, J=7.01 Hz), 4.10 (1H, s), 4.61-4.68 (2H, m), 6.97-7.03 (1H, m), 7.09 (2H, br. s.), 7.33 (1H, dd, J=8.12, 1.34 Hz), 7.45 (1H, d, J=8.04 Hz), 8.33 (1H, s), 8.37 (1H, d, J=5.52 Hz); LC-MS: m/z=+280.00 (M+H)+.

Step 3—Synthesis of 4-[1-(2-aminopyrimidin-4-yl)-2-ethoxy-1H-1,3-benzodiazol-6-yl]-2-(pyrimidin-2-yl)but-3-yn-2-ol To a solution of 4-(2-ethoxy-6-ethynyl-1H-1,3-benzodiazol-1-yl)pyrimidin-2-amine (110 mg, 0.37 mmol) in dry THF (1 mL) at −78° C. was introduced lithium diisopropylamide (0.47 mL of a 2M solution in THF, 0.935 mmol). After 5 minutes, 1-pyrimidin-2-yl-ethanone (81 mg, 0.65 mmol) was added and the reaction mixture maintained at −78° C. for 20 minutes. Following 30 minutes at RT, saturated aqueous ammonium chloride (0.5 ml) was added and the solution concentrated in vacuo. The residue was dissolved in DCM (10 mL), washed with water (2 mL), dried (Na$_2$SO$_4$), filtered and concentrated in vacuo. Purification of the residue by column chromatography (Biotage, DCM containing a 0-8% gradient of methanol) furnished the title compound as a beige solid: $^1$H NMR (500 MHz, DMSO) delta 1.44 (3H, t, J=7.09 Hz), 1.88 (3H, s), 4.63 (2H, q, J=7.09 Hz), 6.14 (1H, s), 6.96 (1H, d, J=5.36 Hz), 7.09 (2H, br.s.), 7.22 (1H, dd, J=8.20, 1.58 Hz), 7.43 (1H, d, J=8.20 Hz), 7.49 (1H, t, J=4.81 Hz), 8.10 (1H, d, J=1.10 Hz), 8.38 (1H, d, J=5.36 Hz), 8.88 (2H, d, J=4.89 Hz); LC-MS: m/z=+402.45 (M+H)+.

Example 116

Preparation of 7-{2-[1-(2-aminopyrimidin-4-yl)-2-ethoxy-1H-1,3-benzodiazol-6-yl]ethynyl}-5H,6H,7H-cyclopenta[b]pyridin-7-ol mono formate salt

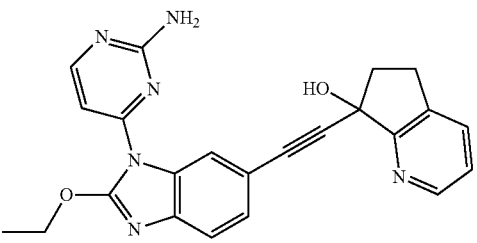 [SMILES: CCOc1nc2ccc(C#CC3(O)CCc4cccnc43)cc2n1-c1ccnc(N)n1]

To a solution of 4-(2-ethoxy-6-iodo-1H-1,3-benzodiazol-1-yl)pyrimidin-2-amine (150 mg, 0.39 mmol) in piperidine (2 mL) was introduced tetrakis(triphenylphosphine)palladium (0) (36.4 mg, 0.03 mmol), copper(I) iodide (6 mg, 0.03 mmol) and 7-ethynyl-5H,6H,7H-cyclopenta[b]pyridin-7-ol (117 mg, 0.59 mmol). The reaction was warmed to 30° C. for 2 hr. After the reaction mixture was concentrated in vacuo, DCM (5 mL) was added and the solution re-evaporated to dryness in vacuo (re-evaporation process repeated twice). Purification of the residue by column chromatography (Biotage, DCM containing a 0-8% gradient of methanol) furnished a partially purified product. Further purification by reverse phase preparative HPLC furnished the title compound as a yellow solid: $^1$H NMR (500 MHz, DMSO) delta 1.44 (3H, t, J=7.1 Hz), 2.36-2.42 (1H, m), 2.52-2.62 (1H, m), 2.83-2.95 (1H, m), 2.94-3.08 (1H, m), 4.63 (2H, q, J=7.0 Hz), 6.96 (1H, d, J=5.5 Hz), 7.08 (2H, s), 7.19-7.32 (2H, m), 7.44 (1H, d, J=8.2 Hz), 7.72 (1H, d, J=7.6 Hz), 8.13 (1H, s), 8.38 (1H, d, J=5.5 Hz), 8.44 (1H, d, J=4.8 Hz), 8.51 (1H, s); LC-MS: m/z=+413.05 (M+H)+.

Example 117

Preparation of (2R)-4-[1-(2-aminopyrimidin-4-yl)-2-(oxetan-3-yloxy)-1H-1,3-benzodiazol-6-yl]-2-(5-methyl-1,2-oxazol-3-yl)but-3-yn-2-ol

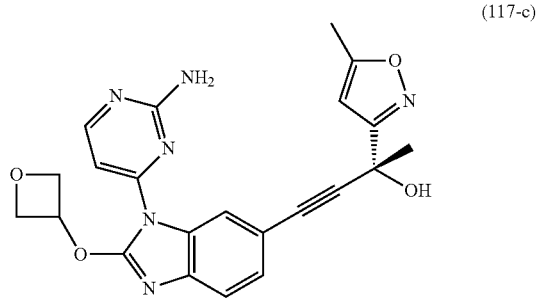 [SMILES: Cc1cc([C@](C)(O)C#Cc2ccc3nc(OC4COC4)n(-c4ccnc(N)n4)c3c2)no1]

(117-c)

Step 1—Synthesis of 4-[6-bromo-2-(trichloromethyl)-1,3-benzodiazol-1-yl]pyrimidin-2-amine

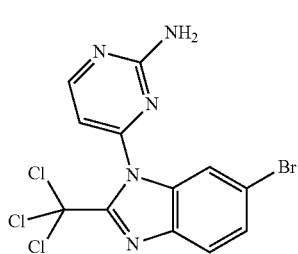

(117-a)

To a solution of 4-N-(2-amino-5-bromophenyl)pyrimidine-2,4-diamine (3.0 g, 10.71 mmol) in acetic acid (10 mL) was added methyl 2,2,2-trichloroethanimidoate (1.4 mL, 11.25 mmol). The reaction was stirred at 45° C. for 7 hr. Water (15 mL) was then added. The precipitate was collected by filtration and dried under vacuum to give the title product (3.94 g as the acetic acid salt); $^1$H NMR (500 MHz, DMSO) delta 1.90 (3H, s), 7.01 (1H, d, J=5.0 Hz), 7.21 (2H, s), 7.75-7.46 (2H, m), 8.09-7.75 (1H, m), 8.58 (1H, d, J=5.0 Hz); LC-MS: m/z=+406/408/410/412 (M+H)+.

Step 2—Synthesis of 4-[6-bromo-2-(oxetan-3-yloxy)-1,3-benzodiazol-1-yl]pyrimidin-2-amine

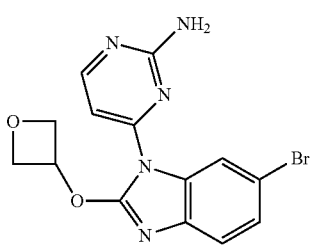

(117-b)

To a solution of oxetan-3-ol (0.04 ml, 0.61 mmol) in DMF (5 ml) at 0° C. was added cesium carbonate (499.75 mg, 1.53 mmol) followed by 4-[6-bromo-2-(trichloromethyl)-1,3-benzodiazol-1-yl]pyrimidin-2-amine (250 mg, 0.61 mmol). The reaction was stirred at RT overnight, then re-charged with oxetan-3-ol (3 eq) and stirred for a total of 5 days at RT. Water was added (15 ml) to the combined reaction mixtures and the product extracted into DCM (2×30 ml). The combined organic extracts were washed with water and brine (10 ml each), dried (Na$_2$SO$_4$), filtered and concentrated in vacuo to give the title compound; $^1$H NMR (500 MHz, DMSO) delta 4.83-4.70 (2H, m), 5.03-4.89 (2H, m), 5.85-5.75 (1H, m), 7.19-7.05 (3H, m), 7.51-7.34 (2H, m), 8.40 (1H, d, J=5.5 Hz), 8.45 (1H, d, J=1.7 Hz); LC-MS: m/z=+362/364 (M+H)+.

Step 3—Synthesis of (2R)-4-[1-(2-aminopyrimidin-4-yl)-2-(oxetan-3-yloxy)-1H-1,3-benzodiazol-6-yl]-2-(5-methyl-1,2-oxazol-3-yl)but-3-yn-2-ol The title compound was prepared by the method described in Example 142-b, by reacting 4-[6-bromo-2-(oxetan-3-yloxy)-1H-1,3-benzodiazol-1-yl]pyrimidin-2-amine with (2R)-2-(5-methyl-1,2-oxazol-3-yl)but-3-yn-2-ol: $^1$H NMR (500 MHz, DMSO) delta 1.81 (3H, s), 2.40 (3H, s), 4.80-4.71 (2H, m), 4.96 (2H, t, J=7.1 Hz), 5.87-5.78 (1H, m), 6.37 (1H, s), 6.46 (1 H, s), 7.22-7.04 (3H, m), 7.28 (1H, dd, J=8.2, 1.5 Hz), 7.45 (1H, d, J=8.2 Hz), 8.18 (1H, s), 8.42 (1 H, d, J=5.5 Hz); LC-MS: m/z=+433.15 (M+H)+.

Example 118

Preparation of 4-[1-(2-aminopyrimidin-4-yl)-2-(oxetan-3-yloxy)-1H-1,3-benzodiazol-6-yl]-2-methyl-but-3-yn-2-ol

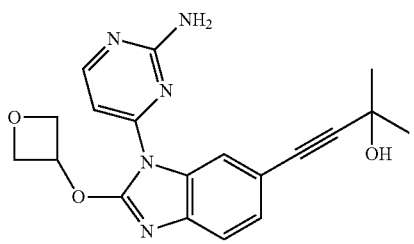 [SMILES: CC(C)(O)C#Cc1ccc2nc(OC3COC3)n(-c3ccnc(N)n3)c2c1]

The title compound was prepared by the method described in Example 142-b, by reacting 4-[6-bromo-2-(oxetan-3-yloxy)-1H-1,3-benzodiazol-1-yl]pyrimidin-2-amine with 2-methyl-3-butyn-2-ol: $^1$H NMR (DMSO, 500 MHz) delta 1.46 (6H, s), 4.73 (2H, dd, J=7.9, 4.9 Hz), 4.94 (2H, t, J=7.1 Hz), 5.40 (1H, s), 5.94-5.68 (1H, m), 7.17-6.99 (3H, m), 7.21 (1H, dd, J=8.2, 1.6 Hz), 7.41 (1H, d, J=8.2 Hz), 8.14 (1H, d, J=1.0 Hz), 8.39 (1H, d, J=5.5 Hz); LC-MS: m/z=+366.1 (M+H)+.

Example 119

Preparation of (2R)-4-[1-(2-aminopyrimidin-4-yl)-2-(2-methoxyethoxy)-1H-1,3-benzodiazol-6-yl]-2-(5-methyl-1,2-oxazol-3-yl)but-3-yn-2-ol

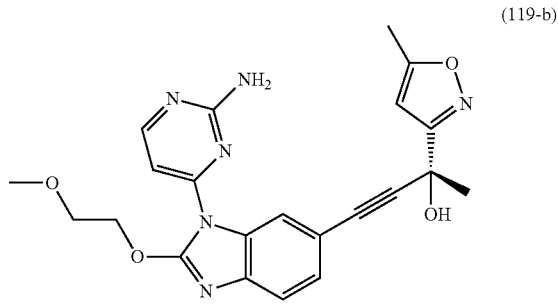 [SMILES: COCCOc1nc2ccc(C#C[C@@](C)(O)c3cc(C)on3)cc2n1-c1ccnc(N)n1]

(119-b)

Step 1—Synthesis of 4-[6-bromo-2-(2-methoxyethoxy)-1H-1,3-benzodiazol-1-yl]pyrimidin-2-amine

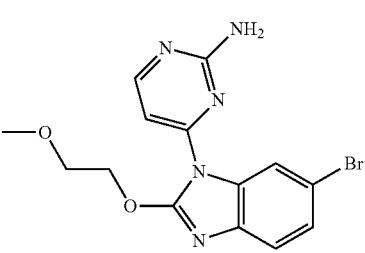

(119-a)

The title compound was prepared by the procedure described for the synthesis of 4-[6-bromo-2-(oxetan-3-yloxy)-1H-1,3-benzodiazol-1-yl]pyrimidin-2-amine, by replacing oxetan-3-ol with 2-methoxyethanol: ¹H NMR (500 MHz, DMSO) delta 3.31 (3H, s), 3.83-3.72 (2 H, m), 4.77-4.61 (2H, m), 7.02 (1H, d, J=5.5 Hz), 7.12 (2H, s), 7.48-7.33 (2H, m), 8.38 (1H, d, J=5.5 Hz), 8.45 (1H, d, J=1.8 Hz); LC-MS: m/z=+364/366 (M+H)+.

Step 2—(2R)-4-[1-(2-aminopyrimidin-4-yl)-2-(2-methoxyethoxy)-1H-1,3-benzodiazol-6-yl]-2-(5-methyl-1,2-oxazol-3-yl)but-3-yn-2-ol The title compound was prepared by the method described in Example 142-b, by reacting 4-[6-bromo-2-(2-methoxyethoxy)-1,3-benzodiazol-1-yl]pyrimidin-2-amine with (2R)-2-(5-methyl-1,2-oxazol-3-yl)but-3-yn-2-ol: ¹H NMR (500 MHz, DMSO) delta 1.81 (3H, s), 2.41 (3H, s), 3.95-3.64 (2H, m), 4.84-4.63 (2H, m), 6.38 (1H, s), 6.46 (1H, s), 6.98 (1H, d, J=5.5 Hz), 7.11 (2H, s), 7.28 (1H, dd, J=8.0, 1.2 Hz), 7.46 (1H, d, J=8.2 Hz), 8.18 (1H, s), 8.40 (1H, d, J=5.4 Hz); LC-MS: m/z=+435.0 (M+H)+.

Example 120

Preparation of (2R)-4-[1-(2-aminopyrimidin-4-yl)-2-[(2-methoxyethyl)amino]-1H-1,3-benzodiazol-6-yl]-2-(5-methyl-1,2-oxazol-3-yl)but-3-yn-2-ol

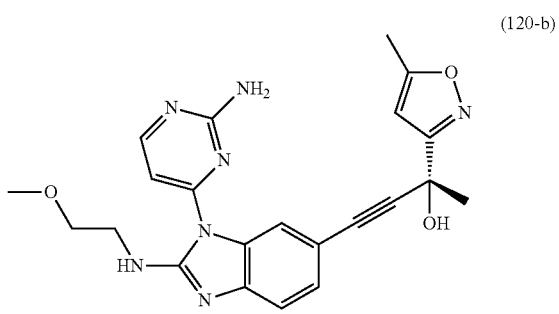

(120-b)

Step 1—Synthesis of 1-(2-aminopyrimidin-4-yl)-6-bromo-N-(2-methoxyethyl)-1H-1,3-benzodiazol-2-amine

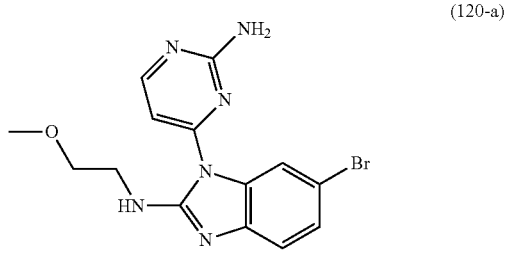 [SMILES: COCCOc1nc2ccc(Br)cc2n1-c1ccnc(N)n1]

(120-a)

A mixture of 2-methoxyethanamine (5 mL) and 4-[6-bromo-2-(trichloromethyl)-1H-1,3-benzodiazol-1-yl]pyrimidin-2-amine (500 mg, 1.23 mmol) were stirred at RT for 3 days. The reaction mixture was then concentrated in vacuo and EtOAc/heptane (2:1) added. The solvent was removed in vacuo and this was repeated (×2). The resulting solid was then triturated from EtOAc:heptane (1:2). The solid was then dissolved in DCM (5 ml) and washed with water (2×2 ml). The organic phase was dried (Na₂SO₄), filtered and concentrated in vacuo to give the title compound (145 mg, 45% yield): ¹H NMR (500 MHz, DMSO) delta 3.28 (3H, s), 3.71-3.53 (4H, m), 6.93 (1H, d, J=5.5), 7.14 (2H, s), 7.31-7.20 (2H, m), 7.67 (1H, d, J=1.6), 8.13 (1H, t, J=5.3), 8.41 (1H, d, J=5.5); LC-MS: m/z=363/365 (M+H)+.

Step 2—Synthesis of (2R)-4-[1-(2-aminopyrimidin-4-yl)-2-[(2-methoxyethyl)amino]-1H-1,3-benzodiazol-6-yl]-2-(5-methyl-1,2-oxazol-3-yl)but-3-yn-2-ol The title compound was prepared by the method described in Example 142-b, by reacting 1-(2-aminopyrimidin-4-yl)-6-bromo-N-(2-methoxyethyl)-1H-1,3-benzodiazol-2-amine with (2R)-2-(5-methyl-1,2-oxazol-3-yl)but-3-yn-2-ol: ¹H NMR (250 MHz, DMSO) delta 1.79 (3H, s), 2.40 (3H, s), 3.28 (3H, s), 3.72-3.53 (4H, m), 6.35 (1H, s), 6.41 (1H, s), 6.91 (1H, d, J=5.5 Hz), 7.34-7.07 (4H, m), 7.50 (1H, d, J=1.0 Hz), 8.23 (1H, t, J=5.5 Hz), 8.43 (1H, d, J=5.5 Hz); LC-MS: m/z=+434.15 (M+H)+.

Example 121

Preparation of 4-[1-(2-aminopyrimidin-4-yl)-2-(2-methoxyethoxy)-1H-1,3-benzodiazol-6-yl]-2-(pyrimidin-2-yl)but-3-yn-2-ol

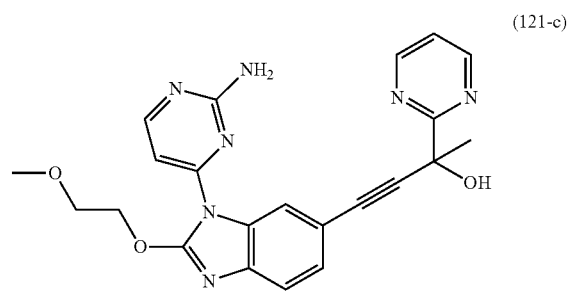 [SMILES: COCCOc1nc2ccc(C#CC(C)(O)c3ncccn3)cc2n1-c1ccnc(N)n1]

(121-c)

Step 1—Synthesis of 4-[6-iodo-2-(trichloromethyl)-1H-1,3-benzodiazol-1-yl]pyrimidin-2-amine

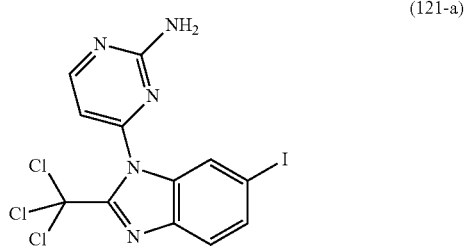 [SMILES: Nc1nccc(-n2c(C(Cl)(Cl)Cl)nc3ccc(I)cc32)n1]

(121-a)

The title compound was prepared by procedure described for 4-[6-bromo-2-(trichloromethyl)-1H-1,3-benzodiazol-1-yl]pyrimidin-2-amine, by replacing 4-N-(2-amino-5-bromophenyl)pyrimidine-2,4-diamine with 4-N-(2-amino-5-iodophenyl)pyrimidine-2,4-diamine: ¹H NMR (500 MHz, DMSO) delta 1.91 (3H, s), 7.01 (1H, d, J=5.1 Hz), 7.22 (2H, s), 7.77-7.69 (3H, m), 8.58 (1H, d, J=5.0 Hz), 11.97 (1H, s); LC-MS: m/z=+454/456/458 (M+H)+.

Step 2—Synthesis of 4-[6-iodo-2-(2-methoxy-ethoxy)-1H-1,3-benzodiazol-1-yl]pyrimidin-2-amine

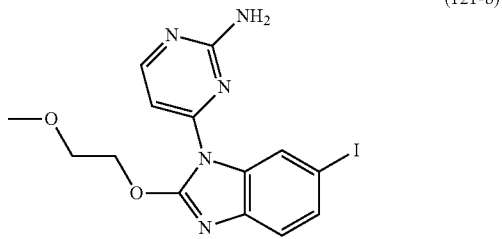

(121-b)

The title compound was prepared by the procedure described for the synthesis of 4-[6-bromo-2-(oxetan-3-yloxy)-1H-1,3-benzodiazol-1-yl]pyrimidin-2-amine by reacting 4-[6-iodo-2-(trichloromethyl)-1H-1,3-benzodiazol-1-yl]pyrimidin-2-amine with 2-methoxyethanol: LC-MS: m/z=+412 (M+H)+.

Step 3—Synthesis of 4-[1-(2-aminopyrimidin-4-yl)-2-(2-methoxyethoxy)-1H-1,3-benzodiazol-6-yl]-2-(pyrimidin-2-yl)but-3-yn-2-ol To a pressure tube was added 4-[6-iodo-2-(2-methoxy-ethoxy)-1H-1,3-benzodiazol-1-yl]pyrimidin-2-amine (70%, 120 mg, 0.2 mmol) followed by piperidine (1.0 mL), tetrakis(triphenylphosphine)palladium(0) (23.61 mg, 0.02 mmol), copper(I) iodide (3.89 mg, 0.02 mmol) and 2-(pyrimidin-2-yl)but-3-yn-2-ol (60.53 mg, 0.41 mmol). The reaction was capped and stirred at RT for 1 h. The reaction mixture was concentrated in vacuo. The crude material was purified by flash column chromatography (1-10% MeOH gradient in DCM), followed by trituration with EtOAc/heptanes/DCM to give the title compound: $^1$H NMR (500 MHz, DMSO) delta 1.88 (3H, s), 3.92-3.64 (2H, m), 4.84-4.59 (2H, m), 6.13 (1H, s), 6.97 (1H, d, J=5.5 Hz), 7.10 (2H, s), 7.23 (1H, dd, J=8.2, 1.5 Hz), 7.44 (1H, d, J=8.1 Hz), 7.49 (1H, t, J=4.8 Hz), 8.13 (1H, s), 8.39 (1H, d, J=5.5 Hz), 8.89 (2H, d, J=4.9 Hz); LC-MS: m/z=+432.05 (M+H)+.

Example 122

Preparation of (2R)-4-[1-(2-aminopyrimidin-4-yl)-2-(2-methoxyethoxy)-1H-1,3-benzodiazol-6-yl]-2-(5-methyl-1,2,4-oxadiazol-3-yl)but-3-yn-2-ol

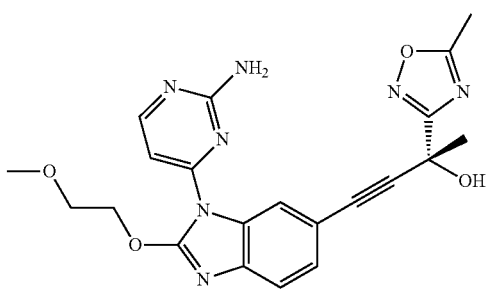

The title compound was prepared by the procedure described for the synthesis of 4-[1-(2-aminopyrimidin-4-yl)-2-(2-methoxyethoxy)-1H-1,3-benzodiazol-6-yl]-2-(pyrimidin-2-yl)but-3-yn-2-ol (Example 121-c), by reacting 4-[6-iodo-2-(2-methoxyethoxy)-1,3-benzodiazol-1-yl]pyrimidin-2-amine with (2R)-2-(5-methyl-1,2,4-oxadiazol-3-yl)but-3-yn-2-ol: $^1$H NMR (500 MHz, DMSO) delta 1.84 (3H, s), 2.61 (3H, s), 3.31 (3H, s), 3.84-3.69 (2H, m), 4.76-4.63 (2H, m), 6.66 (1H, s), 6.97 (1H, d, J=5.5 Hz), 7.09 (2H, s), 7.28 (1H, dd, J=8.2, 1.5 Hz), 7.46 (1H, d, J=8.2 Hz), 8.18 (1H, d, J=1.0 Hz), 8.39 (1H, d, J=5.5 Hz); LC-MS: m/z=+436.1 (M+H)+.

Example 123

Preparation of 4-(3-(2-aminopyrimidin-4-yl)-2-(2,2,2-trifluoroethoxy)-3H-benzo[d]imidazol-5-yl)-2-(5-methylisoxazol-3-yl)but-3-yn-2-ol

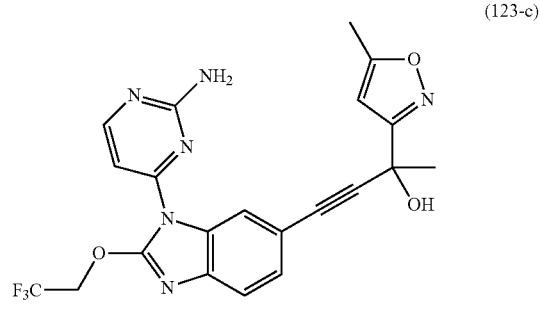 [SMILES: Cc1cc(C(C)(O)C#Cc2ccc3nc(OCC(F)(F)F)n(-c4ccnc(N)n4)c3c2)no1]

(123-c)

Step 1: Synthesis of 4-(6-bromo-2-(trichloromethyl)-1H-benzo[d]imidazol-1-yl)pyrimidin-2-amine

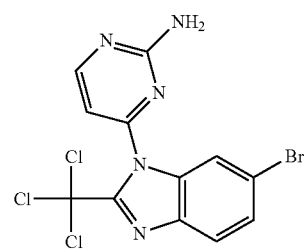

(123-a)

To a solution of 4-N-(2-amino-5-bromophenyl)pyrimidine-2,4-diamine (16.5 g, 58.90 mmol) in acetic acid (55 mL) was added methyl 2,2,2-trichloroethanecarboximidate (11 g, 62.35 mmol) dropwise with stirring. The reaction mixture was stirred at room temperature for 3 hr and then at 45° C. overnight. The resulting solution was diluted with 100 mL of water and the precipitate was collected by filtration. The solid was dried in a vacuum oven to give 19.5 g (81%) of 4-[6-bromo-2-(trichloromethyl)-1H-1,3-benzodiazol-1-yl]pyrimidin-2-amine as a light brown solid: $^1$H NMR (300 MHz, DMSO) delta 8.58 (d, J=4.8 Hz, 1H), 7.68 (t, J=4.5 Hz, 1H), 7.61-7.58 (m, 2H), 7.21 (s, 2H), 7.01 (d, J=5.1 Hz, 3H); LC-MS: m/z=+408 (M+H)+.

Step 2: Synthesis of 4-(6-bromo-2-(2,2,2-trifluoroethoxy)-1H-benzo[d]imidazol-1-yl)pyrimidin-2-amine

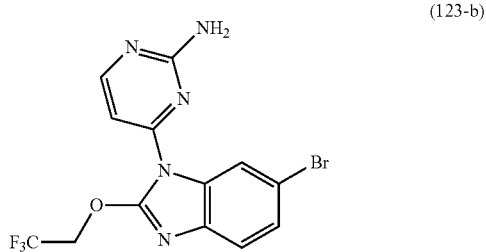 [SMILES: Nc1nccc(-n2c(OCC(F)(F)F)nc3ccc(Br)cc32)n1]

(123-b)

A mixture of 4-[6-bromo-2-(trichloromethyl)-1H-1,3-benzodiazol-1-yl]pyrimidin-2-amine (500 mg, 1.23 mmol), 2,2,2-trifluoroethan-1-ol (500 mg, 5.00 mmol) and cesium carbonate (2.5 g, 7.67 mmol) in N,N-dimethylformamide (5 mL) placed in a 10-mL sealed tube maintained under nitrogen was irradiated with microwave radiation at 70° C. for 2 hr. The residue was purified on a C18 column (acetonitrile/water, 5:95-80:20) to yield 260 mg (46%) of 4-[6-bromo-2-(2,2,2-trifluoroethoxy)-1H-1,3-benzodiazol-1-yl]pyrimidin-2-amine as a yellow solid. LC-MS: m/z=+388 (M+H)+.

Step 3: Synthesis of 4-(3-(2-aminopyrimidin-4-yl)-2-(2,2,2-trifluoroethoxy)-3H-benzo[d]imidazol-5-yl)-2-(5-methylisoxazol-3-yl)but-3-yn-2-ol A mixture of 4-[6-bromo-2-(2,2,2-trifluoroethoxy)-1H-1,3-benzodiazol-1-yl]pyrimidin-2-amine (120 mg, 0.31 mmol), 2-(5-methyl-1,2-oxazol-3-yl)but-3-yn-2-ol (120 mg, 0.79 mmol) and bis(triphenylphosphine)palladium(II) dichloride (200 mg, 0.28 mmol) in dimethylsulfoxide (2 mL) and triethylamine (1 mL) kept in a 10-mL vial under nitrogen was irradiated with microwave radiation for 2 h at 70° C. The reaction mixture was concentrated in vacuo. The crude product (120 mg) was purified by preparative HPLC to give 55 mg (39%) of 4-[1-(2-aminopyrimidin-4-yl)-2-(2,2,2-trifluoroethoxy)-1H-1,3-benzodiazol-6-yl]-2-(5-methyl-1,2-oxazol-3-yl)but-3-yn-2-ol as a light yellow solid: $^1$H NMR (400 MHz, DMSO) delta 8.45 (d, J=5.2 Hz, 1H), 8.17 (s, 1H), 7.53 (d, J=8.0 Hz, 1H), 7.33 (d, J=8.0 Hz, 1H), 7.17 (s, 2H), 6.86 (d, J=5.2 Hz, 1H), 6.46 (s, 1H), 6.38 (s, 1H), 5.37-5.30 (m, 2H), 2.41 (s, 3H), 1.82 (s, 3H); LC-MS: m/z=+459 (M+H)+.

Example 124

Preparation of 4-(3-(2-aminopyrimidin-4-yl)-2-(2-hydroxyethoxy)-3H-benzo[d]imidazol-5-yl)-2-(5-methylisoxazol-3-yl)but-3-yn-2-ol

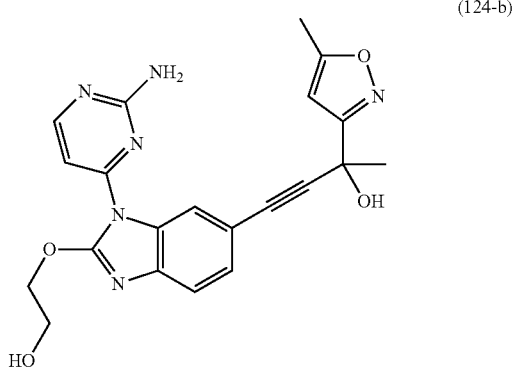 [SMILES: Cc1cc(C(C)(O)C#Cc2ccc3nc(OCCO)n(-c4ccnc(N)n4)c3c2)no1]

(124-b)

Step 1—Synthesis of 2-(1-(2-aminopyrimidin-4-yl)-6-bromo-1H-benzo[d]imidazol-2-yloxy)ethanol

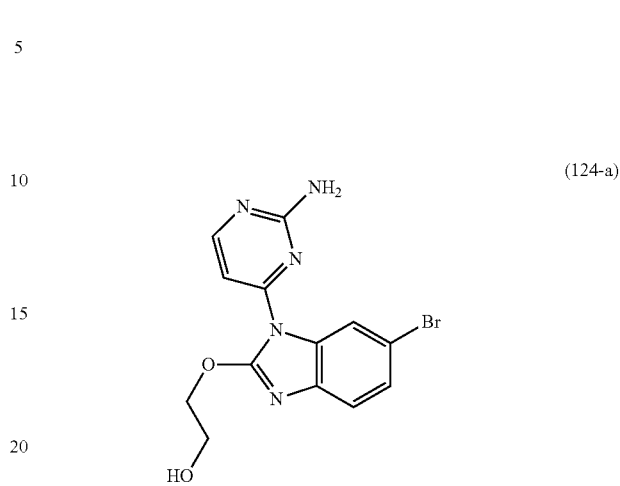

(124-a)

A mixture of 4-[6-bromo-2-(trichloromethyl)-1H-1,3-benzodiazol-1-yl]pyrimidin-2-amine (1 g, 2.45 mmol), ethane-1,2-diol (15 mL) and cesium carbonate (3 g, 9.18 mmol) was stirred overnight at room temperature and then diluted with 200 mL of water. The resulting solution was extracted with 2×200 mL of dichloromethane. The combined organic layers were washed with 3×200 mL of water, dried over anhydrous sodium sulfate and concentrated under vacuum to afford 300 mg (34%) of 2-[[1-(2-aminopyrimidin-4-yl)-6-bromo-1H-1,3-benzodiazol-2-yl]oxy]ethan-1-ol as a yellow solid. $^1$H NMR (300 MHz, DMSO) delta 8.39 (d, J=5.4 Hz, 1H), 8.30 (s, 1H), 7.51 (s, 2H), 7.09 (d, J=5.4 Hz, 1H), 4.78 (t, J=5.2 Hz, 2H), 4.08 (t, J=4.2 Hz, 2H); LC-MS: m/z=+350 (M+H)+.

Step 2—Synthesis of 4-(3-(2-aminopyrimidin-4-yl)-2-(2-hydroxyethoxy)-3H-benzo[d]imidazol-5-yl)-2-(5-methylisoxazol-3-yl)but-3-yn-2-ol A solution of 2-[[1-(2-aminopyrimidin-4-yl)-6-bromo-1H-1,3-benzodiazol-2-yl]oxy]ethan-1-ol (80 mg, 0.19 mmol), 2-(5-methyl-1,2-oxazol-3-yl)but-3-yn-2-ol (80 mg, 0.53 mmol), bis(triphenylphosphine)palladium(II) dichloride (20 mg, 0.03 mmol) and triethylamine (0.7 mL) in dimethylsulfoxide (3 mL) under nitrogen in a 10-mL sealed tube was irradiated with microwave radiation for 30 min at 70° C. The reaction mixture was concentrated and the crude product (80 mg) was purified by Flash-Preparative HPLC to give 24 mg (28%) of 4-[1-(2-aminopyrimidin-4-yl)-2-(2-hydroxyethoxy)-1H-1,3-benzodiazol-6-yl]-2-(5-methyl-1,2-oxazol-3-yl)but-3-yn-2-ol as a yellow solid. $^1$H NMR (400 MHz, DMSO-d6) delta 8.39 (d, J=5.6 Hz, 1H), 8.19 (s, 1H), 7.46 (d, J=8.0 Hz, 1H), 7.27 (d, J=8.0 Hz, 1H), 7.06 (s, 3H), 6.43 (s, 1H), 6.37 (s, 1H), 5.03 (t, J=5.2 Hz, 1H), 4.62 (s, 2H), 3.82 (d, J=4.0 Hz, 2H), 2.41 (s, 3H), 1.81 (s, 3H); LC-MS: m/z=+455 (M+H)+.

Example 125

Preparation of 1-(3-[[1-(2-aminopyrimidin-4-yl)-6-[3-hydroxy-3-(5-methyl-1,2-oxazol-3-yl)but-1-yn-1-yl]-1H-1,3-benzodiazol-2-yl]oxy]azetidin-1-yl)ethan-1-one

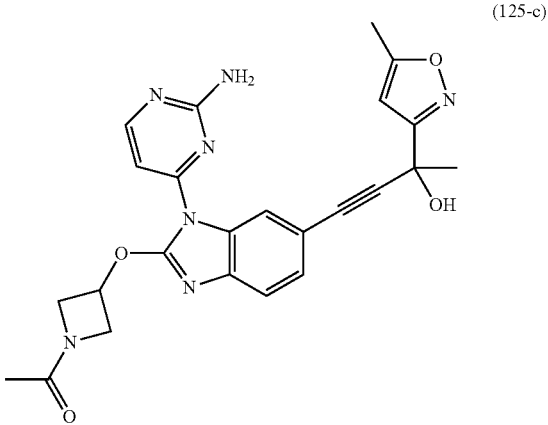 [SMILES: CC(=O)N1CC(Oc2nc3ccc(C#CC(C)(O)c4cc(C)on4)cc3n2-c2ccnc(N)n2)C1]

(125-c)

Step 1—Synthesis of 1-(3-hydroxyazetidin-1-yl)ethan-1-one

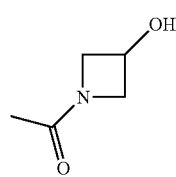

(125-a)

To a solution of azetidin-3-ol (3.0 g, 27.40 mmol) and triethylamine (8.33 g, 82.48 mmol) in tetrahydrofuran (150 mL) was added acetyl chloride (2.15 g, 27.39 mmol) drop-wise with stirring at −78° C. over 10 min. The resulting solution was stirred for 3 h at 20-30° C. The solid material was removed by filtration. The filtrate was concentrated under vacuum and purified on a silica gel column (methanol/ethyl acetate (1/10)) to afford 500 mg (14%) of 1-(3-hydroxyazetidin-1-yl)ethan-1-one as yellow oil. $^1$H NMR (400 MHz, DMSO) delta 3.60 (t, J=4.8 Hz, 2H), 2.83 (t, J=4.8 Hz, 2H), 2.21 (s, 3H).

Step 2—Synthesis of 1-(3-[[1-(2-aminopyrimidin-4-yl)-6-bromo-1H-1,3-benzodiazol-2-yl]oxy]azetidin-1-yl)ethan-1-one

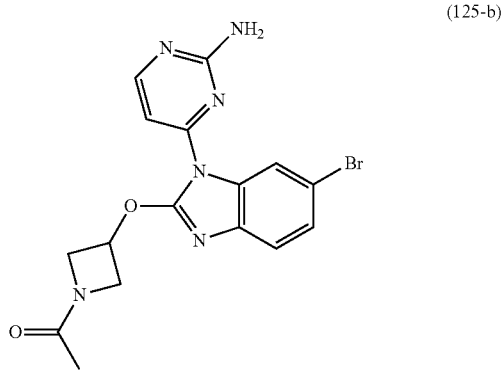 [SMILES: CC(=O)N1CC(Oc2nc3ccc(Br)cc3n2-c2ccnc(N)n2)C1]

(125-b)

A mixture of 4-[6-bromo-2-(trichloromethyl)-1H-1,3-benzodiazol-1-yl]pyrimidin-2-amine (500 mg, 1.23 mmol), 1-(3-hydroxyazetidin-1-yl)ethan-1-one (1 g, 8.69 mmol) and potassium t-butoxide (500 mg, 5.21 mmol) in N,N-dimethylformamide (5 mL) kept under nitrogen in a 30-mL sealed tube was stirred overnight at room temperature. The reaction mixture was filtered through a frit filter and the filtrate was purified on a C18 column (acetonitrile/water, 5:95-80:20) to yield 160 mg (29%) of 1-(3-[[1-(2-aminopyrimidin-4-yl)-6-bromo-1H-1,3-benzodiazol-2-yl]oxy]azetidin-1-yl)ethan-1-one as a yellow solid. LC-MS: m/z=+403 (M+H)+.

Step 3—Synthesis of 1-(3-[[1-(2-aminopyrimidin-4-yl)-6-[3-hydroxy-3-(5-methyl-1,2-oxazol-3-yl)but-1-yn-1-yl]-1H-1,3-benzodiazol-2-yl]oxy]azetidin-1-yl)ethan-1-one A mixture of 1-(3-[[1-(2-aminopyrimidin-4-yl)-6-bromo-1H-1,3-benzodiazol-2-yl]oxy]azetidin-1-yl)ethan-1-one (130 mg, 0.29 mmol), 2-(5-methyl-1,2-oxazol-3-yl)but-3-yn-2-ol (200 mg, 1.32 mmol), bis(triphenylphosphine)palladium(II) dichloride (250 mg, 0.36 mmol) and triethylamine (1 mL) in DMSO (2 mL) was stirred under nitrogen for 5 h at 70° C. The reaction mixture was cooled to room temperature then filtered through a frit filter. The filtrate was purified by preparative HPLC to give 30 mg (21%) of 1-(3-[[1-(2-aminopyrimidin-4-yl)-6-[3-hydroxy-3-(5-methyl-1,2-oxazol-3-yl)but-1-yn-1-yl]-1H-1,3-benzodiazol-2-yl]oxy]azetidin-1-yl)ethan-1-one as a white solid: $^1$H NMR (400 MHz, DMSO) delta 8.41 (d, J=5.6 Hz, 1H), 8.19 (s, 1H), 7.48 (d, J=8.4 Hz, 1H), 7.29 (d, J=8.0 Hz, 1H), 7.11-7.07 (m, 3H), 6.45 (s, 1H), 6.38 (s, 1H), 5.57 (t, J=3.6 Hz, 1H), 4.61 (t, J=8.0 Hz, 1H), 4.37-4.29 (m, 2H), 4.03 (t, J=5.2 Hz, 1H), 2.41 (s, 3H), 1.81 (d, J=4.4 Hz, 6H); LC-MS: m/z=+474 (M+H)+.

Example 126

Preparation of 4-[1-(2-aminopyrimidin-4-yl)-2-(oxan-4-yloxy)-1H-1,3-benzodiazol-6-yl]-2-(5-methyl-1,2-oxazol-3-yl)but-3-yn-2-ol

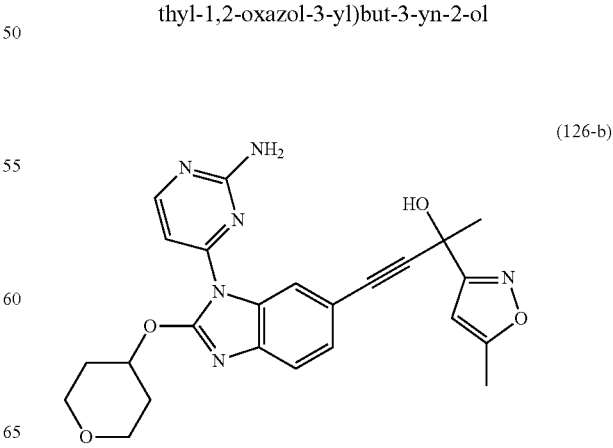

(126-b)

Step 1—Synthesis of 4-[6-bromo-2-(oxan-4-yloxy)-1H-1,3-benzodiazol-1-yl]pyrimidin-2-amine (126-a)

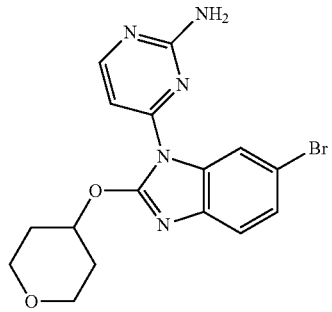

Sodium hydride (200 mg, 5.00 mmol, 60% dispersion in mineral oil) was added in several portions into a solution of 4-[6-bromo-2-(trichloromethyl)-1H-1,3-benzodiazol-1-yl]pyrimidin-2-amine (500 mg, 1.23 mmol) and oxan-4-ol (1.00 g, 9.79 mmol) in N,N-dimethylformamide (10 mL) under an atmosphere of nitrogen. The reaction mixture was stirred overnight at room temperature and then filtered through a frit filter. The filtrate was purified on a C18 column (acetonitrile/water, 5:95-80:20) to give 170 mg (28%) of 4-[6-bromo-2-(oxan-4-yloxy)-1H-1,3-benzodiazol-1-yl]pyrimidin-2-amine as a brown solid. LC-MS: m/z=+390 (M+H)+.

Step 2—Synthesis of 4-[1-(2-aminopyrimidin-4-yl)-2-(oxan-4-yloxy)-1H-1,3-benzodiazol-6-yl]-2-(5-methyl-1,2-oxazol-3-yl)but-3-yn-2-ol A mixture of 4-[6-bromo-2-(oxan-4-yloxy)-1H-1,3-benzodiazol-1-yl]pyrimidin-2-amine (150 mg, 0.27 mmol, 70%), 2-(5-methyl-1,2-oxazol-3-yl)but-3-yn-2-ol (200 mg, 1.32 mmol), bis(triphenylphosphine)palladium(II) dichloride (220 mg, 0.31 mmol) and triethylamine (1 mL) in dimethylsulfoxide (2 mL) was stirred under nitrogen atmosphere for 5 hr at 70° C. The reaction mixture was cooled to room temperature then filtered through a frit filter to remove the catalyst. The filtrate was purified by preparative HPLC to give 30 mg (24%) of 4-[1-(2-aminopyrimidin-4-yl)-2-(oxan-4-yloxy)-1H-1,3-benzodiazol-6-yl]-2-(5-methyl-1,2-oxazol-3-yl)but-3-yn-2-ol as a white solid. $^1$H NMR (400 MHz, DMSO) delta 8.41 (d, J=5.6 Hz, 1H), 8.15 (s, 1H), 7.46 (d, J=8.0 Hz, 1H), 7.28-7.07 (m, 1H), 7.08 (s, 2H), 6.99 (d, J=5.6 Hz, 1H), 6.46 (s, 1H), 6.37 (s, 1H), 5.39-5.35 (m, 1H), 3.88-3.82 (m, 2H), 3.06-3.55 (m, 2H), 2.51 (s, 3H), 2.24-2.16 (m, 2H), 1.88-1.82 (m, 5H); LC-MS: m/z=+461 (M+H)+.

Example 127

Preparation of 3-[[1-(2-aminopyrimidin-4-yl)-6-[3-hydroxy-3-(5-methyl-1,2-oxazol-3-yl)but-1-yn-1-yl]-1H-1,3-benzodiazol-2-yl]oxy]propane-1,2-diol (127-b)

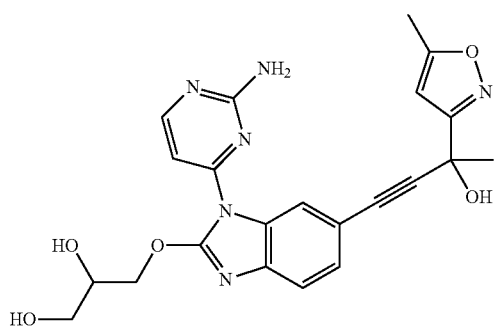

Step 1—Synthesis of 3-[[1-(2-aminopyrimidin-4-yl)-6-bromo-1H-1,3-benzodiazol-2-yl]oxy]propane-1,2-diol (127-a)

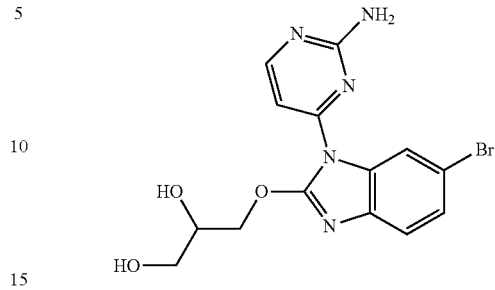

A mixture of 4-[6-bromo-2-(trichloromethyl)-1H-1,3-benzodiazol-1-yl]pyrimidin-2-amine (500 mg, 1.23 mmol), cesium carbonate (3.2 g, 9.82 mmol) and propane-1,2,3-triol (565 mg, 6.14 mmol) in N,N-dimethylformamide (3 mL) was stirred for 12 h at room temperature. The reaction mixture was filtered through a frit filter to remove any solid material and the filtrate was purified by Flash-Preparative HPLC to give 90 mg (19%) of 3-[[1-(2-aminopyrimidin-4-yl)-6-bromo-1H-1,3-benzodiazol-2-yl]oxy]propane-1,2-diol as a yellow solid. $^1$H NMR (400 MHz, DMSO) delta 8.46 (s, 1H), 8.37 (d, J=5.2 Hz, 1H), 7.44-7.38 (m, 2H), 7.13-7.09 (m, 3H), 5.18 (d, J=5.2 Hz, 1H), 4.80 (d, J=6.0 Hz, 1H), 4.68-4.64 (m, 1H), 4.52-4.48 (m, 1H), 3.93 (d, J=4.8 Hz, 1H), 3.52-3.46 (m, 2H); LC-MS: m/z=+380 (M+H)+.

Step 2—Synthesis of 3-[[1-(2-aminopyrimidin-4-yl)-6-[3-hydroxy-3-(5-methyl-1,2-oxazol-3-yl)but-1-yn-1-yl]-1H-1,3-benzodiazol-2-yl]oxy]propane-1,2-diol A mixture of 3-[[1-(2-aminopyrimidin-4-yl)-6-bromo-1H-1,3-benzodiazol-2-yl]oxy]propane-1,2-diol (80 mg, 0.21 mmol), 2-(5-methyl-1,2-oxazol-3-yl)but-3-yn-2-ol (160 mg, 1.06 mol), bis(triphenylphosphine)palladium(II) dichloride (160 mg, 0.22 mmol) and triethylamine (1 mL) in DMSO (2 mL) was stirred for 5 h at 70° C. under nitrogen atmosphere. The reaction mixture was cooled to room temperature and filtered through a frit filter. The filtrate was purified by preparative HPLC to afford 23 mg (24%) of 3-[[1-(2-aminopyrimidin-4-yl)-6-[3-hydroxy-3-(5-methyl-1,2-oxazol-3-yl)but-1-yn-1-yl]-1H-1,3-benzodiazol-2-yl]oxy]propane-1,2-diol as a white solid. $^1$H NMR (300 MHz, DMSO) delta 8.38 (d, J=5.4 Hz, 1H), 8.20 (s, 1H), 7.46 (d, J=8.1 Hz, 1H), 7.28 (d, J=8.1 Hz, 1H), 7.07-7.05 (m, 3H), 6.46 (s, 1H), 6.38 (s, 1H), 5.19 (d, J=5.4 Hz, 1H), 4.83-4.80 (m, 1H), 4.64 (d, J=3.6 Hz, 1H), 4.52 (d, J=6.3 Hz, 1H), 3.93 (d, J=4.5 Hz, 1H), 3.52-3.49 (m, 3H), 2.40 (s, 3H), 1.82 (s, 3H); LC-MS: m/z=451 (M+H)+.

Example 128

Preparation of 4-[1-(2-aminopyrimidin-4-yl)-2-(2,2,2-trifluoroethoxy)-1H-1,3-benzodiazol-6-yl]-2-(pyrimidin-2-yl)but-3-yn-2-ol

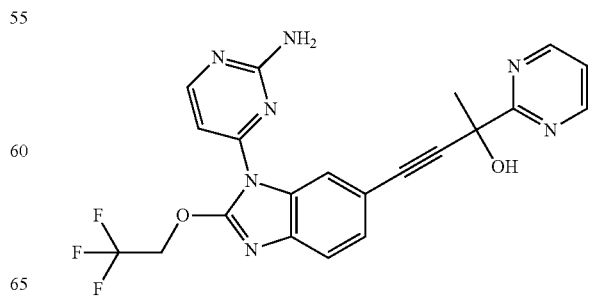

A mixture of 4-[6-bromo-2-(2,2,2-trifluoroethoxy)-1H-1,3-benzodiazol-1-yl]pyrimidin-2-amine (150 mg, 0.31 mmol, 80% purity), 2-(pyrimidin-2-yl)but-3-yn-2-ol (300 mg, 2.02 mmol), bis(triphenylphosphine)palladium(II) dichloride (220 mg, 0.31 mmol) and triethylamine (2 mL) in dimethylsulfoxide (3 mL) was stirred for 1.5 hr at 90° C. under nitrogen. The reaction mixture was cooled to room temperature then filtered through a frit filter to remove the catalyst. The filtrate was purified by preparative HPLC to afford 18 mg (13%) of 4-[1-(2-aminopyrimidin-4-yl)-2-(2,2,2-trifluoroethoxy)-1H-1,3-benzodiazol-6-yl]-2-(pyrimidin-2-yl)but-3-yn-2-ol as a light brown solid: $^1$H NMR (400 MHz, DMSO) delta 8.89 (d, J=4.8 Hz, 2H), 8.44 (d, J=5.6 Hz, 1H), 8.12 (s, 1H), 7.51-7.48 (m, 2H), 7.28 (d, J=8.0 Hz, 1H), 7.16 (s, 2H), 6.85 (d, J=5.2 Hz, 1H), 6.13 (s, 1H), 5.36-5.29 (m, 2H), 1.89 (s, 3H); LC-MS: m/z=+456 (M+H)+.

Example 129

Preparation of 4-[1-(2-aminopyrimidin-4-yl)-2-[(2,2-dimethyl-1,3-dioxolan-4-yl)methoxy]-1H-1,3-benzodiazol-6-yl]-2-(5-methyl-1,2-oxazol-3-yl)but-3-yn-2-ol

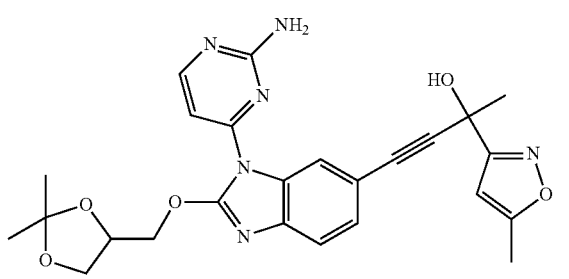
(129-b)

Step 1—Synthesis of 4-[6-bromo-2-[(2,2-dimethyl-1,3-dioxolan-4-yl)methoxy]-1H-1,3-benzodiazol-1-yl]pyrimidin-2-amine

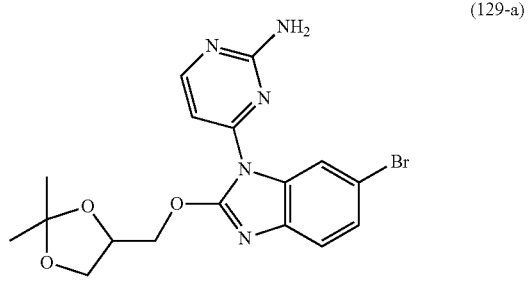 [SMILES: CC1(C)OCC(COc2nc3ccc(Br)cc3n2-c2ccnc(N)n2)O1]
(129-a)

A mixture of (2,2-dimethyl-1,3-dioxolan-4-yl)methanol (800 mg, 6.05 mmol), cesium carbonate (1.7 g, 5.22 mmol) and 4-[6-bromo-2-(trichloromethyl)-1H-1,3-benzodiazol-1-yl]pyrimidin-2-amine (500 mg, 1.23 mmol) in N,N-dimethylformamide (4 mL) was stirred for 12 hr at room temperature. The reaction mixture was quenched with 20 mL of water and the precipitate was collected by filtration. The solid was dried in a vacuum oven to afford 385 mg (75%) of 4-[6-bromo-2-[(2,2-dimethyl-1,3-dioxolan-4-yl)methoxy]-1H-1,3-benzodiazol-1-yl]pyrimidin-2-amine as a yellow solid. $^1$H NMR (400 MHz, CDCl$_3$) delta 8.40 (d, J=5.2 Hz, 2H), 7.40 (s, 2H), 7.21 (d, J=6.0 Hz, 1H), 5.28 (s, 2H), 4.77-4.60 (m, 3H), 4.22-4.20 (m, 1H), 3.96-3.92 (m, 1H), 1.49 (s, 3H), 1.42 (s, 3H); LC-MS: m/z=+420 (M+H)+.

Step 2—Synthesis of 4-[1-(2-aminopyrimidin-4-yl)-2-[(2,2-dimethyl-1,3-dioxolan-4-yl)methoxy]-1H-1,3-benzodiazol-6-yl]-2-(5-methyl-1,2-oxazol-3-yl)but-3-yn-2-ol A mixture of 4-[6-bromo-2-[(2,2-dimethyl-1,3-dioxolan-4-yl)methoxy]-1H-1,3-benzodiazol-1-yl]pyrimidin-2-amine (150 mg, 0.32 mmol), 2-(5-methyl-1,2-oxazol-3-yl)but-3-yn-2-ol (300 mg, 1.98 mmol), bis(triphenylphosphine)palladium(II) dichloride (300 mg, 0.43 mmol) and triethylamine (2 mL) in dimethylsulfoxide (3 mL) was stirred for 1 h at 70° C. under a nitrogen atmosphere. The reaction mixture was cooled to room temperature then filtered through a frit filter to remove the catalyst. The filtrate was purified on a C18 column (acetonitrile/water, 5:95-80:20) to yield 27 mg (17%) of 4-[1-(2-aminopyrimidin-4-yl)-2-[(2,2-dimethyl-1,3-dioxolan-4-yl)methoxy]-1H-1,3-benzodiazol-6-yl]-2-(5-methyl-1,2-oxazol-3-yl)but-3-yn-2-ol as a white solid: $^1$H NMR (400 MHz, DMSO) delta 8.38 (d, J=5.2 Hz, 1H), 8.18 (s, 1H), 7.56 (d, J=8.0 Hz, 1H), 7.28 (d, J=8.0 Hz, 1H), 7.09 (s, 2H), 7.02 (d, J=5.2 Hz, 1H), 6.44 (s, 1H), 6.38 (s, 1H), 4.69-4.54 (m, 3H), 4.11 (t, J=7.4 Hz, 1H), 3.89 (t, J=7.2 Hz, 1H), 2.41 (s, 3H), 1.81 (s, 3H), 1.32 (d, J=16 Hz, 6H); LC-MS: m/z=+491 (M+H)+.

Example 130

Preparation of 4-[1-(2-aminopyrimidin-4-yl)-2-(2-hydroxyethoxy)-1H-1,3-benzodiazol-6-yl]-2-(pyrimidin-2-yl)but-3-yn-2-ol

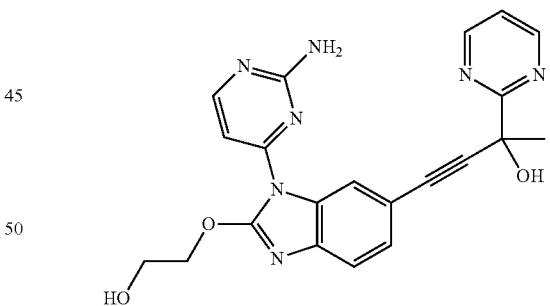

A mixture of 2-[[1-(2-aminopyrimidin-4-yl)-6-bromo-1H-1,3-benzodiazol-2-yl]oxy]ethan-1-ol (420 mg, 1.08 mmol), 2-(pyrimidin-2-yl)but-3-yn-2-ol (1 g, 6.75 mmol, 6.25 equiv), bis(triphenylphosphine)palladium(II) dichloride (800 mg, 1.14 mmol) and triethylamine (2 mL) in dimethylsulfoxide (3 mL) was stirred under nitrogen for 1 hr at 90° C. The resulting mixture was concentrated under vacuum and the residue was purified by preparative HPLC to yield 18 mg (4%) of 4-[1-(2-aminopyrimidin-4-yl)-2-(2-hydroxyethoxy)-1H-1,3-benzodiazol-6-yl]-2-(pyrimidin-2-yl)but-3-yn-2-ol as a light brown solid: $^1$H NMR (400 MHz, D$_2$O) delta 8.75 (d, J=5.2 Hz, 2H), 7.52 (d, J=5.6 Hz, 1H), 7.46 (t, J=5 Hz, 1H), 7.30 (s, 1H), 6.76 (d, J=8.0 Hz, 1H), 6.55 (d, J=8.0 Hz, 1H), 6.24 (d, J=5.2 Hz, 1H), 3.90 (s, 2H), 3.61 (s, 2H), 1.80 (s, 3H); LC-MS: m/z=+418 (M+H)+.

Example 131

Preparation of 1-[2-[1-(2-aminopyrimidin-4-yl)-2-[(2-methoxyethyl)amino]-1H-1,3-benzodiazol-6-yl]ethynyl]cyclohexan-1-ol

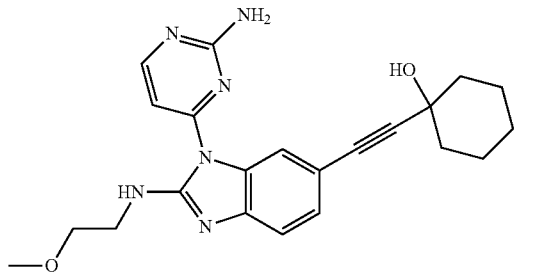

(131-b)

Step 1—Synthesis of 1-(2-aminopyrimidin-4-yl)-6-bromo-N-(2-methoxyethyl)-1H-1,3-benzodiazol-2-amine

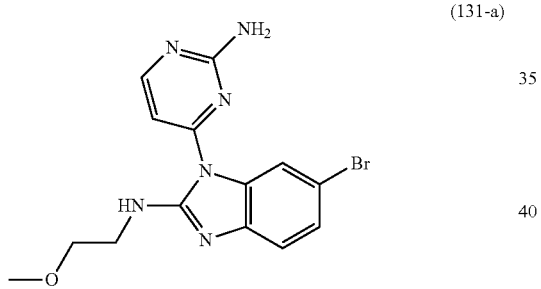

(131-a)

A mixture of 4-[6-bromo-2-(trichloromethyl)-1H-1,3-benzodiazol-1-yl]pyrimidin-2-amine (1.5 g, 3.68 mmol) and cesium carbonate (2.5 g, 7.67 mmol) in 2-methoxyethan-1-amine (15 mL) was stirred under nitrogen for 3 days at room temperature. The reaction mixture was concentrated under vacuum and the residue was purified on a C18 column (acetonitrile/water, 5:95-80:20) to give 0.55 g (39%) of 1-(2-aminopyrimidin-4-yl)-6-bromo-N-(2-methoxyethyl)-1H-1,3-benzodiazol-2-amine as a yellow solid. LC-MS: m/z=+363 (M+H)+.

Step 2—Synthesis of 1-[2-[1-(2-aminopyrimidin-4-yl)-2-[(2-methoxyethyl)amino]-1H-1,3-benzodiazol-6-yl]ethynyl]cyclohexan-1-ol A mixture of 1-(2-aminopyrimidin-4-yl)-6-bromo-N-(2-methoxyethyl)-1H-1,3-benzodiazol-2-amine (150 mg, 0.39 mmol, 95%), triethylamine (2 mL), 1-ethynylcyclohexan-1-ol (300 mg, 2.42 mmol) and bis(triphenylphosphine)palladium(II) dichloride (300 mg, 0.43 mmol) in dimethylsulfoxide (3 mL) was stirred under nitrogen for 1 hr at 70° C. The reaction mixture was purified on a C18 column (acetonitrile/water, 5:95-80:20) to give 30 mg (19%) of 1-[2-[1-(2-aminopyrimidin-4-yl)-2-[(2-methoxyethyl)amino]-1H-1,3-benzodiazol-6-yl]ethynyl]cyclohexan-1-ol as a white solid: ¹H NMR (300 MHz, DMSO) delta 8.43 (d, J=5.4 Hz, 1H), 8.22 (d, J=5.4 Hz, 1H), 7.50 (s, 1H), 7.30-7.10 (m, 4H), 6.91 (s, 1H), 5.33 (s, 1H), 4.69-4.55 (m, 4H), 3.30 (s, 3H), 1.90-1.20 (m, 10H); LC-MS: m/z=407 (M+H)+.

Example 132

Preparation of 4-[1-(2-aminopyrimidin-4-yl)-2-[[1-(2-hydroxyethyl)azetidin-3-yl]oxy]-1H-1,3-benzodiazol-6-yl]-2-(5-methyl-1,2-oxazol-3-yl)but-3-yn-2-ol

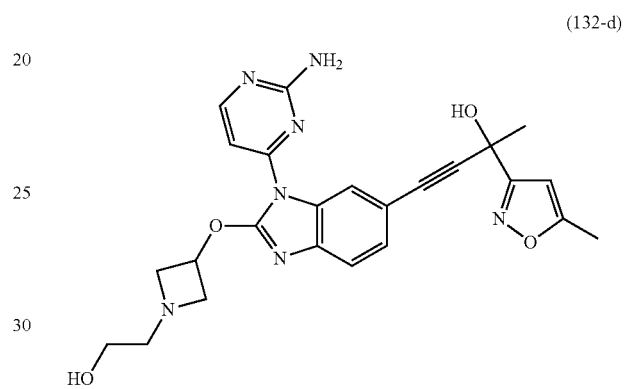

(132-d)

Step 1—Synthesis of tert-butyl 3-[[1-(2-aminopyrimidin-4-yl)-6-bromo-1H-1,3-benzodiazol-2-yl]oxy]azetidine-1-carboxylate

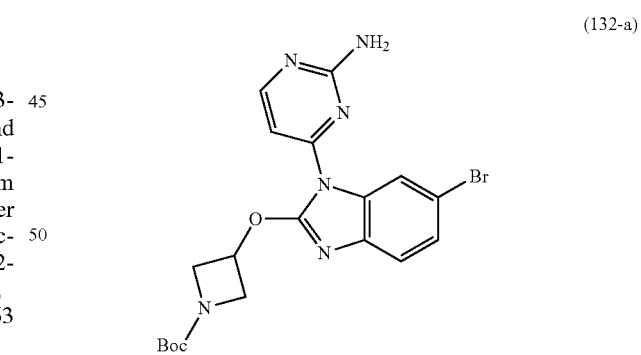

(132-a)

A mixture of 4-[6-bromo-2-(trichloromethyl)-1H-1,3-benzodiazol-1-yl]pyrimidin-2-amine (1 g, 2.45 mmol), tert-butyl 3-hydroxyazetidine-1-carboxylate (2 g, 11.55 mmol) and cesium carbonate (4 g, 12.28 mmol) in N,N-dimethylformamide (15 mL) was stirred under nitrogen overnight at room temperature. The resulting solution was quenched with 200 mL of water. The precipitate was collected by filtration, washed with 200 mL of water and dried in a vacuum oven to give 750 mg (60%) of tert-butyl 3-[[1-(2-aminopyrimidin-4-yl)-6-bromo-1H-1,3-benzodiazol-2-yl]oxy]azetidine-1-carboxylate as a yellow solid: LC-MS: m/z=+461 (M+H)+.

Step 2: Synthesis of 4-[2-(azetidin-3-yloxy)-6-bromo-1H-1,3-benzodiazol-1-yl]pyrimidin-2-amine

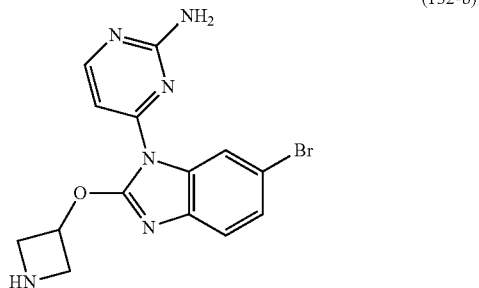

(132-b)

Trifluoroacetic acid (0.5 mL) was added dropwise into a solution of tert-butyl 3-[[1-(2-aminopyrimidin-4-yl)-6-bromo-1H-1,3-benzodiazol-2-yl]oxy]azetidine-1-carboxylate (250 mg, 0.49 mmol, 90%) in dichloromethane (2 mL) at 0° C. The reaction mixture was stirred at room temperature for 2 hr. Triethylamine was then added to adjust the pH of the solution to 8. The mixture was concentrated under vacuum to give 2 g (88%) of 4-[2-(azetidin-3-yloxy)-6-bromo-1H-1,3-benzodiazol-1-yl]pyrimidin-2-amine as dark red oil: LC-MS: m/z=+361 (M+H)+.

Step 3: Synthesis of 2-(3-[[1-(2-aminopyrimidin-4-yl)-6-bromo-1H-1,3-benzodiazol-2-yl]oxy]azetidin-1-yl)ethan-1-ol

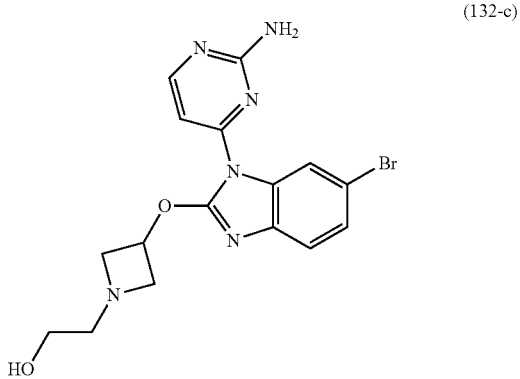 [SMILES: Nc1nccc(-n2c(OC3CN(CCO)C3)nc3ccc(Br)cc32)n1]

(132-c)

A mixture of 4-[2-(azetidin-3-yloxy)-6-bromo-1H-1,3-benzodiazol-1-yl]pyrimidin-2-amine (2 g, 0.44 mmol, 8% purity) and triethylamine (1.5 mL) in 2-bromoethan-1-ol (1.5 mL) was stirred at room temperature for 12 h. The reaction mixture was purified on a C18 column (water/acetonitrile, 5:95-80:20) to yield 100 mg (50%) of 2-(3-[[1-(2-aminopyrimidin-4-yl)-6-bromo-1H-1,3-benzodiazol-2-yl]oxy]azetidin-1-yl)ethan-1-ol as a yellow solid: LC-MS: m/z=+405 (M+H)+.

Step 4: Synthesis of 4-[1-(2-aminopyrimidin-4-yl)-2-[[1-(2-hydroxyethyl)azetidin-3-yl]oxy]-1H-1,3-benzodiazol-6-yl]-2-(5-methyl-1,2-oxazol-3-yl)but-3-yn-2-ol A mixture of 2-(3-[[1-(2-aminopyrimidin-4-yl)-6-bromo-1H-1,3-benzodiazol-2-yl]oxy]azetidin-1-yl)ethan-1-ol (80 mg, 0.20 mmol), 2-(5-methyl-1,2-oxazol-3-yl)but-3-yn-2-ol (160 mg, 1.06 mmol), bis(triphenylphosphine)palladium(II) dichloride (160 mg, 0.23 mmol) and triethylamine (1 mL) in dimethylsulfoxide (2 mL) was stirred under nitrogen for 2 hr at 70° C. The reaction mixture was cooled to room temperature then filtered through a frit filter to remove the catalyst. The filtrate was purified by preparative HPLC to give 7 mg (7%) of 4-[1-(2-aminopyrimidin-4-yl)-2-[[1-(2-hydroxyethyl)azetidin-3-yl]oxy]-1H-1,3-benzodiazol-6-yl]-2-(5-methyl-1,2-oxazol-3-yl)but-3-yn-2-ol as a white solid: $^1$H NMR (400 MHz, DMSO) delta 8.41 (d, J=5.6 Hz, 1H), 8.17 (s, 1H), 7.46 (d, J=8.4 Hz, 1H), 7.27 (d, J=8.4 Hz, 1H), 7.10 (s, 2H), 7.01 (d, J=5.6 Hz, 1H), 6.45 (s, 1H), 6.37 (s, 1H), 5.37 (t, J=5.2 Hz, 1H), 4.44 (t, J=5.4 Hz, 1H), 3.75 (t, J=7.2 Hz, 2H), 3.41 (t, J=6.0 Hz, 2H), 3.28 (t, J=6.8 Hz, 2H), 2.57 (s, 2H), 2.41 (s, 3H), 1.81 (s, 3H); LC-MS: m/z=+476 (M+H)+.

Example 133

Preparation of 4-[1-(2-aminopyrimidin-4-yl)-2-[(2-methoxyethyl)amino]-1H-1,3-benzodiazol-6-yl]-2-methylbut-3-yn-2-ol

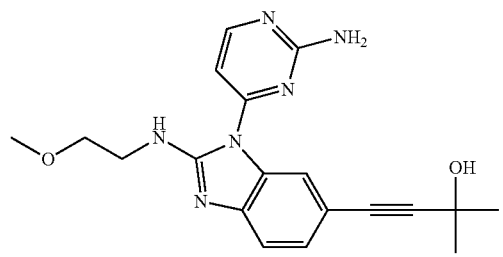 [SMILES: COCCNc1nc2ccc(C#CC(C)(C)O)cc2n1-c1ccnc(N)n1]

A mixture of 1-(2-aminopyrimidin-4-yl)-6-bromo-N-(2-methoxyethyl)-1H-1,3-benzodiazol-2-amine (120 mg, 0.33 mmol), 2-methylbut-3-yn-2-ol (277.2 mg, 3.30 mmol), bis(triphenylphosphine)palladium(II) dichloride (231.67 mg) and triethylamine (2.4 mL) in dimethylsulfoxide (1 mL) was stirred under nitrogen for 1 hr at 70° C. The reaction mixture was cooled to room temperature and the solid material was removed by filtration. The filtrate was diluted with 5 mL of water then extracted with 3×30 mL of ethyl acetate. The combined organic layers was dried over anhydrous sodium sulfate and concentrated under vacuum. The residue was purified by preparative HPLC to give 5.0 mg (4%) of 4-[1-(2-aminopyrimidin-4-yl)-2-[(2-methoxyethyl)amino]-1H-1,3-benzodiazol-6-yl]-2-methylbut-3-yn-2-ol as a white solid: $^1$H NMR (300 MHz, DMSO) delta 8.43 (d, J=5.4 Hz, 1H), 8.21 (d, J=5.4 Hz, 1H), 7.47 (s, 1H), 7.25 (s, 1H), 7.16-7.12 (m, 3H), 6.91 (d, 1H), 5.40 (s, 1H), 3.63-3.57 (m, 4H), 3.35 (s, 3H), 1.47 (s, 6H); LC-MS: m/z=+367 (M+H)+.

Example 134

Preparation of 4-[1-(2-aminopyrimidin-4-yl)-2-[(2-methoxyethyl)amino]-1H-1,3-benzodiazol-6-yl]-2-(4-methyl-1,3-thiazol-2-yl)but-3-yn-2-ol

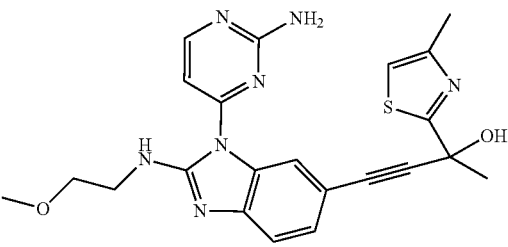 [SMILES: COCCNc1nc2ccc(C#CC(C)(O)c3nc(C)cs3)cc2n1-c1ccnc(N)n1]

A mixture of 1-(2-aminopyrimidin-4-yl)-6-bromo-N-(2-methoxyethyl)-1H-1,3-benzodiazol-2-amine (150 mg, 0.37 mmol), 2-(4-methyl-1,3-thiazol-2-yl)but-3-yn-2-ol (137.6 mg, 0.82 mmol), bis(triphenylphosphine)palladium(II) dichloride (150 mg, 0.21 mmol) and triethylamine (0.7 mL) in dimethylsulfoxide (1 mL) under nitrogen in a 10-mL sealed tube was stirred for 1 hr at 70° C. The reaction mixture was cooled to room temperature then purified on a silica gel column (dichloromethane/methanol, 8:1) to give 19.6 mg (11%) of 4-[1-(2-aminopyrimidin-4-yl)-2-[(2-methoxyethyl)amino]-1H-1,3-benzodiazol-6-yl]-2-(4-methyl-1,3-thiazol-2-yl)but-3-yn-2-ol as yellow oil: $^1$H NMR (300 MHz, DMSO) delta 8.40 (d, J=5.4 Hz, 2H), 8.22 (t, J=5.0 Hz 1H), 7.49 (s, 1H), 7.27 (d, J=8.1 Hz, 1H), 7.16 (t, J=10.5 Hz, 2H), 6.91 (d, J=5.4 Hz, 1H), 6.89 (s, 1H), 6.86 (s, 1H), 3.62-3.59 (m, 4H), 3.32 (d, J=12.3 Hz, 3H), 2.35 (s, 3H), 1.85 (s, 3H); LC-MS: m/z=+450 (M+H)+.

Example 135

Preparation of 4-[1-(2-aminopyrimidin-4-yl)-2-(2-hydroxyethoxy)-1H-1,3-benzodiazol-6-yl]-2-(5-fluoropyridin-2-yl)but-3-yn-2-ol

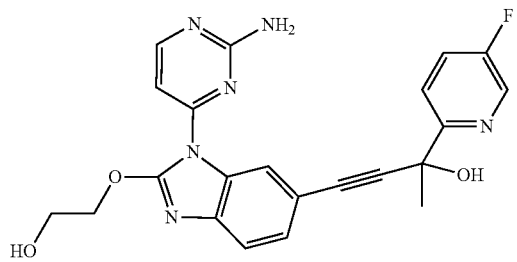 [SMILES: CC(O)(C#Cc1ccc2nc(OCCO)n(-c3ccnc(N)n3)c2c1)c1ccc(F)cn1]

A mixture of 2-[[1-(2-aminopyrimidin-4-yl)-6-bromo-1H-1,3-benzodiazol-2-yl]oxy]ethan-1-ol (200 mg, 0.57 mmol), 2-(5-fluoropyridin-2-yl)but-3-yn-2-ol (940 mg, 5.69 mmol), bis(triphenylphosphine)palladium(II) dichloride (200 mg, 0.28 mmol) and triethylamine (0.5 mL) in dimethylsulfoxide (1 mL) was irradiated with microwave radiation under nitrogen for 1 hr at 120° C. The reaction mixture was cooled to room temperature then filtered through a frit filter to remove the catalyst. The filtrate was concentrated under vacuum and the crude product (80 mg) was purified by preparative HPLC to give 3.7 mg (1%) of 4-[1-(2-aminopyrimidin-4-yl)-2-(2-hydroxyethoxy)-1H-1,3-benzodiazol-6-yl]-2-(5-fluoropyridin-2-yl)but-3-yn-2-ol as a light yellow solid: $^1$H NMR (300 MHz, DMSO) delta 8.54 (d, J=2.7 Hz, 1H), 8.37 (d, J=5.7 Hz, 1H), 8.15 (d, J=1.2 Hz, 1H), 7.84 (q, 1H), 7.78-7.72 (m, 1H), 7.43 (d, J=8.1 Hz, 1H), 7.24 (q, 1H), 7.10-7.04 (m, 3H), 6.37 (s, 1H), 5.03 (s, 1H), 4.60 (t, J=4.5 Hz, 2H), 3.81 (d, J=4.5 Hz, 2H), 1.82 (s, 3H); LC-MS: m/z=+435 (M+H)+.

Example 136

Preparation of (2R)-4-[1-(2-aminopyrimidin-4-yl)-2-(2-fluoroethoxy)-1H-1,3-benzodiazol-6-yl]-2-(5-methyl-1,2,4-oxadiazol-3-yl)but-3-yn-2-ol

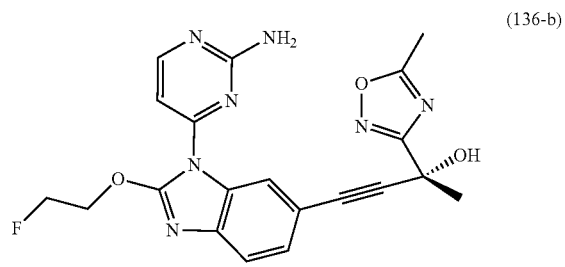 [SMILES: Cc1nc([C@](C)(O)C#Cc2ccc3nc(OCCF)n(-c4ccnc(N)n4)c3c2)no1]

(136-b)

Step 1—Synthesis of 4-[2-(2-fluoroethoxy)-6-iodo-1H-1,3-benzodiazol-1-yl]pyrimidin-2-amine

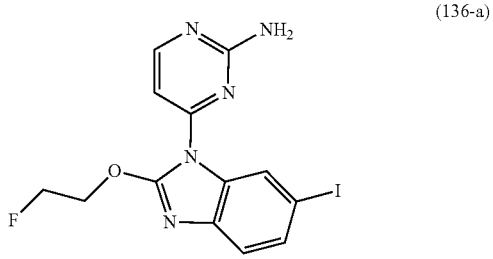 [SMILES: Nc1nccc(-n2c(OCCF)nc3ccc(I)cc32)n1]

(136-a)

A solution of 4-[6-iodo-2-(trichloromethyl)-1H-1,3-benzodiazol-1-yl]pyrimidin-2-amine (1 g, 2.20 mmol), 2-fluoroethan-1-ol (900 mg, 14.05 mmol) and cesium carbonate (4.3 g, 13.20 mmol) in N,N-dimethylformamide (10 mL) was stirred for 14 hr at room temperature. The reaction mixture was diluted with 50 mL of ethyl acetate then washed with 5×10 mL of water. The organic layer was dried over anhydrous sodium sulfate and concentrated under vacuum. The residue was purified on a silica gel column (ethyl acetate/petroleum ether, 10:1) to afford 150 mg (17%) of 4-[2-(2-fluoroethoxy)-6-iodo-1H-1,3-benzodiazol-1-yl]pyrimidin-2-amine as brown oil: LC-MS: m/z=400 (M+H)+.

Step 2—Synthesis of (2R)-4-[1-(2-aminopyrimidin-4-yl)-2-(2-fluoroethoxy)-1H-1,3-benzodiazol-6-yl]-2-(5-methyl-1,2,4-oxadiazol-3-yl)but-3-yn-2-ol A solution of 4-[2-(2-fluoroethoxy)-6-iodo-1H-1,3-benzodiazol-1-yl]pyrimidin-2-amine (130 mg, 0.33 mmol), (2R)-2-(5-methyl-1,2,4-oxadiazol-3-yl)but-3-yn-2-ol (148 mg, 0.97 mmol), bis(triphenylphosphine)palladium(II) dichloride (34 mg, 0.05 mmol) in triethylamine (1 mL) and dimethylsulfoxide (1 mL) was irradiated with microwave radiation under nitrogen in a 8-mL vial at 90° C. for 30 min. The resulting solution was cooled to room temperature and diluted with 30 mL of ethyl acetate. The solid material was removed by filtration. The residue was concentrated under vacuum then purified on a silica gel column (ethyl acetate/ petroleum ether, 2:1) to give 10 mg (7%) of (2R)-4-[1-(2-aminopyrimidin-4-yl)-2-(2-fluoroethoxy)-1H-1,3-benzodiazol-6-yl]-2-(5-methyl-1,2,4-oxadiazol-3-yl)but-3-yn-2-ol as a light brown solid. ¹H NMR (400 MHz, MeOD) delta 8.47 (s, 1H), 8.35 (d, J=5.6 Hz, 1H), 7.44 (d, J=8.4 Hz, 1H), 7.39-7.36 (m, 1H), 7.15 (d, J=5.6 Hz, 1H), 4.95-4.90 (m, 2H), 4.85-4.81 (m, 2H), 2.63 (s, 3H), 1.96 (s, 3H); LC-MS: m/z=+424 (M+H)+.

Example 137

Preparation of 4-[1-(2-aminopyrimidin-4-yl)-2-(2-hydroxyethoxy)-1H-1,3-benzodiazol-6-yl]-2-(5-chloropyridin-2-yl)but-3-yn-2-ol

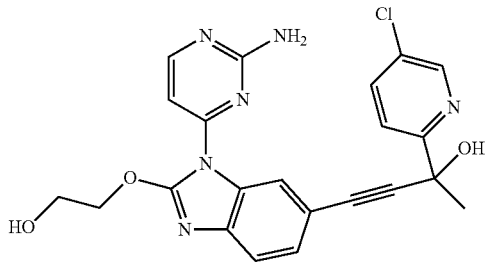 [SMILES: CC(O)(C#Cc1ccc2nc(OCCO)n(-c3ccnc(N)n3)c2c1)c1ccc(Cl)cn1]

A solution of 2-[[1-(2-aminopyrimidin-4-yl)-6-bromo-1H-1,3-benzodiazol-2-yl]oxy]ethan-1-ol (200 mg, 0.57 mmol), 2-(5-chloropyridin-2-yl)but-3-yn-2-ol (518 mg, 2.85 mmol), bis(triphenylphosphine)palladium(II) dichloride (400 mg, 0.57 mmol) and triethylamine (0.5 mL) in DMSO (0.5 mL) was irradiated under nitrogen in a 10-mL sealed tube with microwave radiation for 2 h at 100° C. The reaction mixture was cooled to room temperature and the solid material was removed by filtration. The filtrate was concentrated under vacuum and the crude product (50 mg) was purified by preparative HPLC to give 2 mg (1%) of 4-[1-(2-aminopyrimidin-4-yl)-2-(2-hydroxyethoxy)-1H-1,3-benzodiazol-6-yl]-2-(5-chloropyridin-2-yl)but-3-yn-2-ol as a light yellow solid: ¹H NMR (400 MHz, DMSO) delta 8.61 (s, 1H), 8.38 (d, J=5.6 Hz, 1H), 8.16 (s, 1H), 7.98-7.82 (m, 1H), 7.81 (d, J=8.4 Hz, 1H), 7.43 (d, J=8.4 Hz, 1H), 7.26-7.24 (m, 1H), 7.06 (d, J=5.2 Hz, 3H), 6.44 (s, 1H), 5.06 (t, J=5.6 Hz, 1H), 4.61 (t, J=4.8 Hz, 2H), 3.83-3.80 (m, 2H), 1.82 (s, 3H); LC-MS: m/z=+451 (M+H)+.

Example 138

Preparation of 4-[1-(2-aminopyrimidin-4-yl)-2-(oxetan-3-yloxy)-1H-1,3-benzodiazol-6-yl]-2-(pyrimidin-2-yl)but-3-yn-2-ol

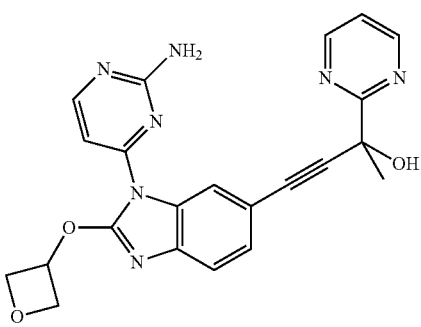
(138-c)

Step 1—Synthesis of 4-[2-(oxetan-3-yloxy)-6-[2-(trimethylsilyl)ethynyl]-1H-1,3-benzodiazol-1-yl]pyrimidin-2-amine

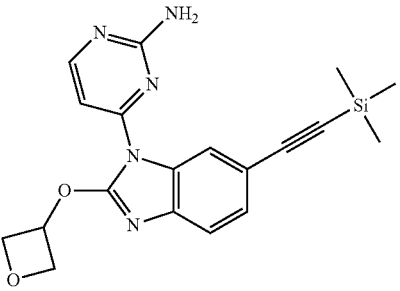 [SMILES: C[Si](C)(C)C#Cc1ccc2nc(OC3COC3)n(-c3ccnc(N)n3)c2c1]
(138-a)

To a solution of 4-[6-bromo-2-(oxetan-3-yloxy)-1H-1,3-benzodiazol-1-yl]pyrimidin-2-amine (900 mg, 2.48 mmol) in piperidine (7.3 mL) was introduced tetrakis(triphenylphosphine)palladium(0) (172 mg, 0.15 mmol), copper(I) iodide (28 mg, 0.15 mmol) and ethynyltrimethylsilane (0.88 mL, 6.21 mmol). The reaction mixture was warmed to 65° C. for 5 hr. After cooling to RT, the reaction mixture was concentrated in vacuo, DCM (5 mL) was added and the solution re-evaporated to dryness in vacuo (re-evaporation process repeated twice). Purification of the residue by column chromatography (Biotage, DCM containing a 3-8% gradient of methanol) furnished the title compound as a brown solid: LC-MS: m/z=+380.05 (M+H)+.

Step 2—Synthesis of 4-[6-ethynyl-2-(oxetan-3-yloxy)-1H-1,3-benzodiazol-1-yl]pyrimidin-2-amine

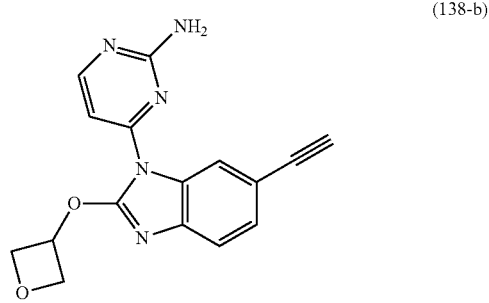 [SMILES: C#Cc1ccc2nc(OC3COC3)n(-c3ccnc(N)n3)c2c1]
(138-b)

To a solution of 4-[2-(oxetan-3-yloxy)-6-[2-(trimethylsilyl)ethynyl]-1H-1,3-benzodiazol-1-yl]pyrimidin-2-amine (450 mg, 1.19 mmol) in dry THF (5 mL) at RT was introduced TBAF (0.88 mL of a 1M solution in THF, 0.88 mmol). After 20 minutes, the reaction mixture was concentrated in vacuo, DCM (5 mL) added and the solution re-evaporated to dryness in vacuo (re-evaporation process repeated twice). Purification of the residue by silica gel flash column chromatography (eluent: DCM containing a 2-10% gradient of methanol) furnished the title compound as a yellow solid: ¹H (500 MHz, DMSO) delta 4.83-4.70 (2H, m), 5.04-4.93 (2H, m), 5.85-5.77 (1H, m), 7.18-7.07 (3H, m), 7.33 (1H, dd, J=8.2, 1.5 Hz), 7.45 (1H, d, J=8.2 Hz), 8.36 (1H, s), 8.40 (1H, d, J=5.5 Hz); LCMS: m/z=+307.95 (M+H)+.

Step 3—Synthesis of 4-[1-(2-aminopyrimidin-4-yl)-2-(oxetan-3-yloxy)-1H-1,3-benzodiazol-6-yl]-2-(pyrimidin-2-yl)but-3-yn-2-ol To a solution of 4-[6-ethynyl-2-(oxetan-3-yloxy)-1H-1,3-benzodiazol-1-yl]pyrimidin-2-amine (270 mg, 0.88 mmol) in dry THF (5 mL) at −78° C. was introduced lithium diisopropylamide (1.10 mL of a 2M solution in THF, 2.20 mmol). After 15 minutes, 1-pyrimidin-2-yl-ethanone (107 mg, 0.88 mmol) was added and the reaction mixture maintained at −78° C. for 15 minutes. Following 2 hr at RT, saturated aqueous ammonium chloride (0.5 ml) was added and the solution concentrated in vacuo. The residue was dissolved in DCM (10 mL), washed with water (2 mL), dried (Na$_2$SO$_4$), filtered and concentrated in vacuo. Purification of the residue by column chromatography (Biotage, DCM containing a 0-12% gradient of methanol) furnished the title compound as a yellow solid: $^1$H NMR (500 MHz, DMSO) delta 1.90 (3H, s), 4.78 (2H, dd, J=7.8, 4.9 Hz), 4.98 (2H, t, J=7.1 Hz), 5.87-5.80 (1H, m), 6.16 (1 H, s), 7.11 (1H, d, J=5.5 Hz), 7.14 (2H, s), 7.25 (1H, dd, J=8.2, 1.2 Hz), 7.45 (1H, d, J=8.2 Hz), 7.52 (1H, t, J=4.8 Hz), 8.16 (1H, s), 8.44 (1H, d, J=5.5 Hz), 8.91 (2H, d, J=4.8 Hz); LC-MS: m/z=+430.05 (M+H)+.

Example 139

Preparation of 4-[1-(2-aminopyrimidin-4-yl)-2-(2-fluoroethoxy)-1H-1,3-benzodiazol-6-yl]-2-(pyrimidin-2-yl)but-3-yn-2-ol

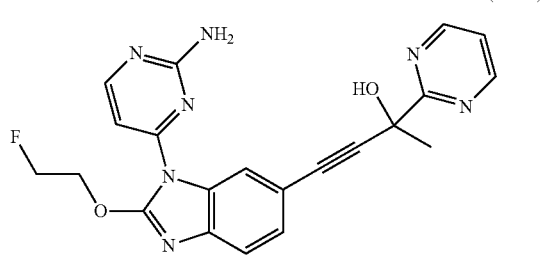

(139-d)

Step 1—Synthesis of 4-[6-bromo-2-(2-fluoroethoxy)-1H-1,3-benzodiazol-1-yl]pyrimidin-2-amine

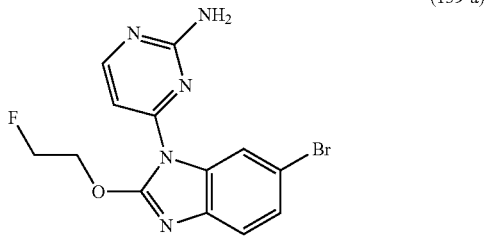

(139-a)

A solution of 4-[6-bromo-2-(trichloromethyl)-1H-1,3-benzodiazol-1-yl]pyrimidin-2-amine (500 mg, 1.23 mmol), 2-fluoroethan-1-ol (236 mg, 3.68 mmol) and cesium carbonate (1.2 g, 3.68 mmol) in N,N-dimethylformamide (3 mL) was stirred in a 20-mL sealed tube under nitrogen overnight at room temperature. The reaction mixture was diluted with 30 mL of water and the precipitate was collected by filtration to give 340 mg (79%) of 4-[6-bromo-2-(2-fluoroethoxy)-1H-1,3-benzodiazol-1-yl]pyrimidin-2-amine as a yellow solid; LC-MS: m/z=+352 (M+H)+.

Step 2: Synthesis of 4-[2-(2-fluoroethoxy)-6-[2-(trimethylsilyl)ethynyl]-1H-1,3-benzodiazol-1-yl]pyrimidin-2-amine

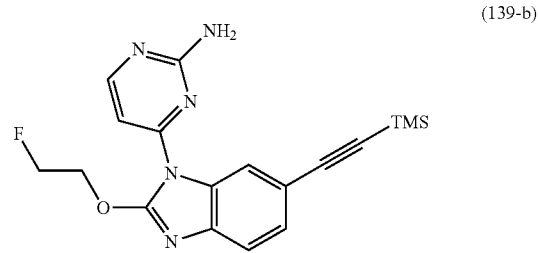 [SMILES: C[Si](C)(C)C#Cc1ccc2nc(OCCF)n(-c3ccnc(N)n3)c2c1]

(139-b)

A solution of 4-[6-bromo-2-(2-fluoroethoxy)-1H-1,3-benzodiazol-1-yl]pyrimidin-2-amine (150 mg, 0.43 mmol), ethynyltrimethylsilane (126 mg, 1.28 mmol), bis(triphenylphosphine) palladium(II) dichloride (120 mg, 0.17 mmol) and triethylamine (0.5 mL) in dimethylsulfoxide (1 mL) was irradiated with microwave radiation under nitrogen in a sealed tube at 80° C. for 40 min. The reaction mixture was diluted with 10 mL of dichloromethane and the solid material was removed by filtration. The filtrate was concentrated under vacuum and the residue was purified on a silica gel column (ethyl acetate/petroleum ether, 3:1) to give 60 mg (38%) of 4-[2-(2-fluoroethoxy)-6-[2-(trimethylsilyl)ethynyl]-1H-1,3-benzodiazol-1-yl]pyrimidin-2-amine as a yellow solid: LC-MS: m/z=+370 (M+H)+.

Step 3: Synthesis of 4-[6-ethynyl-2-(2-fluoroethoxy)-1H-1,3-benzodiazol-1-yl]pyrimidin-2-amine

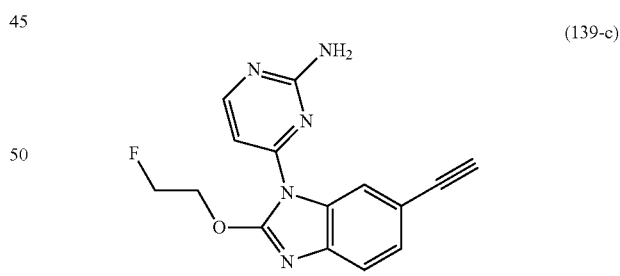

(139-c)

A solution of 4-[2-(2-fluoroethoxy)-6-[2-(trimethylsilyl)ethynyl]-1H-1,3-benzodiazol-1-yl]pyrimidin-2-amine (100 mg, 0.27 mmol) and potassium fluoride (64 mg, 0.68 mmol) in methanol (3 mL) was stirred at 50° C. for 3 hr. The reaction mixture was concentrated under vacuum and the residue was diluted with 30 mL of ethyl acetate. The resulting mixture was washed with 3×10 mL of water and the organic layer was dried over anhydrous sodium sulfate and concentrated under vacuum to give 70 mg (87%) of 4-[6-ethynyl-2-(2-fluoroethoxy)-1H-1,3-benzodiazol-1-yl]pyrimidin-2-amine as a yellow solid: LC-MS: m/z=+298 (M+H)+.

Step 4: Synthesis of 4-[1-(2-aminopyrimidin-4-yl)-2-(2-fluoroethoxy)-1H-1,3-benzodiazol-6-yl]-2-(pyrimidin-2-yl)but-3-yn-2-ol To a solution of 4-[6-ethynyl-2-(2-fluoroethoxy)-1H-1,3-benzodiazol-1-yl]pyrimidin-2-amine (30 mg, 0.10 mmol) in tetrahydrofuran (0.5 mL) under a nitrogen atmosphere at −78° C. was added a lithium diisopropylamide solution (0.3 mL, 3.00 equiv) dropwise with stirring. The reaction mixture was stirred at −78° C. for 15 min. A solution of 1-(pyrimidin-2-yl)ethan-1-one (48.8 mg, 0.40 mmol) in tetrahydrofuran (0.5 mL) was then added and the mixture was stirred at −78° C. for another 20 min. The resulting solution was then stirred at room temperature for 13 h. The reaction was then quenched by the addition of saturated ammonium chloride solution (1 mL) and the mixture was extracted with 10 mL of ethyl acetate. The organic layer was dried over anhydrous sodium sulfate and concentrated under vacuum. The residue was purified on a silica gel column (ethyl acetate/petroleum ether, 1:3) to give 3.7 mg (9%) of 4-[1-(2-aminopyrimidin-4-yl)-2-(2-fluoroethoxy)-1H-1,3-benzodiazol-6-yl]-2-(pyrimidin-2-yl)but-3-yn-2-ol as an off-white solid: $^1$H NMR (400 MHz, DMSO) delta 8.89 (d, J=4.8 Hz, 2H), 8.40 (d, J=5.6 Hz, 1H), 8.13 (d, J=1.2 Hz, 1H), 7.51-7.44 (m, 2H), 7.25-7.22 (m, 1H), 7.10 (s, 1H), 6.96 (d, J=5.2 Hz, 1H), 6.12 (s, 1H), 4.93-4.88 (m, 2H), 4.80 (s, 2H), 1.88 (s, 3H); LC-MS: m/z=+420 (M+H)+.

Example 140

Preparation of 4-[1-(2-aminopyrimidin-4-yl)-2-[(pyrrolidin-1-yl)carbonyl]-1H-1,3-benzodiazol-6-yl]-2-(5-methyl-1,2-oxazol-3-yl)but-3-yn-2-ol

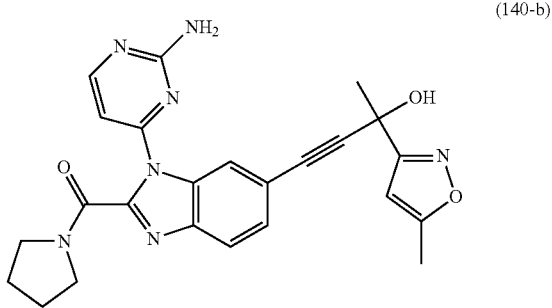 [SMILES: Cc1cc(C(C)(O)C#Cc2ccc3nc(C(=O)N4CCCC4)n(-c4ccnc(N)n4)c3c2)no1]

(140-b)

Step 1—Synthesis of 4-[6-bromo-2-[(pyrrolidin-1-yl)carbonyl]-1H-1,3-benzodiazol-1-yl]pyrimidin-2-amine

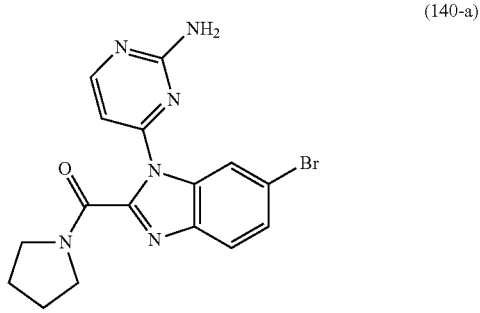 [SMILES: Nc1nccc(-n2c(C(=O)N3CCCC3)nc3ccc(Br)cc32)n1]

(140-a)

A mixture of 4-[6-bromo-2-(trichloromethyl)-1H-1,3-benzodiazol-1-yl]pyrimidin-2-amine (500 mg, 1.23 mmol), pyrrolidine (1 mL) and cesium carbonate (2 g, 6.14 mmol) in N,N-dimethylformamide (5 mL) was stirred for 24 h at room temperature. The reaction mixture was purified on a C18 column (acetonitrile/water, 5:95-80:20) to give 240 mg (51%) of 4-[6-bromo-2-[(pyrrolidin-1-yl)carbonyl]-1H-1,3-benzodiazol-1-yl]pyrimidin-2-amine as a white solid: $^1$H NMR (300 MHz, DMSO) delta 8.42 (d, J=5.1 Hz, 1H), 8.11 (d, J=1.8 Hz, 1H), 7.77 (d, J=8.7 Hz, 1H), 7.57-7.53 (m, 1H), 7.07 (s, 2H), 6.71 (d, J=5.4 Hz, 1H), 3.60 (d, J=6.3 Hz, 2H), 3.50 (t, J=6.6 Hz, 2H), 1.92 (s, 4H); LC-MS: m/z=+387 (M+H)+.

Step 2—Synthesis of 4-[1-(2-aminopyrimidin-4-yl)-2-[(pyrrolidin-1-yl)carbonyl]-1H-1,3-benzodiazol-6-yl]-2-(5-methyl-1,2-oxazol-3-yl)but-3-yn-2-ol A mixture of 4-[6-bromo-2-[(pyrrolidin-1-yl)carbonyl]-1H-1,3-benzodiazol-1-yl]pyrimidin-2-amine (200 mg, 0.49 mmol), 2-(5-methyl-1,2-oxazol-3-yl)but-3-yn-2-ol (200 mg, 1.32 mmol), bis(triphenylphosphine)palladium(II) dichloride (350 mg, 0.50 mmol) and triethylamine (2 mL) in dimethylsulfoxide (3 mL) was stirred under nitrogen at 70° C. for 2 hr. The reaction mixture was cooled to room temperature and purified on a C18 column (acetonitrile/water, 5:95-80:20) to afford 88 mg (38%) of 4-[1-(2-aminopyrimidin-4-yl)-2-[(pyrrolidin-1-yl)carbonyl]-1H-1,3-benzodiazol-6-yl]-2-(5-methyl-1,2-oxazol-3-yl)but-3-yn-2-ol as a light yellow solid. $^1$H NMR (300 MHz, DMSO) delta 8.42 (d, J=5.1 Hz, 1H), 7.86 (s, 1H), 7.79 (d, J=8.4 Hz, 1H), 7.41 (d, J=8.7 Hz, 1H), 7.03 (s, 2H), 6.74 (d, J=5.1 Hz, 1H), 6.50 (s, 1H), 6.36 (s, 1H), 3.61 (d, J=6.6 Hz, 2H), 3.48 (d, J=6.6 Hz, 2H), 2.40 (s, 3H), 1.92 (s, 4H), 1.80 (s, 3H); LC-MS: m/z=+458 (M+H)+.

Example 141

Preparation (2R)-4-[1-(4-amino-1,3,5-triazin-2-yl)-2-methyl-1H-1,3-benzodiazol-6-yl]-2-(5-methyl-1,2-oxazol-3-yl)but-3-yn-2-ol

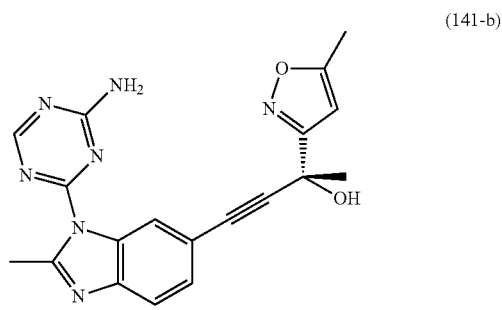

(141-b)

Step 1—Synthesis of 4-(6-bromo-2-methyl-1,3-benzodiazol-1-yl)-1,3,5-triazin-2-amine

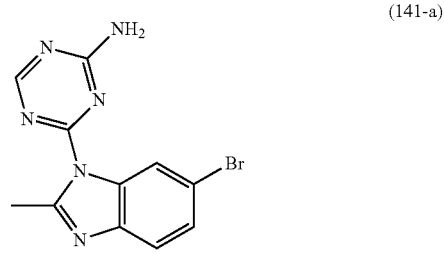 [SMILES: Cc1nc2ccc(Br)cc2n1-c1ncnc(N)n1]

(141-a)

To a solution of 2-N-(2-amino-5-bromophenyl)-1,3,5-triazine-2,4-diamine (2.50 g, 8.89 mmol) in methanol (25 mL) and THF (100 mL) was added trimethyl orthoacetate (16.77 ml, 133.4 mmol) and TsOH (153.14 mg, 0.89 mmol). The reaction mixture was stirred at 70° C. for 1 hr then allowed to cool to RT overnight. Saturated aqueous sodium bicarbonate (30 mL) was introduced and the resulting precipitous solution filtered. The filtrate was extracted into DCM (3×100 mL extractions). The combined organic extracts were washed with brine (30 mL), dried (Na₂SO₄), filtered and concentrated in vacuo. The orange/yellow solid residue was then triturated from a mixture of DCM and MeOH to give the title compound as a pale yellow powder (400 mg): ¹H NMR (500 MHz, DMSO) delta 2.89 (3H, s), 7.46 (1H, dd, J=8.5, 1.9 Hz), 7.57 (1H, d, J=8.4 Hz), 8.02 (1 H, s), 8.10 (1H, s), 8.61 (1H, d, J=1.8 Hz), 8.64 (1H, s); LC-MS: m/z=+306.7 (M+H)+.

Step 2—Synthesis of (2R)-4-[1-(4-amino-1,3,5-triazin-2-yl)-2-methyl-1H-1,3-benzodiazol-6-yl]-2-(5-methyl-1,2-oxazol-3-yl)but-3-yn-2-ol To a solution of 4-(6-bromo-2-methyl-1,3-benzodiazol-1-yl)-1,3,5-triazin-2-amine (160 mg, 0.52 mmol) in piperidine (2 mL) was introduced tetrakis(triphenylphosphine)palladium(0) (60.59 mg, 0.05 mmol), copper(I) iodide (9.99 mg, 0.05 mmol) and (2R)-2-(5-methyl-1,2-oxazol-3-yl)but-3-yn-2-ol (118.9 mg, 0.79 mmol). The reaction was then warmed to 95° C. for 40 minutes (75 W, microwave heating). The reaction mixture was then cooled to RT and concentrated in vacuo. Purification of the residue by flash column chromatography (4-8% MeOH gradient in DCM) gave the title compound as a pale brown solid (77 mg): ¹H NMR (500 MHz, DMSO) delta 1.81 (3H, s), 2.41 (3H, s), 2.90 (3H, s), 6.37 (1H, s), 6.51 (1H, s), 7.33 (1H, dd, J=8.28, 1.50 Hz), 7.60 (1H, d, J=8.20 Hz), 8.01 (1H, br. s.), 8.06 (1H, br. s.), 8.40 (1H, s), 8.66 (1H, s); LC-MS: m/z=+376.45 (M+H)+.

Example 142

Preparation of (2R)-4-[1-(4-amino-1,3,5-triazin-2-yl)-2-cyclopropyl-1H-1,3-benzodiazol-6-yl]-2-(1,3-thiazol-2-yl)but-3-yn-2-ol

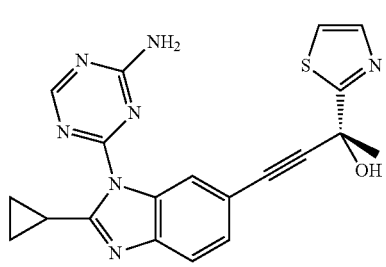

(142-b)

Step 1—Synthesis of 4-(6-bromo-2-cyclopropyl-1,3-benzodiazol-1-yl)-1,3,5-triazin-2-amine

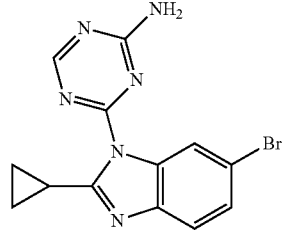

(142-a)

To a solution of 2-N-(2-amino-5-bromophenyl)-1,3,5-triazine-2,4-diamine (6 g, 21.34 mmol) in DMF (60 mL) was added cyclopropanecarbaldehyde (2.07 ml, 27.75 mmol) followed by oxone (7.83 g, 12.81 mmol). The reaction mixture was stirred at RT for 24 hr. The reaction mixture was then cooled to 0° C. and saturated aqueous sodium bicarbonate introduced. A brown precipitate was removed by vacuum filtration. The solid was washed with DCM (100 ml). The organic phase of the filtrate was separated and the aqueous phase extracted with DCM (2×100 mL extractions). The combined organics were washed with brine and then dried (Na₂SO₄), filtered and concentrated in vacuo to furnish the crude title compound as a brown solid: ¹H NMR (500 MHz, DMSO) delta 1.32-1.02 (4H, m), 7.41 (1H, dd, J=8.5, 1.9 Hz), 7.50 (1H, d, J=8.5), 8.05 (1H, s), 8.11 (1H, s), 8.49 (1H, d, J=1.8 Hz), 8.66 (1H, s); LC-MS: m/z=+330.90 (M+H)+. This compound of 85% purity LC-MS (UV) was used without further purification.

Step 2—Synthesis of (2R)-4-[1-(4-amino-1,3,5-triazin-2-yl)-2-cyclopropyl-1H-1,3-benzodiazol-6-yl]-2-(1,3-thiazol-2-yl)but-3-yn-2-ol To a microwave vessel was added 4-(6-bromo-2-cyclopropyl-1,3-benzodiazol-1-yl)-1,3,5-triazin-2-amine (0.3 g, 0.91 mmol) followed by piperidine (2.5 mL), tetrakis(triphenylphosphine)palladium(0) (104.68 mg, 0.09 mmol), copper(I) iodide (17.25 mg, 0.09 mmol) and (2R)-2-(1,3-thiazol-2-yl)but-3-yn-2-ol (0.28 g, 1.81 mmol). The reaction was capped and stirred in the microwave at 95° C. for 25 minutes (55 W). The reaction mixture was cooled to RT and concentrated in vacuo. The residue was re-dissolved in EtOAc and re-evaporated in vacuo (twice). The crude residue was subjected to column chromatography (Biotage, 0-8% methanol gradient in DCM) and the partially purified product triturated with a mixture of EtOAc/heptane to give the title compound as a beige solid: ¹H NMR (DMSO, 500 MHz) delta 1.06-1.20 (4H, m), 1.89 (3H, s), 3.24-3.29 (1H, m), 7.04 (1H, s), 7.30 (1H, dd, J=8.2, 1.4 Hz), 7.53 (1H, d, J=8.2 Hz), 7.69 (1H, d, J=3.2 Hz), 7.78 (1H, d, J=3.2 Hz), 8.05 (1H, s), 8.09 (1H, s), 8.29 (1H, s), 8.68 (1H, s); LC-MS: m/z=+400 (M+H)+.

Example 143

Examples in Table 15 were prepared by procedure described in Example 142-b by reacting 4-(6-bromo-2-methyl-1,3-benzodiazol-1-yl)-1,3,5-triazin-2-amine or 4-(6-bromo-2-cyclopropyl-1,3-benzodiazol-1-yl)-1,3,5-triazin-2-amine with the appropriate but-3-yn-2-ol in Step 2.

TABLE 15

| No | Structure | Name | ¹H NMR | LC-MS (M + H) |
|---|---|---|---|---|
| T15-143.1 | 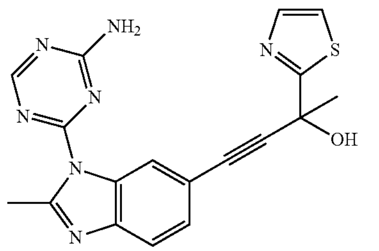 [SMILES: Cc1nc2ccc(C#CC(C)(O)c3nccs3)cc2n1-c1ncnc(N)n1] | 4-[1-(4-amino-1,3,5-triazin-2-yl)-2-methyl-1H-1,3-benzodiazol-6-yl]-2-(1,3-thiazol-2-yl)but-3-yn-2-ol | (500 MHz, DMSO) delta 1.90 (3 H, s), 2.90 (3 H, s), 7.33 (1 H, dd, J = 8.28, 1.50 Hz), 7.60 (1 H, d, J = 8.20 Hz), 7.69 (1 H, d, J = 3.15 Hz), 7.78 (1H, d, J = 3.31 Hz), 7.95-8.02 (1 H, m), 8.03 - 8.09 (1 H, m), 8.34-8.43 (1 H, m), 8.66 (1 H, s) | 378 |
| T15-143.2 | 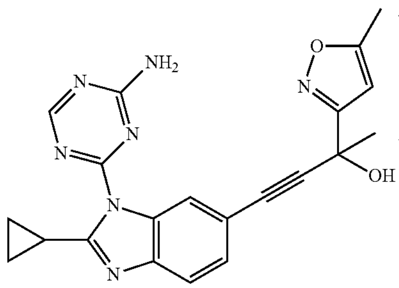 | 4-[1-(4-amino-1,3,5-triazin-2-yl)-2-cyclopropyl-1H-1,3-benzodiazol-6-yl]-2-(5-methyl-1,2-oxazol-3-yl)but-3-yn-2-ol | (500 MHz, DMSO) delta 1.08-1.21 (4 H, m), 1.81 (3 H, s), 2.41 (3 H, s), 6.35-6.38 (1 H, m), 6.50 (1 H, s), 7.31 (1 H, dd, J = 8.20, 1.58 Hz), 7.54 (1 H, d, J = 8.35 Hz), 8.04 (1 H, s), 8.08 (1 H, s), 8.28-8.31 (1 H, m), 8.67-8.70 (1 H, m) | 402 |
| T15-143.3 | 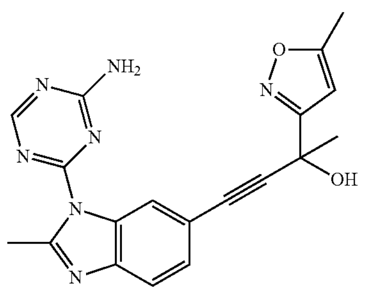 | 4-[1-(4-amino-1,3,5-triazin-2-yl)-2-methyl-1H-1,3-benzodiazol-6-yl]-2-(5-methyl-1,2-oxazol-3-yl)but-3-yn-2-ol | (500 MHz, MeOD) delta 1.91 (3 H, s), 2.48 (3 H, s), 3.00 (3 H, s), 6.34 (1 H, s), 7.44 (1 H, d, J = 9.46 Hz), 7.58 (1 H, d, J = 8.20 Hz), 8.49-8.76 (2 H, m) | 376 |
| T15-143.4 | 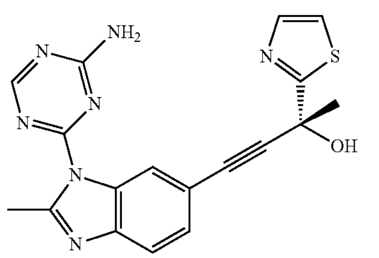 [SMILES: Cc1nc2ccc(C#C[C@@](C)(O)c3nccs3)cc2n1-c1ncnc(N)n1] | (2R)-4-[1-(4-amino-1,3,5-triazin-2-yl)-2-methyl-1H-1,3-benzodiazol-6-yl]-2-(1,3-thiazol-2-yl)but-3-yn-2-ol | (500 MHz, DMSO) delta 1.90 (3 H, s), 2.90 (3 H, s), 7.05 (1 H, s), 7.33 (1 H, dd, J = 8.2, 1.5 Hz), 7.60 (1 H, d, J = 8.2 Hz), 7.69 (1 H, d, J = 3.2 Hz), 7.78 (1 H, d, J = 3.2 Hz), 8.16-7.94 (2 H, m), 8.40 (1 H, s), 8.66 (1 H, s). | 378.4 |
| T15-143.5 | 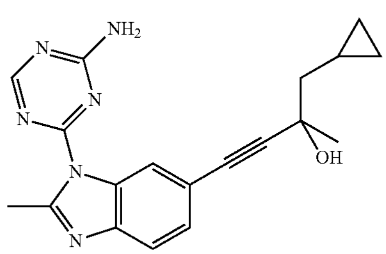 [SMILES: Cc1nc2ccc(C#CC(C)(O)CC3CC3)cc2n1-c1ncnc(N)n1] | 4-[1-(4-amino-1,3,5-triazin-2-yl)-2-methyl-1H-1,3-benzodiazol-6-yl]-1-cyclopropyl-2-methylbut-3-yn-2-ol | (500 MHz, MeOD) delta 0.13-0.31 (2 H, m), 0.48-0.64 (2 H, m), 0.92-1.10 (1 H, m), 1.54 -1.68 (4 H, m), 1.79 (1 H, dd, J = 13.64, 6.38 Hz), 2.97 (3 H, s), 4.59 (1 H, br. s.), 7.37 (1 H, dd, J = 8.35, 1.26 Hz), 7.53(1 H, d, J = 8.20 Hz), 8.52 (1 H, s), 8.59 (1 H, s) | 349.1 |

Example 144

Preparation of 2-((1-(4-amino-1,3,5-triazin-2-yl)-2-methyl-1H-benzo[d]imidazol-6-yl)ethynyl)bicyclo[2.2.1]heptan-2-ol

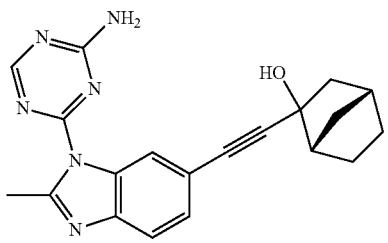 [SMILES: Cc1nc2ccc(C#CC3(O)C[C@@H]4CC[C@H]3C4)cc2n1-c1ncnc(N)n1]

A mixture of 4-(6-bromo-2-methyl-1H-benzo[d]imidazol-1-yl)-1,3,5-triazin-2-amine (200 mg, 0.66 mmol) and 2-ethynylbicyclo[2.2.1]heptan-2-ol (85 mg, 1.3 mmol) in DMF (2.5 mL) was treated with palladium(II) acetate (16 mg, 0.07 mmol), DPPP (58 mg, 0.14 mmol), copper(I) iodide (5 mg, 0.04 mmol) and potassium carbonate (180 mg, 1.3 mmol), then the mixture was heated at 120° C. for 40 min under microwave irradiation. After cooling to RT, the reaction mixture was filtered and the filtrate concentrated in vacuo. Purification of the residue by silica gel column chromatography furnished the title compound (18.5 mg, yield 8%): $^1$H NMR: (400 MHz, MeOD) delta 1.30-1.47 (m, 4H), 1.56-1.67 (m, 1H), 1.92-2.48 (m, 5H), 2.97 (s, 3H), 7.36 (dd, J=1.6, 8.4 Hz, 1H), 7.53 (d, J=8.4 Hz, 1H), 8.50 (s, 1H), 8.60 (s, 1H); LC-MS: m/z=+361.0 (M+H)$^+$.

Example 145

Preparation of 3-((1-(4-amino-1,3,5-triazin-2-yl)-2-methyl-1H-benzo[d]imidazol-6-yl)ethynyl)tetrahydro-2H-pyran-3-ol

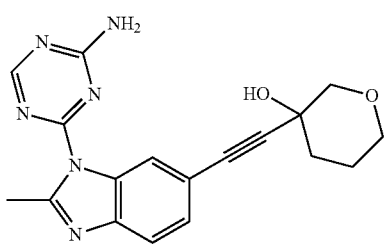 [SMILES: Cc1nc2ccc(C#CC3(O)CCCOC3)cc2n1-c1ncnc(N)n1]

The title compound was prepared by the procedure described for 2-((1-(4-amino-1,3,5-triazin-2-yl)-2-methyl-1H-benzo[d]imidazol-6-yl)ethynyl)bicyclo[2.2.1]heptan-2-ol, by substituting 2-ethynylbicyclo [2.2.1]heptan-2-ol (1-b) with 3-ethynyltetrahydro-2H-pyran-3-ol. The title product, 3-((1-(4-amino-1,3,5-triazin-2-yl)-2-methyl-1H-benzo[d]imidazol-6-yl)ethynyl)tetrahydro-2H-pyran-3-ol was purified by silica gel chromatography: $^1$H NMR (400 MHz, DMSO) delta 1.66-1.78 (m, 4H), 1.97-2.05 (m, 1H), 3.01 (s, 3H), 3.36-3.71 (m, 4H), 7.47 (dd, J=1.6, 8.4 Hz, 1H), 7.71 (dd, J=0.4, 8.4 Hz, 1H), 8.17 (s, 1H), 8.24 (s, 1H), 8.48 (dd, J=0.4, 1.6 Hz, 1H), 8.71 (s, 1H); LC-MS: m/z=+350.9 (M+H)+.

Example 146

Preparation of 3-((1-(4-amino-1,3,5-triazin-2-yl)-2-methyl-1H-benzo[d]imidazol-6-yl)ethynyl)oxetan-3-ol

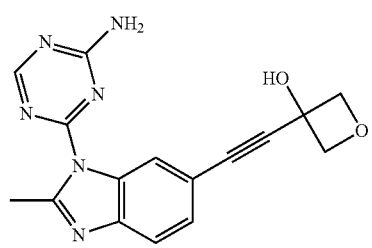 [SMILES: Cc1nc2ccc(C#CC3(O)COC3)cc2n1-c1ncnc(N)n1]

The title compound was prepared by procedure described for Example 144, by substituting 2-ethynyl-bicyclo[2.2.1]heptan-2-ol (1-b) with 3-ethynyloxetan-3-ol (3-a). The title product, 3-((1-(4-amino-1,3,5-triazin-2-yl)-2-methyl-1H-benzo[d]imidazol-6-yl)ethynyl)oxetan-3-ol was purified by reverse phase preparative HPLC (37.5 mg, yield 35%): $^1$H NMR (400 MHz, DMSO) delta 2.88 (s, 3H), 4.60 (d, J=6.8 Hz, 2H), 4.78 (d, J=6.8 Hz, 2H), 6.59 (s, 1H), 7.37 (dd, J=1.6, 8.0 Hz, 1H), 7.60 (dd, J=0.4, 8.4 Hz, 1H), 7.99 (s, 1H), 8.04 (s, 1H), 8.47 (dd, J=0.8, 1.6 Hz, 1H), 8.62 (s, 1H); LC-MS: m/z=+323.0 (M+H)+.

Example 147

Preparation of 3-((1-(4-amino-1,3,5-triazin-2-yl)-2-methyl-1H-benzo[d]imidazol-6-yl)ethynyl)-3-hydroxycyclobutanecarbonitrile

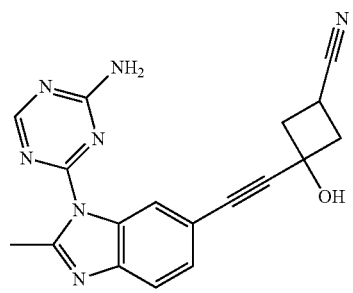 [SMILES: Cc1nc2ccc(C#CC3(O)CC(C#N)C3)cc2n1-c1ncnc(N)n1]

The title compound was prepared by procedure described for Example 144, by substituting 2-ethynylbicyclo [2.2.1]heptan-2-ol (1-b) with 3-ethynyl-3-hydroxycyclobutanecarbonitrile. The product was purified by SFC chromatography (yield 6.2%) to give the title product: $^1$H NMR (400 MHz, MeOD) delta 2.62-2.67 (m, 2H), 2.94-3.00 (m, 5H), 3.17-3.25 (m, 1H), 7.44 (d, J=8.4 Hz), 7.58 (d, J=8.4 Hz), 8.61-8.62 (m, 2H). LCMS: m/z=+346.1 (M+H)+.

Example 148

Preparation of 4-(1-(4-amino-1,3,5-triazin-2-yl)-2-methyl-1H-benzo[d]imidazol-6-yl)-2-methyl-1-(1H-pyrazol-1-yl)but-3-yn-2-ol

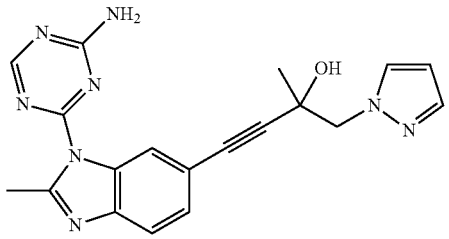 [SMILES: Cc1nc2ccc(C#CC(C)(O)Cn3cccn3)cc2n1-c1ncnc(N)n1]

The title compound was prepared by the procedure described in Example 144, by substituting 2-ethynylbicyclo[2.2.1]heptan-2-ol (1-b) with 2-methyl-1-(1H-pyrazol-1-yl)but-3-yn-2-ol in Step 3. The residue was purified by Prep-HPLC to get 4-(1-(4-amino-1,3,5-triazin-2-yl)-2-methyl-1H-benzo[d]imidazol-6-yl)-2-methyl-1-(1H-pyrazol-1-yl)but-3-yn-2-ol (12.2 mg, yield 5%). $^1$H NMR (400 MHz, MeOD) delta 1.51 (s, 3H), 3.09 (s, 3H), 4.42 (s, 2H), 6.36 (s, 1H), 7.46-7.80 (m, 4H), 8.63 (dd, J=0.4, 1.6 Hz, 1H), 8.66 (s, 1H). LCMS: m/z=+374.9 (M+H)+.

Example 149

Preparation of 4-[1-(4-amino-1,3,5-triazin-2-yl)-2-methyl-1H-1,3-benzodiazol-6-yl]-2-(pyrazin-2-yl)but-3-yn-2-ol

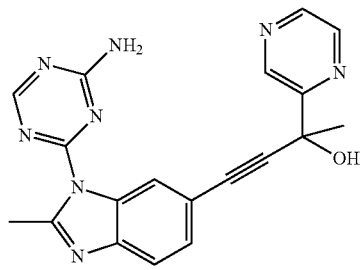
(149-c)

Step 1—Synthesis of 4-{2-methyl-6-[2-(trimethylsilyl)ethynyl]-1,3-benzodiazol-1-yl}-1,3,5-triazin-2-amine

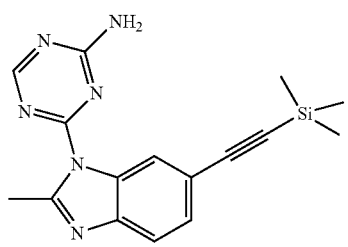
(149-a)

To a mixture of 4-(6-bromo-2-methyl-1,3-benzodiazol-1-yl)-1,3,5-triazin-2-amine (250 mg, 0.74 mmol), tetrakis(triphenylphosphine)palladium(0) (70 mg, 0.06 mmol), copper(I) iodide (11 mg, 0.06 mmol) and ethynyl(trimethyl)silane 0.230 ml, 1.51 mmol) was added triethylamine (2.6 mL). The mixture was purged with nitrogen for 2 minutes and was stirred at 80° C. for 15 min in the microwave. LC-MS shows 50% conversion. The mixture was retreated with another equivalent of tetrakis(triphenylphosphine)palladium (70 mg) copper(I) iodide (11 mg) and ethynyl(trimethyl)silane (0.230 ml). Heating in the microwave at 90° C. was continued for another 30 mins. Purification by Biotage column chromatography (DCM to 5% MeOH/DCM to give the title compound; LC-MS: m/z+323.40 (M+H)+.

Step 2—Synthesis of 4-(6-ethynyl-2-methyl-1,3-benzodiazol-1-yl)-1,3,5-triazin-2-amine

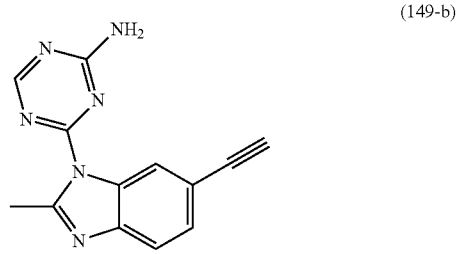 [SMILES: C#Cc1ccc2nc(C)n(-c3ncnc(N)n3)c2c1]
(149-b)

To a solution of 4-{2-methyl-6-[2-(trimethylsilyl)ethynyl]-1,3-benzodiazol-1-yl}-1,3,5-triazin-2-amine (90 mg, 0.279 mmol) in THF (1 mL) was added 1M TBAF in THF (0.33 mL, 0.33 mmol). The mixture was allowed to stand at RT for 1 hr, the mixture was concentrated in vacuo and purified by column chromatography (Biotage 5-8% MeOH/DCM) to give the title compound; LC-MS: m/z+250.95 (M+H)+.

Step 3—Synthesis of 4-[1-(4-amino-1,3,5-triazin-2-yl)-2-methyl-1H-1,3-benzodiazol-6-yl]-2-(pyrazin-2-yl)but-3-yn-2-ol To a solution of 4-(6-ethynyl-2-methyl-1,3-benzodiazol-1-yl)-1,3,5-triazin-2-amine (80 mg, 0.29 mmol) in THF (0.5 mL) at −78° C. under $N_2$ (g) was added 2M LDA in THF (0.43 mL, 0.86 mmol). After 5 min 1-pyrazin-2-yl-ethanone (105 mg, 0.86 mmol) in THF (0.5 mL) was added. After 20 min, the mixture was allowed to warm to RT and was stirred for 1 hr. The reaction mixture was quenched by addition of sat aq NH$_4$Cl (0.5 mL). The volatiles were removed by evaporation under reduced pressure. The mixture was diluted with EtOAc (10 ml) and washed with water (2 mL), dried (Na$_2$SO$_4$), filtered and concentrated in vacuo. Purification by Biotage chromatography (100% DCM to 8% MeOH/DCM) gave the title compound (15 mg, 14% yield); $^1$H NMR (250 MHz, DMSO) delta 1.86 (3H, s), 2.89 (3H, s), 6.63 (1H, s), 7.32 (1H, dd, J=8.22, 1.52 Hz), 7.58 (1H, d, J=8.22 Hz), 7.96 (1H, s), 7.98 (1H, s), 8.39 (1H, d, J=1.22 Hz), 8.59-8.63 (1H, m), 8.63-8.67 (2 H, m), 9.02 (1H, d, J=1.37 Hz); LC-MS: m/z+ 373.4 (M+H)+.

Example 150

Preparation of 4-[1-(4-amino-1,3,5-triazin-2-yl)-2-methyl-1H-1,3-benzodiazol-6-yl]-2-(pyrimidin-2-yl)but-3-yn-2-ol

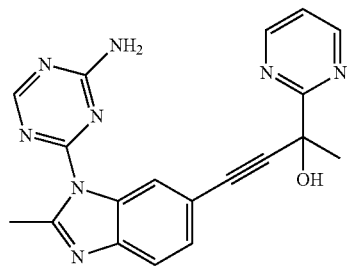 [SMILES: Cc1nc2ccc(C#CC(C)(O)c3ncccn3)cc2n1-c1ncnc(N)n1]

The title compound was prepared by procedure described for Example 149-c, by replacing 1-pyrazin-2-yl-ethanone with 1-(pyrimidin-2-yl)ethanone in Step 3; $^1$H NMR (500 MHz, DMSO) delta 1.88 (3H, s), 2.89 (3H, s), 6.06-6.35 (1H, m), 7.29 (1H, dd, J=8.28, 1.50 Hz), 7.50 (1H, t, J=4.89 Hz), 7.57 (1H, d, J=8.20 Hz), 8.01 (1H, s), 8.07 (1H, s), 8.37 (1H, d, J=0.95 Hz), 8.65 (1H, s), 8.89 (2H, d, J=4.73 Hz); LC-MS: m/z+373.4 (M+H)+.

Example 151

Preparation of 1-[3-(4-Amino-[1,3,5]triazin-2-yl)-2-methyl-3H-benzoimidazol-5-ylethynyl]-3-hydroxymethyl-cyclobutanol (151-b1) and 3-{3-[3-(4-Amino-[1,3,5]triazin-2-yl)-2-methyl-3H-benzoimidazol-5-yl]-1-hydroxy-prop-2-ynyl}-cyclobutanol (151-b2)

(151-b1)

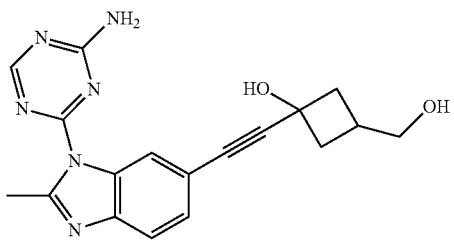

(151-b2)

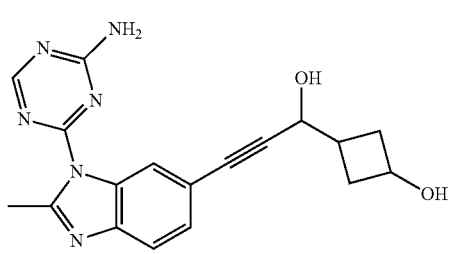

Step 1—Synthesis of 1-[3-(4-amino-[1,3,5]triazin-2-yl)-2-methyl-3H-benzoimidazol-5-ylethynyl]-3-(tert-butyl-dimethyl-silanyloxymethyl)-cyclobutanol and 3-[3-(4-amino-[1,3,5]triazin-2-yl)-2-methyl-3H-benzoimidazol-5-yl]-1-[3-(tert-butyl-dimethyl-silanyloxy)-cyclobutyl]-prop-2-yn-1-ol (151-a1)

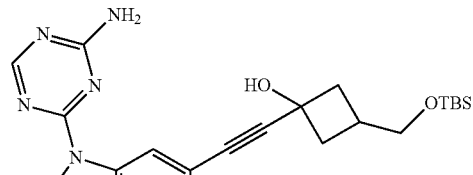

(151-a2)

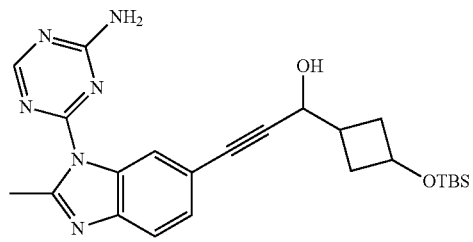

To a solution of the crude product from Example 36-d (0.24 g, 1.0 mmol) in N,N-dimethyl-formamide (3 mL) was added 1,3-bis(diphenylphosphino)propane (40 mg, 0.1 mmol), Pd(OAc)$_2$ (10 mg, 0.05 mmol), K$_2$CO$_3$ (207 mg, 1.5 mmol), 4-(6-bromo-2-methyl-benzoimidazol-1-yl)-[1,3,5]triazin-2-ylamine (150 mg, 1 mmol) and CuI (5 mg, 0.025 mmol). Then the solution was bubbled with N$_2$ for 5 min and microwaved for 1 h at 120° C. under nitrogen. The reaction mixture was filtrated and the filtrate was purified by column to afford 1-[3-(4-amino-[1,3,5]triazin-2-yl)-2-methyl-3H-benzoimidazol-5-ylethynyl]-3-(tert-butyl-dimethyl-silanyloxymethyl)-cyclobutanol (55 mg, 24%) and 3-[3-(4-amino-[1,3,5]triazin-2-yl)-2-methyl-3H-benzoimidazol-5-yl]-1-[3-(tert-butyl-dimethyl-silanyloxy)-cyclobutyl]-prop-2-yn-1-ol (50 mg, 22%): LCMS m/z=+465.1 (M+H)$^+$.

Step 2—Synthesis of 1-[3-(4-amino-[1,3,5]triazin-2-yl)-2-methyl-3H-benzoimidazol-5-ylethynyl]-3-hydroxymethyl-cyclobutanol (151-b1)

In a solution of 1-[3-(4-amino-[1,3,5]triazin-2-yl)-2-methyl-3H-benzoimidazol-5-ylethynyl]-3-(tert-butyl-dimethyl-silanyloxymethyl)-cyclobutanol (55 mg, 0.1 mmol) in tetrahydrofuran (20 ml) was added tetrabutylammonium fluoride (70 mg, 0.3 mmol). Then the solution stirred overnight at room temperature. The reaction mixture was washed with water and purified by column to afford title compound (30 mg, 86%): $^1$H NMR (400 MHz, MeOD) delta 2.05-2.10 (m, 2H), 2.36-2.38 (m, 1H), 2.57-2.62 (m, 2H), 3.59 (d, J=6.4 Hz, 2H), 7.40 (dd, J=1.6, 8.0 Hz, 1H), 7.55 (dd, J=0.4, 8.4 Hz, 1H), 8.56 (dd, J=0.4, 1.6 Hz, 1H), 8.59 (s, 1H). LCMS: m/z=+351.1 (M+H)$^+$.

Synthesis of 1 3-{3-[3-(4-amino-[1,3,5]triazin-2-yl)-2-methyl-3H-benzoimidazol-5-yl]-1-hydroxy-prop-2-ynyl}-cyclobutanol (151-b2)

In a solution of 3-[3-(4-amino-[1,3,5]triazin-2-yl)-2-methyl-3H-benzoimidazol-5-yl]-1-[3-(tert-butyl-dimethyl-silanyloxy)-cyclobutyl]-prop-2-yn-1-ol (50 mg, 0.1 mmol) in tetrahydrofuran (20 ml) was added tetrabutylammonium fluoride (70 mg, 0.3 mmol). Then the solution stirred overnight at room temperature. The reaction mixture was washed with water and purified by column to afford title compound (20 mg, 57%): $^1$H NMR (400 MHz, MeOD) delta 1.80-2.20 (m, 3H), 2.32-2.43 (m, 2H), 2.94 (s, 3H), 3.56-3.70 (m, 0.5H), 4.05-4.17 (m, 0.5H), 4.45-4.48 (m, 0.5H), 7.35-7.51 (m, 2H), 8.53-8.57 (m, 2H). LCMS: m/z=+350.9 (M+H)+.

Example 152

Preparation of 4-[3-(4-amino-[1,3,5]triazin-2-yl)-2-methyl-3H-benzoimidazol-5-yl]-2,2-dimethyl-but-3-yn-1-ol

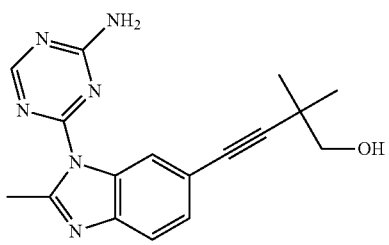
(152-b)

Step 1—Synthesis of 4-{6-[4-(tert-butyl-dimethyl-silanyloxy)-3,3-dimethyl-but-1-ynyl]-2-methyl-benzoimidazol-1-yl}-[1,3,5]triazin-2-ylamine

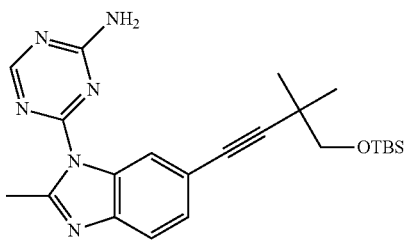
(152-a)

In a solution of 4-(6-bromo-2-methyl-benzoimidazol-1-yl)-[1,3,5]triazin-2-ylamine (0.15 g, 0.5 mmol) in N,N-dimethyl-formamide (3 ml) were added 1,3-bis(diphenylphosphino)propane (40 mg, 0.1 mmol), Pd(OAc)$_2$ (10 mg, 0.05 mmol), K$_2$CO$_3$ (207 mg, 1.5 mmol), tert-butyl-(2,2-dimethyl-but-3-ynyloxy)-dimethyl-silane (150 mg, 1 mmol) and CuI (5 mg, 0.025 mmol). Then the solution bubbled N$_2$ for 5 min and was microwaved for 1 h at 120° C. under nitrogen. The reaction mixture was filtrated and the filtrate was purified by column to afford 4-{6-[4-(tert-butyl-dimethyl-silanyloxy)-3,3-dimethyl-but-1-ynyl]2-methyl-benzoimidazol-1-yl}-[1,3,5]triazin-2-ylamine (140 mg, 66%): LCMS m/z=+ 437.0 (M+H)+.

Step 2—Synthesis of 4-[3-(4-amino-[1,3,5]triazin-2-yl)-2-methyl-3H-benzoimidazol-5-yl]-2,2-dimethyl-but-3-yn-1-ol In a solution of 4-{6-[4-(tert-butyl-dimethyl-silanyloxy)-3,3-dimethyl-but-1-ynyl]2-methyl-benzoimidazol-1-yl}-[1,3,5]triazin-2-ylamine (140 mg, 0.32 mmol) in THF (10 ml) was added tetrabutyl-ammonium fluoride (170 mg, 0.64 mmol). Then the solution stirred overnight at room temperature. The reaction mixture was washed with water and purified by column to afford the title compound 4-[3-(4-amino-[1,3,5]triazin-2-yl)-2-methyl-3H-benzoimidazol-5-yl]-2,2-dimethyl-but-3-yn-1-ol (5-e) (30 mg, 29%): $^1$H NMR (400 MHz, DMSO) delta 1.23 (s, 6H), 2.89 (s, 3H), 3.39 (d, J=6.0 Hz, 2H), 5.00 (t, J=5.6 Hz, 2H), 7.29 (dd, J=1.6, 8.4 Hz, 1H), 7.55 (d, J=8.4 Hz, 1H), 7.99 (s, 1H), 8.02 (s, 1H), 8.33 (t, J=0.4 Hz, 1H), 8.65 (s, 1H). LCMS m/z=+323.1 (M+H)+.

Example 153

Preparation of {1-[3-(4-amino-[1,3,5]triazin-2-yl)-2-methyl-3H-benzoimidazol-5-ylethynyl]-cyclopentyl}-methanol (6-f)

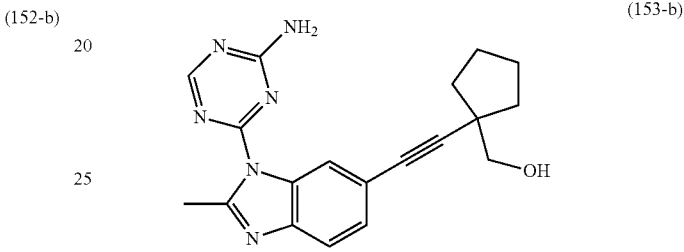
(153-b)

Step 1—Synthesis of 4-{6-[1-(tert-butyl-dimethyl-silanyloxymethyl)-cyclopentylethynyl]-2-methyl-benzoimidazol-1-yl}-[1,3,5]triazin-2-ylamine

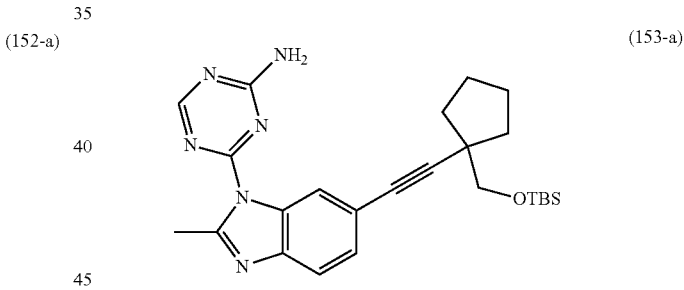
(153-a)

The title compound was prepared by procedure described in Example 144, by substituting 2-ethynylbicyclo[2.2.1]heptan-2-ol (1-b) with tert-butyl-(1-ethynyl-cyclopentyl-methoxy)-dimethyl-silane. 4-(6-bromo-2-methyl-benzoimidazol-1-yl)-[1,3,5]triazin-2-ylamine (200 mg, 0.66 mmol), tert-butyl-(1-ethynyl-cyclopentylmethoxy)-dimethylsilane (313 mg, 1.3 mmol), Pd(OAc)$_2$(29 mg, 0.13 mmol), CuI (25 mg, 0.13 mmol), DPPP (102 mg, 0.26 mmol) and K$_2$CO$_3$ (181 mg, 1.31 mmol) were combined in a flask, and DMF (10 mL) was added. The resulting mixture was stirred at 120° C. for 3 h under N$_2$. The reaction mixture was filtered via silica gel, the filtrate was concentrated, and the residue was washed with EtOAc and MeOH to afford the desired product (80 mg, 26%). LCMS: m/z=+463.1 (M+H)+.

Step 2—Synthesis of {1-[3-(4-amino-[1,3,5]triazin-2-yl)-2-methyl-3H-benzoimidazol-5-ylethynyl]-cyclopentyl}-methanol 4-{6-[1-(tert-butyl-dimethyl-silanyloxymethyl)-cyclopentylethynyl]-2-methyl-benzoimidazol-1-yl}-[1,3,5]triazin-2-ylamine (6-e) (80 mg, 0.17 mmol) was dissolved in THF (100 mL), TBAF (113 mg, 0.43 mmol) was added. The resulting mixture was stirred at room temperature for 12 h. Water (5 mL) was added, extracted with EtOAc. The organic phase was concentrated, purified via prep-TLC separation to afford the title target (27.5 mg, 47%): $^1$H NMR (400 MHz, DMSO) delta 1.55-1.76 (m, 8H), 2.86 (s, 3H), 3.40 (d, J=4.8 Hz, 2H), 4.96 (t, J=4.8 Hz, 1H), 7.25 (d, J=8.4 Hz, 1H), 7.50 (d, J=8.4 Hz, 1H), 7.90-8.10 (m, 2H), 8.30 (t, J=0.8 Hz, 1H), 8.63 (s, 1H). LCMS: m/z=+349.1 (M+H)+.

Example 154

Preparation of 4-[3-(4-amino-[1,3,5]triazin-2-yl)-2-methyl-3H-benzoimidazol-5-yl]-2-methyl-but-3-yne-1,2-diol

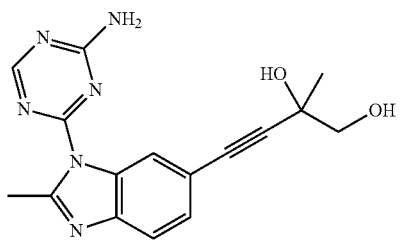

(154-b)

Step 1—Synthesis of 4-[3-(4-amino-[1,3,5]triazin-2-yl)-2-methyl-3H-benzoimidazol-5-yl]-1-(tert-butyl-dimethyl-silanyloxy)-2-methyl-but-3-yn-2-ol

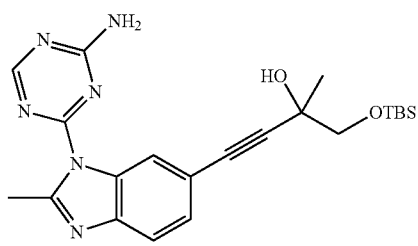

(154-a)

The title compound was prepared by procedure described in Example 144, by substituting 2-ethynylbicyclo[2.2.1]heptan-2-ol with 1-(tert-butyl-dimethyl-silanyloxy)-2-methyl-but-3-yn-2-ol. A mixture of 4-(6-bromo-2-methyl-benzoimidazol-1-yl)-[1,3,5]triazin-2-ylamine (300 mg, 0.98 mmol), 1-(tert-butyl-dimethyl-silanyloxy)-2-methyl-but-3-yn-2-ol (380 mg, 1.9 mmol) in DMF (2.5 mL) was treated with Pd(OAc)$_2$ (20 mg, 0.1 mmol), dppp (60 mg, 0.2 mmol), CuI (5 mg, 0.05 mmol) and K$_2$CO$_3$ (280 mg, 2.0 mmol), then the mixture was heated at 120° C. for 40 min under microwave. After filtrated and concentrated by vacuum, the residue was purified by silica gel chromatography (DCM: MeOH=20:1) to get the title compound 4-[3-(4-amino-[1,3,5]triazin-2-yl)-2-methyl-3H-benzoimidazol-5-yl]-1-(tert-butyl-dimethyl-silanyloxy)-2-methyl-but-3-yn-2-ol (7-b) (300 mg, yield 68%).

Step 2—Synthesis of 4-[3-(4-amino-[1,3,5]triazin-2-yl)-2-methyl-3H-benzoimidazol-5-yl]-1-(tert-butyl-dimethyl-silanyloxy)-2-methyl-but-3-yn-2-ol To a solution of 4-[3-(4-amino-[1,3,5]triazin-2-yl)-2-methyl-3H-benzoimidazol-5-yl]-1-(tert-butyl-dimethyl-silanyloxy)-2-methyl-but-3-yn-2-ol (300 mg, 0.68 mmol) in THF (20 mL) was added TBAF (dissolved in 5 mL THF) at 0° C. for about 1 h. After washing with water and extracting with EtOAc, the crude product was obtained and further purified by Prep-TLC (DCM: MeOH=10:1) to get the title compound (22.8 mg, yield 10%): $^1$H NMR (400 MHz, MeOD) delta 1.54 (s, 3H), 2.98 (s, 3H), 3.61 (s, 2H), 7.43 (d, J=8.0 Hz, 1H), 7.54 (d, J=8.0 Hz, 1H), 8.60 (s, 2H). LCMS: m/z=+325.1 (M+H)+.

Example 155

Preparation of (2R)-4-[1-(4-amino-1,3,5-triazin-2-yl)-2-(methoxymethyl)-1H-1,3-benzodiazol-6-yl]-2-(1,3-thiazol-2-yl)but-3-yn-2-ol

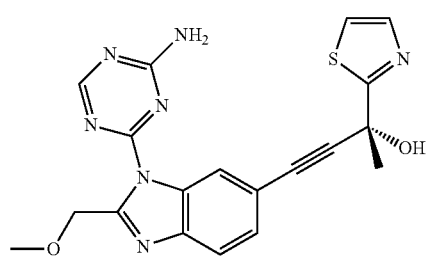

(155-b)

Step 1—Synthesis of 4-[6-bromo-2-(methoxymethyl)-1H-1,3-benzodiazol-1-yl]-1,3,5-triazin-2-amine

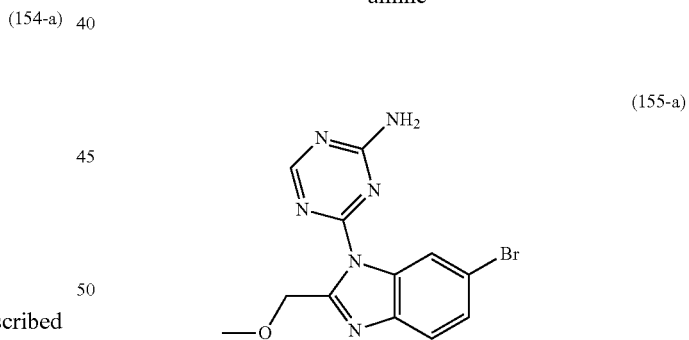

(155-a)

To a solution of 2-N-(2-amino-5-bromophenyl)-1,3,5-triazine-2,4-diamine (1.00 g, 3.56 mmol) in DMF (5 mL) was introduced methoxyacetic acid (320 mg, 3.56 mmol), N-(3-dimethylaminopropyl)-N'-ethylcarbodiimide hydrochloride (750 mg, 3.91 mmol), 1-hydroxy-7-azabenzotriazole (533 mg, 3.91 mmol) and triethylamine (720 mg, 7.11 mmol). The reaction mixture was stirred for 18 hr at RT and concentrated in vacuo. The residue was suspended in water (100 mL) and the resulting precipitate collected by filtration. After washing the filter cake with EtOAc (10 mL) and methanol (10 mL), the crude amide was dried on the filter. The intermediate amide was dissolved in glacial acetic acid (20 mL) and warmed to 140° C. for 15 minutes (microwave heating in 4 batches of equal volume). Following concentration of the reaction mixture in vacuo, toluene (20 mL) was introduced and the suspension concentrated in vacuo (repeated twice) to furnish the crude title compound as a brown oil: LC-MS: m/z=+334.90/336.75 (M+H)+. This compound, with LC-MS purity=86% UV, was used in the next step without further purification.

Step 2—Synthesis of (2R)-4-[1-(4-amino-1,3,5-triazin-2-yl)-2-(methoxymethyl)-1H-1,3-benzodiazol-6-yl]-2-(1,3-thiazol-2-yl)but-3-yn-2-ol To a solution of 4-[6-bromo-2-(methoxymethyl)-1H-1,3-benzodiazol-1-yl]-1,3,5-triazin-2-amine (150 mg at 86% purity, 0.38 mmol) in piperidine (3 mL) was introduced tetrakis(triphenylphosphine)palladium(0) (22.2 mg, 0.02 mmol), copper(I) iodide (7.3 mg, 0.04 mmol) and (2R)-2-(1,3-thiazol-2-yl)but-3-yn-2-ol (118 mg, 0.77 mmol). The reaction was warmed to 70° C. for 1 hr. After cooling to RT, additional tetrakis(triphenylphosphine)palladium(0) (22.2 mg, 0.02 mmol) was introduced and the reaction mixture warmed to 70° C. for a further 1 hr. The reaction mixture was concentrated in vacuo and the residue purified by silica gel flash chromatography (DCM containing a 0-3% gradient of methanol) to furnish the title compound as a brown oil: $^1$H NMR (500 MHz, DMSO) delta 1.90 (3H, s), 5.10 (2H, s), 7.06 (1H, br. s.), 7.31-7.40 (1H, m), 7.64-7.73 (2H, m), 7.75-7.80 (1H, m), 8.02 (1H, br. s.), 8.08 (1H, br. s.), 8.30 (1H, s), 8.40-8.45 (1H, m), 8.65 (1H, s); LC-MS: m/z=+408.00 (M+H)+.

Example 156

Preparation of 4-[3-(2-aminopyrimidin-4-yl)-6-fluoro-1,3-benzodiazol-5-yl]-2-(1,3-thiazol-2-yl)but-3-yn-2-ol

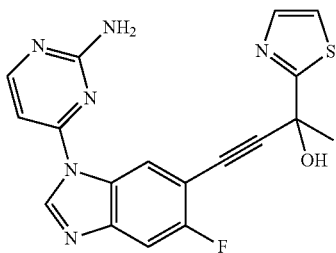

(156-e)

Step 1—Synthesis of N-(5-bromo-4-fluoro-2-nitrophenyl)-2-chloropyrimidin-4-amine

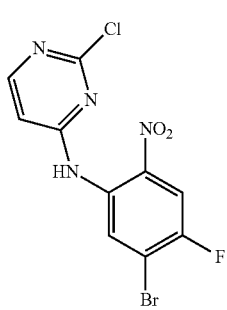

(156-a)

To a solution of 2-chloropyrimidin-4-amine (1.31 g, 10.08 mmol) in THF (55 mL) at 0° C. was added sodium hydride (60% in oil, 806.69 mg, 20.17 mmol) portion-wise. The reaction mixture was stirred at 0° C. to RT for 10 minutes and 1-bromo-2,5-difluoro-4-nitrobenzene (1.2 g, 5.04 mmol) was added. The reaction mixture was stirred at 65° C. for 1 h. The reaction mixture was cooled to RT and water (30 mL) was added. Product extracted into DCM (2×30 mL) and washed with water (20 mL). The combined organics were dried (Na$_2$SO$_4$), filtered and concentrated in vacuo. The crude product was purified by column chromatography (Biotage) eluted with DCM:MeOH gradient (99:1 to 95:05) to afford the title compound as an orange solid (1005 mg, 56% yield); $^1$H NMR (250 MHz, DMSO) delta 6.87 (1H, d, J=5.83 Hz), 8.08 (1H, d, J=6.31 Hz), 8.18 (1H, d, J=8.35 Hz), 8.27 (1H, d, J=5.83 Hz), 10.32 (1H, br. s.); LC-MS: m/z+348.70 (M+H)+.

Step 2—Synthesis of 4-N-(5-bromo-4-fluoro-2-nitrophenyl)pyrimidine-2,4-diamine

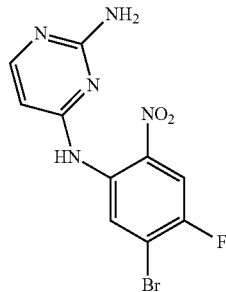

(156-b)

To a solution of N-(5-bromo-4-fluoro-2-nitrophenyl)-2-chloropyrimidin-4-amine (1.05 g, 3.02 mmol) in 2-propanol (12 mL) in a pressure vessel was added ammonium hydroxide (12 mL, 303 mmol) carefully at RT. The reaction vessel was sealed and stirred at 90° C. for 15 hr (4 bar). Extra aqueous ammonium (4 mL, 100 mmol) was added and the reaction heated at 90° C. for 1 hr then cooled to 0° C. The resultant orange precipitate was filtered and dried by suction filtration to afford the title compound as an orange solid (713 mg, 63% yield); $^1$H NMR (500 MHz, DMSO) delta 9.55 (s, 1H), 8.44 (d, J=6.6 Hz, 1H), 8.17 (d, J=8.6 Hz, 1H), 7.98 (d, J=5.6 Hz, 1H), 6.31 (s, 2H), 6.19 (d, J=5.6 Hz, 1H); LC-MS: m/z+ 329.80 (M+H)+.

Step 3—Synthesis of 4-N-(2-amino-5-bromo-4-fluorophenyl)pyrimidine-2,4-diamine

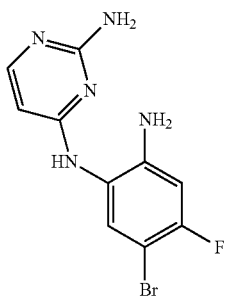

(156-c)

To a solution of 4-N-(5-bromo-4-fluoro-2-nitrophenyl)pyrimidine-2,4-diamine (713 mg, 2.17 mmol) in ethanol (30 mL) was added tin(II) chloride dihydrate (1.72 g, 7.61 mmol) The reaction mixture was stirred at 60° C. for 1 hr. Upon completion, reaction mixture was evaporated to dryness and added to ice water (20 mL). The pH was adjusted to pH10 using sat Na₂CO₃ solution (30 mL) and EtOAc (30 mL) was added. Saturated Rochelle's salt (20 mL) was added and the mixture stirred until separate layers were observed. The organic layer was separated and the aqueous layer extracted with EtOAc (2×5 mL). Combined organics were washed with saturated Rochelles salt (15 mL) followed by brine solution (15 mL) and dried over Na₂SO₄, filtered and concentrated in vacuo to afford the title compound as a pale orange solid (500 mg, 68.7% yield); ¹H NMR (250 MHz, DMSO) delta 8.11 (s, 1H), 7.75 (d, J=5.7 Hz, 1H), 7.37 (d, J=7.6 Hz, 1H), 6.67 (d, J=11.1 Hz, 1H), 6.08 (s, 2H), 5.75 (d, J=5.7 Hz, 1H), 5.37 (s, 2H); LC-MS: m/z+299.75 (M+H)+.

Step 4—Synthesis of 4-(6-Bromo-5-fluoro-benzoimidazol-1-yl)-pyrimidin-2-ylamine

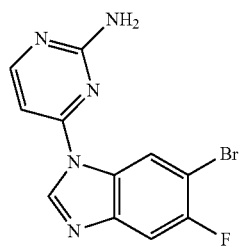

(156-d)

To a solution of 4-N-(2-amino-5-bromo-4-fluorophenyl)pyrimidine-2,4-diamine (500 mg, 1.68 mmol) in methanol (6 mL) and THF (20 mL) was added trimethyl orthoformate (5.59 ml, 50.32 mmol) and TsOH (0.03 ml, 0.17 mmol). The reaction mixture was stirred at 70° C. for 1.5 hr. Reaction had only progressed 6% by LC-MS. Extra trimethyl orthoformate (6 mL, 54.23 mmol) was added and stirred at 70° C. for 1 hr. Reaction mixture was cooled and sat NaHCO₃ (10 mL) was added. The product was extracted with DCM (3×10 mL) and the organics were washed with brine and then dried (Na₂SO₄), filtered and concentrated in vacuo to obtain title compound as a beige solid (500 mg, 63.8% yield); ¹H NMR (500 MHz, DMSO) delta 9.17 (s, 1H), 8.97 (d, J=6.7 Hz, 1H), 8.37 (d, J=5.5 Hz, 1H), 7.81 (d, J=9.1 Hz, 1H), 7.20 (s, 2H), 7.14 (d, J=5.6 Hz, 1H); LC-MS: m/z=+309.75 (M+H)+.

Step 5—Synthesis of 4-[3-(2-aminopyrimidin-4-yl)-6-fluoro-1,3-benzodiazol-5-yl]-2-(1,3-thiazol-2-yl)but-3-yn-2-ol To a pressure tube was added 4-(6-Bromo-5-fluoro-benzoimidazol-1-yl)-pyrimidin-2-ylamine (66%, 250 mg, 0.54 mmol), piperidine (1.5 mL), tetrakis(triphenylphosphine)palladium (61.9 mg, 0.05 mmol), copper(I) iodide (10.2 mg, 0.05 mmol) and 2-(1,3-thiazol-2-yl)but-3-yn-2-ol (164.09 mg, 1.07 mmol), degassed with N₂ for 5 min and stirred at 75° C. for 3 hr before concentrating in vacuo. The crude product was purified by column chromatography (Biotage) eluted with DCM: methanol gradient (98:2 to 90:10). The product obtained was triturated with methanol to obtain the title compound as an off-white solid (35 mg, 17.1% yield). ¹H NMR (500 MHz, DMSO) delta 1.94 (3H, s), 7.08 (1H, s), 7.13 (1H, d, J=5.36 Hz), 7.18 (2H, br. s.), 7.65-7.73 (2H, m), 7.78 (1H, d, J=3.15 Hz), 8.39 (1H, br. s.), 8.64 (1 H, d, J=6.46 Hz), 9.17 (1H, s); LC-MS: m/z+381.40 (M+H)+.

Example 156

Preparation of 4-[3-(2-aminopyrimidin-4-yl)-6-fluoro-1,3-benzodiazol-5-yl]-2-methylbut-3-yn-2-ol

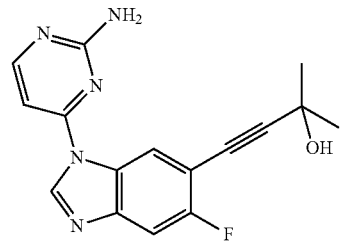 [SMILES: CC(C)(O)C#Cc1cc2c(cc1F)ncn2-c1ccnc(N)n1]

To a pressure tube was added 3-(2-aminopyrimidin-4-yl)-7-bromo-6-fluoro-1,3benzodiazol-4-amine (66%, 250 mg, 0.54 mmol), piperidine (1.5 mL), tetrakis(triphenylphosphine)palladium (61.9 mg, 0.05 mmol), copper(I) iodide (10.2 mg, 0.05 mmol) and 2-methylbut-3-yn-2-ol (0.1 ml, 1.07 mmol). The reaction was stirred at 75° C. for 2.5 h before concentrating in vacuo. The crude product was purified by column chromatography (Biotage) eluted with DCM: methanol gradient (98:3 to 90:10). Material obtained triturated with methanol to obtain the title compound as an off-white solid. (45 mg, 26.7% yield); ¹H NMR (500 MHz, DMSO) delta 1.52 (6H, s), 5.53 (1H, s), 7.14 (1H, d, J=5.20 Hz), 7.18 (2H, br. s.), 7.67 (1H, d, J=9.62 Hz), 8.40 (1H, br. s.), 8.63 (1H, d, J=6.62 Hz), 9.16 (1H, s); LC-MS m/z+312.5 (M+H)+.

Example 157

Preparation of 4-[1-(4-aminopyrimidin-2-yl)-1H-1,3-benzodiazol-6-yl]-2-(1,3-thiazol-2-yl)but-3-yn-2-ol

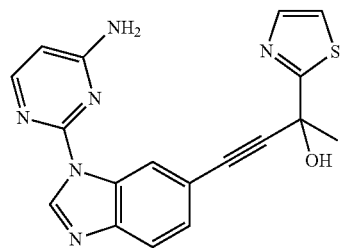 [SMILES: CC(O)(C#Cc1ccc2ncn(-c3nccc(N)n3)c2c1)c1nccs1]

To a pressure tube was added 2-(6-bromo-1,3-benzodiazol-1-yl)pyrimidin-4-amine (300 mg, 1.03 mmol), piperidine (2 mL), tetrakis(triphenylphosphine)palladium (119.5 mg, 0.10 mmol), copper(I) iodide (19.7 mg, 0.10 mmol) and 2-(1,3-thiazol-2-yl)but-3-yn-2-ol (316.84 mg, 2.07 mmol). The reaction was stirred at 75° C. for 18 h. The reaction mixture was cooled before concentrating in vacuo. The crude product was purified by column chromatography (Biotage) eluted with DCM: methanol gradient (97:3 to 90:1). Material obtained was triturated with methanol to afford the title compound as a beige solid. (43 mg, 11.5% yield); ¹H NMR (250 MHz, DMSO) delta 1.91 (3H, s), 6.41 (1H, d, J=5.79 Hz), 7.06 (1H, s), 7.37 (1H, d, J=1.52 Hz), 7.45 (2H, br. s.), 7.65-7.84 (3H, m), 8.19 (1H, d, J=5.79 Hz), 8.62 (1H, d, J=1.07 Hz), 9.00 (1H, s); LC-MS m/z+3.

Example 158

Preparation of 4-[1-[2-amino-5-(1-methylpyrazol-4-yl)pyrimidin-4-yl]indazol-6-yl]-2-methyl-but-3-yn-2-ol (158-b)

Synthesis of 5-bromo-4-(6-bromo-1H-indazol-1-yl)pyrimidin-2-amine

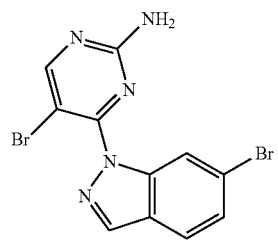

(158-a)

To a solution of 6-bromo-1H-indazole (1.01 eq) in DMF (50 mL) at 0° C. was added sodium hydride in oil (1.3 eq). The ice bath was removed after 10 minutes and the reaction mixture was stirred for 30 minutes before the addition of 5-bromo-4-chloro-pyrimidin-2-amine (5.2 g). The reaction was judged to be complete by LC-MS after heating overnight at 50° C. The crude reaction mixture was subsequently concentrated to dryness whereupon the product was triterated from by sonication from Methanol to afford 7 g of 5-bromo-4-(6-bromo-1H-indazol-1-yl)pyrimidin-2-amine (158-a) as a light orange solid. $^1$H NMR (400 MHz, DMSO-d6) δ 8.48 (s, 1H), 8.41 (d, J=1.3 Hz, 1H), 7.86 (d, J=8.5 Hz, 1H), 7.49 (dd, J=8.5, 1.6 Hz, 1H), 7.30 (s, 2H).

Synthesis of 4-[1-(2-amino-5-bromo-pyrimidin-4-yl)indazol-6-yl]-2-methyl-but-3-yn-2-ol (158-b)

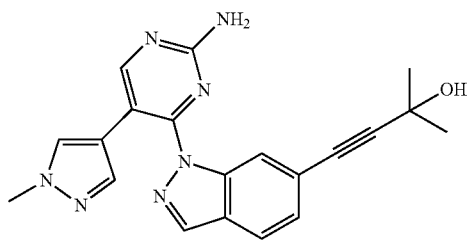

(158-b)

5-bromo-4-(6-bromoindazol-1-yl)pyrimidin-2-amine (3 g) was reacted with 2-methyl-3-butyn-2-ol (1 eq) via General Procedure Sonagashira Coupling (See, Chinchilla, R.; Najera, C. (2007), "The Sonogashira Reaction: A Booming Methodology in Synthetic Organic Chemistry", Chem. Rev. 107: 874-922) to afford 0.7 g of 4-[1-(2-amino-5-bromo-pyrimidin-4-yl)indazol-6-yl]-2-methyl-but-3-yn-2-ol following flash column chromatography. 4-[1-(2-amino-5-bromo-pyrimidin-4-yl)indazol-6-yl]-2-methyl-but-3-yn-2-ol (0.1 g) was reacted with 1-methyl-4-pyrazoleboronic acid pinacol ester via General Procedure Suzuki Coupling to afford 12.2 mg of 4-[1-[2-amino-5-(1-methylpyrazol-4-yl)pyrimidin-4-yl]indazol-6-yl]-2-methyl-but-3-yn-2-ol following reverse phase hplc purification. MS (Q1) 374. $^1$H NMR (400 MHz, DMSO-d6) δ 8.57 (s, 1H), 8.30 (s, 1H), 7.88-7.81 (m, 2H), 7.48 (s, 1H), 7.24 (dd, J=8.3, 1.1 Hz, 1H), 7.05 (s, 2H), 6.98 (s, 1H), 5.47 (s, 1H), 3.73 (s, 3H), 1.48 (s, 6H).

Example 159

Preparation of 4-[1-[2-amino-5-(1-methylpyrazol-4-yl)pyrimidin-4-yl]indazol-6-yl]-2-methyl-but-3-yn-2-ol (159-a)

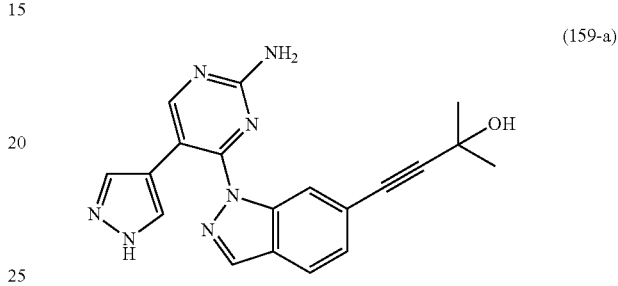

(159-a)

4-[1-(2-amino-5-bromo-pyrimidin-4-yl)indazol-6-yl]-2-methyl-but-3-yn-2-ol (0.075 g) was reacted 1-Boc-4-pyrazoleboronic acid pinacol ester via General Procedure Suzuki Coupling to afford 9.5 mg of 4-[1-[2-amino-5-(1-methylpyrazol-4-yl)pyrimidin-4-yl]indazol-6-yl]-2-methyl-but-3-yn-2-ol following reverse phase hplc purification. MS (Q1) 360. $^1$H NMR (400 MHz, DMSO-d6) δ 12.71 (s, 1H), 8.62 (s, 1H), 8.30 (s, 1H), 7.84 (d, J=8.3 Hz, 1H), 7.76 (s, 1H), 7.46 (s, 1H), 7.23 (d, J=8.2 Hz, 1H), 7.02 (s, 2H), 5.45 (s, 1H), 1.47 (s, 6H).

Example 160

NIK Enzyme Inhibition Assay: The ability of the nuclear factor-kappa B (NF-kB)-inducing kinase (NIK) to catalyze the hydrolysis of adenosine-5'-triphosphate (ATP) was monitored using the Transcreener ADP (adenosine-5'-diphosphate) assay (BellBrook Labs). Purified NIK (0.2-1 nM) derived from a baculovirus-infected insect cell expression system was incubated with test compounds for 1-3.5 hours in 50 mM 2-[4-(2-hydroxyethyl)piperazin-1-yl]ethanesulfonic acid buffer (pH 7.2) containing 10 mM $MgCl_2$, 2 mM dithiothreitol, 10 uM ATP, 0.01% Triton X-100, 0.1% gamma-globulins from bovine blood, 1% dimethylsulfoxide (DMSO), 12 ug/mL ADP antibody and 4 nM ADP-AlexaFluor® 633 tracer. Reactions were quenched by the addition of 20 mM 2,2',2'', 2'''-(ethane-1,2-diyldinitrilo)tetraacetic acid and 0.01% Brij 35. The tracer bound to the antibody was displaced by the ADP generated during the NIK reaction, which causes a decrease in fluorescence polarization that was measured by laser excitation at 633 nm with a Fluorescence Correlation Spectroscopy Plus reader (Evotec AG). Equilibrium dissociation constant ($K_i$) values for NIK inhibitors are calculated from plots of activity vs. inhibitor concentration using Morrison's quadratic equation that accounts for the potential of tight binding, and by also applying the conversion factor that accounted for competitive inhibition and the concentration of substrate used in the assay relative to its Michaelis constant ($K_m$). The compounds in listed in Table 1 have the corresponding inhibitory value (Ki in micromolar) for NIK (values for compounds are presented in the same order as found in Table 1): na, na, na, na, na, 0.00014, 0.00028, 0.411, 0.0459, 0.0143, 0.559, 0.0093, 0.000262, 0.0069, 0.00032, 0.027, 2.9, 0.0017, 0.19, 0.049, 0.0003, 0.0001, >5, 2.1, 0.012, 0.061, 0.57, 0.00042, 0.0009, 0.060, 4.6, 0.0013, 0.023, 0.0921, 0.018, 0.85, 0.0023, 0.016, 0.00025, 0.003, 0.0085, 0.00014, 0.0002, 0.0435, 0.000045, 0.00016 and 0.00011, 0.013, 0.847, 0.152, 0.575, 0.01, 0.0004, 0.105, 0.0002, 0.0016, 0.002, 0.00015, 0.00049, 0.0022, 0.383, 0.017, 0.00023, 0.005, 0.00265, 0.00127, 0.004, 0.0027, 5 and 0.0005. The compounds in listed in Table 1.1 have the corresponding inhibitory value (Ki in micromolar) for NIK (values for compounds are presented in the same order as found in Table 1.1): 0.0001, 0.0002, 0.0002, 0.00022, 0.00032, 0.00032, 0.0004, 0.0005, 0.0005, 0.0005, 0.0005, 0.0006, 0.0006, 0.0008, 0.001, 0.001, 0.001, 0.001, 0.001, 0.001, 0.001, 0.001, 0.001, 0.001, 0.001, 0.001, 0.002, 0.002, 0.002, 0.002, 0.002, 0.002, 0.002, 0.002, 0.002, 0.002, 0.002, 0.002, 0.002, 0.002, 0.002, 0.002, 0.002, 0.002, 0.002, 0.002, 0.003, 0.003, 0.003, 0.003, 0.003, 0.003, 0.003, 0.004, 0.004, 0.004, 0.004, 0.004, 0.004, 0.004, 0.004, 0.005, 0.005 0.005, 0.006, 0.006, 0.006, 0.006, 0.006, 0.007, 0.007, 0.008, 0.009, 0.009, 0.009, 0.010, 0.012, 0.012, 0.013, 0.014, 0.016, 0.020, 0.020, 0.022, 0.024, 0.025, 0.025, 0.027, 0.027, 0.031, 0.039, 0.046, 0.052, 0.054, 0.069, 0.070, 0.078, 0.085, 0.087, 0.100, 0.102, 0.111, 0.129, 0.13, 0.15, 0.31, 0.315, 0.342, 0.491, 0.775, 0.913, 1.6, 1.6, 1.7, 1.7, 1.8, 2.4, 2.6, 3.9, 5, 5, 5, 5, 5, 5, 0.0003, 5, na, 0.001, 5, na, 4.9, na, 5, 0.009, 0.841, 0.0004, 0.002, 0.004, 0.002, 0.007, 0.0002, 0.020, 0.00528, 0.0002, 0.007, 0.002, 0.003, 0.011, 3.4, 0.004, 0.0001 and 0.0003.

Example 161

Cellular Assay: Several Assays were Developed to Profile the Cellular Activities of NIK Inhibitors (1) The first assay was used to profile whether a test compound can inhibit the NF-kB signally through NIK inhibition without affecting cell viability. In this assay, human embryonic kidney 293 cells was stably transfected with a tetracycline-inducible NIK DNA construct containing a cytomegalovirus promoter plus two reporter DNA constructs. One reporter encoded firefly luciferase under the control of three repeats of an NF-kB response element from the ELAM-1 gene and reflects the level of NIK activity in the cells, whereas the other reporter constitutively expressed *Renilla* luciferase under the control of the herpes simplex virus thymidine kinase promoter and served as a general measure of cell viability. Cells were incubated with different concentrations of compounds (0.2% DMSO final) in medium containing 1 ug/mL doxycycline and 10% tet-system approved fetal bovine serum (Clontech) for 24 hours, after which the reporters' signals were detected using the Dual Glo luciferase detection system (Promega) according to the vendor's protocol. The compounds listed in Table 1 have the corresponding inhibitory value ($IC_{50}$ in micromolar) for 293-NIK NF-kB-Luciferase activity (values for compounds are presented in the same order as found in Table 1): na, 0.059, na, na, na, 0.105, 0.027, na, 20, 1.2, na, 1.8, 0.0231, 0.879, 0.0361, 0.582, na, 0.142, na, 0.403, 0.059, 0.0331, na, na, 0.0573, 1.5, na, na, 0.0722, na, na, 0.589, 12.7, 3.7, 14.9, na, 0.707, 1, 0.0311, 0.332, 0.309, 0.0142, 0.051, 2.8, 0.129, na, na, 1.5, na, na, na, 1.3, 0.062, 20, 0.31, 0.104, 0.091, 0.037, 0.085, 0.279, na, 0.305, 0.064, 0.332, 0.133, 0.168, 0.217, 0.553, na and na.

The compounds in listed in Table 1 have the corresponding inhibitory value ($IC_{50}$ in micromolar) for 293-NIK TK *Renilla* Luciferase activity: (values for compounds are presented in the same order as found in Table 1): 6.4, 3.6, 20, na, 1.6, 9.3, 18.5, na, na, 2.6, na, na, na, na, na, na, na, na, na, na, na, na, na, na, na, na, na, na, na, na, na, na, na, na, na, na, na, na, na, >20, na, na, na, 20, >20, 17, 1.3, 15.6, 0.967, 2.7, 11.2, 5.1, na, 20, 20, 20, 20, 20, 17.6, 20, na and na.

(2) A second set of cell assay was used to define the selectivity of NIK inhibitors toward inhibition of classical vs. non-classical NF-kB signaling and rely on quantification of the nuclear translocation of p52 (NF-kB2) and REL-A (p65) using high content cellular imaging. For the p52 (non-classical NF-kB signaling) nuclear translocation assay, HeLa cells were treated with different concentrations of compounds (0.2% DMSO final) in medium containing 10% fetal bovine serum and then stimulated with 100 ng/mL of an anti-lymphotoxin beta receptor antibody (R&D Systems) for 5 hours. In the REL-A nuclear translocation assay, HeLa cells were incubated with compounds (0.2% DMSO final) for 4.5 hours in medium containing 10% fetal bovine serum before stimulating them with 10 ng/mL tumor necrosis factor (TNF)-α (R&D Systems) for 30 minutes. Cells were fixed with 4% paraformaldehyde, permeabilized by adding 0.1% Triton X-100 in phosphate buffered saline, and then incubated with either 2 ug/mL anti-p52 antibody (Millipore) or 400 ng/mL anti-REL-A (p65) antibody (Santa Cruz Biotechnology). Finally, the cells were incubated with an Alexa488-labeled secondary antibody (Invitrogen) and DRAQ5 DNA stain (Biostatus). Imaging was carried out using an Opera reader (Perkin Elmer) and data are analyzed with the aid of Acapella software (Perkin Elmer). The p52 or REL-A translocation into the nucleus was quantified by the ratio of the nuclear to cytoplasmic signal intensity. The concentration of inhibitor required for 50% inhibition ($IC_{50}$ values) in these cell assays were derived from the plots of signal vs. inhibitor concentration. The compounds in listed in Table 1 have the corresponding inhibitory value ($IC_{50}$ in micromolar) for NIK p52 Translocation Assay (values for compounds are presented in the same order as found in Table 1, and "na" means the data for this assay is to be determined): 0.326, 0.33, na, na, na, 0.218, 0.07, na, na, na, 0.129, 7.6, 0.077, 3.4, na, 0.518, na, 0.059, 0.514, 0.127, na, na, 0.010, na, na, 0.313, 0.275, na, 0.0727, na, na, na, na, na, na, 0.194, na, 6.4, 0.22, 0.346, na, na, na and na, na, na, na, na, na, 0.447, na, 0.089, 0.479, 0.489, 0.243, 0.747, 1, na, 1.9, 0.552, 2.1, na. na, na, na, na and na.

The compounds in listed in Table 1 has the corresponding inhibitory value ($IC_{50}$ in micromolar) for NIK RelA Translocation Assay (values for compounds are presented in the same order as found in Table 1): 0.326, 0.33, na, na, na, 0.218, 0.07, na, na, na, na, 0.129, 7.6, 0.077, 3.4, na, 0.518, na, 0.059, 0.514, 0.127, na, na, 0.010, na, na, 0.313, 0.275, na, na, 0.0727, na, na, na, na, na, na, 0.194, na, 6.4, 0.22, 0.346, na, na, na, na, na, na, na, na, na, 0.447, na, 0.089, 0.479, 0.489, 0.243, 0.747, 1, na, 1.9, 0.552, 2.1, na, na, na, na, na and na.

Example 162

Comparative data: PCT Application (WO 2009/158011) to Amgen, Inc. describes certain alkynyl alcohol formula as NIK inhibitors. Compounds of the invention of Formula I, in which "A" group in Formula I is as disclosed herein exhibit unexpectedly, superior properties in the assays described hereinabove as compared to compounds described in WO 2009/158011 (See Table 16A-16D):

TABLE 16A

| Assay (micromolar) | 4-(1-(2-aminopyrimidin-4-yl)indolin-6-yl)-2-(thiazol-2-yl)but-3-yn-2-ol (WO2009/158011) | 4-(1-(2-aminopyrimidin-4-yl)-1H-benzo[d]imidazol-6-yl)-2-(thiazol-2-yl)but-3-yn-2-ol |
|---|---|---|
| NIK ADP (Ki) | 0.0027 | 0.0003 |
| 293-NIK NF-kB-Luciferase (IC$_{50}$) | 0.126 | 0.027 |
| 293-NIK TK Renilla Luciferase (IC$_{50}$) | 3.9 | 4.9 |
| NIK p52 Translocation (IC$_{50}$) | 0.862 | 0.070 |
| NIK RelA Translocation (IC$_{50}$) | >20 | >20 |

TABLE 16B

| Assay (micromolar) | 4-(1-(2-aminopyrimidin-4-yl)-3-methyl-1H-indazol-6-yl)-2-(thiazol-2-yl)but-3-yn-2-ol | 1-(2-aminopyrimidin-4-yl)-6-(3-hydroxy-3-(thiazol-2-yl)but-1-ynyl)-1H-benzo[d]imidazol-2( |
|---|---|---|
| NIK ADP (Ki) | 0.0001 | 0.0003 |
| 293-NIK NF-kB-Luciferase (IC$_{50}$) | 0.011 | 0.59 |
| 293-NIK TK Renilla Luciferase (IC$_{50}$) | 1.2 | 5.2 |
| NIK p52 Translocation (IC$_{50}$) | 0.222 | 0.514 |
| NIK RelA Translocation (IC$_{50}$) | >20 | >20 |

TABLE 16C

| Assay (micromolar) | 4-(1-(2-aminopyrimidin-4-yl)-1H-benzo[d]imidazol-6-yl)-2-(oxazol-2-yl)but-3-yn-2-ol | 4-(1-(2-aminopyrimidin-4-yl)-1H-indazol-6-yl)-2-(oxazol-2-yl)but-3-yn-2-ol |
|---|---|---|
| NIK ADP (Ki) | 0.0001 | 0.0003 |
| 293-NIK NF-kB-Luciferase (IC$_{50}$) | 0.033 | 0.036 |
| 293-NIK TK Renilla Luciferase (IC$_{50}$) | 3.1 | 0.514 |
| NIK p52 Translocation (IC$_{50}$) | 0.127 | 0.077 |
| NIK RelA Translocation (IC$_{50}$) | >20 | >20 |

TABLE 16D

| Assay (micromolar) | 1-(2-aminopyrimidin-4-yl)-6-(3-hydroxy-3-(oxazol-2-yl)but-1-ynyl)-N,N-dimethyl-1H-indazole-3-carboxamide |
|---|---|
| NIK ADP (Ki) | 0.0002 |
| 293-NIK NF-kB-Luciferase (IC$_{50}$) | 0.051 |
| 293-NIK TK Renilla Luciferase (IC$_{50}$) | 0.583 |
| NIK p52 Translocation (IC$_{50}$) | 0.346 |
| NIK RelA Translocation (IC$_{50}$) | >20 |

We claim:

1. A compound of formula (I)

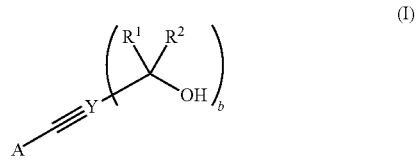

or a stereoisomer or pharmaceutically acceptable salt thereof,
wherein in formula I:
Y is carbon and the subscript b is the integer 1;
R$^1$ is C$_{1-2}$ alkyl, C$_{1-2}$ haloalkyl or —CH$_2$—OH;
R$^2$ is C$_{1-6}$ alkyl, C$_{1-6}$ haloalkyl, 3-7 membered cycloalkyl, C$_{1-6}$ alkylene-C$_{3-7}$ membered cycloalkyl, phenyl, 5-6 membered heteroaryl, —C(=O)R$^{x2a}$, —C(=O)OR$^{x2a}$ or —C(=O)NR$^{x2a}$R$^{x2b}$, wherein R$^{x2a}$ is selected from the group consisting of hydrogen, C$_{1-6}$ alkyl, C$_{2-6}$ alkenyl, C$_{2-6}$ alkynyl, C$_{1-6}$ heteroalkyl, 3-8 membered cycloalkyl, 3-8 membered heteroalkyl, —(C$_{1-6}$ alkylene)-(3-8 membered cycloalkyl), —(C$_{1-6}$ alkylene)-(3-8 membered heterocycloalkyl), —(C$_{1-6}$ alkylene)-(6-membered aryl) and —(C$_{1-6}$ alkylene)-(5-6 membered heteroaryl) and R$^{x2b}$ is selected from the group consisting of hydrogen, C$_{1-6}$ alkyl, C$_{2-6}$ alkenyl, C$_{2-6}$ alkynyl and C$_{1-6}$ heteroalkyl, and wherein R$^{x2a}$ and R$^{x2b}$, when attached to the same nitrogen atom, are optionally combined to form a 3-7 membered heterocycloalkyl further comprising 0-2 additional heteroatoms selected from N, O and S; or alternatively R$^1$ and R$^2$ are combined to form a 3-8 membered cycloalkyl or 3-8 membered heterocycloalkyl and optionally fused thereto is a 5-6 membered heteroaryl ring comprising 1-3 heteroatoms selected from N, O and S; and
wherein the aliphatic and/or aromatic portions of R$^1$ and R$^2$ either independently or when combined, are optionally substituted with 1 to 5 R$^{R1/2}$ substituents selected from the group consisting of F, Cl, Br, I, —OH, —NH$_2$, —SH, —CF$_3$, —OCF$_3$, —SF$_5$, —OCH$_3$, —(X$^a$)$_{0-1}$—CN, —(X$^a$)$_{0-1}$—NO$_2$, —(X$^a$)$_{0-1}$—N$_3$, —(X$^a$)$_{0-1}$—OH, —(X$^a$)$_{0-1}$—H, —(X$^a$)$_{0-1}$—OR$^a$, —(X$^a$)$_{0-1}$—N(H)R$^a$, —(X$^a$)$_{0-1}$—N(H)$_2$, —(X$^a$)$_{0-1}$—N(R$^a$)$_2$, —(X$^a$)$_{0-1}$—SR$^a$, —(X$^a$)$_{0-1}$—SH, —(X$^a$)$_{0-1}$—C(O)R$^a$, —(X$^a$)$_{0-1}$—S(O)$_2$R$^a$, —(X$^a$)$_{0-1}$—S(O)R$^a$, —(X$^a$)$_{0-1}$—N(H)S(O)$_2$R$^a$, —(X$^a$)$_{0-1}$—N(H)S(O)$_2$R$^a$, —(X$^a$)$_{0-1}$—N(R$^a$)S(O)$_2$R$^a$, —(X$^a$)$_{0-1}$—OC(O)R$^a$, —(X$^a$)$_{0-1}$—N(H)C(O)OR$^a$, —(X$^a$)$_{0-1}$—N(R$^a$)C(O)OR$^a$, —(X$^a$)$_{0-1}$—C(=O)OR$^a$, —(X$^a$)$_{0-1}$—C(=O)OH, —(X$^a$)$_{0-1}$—C(=O)N(H)R$^a$, —(X$^a$)$_{0-1}$—C(=O)N(R$^a$)R$^a$, —(X$^a$)$_{0-1}$—N(H)C(=O)R$^a$, —(X$^a$)$_{0-1}$—N $(R^a)C(=O)R^a$, $—(X^a)_{0-1}—N(H)C(=O)OR^a$ and $—(X^a)_{0-1}—N(R^a)C(=O)OR^a$, wherein $X^a$ is selected from the group consisting of $C_{1-6}$ alkylene, $C_{2-6}$ alkenylene, $C_{2-6}$ alkynylene, $C_{1-6}$ heteroalkylene, 3-6 membered cycloalkylene and 3-6 membered heterocycloalkylene, and $R^a$ at each occurrence is independently selected from the group consisting of $C_{1-6}$ alkyl, $C_{1-6}$ haloalkyl, $C_{1-6}$ heteroalkyl, $C_{2-6}$ alkenyl, $C_{2-6}$ alkynyl, 3-7 membered cycloalkyl and 3-7 membered heterocycloalkyl;

A is selected from the group consisting of:

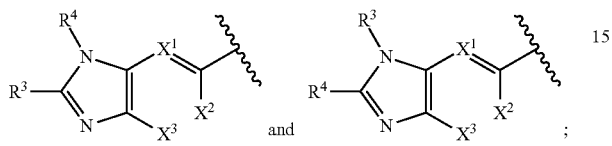

and

;

wherein $X^1$, $X^2$ and $X^3$ are independently $CR^5$, wherein $R^5$ is selected from the group consisting of hydrogen, $C_{1-4}$ alkyl, $C_{1-4}$ haloalkyl, halogen, $—OC_{1-6}$ alkyl, 3-6 membered heterocycloalkyl-$C_{1-3}$ alkyleneoxy-, —CN, —NO$_2$, —NH($C_{1-6}$ alkyl), —NH$_2$ and —N($C_{1-6}$ alkyl)$_2$;

$R^3$ is 5-10 membered heteroaryl optionally substituted with $—NR^{x3a}R^{x3b}$, wherein $R^{x3a}$ and $R^{x3b}$ are each independently selected from the group consisting of hydrogen, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ heteroalkyl, 6-10 membered aryl, 5-10 membered heteroaryl, and wherein $R^3$ and the $R^{x3a}$ and $R^{x3b}$ groups of $R^3$, if present, are further each independently optionally substituted with 1 to 5 $R^{R3}$ substituents selected from the group consisting of F, Cl, Br, I, —OH, —NH$_2$, —SH, —CF$_3$, —OCF$_3$, —SF$_5$, —OCH$_3$, $—(X^b)_{0-1}$—CN, $—(X^b)_{0-1}$—NO$_2$, $—(X^b)_{0-1}$—N$_3$, $—(X^b)$—OH, $—(X^b)$—H, $—(X^b)_{0-1}$—OR$^b$, $—(X^b)_{0-1}$—N(H)R$^b$, $—(X^b)$—N(H)$_2$, $—(X^b)_{0-1}$—N(R$^b$)$_2$, $—(X^b)_{0-1}$—SR$^b$, $—(X^b)_{0-1}$—SH, $—(X^b)_{0-1}$—C(O)R$^b$, $—(X^b)_{0-1}$—S(O)$_2$R$^b$, $—(X^b)_{0-1}$—S(O)R$^b$, $—(X^b)_{0-1}$—N(H)S(O)$_2$R$^b$, $—(X^b)_{0-1}$—N(R$^b$)S(O)$_2$R$^b$, $—(X^b)_{0-1}$—OC(O)R$^b$, $—(X^b)_{0-1}$—N(H)C(O)OR$^b$, $—(X^b)_{0-1}$—N(R$^b$)C(O)OR$^b$, $—(X^b)_{0-1}$—C(=O)OR$^b$, $—(X^b)_{0-1}$—C(=O)OH, $—(X^b)_{0-1}$—C(=O)N(H)R$^b$, $—(X^b)_{0-1}$—C(=O)N(R$^b$)R$^b$, $—(X^b)_{0-1}$—N(H)C(=O)R$^b$, $—(X^b)_{0-1}$—N(R$^b$)C(=O)R$^b$, $—(X^b)_{0-1}$—N(H)C(=O)OR$^b$ and $—(X^b)_{0-1}$—N(R$^b$)C(=O)OR$^b$, wherein $X^b$ is selected from the group consisting of $C_{1-6}$ alkylene, $C_{2-6}$ alkenylene, $C_{2-6}$ alkynylene, $C_{1-6}$ heteroalkylene, $C_{3-6}$ cycloalkylene and $C_{3-6}$ heterocycloalkylene, and $R^b$ at each occurrence is independently selected from the group consisting of $C_{1-6}$ alkyl, $C_{1-6}$ haloalkyl, $C_{1-6}$ heteroalkyl, $C_{2-6}$ alkenyl, $C_{2-6}$ alkynyl, 3-7 membered cycloalkyl and 3-7 membered heterocycloalkyl;

$R^4$ is $-(L)_{0-1}—R^{x4a}$, wherein L is selected from the group consisting of —O—, —N(H)—, —C(=O)—, $C_{1-4}$ alkylene, $C_{1-4}$ haloalkylene, $C_{2-4}$ alkenylene, $C_{2-4}$ alkynylene and $C_{1-4}$ heteroalkylene and $R^{x4a}$ is selected from the group consisting of hydrogen, $C_{1-6}$ alkyl, $C_{1-6}$ haloalkyl, $C_{2-6}$ alkenyl, $C_{2-6}$ alkynyl and $C_{1-6}$ heteroalkyl, 3-6 membered cycloalkyl, 3-9 membered heterocycloalkyl, 6-10 membered aryl and 5-10 membered heteroaryl, wherein the aliphatic or aromatic portions of $R^4$ are independently substituted with 0 to 5 $R^{R4}$ substituents selected from the group consisting of $C_{1-6}$ alkyl, $C_{1-6}$ haloalkyl, $C_{1-6}$ heteroalkyl, $C_{1-6}$ alkoxy, $C_{1-6}$ alkylamino, $C_{1-6}$ dialkylamino, $C_{3-6}$ heterocycloalkyl, F, Cl, Br, I, —OH, —NH$_2$, —SH, —CF$_3$, —OCF$_3$, —SF$_5$, $—(X^c)_{0-1}$—CN, $—(X^c)_{0-1}$—NO$_2$, $—(X^c)_{0-1}$—N$_3$, $—(X^c)$—OH, $—(X^c)_{0-1}$—OR$^c$, $—(X^c)$—H, $—(X^c)_{0-1}$—R$^c$, $—(X^c)_{0-1}$—N(H)R$^c$, $—(X^c)_{0-1}$—N(R$^c$)$_2$, $—(X^c)_{0-1}$—SR$^c$, $—(X^c)_{0-1}$—C(O)R$^c$, $—(X^c)_{0-1}$—S(O)$_2$R$^c$, $—(X^c)_{0-1}$—S(O)R$^c$, $—(X^c)_{0-1}$—N(H)S(O)$_2$R$^c$, $—(X^c)_{0-1}$—N(R$^c$)S(O)$_2$R$^c$, $—(X^c)_{0-1}$—C(=O)OR$^c$, $—(X^c)_{0-1}$—C(=O)OH, $—(X^c)_{0-1}$—C(=O)N(H)R$^c$, $—(X^c)_{0-1}$—C(=O)N(R$^c$)R$^c$, $—(X^c)_{0-1}$—N(H)C(=O)R$^c$, $—(X^c)_{0-1}$—N(R$^c$)C(=O)R$^c$, wherein $X^c$ is selected from the group consisting of $C_{1-6}$ alkylene, $C_{2-6}$ alkenylene, $C_{2-6}$ alkynylene, $C_{1-6}$ heteroalkylene, $C_{3-6}$ cycloalkylene and $C_{3-6}$ heterocycloalkylene, and $R^c$ at each occurrence is independently selected from the group consisting of $C_{1-6}$ alkyl, $C_{1-6}$ haloalkyl, $C_{1-6}$ heteroalkyl, $C_{2-6}$ alkenyl, $C_{2-6}$ alkynyl, 3-7 membered cycloalkyl, 3-7 membered heterocycloalkyl, phenyl and 5-6 membered heteroaryl, wherein any two $R^c$ groups attached to the same nitrogen atom are optionally combined to form a 3-7 membered heterocycloalkyl or 5-10 membered heteroaryl comprising 1-3 heteroatoms selected from N, O and S.

2. The compound of claim 1, wherein $R^3$ is substituted with $—NR^{x3a}R^{x3b}$, wherein and $R^{x3a}$ and $R^{x3b}$ are optionally substituted with 1 to 5 $R^{R3}$ substituents.

3. The compound of claim 1, wherein A is selected from the group consisting of

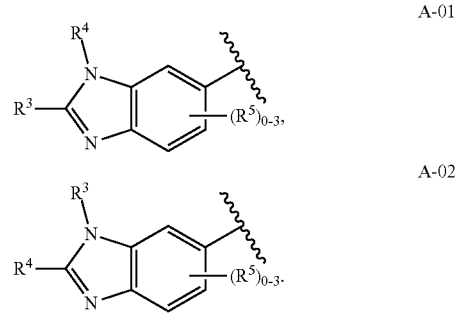

4. The compound of claim 1, wherein $R^3$ is selected from the group consisting of pyridyl, pyrimidinyl, pyrazinyl, pyridazinyl, triazinyl, purinyl, pyrrolopyrimidinyl, triazolopyrimidinyl, pyrazolopyrimidinyl, pyrrolopyrazinyl, pyrazolopyrazinyl, triazolopyrazinyl, imidazolopyrazinyl, pyrrolopyridazinyl, pyrazoloyridazinyl, triazoloyridazinyl, imidazoloyridazinyl, furopyrimidinyl, thienopyrimidinyl, oxazolopyrimidinyl, thiazolopyrimidinyl, pyrrolyl, imidazolyl, pyrazolyl, oxazolyl, isoxazolyl, oxadiazolyl, thiazolyl, isothiazolyl and thiadiazolyl, wherein $R^3$ is substituted with $—NR^{x3a}R^{x3b}$, wherein $R^3$ and the $R^{x3a}$ and $R^{x3b}$ group are each independently further optionally substituted with 1 to 5 $R^{R3}$ substituents.

5. The compound of claim 4, wherein $R^3$ is selected from the group consisting of pyridyl, pyrimidinyl, pyrazinyl, pyridazinyl, triazinyl, pyrrolyl, imidazolyl, pyrazolyl, isoxazolyl, oxadiazolyl, thiazolyl, isothiazolyl and thiadiazolyl and wherein $R^3$ is substituted with $—NR^{x3a}R^{x3b}$, wherein $R^3$ and the $R^{x3a}$ and $R^{x3b}$ group are further each independently optionally substituted with 1 to 3 $R^{R3}$ substituents.

6. The compound of claim 5, wherein $R^{x3a}$ and $R^{x3b}$ is each independently selected from the group consisting of hydrogen, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ heteroalkyl, 6-10 membered aryl and 5-10 membered heteroaryl, wherein at least one of $R^{x3a}$ and $R^{x3b}$ is hydrogen.

7. The compound of claim 6, wherein $R^{x3a}$ and $R^{x3b}$ is each independently selected from the group consisting of hydrogen, methyl, ethyl, propyl, isopropyl, phenyl and pyridyl, and wherein at least one of $R^{x3a}$ and $R^{x3b}$ is hydrogen.

8. The compound of claim 7, wherein $R^{x3a}$ and $R^{x3b}$ are each hydrogen.

9. The compound of claim 5, wherein $R^{R3}$ is selected from the group consisting F, Cl, Br, I, —OH, —NH$_2$, —CF$_3$, —OCF$_3$, —OCH$_3$, —NO$_2$, —X$^b$—NO$_2$, —X$^b$—OH, —X$^b$—H, —X$^b$—OR$^b$, —OR$^b$, —X$^b$—N(H)R$^b$, —N(H)R$^b$, —X$^b$—N(H)$_2$, —X$^b$—N(R$^b$)$_2$, —N(R$^b$)$_2$, —C(=O)N(H)R$^b$, —X$^b$—C(=O)N(H)R$^b$, —C(=O)N(R$^b$)R$^b$, —X$^b$—C(=O)N(R$^b$)R$^b$, —X$^b$—N(H)C(=O)R$^b$, —X$^b$—N(H)C(=O)R$^b$, —X$^b$—N(R$^b$)C(=O)R$^b$ and —N(R$^b$)C(=O)R$^b$, wherein $X^b$ is selected from the group consisting of $C_{1-6}$ alkylene, $C_{2-6}$ alkenylene, $C_{2-6}$ alkynylene, and $C_{1-6}$ heteroalkylene, and $R^b$ at each occurrence is independently selected from the group consisting of $C_{1-6}$ alkyl, $C_{1-6}$ haloalkyl, $C_{1-6}$ heteroalkyl, $C_{2-6}$ alkenyl, $C_{2-6}$ alkynyl, 3-7 membered cycloalkyl and 3-7 membered heterocycloalkyl.

10. The compound of claim 9, wherein $R^{R3}$ is selected from the group consisting of F, Cl, Br, I, —OH, —NH$_2$, —CF$_3$, —OCF$_3$, —OCH$_3$, —NO$_2$, —X$^b$—H, —OR$^b$, —N(H)R$^b$, —N(R$^b$)$_2$, —C(=O)N(H)R$^b$ and —C(=O)N(R$^b$)R$^b$.

11. The compound of claim 10, wherein $R^{R3}$ is selected from the group consisting of F, Cl, Br, I, —OH, —NH$_2$, —CF$_3$, —OCF$_3$, —OCH$_3$, —NO$_2$, —C(=O)N(CH$_3$)$_2$ and 3-methyloxetan-3-yl-(C=O)N(H)—.

12. The compound of claim 1, wherein $R^4$ is -(L)$_{0-1}$—$R^{x4a}$, wherein L is selected from the group consisting of —O—, —N(H)—, —C(=O)—, $C_{1-6}$ alkylene, $C_{1-6}$ haloalkylene and $C_{1-6}$ heteroalkylene, $R^{x4a}$ is selected from the group consisting of hydrogen, 3-6 membered cycloalkyl, 3-9 membered heterocycloalkyl and 5-6 membered heteroaryl, wherein the aliphatic and/or aromatic portions of $R^4$ are independently optionally substituted with 1 to 5 $R^{R4}$ substituents.

13. The compound of claim 12, wherein $R^4$ is -(L)$_{0-1}$—$R^{x4a}$, wherein L is selected from the group consisting of —O—, —N(H)—, —C(=O)—, $C_{1-6}$ alkylene, $C_{1-6}$ haloalkylene and $C_{1-6}$ heteroalkylene, $R^{x4a}$ is selected from the group consisting of hydrogen, cyclopropyl, cyclobutyl, cyclopentyl, cyclohexyl, aziridinyl, oxetanyl, tetrahydropyranyl, tetrahydrothiopyranyl, tetrahydrofuranyl, tetrahydromorpholinyl, piperidinyl, piperazinyl, thiomorpholino and pyrrolidinyl, wherein the aliphatic and/or aromatic portions of $R^4$ are independently optionally substituted with 1 to 5 $R^{R4}$ substituents.

14. The compound of claim 13, wherein $R^4$ is selected from the group consisting of hydrogen, —C(=O)N(CH$_3$)$_2$, —(CH$_2$)N(CH$_3$)$_2$, —(CH$_2$)N(CH$_3$)$_2$, morpholin-4-yl-(CH$_2$)—, cyclopropylmethyl, trifluoromethylethyl, —CH$_2$CH$_2$OCH$_3$, —OCH$_2$CH$_3$, methyl, ethyl, morpholin-4-yl-C(=O)—, pyrrolidin-1-yl-C(=O)—, CH$_3$OCH$_2$—, ethoxy and cyclopropyl.

15. The compound of claim 1, wherein $R^1$ is $C_{1-2}$ alkyl or $C_{1-2}$ haloalkyl; $R^2$ is $C_{1-6}$ alkyl, $C_{1-6}$ haloalkyl, 3-8 membered cycloalkyl, phenyl and 5-6 membered heteroaryl; or alternatively $R^1$ and $R^2$ are combined to form a 3-6 membered cycloalkyl or 3-6 membered heterocycloalkyl; and wherein the aliphatic and/or aromatic portions of $R^1$ and $R^2$ either independently or when combined, are optionally substituted with 1 to 5 $R^{R1/2}$ substituents.

16. The compound of claim 15, wherein $R^2$ is selected from the group consisting of $C_{1-6}$ alkyl, $C_{1-6}$ haloalkyl, cyclopropyl, cyclobutyl, cyclopentyl, cyclohexyl, oxetanyl, tetrahydrofuranyl, tetrahydropyranyl, thiazolyl, oxadiazolyl, triazolyl, tetrazolyl, oxazolyl, pyrazolyl, pyrimidinyl, pyrazinyl and pyrrolyl; or alternatively $R^2$ and $R^1$ are combined to form 3-6 membered ring selected from the group consisting of cyclobutyl, cyclopentyl, cyclohexyl oxetanyl, tetrahydrofuranyl and tetrahydropyranyl, azetidinyl, pyrrolidinyl and piperidinyl, wherein the aliphatic and/or aromatic portions of $R^1$ and $R^2$ either independently or when combined, are optionally substituted with 1 to 5 $R^{R1/2}$ substituents.

17. The compound of claim 1, wherein formula I has a subformula selected from the group consisting of

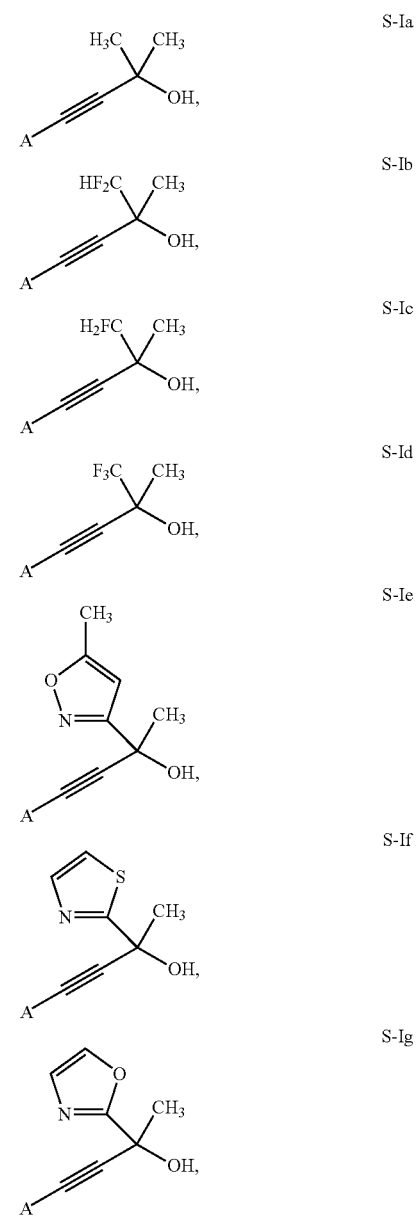

S-Ih 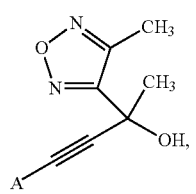

S-Ii 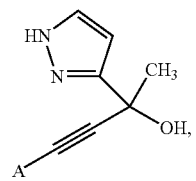

S-Ij 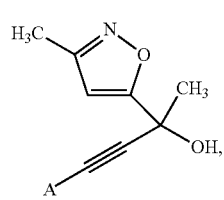

S-Ik 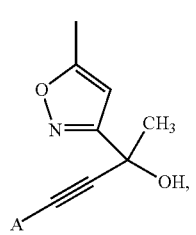

S-Il 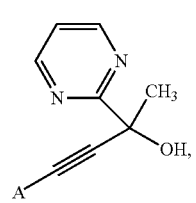

S-Im 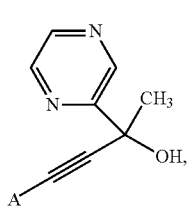

S-In 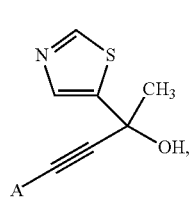

S-Io 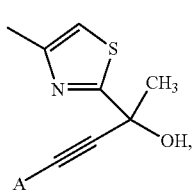

S-Ip 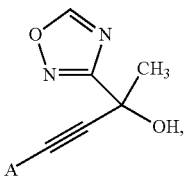

S-Iq 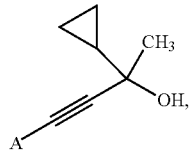

S-Ir 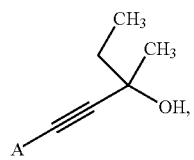

S-Is 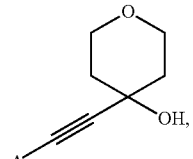

S-It 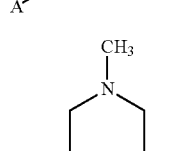

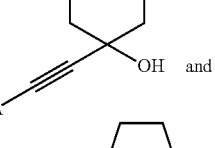 and

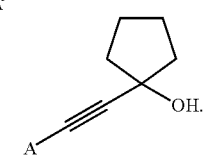

18. The compound of claim 1, wherein $R^1$ is $C_{1-2}$ alkyl, $C_{1-2}$ haloalkyl or $CH_2$—OH; $R^2$ is $C_{1-6}$ alkyl, $C_{1-6}$ haloalkyl, 3-8 membered cycloalkyl, phenyl and 5-6 membered heteroaryl; or alternatively $R^1$ and $R^2$ are combined to form a 3-6 membered cycloalkyl or 3-6 membered heterocycloalkyl; and wherein the aliphatic and/or aromatic portions of $R^1$ and $R^2$ either independently or when combined, are optionally substituted with 1 to 5 $R^{R1/2}$ substituents; A is

A-01

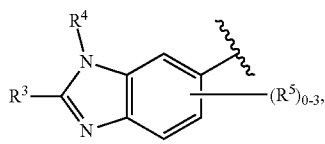

wherein $R^3$ is selected from the group consisting of pyridyl, pyrimidinyl, pyrazinyl, pyridazinyl, triazinyl, purinyl, pyrrolopyrimidinyl, triazolopyrimidinyl, pyrazolopyrimidinyl, pyrrolopyrazinyl, pyrazolopyrazinyl, triazolopyrazinyl, imidazolopyrazinyl, pyrrolopyridazinyl, pyrazoloyridazinyl, triazoloyridazinyl, imidazoloyridazinyl, furopyrimidinyl, thienopyrimidinyl, oxazolopyrimidinyl, thiazolopyrimidinyl, pyrrolyl, imidazolyl, pyrazolyl, oxazolyl, isoxazolyl, oxadiazolyl, thiazolyl, isothiazolyl and thiadiazolyl, wherein $R^3$ is substituted with —$NR^{x3a}R^{x3b}$, wherein $R^3$ and the $R^{x3a}$ and $R^{x3b}$ group are each independently further optionally substituted with 1 to 5 $R^{R3}$ substituents; $R^4$ is -(L)$_{0-1}$—$R^{x4a}$, wherein L is selected from the group consisting of —C(=O)—, $C_{1-6}$ alkylene, $C_{1-6}$ haloalkylene and $C_{1-6}$ heteroalkylene, $R^{x4a}$ is selected from the group consisting of hydrogen, cyclopropyl, cyclobutyl, cyclopentyl, cyclohexyl, aziridinyl, oxetanyl, tetrahydropyranyl, tetrahydrothiopyranyl, tetrahydrofuranyl, morpholinyl, piperidinyl, piperazinyl, thiomorpholino and pyrrolidinyl, wherein the aliphatic and/or aromatic portions of $R^4$ are independently optionally substituted with 1 to 5 $R^{R4}$ substituents; $R^5$ is selected from the group consisting of hydrogen, $C_{1-4}$ alkyl, $C_{1-4}$ haloalkyl, halogen, —$OC_{1-6}$ alkyl and 3-6 membered heterocycloalkyl-$C_{1-3}$ alkyleneoxy.

19. The compound of claim 1, selected from the group consisting of: 4-(1-(2-aminopyrimidin-4-yl)-1H-benzo[d]imidazol-5-yl)-2-(thiazol-2-yl)but-3-yn-2-ol; 4-(1-(2-aminopyrimidin-4-yl)-1H-benzo[d]imidazol-6-yl)-2-(thiazol-2-yl)but-3-yn-2-ol; 4-(1-(2-aminopyrimidin-4-yl)-1H-benzo[d]imidazol-6-yl)-2-(thiazol-2-yl)but-3-yn-2-ol; 4-(1-(2-aminopyrimidin-4-yl)-1H-benzo[d]imidazol-6-yl)-2-methylbut-3-yn-2-ol; 4-(1-(2-aminopyrimidin-4-yl)-2-methyl-1H-benzo[d]imidazol-6-yl)-2-(thiazol-2-yl)but-3-yn-2-ol; 4-(1-(2-aminopyrimidin-4-yl)-2-cyclopropyl-1H-benzo[d]imidazol-6-yl)-2-(thiazol-2-yl)but-3-yn-2-ol; N-(2-amino-4-(6-(3-hydroxy-3-(thiazol-2-yl)but-1-ynyl)-1H-indazol-1-yl)pyrimidin-5-yl)-3-methyloxetane-3-carboxamide; 4-(1-(2-aminopyrimidin-4-yl)-2-cyclopropyl-1H-benzo[d]imidazol-6-yl)-2-methylbut-3-yn-2-ol; 1-(2-aminopyrimidin-4-yl)-6-(3-hydroxy-3-methylbut-1-ynyl)-1H-benzo[d]imidazol-2(3H)-one; 1-(2-aminopyrimidin-4-yl)-6-(3-hydroxy-3-(thiazol-2-yl)but-1-ynyl)-1H-benzo[d]imidazol-2(3H)-one; 4-(1-(2-aminopyrimidin-4-yl)-1H-benzo[d]imidazol-6-yl)-2-(oxazol-2-yl)but-3-yn-2-ol; 4-(1-(2-aminopyrimidin-4-yl)-1H-benzo[d]imidazol-6-yl)-1,1-difluoro-2-methylbut-3-yn-2-ol; 4-(1-(2-aminopyrimidin-4-yl)-1H-benzo[d]imidazol-6-yl)-1,1,1-trifluoro-2-methylbut-3-yn-2-ol; 4-(1-(2-aminopyrimidin-4-yl)-1H-benzo[d]imidazol-6-yl)-2-(5-methylisoxazol-3-yl)but-3-yn-2-ol; 4-(1-(2-aminopyrimidin-4-yl)-1H-benzo[d]imidazol-6-yl)-2-(1H-pyrazol-4-yl)but-3-yn-2-ol; 4-(1-(2-aminopyrimidin-4-yl)-1H-benzo[d]imidazol-6-yl)-2-cyclopropylbut-3-yn-2-ol; 4-(1-(2-aminopyrimidin-4-yl)-1H-benzo[d]imidazol-6-yl)-1-fluoro-2-methylbut-3-yn-2-ol; 4-(1-(2-aminopyrimidin-4-yl)-2-ethoxy-1H-benzo[d]imidazol-6-yl)-2-methylbut-3-yn-2-ol; 4-(1-(2-aminopyrimidin-4-yl)-5-fluoro-1H-benzo[d]imidazol-6-yl)-2-(thiazol-2-yl)but-3-yn-2-ol; 4-(1-(2-aminopyrimidin-4-yl)-5-fluoro-1H-benzo[d]imidazol-6-yl)-2-methylbut-3-yn-2-ol; 4-(1-(2-aminopyrimidin-4-yl)-1H-benzo[d]imidazol-6-yl)-2-(3-methylisoxazol-5-yl)but-3-yn-2-ol; 1 (2 aminopyrimidin-4-yl)-6-(3-hydroxy-3-(oxazol-2-yl)but-1-ynyl)-N,N-dimethyl-1H-indazole-3-carboxamide; 4-(1-(2-aminopyrimidin-4-yl)-1H-benzo[d]imidazol-6-yl)-2-(oxazol-2-yl)but-3-yn-2-ol; 4-(1-(2-aminopyrimidin-4-yl)-1H-benzo[d]imidazol-6-yl)-2-(oxazol-2-yl)but-3-yn-2-ol; 4-(1-(4-aminopyrimidin-2-yl)-1H-benzo[d]imidazol-6-yl)-2-(thiazol-2-yl)but-3-yn-2-ol; 4-(1-(4-amino-1,3,5-triazin-2-yl)-2-methyl-1H-benzo[d]imidazol-6-yl)-2-(thiazol-2-yl)but-3-yn-2-ol; 4-(1-(4-amino-1,3,5-triazin-2-yl)-2-cyclopropyl-1H-benzo[d]imidazol-6-yl)-2-(5-methylisoxazol-3-yl)but-3-yn-2-ol; (R)- 4-(1-(4-amino-1,3,5-triazin-2-yl)-2-cyclopropyl-1H-benzo[d]imidazol-6-yl)-2-(thiazol-2-yl)but-3-yn-2-ol; 4-(1-(4-amino-1,3,5-triazin-2-yl)-2-methyl-1H-benzo[d]imidazol-6-yl)-2-(5-methylisoxazol-3-yl)but-3-yn-2-ol; (R)-4-(1-(4-amino-1,3,5-triazin-2-yl)-2-(methoxymethyl)-1H-benzo[d]imidazol-6-yl)-2-(thiazol-2-yl)but-3-yn-2-ol; 4-(1-(2-aminopyrimidin-4-yl)-2-ethoxy-1H-benzo[d]imidazol-6-yl)-2-(5-methylisoxazol-3-yl)but-3-yn-2-ol; (2R)-4-[3-(4-amino-1,3,5-triazin-2-yl)-2-methyl-benzimidazol-5-yl]-2-thiazol-2-yl-but-3-yn-2-ol; (2R)-4-[3-(4-amino-1,3,5-triazin-2-yl)-2-methyl-benzimidazol-5-yl]-2-(5-methylisoxazol-3-yl)but-3-yn-2-ol; 4-[3-(2-aminopyrimidin-4-yl)-2-ethoxy-benzimidazol-5-yl]-2-(5-methylisoxazol-3-yl)but-3-yn-2-ol; 3-[1-(2-aminopyrimidin-4-yl)-6-[3-hydroxy-3-(5-methylisoxazol-3-yl)but-1-ynyl]benzimidazol-2-yl]oxypropane-1,2-diol; 4-[3-(2-aminopyrimidin-4-yl)-2-ethoxy-benzimidazol-5-yl]-2-[5-(hydroxymethyl)isoxazol-3-yl]but-3-yn-2-ol; (2R)-4-[3-(2-aminopyrimidin-4-yl)-2-(oxetan-3-yloxy)benzimidazol-5-yl]-2-(5-methylisoxazol-3-yl)but-3-yn-2-ol; 4-[3-(2-aminopyrimidin-4-yl)-2-(2-hydroxyethoxy)benzimidazol-5-yl]-2-(5-methylisoxazol-3-yl)but-3-yn-2-ol; 7-[2-[3-(2-aminopyrimidin-4-yl)-2-ethoxy-benzimidazol-5-yl]ethynyl]-5,6-dihydropyrrolo[1,2-a]imidazol-7-ol; 4-[3-(2-aminopyrimidin-4-yl)-2-(2,2,2-trifluoroethoxy)benzimidazol-5-yl]-2-(5-methylisoxazol-3-yl)but-3-yn-2-ol; 4-[3-(2-aminopyrimidin-4-yl)-2-tetrahydropyran-4-yloxy-benzimidazol-5-yl]-2-(5-methylisoxazol-3-yl)but-3-yn-2-ol; (2R)-4-[3-(2-aminopyrimidin-4-yl)-2-(2-methoxyethoxy)benzimidazol-5-yl]-2-(5-methylisoxazol-3-yl)but-3-yn-2-ol; 4-[3-(2-aminopyrimidin-4-yl)-2-(2,2,2-trifluoroethoxy)benzimidazol-5-yl]-2-pyrimidin-2-yl-but-3-yn-2-ol; (2R)-4-[3-(2-aminopyrimidin-4-yl)-2-(oxetan-3-yloxy)benzimidazol-5-yl]-2-(5-methyl-1,2,4-oxadiazol-3-yl)but-3-yn-2-ol; 4-[3-(2-aminopyrimidin-4-yl)-2-ethoxy-benzimidazol-5-yl]-2-pyrimidin-2-yl-but-3-yn-2-ol; (2R)-4-[3-(2-aminopyrimidin-4-yl)-2-(2-methoxyethoxy)benzimidazol-5-yl]-2-(5-methyl-1,2,4-oxadiazol-3-yl)but-3-yn-2-ol; 1-[3-[1-(2-aminopyrimidin-4-yl)-6-[3-hydroxy-3-(5-methylisoxazol-3-yl)but-1-ynyl]benzimidazol-2-yl]oxyazetidin-1-yl]ethanone; 4-[3-(2-aminopyrimidin-4-yl)-2-(2-methoxyethoxy)benzimidazol-5-yl]-2-pyrimidin-2-yl-but-3-yn-2-ol; 4-[3-(2-aminopyrimidin-4-yl)-2-(2-hydroxyethoxy)benzimidazol-5-yl]-2-pyrimidin-2-yl-but-3-yn-2-ol; 4-[3-(4-amino-1,3,5-triazin-2-yl)-2-methyl-benzimidazol-5-yl]-2-pyrimidin-2-yl-but-3-yn-2-ol; 4-[3-(2-aminopyrimidin-4-yl)-2-[(2,2-dimethyl-1,3-dioxolan-4-yl)methoxy]benzimidazol-5-yl]-2-(5-methylisoxazol-3-yl)but-3-yn-2-ol; 4-[3-(2-aminopyrimidin-4-yl)-2-(oxetan-3-yloxy)benzimidazol-5-yl]-2-pyrimidin-2-yl-but-3-yn-2-ol; 4-[3-(4-amino-1,3,5-triazin-2-yl)-2-methyl-benzimidazol-5-yl]-2-pyrazin-2-yl-but-3-yn-2-ol; 4-[3-(2-aminopyrimidin-4-yl)-2-(oxetan-3-yloxy)benzimidazol-5-yl]-2-methyl-but-3-yn-2-ol; 4-[3-(2-aminopyrimidin-4-yl)-2-[1-(2-hydroxyethyl)azetidin-3-yl]oxy-benzimidazol-5-yl]-2-(5-methylisoxazol-3-yl)but-3-yn-2-ol; 4-[3-(4-amino-1,3,5-triazin-2-yl)-2-methyl-benzimidazol-5-yl]-1-cyclopropyl-2-methyl-but-3-yn-2-ol; 4-[3-(4-amino-1,3,5-triazin-2-yl)-2-methyl-benzimidazol-5-yl]-2-methyl-but-3-yne-1,2-diol; [1-(2-aminopyrimidin-4-yl)-6-[3-hydroxy-3-(5-methylisoxazol-3-yl)but-1-ynyl]benzimidazol-2-yl]-pyrrolidin-1-yl-methanone; 1-[2-[3-(4-amino-1,3,5-triazin-2-yl)-2-methyl-benzimidazol-5-yl]ethynyl]cyclohexanol; [1-[2-[3-(4-amino-1,3,5-triazin-2-yl)-2-methyl-benzimidazol-5-yl]ethynyl]cyclopentyl]methanol; 4-[3-(2-aminopyrimidin-4-yl)-2-(2-hydroxyethoxy)benzimidazol-5-yl]-2-(5-fluoro-2-pyridyl)but-3-yn-2-ol; 3-[3-[3-(4-amino-1,3,5- triazin-2-yl)-2-methyl-benzimidazol-5-yl]-1-hydroxy-prop-2-ynyl]cyclobutanol; 2-[2-[3-(4-amino-1,3,5-triazin-2-yl)-2-methyl-benzimidazol-5-yl]ethynyl]norbornan-2-ol; 4-[3-(4-amino-1,3,5-triazin-2-yl)-2-methyl-benzimidazol-5-yl]-2-[4-(hydroxymethyl)thiazol-2-yl]but-3-yn-2-ol; 2-[2-[3-[3-(4-amino-1,3,5-triazin-2-yl)-2-methyl-benzimidazol-5-yl]-1-hydroxy-1-methyl-prop-2-ynyl]thiazol-4-yl]acetonitrile; 3-[2-[3-(4-amino-1,3,5-triazin-2-yl)-2-methyl-benzimidazol-5-yl]ethynyl]-3-hydroxy-cyclobutanecarbonitrile; 3-[2-[3-(4-amino-1,3,5-triazin-2-yl)-2-methyl-benzimidazol-5-yl]ethynyl]tetrahydropyran-3-ol; 1-[2-[3-(4-amino-1,3,5-triazin-2-yl)-2-methyl-benzimidazol-5-yl]ethynyl]-3-(hydroxymethyl)cyclobutanol; 3-[2-[3-(4-amino-1,3,5-triazin-2-yl)-2-methyl-benzimidazol-5-yl]ethynyl]oxetan-3-ol; 4-[3-(4-amino-1,3,5-triazin-2-yl)-2-methyl-benzimidazol-5-yl]-2,2-dimethyl-but-3-yn-1-ol; (2R)-4-[3-(2-aminopyrimidin-4-yl)-2-(2-fluoroethoxy)benzimidazol-5-yl]-2-(5-methyl-1,2,4-oxadiazol-3-yl)but-3-yn-2-ol; 4-[3-(2-aminopyrimidin-4-yl)-2-(2-hydroxyethoxy)benzimidazol-5-yl]-2-(5-chloro-2-pyridyl)but-3-yn-2-ol; 4-[3-(2-aminopyrimidin-4-yl)-2-(2-fluoroethoxy)benzimidazol-5-yl]-2-pyrimidin-2-yl-but-3-yn-2-ol; 4-[3-(4-amino-1,3,5-triazin-2-yl)-2-methyl-benzimidazol-5-yl]-2-methyl-1-pyrazol-1-yl-but-3-yn-2-ol; (2R)-4-[3-(2-aminopyrimidin-4-yl)-2-(2-methoxyethylamino)benzimidazol-5-yl]-2-(5-methylisoxazol-3-yl)but-3-yn-2-ol; 4-[3-(2-aminopyrimidin-4-yl)-2-(2-methoxyethylamino)benzimidazol-5-yl]-2-(4-methylthiazol-2-yl)but-3-yn-2-ol; and 4-[3-(2-aminopyrimidin-4-yl)-2-(2-hydroxyethoxy)benzimidazol-5-yl]-2-(5-chloro-2-pyridyl)but-3-yn-2-ol.

20. A pharmaceutical composition comprising a compound of claim 1 and at least one pharmaceutically acceptable carrier, diluent or excipient.

21. A method for the treatment of rheumatoid arthritis in a mammal, wherein said method comprises administering an effective amount to the mammal of a compound as defined in claim 1.

* * * * *